US011186554B2

(12) United States Patent
Konradi et al.

(10) Patent No.: US 11,186,554 B2
(45) Date of Patent: Nov. 30, 2021

(54) NON-FUSED TRICYCLIC COMPOUNDS

(71) Applicant: VIVACE THERAPEUTICS, INC., San Mateo, CA (US)

(72) Inventors: Andrei W. Konradi, Burlingame, CA (US); Tracy Tzu-Ling Tang Lin, Redwood City, CA (US)

(73) Assignee: VIVACE THERAPEUTICS, INC., San Mateo, CA (US)

( * ) Notice: Subject to any disclaimer, the term of this patent is extended or adjusted under 35 U.S.C. 154(b) by 0 days.

(21) Appl. No.: 16/609,715

(22) PCT Filed: May 2, 2018

(86) PCT No.: PCT/US2018/030721
§ 371 (c)(1),
(2) Date: Oct. 30, 2019

(87) PCT Pub. No.: WO2018/204532
PCT Pub. Date: Nov. 8, 2018

(65) Prior Publication Data
US 2020/0062721 A1  Feb. 27, 2020

Related U.S. Application Data

(60) Provisional application No. 62/500,937, filed on May 3, 2017.

(51) Int. Cl.
| | |
|---|---|
| *C07D 257/04* | (2006.01) |
| *A61P 35/00* | (2006.01) |
| *C07D 231/12* | (2006.01) |
| *C07D 249/08* | (2006.01) |
| *C07D 401/04* | (2006.01) |
| *C07D 401/06* | (2006.01) |
| *C07D 403/04* | (2006.01) |
| *C07D 403/06* | (2006.01) |
| *C07D 405/04* | (2006.01) |
| *C07D 413/06* | (2006.01) |

(52) U.S. Cl.
CPC ............ *C07D 257/04* (2013.01); *A61P 35/00* (2018.01); *C07D 231/12* (2013.01); *C07D 249/08* (2013.01); *C07D 401/04* (2013.01); *C07D 401/06* (2013.01); *C07D 403/04* (2013.01); *C07D 403/06* (2013.01); *C07D 405/04* (2013.01); *C07D 413/06* (2013.01)

(58) Field of Classification Search
CPC ... C07D 257/04; C07D 401/04; C07D 401/06
USPC .................................................... 514/210.18
See application file for complete search history.

(56) References Cited

U.S. PATENT DOCUMENTS

| | | | |
|---|---|---|---|
| 3,895,027 A | 7/1975 | Katner | |
| 3,903,106 A | 9/1975 | Katner et al. | |
| 4,010,273 A | 3/1977 | Bormann et al. | |
| 4,962,119 A | 10/1990 | Boschelli et al. | |
| 5,017,467 A | 5/1991 | Masukawa et al. | |
| 5,066,668 A | 11/1991 | Boschelli et al. | |
| 5,114,958 A | 5/1992 | Boschelli et al. | |
| 5,462,952 A | 10/1995 | Boschelli et al. | |
| 5,670,526 A | 9/1997 | Dodd et al. | |
| 6,211,209 B1 | 4/2001 | Baragi et al. | |
| 6,545,030 B1 | 4/2003 | Barrett et al. | |
| 6,972,287 B1 | 12/2005 | Augelli-Szafran et al. | |
| 7,019,033 B2 | 3/2006 | Barrett et al. | |
| 7,956,191 B2 | 6/2011 | Abel et al. | |
| 8,076,486 B2 | 12/2011 | Goutopoulos et al. | |
| 8,198,457 B2 | 6/2012 | Abel et al. | |
| 8,524,911 B2 | 9/2013 | Abel et al. | |
| 8,841,459 B2 | 9/2014 | Deppe et al. | |
| 9,790,229 B2 | 10/2017 | Bui et al. | |
| 2003/0004193 A1 | 1/2003 | Barrett et al. | |
| 2005/0004186 A1 | 1/2005 | Barrett et al. | |
| 2007/0259051 A1 | 11/2007 | Feinmark et al. | |
| 2009/0048301 A1 | 2/2009 | Chen et al. | |
| 2009/0318438 A1 | 12/2009 | Chen et al. | |
| 2016/0289171 A1 | 10/2016 | Balog et al. | |
| 2017/0137428 A1 | 5/2017 | Spangenberg | |
| 2020/0354325 A1 | 11/2020 | Konradi et al. | |

FOREIGN PATENT DOCUMENTS

| | | |
|---|---|---|
| WO | WO-0042029 A1 | 7/2000 |
| WO | WO-0105391 A2 | 1/2001 |
| WO | WO-03045912 A1 | 6/2003 |
| WO | WO-2004056789 A1 | 7/2004 |
| WO | WO-2005004818 A2 | 1/2005 |
| WO | WO-2007123936 A1 | 11/2007 |
| WO | WO-2009086163 A2 | 7/2009 |
| WO | WO-2013188138 A1 | 12/2013 |
| WO | WO-2016161269 A1 | 10/2016 |

(Continued)

OTHER PUBLICATIONS

Ouyang et al. Bioorganic & Medicinal Chemistry Letters (2005),15(23), 5154-5159.*
Holmes et al., Discovery and structure-activity relationships of novel sulfonamides as potent PTP1B inhibitors. Bioorganic and Medicinal Chemistry Letters 15:4336-4341 (2005).
Pobbati et al. Targeting the Central Pocket in Human Transcription Factor TEAD as a Potential Cancer Therapeutic Strategy. Structure 23:2076-2086 (2015).
Pubchem Compound Summary CID 68170056 deposited Nov. 30, 2012.
Science IP Report 2017 (1079 pgs).

(Continued)

*Primary Examiner* — Kahsay Habte
(74) *Attorney, Agent, or Firm* — Wilson Sonsini Goodrich & Rosati

(57) ABSTRACT

Provided herein are compounds and pharmaceutical compositions comprising said compounds that are useful for treating cancers. Specific cancers include those that are mediated by YAP/TAZ or those that are modulated by the interaction between YAP/TAZ and TEAD.

22 Claims, 2 Drawing Sheets

(56) References Cited

FOREIGN PATENT DOCUMENTS

| WO | WO-2016161279 A1 | 10/2016 |
| WO | WO-2016161286 A1 | 10/2016 |
| WO | WO-2017058716 A1 | 4/2017 |
| WO | WO-2018204532 A1 | 11/2018 |
| WO | WO-2019040380 A1 | 2/2019 |
| WO | WO-2019113236 A1 | 6/2019 |
| WO | WO-2019222431 A1 | 11/2019 |

OTHER PUBLICATIONS

Yokokawa et al., Discovery of potent non-nucleoside inhibitors of dengue viral RNA-dependent RNA polymerase from a fragment hit using structure-based drug design. Journal of Medicinal Chemistry 59(8):3935-3952 (2016).
Berge et al. Pharmaceutical Salts. Journal of Pharmaceutical Sciences 66(1):1-19 (Jan. 1977).
Bundgaard et al. Design of Prodrugs pp. 7-9, 21-24 (1985).
Fleisher et al. Improved oral drug delivery: solubility limitations overcome by the use of prodrugs. Advanced Drug Delivery Reviews 19:115-130 (1996).
PCT/US2018/030721 International Search Report and Written Opinion dated Aug. 28, 2018.
PCT/US2018/030721 Invitation to Pay Additional Fees dated Jul. 3, 2018.
PUBCHEM Substance record for SID 274578875, available date: Dec. 18, 2015 (retrieved on Jun. 22, 2018). Retrieved from https://pubchem.ncbi.nlm.nih.gov/substance/274578875.
Manbeck et al. Photoluminescent Copper(I) Complexes with Amido-Triazolato Ligands. Inorganic Chemistry 50(8):3431-3441 (2011).

\* cited by examiner

NON-FUSED TRICYCLIC COMPOUNDS

CROSS-REFERENCE

This application claims benefit of U.S. Provisional Patent Application No. 62/500,937 filed on May 3, 2017, which is incorporated herein by reference in its entirety.

BACKGROUND OF THE DISCLOSURE

YAP and TAZ are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with transcriptional enhancer associate domain (TEAD) transcription factors and coactivate the expression of target genes and promote cell proliferaction. Hyperactivation of YAP and TAZ and/or mutations in one or more members of the Hippo pathway network have been implicated in numerous cancers. Described herein are inhibitors associated with one or more members of the Hippo pathway network, such as inhibitors of YAP/TAZ or inhibitors that modulate the interaction between YAP/TAZ and TEAD.

SUMMARY OF THE DISCLOSURE

Provided herein are substituted tetrazole compounds and pharmaceutical compositions comprising said compounds. In some embodiments, the subject compounds are useful for the treatment of cancer.

Provided in one aspect is a compound of Formula (I), or a pharmaceutically acceptable salt thereof:

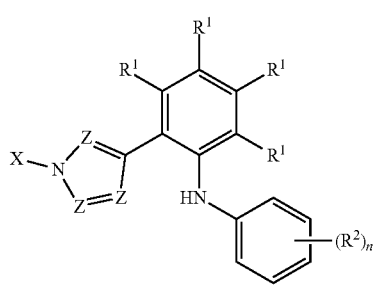

Formula (I)

wherein:
each Z is independently N or $CR^z$;
  each $R^z$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, unsubstituted aryl, substituted or unsubstituted heteroaryl, -$L^1$-$Y^1$, or -$L^2$-$L^3$-$Y^2$;
$L^1$ is substituted or unsubstituted $C_1$-$C_6$alkylene;
$Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;
$L^2$ is absent or substituted or unsubstituted $C_1$-$C_6$alkylene;
$L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —O—$NR^3$(C=O)—, —$NR^3$(C=O)—, —$NR^3$(C=O)$NR^3$—, —O(C=O)$NR^3$—, —$NR^3$(C=O)O—, —$NR^3$($SO_2$)$NR^3$—, —$NR^3$($SO_2$)—, —($SO_2$)$NR^3$—, —($SO_2$)$NR^3$—(C=O)—, —(C=O)—$NR^3$($SO_2$)—, —($SO_2$)$NR^3$—(C=O)O—, —O(C=O)—$NR^3$($SO_2$)—, —$NR^3$($SO_2$)$NR^3$—(C=O)—, —(C=O)—$NR^3$($SO_2$)$NR^3$—, —O(C=O)—$NR^3$($SO_2$)—$NR^3$—, or —$NR^3$($SO_2$)$NR^3$—(C=O)O—;

each $R^3$ is independently H or substituted or unsubstituted $C_1$-$C_6$alkyl;

$Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$ cycloalkyl, substituted or unsubstituted $C_2$-$C_{10}$heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

each $R^1$ is independently H, halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

n is 1, 2, 3, 4 or 5;

each $R^2$ is independently halogen, —$N_3$, —CN, —$OR^5$, —$SR^5$, —($SO_2$)$R^5$, —$N(R^5)_2$, —$CO_2R^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

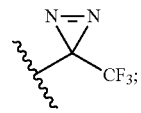

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^5$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

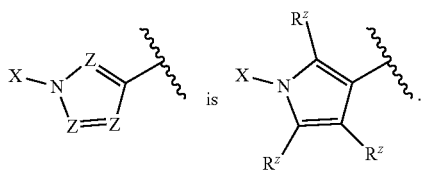

In some embodiments,

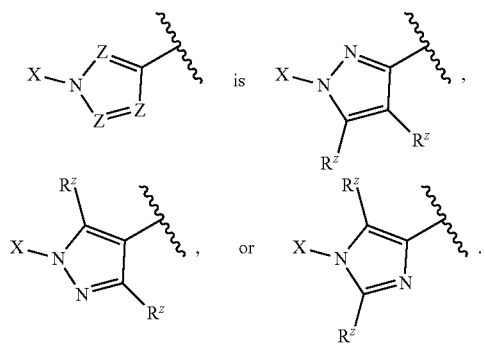

In some embodiments,

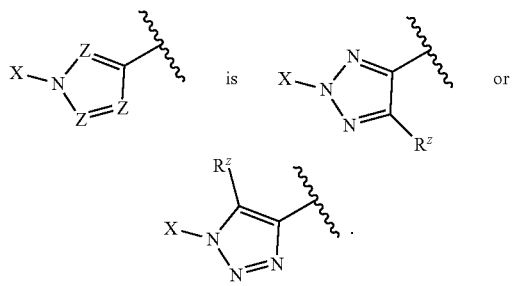

In some embodiments,

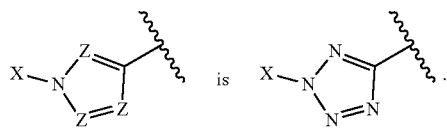

In some embodiments, each $R^z$ is independently H or substituted or unsubstituted $C_1$-$C_6$alkyl.

In some embodiments, X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, unsubstituted aryl, or substituted or unsubstituted heteroaryl. In some embodiments, X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2C_{10}$heterocycloalkyl, or substituted or unsubstituted heteroaryl. In some embodiments, X is —C—$Y^1$. In some embodiments, $L^1$ is substituted or unsubstituted $C_1$-$C_4$alkylene; and $Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl. In some embodiments, $L^1$ is substituted or unsubstituted $C_1$-$C_4$alkylene; and $Y^1$ is substituted or unsubstituted $C_3$-$C_6$cycloalkyl, substituted or unsubstituted $C_2$-$C_6$ heterocycloalkyl, substituted or unsubstituted phenyl, or substituted or unsubstituted monocyclic heteroaryl. In some embodiments, X is -$L^2$-$L^3$-$Y^2$. In some embodiments, $L^2$ is substituted or unsubstituted $C_1$-$C_6$alkylene; $L^3$ is —O—, —S—, —(S=O)—, —(SO_2)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O) NR$^3$—, —NR$^3$(C=O)O—, —NR$^3$(SO_2)NR$^3$—, —NR$^3$ (SO_2)—, —(SO_2)NR$^3$—, —(SO_2)NR$^3$—(C=O)—, —(SO_2)NR$^3$—(C=O)O—, —NR$^3$(SO_2)NR$^3$—(C=O)—, or —NR$^3$(SO_2)NR$^3$—(C=O)O—; each R$^3$ is independently H or substituted or unsubstituted $C_1$-$C_6$alkyl; and $Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl. In some embodiments, $L^2$ is substituted or unsubstituted $C_1$-$C_4$alkylene; $L^3$ is —O—, —S—, —(S=O)—, —(SO_2)—, —NR$^3$—, —(C=O)—, —(C=O)O—, —O(C=O)—, —(C=O) NR$^3$—, —(C=O)NR$^3$—O—, —NR$^3$(C=O)—, —NR$^3$ (C=O)NR$^3$—, —O(C=O)NR$^3$—, —NR$^3$(C=O)O—, —NR$^3$(SO_2)NR$^3$—, —NR$^3$(SO_2)—, —(SO_2)NR$^3$—, —(SO_2)NR$^3$—(C=O)—, —(SO_2)NR$^3$—(C=O)O—, —NR$^3$(SO_2)NR$^3$—(C=O)—, or —NR$^3$(SO_2)NR$^3$—(C=O)O—; each R$^3$ is independently H or substituted or unsubstituted $C_1$-$C_4$alkyl; and $Y^2$ is H, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl.

In some embodiments,

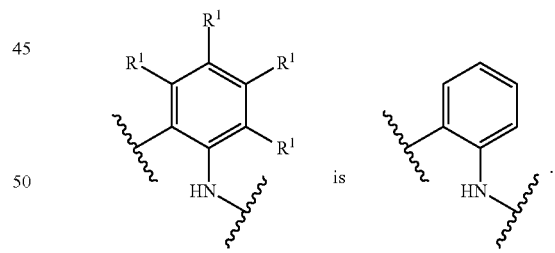

In some embodiments,

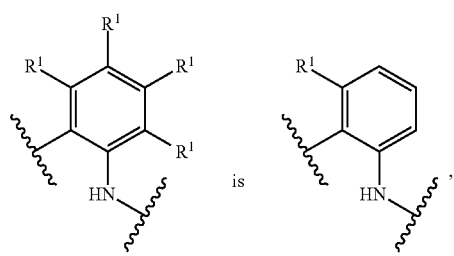

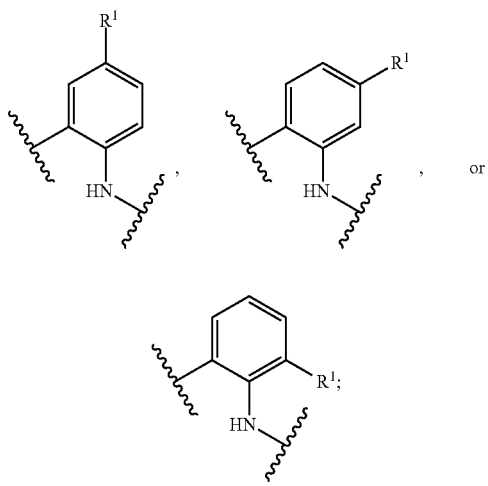

and R[1] is halogen, —CN, —OR[4], —SR[4], —N(R[4])$_2$, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted aryl, or substituted or unsubstituted heteroaryl.

In some embodiments,

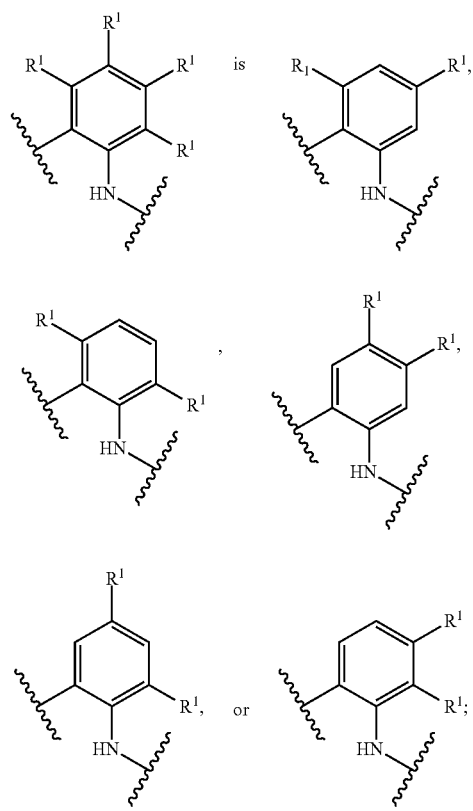

and each R[1] is independently halogen, —CN, —OR[4], —SR[4], —N(R[4])$_2$, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted aryl, or substituted or unsubstituted heteroaryl.

In some embodiments,

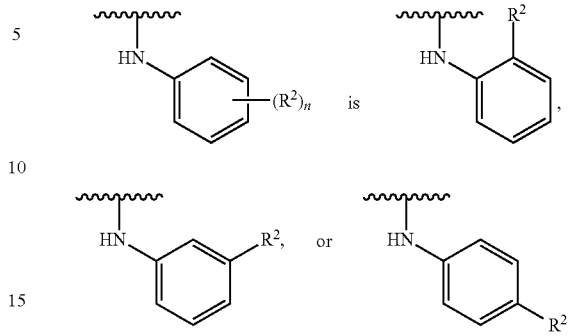

In some embodiments,

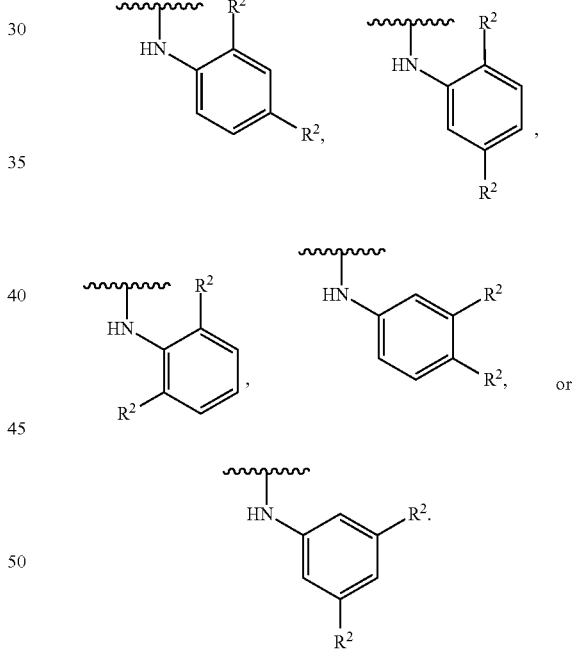

In some embodiments, each R[2] is independently halogen, —N$_3$, —OR[5], —(SO$_2$)R[5], —CO$_2$R[5], substituted or unsubstituted $C_1$-$C_6$alkyl, substituted or unsubstituted $C_1$-$C_6$haloalkyl, or

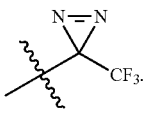 [SMILES: *C1(C(F)(F)F)N=N1]

In some embodiments, the compound has the structure of Formula (Ia), or a pharmaceutically acceptable salt thereof:

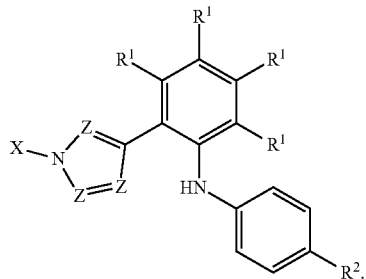

Formula (Ia)

In some embodiments, the compound has the structure of Formula (Ib), or a pharmaceutically acceptable salt thereof:

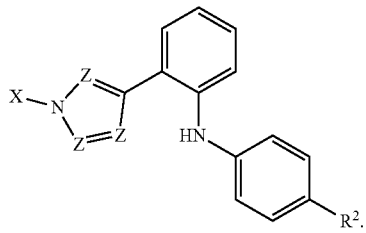

Formula (Ib)

In some embodiments, the compound has the structure of Formula (Ic), or a pharmaceutically acceptable salt thereof:

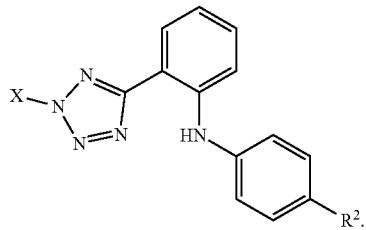

Formula (Ic)

Provided in another aspect is a compound of Formula (II), or a pharmaceutically acceptable salt thereof:

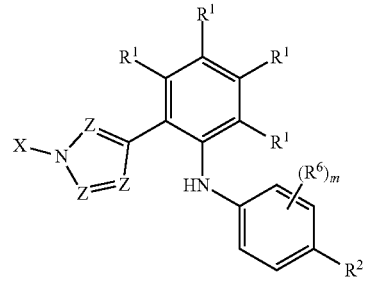

Formula (II)

wherein:
each Z is independently N or $CR^z$;
each $R^z$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

X is methyl;

each $R^1$ is independently H, halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^2$ is halogen, —$N_3$, —CN, —$OR^5$, —$SR^5$, —$(SO_2)R^5$, —$N(R^5)_2$, —$CO_2R^5$, substituted or unsubstituted $C_1$-$C_6$ alkyl, substituted or unsubstituted $C_1$-$C_6$haloalkyl, substituted or unsubstituted $C_1$-$C_6$heteroalkyl, substituted or unsubstituted $C_3$-$C_{10}$ cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

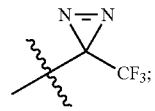

each $R^6$ is independently H, halogen, —$N_3$, —CN, —$OR^7$, —$SR^7$, —$(SO_2)R^7$, —$N(R^7)_2$, —$CO_2R^7$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^5$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^7$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and m is 0, 1, 2, 3, or 4.

In some embodiments,

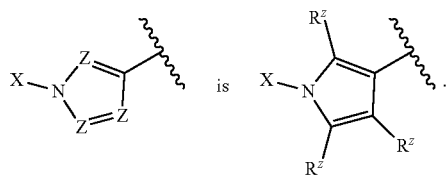

In some embodiments,

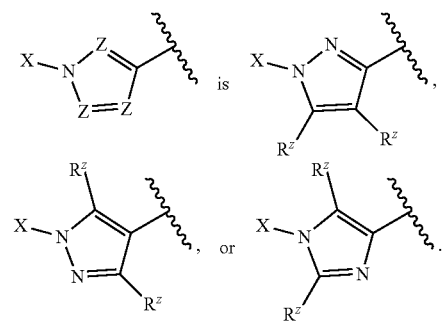

In some embodiments,

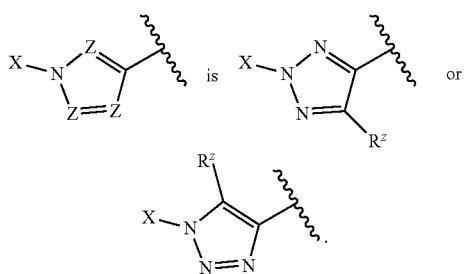

In some embodiments,

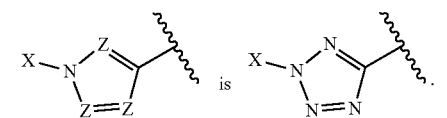

In some embodiments, each $R^z$ is independently H or substituted or unsubstituted $C_1$-$C_6$alkyl.

In some embodiments,

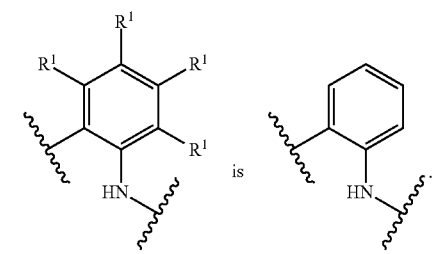

In some embodiments,

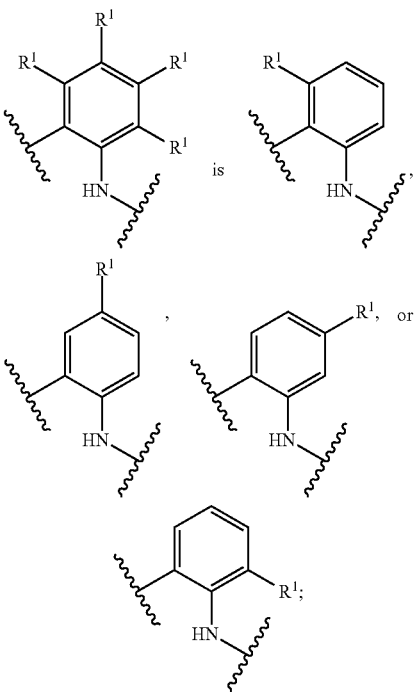

and $R^1$ is halogen, —CN, —OR$^4$, —SR$^4$, —N(R$^4$)$_2$, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted aryl, or substituted or unsubstituted heteroaryl.

In some embodiments,

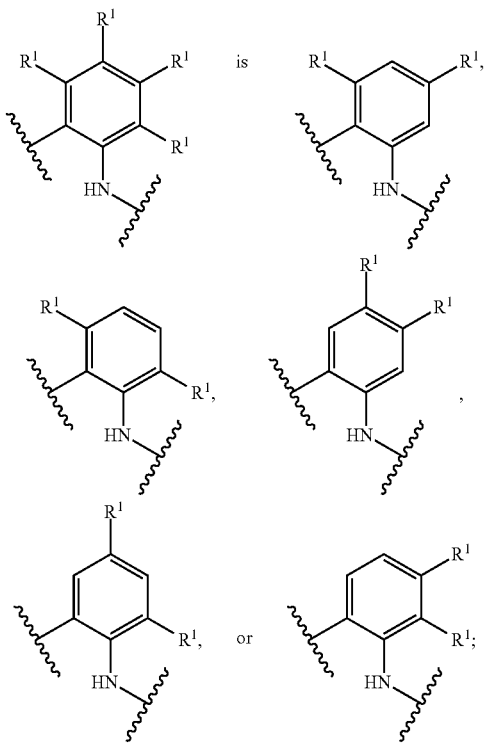

and each R¹ is independently halogen, —CN, —OR⁴, —SR⁴, —N(R⁴)₂, substituted or unsubstituted C₁-C₆alkyl, substituted or unsubstituted C₁-C₆haloalkyl, substituted or unsubstituted C₃-C₁₀cycloalkyl, substituted or unsubstituted aryl, or substituted or unsubstituted heteroaryl.

In some embodiments,

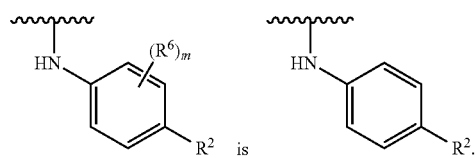

is

In some embodiments,

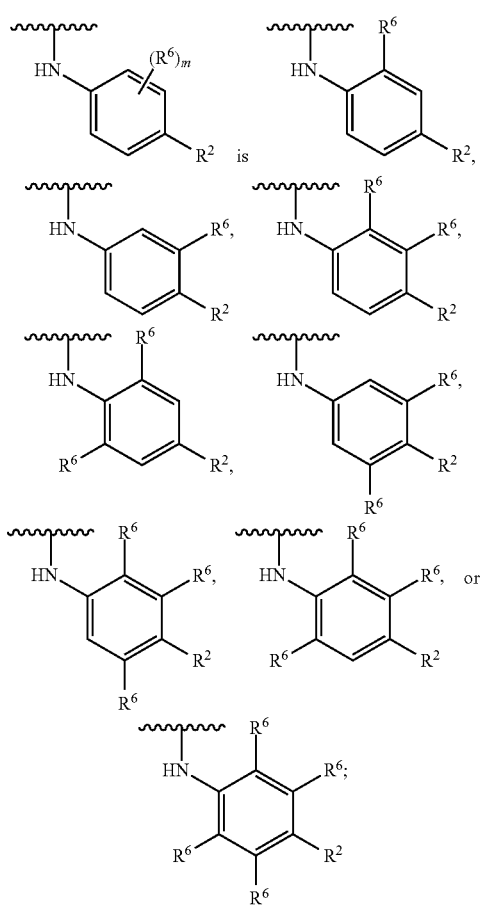

and each R⁶ is independently halogen, —N₃, —CN, —OR⁷, —SR⁷, —(SO₂)R⁷, —N(R⁷)₂, —CO₂R⁷, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl.

In some embodiments, R² is halogen, —N₃, —OR⁵, —(SO₂)R⁵, —CO₂R⁵, substituted or unsubstituted C₁-C₆ alkyl, substituted or unsubstituted C₁-C₆haloalkyl, or

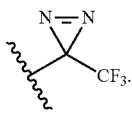 [SMILES: *C1(C(F)(F)F)N=N1]

In some embodiments, the compound has the structure of Formula (IIa), or a pharmaceutically acceptable salt thereof:

Formula (IIa)

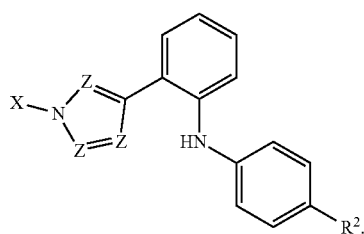

In some embodiments, the compound has the structure of Formula (IIb), or a pharmaceutically acceptable salt thereof:

Formula (IIb)

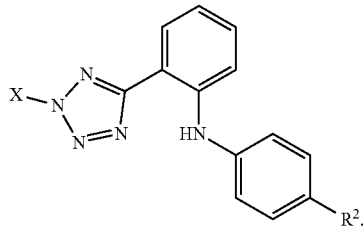

Provided in another aspect is a compound of Formula (III), or a pharmaceutically acceptable salt thereof:

Formula (III)

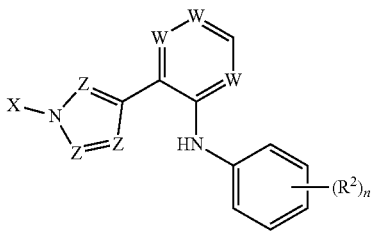

wherein:
each Z is independently N or CR$^z$;
 each R$^z$ is independently H, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;
X is substituted or unsubstituted C₁-C₆alkyl, substituted or unsubstituted C₁-C₆haloalkyl, substituted or unsubstituted C₃-C₁₀cycloalkyl, substituted or unsubstituted C₂-C₁₀heterocycloalkyl, substituted or unsubstituted aryl, substituted or unsubstituted heteroaryl, -L¹-Y¹, or -L²-L³-Y²;

L¹ is substituted or unsubstituted $C_1$-$C_6$alkylene;

Y¹ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;

L² is absent or substituted or unsubstituted $C_1$-$C_6$alkylene;

L³ is —O—, —S—, —(S=O)—, —(SO$_2$)—, —NR³—, —(C=O)—, —(C=O)O—, —O(C=O)—, —(C=O)NR³—, —(C=O)NR³—O—, —O—NR³(C=O)—, —NR³(C=O)—, —NR³(C=O)NR³—, —O(C=O)NR³—, —NR³(C=O)O—, —NR³(SO$_2$)NR³—, —NR³(SO$_2$)—, —(SO$_2$)NR³—, —(SO$_2$)NR³—(C=O)—, —(C=O)—NR³(SO$_2$)—, —(SO$_2$)NR³—(C=O)O—, —O(C=O)—NR³(SO$_2$)—, —NR³(SO$_2$)NR³—(C=O)—, —(C=O)—NR³(SO$_2$)NR³—, —O(C=O)—NR³(SO$_2$)—NR³—, or —NR³(SO$_2$)NR³—(C=O)O—;

each R³ is independently H or substituted or unsubstituted $C_1$-$C_6$alkyl;

Y² is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

or R³ and Y² on the same N atom are taken together with the N atom to which they are attached to form a substituted or unsubstituted N-containing heterocycle;

each W is CR¹ or N with the provision that at least one W is N;

each R¹ is independently H, halogen, —CN, —OR⁴, —SR⁴, —N(R⁴)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

n is 0, 1, 2, 3, 4, or 5;

each R² is independently H, halogen, —N$_3$, —CN, —OR⁵, —SR⁵, —(SO$_2$)R⁵, —N(R⁵)$_2$, —CO$_2$R⁵, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

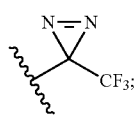 [SMILES: *C1(C(F)(F)F)N=N1]

each R⁴ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each R⁵ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

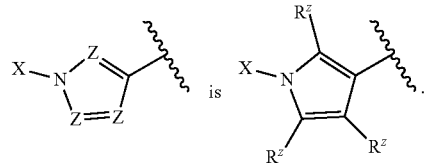

In some embodiments,

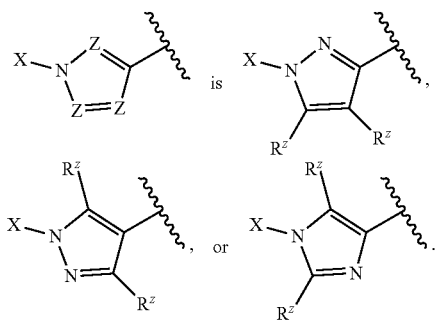

In some embodiments,

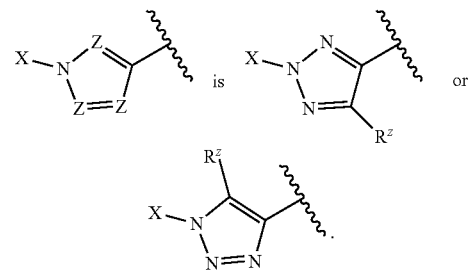

In some embodiments,

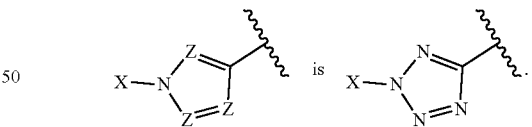

In some embodiments, each R$^z$ is independently H or substituted or unsubstituted $C_1$-$C_6$alkyl. In some embodiments, X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl. In some embodiments, X is -L¹-Y¹. In some embodiments, L¹ is substituted or unsubstituted $C_1$-$C_4$alkylene; and Y¹ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl. In some embodiments, L¹ is substituted or unsubstituted $C_1$-$C_4$alkylene; and Y¹ is substituted or unsubstituted $C_3$-$C_6$cycloalkyl, substituted or unsubstituted C₂-C₆ heterocycloalkyl, substituted or unsubstituted phenyl, or substituted or unsubstituted monocyclic heteroaryl.

In some embodiments, X is -L²-L³-Y². In some embodiments, L² is substituted or unsubstituted C₁-C₆alkylene; L³ is —O—, —S—, —(S=O)—, —(SO₂)—, —NR³—, —(C=O)—, —(C=O)O—, —O(C=O)—, —(C=O)NR³—, —(C=O)NR³—O—, —NR³(C=O)—, —NR³(C=O)NR³—, —O(C=O)NR³—, —NR³(C=O)O—, —NR³(SO₂)NR³—, —NR³(SO₂)—, —(SO₂)NR³—, —(SO₂)NR³—(C=O)—, —(SO₂)NR³—(C=O)O—, —NR³(SO₂)NR³—(C=O)—, or —NR³(SO₂)NR³—(C=O)O—; each R³ is independently H or substituted or unsubstituted C₁-C₆alkyl; and Y² is H, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aryl, or substituted or unsubstituted heteroaryl. In some embodiments, L² is substituted or unsubstituted C₁-C₄alkylene; L³ is —O—, —S—, —(S=O)—, —(SO₂)—, —NR³—, —(C=O)—, —(C=O)O—, —O(C=O)—, —(C=O)NR³—, —(C=O)NR³—O—, —NR³(C=O)—, —NR³(C=O)NR³—, —O(C=O)NR³—, —NR³(C=O)O—, —NR³(SO₂)NR³—, —NR³(SO₂)—, —(SO₂)NR³—, —(SO₂)NR³—(C=O)—, —(SO₂)NR³—(C=O)O—, —NR³(SO₂)NR³—(C=O)—, or —NR³(SO₂)NR³—(C=O)O—; each R³ is independently H or substituted or unsubstituted C₁-C₄alkyl; and Y² is H, substituted or unsubstituted C₁-C₄alkyl, substituted or unsubstituted C₁-C₄haloalkyl, substituted or unsubstituted C₁-C₄heteroalkyl, substituted or unsubstituted C₃-C₆cycloalkyl, substituted or unsubstituted C₂-C₆heterocycloalkyl, substituted or unsubstituted phenyl, or substituted or unsubstituted monocyclic heteroaryl.

In some embodiments,

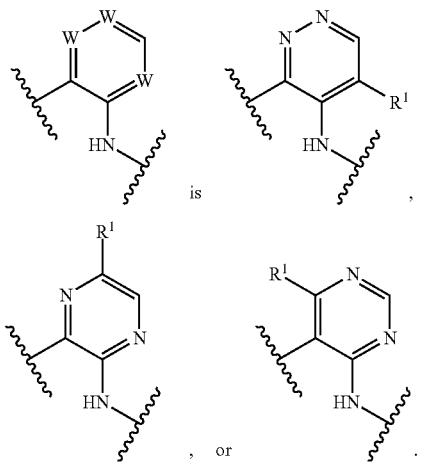

is

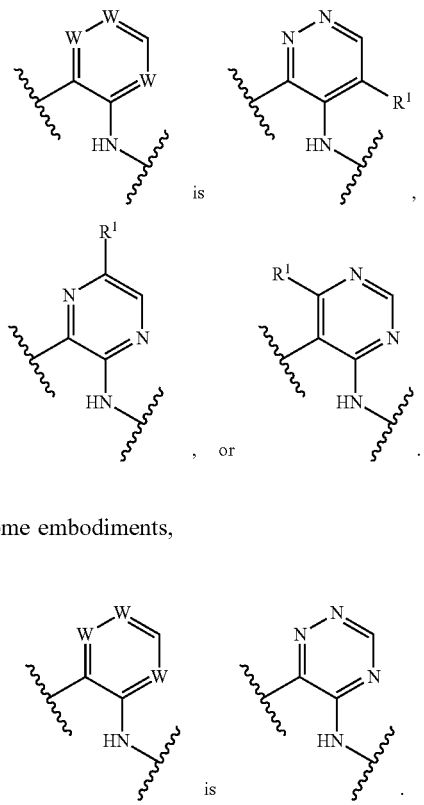

In some embodiments,

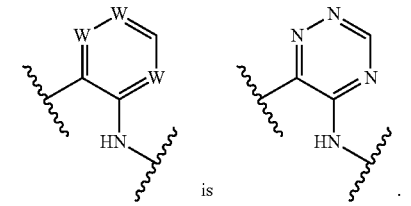

is

In some embodiments, each R¹ is independently H, halogen, —CN, —OR⁴, —SR⁴, —N(R⁴)₂, substituted or unsubstituted C₁-C₆alkyl, substituted or unsubstituted C₁-C₆haloalkyl, substituted or unsubstituted C₃-C₁₀cycloalkyl, substituted or unsubstituted aryl, or substituted or unsubstituted heteroaryl.

In some embodiments,

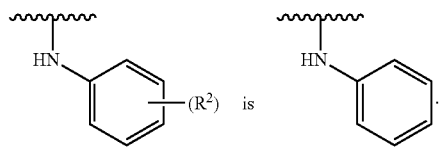

is

In some embodiments,

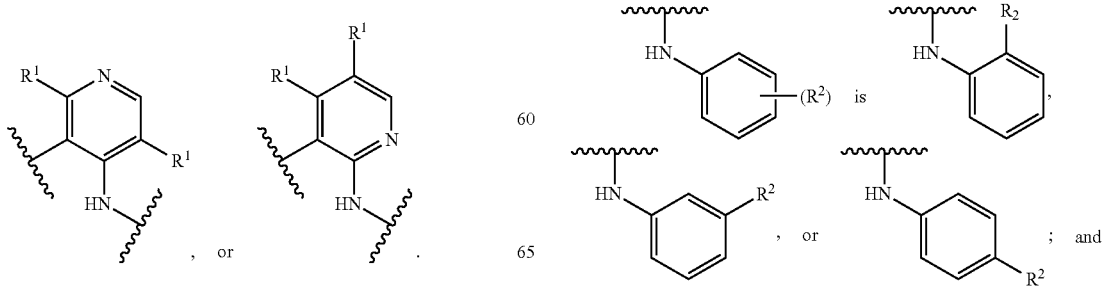

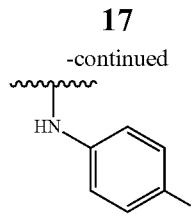

and R² is halogen, —N₃, —OR⁵, —(SO₂)R⁵, —CO₂R⁵, substituted or unsubstituted $C_1$-$C_6$alkyl, substituted or unsubstituted $C_1$-$C_6$haloalkyl, or

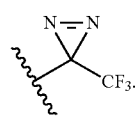

In some embodiments,

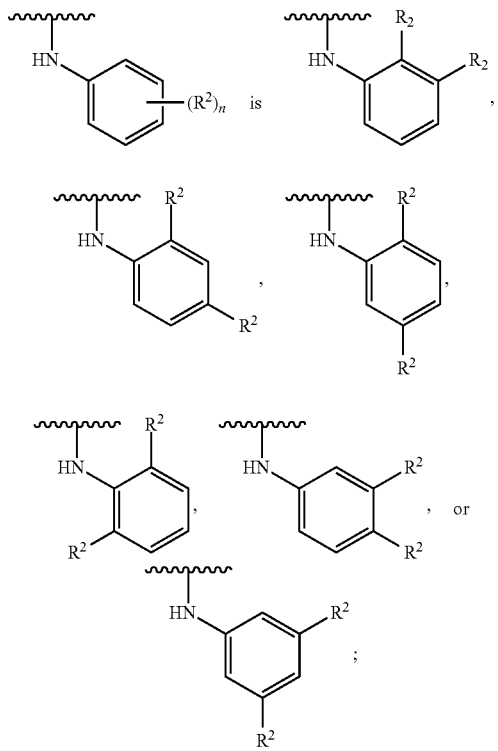

and each R² is independently halogen, —N₃, —OR⁵, —(SO₂)R⁵, —CO₂R⁵, substituted or unsubstituted $C_1$-$C_6$alkyl, substituted or unsubstituted $C_1$-$C_6$haloalkyl, or

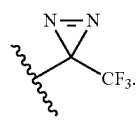

In some embodiments, the compound has the structure of Formula (IIIa), or a pharmaceutically acceptable salt thereof:

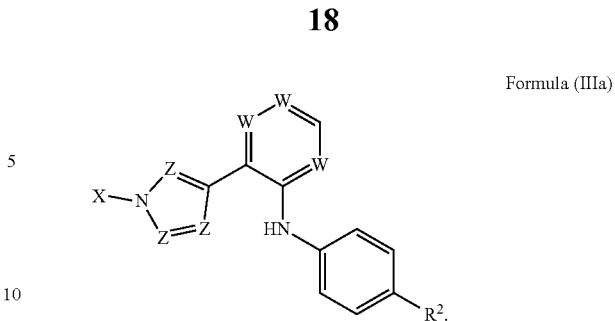

Formula (IIIa)

In some embodiments, the compound has the structure of Formula (IIIb), or a pharmaceutically acceptable salt thereof:

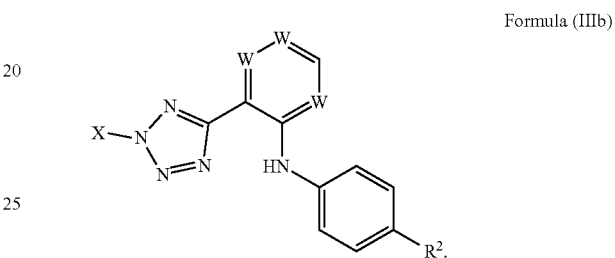

Formula (IIIb)

In some embodiments, the compound exhibits an $IC_{50}$ of no more than about 5.000 µM.

Provided in another aspect is a compound, or pharmaceutically acceptable salt thereof, wherein the compound is a compound from Table 1 or 2, or a pharmaceutically acceptable salt thereof.

Provided in another aspect is a pharmaceutical composition comprising a pharmaceutically acceptable excipient and any one of the compounds disclosed herein or a pharmaceutically acceptable salt thereof.

Provided herein is a method for treating a cancer in a subject in need thereof comprising administering a therapeutically effective amount of a compound of any one of the compounds disclosed herein or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Certain Terminology

Figure 1:
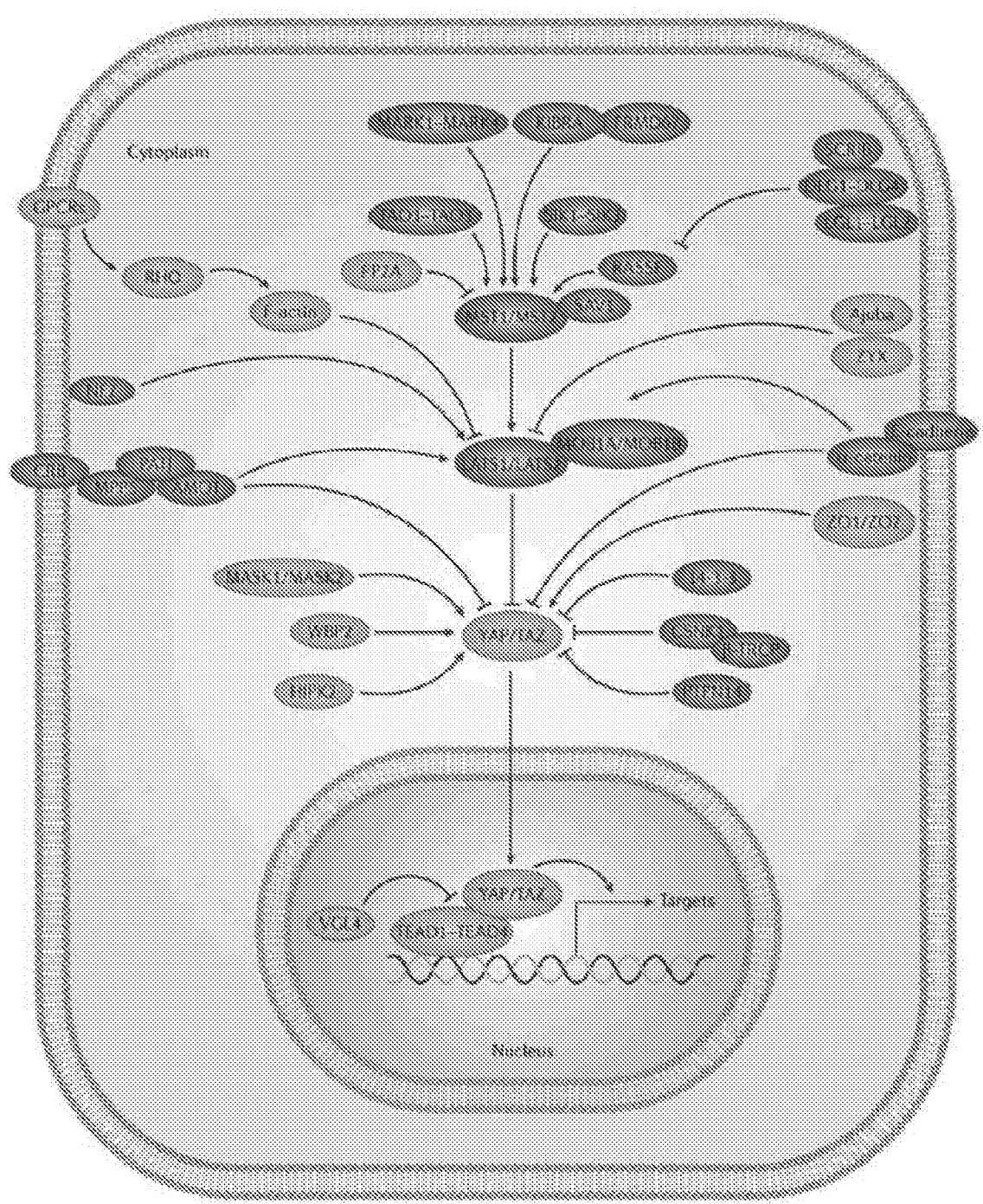
FIG. 1 illustrates a schematic representation of the Hippo signaling network. Hippo pathway components shaded in dark gray indicate components that inhibit YAP/TAZ activity. Hippo pathway components shaded in light gray indicate components that promote YAP/TAZ activity. Pointed and blunt arrowheads indicate activating and inhibitory interactions, respectively. Abbreviations: α-CAT (α-Catenin), AJUB (Ajuba), AMOT (Angiomotin), β-TRCP (β-transducing repeat containing protein), CK1 (Casein Kinase 1), CRB (Crumbs), E-CAD (E-cadherin), EX (Expanded), GPCR (G-protein coupled receptor), HIPK (Homeodomain interacting protein kinase), KIBRA (Kidney brain), LATS (Large tumor suppressor), LGL (Lethal giant larvae), MASK (Multiple ankyrin single KH), MER (Merlin), MOB (Mps one binder), MST (Mammalian sterile 20 like), PALS (Protein Associated with Lin-7), PATJ (Palsl-associated tight junction protein), PP2A (Protein phosphatase 2A), PTPN14 (Protein tyrosine phosphatase non-receptor type 14), RASSF (Ras associated factor), SAV (Salvador), SCRIB (Scribble), SIK (Salt inducible kinase), TAO (Thousand and one amino acid protein), TAZ (transcriptional coactivator with PDZ-binding motif), TEAD (TEA domain protein), VGL4 (Vestigial-like 4), WBP2 (WW domain binding protein 2), YAP (Yes associated protein), ZO (Zonula occludens), ZYX (Zyxin).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, in some embodiments, ranges and amounts are expressed as "about" a particular value or range. About also includes the exact amount. Hence "about 5 μL" means "about 5 μL" and also "5 μL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly, or a hospice worker).

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl. In some embodiments, an alkyl chain is optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Alkoxy" refers to a radical bonded through an oxygen atom of the formula O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$) C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl. In some embodiments, an alkylene chain is optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$) C(O)R$^a$, —R$^b$—N(R$^a$)S(O)$_t$R$^a$ (where t is 1 or 2), —R$^b$—S (O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Htickel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, and in some embodiments, include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. In some embodiments, the carbocyclyl is saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—$OR^a$—, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycle" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocyclyl radical is a monocyclic, bicyclic, tricyclic, or tetracyclic ring system, which include fused or bridged ring systems in some embodiments. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). In some embodiments, the heterocyclyl is saturated, (i.e., containing single bonds only) or unsaturated (i.e., containing one or more double bonds or triple bonds.) A fully saturated heterocyclyl radical is also referred to as "heterocycloalkyl." Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclyl alkyl, optionally substituted heteroaryl, optionally substituted heteroarylalkyl, —CN, —$R^b$—CN, —$R^b$—$OR^a$, —$R^b$—OC(O)—$R^a$—, $R^b$—OC(O)—$OR^a$—, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heteroalkyl" refers to an alkyl group in which one or more skeletal atoms of the alkyl are selected from an atom other than carbon, e.g., oxygen, nitrogen (e.g. NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl. In some embodiments, the alkyl part of the heteroalkyl radical is optionally substituted as defined for an alkyl group.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In one aspect, a heterocycloalkyl is a $C_2$-$C_6$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

"Heterocyclylalkyl" refers to a radical of the formula $R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, in some embodiments, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocyclooocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula O-heteroaryl, where heteroaryl is as defined above.

"Heteroarylalkyl" refers to a radical of the formula $R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

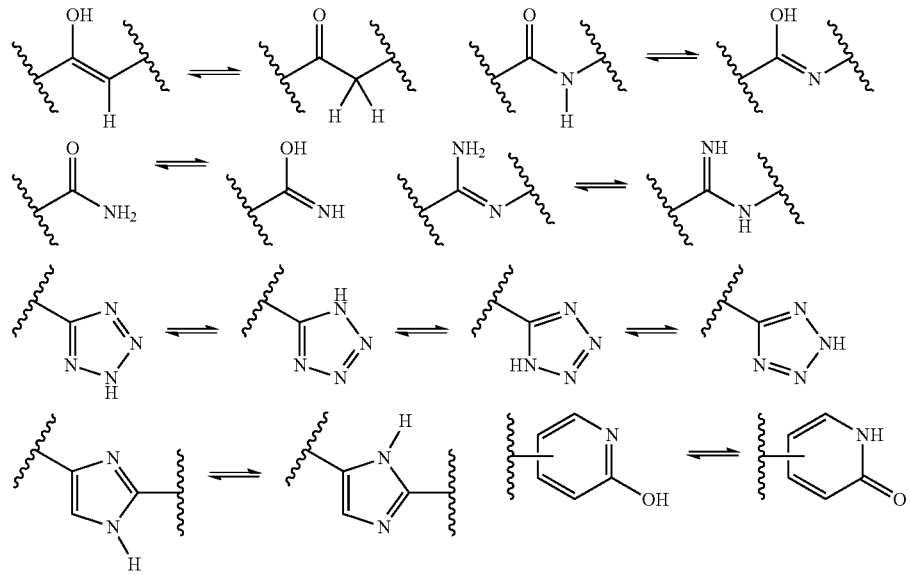

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The term "optionally substituted" or "substituted" means that the referenced group is optionally substituted with one or more additional group(s). In some other embodiments, optional substituents are individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, —CH$_2$CO$_2$H, —CH$_2$CO$_2$alkyl, —CH$_2$C(=O)NH$_2$, —CH$_2$C(=O)NH(alkyl), —CH$_2$C(=O)N(alkyl)$_2$, —CH$_2$S(=O)$_2$NH$_2$, —CH$_2$S(=O)$_2$NH(alkyl), —CH$_2$S(=O)$_2$N(alkyl)$_2$, alkyl, alkenyl, alkynyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups. In some embodiments, an optional substituent on an aliphatic carbon atom (acyclic or cyclic) includes oxo (=O). In some embodiments, an optional substituent on a sulfur atom includes one or two oxo (=O) groups.

"Pharmaceutically acceptable salt" includes both acid and base addition salts. A pharmaceutically acceptable salt of any one of the compounds described herein is intended to encompass any and all pharmaceutically suitable salt forms. Pharmaceutically acceptable salts of the compounds described herein are optionally pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). In some embodiments, acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate, and benzoate derivatives of alcohol or amine functional groups in the active compounds and the like.

Compounds

In some embodiments, the compounds disclosed herein are tetrazole compounds.

Provided in one aspect is a compound of Formula (I), or a pharmaceutically acceptable salt thereof:

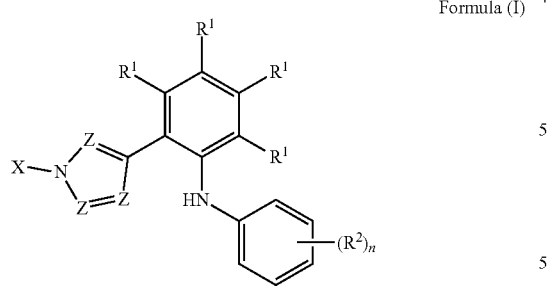

Formula (I)

wherein:
each Z is independently N or $CR^z$;
  each $R^z$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, unsubstituted aryl, substituted or unsubstituted heteroaryl, -$L^1$-$Y^1$, or -$L^2$-$L^3$-$Y^2$;

$L^1$ is substituted or unsubstituted $C_1$-$C_6$alkylene;

$Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;

$L^2$ is absent or substituted or unsubstituted $C_1$-$C_6$alkylene;

$L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—(C=O)—, —(C=O)—NR$^3$(SO$_2$)NR$^3$—, —O(C=O)—NR$^3$(SO$_2$)—NR$^3$—, or —NR$^3$(SO$_2$)NR$^3$—(C=O)O—;

each $R^3$ is independently H or substituted or unsubstituted $C_1$-$C_6$alkyl;

$Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

each $R^1$ is independently H, halogen, —CN, —OR$^4$, —N(R$^4$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

n is 1, 2, 3, 4, or 5;

each $R^2$ is independently halogen, —N$_3$, —CN, —OR$^5$, —SR$^5$, —(SO$_2$)R$^5$, —N(R$^5$)$_2$, —CO$_2$R$^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

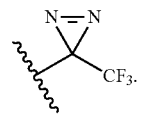 [SMILES: *C1(C(F)(F)F)N=N1]

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^5$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

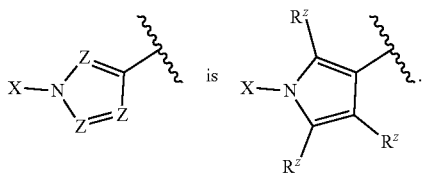

In some embodiments,

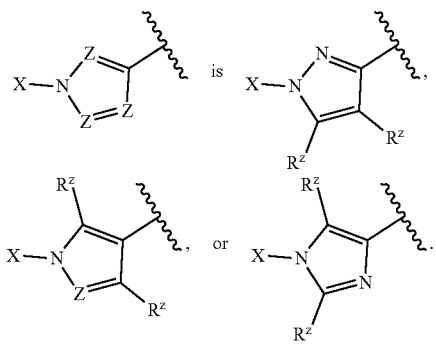

In some embodiments,

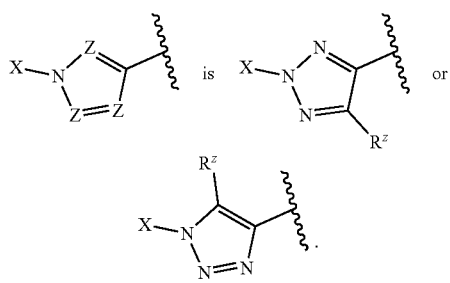

In some embodiments,

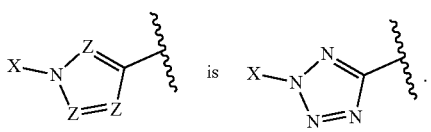

In some embodiments, each $R^z$ is independently H, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted aralkyl, substituted or unsubstituted aryl, or substituted or unsubstituted heteroaryl. In some embodiments, each $R^z$ is independently H, substituted or unsubstituted $C_1$-$C_6$alkyl, or substituted or unsubstituted $C_1$-$C_6$haloalkyl. In some embodiments, each $R^z$ is independently H or substituted or unsubstituted $C_1$-$C_6$alkyl. In some embodiments, each $R^z$ is independently H or substituted or unsubstituted $C_1$-$C_4$alkyl. In some embodiments, each $R^z$ is independently H, —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$.

In some embodiments, each $R^z$ is independently H. In some embodiments, each $R^z$ is independently substituted or unsubstituted $C_1$-$C_6$alkyl. In some embodiments, each $R^z$ is independently substituted or unsubstituted $C_1$-$C_4$alkyl. In some embodiments, each $R^z$ is independently substituted or unsubstituted $C_1$-$C_6$haloalkyl. In some embodiments, each $R^z$ is independently substituted or unsubstituted $C_1$-$C_4$haloalkyl. In some embodiments, each $R^z$ is independently —$CH_2F$, —$CHF_2$, —$CF_3$, or —$CH_2CF_3$. In some embodiments, each $R^z$ is independently substituted or unsubstituted $C_1$-$C_6$heteroalkyl. In some embodiments, each $R^z$ is independently substituted or unsubstituted $C_1$-$C_4$heteroalkyl. In some embodiments, each $R^z$ is independently substituted or unsubstituted $C_3$-$C_{10}$cycloalkyl. In some embodiments, each $R^z$ is independently substituted or unsubstituted $C_3$-$C_6$cycloalkyl. In some embodiments, each $R^z$ is independently substituted or unsubstituted cyclopropyl, substituted or unsubstituted cyclobutyl, substituted or unsubstituted cyclopentyl, or substituted or unsubstituted cyclohexyl. In some embodiments, each $R^z$ is independently substituted or unsubstituted $C_2$-$C_{10}$heterocycloalkyl. In some embodiments, each $R^z$ is independently substituted or unsubstituted $C_2$-$C_6$heterocycloalkyl. In some embodiments, each $R^z$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-only. In some embodiments, each $R^z$ is independently substituted or unsubstituted aralkyl. In some embodiments, each $R^z$ is independently substituted or unsubstituted benzyl. In some embodiments, each $R^z$ is independently substituted or unsubstituted aryl. In some embodiments, each $R^z$ is independently substituted or unsubstituted phenyl. In some embodiments, each $R^z$ is independently substituted or unsubstituted heteroaryl. In some embodiments, each $R^z$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, unsubstituted aryl, or substituted or unsubstituted heteroaryl.

In some embodiments, X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2C_{10}$heterocycloalkyl, or substituted or unsubstituted heteroaryl.

In some embodiments, X is substituted or unsubstituted $C_2$-$C_6$alkyl. In some embodiments, X is substituted or unsubstituted $C_2$-$C_4$alkyl. In some embodiments, X is —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, X is substituted or unsubstituted $C_1$-$C_6$haloalkyl. In some embodiments, X is substituted or unsubstituted $C_1$-$C_4$haloalkyl. In some embodiments, X is —$CH_2F$, —$CHF_2$, —$CF_3$, or —$CH_2CF_3$. In some embodiments, X is substituted or unsubstituted $C_3$-$C_{10}$cycloalkyl. In some embodiments, X is substituted or unsubstituted $C_3$-$C_6$cycloalkyl. In some embodiments, X is substituted or unsubstituted cyclopropyl, substituted or unsubstituted cyclobutyl, substituted or unsubstituted cyclopentyl, or substituted or unsubstituted cyclohexyl. In some embodiments, X is substituted or unsubstituted $C_2$-$C_{10}$heterocycloalkyl. In some embodiments, X is substituted or unsubstituted $C_2$-$C_6$heterocycloalkyl. In some embodiments, X is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, X is unsubstituted aryl. In some embodiments, X is phenyl. In some embodiments, X is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, X is -$L^1$-$Y^1$. In some embodiments, $L^1$ is substituted or unsubstituted $C_1$-$C_6$alkylene. In some embodiments, $L^1$ is substituted or unsubstituted $C_1$-$C_4$alkylene. In some embodiments, $L^1$ is —$CH_2$—, —$CH_2CH_2$—, —$CH_2CH_2CH_2$—, or —$CH_2CH_2CH_2CH_2$—. In some embodiments, $Y^1$ is substituted or unsubstituted $C_3$-$C_{10}$cycloalkyl. In some embodiments, $Y^1$ is substituted or unsubstituted $C_3$-$C_6$cycloalkyl. In some embodiments, $Y^1$ is substituted or unsubstituted cyclopropyl, substituted or unsubstituted cyclobutyl, substituted or unsubstituted cyclopentyl, or substituted or unsubstituted cyclohexyl. In some embodiments, $Y^1$ is substituted or unsubstituted $C_2$-$C_{10}$heterocycloalkyl. In some embodiments, $Y^1$ is substituted or unsubstituted $C_2$-$C_6$heterocycloalkyl. In some embodiments, $Y^1$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, $Y^1$ is substituted or unsubstituted aryl. In some embodiments, $Y^1$ is substituted or unsubstituted phenyl. In some embodiments, $Y^1$ is substituted or unsubstituted heteroaryl. In some embodiments, $Y^1$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, $L^1$ is substituted or unsubstituted $C_1$-$C_4$alkylene; and $Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl. In some embodiments, $L^1$ is substituted or unsubstituted $C_1$-$C_4$alkylene; and $Y^1$ is substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl.

In some embodiments, X is -$L^2$-$L^3$-$Y^2$. In some embodiments, $L^2$ is absent. In some embodiments, $L^2$ is substituted or unsubstituted $C_1$-$C_6$alkylene. In some embodiments, $L^2$ is substituted or unsubstituted $C_1$-$C_4$alkylene. In some embodiments, $L^2$ is —$CH_2$—, —$CH_2CH_2$—, —$CH_2CH_2CH_2$—, or —$CH_2CH_2CH_2CH_2$—. In some embodiments, $L^3$ is —O—. In some embodiments, $L^3$ is —S—. In some embodiments, $L^3$ is —(S=O)—. In some embodiments, $L^3$ is —(SO$_2$)—. In some embodiments, $L^3$ is —$NR^3$—. In some embodiments, $L^3$ is —(C=O)—. In some embodiments, $L^3$ is —(C=O)O—. In some embodiments, $L^3$ is —O(C=O)—. In some embodiments, $L^3$ is —(C=O)$NR^3$—. In some embodiments, $L^3$ is —(C=O)$NR^3$—O—. In some embodiments, $L^3$ is —O—$NR^3$(C=O)—. In some embodiments, $L^3$ is —$NR^3$(C=O)—. In some embodiments, $L^3$ is —$NR^3$(C=O)$NR^3$—. In some embodiments, $L^3$ is —O(C=O)$NR^3$—. In some embodiments, $L^3$ is —$NR^3$(C=O)O—. In some embodiments, $L^3$ is —$NR^3$(SO$_2$)$NR^3$—. In some embodiments, $L^3$ is —$NR^3$(SO$_2$)—. In some embodiments, $L^3$ is —(SO$_2$)$NR^3$—. In some embodiments, $L^3$ is —(SO$_2$)$NR^3$—(C=O)—. In some embodiments, $L^3$ is —(C=O)—$NR^3$(SO$_2$)—. In some embodiments, $L^3$ is —(SO$_2$)$NR^3$—(C=O)O—. In some embodiments, $L^3$ is —O(C=O)—$NR^3$(SO$_2$)—. In some embodiments, $L^3$ is —$NR^3$(SO$_2$)$NR^3$—(C=O)—. In some embodiments, $L^3$ is —(C=O)—$NR^3$(SO$_2$)$NR^3$—. In some embodiments, $L^3$ is —O(C=O)—$NR^3$(SO$_2$)—$NR^3$—. In some embodiments, $L^3$ is —$NR^3$(SO$_2$)$NR^3$—(C=O)O—. In some embodiments, each $R^3$ is independently H. In some embodiments, each $R^3$ substituted or unsubstituted $C_1$-$C_6$alkyl. In some embodiments, each $R^3$ is substituted or unsubstituted $C_1$-$C_4$alkyl. In some embodiments, each $R^3$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —C(CH$_3$)$_3$.

In some embodiments, Y$^2$ is H. In some embodiments, Y$^2$ is substituted or unsubstituted C$_1$-C$_6$alkyl. In some embodiments, Y$^2$ is substituted or unsubstituted C$_1$-C$_4$alkyl. In some embodiments, Y$^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —C(CH$_3$)$_3$. In some embodiments, Y$^2$ is substituted or unsubstituted C$_1$-C$_6$haloalkyl. In some embodiments, Y$^2$ is substituted or unsubstituted C$_1$-C$_4$haloalkyl. In some embodiments, Y$^2$ is —CH$_2$F, —CHF$_2$, —CF$_3$, or —CH$_2$CF$_3$. In some embodiments, Y$^2$ is substituted or unsubstituted C$_1$-C$_6$heteroalkyl. In some embodiments, Y$^2$ is substituted or unsubstituted C$_1$-C$_4$heteroalkyl. In some embodiments, Y$^2$ is substituted or unsubstituted C$_3$-C$_{10}$cycloalkyl. In some embodiments, Y$^2$ is substituted or unsubstituted C$_3$-C$_6$cycloalkyl. In some embodiments, Y$^2$ is substituted or unsubstituted cyclopropyl, substituted or unsubstituted cyclobutyl, substituted or unsubstituted cyclopentyl, or substituted or unsubstituted cyclohexyl. In some embodiments, Y$^2$ is substituted or unsubstituted C$_2$-C$_{10}$heterocycloalkyl. In some embodiments, Y$^2$ is substituted or unsubstituted C$_2$-C$_6$heterocycloalkyl. In some embodiments, Y$^2$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, Y$^2$ is substituted or unsubstituted aryl. In some embodiments, Y$^2$ is substituted or unsubstituted phenyl. In some embodiments, Y$^2$ is substituted or unsubstituted heteroaryl. In some embodiments, Y$^2$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, R$^3$ and Y$^2$ on the same N atom are taken together with the N atom to which they are attached to form a substituted or unsubstituted N-containing heterocycle.

In some embodiments, L$^2$ is substituted or unsubstituted C$_1$-C$_6$alkylene; L$^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, or —NR$^3$(SO$_2$)NR$^3$—(C=O)O—; each R$^3$ is independently H or substituted or unsubstituted C$_1$-C$_6$alkyl; and Y$^2$ is H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl. In some embodiments, L$^2$ is substituted or unsubstituted C$_1$-C$_4$alkylene; L$^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, or —NR$^3$(SO$_2$)NR$^3$—(C=O)O—; each R$^3$ is independently H or substituted or unsubstituted C$_1$-C$_4$alkyl; and Y$^2$ is H, substituted or unsubstituted C$_1$-C$_4$alkyl, substituted or unsubstituted C$_1$-C$_4$haloalkyl, substituted or unsubstituted C$_1$-C$_4$heteroalkyl, substituted or unsubstituted C$_3$-C$_6$cycloalkyl, substituted or unsubstituted C$_2$-C$_6$heterocycloalkyl, substituted or unsubstituted phenyl, or substituted or unsubstituted monocyclic heteroaryl.

In some embodiments, each R$^1$ is independently H. In some embodiments, each R$^1$ is independently halogen. In some embodiments, each R$^1$ is independently F, Cl, Br, or I. In some embodiments, each R$^1$ is independently —CN. In some embodiments, each R$^1$ is —OR$^4$. In some embodiments, each R$^1$ is —SR$^4$. In some embodiments, each R$^1$ independently is —N(R$^4$)$_2$. In some embodiments, each R$^1$ is independently substituted or unsubstituted C$_1$-C$_6$alkyl. In some embodiments, each R$^1$ is independently substituted or unsubstituted C$_1$-C$_4$alkyl. In some embodiments, R$^1$ is independently —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —C(CH$_3$)$_3$. In some embodiments, each R$^1$ is independently substituted or unsubstituted C$_1$-C$_6$haloalkyl. In some embodiments, each R$^1$ is independently substituted or unsubstituted C$_1$-C$_4$haloalkyl. In some embodiments, each R$^1$ is independently —CH$_2$F, —CHF$_2$, —CF$_3$, or —CH$_2$CF$_3$. In some embodiments, each R$^1$ is independently substituted or unsubstituted C$_1$-C$_6$heteroalkyl. In some embodiments, each R$^1$ is independently substituted or unsubstituted C$_1$-C$_4$heteroalkyl. In some embodiments, each R$^1$ is independently substituted or unsubstituted C$_3$-C$_{10}$cycloalkyl. In some embodiments, each R$^1$ is independently substituted or unsubstituted C$_3$-C$_6$cycloalkyl. In some embodiments, each R$^1$ is independently substituted or unsubstituted cyclopropyl, substituted or unsubstituted cyclobutyl, substituted or unsubstituted cyclopentyl, or substituted or unsubstituted cyclohexyl. In some embodiments, each R$^1$ is independently substituted or unsubstituted C$_2$-C$_{10}$heterocycloalkyl. In some embodiments, each R$^1$ is independently substituted or unsubstituted C$_2$-C$_6$heterocycloalkyl. In some embodiments, each R$^1$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each R$^1$ is independently substituted or unsubstituted aralkyl. In some embodiments, each R$^1$ is independently substituted or unsubstituted benzyl. In some embodiments, each R¹ is independently substituted or unsubstituted aryl. In some embodiments, each R¹ is independently substituted or unsubstituted phenyl. In some embodiments, each R¹ is independently substituted or unsubstituted heteroaryl. In some embodiments, each R¹ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments,

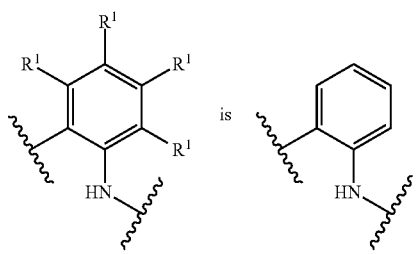

In some embodiments,

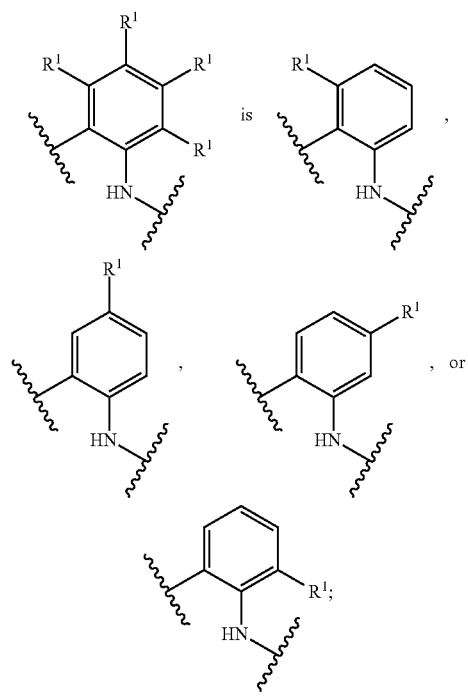

and R¹ is halogen, —CN, —OR⁴, —SR⁴, —N(R⁴)₂, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

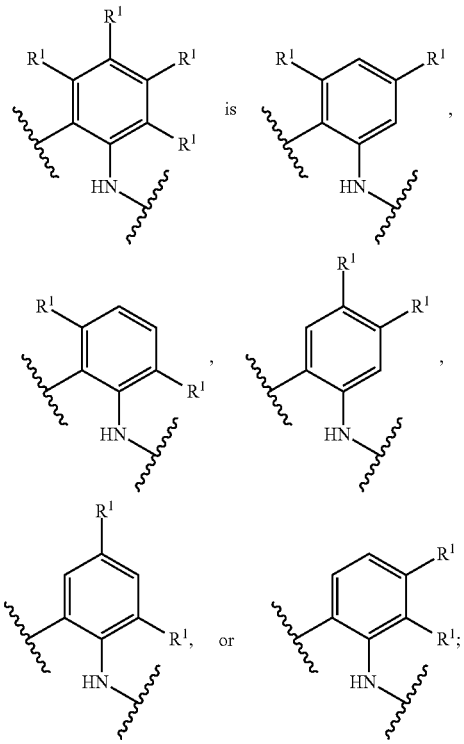

and each R¹ is independently halogen, —CN, —OR⁴, —SR⁴, —N(R⁴)₂, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, each R⁴ is independently H. In some embodiments, each R⁴ is independently substituted or unsubstituted $C_1$-$C_6$alkyl. In some embodiments, each R⁴ is independently substituted or unsubstituted $C_1$-$C_4$alkyl. In some embodiments, each R⁴ is independently —CH₃, —CH₂CH₃, —CH₂CH₂CH₃, —CH(CH₃)₂, —CH₂CH₂CH₂CH₃, —CH₂CH(CH₃)₂, or —C(CH₃)₃. In some embodiments, each R⁴ is independently substituted or unsubstituted $C_1$-$C_6$haloalkyl. In some embodiments, each R⁴ is independently substituted or unsubstituted $C_1$-$C_4$haloalkyl. In some embodiments, each R⁴ is independently —CH₂F, —CHF₂, —CF₃, or —CH₂CF₃. In some embodiments, each R⁴ is independently substituted or unsubstituted $C_1$-$C_6$heteroalkyl. In some embodiments, each R⁴ is independently substituted or unsubstituted $C_1$-$C_4$heteroalkyl. In some embodiments, each R⁴ is independently substituted or unsubstituted $C_3$-$C_{10}$cycloalkyl. In some embodiments, each R⁴ is independently substituted or unsubstituted $C_3$-$C_6$cycloalkyl. In some embodiments, each R⁴ is independently substituted or unsubstituted cyclopropyl, substituted or unsubstituted cyclobutyl, substituted or unsubstituted cyclopentyl, or substituted or unsubstituted cyclohexyl. In some embodiments, each R⁴ is independently substituted or unsubstituted $C_2$-$C_{10}$heterocycloalkyl. In some embodiments, each $R^4$ is independently substituted or unsubstituted $C_2$-$C_6$heterocycloalkyl. In some embodiments, each $R^4$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^4$ is independently substituted or unsubstituted aralkyl. In some embodiments, each $R^4$ is independently substituted or unsubstituted benzyl. In some embodiments, each $R^4$ is independently substituted or unsubstituted aryl. In some embodiments, each $R^4$ is independently substituted or unsubstituted phenyl. In some embodiments, each $R^4$ is independently substituted or unsubstituted heteroaryl. In some embodiments, each $R^4$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, n is 1. In some embodiments, n is 2. In some embodiments, n is 3. In some embodiments, n is 4. In some embodiments, n is 5.

In some embodiments,

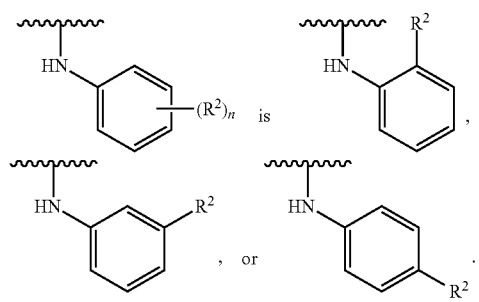

In some embodiments,

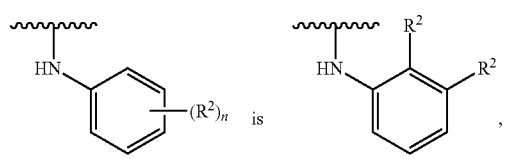

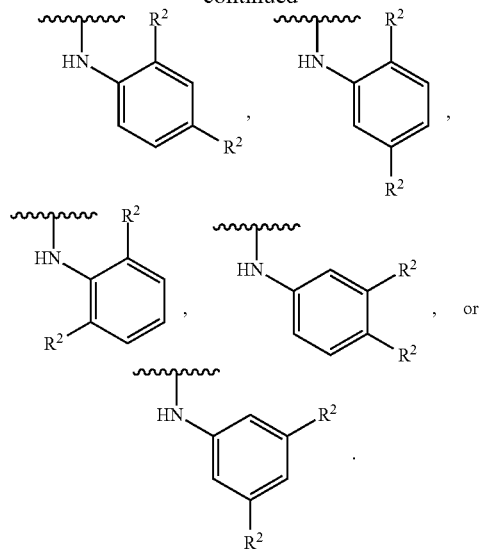

In some embodiments, each $R^2$ is independently halogen. In some embodiments, each $R^2$ is independently F, Cl, Br, or I. In some embodiments, each $R^2$ is independently —$N_3$. In some embodiments, each $R^2$ is independently —CN. In some embodiments, each $R^2$ is independently —$OR^5$. In some embodiments, each $R^2$ is independently —$SR^5$. In some embodiments, each $R^2$ is independently —$(SO_2)R^5$. In some embodiments, each $R^2$ is independently —$N(R^5)_2$. In some embodiments, each $R^2$ is independently —$CO_2R^5$. In some embodiments, each $R^2$ is independently substituted or unsubstituted $C_1$-$C_6$alkyl. In some embodiments, each $R^2$ is independently substituted or unsubstituted $C_1$-$C_4$alkyl. In some embodiments, each $R^2$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^2$ is independently substituted or unsubstituted $C_1$-$C_6$haloalkyl. In some embodiments, each $R^2$ is independently substituted or unsubstituted $C_1$-$C_4$haloalkyl. In some embodiments, each $R^2$ is independently —$CH_2F$, —$CHF_2$, —$CF_3$, or —$CH_2CF_3$. In some embodiments, each $R^2$ is independently substituted or unsubstituted $C_1$-$C_6$heteroalkyl. In some embodiments, each $R^2$ is independently substituted or unsubstituted $C_1$-$C_4$heteroalkyl. In some embodiments, each $R^2$ is independently substituted or unsubstituted $C_3$-$C_{10}$cycloalkyl. In some embodiments, each $R^2$ is independently substituted or unsubstituted $C_3$-$C_6$cycloalkyl. In some embodiments, each $R^2$ is independently substituted or unsubstituted cyclopropyl, substituted or unsubstituted cyclobutyl, substituted or unsubstituted cyclopentyl, or substituted or unsubstituted cyclohexyl. In some embodiments, each $R^2$ is independently substituted or unsubstituted $C_2$-$C_{10}$heterocycloalkyl. In some embodiments, each $R^2$ is independently substituted or unsubstituted $C_2$-$C_6$heterocycloalkyl. In some embodiments, each $R^2$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^2$ is independently substituted or unsubstituted aralkyl. In some embodiments, each $R^2$ is independently benzyl. In some embodiments, each $R^2$ is independently substituted or unsubstituted aryl. In some embodiments, each $R^2$ is independently substituted or unsubstituted phenyl. In some embodiments, each $R^2$ is independently substituted or unsubstituted heteroaryl. In some embodiments, each $R^2$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, each $R^2$ is independently

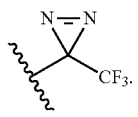

In some embodiments, each $R^2$ is independently halogen, $-N_3$, $-OR^5$, $-(SO_2)R^5$, $-CO_2R^5$, substituted or unsubstituted $C_1$-$C_6$alkyl, substituted or unsubstituted $C_1$-$C_6$haloalkyl, or

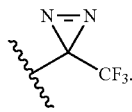 [SMILES: *C1(C(F)(F)F)N=N1]

In some embodiments, each $R^5$ is independently H. In some embodiments, each $R^5$ is independently substituted or unsubstituted $C_1$-$C_6$alkyl. In some embodiments, each $R^5$ is independently substituted or unsubstituted $C_1$-$C_4$alkyl. In some embodiments, each $R^5$ is independently $-CH_3$, $-CH_2CH_3$, $-CH_2CH_2CH_3$, $-CH(CH_3)_2$, $-CH_2CH_2CH_2CH_3$, $-CH_2CH(CH_3)_2$, or $-C(CH_3)_3$. In some embodiments, each $R^5$ is independently substituted or unsubstituted $C_1$-$C_6$haloalkyl. In some embodiments, each $R^5$ is independently substituted or unsubstituted $C_1$-$C_4$haloalkyl. In some embodiments, each $R^5$ is independently $-CH_2F$, $-CHF_2$, $-CF_3$, or $-CH_2CF_3$. In some embodiments, each $R^5$ is independently substituted or unsubstituted $C_1$-$C_6$heteroalkyl. In some embodiments, each $R^5$ is independently substituted or unsubstituted $C_1$-$C_4$heteroalkyl. In some embodiments, each $R^5$ is independently substituted or unsubstituted $C_3$-$C_{10}$cycloalkyl. In some embodiments, each $R^5$ is independently substituted or unsubstituted $C_3$-$C_6$cycloalkyl. In some embodiments, each $R^5$ is independently substituted or unsubstituted cyclopropyl, substituted or unsubstituted cyclobutyl, substituted or unsubstituted cyclopentyl, or substituted or unsubstituted cyclohexyl. In some embodiments, each $R^5$ is independently substituted or unsubstituted $C_2$-$C_{10}$heterocycloalkyl. In some embodiments, each $R^5$ is independently substituted or unsubstituted $C_2$-$C_6$heterocycloalkyl. In some embodiments, each $R^5$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^5$ is independently substituted or unsubstituted aralkyl. In some embodiments, each $R^5$ is independently substituted or unsubstituted benzyl. In some embodiments, each $R^5$ is independently substituted or unsubstituted aryl. In some embodiments, each $R^5$ is independently substituted or unsubstituted phenyl. In some embodiments, each $R^5$ is independently substituted or unsubstituted heteroaryl. In some embodiments, each $R^5$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, the compound has the structure of Formula (Ia), or a pharmaceutically acceptable salt thereof:

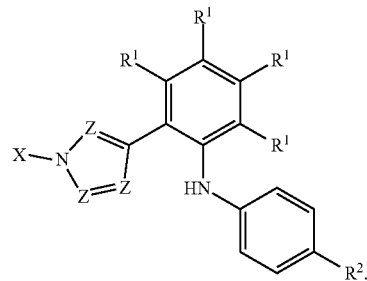

Formula (Ia)

In some embodiments, the compound has the structure of Formula (Ib), or a pharmaceutically acceptable salt thereof:

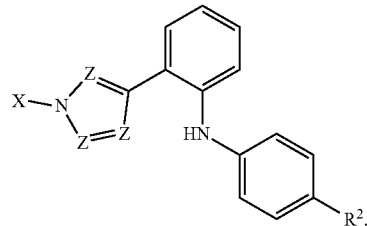

Formula (Ib)

In some embodiments, $R^2$ is substituted or unsubstituted $C_1$-$C_6$haloalkyl. In some embodiments, $R^2$ is substituted or unsubstituted $C_1$-$C_4$haloalkyl. In some embodiments, $R^2$ is $-CH_2F$, $-CHF_2$, $-CF_3$, or $-CH_2CF_3$. In some embodiments, $R^2$ is $-CF_3$.

In some embodiments, the compound has the structure of Formula (Ic), or a pharmaceutically acceptable salt thereof:

Formula (Ic)

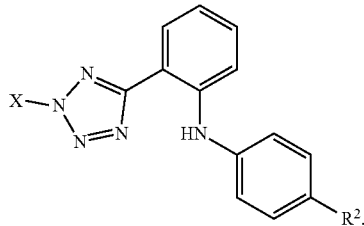

In some embodiments, $R^2$ is substituted or unsubstituted $C_1$-$C_6$haloalkyl. In some embodiments, $R^2$ is substituted or unsubstituted $C_1$-$C_4$haloalkyl. In some embodiments, $R^2$ is —$CH_2F$, —$CHF_2$, —$CF_3$, or —$CH_2CF_3$. In some embodiments, $R^2$ is —$CF_3$.

In some embodiments, X is —$(CH_2)_r$—OH, —$(CH_2)_r$—OR", —$(CH_2)_r$—N(R')$_2$, —$(CH_2)_r$—NR'S(=O)$_2$R", —$(CH_2)_r$—S(=O)$_2$N(R')$_2$, —$(CH_2)_r$—SR', —$(CH_2)_r$—S(=O)R", —$(CH_2)_r$—S(=O)$_2$R", —$(CH_2)_r$—C(=O)R", —$(CH_2)_r$—OC(=O)R", —$(CH_2)_r$—CO$_2$H, —$(CH_2)_r$—CO$_2$R", —$(CH_2)_r$—OC(=O)OR", —$(CH_2)_r$—NR'C(=O)R", —$(CH_2)_r$—C(=O)N(R')$_2$, —$(CH_2)_r$—NR"C(=O)OR', —$(CH_2)_r$—OC(=O)N(R")$_2$; r is 1, 2, 3, or 4; each R' is independently H substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted aryl, or substituted or unsubstituted heteroaryl; and each R" is independently unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted aryl, or substituted or unsubstituted heteroaryl.

Provided in another aspect is a compound of Formula (II), or a pharmaceutically acceptable salt thereof:

Formula (II)

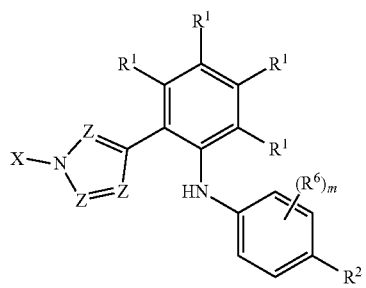

wherein:

each Z is independently N or $CR^z$;

each $R^z$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

X is methyl;

each $R^1$ is independently H, halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^2$ is halogen, —$N_3$, —CN, —$OR^5$, —$SR^5$, —$(SO_2)R^5$, —$N(R^5)_2$, —$CO_2R^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

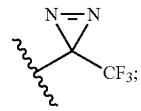 [SMILES: *C1(C(F)(F)F)N=N1]

each $R^6$ is independently H, halogen, —$N_3$, —CN, —$OR^7$, —$SR^7$, —$(SO_2)R^7$, —$N(R^7)_2$, —$CO_2R^7$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^5$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^7$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and m is 0, 1, 2, 3, or 4.

In some embodiments,

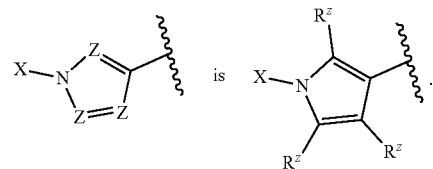

In some embodiments,

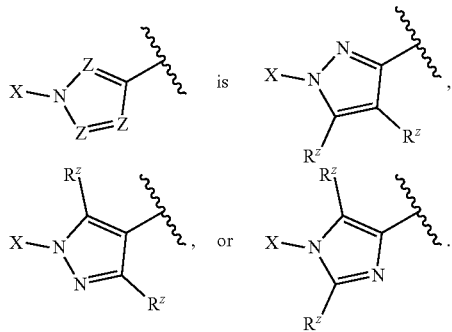

In some embodiments,

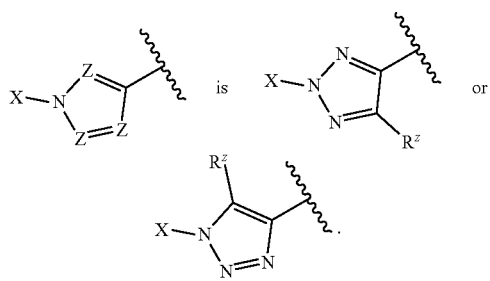

In some embodiments,

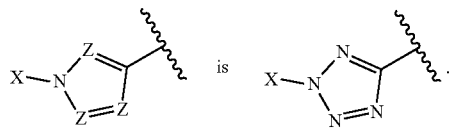

In some embodiments, each $R^z$ is independently H, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted aralkyl, substituted or unsubstituted aryl, or substituted or unsubstituted heteroaryl. In some embodiments, each $R^z$ is independently H, substituted or unsubstituted $C_1$-$C_6$alkyl, or substituted or unsubstituted $C_1$-$C_6$haloalkyl. In some embodiments, each $R^z$ is independently H or substituted or unsubstituted $C_1$-$C_6$alkyl. In some embodiments, each $R^z$ is independently H or substituted or unsubstituted $C_1$-$C_4$alkyl. In some embodiments, each $R^z$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$.

In some embodiments, each $R^z$ is independently H. In some embodiments, each $R^z$ is independently substituted or unsubstituted $C_1$-$C_6$alkyl. In some embodiments, each $R^z$ is independently substituted or unsubstituted $C_1$-$C_4$alkyl. In some embodiments, each $R^z$ is independently substituted or unsubstituted $C_1$-$C_6$haloalkyl. In some embodiments, each $R^z$ is independently substituted or unsubstituted $C_1$-$C_4$haloalkyl. In some embodiments, each $R^z$ is independently —$CH_2F$, —$CHF_2$, —$CF_3$, or —$CH_2CF_3$. In some embodiments, each $R^z$ is independently substituted or unsubstituted $C_1$-$C_6$heteroalkyl. In some embodiments, each $R^z$ is independently substituted or unsubstituted $C_1$-$C_4$heteroalkyl. In some embodiments, each $R^z$ is independently substituted or unsubstituted $C_3$-$C_{10}$cycloalkyl. In some embodiments, each $R^z$ is independently substituted or unsubstituted $C_3$-$C_6$cycloalkyl. In some embodiments, each $R^z$ is independently substituted or unsubstituted cyclopropyl, substituted or unsubstituted cyclobutyl, substituted or unsubstituted cyclopentyl, or substituted or unsubstituted cyclohexyl. In some embodiments, each $R^z$ is independently substituted or unsubstituted $C_2$-$C_{10}$heterocycloalkyl. In some embodiments, each $R^z$ is independently substituted or unsubstituted $C_2$-$C_6$heterocycloalkyl. In some embodiments, each $R^z$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^z$ is independently substituted or unsubstituted aralkyl. In some embodiments, each $R^z$ is independently substituted or unsubstituted benzyl. In some embodiments, each $R^z$ is independently substituted or unsubstituted aryl. In some embodiments, each $R^z$ is independently substituted or unsubstituted phenyl. In some embodiments, each $R^z$ is independently substituted or unsubstituted heteroaryl. In some embodiments, each $R^z$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, each $R^1$ is independently H. In some embodiments, each $R^1$ is independently halogen. In some embodiments, each $R^1$ is independently F, Cl, Br, or I. In some embodiments, each $R^1$ is independently —CN. In some embodiments, each $R^1$ is independently —$OR^4$. In some embodiments, each $R^1$ is independently —$SR^4$. In some embodiments, each $R^1$ is independently —$N(R^4)_2$. In some embodiments, each $R^1$ is independently substituted or unsubstituted $C_1$-$C_6$alkyl. In some embodiments, each $R^1$ is independently substituted or unsubstituted $C_1$-$C_4$alkyl. In some embodiments, each $R^1$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^1$ is independently substituted or unsubstituted $C_1$-$C_6$haloalkyl. In some embodiments, each $R^1$ is independently substituted or unsubstituted $C_1$-$C_4$haloalkyl. In some embodiments, each $R^1$ is independently —$CH_2F$, —$CHF_2$, —$CF_3$, or —$CH_2CF_3$. In some embodiments, each $R^1$ is independently substituted or unsubstituted $C_1$-$C_6$heteroalkyl. In some embodiments, each $R^1$ is independently substituted or unsubstituted $C_1$-$C_4$heteroalkyl. In some embodiments, each $R^1$ is independently substituted or unsubstituted $C_3$-$C_{10}$cycloalkyl. In some embodiments, each $R^1$ is independently substituted or unsubstituted $C_3$-$C_6$cycloalkyl. In some embodiments, each $R^1$ is independently substituted or unsubstituted cyclopropyl, substituted or unsubstituted cyclobutyl, substituted or unsubstituted cyclopentyl, or substituted or unsubstituted cyclohexyl. In some embodiments, each $R^1$ is independently substituted or unsubstituted $C_2$-$C_{10}$heterocycloalkyl. In some embodiments, each $R^1$ is independently substituted or unsubstituted $C_2$-$C_6$heterocycloalkyl. In some embodiments, each $R^1$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^1$ is independently substituted or unsubstituted aralkyl. In some embodiments, each $R^1$ is independently substituted or unsubstituted benzyl. In some embodiments, each $R^1$ is independently substituted or unsubstituted aryl. In some embodiments, each $R^1$ is independently substituted or unsubstituted phenyl. In some embodiments, each $R^1$ is independently substituted or unsubstituted heteroaryl. In some embodiments, each $R^1$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments,

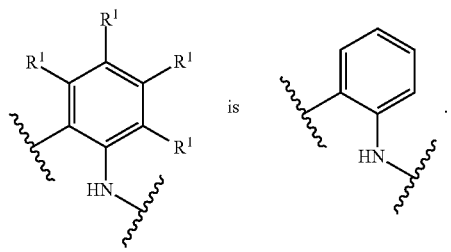

In some embodiments,

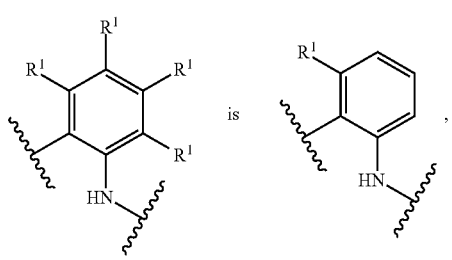

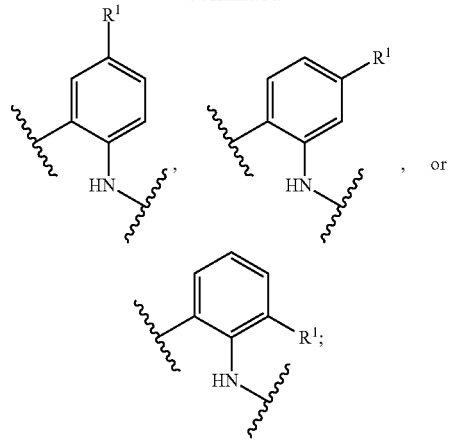

and $R^1$ is halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

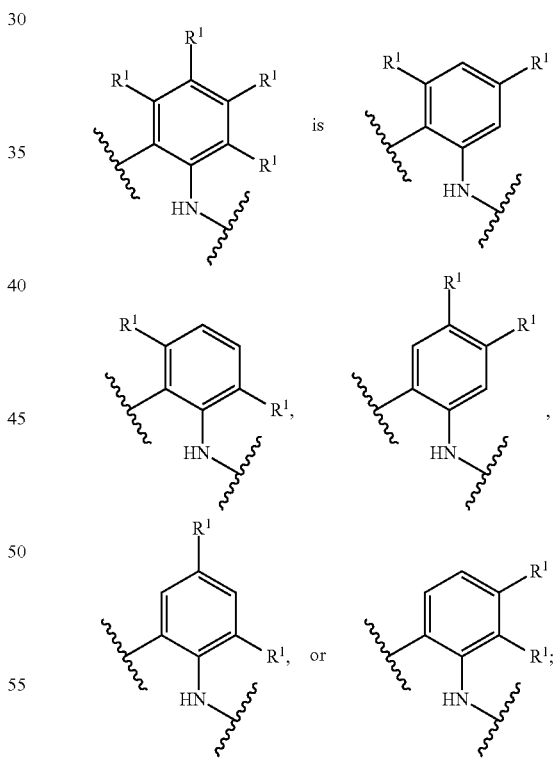

and each $R^1$ is independently halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, each R⁴ is independently H. In some embodiments, each R⁴ is independently substituted or unsubstituted $C_1$-$C_6$alkyl. In some embodiments, each R⁴ is independently substituted or unsubstituted $C_1$-$C_4$alkyl. In some embodiments, each R⁴ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each R⁴ is independently substituted or unsubstituted $C_1$-$C_6$haloalkyl. In some embodiments, each R⁴ is independently substituted or unsubstituted $C_1$-$C_4$haloalkyl. In some embodiments, each R⁴ is independently —$CH_2F$, —$CHF_2$, —$CF_3$, or —$CH_2CF_3$. In some embodiments, each R⁴ is independently substituted or unsubstituted $C_1$-$C_6$heteroalkyl. In some embodiments, each R⁴ is independently substituted or unsubstituted $C_1$-$C_4$heteroalkyl. In some embodiments, each R⁴ is independently substituted or unsubstituted $C_3$-$C_{10}$cycloalkyl. In some embodiments, each R⁴ is independently substituted or unsubstituted $C_3$-$C_6$cycloalkyl. In some embodiments, each R⁴ is independently substituted or unsubstituted cyclopropyl, substituted or unsubstituted cyclobutyl, substituted or unsubstituted cyclopentyl, or substituted or unsubstituted cyclohexyl. In some embodiments, each R⁴ is independently substituted or unsubstituted $C_2$-$C_{10}$heterocycloalkyl. In some embodiments, each R⁴ is independently substituted or unsubstituted $C_2$-$C_6$heterocycloalkyl. In some embodiments, each R⁴ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each R⁴ is independently substituted or unsubstituted aralkyl. In some embodiments, each R⁴ is independently substituted or unsubstituted benzyl. In some embodiments, each R⁴ is independently substituted or unsubstituted aryl. In some embodiments, each R⁴ is independently substituted or unsubstituted phenyl. In some embodiments, each R⁴ is independently substituted or unsubstituted heteroaryl. In some embodiments, each R⁴ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments,

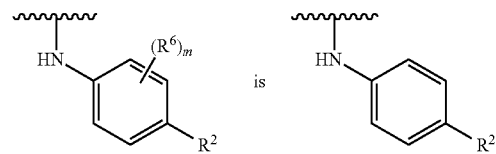

In some embodiments,

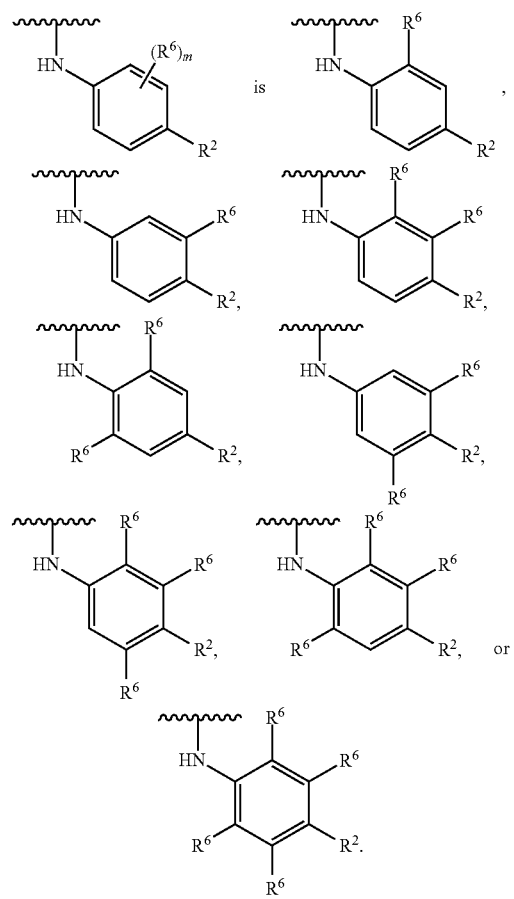

In some embodiments, R² is halogen. In some embodiments, R² is F, Cl, Br, or I. In some embodiments, R² is —$N_3$. In some embodiments, R² is —CN. In some embodiments, R² is —OR⁵. In some embodiments, R² is —SR⁵. In some embodiments, R² is —$(SO_2)R^5$. In some embodiments, R² is —$N(R^5)_2$. In some embodiments, R² is —$CO_2R^5$. In some embodiments, R² is substituted or unsubstituted $C_1$-$C_6$alkyl. In some embodiments, R² is substituted or unsubstituted $C_1$-$C_4$alkyl. In some embodiments, R² is —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, R² is substituted or unsubstituted $C_1$-$C_6$haloalkyl. In some embodiments, R² is substituted or unsubstituted $C_1$-$C_4$haloalkyl. In some embodiments, R² is —$CH_2F$, —$CHF_2$, —$CF_3$, or —$CH_2CF_3$. In some embodiments, R² is substituted or unsubstituted $C_1$-$C_6$heteroalkyl. In some embodiments, R² is substituted or unsubstituted $C_1$-$C_4$heteroalkyl. In some embodiments, R² is substituted or unsubstituted $C_3$-$C_{10}$cycloalkyl. In some embodiments, R² is substituted or unsubstituted $C_3$-$C_6$cycloalkyl. In some embodiments, R² is substituted or unsubstituted cyclopropyl, substituted or unsubstituted cyclobutyl, substituted or unsubstituted cyclopentyl, or substituted or unsubstituted cyclohexyl. In some embodiments, $R^2$ is substituted or unsubstituted $C_2$-$C_{10}$heterocycloalkyl. In some embodiments, $R^2$ is substituted or unsubstituted $C_2$-$C_6$heterocycloalkyl. In some embodiments, $R^2$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, $R^2$ is substituted or unsubstituted aralkyl. In some embodiments, $R^2$ is substituted or unsubstituted benzyl. In some embodiments, $R^2$ is substituted or unsubstituted aryl. In some embodiments, $R^2$ is substituted or unsubstituted phenyl. In some embodiments, $R^2$ is substituted or unsubstituted heteroaryl. In some embodiments, $R^2$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, $R^2$ is

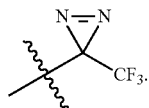

In some embodiments, $R^2$ is halogen, —$N_3$, —$OR^5$, —$(SO_2)R^5$, —$CO_2R^5$, substituted or unsubstituted $C_1$-$C_6$alkyl, substituted or unsubstituted $C_1$-$C_6$haloalkyl, or

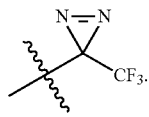

In some embodiments, each $R^5$ is independently H. In some embodiments, each $R^5$ is independently substituted or unsubstituted $C_1$-$C_6$alkyl. In some embodiments, each $R^5$ is independently substituted or unsubstituted $C_1$-$C_4$alkyl. In some embodiments, each $R^5$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^5$ is independently substituted or unsubstituted $C_1$-$C_6$haloalkyl. In some embodiments, each $R^5$ is independently substituted or unsubstituted $C_1$-$C_4$haloalkyl. In some embodiments, each $R^5$ is independently —$CH_2F$, —$CHF_2$, —$CF_3$, or —$CH_2CF_3$. In some embodiments, each $R^5$ is independently substituted or unsubstituted $C_1$-$C_6$heteroalkyl. In some embodiments, each $R^5$ is independently substituted or unsubstituted $C_1$-$C_4$heteroalkyl. In some embodiments, each $R^5$ is independently substituted or unsubstituted $C_3$-$C_{10}$cycloalkyl. In some embodiments, each $R^5$ is independently substituted or unsubstituted $C_3$-$C_6$cycloalkyl. In some embodiments, each $R^5$ is independently substituted or unsubstituted cyclopropyl, substituted or unsubstituted cyclobutyl, substituted or unsubstituted cyclopentyl, or substituted or unsubstituted cyclohexyl. In some embodiments, each $R^5$ is independently substituted or unsubstituted $C_2$-$C_{10}$heterocycloalkyl. In some embodiments, each $R^5$ is independently substituted or unsubstituted $C_2$-$C_6$heterocycloalkyl. In some embodiments, each $R^5$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^5$ is independently substituted or unsubstituted aralkyl. In some embodiments, each $R^5$ is independently substituted or unsubstituted benzyl. In some embodiments, each $R^5$ is independently substituted or unsubstituted aryl. In some embodiments, each $R^5$ is independently substituted or unsubstituted phenyl. In some embodiments, each $R^5$ is independently substituted or unsubstituted heteroaryl. In some embodiments, each $R^5$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, m is 0. In some embodiments, m is 1. In some embodiments, m is 2. In some embodiments, m is 3. In some embodiments, m is 4.

In some embodiments, each $R^6$ is independently H. In some embodiments, each $R^6$ is independently halogen. In some embodiments, each $R^6$ is independently F, Cl, Br, or I. In some embodiments, each $R^6$ is independently —$N_3$. In some embodiments, each $R^6$ is independently —CN. In some embodiments, each $R^6$ is independently —$OR^5$. In some embodiments, each $R^6$ is independently —$SR^5$. In some embodiments, each $R^6$ is independently —$(SO_2)R^5$. In some embodiments, each $R^6$ is independently —$N(R^5)_2$. In some embodiments, each $R^6$ is independently —$CO_2R^5$. In some embodiments, each $R^6$ is independently substituted or unsubstituted $C_1$-$C_6$alkyl. In some embodiments, each $R^6$ is independently substituted or unsubstituted $C_1$-$C_4$alkyl. In some embodiments, each $R^6$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^6$ is independently substituted or unsubstituted $C_1$-$C_6$haloalkyl. In some embodiments, each $R^6$ is independently substituted or unsubstituted $C_1$-$C_4$haloalkyl. In some embodiments, each $R^6$ is independently —$CH_2F$, —$CHF_2$, —$CF_3$, or —$CH_2CF_3$. In some embodiments, each $R^6$ is independently substituted or unsubstituted $C_1$-$C_6$heteroalkyl. In some embodiments, each $R^6$ is independently substituted or unsubstituted $C_1$-$C_4$heteroalkyl. In some embodiments, each $R^6$ is independently substituted or unsubstituted $C_3$-$C_{10}$cycloalkyl. In some embodiments, each $R^6$ is independently substituted or unsubstituted $C_3$-$C_6$cycloalkyl. In some embodiments, each $R^6$ is independently substituted or unsubstituted cyclopropyl, substituted or unsubstituted cyclobutyl, substituted or unsubstituted cyclopentyl, or substituted or unsubstituted cyclohexyl. In some embodiments, each $R^6$ is independently substituted or unsubstituted $C_2$-$C_{10}$heterocycloalkyl. In some embodiments, each $R^6$ is independently substituted or unsubstituted $C_2$-$C_6$heterocycloalkyl. In some embodiments, each $R^6$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^6$ is independently substituted or unsubstituted aralkyl. In some embodiments, each $R^6$ is independently substituted or unsubstituted benzyl. In some embodiments, each $R^6$ is independently substituted or unsubstituted aryl. In some embodiments, each $R^6$ is independently substituted or unsubstituted phenyl. In some embodiments, each $R^6$ is independently substituted or unsubstituted heteroaryl. In some embodiments, each $R^6$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, each $R^7$ is independently H. In some embodiments, each $R^7$ is independently substituted or unsubstituted $C_1$-$C_6$alkyl. In some embodiments, each $R^7$ is independently substituted or unsubstituted $C_1$-$C_4$alkyl. In some embodiments, each $R^7$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^7$ is independently substituted or unsubstituted $C_1$-$C_6$haloalkyl. In some embodiments, each $R^7$ is independently substituted or unsubstituted $C_1$-$C_4$haloalkyl. In some embodiments, each $R^7$ is independently —$CH_2F$, —$CHF_2$, —$CF_3$, or —$CH_2CF_3$. In some embodiments, each $R^7$ is independently substituted or unsubstituted $C_1$-$C_6$heteroalkyl. In some embodiments, each $R^7$ is independently substituted or unsubstituted $C_1$-$C_4$heteroalkyl. In some embodiments, each $R^7$ is independently substituted or unsubstituted $C_3$-$C_{10}$cycloalkyl. In some embodiments, each $R^7$ is independently substituted or unsubstituted $C_3$-$C_6$cycloalkyl. In some embodiments, each $R^7$ is independently substituted or unsubstituted cyclopropyl, substituted or unsubstituted cyclobutyl, substituted or unsubstituted cyclopentyl, or substituted or unsubstituted cyclohexyl. In some embodiments, each $R^7$ is independently substituted or unsubstituted $C_2$-$C_{10}$heterocycloalkyl. In some embodiments, each $R^7$ is independently substituted or unsubstituted $C_2$-$C_6$heterocycloalkyl. In some embodiments, each $R^7$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^7$ is independently substituted or unsubstituted aralkyl. In some embodiments, each $R^7$ is independently substituted or unsubstituted benzyl. In some embodiments, each $R^7$ is independently substituted or unsubstituted aryl. In some embodiments, each $R^7$ is independently substituted or unsubstituted phenyl. In some embodiments, each $R^7$ is independently substituted or unsubstituted heteroaryl. In some embodiments, each $R^7$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, the compound has the structure of Formula (IIa), or a pharmaceutically acceptable salt thereof:

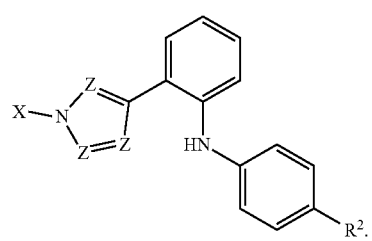

Formula (IIa)

In some embodiments, $R^2$ is substituted or unsubstituted $C_1$-$C_6$haloalkyl. In some embodiments, $R^2$ is substituted or unsubstituted $C_1$-$C_4$haloalkyl. In some embodiments, $R^2$ is —$CH_2F$, —$CHF_2$, —$CF_3$, or —$CH_2CF_3$. In some embodiments, $R^2$ is —$CF_3$.

In some embodiments, the compound has the structure of Formula (IIb), or a pharmaceutically acceptable salt thereof:

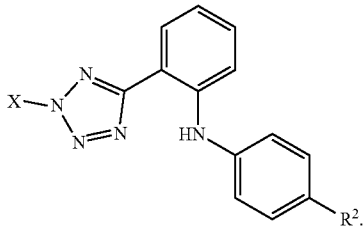

Formula (IIb)

In some embodiments, $R^2$ is substituted or unsubstituted $C_1$-$C_6$haloalkyl. In some embodiments, $R^2$ is substituted or unsubstituted $C_1$-$C_4$haloalkyl. In some embodiments, $R^2$ is —$CH_2F$, —$CHF_2$, —$CF_3$, or —$CH_2CF_3$. In some embodiments, $R^2$ is —$CF_3$.

In some embodiments, X is —$(CH_2)_r$—OH, —$(CH_2)_r$—OR", —$(CH_2)_r$—$N(R')_2$, —$(CH_2)_r$—NR'S(=O)$_2$R", —$(CH_2)_r$—S(=O)$_2$N$(R')_2$, —$(CH_2)_r$—SR', —$(CH_2)_r$—S(=O)R", —$(CH_2)_r$—S(=O)$_2$R", —$(CH_2)_r$—C(=O)R"—$(CH_2)_r$—OC(=O)R"—$(CH_2)_r$—$CO_2$H, —$(CH_2)_r$—$CO_2$R", —$(CH_2)_r$—OC(=O)OR"—$(CH_2)_r$—NR'C(=O)R", —$(CH_2)_r$—C(=O)N$(R')_2$, —$(CH_2)_r$—NR"C(=O)OR', —$(CH_2)_r$—OC(=O)N$(R")_2$; r is 1, 2, 3, or 4; each R' is independently H substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted aryl, or substituted or unsubstituted heteroaryl; and each R" is independently unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted aryl, or substituted or unsubstituted heteroaryl.

Provided in another aspect is a compound of Formula (III), or a pharmaceutically acceptable salt thereof:

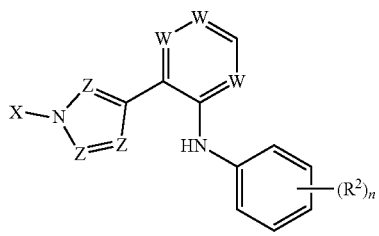

Formula (III)

wherein:
each Z is independently N or $CR^z$;
  each $R^z$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, -$L^1$-$Y^1$, or -$L^2$-$L^3$-$Y^2$;
$L^1$ is substituted or unsubstituted $C_1$-$C_6$alkylene;
$Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;
$L^2$ is absent or substituted or unsubstituted $C_1$-$C_6$alkylene;
$L^3$ is —O—, —S—, —(S=O)—, —(SO$_2$)—, —$NR^3$—, —(C=O)—, —(C=O)O—, —O(C=O)—, —(C=O)$NR^3$—, —(C=O)$NR^3$—O—, —O—$NR^3$(C=O)—, —$NR^3$(C=O)—, —$NR^3$(C=O)$NR^3$—, —O(C=O)$NR^3$—, —$NR^3$(C=O)O—, —$NR^3$(SO$_2$)$NR^3$—, —$NR^3$(SO$_2$)—, —(SO$_2$)$NR^3$—, —(SO$_2$)$NR^3$—(C=O)—, —(C=O)—$NR^3$(SO$_2$)—, —(SO$_2$)$NR^3$—(C=O)O—, —O(C=O)—$NR^3$(SO$_2$)—, —$NR^3$(SO$_2$)$NR^3$—(C=O)—, —(C=O)—$NR^3$(SO$_2$)$NR^3$—, —O(C=O)—$NR^3$(SO$_2$)—$NR^3$—, or —$NR^3$(SO$_2$)$NR^3$—(C=O)O—;
each $R^3$ is independently H or substituted or unsubstituted $C_1$-$C_6$alkyl;
$Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;
or $R^3$ and $Y^2$ on the same N atom are taken together with the N atom to which they are attached to form a substituted or unsubstituted N-containing heterocycle;
each W is $CR^1$ or N with the provision that at least one W is N;
each $R^1$ is independently H, halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
n is 0, 1, 2, 3, 4, or 5;
each $R^2$ is independently H, halogen, —$N_3$, —CN, —$OR^5$, —$SR^5$, —(SO$_2$)$R^5$, —$N(R^5)_2$, —$CO_2R^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

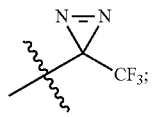 [SMILES: *C1(C(F)(F)F)N=N1]

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and
each $R^5$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

Provided in another aspect is a compound of Formula (III), or a pharmaceutically acceptable salt thereof:

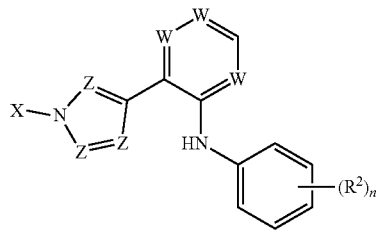

Formula (III)

wherein:
each Z is independently N or $CR^z$;
each $R^z$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, -$L^1$-$Y^1$, or -$L^2$-$L^3$-$Y^2$;
$L^1$ is substituted or unsubstituted $C_1$-$C_6$alkylene;
$Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;
$L^2$ is absent or substituted or unsubstituted $C_1$-$C_6$alkylene;
$L^3$ is —O—, —S—, —(S=O)—, —($SO_2$)—, —$NR^3$—, —(C=O)—, —(C=O)O—, —O(C=O)—, —(C=O)$NR^3$—, —(C=O)$NR^3$—O—, —O—$NR^3$(C=O)—, —$NR^3$(C=O)—, —$NR^3$(C=O)$NR^3$—, —O(C=O)$NR^3$—, —$NR^3$(C=O)O—, —$NR^3$($SO_2$)$NR^3$—, —$NR^3$($SO_2$)—, —($SO_2$)$NR^3$—, —($SO_2$)$NR^3$—(C=O)—, —(C=O)—$NR^3$($SO_2$)—, —($SO_2$)$NR^3$—(C=O)O—, —O(C=O)—$NR^3$($SO_2$)—, —$NR^3$($SO_2$)$NR^3$—(C=O)—, —(C=O)—$NR^3$($SO_2$)$NR^3$—, —O(C=O)—$NR^3$($SO_2$)—$NR^3$—, or —$NR^3$($SO_2$)$NR^3$—(C=O)O—;
each $R^3$ is independently H or substituted or unsubstituted $C_1$-$C_6$alkyl;
$Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;
or $R^3$ and $Y^2$ on the same N atom are taken together with the N atom to which they are attached to form a substituted or unsubstituted N-containing heterocycle;
each W is $CR^1$ or N with the provision that at least one W is N;
each $R^1$ is independently H, halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

n is 0, 1, 2, 3, 4, or 5;
each $R^2$ is independently H, halogen, —$N_3$, —CN, —$OR^5$, —$SR^5$, —($SO_2$)$R^5$, —$N(R^5)_2$, —$CO_2R^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

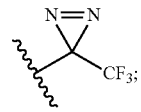

each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and
each $R^5$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

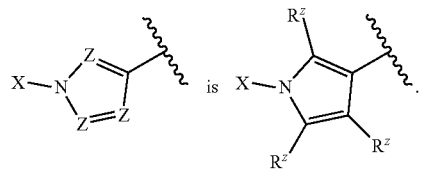

In some embodiments,

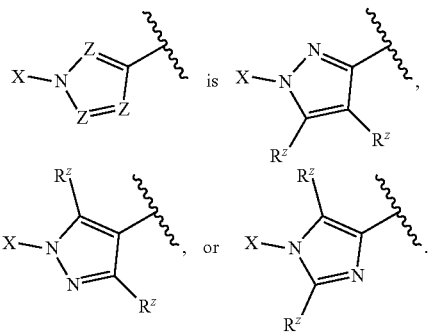

In some embodiments,

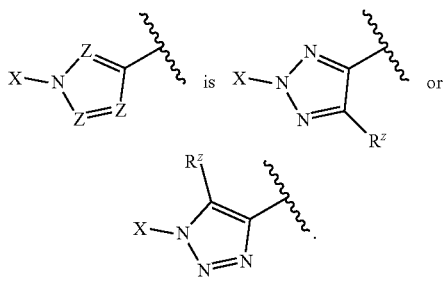

In some embodiments,

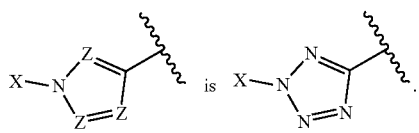

In some embodiments, each $R^z$ is independently H, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted aralkyl, substituted or unsubstituted aryl, or substituted or unsubstituted heteroaryl. In some embodiments, each $R^z$ is independently H, substituted or unsubstituted $C_1$-$C_6$alkyl, or substituted or unsubstituted $C_1$-$C_6$haloalkyl. In some embodiments, each $R^z$ is independently H or substituted or unsubstituted $C_1$-$C_6$alkyl. In some embodiments, each $R^z$ is independently H or substituted or unsubstituted $C_1$-$C_4$alkyl. In some embodiments, each $R^z$ is independently H, —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$.

In some embodiments, each $R^z$ is independently H. In some embodiments, each $R^z$ is independently substituted or unsubstituted $C_1$-$C_6$alkyl. In some embodiments, each $R^z$ is independently substituted or unsubstituted $C_1$-$C_4$alkyl. In some embodiments, each $R^z$ is independently substituted or unsubstituted $C_1$-$C_6$haloalkyl. In some embodiments, each $R^z$ is independently substituted or unsubstituted $C_1$-$C_4$haloalkyl. In some embodiments, each $R^z$ is independently —$CH_2F$, —$CHF_2$, —$CF_3$, or —$CH_2CF_3$. In some embodiments, each $R^z$ is independently substituted or unsubstituted $C_1$-$C_6$heteroalkyl. In some embodiments, each $R^z$ is independently substituted or unsubstituted $C_1$-$C_4$heteroalkyl. In some embodiments, each $R^z$ is independently substituted or unsubstituted $C_3$-$C_{10}$cycloalkyl. In some embodiments, each $R^z$ is independently substituted or unsubstituted $C_3$-$C_6$cycloalkyl. In some embodiments, each $R^z$ is independently substituted or unsubstituted cyclopropyl, substituted or unsubstituted cyclobutyl, substituted or unsubstituted cyclopentyl, or substituted or unsubstituted cyclohexyl. In some embodiments, each $R^z$ is independently substituted or unsubstituted $C_2$-$C_{10}$heterocycloalkyl. In some embodiments, each $R^z$ is independently substituted or unsubstituted $C_2$-$C_6$heterocycloalkyl. In some embodiments, each $R^z$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^z$ is independently substituted or unsubstituted aralkyl. In some embodiments, each $R^z$ is independently substituted or unsubstituted benzyl. In some embodiments, each $R^z$ is independently substituted or unsubstituted aryl. In some embodiments, each $R^z$ is independently substituted or unsubstituted phenyl. In some embodiments, each $R^z$ is independently substituted or unsubstituted heteroaryl. In some embodiments, each $R^z$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, X is substituted or unsubstituted $C_2$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, X is substituted or unsubstituted $C_1$-$C_6$alkyl. In some embodiments, X is substituted or unsubstituted $C_1$-$C_4$alkyl. In some embodiments, X is —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, X is substituted or unsubstituted $C_2$-$C_6$alkyl. In some embodiments, X is substituted or unsubstituted $C_2$-$C_4$alkyl. In some embodiments, X is —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, X is substituted or unsubstituted $C_1$-$C_6$haloalkyl. In some embodiments, X is substituted or unsubstituted $C_1$-$C_4$haloalkyl. In some embodiments, X is —$CH_2F$, —$CHF_2$, —$CF_3$, or —$CH_2CF_3$. In some embodiments, X is substituted or unsubstituted $C_3$-$C_{10}$cycloalkyl. In some embodiments, X is substituted or unsubstituted $C_3$-$C_6$cycloalkyl. In some embodiments, X is substituted or unsubstituted cyclopropyl, substituted or unsubstituted cyclobutyl, substituted or unsubstituted cyclopentyl, or substituted or unsubstituted cyclohexyl. In some embodiments, X is substituted or unsubstituted $C_2$-$C_{10}$heterocycloalkyl. In some embodiments, X is substituted or unsubstituted $C_2$-$C_6$heterocycloalkyl. In some embodiments, X is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, X is substituted or unsubstituted aryl. In some embodiments, X is substituted or unsubstituted phenyl. In some embodiments, X is substituted or unsubstituted heteroaryl. In some embodiments, X is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, X is -$L^1$-$Y^1$. In some embodiments, $L^1$ is substituted or unsubstituted $C_1$-$C_6$alkylene. In some embodiments, $L^1$ is substituted or unsubstituted $C_1$-$C_4$alkylene. In some embodiments, $L^1$ is —$CH_2$—, —$CH_2CH_2$—, —$CH_2CH_2CH_2$—, or —$CH_2CH_2CH_2CH_2$—. In some embodiments, $Y^1$ is substituted or unsubstituted $C_3$-$C_{10}$cycloalkyl. In some embodiments, $Y^1$ is substituted or unsubstituted $C_3$-$C_6$cycloalkyl. In some embodiments, $Y^1$ is substituted or unsubstituted cyclopropyl, substituted or unsubstituted cyclobutyl, substituted or unsubstituted cyclopentyl, or substituted or unsubstituted cyclohexyl. In some embodiments, $Y^1$ is substituted or unsubstituted $C_2$-$C_{10}$heterocycloalkyl. In some embodiments, $Y^1$ is substituted or unsubstituted $C_2$-$C_6$heterocycloalkyl. In some embodiments, $Y^1$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, $Y^1$ is substituted or unsubstituted aryl. In some embodiments, $Y^1$ is substituted or unsubstituted phenyl. In some embodiments, $Y^1$ is substituted or unsubstituted heteroaryl. In some embodiments, $Y^1$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, $L^1$ is substituted or unsubstituted $C_1$-$C_4$alkylene; and $Y^1$ is substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl. In some embodiments, $L^1$ is substituted or unsubstituted $C_1$-$C_4$alkylene; and $Y^1$ is substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl.

In some embodiments, X is -$L^2$-$L^3$-$Y^2$. In some embodiments, $L^2$ is absent. In some embodiments, $L^2$ is substituted or unsubstituted $C_1$-$C_6$alkylene. In some embodiments, $L^2$ is substituted or unsubstituted $C_1$-$C_4$alkylene. In some embodiments, $L^2$ is —$CH_2$—, —$CH_2CH_2$—, —$CH_2CH_2CH_2$—, or —$CH_2CH_2CH_2CH_2$—. In some embodiments, $L^3$ is —O—. In some embodiments, $L^3$ is —S—. In some embodiments, $L^3$ is —(S=O)—. In some embodiments, $L^3$ is —($SO_2$)—. In some embodiments, $L^3$ is —$NR^3$—. In some embodiments, $L^3$ is —(C=O)—. In some embodiments, $L^3$ is —(C=O)O—. In some embodiments, $L^3$ is —O(C=O)—. In some embodiments, $L^3$ is —(C=O)$NR^3$—. In some embodiments, $L^3$ is —(C=O)$NR^3$—O—. In some embodiments, $L^3$ is —O—$NR^3$(C=O)—. In some embodiments, $L^3$ is —$NR^3$(C=O)—. In some embodiments, $L^3$ is —$NR^3$(C=O)$NR^3$—. In some embodiments, $L^3$ is —O(C=O)$NR^3$—. In some embodiments, $L^3$ is —$NR^3$(C=O)O—. In some embodiments, $L^3$ is —$NR^3$($SO_2$)$NR^3$—. In some embodiments, $L^3$ is —$NR^3$($SO_2$)—. In some embodiments, $L^3$ is —($SO_2$)$NR^3$—. In some embodiments, $L^3$ is —($SO_2$)$NR^3$—(C=O)—. In some embodiments, $L^3$ is —(C=O)—$NR^3$($SO_2$)—. In some embodiments, $L^3$ is —($SO_2$)$NR^3$—(C=O)O—. In some embodiments, $L^3$ is —O(C=O)—$NR^3$($SO_2$)—. In some embodiments, $L^3$ is —$NR^3$($SO_2$)$NR^3$—(C=O)—. In some embodiments, $L^3$ is —(C=O)—$NR^3$($SO_2$)$NR^3$—. In some embodiments, $L^3$ is —O(C=O)—$NR^3$($SO_2$)—$NR^3$—. In some embodiments, $L^3$ is —$NR^3$($SO_2$)$NR^3$—(C=O)O—. In some embodiments, each $R^3$ is independently H. In some embodiments, each $R^3$ substituted or unsubstituted $C_1$-$C_6$alkyl. In some embodiments, $R^3$ is substituted or unsubstituted $C_1$-$C_4$alkyl. In some embodiments, $R^3$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$.

In some embodiments, $Y^2$ is independently H. In some embodiments, $Y^2$ substituted or unsubstituted $C_1$-$C_6$alkyl. In some embodiments, $Y^2$ substituted or unsubstituted $C_1$-$C_4$alkyl. In some embodiments, $Y^2$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, $Y^2$ is substituted or unsubstituted $C_1$-$C_6$haloalkyl. In some embodiments, $Y^2$ is substituted or unsubstituted $C_1$-$C_4$haloalkyl. In some embodiments, $Y^2$ is —$CH_2F$, —$CHF_2$, —$CF_3$, or —$CH_2CF_3$. In some embodiments, $Y^2$ is substituted or unsubstituted $C_1$-$C_6$heteroalkyl. In some embodiments, $Y^2$ is substituted or unsubstituted $C_1$-$C_4$heteroalkyl. In some embodiments, $Y^2$ is substituted or unsubstituted $C_3$-$C_{10}$cycloalkyl. In some embodiments, $Y^2$ is substituted or unsubstituted $C_3$-$C_6$cycloalkyl. In some embodiments, $Y^2$ is substituted or unsubstituted cyclopropyl, substituted or unsubstituted cyclobutyl, substituted or unsubstituted cyclopentyl, or substituted or unsubstituted cyclohexyl. In some embodiments, $Y^2$ is substituted or unsubstituted $C_2$-$C_{10}$heterocycloalkyl. In some embodiments, $Y^2$ is substituted or unsubstituted $C_2$-$C_6$heterocycloalkyl. In some embodiments, $Y^2$ is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, $Y^2$ is substituted or unsubstituted aryl. In some embodiments, $Y^2$ is substituted or unsubstituted phenyl. In some embodiments, $Y^2$ is substituted or unsubstituted heteroaryl. In some embodiments, $Y^2$ is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, $R^3$ and $Y^2$ on the same N atom are taken together with the N atom to which they are attached to form a substituted or unsubstituted N-containing heterocycle.

In some embodiments, $L^2$ is substituted or unsubstituted $C_1$-$C_6$alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, or —NR$^3$(SO$_2$)NR$^3$—(C=O)O—; each $R^3$ is independently H or substituted or unsubstituted $C_1$-$C_6$alkyl; and $Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, $L^2$ is substituted or unsubstituted $C_1$-$C_4$alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, or —NR$^3$(SO$_2$)NR$^3$—(C=O)O—; each $R^3$ is independently H or substituted or unsubstituted $C_1$-$C_4$alkyl; and $Y^2$ is H, substituted or unsubstituted $C_1$-$C_4$alkyl, substituted or unsubstituted $C_1$-$C_4$haloalkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl.

In some embodiments, one W is N. In some embodiments, two W are N. In some embodiments, three W are N.

In some embodiments,

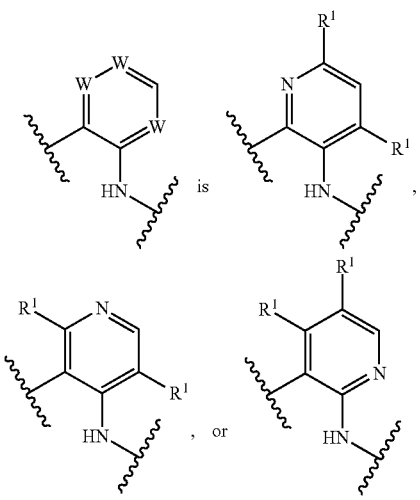

In some embodiments,

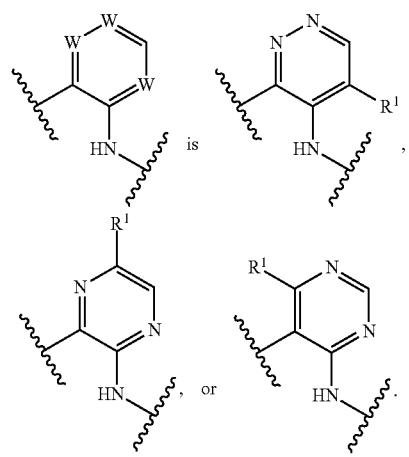

In some embodiments,

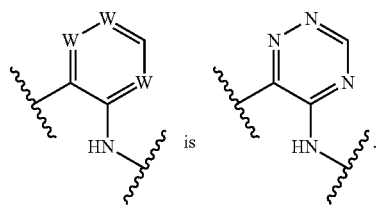

In some embodiments, each $R^1$ is independently H. In some embodiments, each $R^1$ is halogen. In some embodiments, each $R^1$ is independently F, Cl, Br, or I. In some embodiments, each $R^1$ is independently —CN. In some embodiments, each $R^1$ is independently —OR$^4$. In some embodiments, each $R^1$ is independently —SR$^4$. In some embodiments, each $R^1$ is independently —N(R$^4$)$_2$. In some embodiments, each $R^1$ is independently substituted or unsubstituted $C_1$-$C_6$alkyl. In some embodiments, each $R^1$ is independently substituted or unsubstituted $C_1$-$C_4$alkyl. In some embodiments, each $R^1$ is independently —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —C(CH$_3$)$_3$. In some embodiments, each $R^1$ is independently substituted or unsubstituted $C_1$-$C_6$haloalkyl. In some embodiments, each $R^1$ is independently substituted or unsubstituted $C_1$-$C_4$haloalkyl. In some embodiments, each $R^1$ is independently —CH$_2$F, —CHF$_2$, —CF$_3$, or —CH$_2$CF$_3$. In some embodiments, each $R^1$ is independently substituted or unsubstituted $C_1$-$C_6$heteroalkyl. In some embodiments, each $R^1$ is independently substituted or unsubstituted $C_1$-$C_4$heteroalkyl. In some embodiments, each $R^1$ is independently substituted or unsubstituted $C_3$-$C_{10}$cycloalkyl. In some embodiments, each $R^1$ is independently substituted or unsubstituted $C_3$-$C_6$cycloalkyl. In some embodiments, each $R^1$ is independently substituted or unsubstituted cyclopropyl, substituted or unsubstituted cyclobutyl, substituted or unsubstituted cyclopentyl, or substituted or unsubstituted cyclohexyl. In some embodiments, each $R^1$ is independently substituted or unsubstituted $C_2$-$C_{10}$heterocycloalkyl. In some embodiments, each $R^1$ is independently substituted or unsubstituted $C_2$-$C_6$heterocycloalkyl. In some embodiments, each $R^1$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^1$ is independently substituted or unsubstituted aralkyl. In some embodiments, each $R^1$ is independently substituted or unsubstituted benzyl. In some embodiments, each $R^1$ is independently substituted or unsubstituted aryl. In some embodiments, each $R^1$ is independently substituted or unsubstituted phenyl. In some embodiments, each $R^1$ is independently substituted or unsubstituted heteroaryl. In some embodiments, each $R^1$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, each $R^1$ is independently H, halogen, —CN, —OR$^4$, —SR$^4$, —N(R$^4$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, each $R^4$ is independently H. In some embodiments, each $R^4$ is independently substituted or unsubstituted $C_1$-$C_6$alkyl. In some embodiments, each $R^4$ is independently substituted or unsubstituted $C_1$-$C_4$alkyl. In some embodiments, each $R^4$ is independently —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, or —C(CH$_3$)$_3$. In some embodiments, each $R^4$ is independently substituted or unsubstituted $C_1$-$C_6$haloalkyl. In some embodiments, each $R^4$ is independently substituted or unsubstituted $C_1$-$C_4$haloalkyl. In some embodiments, each $R^4$ is independently —CH$_2$F, —CHF$_2$, —CF$_3$, or —CH$_2$CF$_3$. In some embodiments, each $R^4$ is independently substituted or unsubstituted $C_1$-$C_6$heteroalkyl. In some embodiments, each $R^4$ is independently substituted or unsubstituted $C_1$-$C_4$heteroalkyl. In some embodiments, each $R^4$ is independently substituted or unsubstituted $C_3$-$C_{10}$cycloalkyl. In some embodiments, each $R^4$ is independently substituted or unsubstituted $C_3$-$C_6$cycloalkyl. In some embodiments, each $R^4$ is independently substituted or unsubstituted cyclopropyl, substituted or unsubstituted cyclobutyl, substituted or unsubstituted cyclopentyl, or substituted or unsubstituted cyclohexyl. In some embodiments, each $R^4$ is independently substituted or unsubstituted $C_2$-$C_{10}$heterocycloalkyl. In some embodiments, each $R^4$ is independently substituted or unsubstituted $C_2$-$C_6$heterocycloalkyl. In some embodiments, each $R^4$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^4$ is independently substituted or unsubstituted aralkyl. In some embodiments, each $R^4$ is independently substituted or unsubstituted benzyl. In some embodiments, each $R^4$ is independently substituted or unsubstituted aryl. In some embodiments, each $R^4$ is independently substituted or unsubstituted phenyl. In some embodiments, each $R^4$ is independently substituted or unsubstituted heteroaryl. In some embodiments, each $R^4$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments,

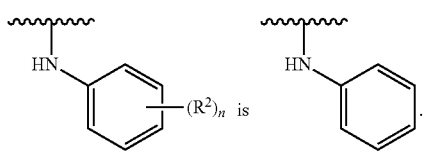

In some embodiments,

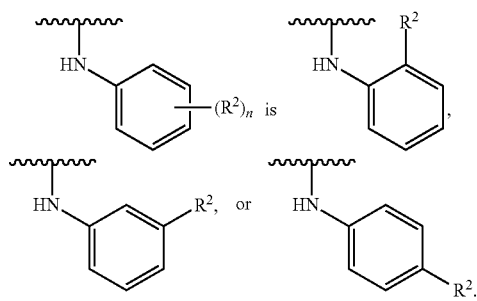

In some embodiments,

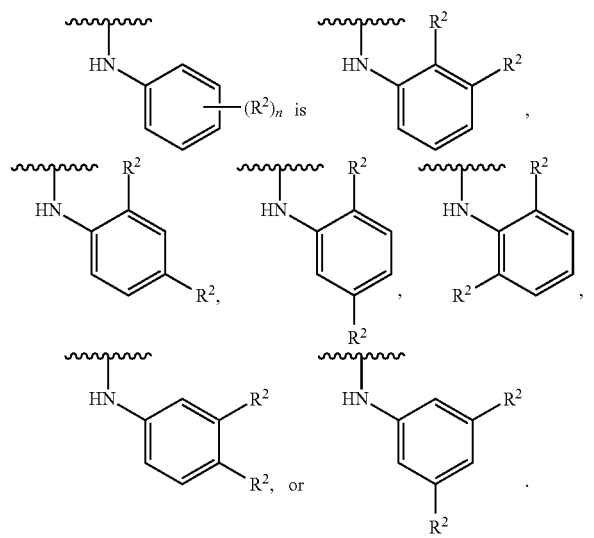

In some embodiments, n is 0. In some embodiments, n is 1. In some embodiments, n is 2. In some embodiments, n is 3. In some embodiments, n is 4. In some embodiments, n is 5.

In some embodiments, each $R^2$ is independently H. In some embodiments, each $R^2$ is independently halogen. In some embodiments, each $R^2$ is independently F, Cl, Br, or I. In some embodiments, each $R^2$ is independently —$N_3$. In some embodiments, each $R^2$ is independently —CN. In some embodiments, each $R^2$ is independently —$OR^5$. In some embodiments, each $R^2$ is independently —$SR^5$. In some embodiments, each $R^2$ is independently —$(SO_2)R^5$. In some embodiments, each $R^2$ is independently —$N(R^5)_2$. In some embodiments, each $R^2$ is independently —$CO_2R^5$. In some embodiments, each $R^2$ is independently substituted or unsubstituted $C_1$-$C_6$alkyl. In some embodiments, each $R^2$ is independently substituted or unsubstituted $C_1$-$C_4$alkyl. In some embodiments, each $R^2$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^2$ is independently substituted or unsubstituted $C_1$-$C_6$haloalkyl. In some embodiments, each $R^2$ is independently substituted or unsubstituted $C_1$-$C_4$haloalkyl. In some embodiments, each $R^2$ is independently —$CH_2F$, —$CHF_2$, —$CF_3$, or —$CH_2CF_3$. In some embodiments, each $R^2$ is independently substituted or unsubstituted $C_1$-$C_6$heteroalkyl. In some embodiments, each $R^2$ is independently substituted or unsubstituted $C_1$-$C_4$heteroalkyl. In some embodiments, each $R^2$ is independently substituted or unsubstituted $C_3$-$C_{10}$cycloalkyl. In some embodiments, each $R^2$ is independently substituted or unsubstituted $C_3$-$C_6$cycloalkyl. In some embodiments, each $R^2$ is independently substituted or unsubstituted cyclopropyl, substituted or unsubstituted cyclobutyl, substituted or unsubstituted cyclopentyl, or substituted or unsubstituted cyclohexyl. In some embodiments, each $R^2$ is independently substituted or unsubstituted $C_2$-$C_{10}$heterocycloalkyl. In some embodiments, each $R^2$ is independently substituted or unsubstituted $C_2$-$C_6$heterocycloalkyl. In some embodiments, each $R^2$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^2$ is independently substituted or unsubstituted aralkyl. In some embodiments, each $R^2$ is independently substituted or unsubstituted benzyl. In some embodiments, each $R^2$ is independently substituted or unsubstituted aryl. In some embodiments, each $R^2$ is independently substituted or unsubstituted phenyl. In some embodiments, each $R^2$ is independently substituted or unsubstituted heteroaryl. In some embodiments, each $R^2$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl. In some embodiments, each $R^2$ is independently

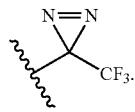

In some embodiments, each $R^2$ is independently H, halogen, —$N_3$, —$OR^5$, —$(SO_2)R^5$, —$CO_2R^5$, substituted or unsubstituted $C_1$-$C_6$alkyl, substituted or unsubstituted $C_1$-$C_6$haloalkyl, or

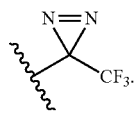 [SMILES: *C1(C(F)(F)F)N=N1]

In some embodiments, each $R^5$ is independently H. In some embodiments, each $R^5$ is independently substituted or unsubstituted $C_1$-$C_6$alkyl. In some embodiments, each $R^5$ is independently substituted or unsubstituted $C_1$-$C_4$alkyl. In some embodiments, each $R^5$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, or —$C(CH_3)_3$. In some embodiments, each $R^5$ is independently substituted or unsubstituted $C_1$-$C_6$haloalkyl. In some embodiments, each $R^5$ is independently substituted or unsubstituted $C_1$-$C_4$haloalkyl. In some embodiments, each $R^5$ is independently —$CH_2F$, —$CHF_2$, —$CF_3$, or —$CH_2CF_3$. In some embodiments, each $R^5$ is independently substituted or unsubstituted $C_1$-$C_6$heteroalkyl. In some embodiments, each $R^5$ is independently substituted or unsubstituted $C_1$-$C_4$heteroalkyl. In some embodiments, each $R^5$ is independently substituted or unsubstituted $C_3$-$C_{10}$cycloalkyl. In some embodiments, each $R^5$ is independently substituted or unsubstituted $C_3$-$C_6$cycloalkyl. In some embodiments, each $R^5$ is independently substituted or unsubstituted cyclopropyl, substituted or unsubstituted cyclobutyl, substituted or unsubstituted cyclopentyl, or substituted or unsubstituted cyclohexyl. In some embodiments, each $R^5$ is independently substituted or unsubstituted $C_2$-$C_{10}$heterocycloalkyl. In some embodiments, each $R^5$ is independently substituted or unsubstituted $C_2$-$C_6$heterocycloalkyl. In some embodiments, each $R^5$ is independently substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl. In some embodiments, each $R^5$ is independently substituted or unsubstituted aralkyl. In some embodiments, each $R^5$ is independently substituted or unsubstituted benzyl. In some embodiments, each $R^5$ is independently substituted or unsubstituted aryl. In some embodiments, each $R^5$ is independently substituted or unsubstituted phenyl. In some embodiments, each $R^5$ is independently substituted or unsubstituted heteroaryl. In some embodiments, each $R^5$ is independently substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

In some embodiments, the compound has the structure of Formula (IIIa), or a pharmaceutically acceptable salt thereof:

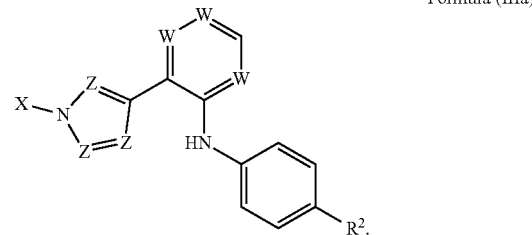

Formula (IIIa)

In some embodiments, $R^2$ is substituted or unsubstituted $C_1$-$C_6$haloalkyl. In some embodiments, $R^2$ is substituted or unsubstituted $C_1$-$C_4$haloalkyl. In some embodiments, $R^2$ is —$CH_2F$, —$CHF_2$, —$CF_3$, or —$CH_2CF_3$. In some embodiments, $R^2$ is —$CF_3$.

In some embodiments, the compound has the structure of Formula (IIIb), or a pharmaceutically acceptable salt thereof:

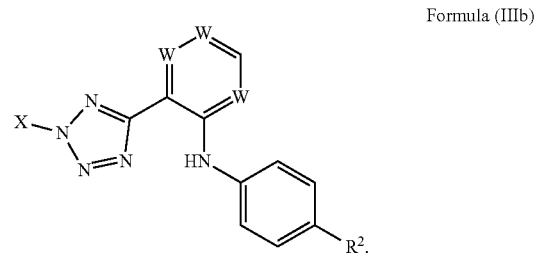

Formula (IIIb)

In some embodiments, $R^2$ is substituted or unsubstituted $C_1$-$C_6$haloalkyl. In some embodiments, $R^2$ is substituted or unsubstituted $C_1$-$C_4$haloalkyl. In some embodiments, $R^2$ is —$CH_2F$, —$CHF_2$, —$CF_3$, or —$CH_2CF_3$. In some embodiments, $R^2$ is —$CF_3$.

In some embodiments, X is —$(CH_2)_r$—OH, —$(CH_2)_r$—OR", —$(CH_2)_r$—N(R')$_2$, —$(CH_2)_r$—NR'S(=O)$_2$R", —$(CH_2)_r$—S(=O)$_2$N(R')$_2$, —$(CH_2)_r$—SR', —$(CH_2)_r$—S(=O)R", —$(CH_2)_r$—S(=O)$_2$R"—$(CH_2)_r$—C(=O)R", —$(CH_2)_r$—OC(=O)R", —$(CH_2)_r$—CO$_2$H, —$(CH_2)_r$—CO$_2$R", —$(CH_2)_r$—OC(=O)OR", —$(CH_2)_r$—NR'C(=O)R", —$(CH_2)_r$—C(=O)N(R')$_2$, —$(CH_2)_r$—NR"C(=O)OR', —$(CH_2)_r$—OC(=O)N(R")$_2$; r is 1, 2, 3, or 4; each R' is independently H substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted aryl, or substituted or unsubstituted heteroaryl; and each R" is independently unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted aryl, or substituted or unsubstituted heteroaryl.

In some embodiments, the compound disclosed herein has the structure provided in Table 1 or Table 2.
TABLE 1
| Compound No. | Structure | Name |
| --- | --- | --- |
| 1 | 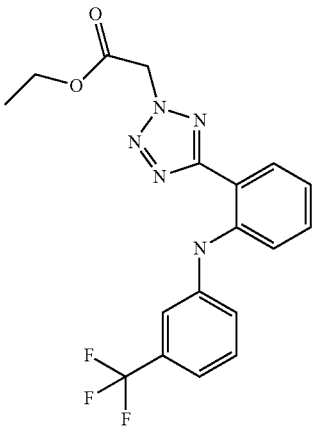 [SMILES: CCOC(=O)Cn1nnc(-c2ccccc2Nc2cccc(C(F)(F)F)c2)n1] | ethyl 2-[5-[2-[3-(trifluoromethyl)anilino]phenyl]tetrazol-2-yl]acetate |
| 2 | 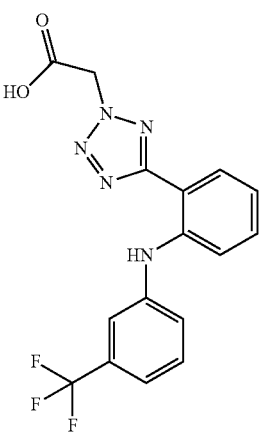 [SMILES: O=C(O)Cn1nnc(-c2ccccc2Nc2cccc(C(F)(F)F)c2)n1] | 2-[5-[2-[3-(trifluoromethyl)anilino]phenyl]tetrazol-2-yl]acetic acid |
| 3 | 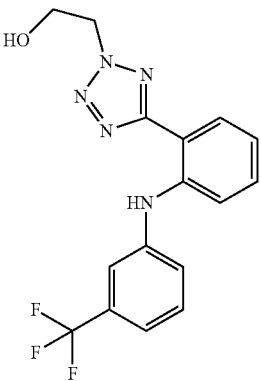 [SMILES: OCCn1nnc(-c2ccccc2Nc2cccc(C(F)(F)F)c2)n1] | 2-[5-[2-[3-(trifluoromethyl)anilino]phenyl]tetrazol-2-yl]ethanol |

TABLE 1-continued
| Compound No. | Structure | Name |
|---|---|---|
| 4 | 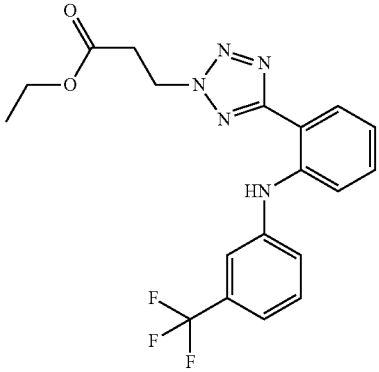 [SMILES: CCOC(=O)CCn1nnc(-c2ccccc2Nc2cccc(C(F)(F)F)c2)n1] | ethyl 3-[5-[2-[3-(trifluoromethyl)anilino]phenyl]tetrazol-2-yl]propanoate |
| 5 | 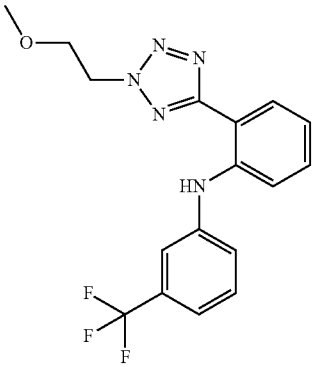 [SMILES: COCCn1nnc(-c2ccccc2Nc2cccc(C(F)(F)F)c2)n1] | 2-[2-(2-methoxyethyl)tetrazol-5-yl]-N-[3-(trifluoromethyl)phenyl]aniline |
| 6 | 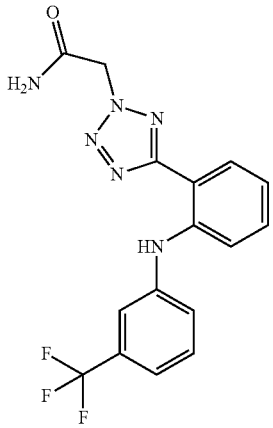 [SMILES: NC(=O)Cn1nnc(-c2ccccc2Nc2cccc(C(F)(F)F)c2)n1] | 2-[5-[2-[3-(trifluoromethyl)anilino]phenyl]tetrazol-2-yl]acetamide |
| 7 | 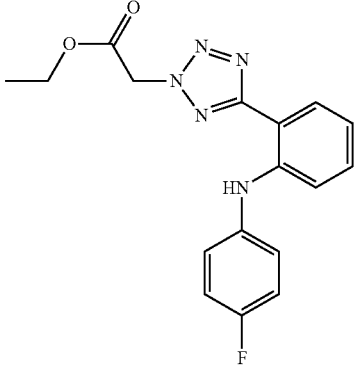 [SMILES: CCOC(=O)Cn1nnc(-c2ccccc2Nc2ccc(F)cc2)n1] | ethyl 2-[5-[2-(4-fluoroanilino)phenyl]tetrazol-2-yl]acetate |

TABLE 1-continued

| Compound No. | Structure | Name |
|---|---|---|
| 8 | 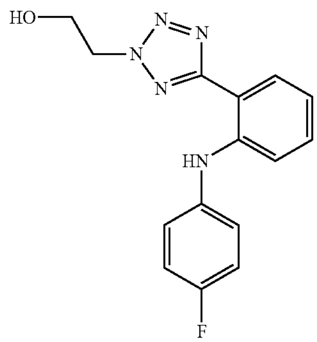 [SMILES: OCCn1nnc(-c2ccccc2Nc2ccc(F)cc2)n1] | 2-[5-[2-(4-fluoroanilino)phenyl]tetrazol-2-yl]ethanol |
| 9 | 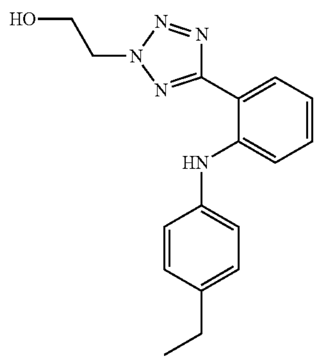 [SMILES: CCc1ccc(Nc2ccccc2-c2nnn(CCO)n2)cc1] | 2-[5-[2-(4-ethylanilino)phenyl]tetrazol-2-yl]ethanol |
| 10 | 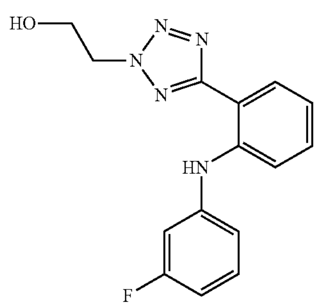 [SMILES: OCCn1nnc(-c2ccccc2Nc2cccc(F)c2)n1] | 2-(5-(2-((3-fluorophenyl)amino)phenyl)-2H-tetrazol-2-yl)ethanol |
| 11 | 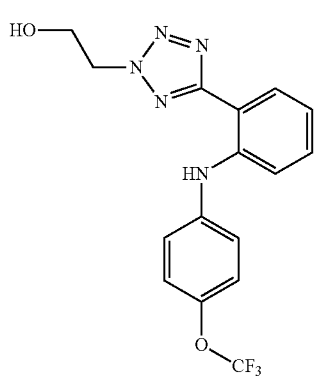 [SMILES: OCCn1nnc(-c2ccccc2Nc2ccc(OC(F)(F)F)cc2)n1] | 2-(5-(2-((4-(Trifluoromethoxy)phenyl)amino)phenyl)-2H-tetrazol-2-yl)ethanol |

TABLE 1-continued

| Compound No. | Structure | Name |
|---|---|---|
| 12 | 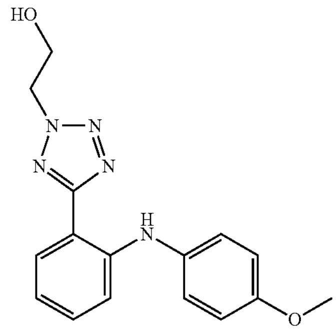 [SMILES: COc1ccc(Nc2ccccc2-c2nnn(CCO)n2)cc1] | 2-[5-[2-(4-methoxyanilino)phenyl]tetrazol-2-yl]ethanol |
| 13 | 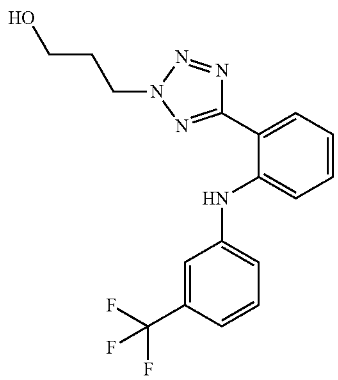 [SMILES: OCCCn1nnc(-c2ccccc2Nc2cccc(C(F)(F)F)c2)n1] | 3-[5-[2-[3-(trifluoromethyl)anilino]phenyl]tetrazol-2-yl]propan-1-ol |
| 14 | 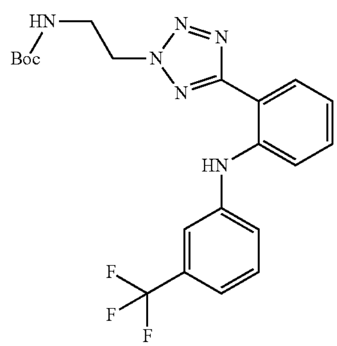 [SMILES: CC(C)(C)OC(=O)NCCn1nnc(-c2ccccc2Nc2cccc(C(F)(F)F)c2)n1] | tert-butyl N-[2-[5-[2-[3-(trifluoromethyl)anilino]phenyl]tetrazol-2-yl]ethyl]carbamate |
| 15 | 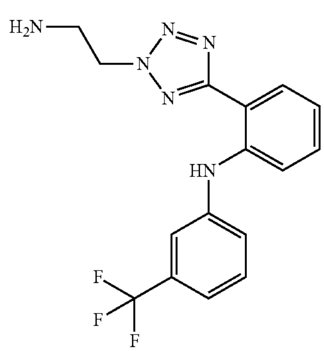 [SMILES: NCCn1nnc(-c2ccccc2Nc2cccc(C(F)(F)F)c2)n1] | 2-[2-(2-aminoethyl)tetrazol-5-yl]-N-[3-(trifluoromethyl)phenyl]aniline |

TABLE 1-continued

| Compound No. | Structure | Name |
|---|---|---|
| 16 | 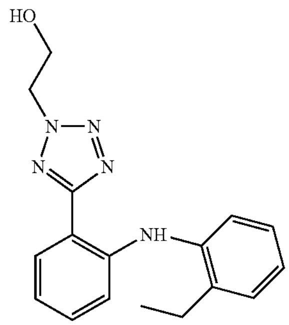 [SMILES: CCc1ccccc1Nc1ccccc1-c1nnn(CCO)n1] | 2-[5-[2-(2-ethylanilino)phenyl]tetrazol-2-yl]ethanol |
| 17 | 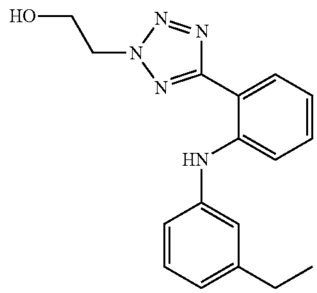 [SMILES: CCc1cccc(Nc2ccccc2-c2nnn(CCO)n2)c1] | 2-[5-[2-(3-ethylanilino)phenyl]tetrazol-2-yl]ethanol |
| 18 | 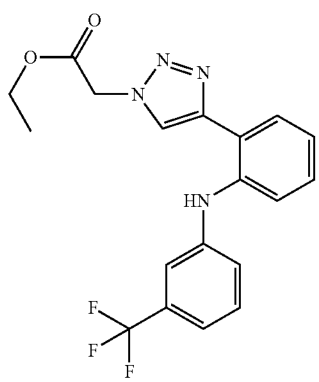 [SMILES: CCOC(=O)Cn1cc(-c2ccccc2Nc2cccc(C(F)(F)F)c2)nn1] | Ethyl 2-[4-[2-[3-(trifluoromethyl)anilino]phenyl]triazol-1-yl]acetate |
| 19 | 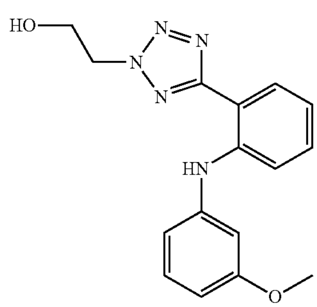 [SMILES: COc1cccc(Nc2ccccc2-c2nnn(CCO)n2)c1] | 2-(5-(2-((3-methoxyphenyl)amino)phenyl)-2H-tetrazol-2-yl)ethan-1-ol |

TABLE 1-continued

| Compound No. | Structure | Name |
|---|---|---|
| 20 | 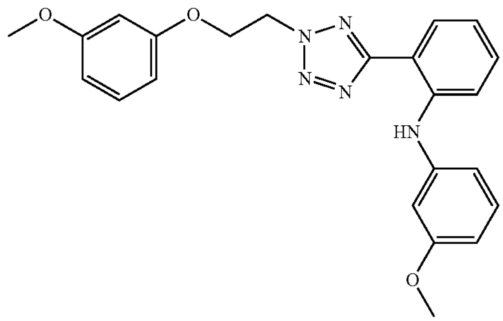 [SMILES: COc1cccc(Nc2ccccc2-c2nnn(CCOc3cccc(OC)c3)n2)c1] | 2-[2-[2-(3-methoxyphenoxy)ethyl]tetrazol-5-yl]-N-(3-methoxyphenyl)aniline |
| 21 | 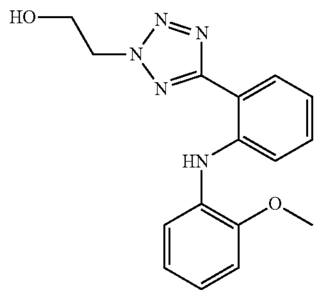 [SMILES: COc1ccccc1Nc1ccccc1-c1nnn(CCO)n1] | 2-[5-[2-(2-methoxyanilino)phenyl]tetrazol-2-yl]ethanol |
| 22 | 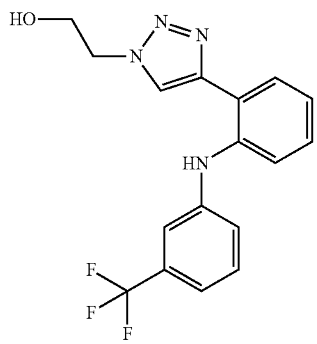 [SMILES: OCCn1cc(-c2ccccc2Nc2cccc(C(F)(F)F)c2)nn1] | 2-[4-[2-[3-(trifluoromethyl)anilino]phenyl]triazol-1-yl]ethanol |
| 23 | 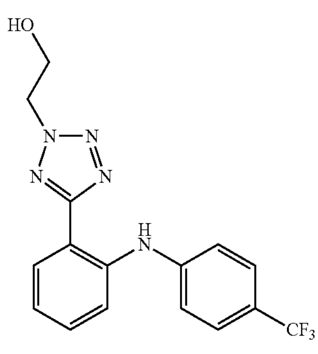 [SMILES: OCCn1nnc(-c2ccccc2Nc2ccc(C(F)(F)F)cc2)n1] | 2-(5-(2-((4-(Trifluoromethyl)phenyl)amino)phenyl)-2H-tetrazol-2-yl)ethanol |

TABLE 1-continued

| Compound No. | Structure | Name |
|---|---|---|
| 24 | 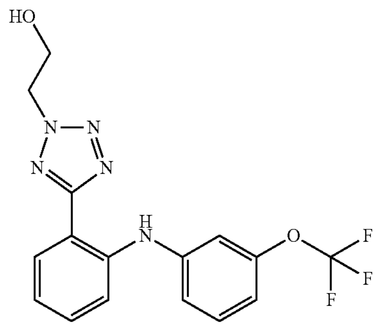 [SMILES: OCCn1nnc(-c2ccccc2Nc2cccc(OC(F)(F)F)c2)n1] | 2-(5-(2-((3-(Trifluoromethoxy)phenyl)amino)phenyl)-2H-tetrazol-2-yl)ethanol |
| 25 | 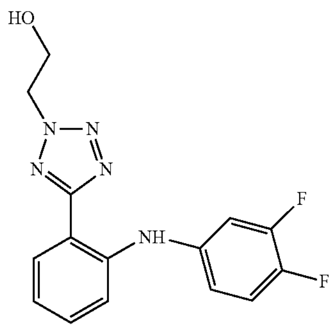 [SMILES: OCCn1nnc(-c2ccccc2Nc2ccc(F)c(F)c2)n1] | 2-[5-[2-(3,4-difluoroanilino)phenyl]tetrazol-2-yl]ethanol |
| 26 | 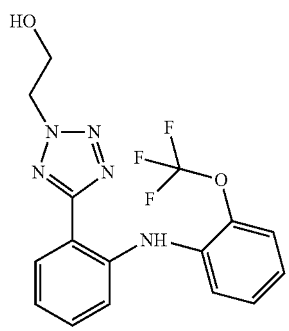 [SMILES: OCCn1nnc(-c2ccccc2Nc2ccccc2OC(F)(F)F)n1] | 2-[5-[2-[2-(trifluoromethoxy)anilino]phenyl]tetrazol-2-yl]ethanol |
| 27 | 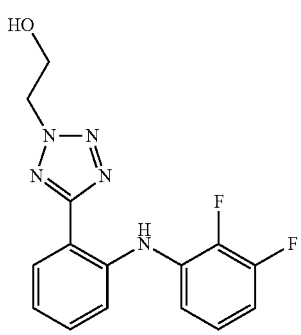 [SMILES: OCCn1nnc(-c2ccccc2Nc2cccc(F)c2F)n1] | 2-(5-(2-((2,3-difluorophenyl)amino)phenyl)-2H-tetrazol-2-yl)ethan-1-ol |

TABLE 1-continued

| Compound No. | Structure | Name |
|---|---|---|
| 28 | 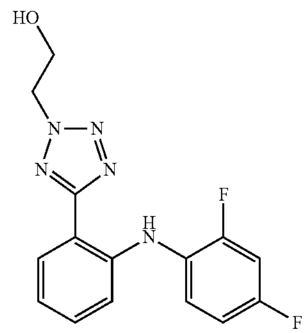 [SMILES: OCCn1nnc(-c2ccccc2Nc2ccc(F)cc2F)n1] | 2-(5-(2-((2,4-difluorophenyl)amino)phenyl)-2H-tetrazol-2-yl)ethan-1-ol |
| 29 | 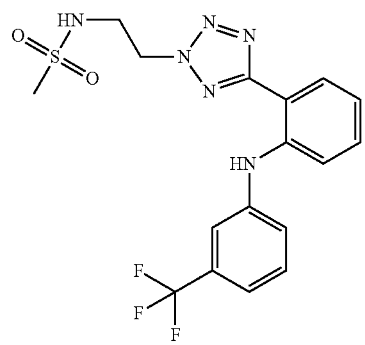 [SMILES: CS(=O)(=O)NCCn1nnc(-c2ccccc2Nc2cccc(C(F)(F)F)c2)n1] | N-[2-[5-[2-[3-(trifluoromethyl)anilino]phenyl]tetrazol-2-yl]ethyl]methanesulfonamide |
| 30 | 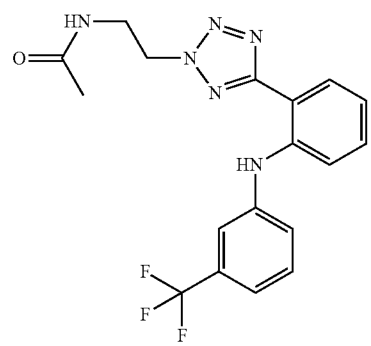 [SMILES: CC(=O)NCCn1nnc(-c2ccccc2Nc2cccc(C(F)(F)F)c2)n1] | N-[2-[5-[2-[3-(trifluoromethyl)anilino]phenyl]tetrazol-2-yl]ethyl]acetamide |
| 31 | 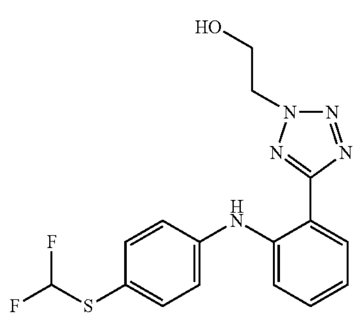 [SMILES: OCCn1nnc(-c2ccccc2Nc2ccc(SC(F)F)cc2)n1] | 2-[5-[2-[4-(difluoromethylsulfanyl)anilino]phenyl]tetrazol-2-yl]ethanol |

TABLE 1-continued

| Compound No. | Structure | Name |
|---|---|---|
| 32 | 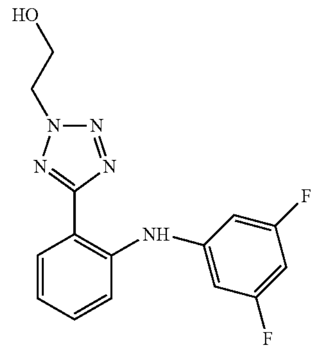 [SMILES: OCCn1nnc(-c2ccccc2Nc2cc(F)cc(F)c2)n1] | 2-(5-(2-((3,5-difluorophenyl)amino)phenyl)-2H-tetrazol-2-yl)ethanol |
| 33 | 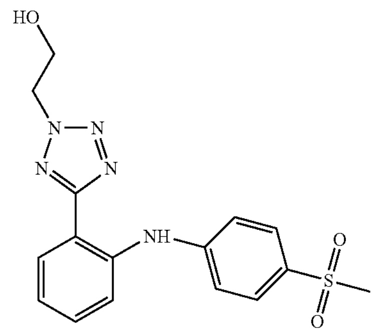 [SMILES: CS(=O)(=O)c1ccc(Nc2ccccc2-c2nnn(CCO)n2)cc1] | 2-(5-(2-((4-(methylsulfonyl)phenyl)amino)phenyl)-2H-tetrazol-2-yl)ethanol |
| 34 | 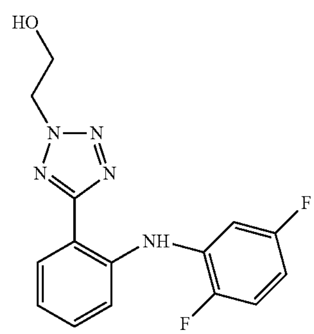 [SMILES: OCCn1nnc(-c2ccccc2Nc2cc(F)ccc2F)n1] | 2-(5-(2-((2,5-difluorophenyl)amino)phenyl)-2H-tetrazol-2-yl)ethanol |
| 35 | 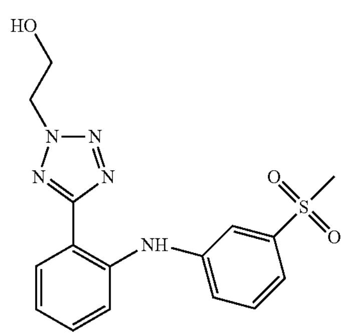 [SMILES: CS(=O)(=O)c1cccc(Nc2ccccc2-c2nnn(CCO)n2)c1] | 2-(5-(2-((3-(methylsulfonyl)phenyl)amino)phenyl)-2H-tetrazol-2-yl)ethanol |

TABLE 1-continued
| Compound No. | Structure | Name |
|---|---|---|
| 36 | 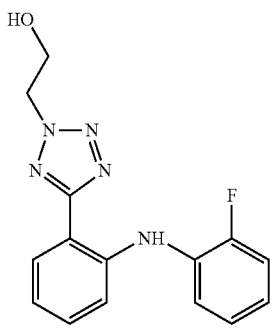 [SMILES: OCCn1nnc(-c2ccccc2Nc2ccccc2F)n1] | 2-(5-(2-((2-fluorophenyl)amino)phenyl)-2H-tetrazol-2-yl)ethanol |
| 37 | 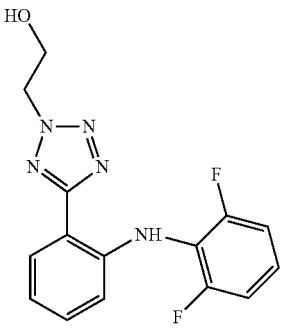 [SMILES: OCCn1nnc(-c2ccccc2Nc2c(F)cccc2F)n1] | 2-[5-[2-(2,6-difluoroanilino)phenyl]tetrazol-2-yl]ethanol |
| 38 | 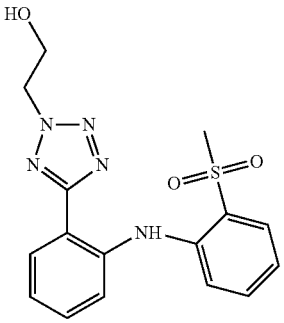 [SMILES: CS(=O)(=O)c1ccccc1Nc1ccccc1-c1nnn(CCO)n1] | 2-[5-[2-(2-methylsulfonylanilino)phenyl]tetrazol-2-yl]ethanol |
| 39 | 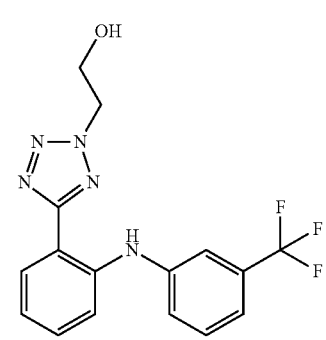 [SMILES: OCCn1nnc(-c2ccccc2Nc2cccc(C(F)(F)F)c2)n1] | 2-(3-(2-((3-(trifluoromethyl)phenyl)amino)phenyl)-1H-1,2,4-triazol-1-yl)ethanol |

TABLE 1-continued

| Compound No. | Structure | Name |
|---|---|---|
| 40 | 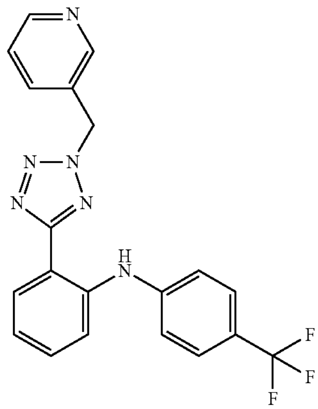 [SMILES: FC(F)(F)c1ccc(Nc2ccccc2-c2nnn(Cc3cccnc3)n2)cc1] | 2-[2-(3-pyridylmethyl)tetrazol-5-yl]-N-[4-(trifluoromethyl)phenyl]aniline |
| 41 | 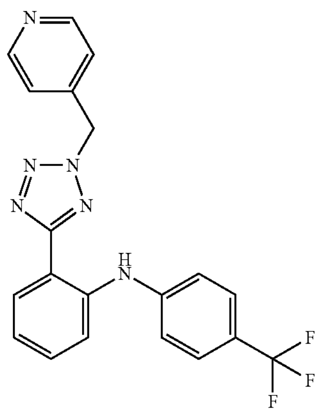 [SMILES: FC(F)(F)c1ccc(Nc2ccccc2-c2nnn(Cc3ccncc3)n2)cc1] | 2-[2-(4-pyridylmethyl)tetrazol-5-yl]-N-[4-(trifluoromethyl)phenyl]aniline |
| 42 | 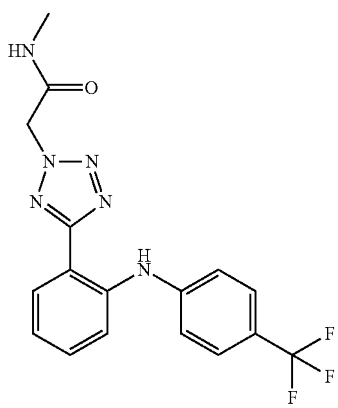 [SMILES: CNC(=O)Cn1nnc(-c2ccccc2Nc2ccc(C(F)(F)F)cc2)n1] | N-methyl-2-[5-[2-[4-(trifluoromethyl)anilino]phenyl]tetrazol-2-yl]acetamide |
| 43 | 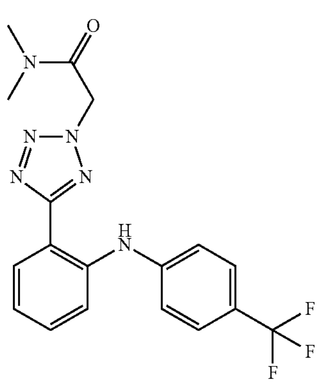 [SMILES: CN(C)C(=O)Cn1nnc(-c2ccccc2Nc2ccc(C(F)(F)F)cc2)n1] | N,N-dimethyl-2-[5-[2-[4-(trifluoromethyl)anilino]phenyl]tetrazol-2-yl]acetamide |

TABLE 1-continued

| Compound No. | Structure | Name |
|---|---|---|
| 44 | 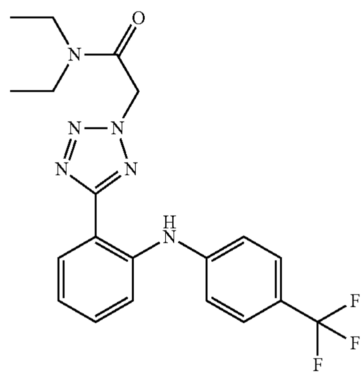 [SMILES: CCN(CC)C(=O)Cn1nnc(-c2ccccc2Nc2ccc(C(F)(F)F)cc2)n1] | N,N-diethyl-2-[5-[2-[4-(trifluoromethyl)anilino]phenyl]tetrazol-2-yl]acetamide |
| 45 | 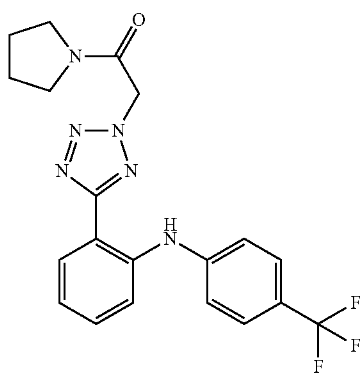 [SMILES: O=C(Cn1nnc(-c2ccccc2Nc2ccc(C(F)(F)F)cc2)n1)N1CCCC1] | 1-pyrrolidin-1-yl-2-[5-[2-[4-(trifluoromethyl)anilino]phenyl]tetrazol-2-yl]ethanone |
| 46 | 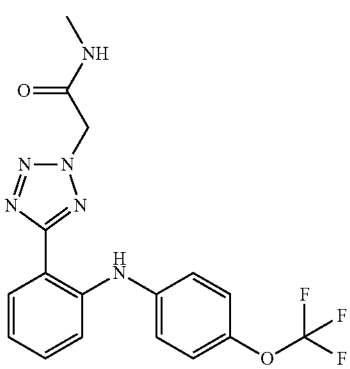 [SMILES: CNC(=O)Cn1nnc(-c2ccccc2Nc2ccc(OC(F)(F)F)cc2)n1] | N-methyl-2-[5-[2-[4-(trifluoromethoxy)anilino]phenyl]tetrazol-2-yl]acetamide |
| 47 | 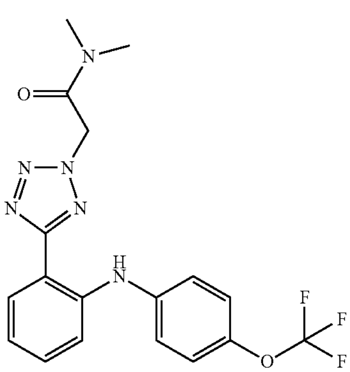 [SMILES: CN(C)C(=O)Cn1nnc(-c2ccccc2Nc2ccc(OC(F)(F)F)cc2)n1] | N,N-dimethyl-2-[5-[2-[4-(trifluoromethoxy)anilino]phenyl]tetrazol-2-yl]acetamide |

TABLE 1-continued

| Compound No. | Structure | Name |
|---|---|---|
| 48 | 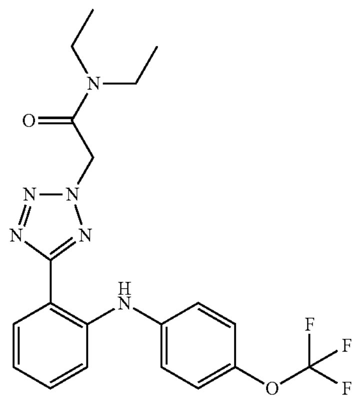 [SMILES: CCN(CC)C(=O)Cn1nnc(-c2ccccc2Nc2ccc(OC(F)(F)F)cc2)n1] | N,N-diethyl-2-[5-[2-[4-(trifluoromethoxy)anilino]phenyl]tetrazol-2-yl]acetamide |
| 49 | 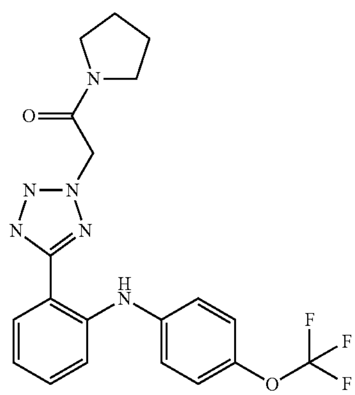 [SMILES: O=C(CN1N=C(c2ccccc2Nc2ccc(OC(F)(F)F)cc2)NN1)N1CCCC1] | 1-(pyrrolidin-1-yl)-2-(5-(2-((4-(trifluoromethoxy)phenyl)amino)phenyl)-2H-tetrazol-2-yl)ethan-1-one |
| 50 | 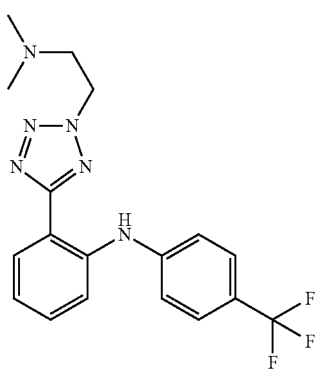 [SMILES: CN(C)CCn1nnc(-c2ccccc2Nc2ccc(C(F)(F)F)cc2)n1] | 2-[2-[2-(dimethylamino)ethyl]tetrazol-5-yl]-N-[4-(trifluoromethyl)phenyl]aniline |
| 51 | 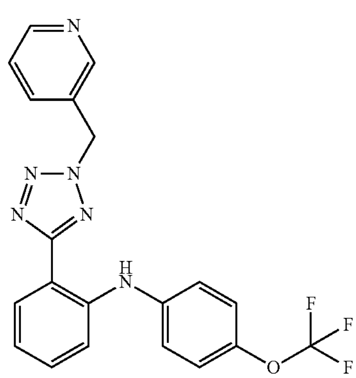 [SMILES: FC(F)(F)Oc1ccc(Nc2ccccc2-c2nnn(Cc3cccnc3)n2)cc1] | 2-[2-(3-pyridylmethyl)tetrazol-5-yl]-N-[4-(trifluoromethoxy)phenyl]aniline |

TABLE 1-continued

| Compound No. | Structure | Name |
|---|---|---|
| 52 | 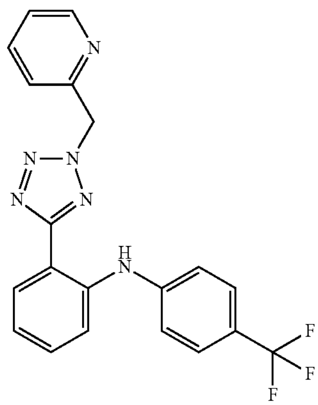 [SMILES: FC(F)(F)c1ccc(Nc2ccccc2-c2nnn(Cc3ccccn3)n2)cc1] | 2-[2-(2-pyridylmethyl)tetrazol-5-yl]-N-[4-(trifluoromethyl)phenyl]aniline |
| 53 | 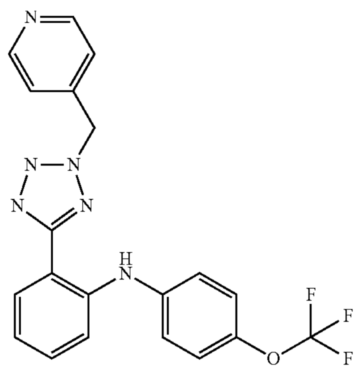 [SMILES: FC(F)(F)Oc1ccc(Nc2ccccc2C2=NN(Cc3ccncc3)NN2)cc1] | 2-[2-(4-pyridylmethyl)tetrazol-5-yl]-N-[4-(trifluoromethoxy)phenyl]aniline |
| 54 | 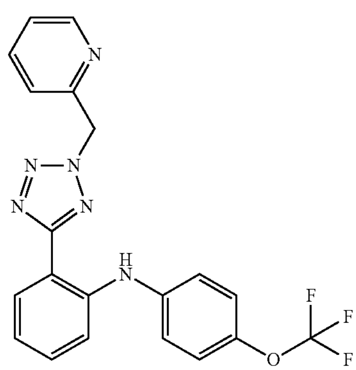 [SMILES: FC(F)(F)Oc1ccc(Nc2ccccc2-c2nnn(Cc3ccccn3)n2)cc1] | 2-[2-(2-pyridylmethyl)tetrazol-5-yl]-N-[4-(trifluoromethoxy)phenyl]aniline |
| 55 | 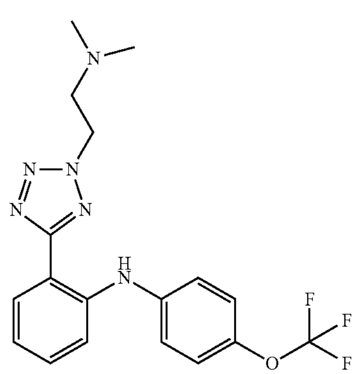 [SMILES: CN(C)CCn1nnc(-c2ccccc2Nc2ccc(OC(F)(F)F)cc2)n1] | 2-[2-[2-(dimethylamino)ethyl]tetrazol-5-yl]-N-4-[trifluoromethoxy)phenyl]aniline |

TABLE 1-continued

| Compound No. | Structure | Name |
|---|---|---|
| 56 | 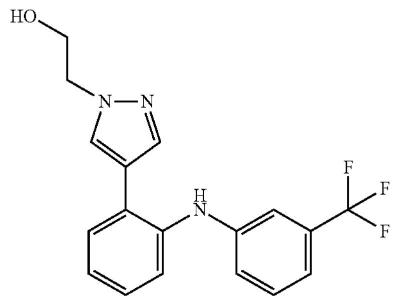 [SMILES: OCCn1cc(-c2ccccc2Nc2cccc(C(F)(F)F)c2)cn1] | 2-[4-[2-[3-(trifluoromethyl)anilino]phenyl]pyrazol-1-yl]ethanol |
| 57 | 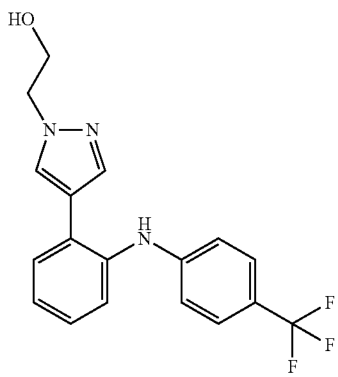 [SMILES: OCCn1cc(-c2ccccc2Nc2ccc(C(F)(F)F)cc2)cn1] | 2-[4-[2-[3-(trifluoromethyl)anilino]phenyl]pyrazol-1-yl]ethanol |
| 58 | 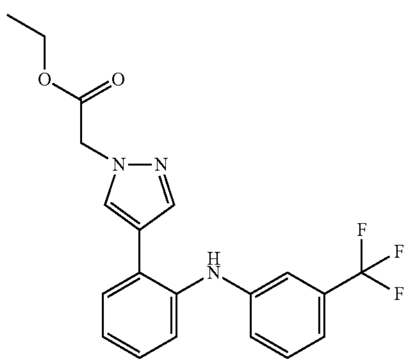 [SMILES: CCOC(=O)Cn1cc(-c2ccccc2Nc2cccc(C(F)(F)F)c2)cn1] | ethyl 2-(4-(2-((3-(trifluoromethyl)phenyl)amino)phenyl)-1H-pyrazol-1-yl)acetate |
| 59 | 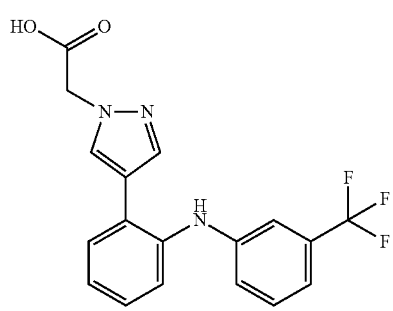 [SMILES: O=C(O)Cn1cc(-c2ccccc2Nc2cccc(C(F)(F)F)c2)cn1] | 2-(4-(2-((3-(trifluoromethyl)phenyl)amino)phenyl)-1H-pyrazol-1-yl)acetic acid |

TABLE 1-continued
| Compound No. | Structure | Name |
|---|---|---|
| 60 | 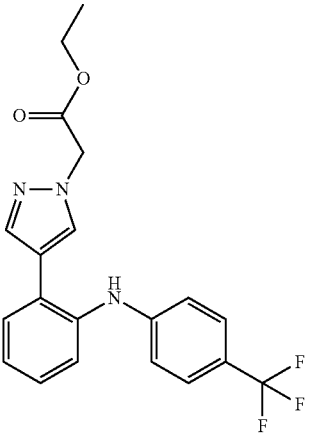 [SMILES: CCOC(=O)Cn1cc(-c2ccccc2Nc2ccc(C(F)(F)F)cc2)cn1] | ethyl 2-(4-(2-((4-(trifluoromethyl)phenyl)amino)phenyl)-1H-pyrazol-1-yl)acetate |
| 61 | 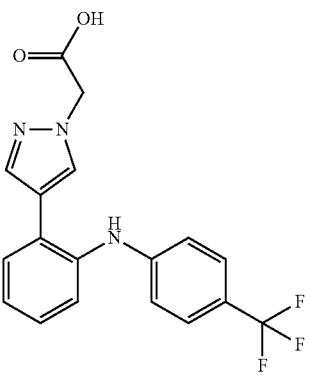 [SMILES: O=C(O)Cn1cc(-c2ccccc2Nc2ccc(C(F)(F)F)cc2)cn1] | 2-(4-(2-((4-(trifluoromethyl)phenyl)amino)phenyl)-1H-pyrazol-1-yl)acetic acid |
| 62 | 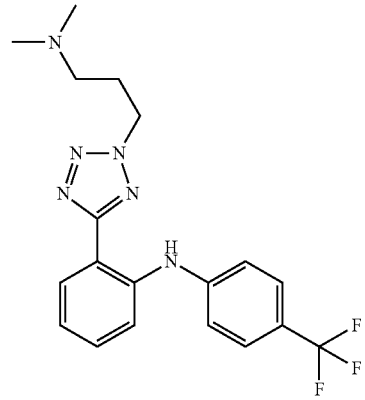 [SMILES: CN(C)CCCn1nnc(-c2ccccc2Nc2ccc(C(F)(F)F)cc2)n1] | 2-(2-(3-(dimethylamino)propyl)-2H-tetrazol-5-yl)-N-(4-(trifluoromethyl)phenyl)aniline |
| 63 | 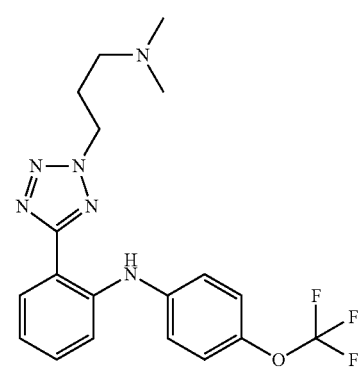 [SMILES: CN(C)CCCn1nnc(-c2ccccc2Nc2ccc(OC(F)(F)F)cc2)n1] | 2-(2-(3-(dimethylamino)propyl)-2H-tetrazol-5-yl)-N-(4-(trifluoromethoxy)phenyl)aniline |

TABLE 1-continued

| Compound No. | Structure | Name |
|---|---|---|
| 64 | 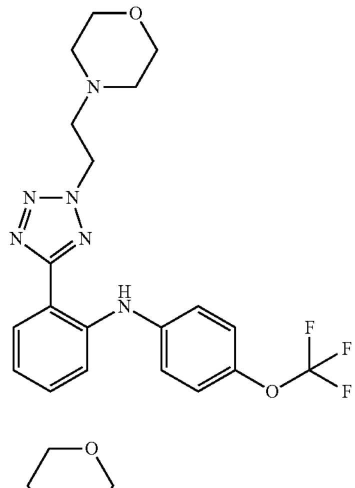 | 2-(2-(2-morpholinoethyl)-2H-tetrazol-5-yl)-N-(4-(trifluoromethoxy)phenyl)aniline |
| 65 | 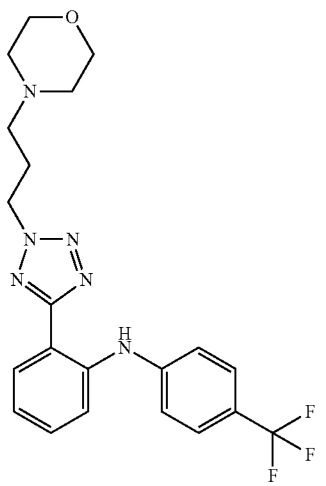 [SMILES: FC(F)(F)c1ccc(Nc2ccccc2-c2nnn(CCCN3CCOCC3)n2)cc1] | 2-(2-(3-morpholinopropyl)-2H-tetrazol-5-yl)-N-(4-(trifluoromethyl)phenyl)aniline |
| 66 | 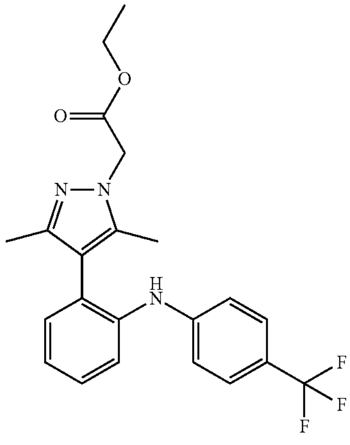 [SMILES: CCOC(=O)Cn1nc(C)c(-c2ccccc2Nc2ccc(C(F)(F)F)cc2)c1C] | ethyl 2-(3,5-dimethyl-4-(2-((4-(trifluoromethyl)phenyl)amino)phenyl)-1H-pyrazol-1-yl)acetate |

TABLE 1-continued

| Compound No. | Structure | Name |
|---|---|---|
| 67 | 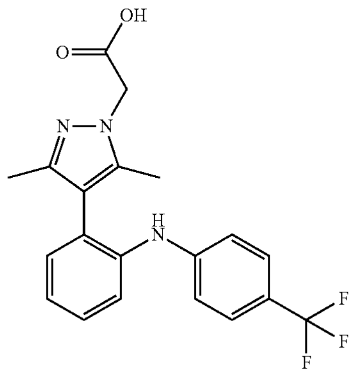 [SMILES: Cc1nn(CC(=O)O)c(C)c1-c1ccccc1Nc1ccc(C(F)(F)F)cc1] | 2-(3,5-dimethyl-4-(2-((4-(trifluoromethyl)phenyl)amino)phenyl)-1H-pyrazol-1-yl)acetic acid |
| 68 | 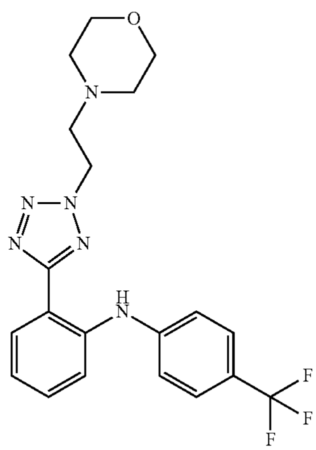 [SMILES: FC(F)(F)c1ccc(Nc2ccccc2-c2nnn(CCN3CCOCC3)n2)cc1] | 2-(2-(2-morpholinoethyl)-2H-tetrazol-5-yl)-N-(4-(trifluoromethyl)phenyl)aniline |
| 69 | 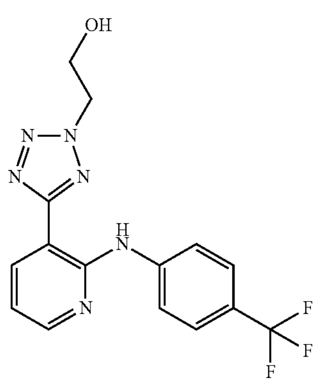 [SMILES: OCCn1nnc(-c2cccnc2Nc2ccc(C(F)(F)F)cc2)n1] | 2-(5-(2-((4-(trifluoromethyl)phenyl)amino)pyridin-3-yl)-2H-tetrazol-2-yl)ethanol |

TABLE 1-continued

| Compound No. | Structure | Name |
|---|---|---|
| 70 | 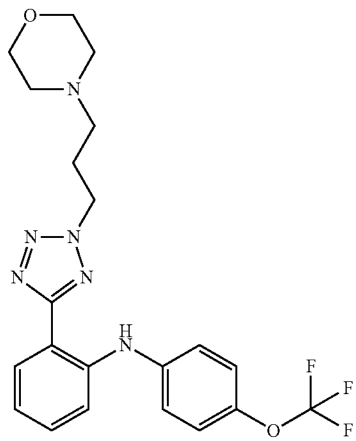 [SMILES: FC(F)(F)Oc1ccc(Nc2ccccc2-c2nnn(CCCN3CCOCC3)n2)cc1] | 2-(2-(3-morpholinopropyl)-2H-tetrazol-5-yl)-N-(4-(trifluoromethoxy)phenyl)aniline |
| 71 | 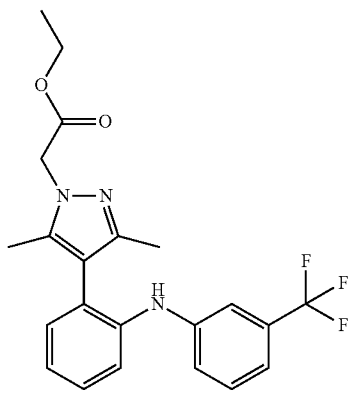 [SMILES: CCOC(=O)Cn1nc(C)c(-c2ccccc2Nc2cccc(C(F)(F)F)c2)c1C] | ethyl 2-(3,5-dimethyl-4-(2-((3-(trifluoromethyl)phenyl)amino)phenyl)-1H-pyrazol-1-yl)acetate |
| 72 | 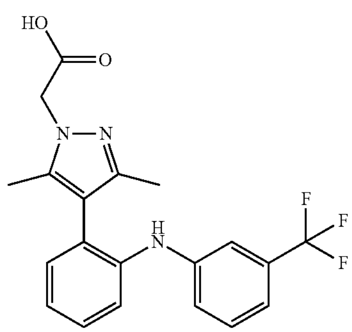 [SMILES: Cc1nn(CC(=O)O)c(C)c1-c1ccccc1Nc1cccc(C(F)(F)F)c1] | 2-(3,5-dimethyl-4-(2-((3-(trifluoromethyl)phenyl)amino)phenyl)-1H-pyrazol-1-yl)acetic acid |
| 73 | 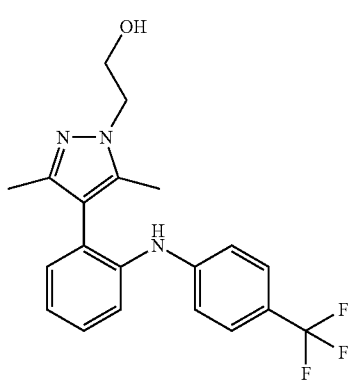 [SMILES: Cc1nn(CCO)c(C)c1-c1ccccc1Nc1ccc(C(F)(F)F)cc1] | 2-(3,5-dimethyl-4-(2-((4-(trifluoromethyl)phenyl)amino)phenyl)-1H-pyrazol-1-yl)ethanol |

TABLE 1-continued

| Compound No. | Structure | Name |
|---|---|---|
| 74 | 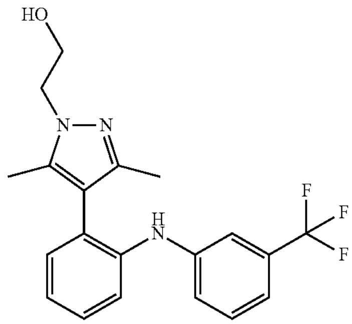 [SMILES: Cc1nn(CCO)c(C)c1-c1ccccc1Nc1cccc(C(F)(F)F)c1] | 2-(3,5-dimethyl-4-(2-((3-(trifluoromethyl)phenyl)amino)phenyl)-1H-pyrazol-1-yl)ethanol |
| 75 | 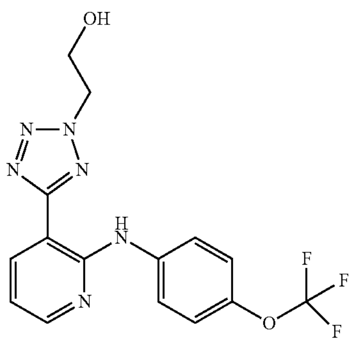 [SMILES: OCCn1nnc(-c2cccnc2Nc2ccc(OC(F)(F)F)cc2)n1] | 2-(5-(2-((4-(trifluoromethoxy)phenyl)amino)pyridin-3-yl)-2H-tetrazol-2-yl)ethanol |
| 76 | 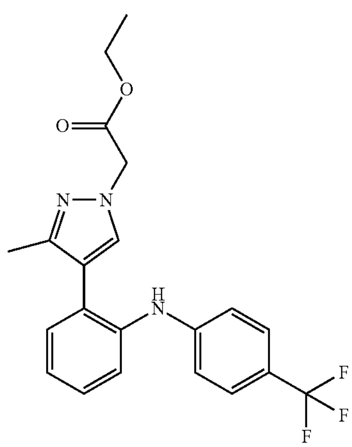 [SMILES: CCOC(=O)Cn1cc(-c2ccccc2Nc2ccc(C(F)(F)F)cc2)c(C)n1] | ethyl 2-[3-methyl-4-[2-[4-(trifluoromethyl)anilino]phenyl]pyrazol-1-yl]acetate |
| 77 | 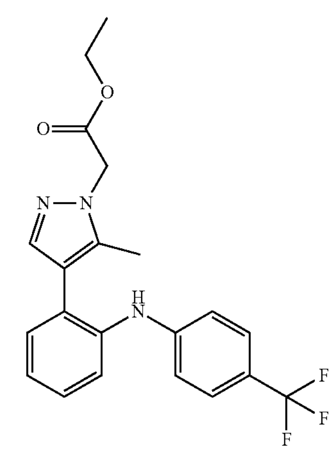 [SMILES: CCOC(=O)Cn1ncc(-c2ccccc2Nc2ccc(C(F)(F)F)cc2)c1C] | ethyl 2-[5-methyl-4-[2-[4-(trifluoromethyl)anilino]phenyl]pyrazol-1-yl]acetate |

TABLE 1-continued

| Compound No. | Structure | Name |
|---|---|---|
| 78 | 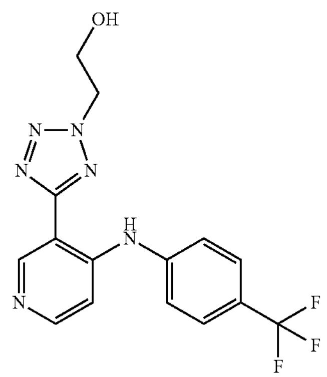 [SMILES: OCCn1nnc(-c2cnccc2Nc2ccc(C(F)(F)F)cc2)n1] | 2-[5-[4-[4-(trifluoromethyl)anilino]-3-pyridyl]tetrazol-2-yl]ethanol |
| 79 | 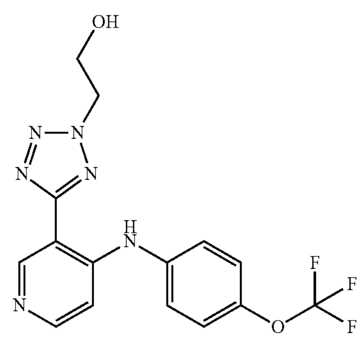 [SMILES: OCCn1nnc(-c2cnccc2Nc2ccc(OC(F)(F)F)cc2)n1] | 2-[5-[4-[4-(trifluoromethoxy)anilino]-3-pyridyl]tetrazol-2-yl]ethanol |
| 80 | 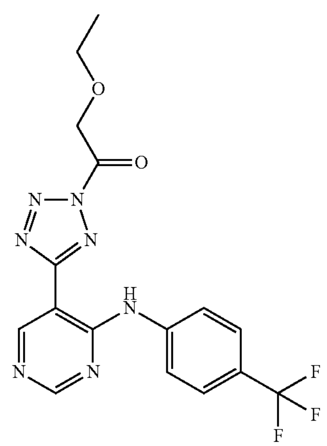 [SMILES: CCOCC(=O)n1nnc(-c2cncnc2Nc2ccc(C(F)(F)F)cc2)n1] | ethyl 2-[5-[4-[4-(trifluoromethyl)anilino]pyrimidin-5-yl]tetrazol-2-yl]acetate |
| 81 | 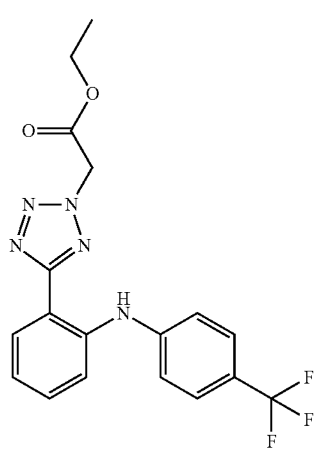 [SMILES: CCOC(=O)Cn1nnc(-c2ccccc2Nc2ccc(C(F)(F)F)cc2)n1] | ethyl 2-(5-(2-((4-(trifluoromethyl)phenyl)amino)phenyl)-2H-tetrazol-2-yl)acetate |

TABLE 1-continued
| Compound No. | Structure | Name |
|---|---|---|
| 82 | 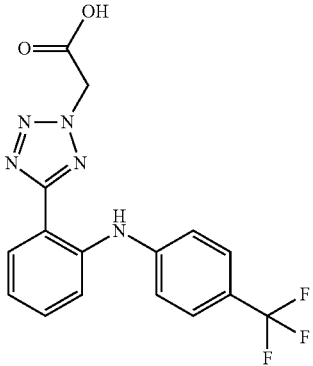 [SMILES: O=C(O)Cn1nnc(-c2ccccc2Nc2ccc(C(F)(F)F)cc2)n1] | 2-[5-[2-[4-(trifluoromethyl)anilino]phenyl]tetrazol-2-yl]acetic acid |
| 83 | 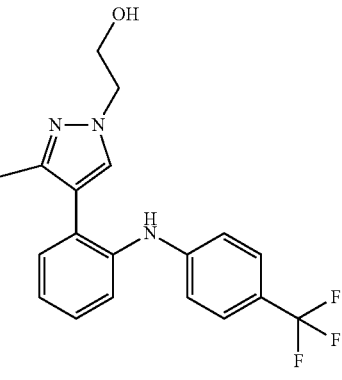 [SMILES: Cc1nn(CCO)cc1-c1ccccc1Nc1ccc(C(F)(F)F)cc1] | 2-[3-methyl-4-[2-[4-(trifluoromethyl)anilino]phenyl]pyrazol-1-yl]ethanol |
| 84 | 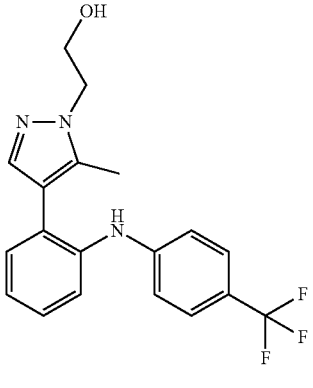 [SMILES: Cc1c(-c2ccccc2Nc2ccc(C(F)(F)F)cc2)cnn1CCO] | 2-[5-methyl-4-[2-[4-(trifluoromethyl)anilino]phenyl]pyrazol-1-yl]ethanol |
| 85 | 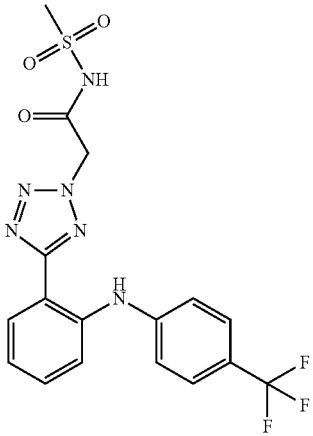 [SMILES: CS(=O)(=O)NC(=O)Cn1nnc(-c2ccccc2Nc2ccc(C(F)(F)F)cc2)n1] | N-methylsulfonyl-2-[5-[2-[4-(trifluoromethyl)anilino]phenyl]tetrazol-2-yl]acetamide |

TABLE 1-continued

| Compound No. | Structure | Name |
|---|---|---|
| 86 | 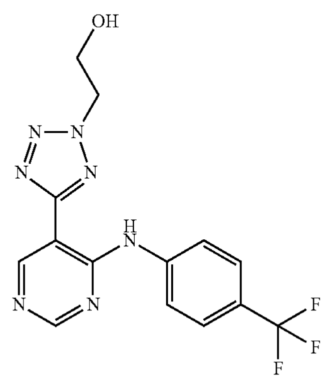 [SMILES: OCCn1nnc(-c2cncnc2Nc2ccc(C(F)(F)F)cc2)n1] | 2-(5-(4-((4-(trifluoromethyl)phenyl)amino)pyrimidin-5-yl)-2H-tetrazol-2-yl)ethan-1-ol |
| 87 | 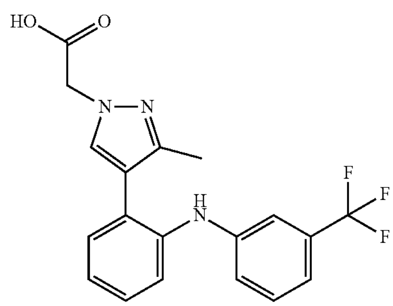 [SMILES: Cc1nn(CC(=O)O)cc1-c1ccccc1Nc1cccc(C(F)(F)F)c1] | 2-(3-methyl-4-(2-((3-(trifluoromethyl)phenyl)amino)phenyl)-1H-pyrazol-1-yl)acetic acid |
| 88 | 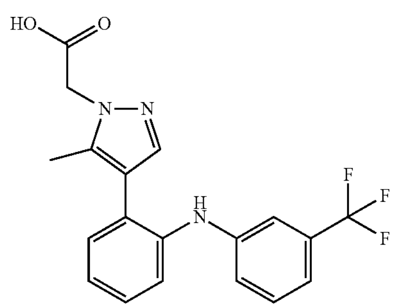 [SMILES: Cc1c(-c2ccccc2Nc2cccc(C(F)(F)F)c2)cnn1CC(=O)O] | 2-(5-methyl-4-(2-((3-(trifluoromethyl)phenyl)amino)phenyl)-1H-pyrazol-1-yl)acetic acid |
| 89 | 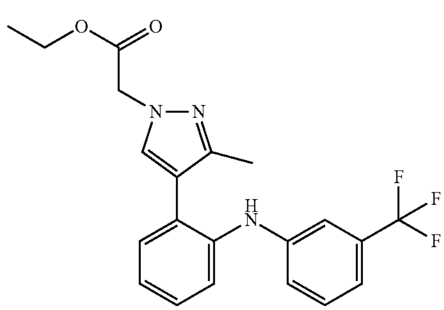 [SMILES: CCOC(=O)Cn1cc(-c2ccccc2Nc2cccc(C(F)(F)F)c2)c(C)n1] | ethyl 2-(3-methyl-4-(2-((3-(trifluoromethyl)phenyl)amino)phenyl)-1H-pyrazol-1-yl)acetate |

TABLE 1-continued

| Compound No. | Structure | Name |
|---|---|---|
| 90 | 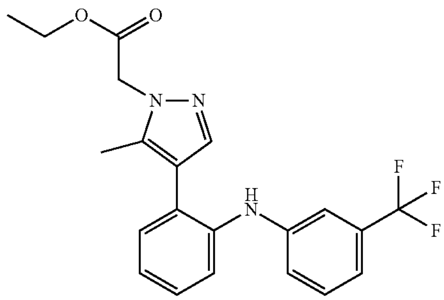 [SMILES: CCOC(=O)Cn1ncc(-c2ccccc2Nc2cccc(C(F)(F)F)c2)c1C] | ethyl 2-(5-methyl-4-(2-((3-(trifluoromethyl)phenyl)amino)phenyl)-1H-pyrazol-1-yl)acetate |
| 91 | 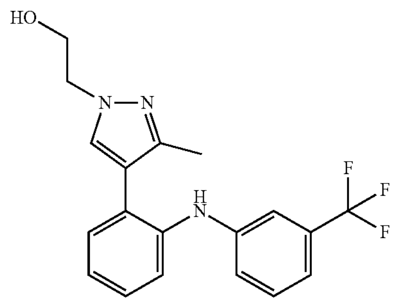 [SMILES: Cc1nn(CCO)cc1-c1ccccc1Nc1cccc(C(F)(F)F)c1] | 2-(3-methyl-4-(2-((3-(trifluoromethyl)phenyl)amino)phenyl)-1H-pyrazol-1-yl)ethanol |
| 92 | 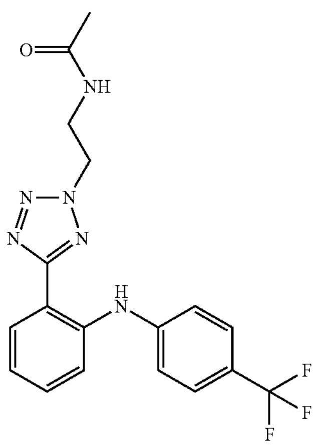 [SMILES: CC(=O)NCCn1nnc(-c2ccccc2Nc2ccc(C(F)(F)F)cc2)n1] | N-[2-[5-[2-[4-(trifluoromethyl)anilino]phenyl]tetrazol-2-yl]ethyl]acetamide |
| 93 | 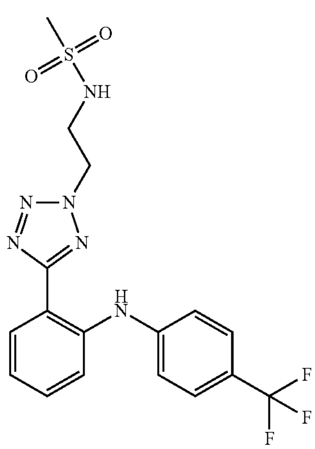 [SMILES: CS(=O)(=O)NCCn1nnc(-c2ccccc2Nc2ccc(C(F)(F)F)cc2)n1] | N-[2-[5-[2-[4-(trifluoromethyl)anilino]phenyl]tetrazol-2-yl]ethyl]methanesulfonamide |

TABLE 1-continued

| Compound No. | Structure | Name |
|---|---|---|
| 94 | 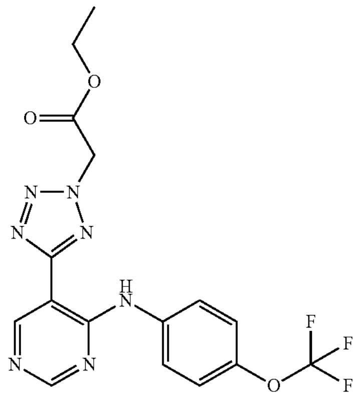 [SMILES: CCOC(=O)Cn1nnc(-c2cncnc2Nc2ccc(OC(F)(F)F)cc2)n1] | ethyl 2-[5-[4-[4-(trifluoromethoxy)anilino]pyrimidin-5-yl]tetrazol-2-yl]acetate |
| 95 | 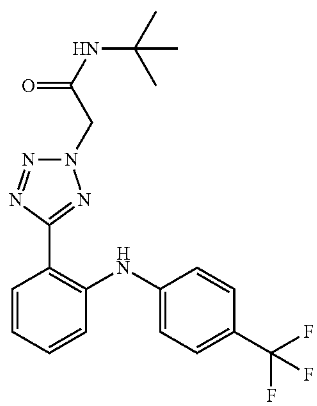 [SMILES: CC(C)(C)NC(=O)Cn1nnc(-c2ccccc2Nc2ccc(C(F)(F)F)cc2)n1] | N-tert-butyl-2-[5-[2-[4-(trifluoromethyl)anilino]phenyl]tetrazol-2-yl]acetamide |
| 96 | 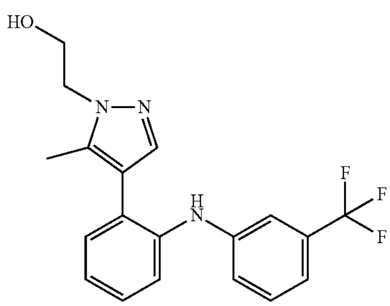 [SMILES: Cc1c(-c2ccccc2Nc2cccc(C(F)(F)F)c2)cnn1CCO] | 2-(5-methyl-4-(2-((3-(trifluoromethyl)phenyl)amino)phenyl)-1H-pyrazol-1-yl)ethanol |
| 97 | 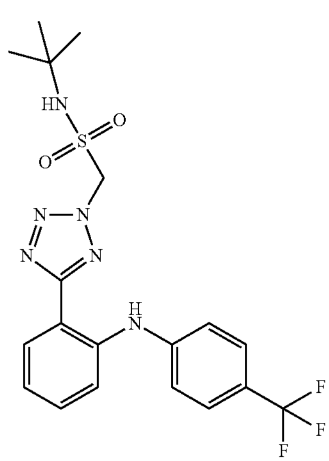 [SMILES: CC(C)(C)NS(=O)(=O)Cn1nnc(-c2ccccc2Nc2ccc(C(F)(F)F)cc2)n1] | N-tert-blityl-1-(5-(2-((4-(trifluoromethyl)phenyl)amino)phenyl)-2H-tetrazol-2-yl)methanesulfonamide |

TABLE 1-continued

| Compound No. | Structure | Name |
|---|---|---|
| 98 | 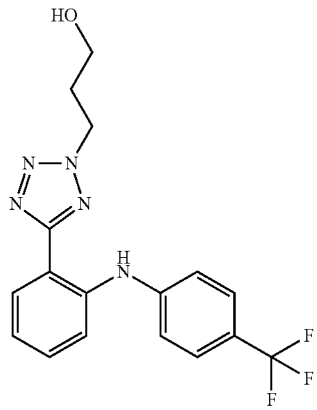 [SMILES: OCCCn1nnc(-c2ccccc2Nc2ccc(C(F)(F)F)cc2)n1] | 3-(5-(2-((4-(trifluoromethyl)phenyl)amino)phenyl)-2H-tetrazol-2-yl)propan-1-ol |
| 99 | 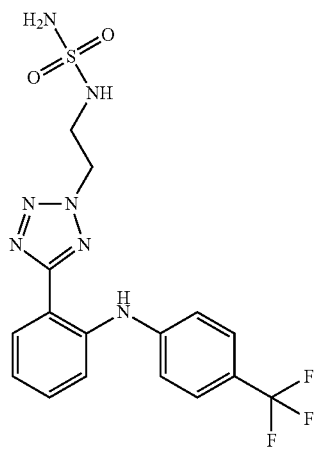 [SMILES: NS(=O)(=O)NCCn1nnc(-c2ccccc2Nc2ccc(C(F)(F)F)cc2)n1] | 2-[2-(sulfamoylamino)ethyl]-5-[2-[4-(trifluoromethyl)anilino]phenyl]tetrazole |
| 100 | 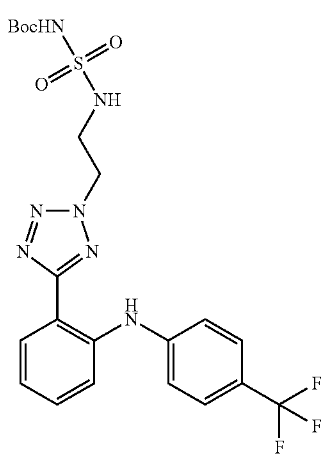 [SMILES: CC(C)(C)OC(=O)NS(=O)(=O)NCCn1nnc(-c2ccccc2Nc2ccc(C(F)(F)F)cc2)n1] | tert-butyl N-[2-[5-[2-[4-(trifluoromethyl)anilino]phenyl]tetrazol-2-yl]ethylsulfamoyl]carbamate |

TABLE 1-continued

| Compound No. | Structure | Name |
|---|---|---|
| 101 | 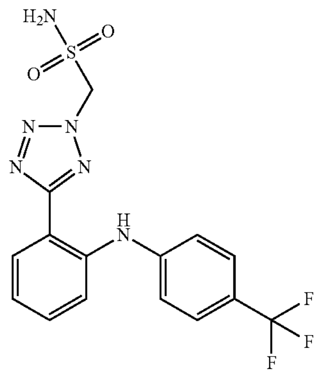 [SMILES: NS(=O)(=O)Cn1nnc(-c2ccccc2Nc2ccc(C(F)(F)F)cc2)n1] | (5-(2-((4-(trifluoromethyl)phenyl)amino)phenyl)-2H-tetrazol-2-yl)methanesulfonamide |
| 102 | 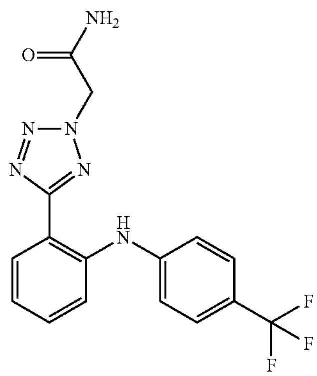 | 2-[5-[2-[4-(trifluoromethyl)anilino]phenyl]tetrazol-2-yl]acetamide |
| 103 | 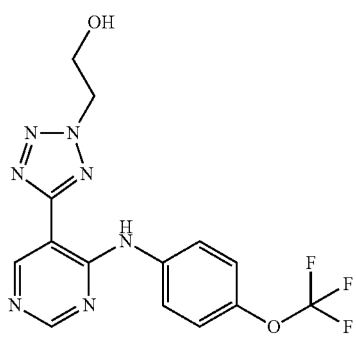 [SMILES: OCCn1nnc(-c2cncnc2Nc2ccc(OC(F)(F)F)cc2)n1] | 2-[5-[4-[4-(trifluoromethoxy)anilino]pyrimidin-5-yl]tetrazol-2-yl]ethanol |
| 104 | 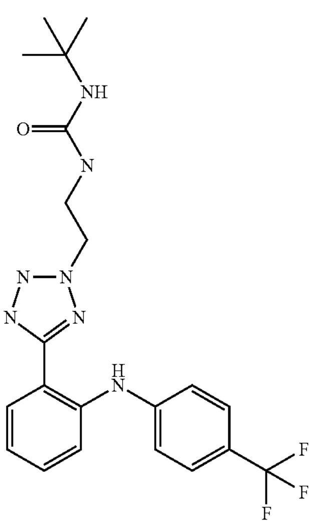 [SMILES: CC(C)(C)NC(=O)NCCN1N=C(c2ccccc2Nc2ccc(C(F)(F)F)cc2)NN1] | 1-tert-butyl-3-[2-[5-[2-[4-(trifluoromethyl)anilino]phenyl]tetrazol-2-yl]ethyl]urea |

TABLE 1-continued

| Compound No. | Structure | Name |
|---|---|---|
| 105 | 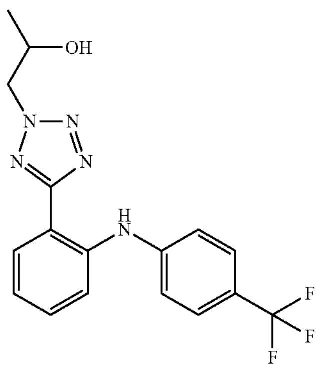 [SMILES: CC(O)Cn1nnc(-c2ccccc2Nc2ccc(C(F)(F)F)cc2)n1] | 1-[5-[2-[4-(trifluoromethyl)anilino]phenyl]tetrazol-2-yl]propan-2-ol |
| 106 | 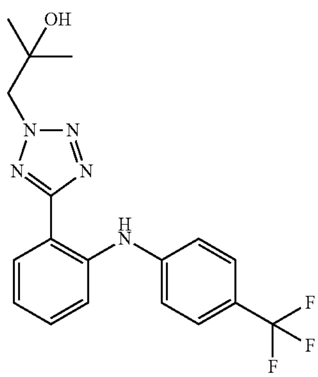 [SMILES: CC(C)(O)Cn1nnc(-c2ccccc2Nc2ccc(C(F)(F)F)cc2)n1] | 1-[5-[2-[4-(trifluoromethyl)anilino]phenyl]tetrazol-2-yl]propan-2-ol |
| 107 | 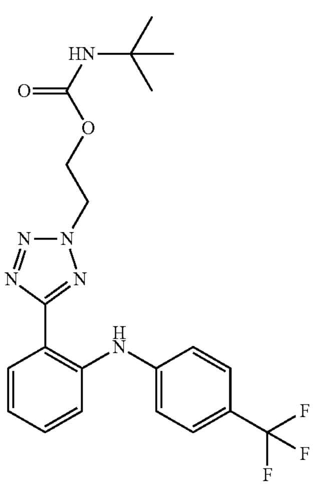 [SMILES: CC(C)(C)NC(=O)OCCn1nnc(-c2ccccc2Nc2ccc(C(F)(F)F)cc2)n1] | 2-[5-[2-[4-(trifluoromethyl)anilino]phenyl]tetrazol-2-yl]ethyl N-tert-butylcarbamate |

TABLE 1-continued

| Compound No. | Structure | Name |
|---|---|---|
| 108 | 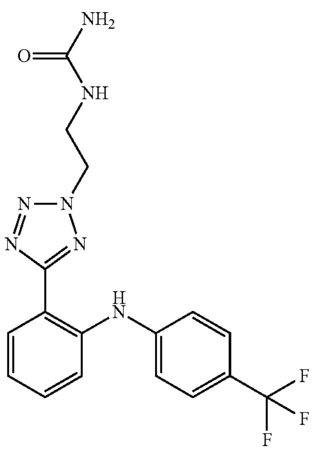 [SMILES: NC(=O)NCCn1nnc(-c2ccccc2Nc2ccc(C(F)(F)F)cc2)n1] | 2-[5-[2-[4-(trifluoromethyl)anilino]phenyl]tetrazol-2-yl]ethylurea |
| 109 | 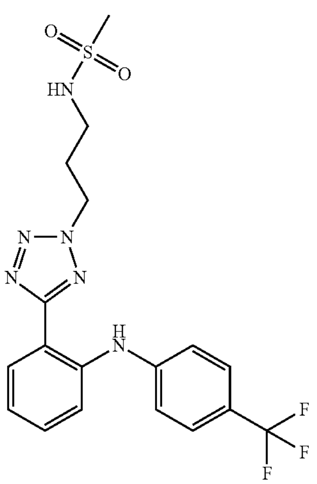 [SMILES: CS(=O)(=O)NCCCn1nnc(-c2ccccc2Nc2ccc(C(F)(F)F)cc2)n1] | N-(3-(5-(2-((4-(trifluoromethyl)phenyl)amino)phenyl)-2H-tetrazol-2-yl)propyl)methanesulfonamide |
| 110 | 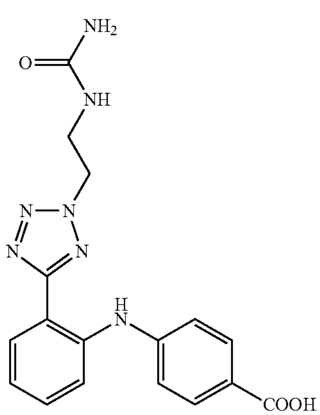 [SMILES: NC(=O)NCCn1nnc(-c2ccccc2Nc2ccc(C(=O)O)cc2)n1] | 4-[2-[2-(2-ureidoethyl)tetrazol-5-yl]anilino]benzoic acid |

TABLE 1-continued

| Compound No. | Structure | Name |
| --- | --- | --- |
| 111 | 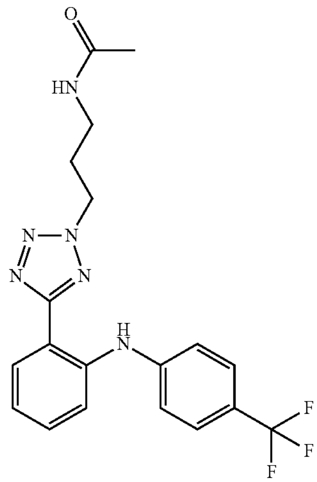 [SMILES: CC(=O)NCCCn1nnc(-c2ccccc2Nc2ccc(C(F)(F)F)cc2)n1] | N-[3-[5-[2-[4-(trifluoromethyl)anilino]phenyl]tetrazol-2-yl]propyl]acetamide |
| 112 | 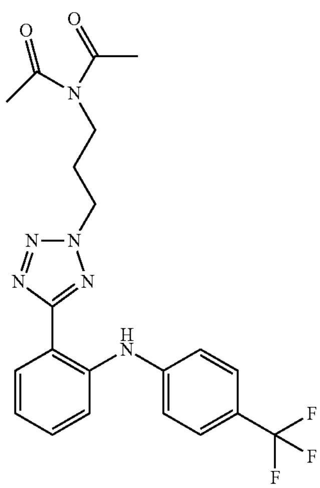 [SMILES: CC(=O)N(CCCn1nnc(-c2ccccc2Nc2ccc(C(F)(F)F)cc2)n1)C(C)=O] | N-acetyl-N-[3-[5-[2-[4-(trifluoromethyl)anilino]phenyl]tetrazol-2-yl]propyl]acetamide |
| 113 | 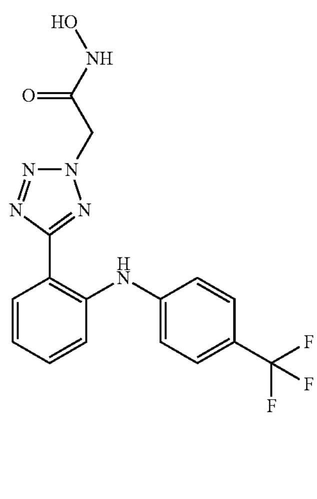 [SMILES: O=C(Cn1nnc(-c2ccccc2Nc2ccc(C(F)(F)F)cc2)n1)NO] | 2-[5-[2-[4-(trifluoromethyl)anilino]phenyl]tetrazol-2-yl]ethanehydroxamic acid |

TABLE 1-continued

| Compound No. | Structure | Name |
| --- | --- | --- |
| 114 | 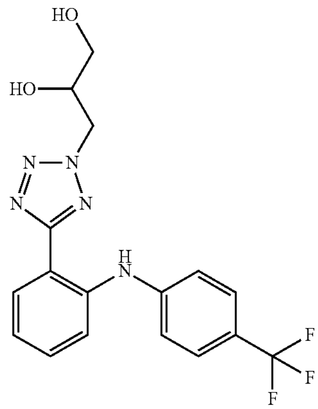 [SMILES: OCC(O)Cn1nnc(-c2ccccc2Nc2ccc(C(F)(F)F)cc2)n1] | 3-(5-(2-((4-(trifluoromethyl)phenyl)amino)phenyl)-2H-tetrazol-2-yl)propane-1,2-diol |
| 115 | 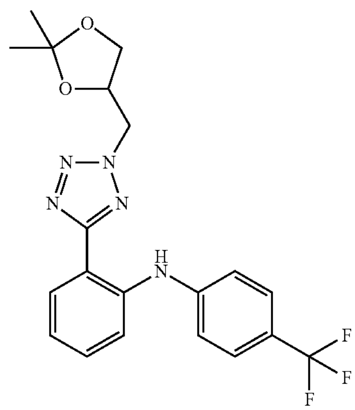 [SMILES: CC1(C)OCC(Cn2nnc(-c3ccccc3Nc3ccc(C(F)(F)F)cc3)n2)O1] | 2-(2-((2,2-dimethyl-1,3-dioxolan-4-yl)methyl)-2H-tetrazol-5-yl)-N-(4-(trifluoromethyl)phenyl)aniline |
| 116 | 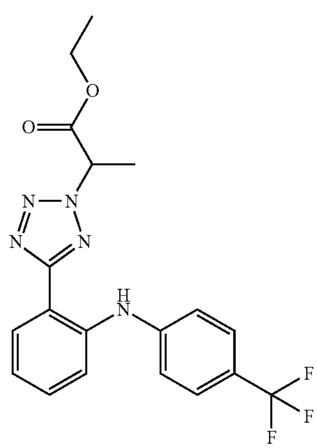 [SMILES: CCOC(=O)C(C)n1nnc(-c2ccccc2Nc2ccc(C(F)(F)F)cc2)n1] | ethyl 2-[5-[2-[4-(trifluoromethyl)anilino]phenyl]tetrazol-2-yl]propanoate |

TABLE 1-continued

| Compound No. | Structure | Name |
|---|---|---|
| 117 | 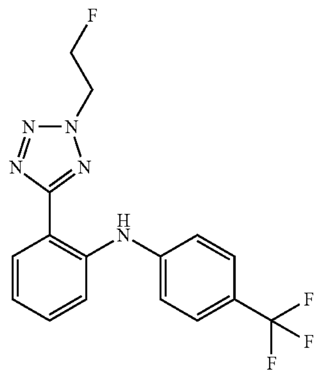 [SMILES: FCCn1nnc(-c2ccccc2Nc2ccc(C(F)(F)F)cc2)n1] | 2-[2-(2-fluoroethyl)tetrazol-5-yl]-N-[4-(trifluoromethyl)phenyl]aniline |
| 118 | 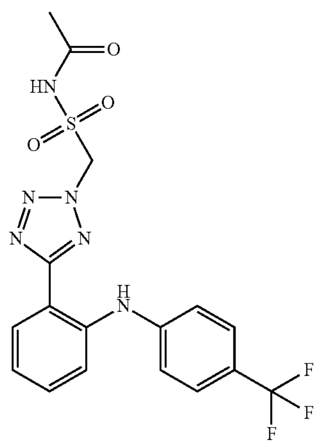 [SMILES: CC(=O)NS(=O)(=O)Cn1nnc(-c2ccccc2Nc2ccc(C(F)(F)F)cc2)n1] | N-[[5-[2-[4-(trifluoromethyl)anilino]phenyl]tetrazol-2-yl]methylsulfonyl]acetamide |
| 119 | 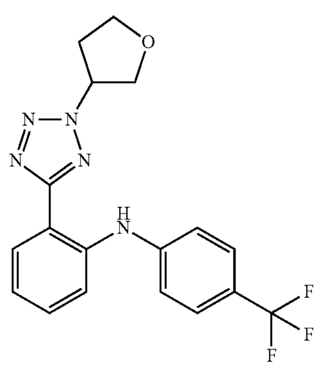 [SMILES: FC(F)(F)c1ccc(Nc2ccccc2-c2nnn(C3CCOC3)n2)cc1] | 2-(2-(tetrahydrofuran-3-yl)-2H-tetrazol-5-yl)-N-(4-(trifluoromethyl)phenyl)aniline |
| 120 | 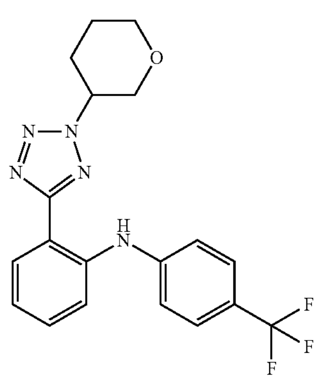 [SMILES: FC(F)(F)c1ccc(Nc2ccccc2-c2nnn(C3CCCOC3)n2)cc1] | 2-(2-tetrahydropyran-3-yltetrazol-5-yl)-N-[4-(trifluoromethyl)phenyl]aniline |

TABLE 1-continued

| Compound No. | Structure | Name |
|---|---|---|
| 121 | 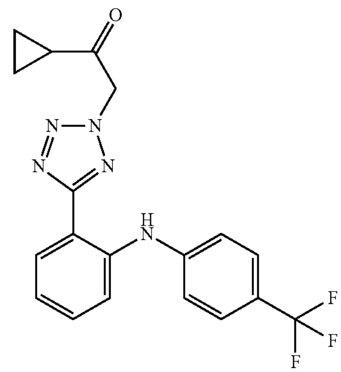 [SMILES: O=C(Cn1nnc(-c2ccccc2Nc2ccc(C(F)(F)F)cc2)n1)C1CC1] | 1-cyclopropyl-2-[5-[2-[4-(trifluoromethyl)anilino]phenyl]tetrazol-2-yl]ethanone |
| 122 | 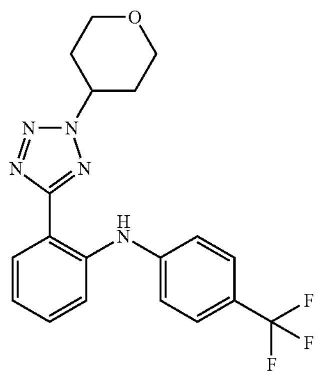 [SMILES: FC(F)(F)c1ccc(Nc2ccccc2-c2nnn(C3CCOCC3)n2)cc1] | 2-(2-tetrahydropyran-4-yltetrazol-5-yl)-N-[4-(trifluoromethyl)phenyl]aniline |
| 123 | 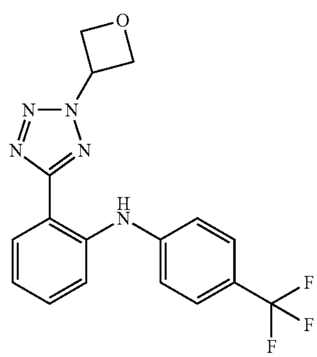 [SMILES: FC(F)(F)c1ccc(Nc2ccccc2-c2nnn(C3COC3)n2)cc1] | 2-[2-(oxetan-3-yl)tetrazol-5-yl]-N-[4-(trifluoromethyl)phenyl]aniline |
| 124 | 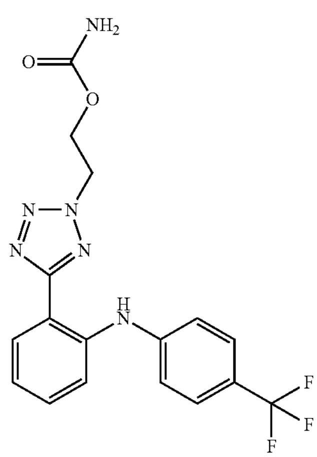 [SMILES: NC(=O)OCCn1nnc(-c2ccccc2Nc2ccc(C(F)(F)F)cc2)n1] | 2-[5-[2-[4-(trifluoromethyl)anilino]phenyl]tetrazol-2-yl]ethylcarbamate |

TABLE 1-continued

| Compound No. | Structure | Name |
|---|---|---|
| 125 | 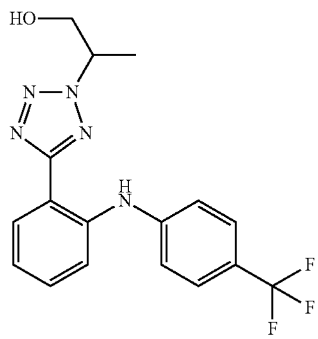 [SMILES: CC(CO)n1nnc(-c2ccccc2Nc2ccc(C(F)(F)F)cc2)n1] | 2-[5-[2-[4-(trifluoromethyl)anilino]phenyl]tetrazol-2-yl]propan-1-ol |
| 126 | 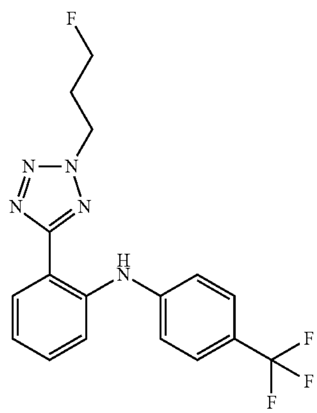 [SMILES: FCCCn1nnc(-c2ccccc2Nc2ccc(C(F)(F)F)cc2)n1] | 2-[2-(3-fluoropropyl)tetrazol-5-yl]-N-[4-(trifluoromethyl)phenyl]aniline |
| 127 | 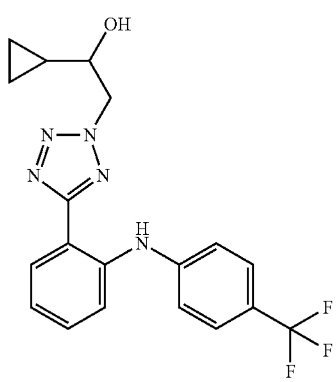 [SMILES: OC(Cn1nnc(-c2ccccc2Nc2ccc(C(F)(F)F)cc2)n1)C1CC1] | 1-cyclopropyl-2-[5-[2-[4-(trifluoromethyl)anilino]phenyl]tetrazol-2-yl]ethanol |
| 128 | 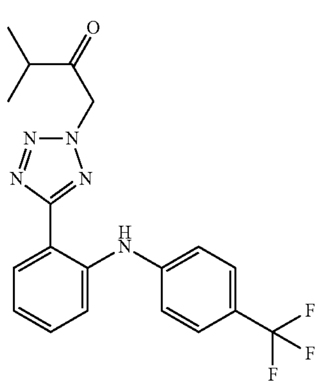 [SMILES: CC(C)C(=O)Cn1nnc(-c2ccccc2Nc2ccc(C(F)(F)F)cc2)n1] | 3-methyl-1-[5-[2-[4-(trifluoromethyl)anilino]phenyl]tetrazol-2-yl]butan-2-one |

TABLE 1-continued

| Compound No. | Structure | Name |
|---|---|---|
| 129 | 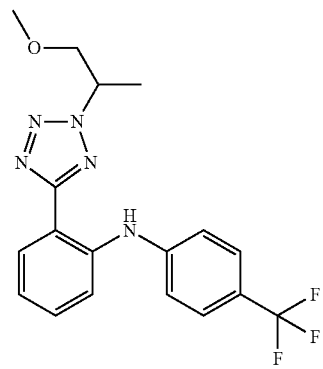 [SMILES: COCC(C)n1nnc(-c2ccccc2Nc2ccc(C(F)(F)F)cc2)n1] | 2-(2-(1-methoxypropan-2-yl)-2H-tetrazol-5-yl)-N-(4-(trifluoromethyl)phenyl)aniline |
| 130 | 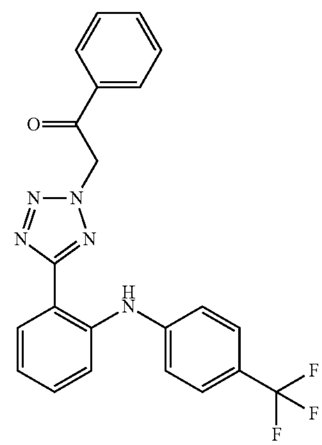 [SMILES: O=C(Cn1nnc(-c2ccccc2Nc2ccc(C(F)(F)F)cc2)n1)c1ccccc1] | 1-phenyl-2-[5-[2-[4-(trifluoromethyl)anilino]phenyl]tetrazol-2-yl]ethanone |
| 131 | 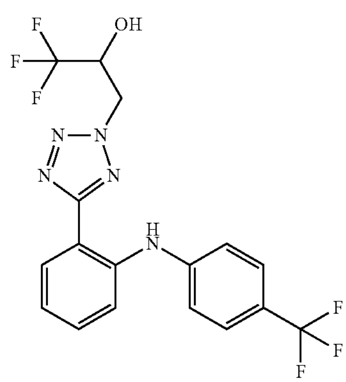 [SMILES: OC(Cn1nnc(-c2ccccc2Nc2ccc(C(F)(F)F)cc2)n1)C(F)(F)F] | 1,1,1-trifluoro-3-[5-[2-[4-(trifluoromethyl)anilino]phenyl]tetrazol-2-yl]propan-2-ol |

TABLE 1-continued

| Compound No. | Structure | Name |
|---|---|---|
| 132 | 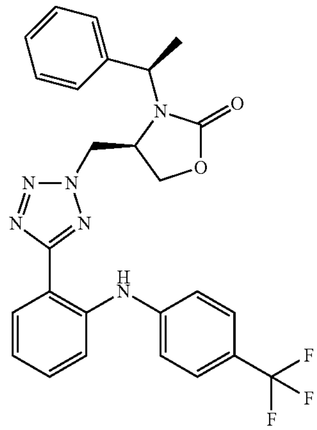 [SMILES: C[C@H](c1ccccc1)N1C(=O)OC[C@H]1Cn1nnc(-c2ccccc2Nc2ccc(C(F)(F)F)cc2)n1] | (4R)-3-[(1R)-1-phenylethyl]-4-[[5-[2-[4-(trifluoromethyl)anilino]phenyl]tetrazol-2-yl]methyl]oxazolidin-2-one |
| 133 | 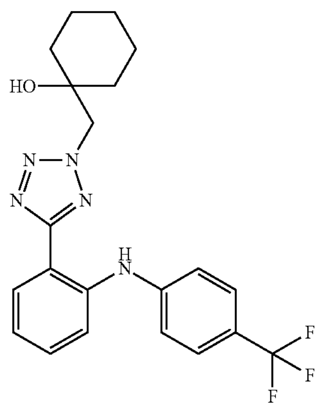 [SMILES: OC1(Cn2nnc(-c3ccccc3Nc3ccc(C(F)(F)F)cc3)n2)CCCCC1] | 1-[[5-[2-[4-(trifluoromethyl)anilino]phenyl]tetrazol-2-yl]methyl]cyclohexanol |
| 134 | 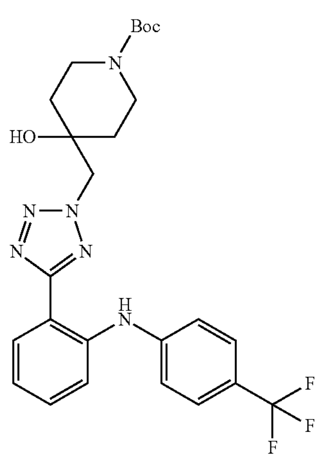 [SMILES: CC(C)(C)OC(=O)N1CCC(O)(Cn2nnc(-c3ccccc3Nc3ccc(C(F)(F)F)cc3)n2)CC1] | tert-butyl 4-hydroxy-4-[[5-[2-[4-(trifluoromethyl)anilino]phenyl]tetrazol-2-yl]methyl]piperidine-1-carboxylate |

TABLE 1-continued

| Compound No. | Structure | Name |
|---|---|---|
| 135 | 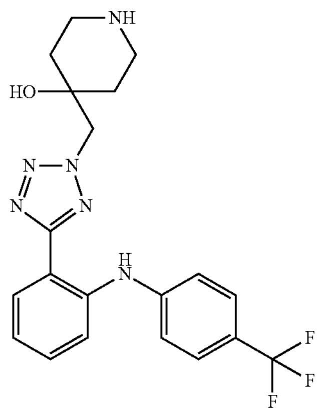 [SMILES: OC1(Cn2nnc(-c3ccccc3Nc3ccc(C(F)(F)F)cc3)n2)CCNCC1] | 4-[[5-[2-[4-(trifluoromethyl)anilino]phenyl]tetrazol-2-yl]methyl]piperidin-4-ol |
| 136 | 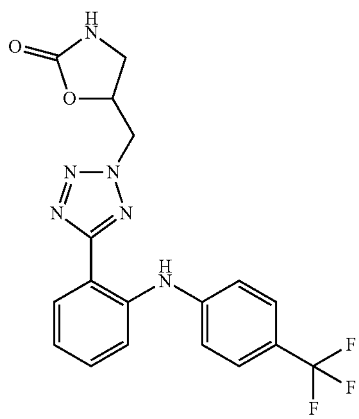 [SMILES: O=C1NCC(Cn2nnc(-c3ccccc3Nc3ccc(C(F)(F)F)cc3)n2)O1] | 5-((5-(2-((4-(trifluoromethyl)phenyl)amino)phenyl)-2H-tetrazol-2-yl)methyl)oxazolidin-2-one |
| 137 | 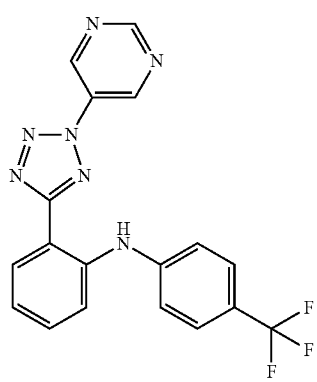 [SMILES: FC(F)(F)c1ccc(Nc2ccccc2-c2nnn(-c3cncnc3)n2)cc1] | 2-(2-pyrimidin-5-yltetrazol-5-yl)-N-[4-(trifluoromethyl)phenyl]aniline |

TABLE 1-continued

| Compound No. | Structure | Name |
|---|---|---|
| 138 | 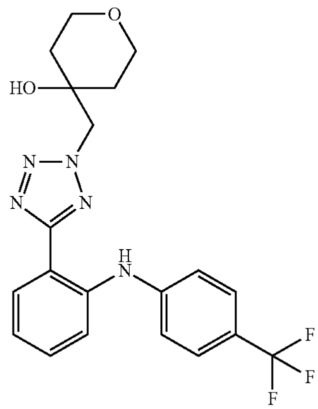 [SMILES: OC1(Cn2nnc(-c3ccccc3Nc3ccc(C(F)(F)F)cc3)n2)CCOCC1] | 4-[[5-[2-[4-(trifluoromethyl)anilino]phenyl]tetrazol-2-yl]methyl]tetrahydropyran-4-ol |
| 139 | 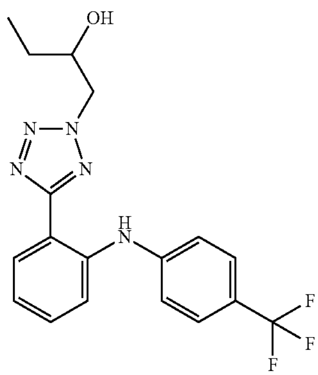 [SMILES: CCC(O)Cn1nnc(-c2ccccc2Nc2ccc(C(F)(F)F)cc2)n1] | 1-(5-(2-((4-(trifluoromethyl)phenyl)amino)phenyl)-2H-tetrazol-2-yl)butan-2-ol |
| 140 | 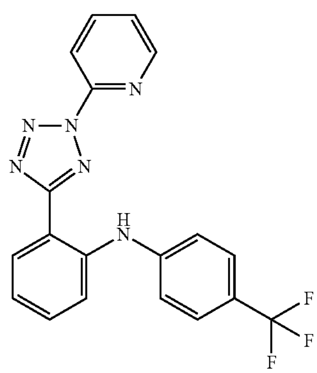 [SMILES: FC(F)(F)c1ccc(Nc2ccccc2-c2nnn(-c3ccccn3)n2)cc1] | 2-[2-(2-pyridyl)tetrazol-5-yl]-N-[4-(trifluoromethyl)phenyl]aniline |
| 141 | 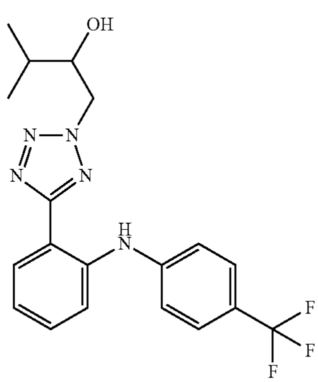 [SMILES: CC(C)C(O)Cn1nnc(-c2ccccc2Nc2ccc(C(F)(F)F)cc2)n1] | 3-methyl-1-[5-[2-[4-(trifluoromethyl)anilino]phenyl]tetrazol-2-yl]butan-2-ol |

TABLE 1-continued

| Compound No. | Structure | Name |
|---|---|---|
| 142 | 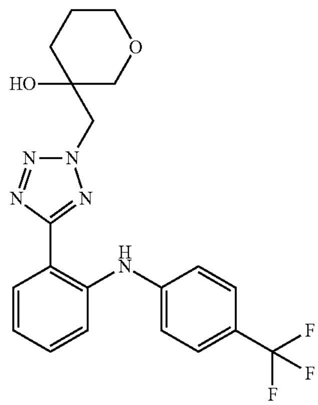 [SMILES: OC1(Cn2nnc(-c3ccccc3Nc3ccc(C(F)(F)F)cc3)n2)CCCOC1] | 3-[[5-[2-[4-(trifluoromethyl)anilino]phenyl]tetrazol-2-yl]methyl]tetrahydropyran-3-ol |
| 143 | 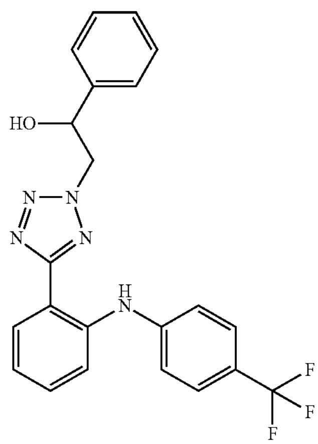 [SMILES: OC(Cn1nnc(-c2ccccc2Nc2ccc(C(F)(F)F)cc2)n1)c1ccccc1] | 1-phenyl-2-[5-[2-[4-(trifluoromethyl)anilino]phenyl]tetrazol-2-yl]ethanol |
| 144 | 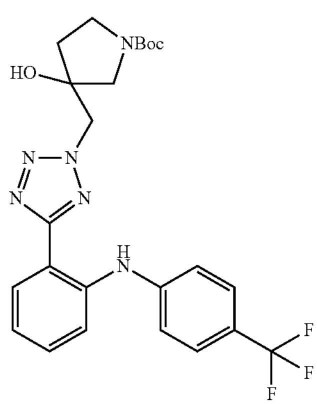 [SMILES: CC(C)(C)OC(=O)N1CCC(O)(Cn2nnc(-c3ccccc3Nc3ccc(C(F)(F)F)cc3)n2)C1] | tert-butyl 3-hydroxy-3-((5-(2-((4-(trifluoromethyl)phenyl)amino)phenyl)-2H-tetrazol-2-yl)methyl)pyrrolidine-1-carboxylate |

TABLE 1-continued

| Compound No. | Structure | Name |
| --- | --- | --- |
| 145 | 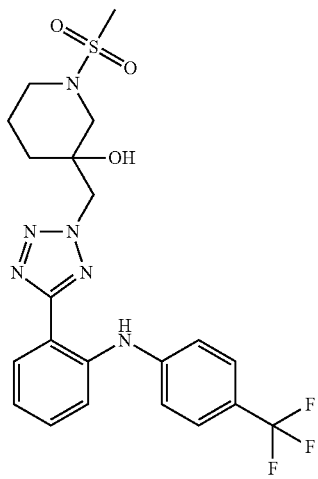 [SMILES: CS(=O)(=O)N1CCCC(O)(Cn2nnc(-c3ccccc3Nc3ccc(C(F)(F)F)cc3)n2)C1] | 1-(methylsulfonyl)-3-((5-(2-((4-(trifluoromethyl)phenyl)amino)phenyl)-2H-tetrazol-2-yl)methyl)piperidin-3-ol |
| 146 | 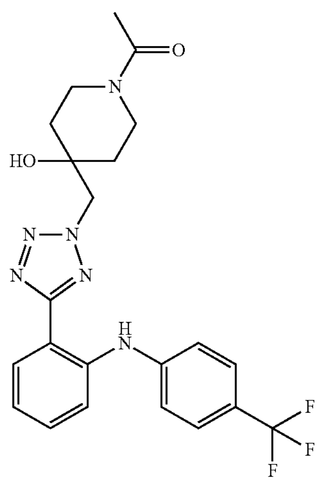 [SMILES: CC(=O)N1CCC(O)(Cn2nnc(-c3ccccc3Nc3ccc(C(F)(F)F)cc3)n2)CC1] | 1-[4-hydroxy-4-[[5-[2-[4-(trifluoromethyl)anilino]phenyl]tetrazol-2-yl]methyl]-1-piperidyl]ethanone |
| 147 | 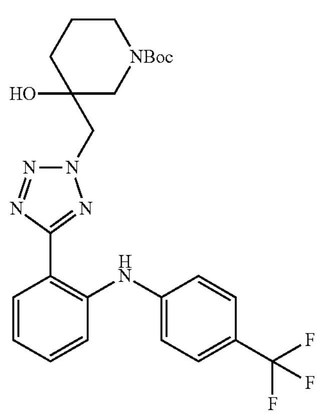 [SMILES: CC(C)(C)OC(=O)N1CCCC(O)(Cn2nnc(-c3ccccc3Nc3ccc(C(F)(F)F)cc3)n2)C1] | tert-butyl 3-hydroxy-3-((5-(2-((4-(trifluoromethyl)phenyl)amino)phenyl)-2H-tetrazol-2-yl)methyl)piperidine-1-carboxylate |

TABLE 1-continued

| Compound No. | Structure | Name |
|---|---|---|
| 148 | 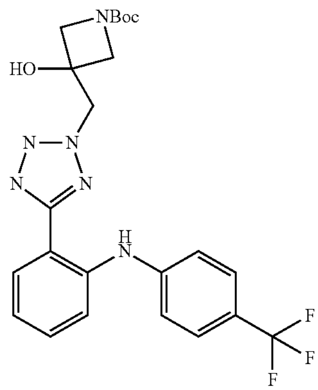 [SMILES: CC(C)(C)OC(=O)N1CC(O)(CN2N=C(c3ccccc3Nc3ccc(C(F)(F)F)cc3)NN2)C1] | tert-butyl 3-hydroxy-3-[[5-[2-[4-(trifluoromethyl)anilino]phenyl]tetrazol-2-yl]methyl]azetidine-1-carboxylate |
| 149 | 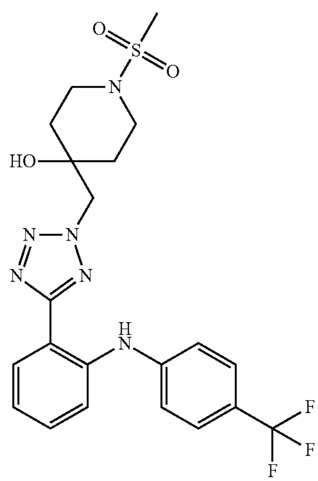 [SMILES: CS(=O)(=O)N1CCC(O)(Cn2nnc(-c3ccccc3Nc3ccc(C(F)(F)F)cc3)n2)CC1] | 1-methylsulfonyl-4-[[5-[2-[4-(trifluoromethyl)anilino]phenyl]tetrazol-2-yl]methyl]piperidin-4-ol; |
| 150 | 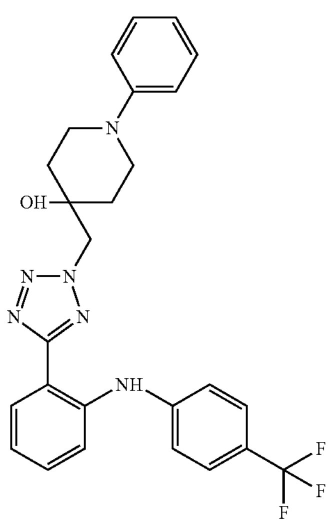 [SMILES: OC1(Cn2nnc(-c3ccccc3Nc3ccc(C(F)(F)F)cc3)n2)CCN(c2ccccc2)CC1] | 1-phenyl-4-[[5-[2-[4-(trifluoromethyl)anilino]phenyl]tetrazol-2-yl]methyl]piperidin-4-ol |

TABLE 1-continued

| Compound No. | Structure | Name |
|---|---|---|
| 151 | 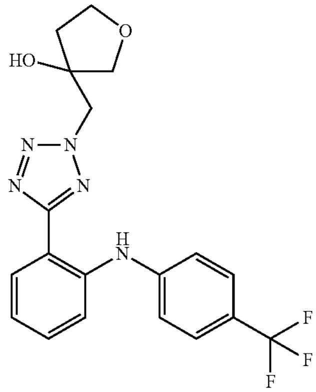 [SMILES: OC1(Cn2nnc(-c3ccccc3Nc3ccc(C(F)(F)F)cc3)n2)CCOC1] | 3-[[5-[2-[4-(trifluoromethyl)anilino]phenyl]tetrazol-2-yl]methyl]tetrahydrofuran-3-ol |
| 152 | 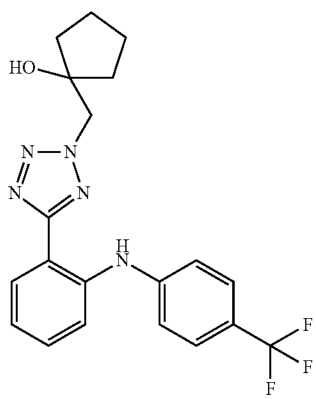 [SMILES: OC1(Cn2nnc(-c3ccccc3Nc3ccc(C(F)(F)F)cc3)n2)CCCC1] | 1-((5-(2-((4-(Trifluoromethyl)phenyl)amino)phenyl)-2H-tetrazol-2-yl)methyl)cyclopentanol |
| 153 | 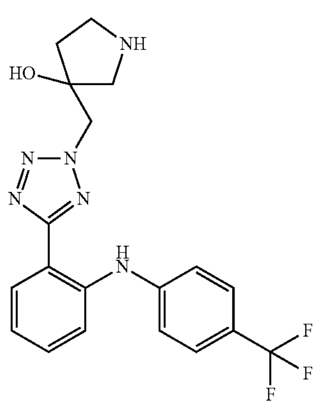 [SMILES: OC1(Cn2nnc(-c3ccccc3Nc3ccc(C(F)(F)F)cc3)n2)CCNC1] | 3-((5-(2-((4-(trifluoromethyl)phenyl)amino)phenyl)-2H-tetrazol-2-yl)methyl)pyrrolidin-3-ol |

TABLE 1-continued

| Compound No. | Structure | Name |
|---|---|---|
| 154 | 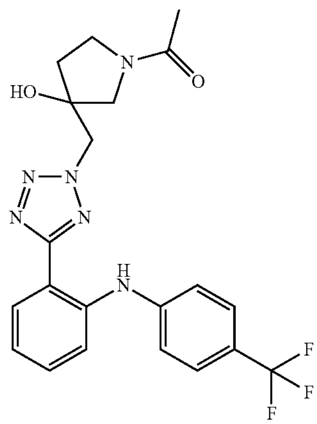 [SMILES: CC(=O)N1CCC(O)(Cn2nnc(-c3ccccc3Nc3ccc(C(F)(F)F)cc3)n2)C1] | 1-(3-hydroxy-3-((5-(2-((4-(trifluoromethyl)phenyl)amino)phenyl)-2H-tetrazol-2-yl)methyl)pyrrolidin-1-yl)ethanone |
| 155 | 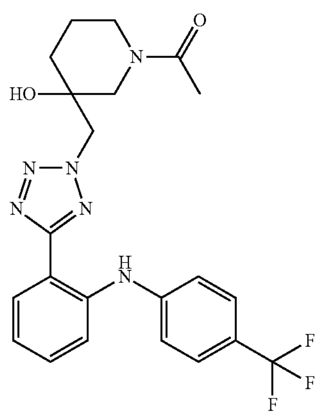 [SMILES: CC(=O)N1CCCC(O)(Cn2nnc(-c3ccccc3Nc3ccc(C(F)(F)F)cc3)n2)C1] | 1-(3-hydroxy-3-[5-(2-((4-(trifluoromethyl)phenyl)amino)phenyl)-2H-tetrazol-2-yl)methyl)piperidin-1-yl)ethanone |
| 156 | 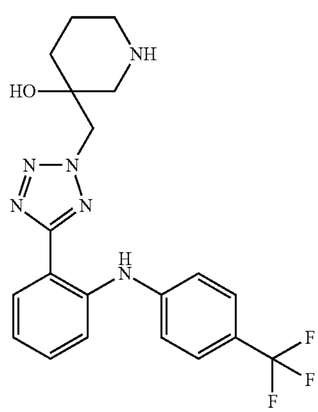 [SMILES: OC1(Cn2nnc(-c3ccccc3Nc3ccc(C(F)(F)F)cc3)n2)CCCNC1] | 3-((5-(2-((4-(trifluoromethyl)phenyl)amino)phenyl)-2H-tetrazol-2-yl)methyl)piperidin-3-ol |

TABLE 1-continued

| Compound No. | Structure | Name |
|---|---|---|
| 157 | 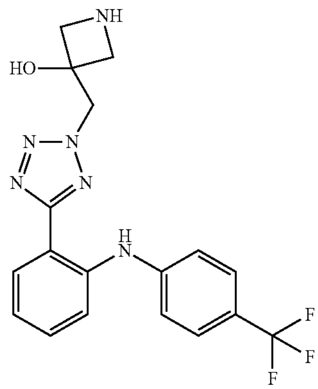 [SMILES: OC1(Cn2nnc(-c3ccccc3Nc3ccc(C(F)(F)F)cc3)n2)CNC1] | 3-[[5-[2-[4-(trifluoromethyl)anilino]phenyl]tetrazol-2-yl]methyl]azetidin-3-ol |
| 158 | 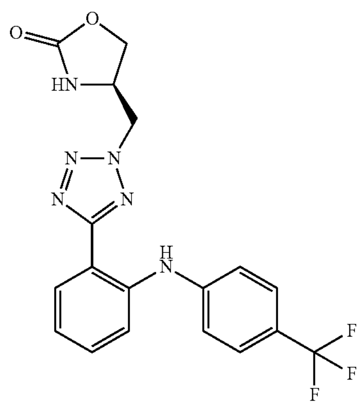 [SMILES: O=C1N[C@H](Cn2nnc(-c3ccccc3Nc3ccc(C(F)(F)F)cc3)n2)CO1] | (R)-4-((5-(2-((4-(trifluoromethyl)phenyl)amino)phenyl)-2H-tetrazol-2-yl)methyl)oxazolidin-2-one |
| 159 | 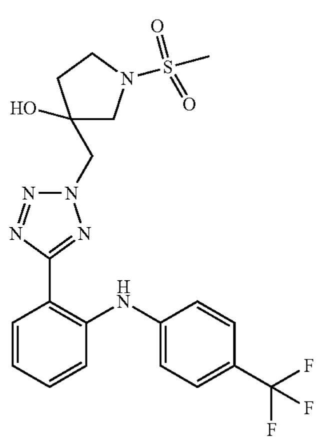 [SMILES: CS(=O)(=O)N1CCC(O)(Cn2nnc(-c3ccccc3Nc3ccc(C(F)(F)F)cc3)n2)C1] | 1-(methylsulfonyl)-3-((5-(2-((4-(trifluoromethyl)phenyl)amino)phenyl)-2H-tetrazol-2-yl)methyl)pyrrolidin-3-ol |

TABLE 1-continued

| Compound No. | Structure | Name |
|---|---|---|
| 160 | 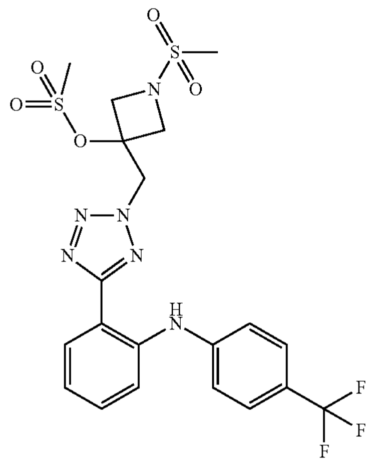 [SMILES: CS(=O)(=O)OC1(Cn2nnc(-c3ccccc3Nc3ccc(C(F)(F)F)cc3)n2)CN(S(C)(=O)=O)C1] | [1-methylsulfonyl-3-[[5-[2-[4-(trifluoromethyl)anilino]phenyl]tetrazol-2-yl]methyl]azetidin-3-yl]methanesulfonate |
| 161 | 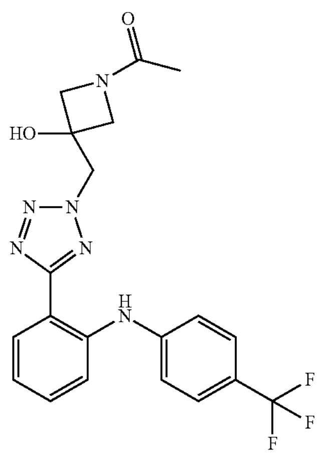 [SMILES: CC(=O)N1CC(O)(Cn2nnc(-c3ccccc3Nc3ccc(C(F)(F)F)cc3)n2)C1] | 1-[3-hydroxy-3-[[5-[2-[4-(trifluoromethyl)anilino]phenyl]tetrazol-2-yl]methyl]azetidin-1-yl]ethanone |
| 162 | 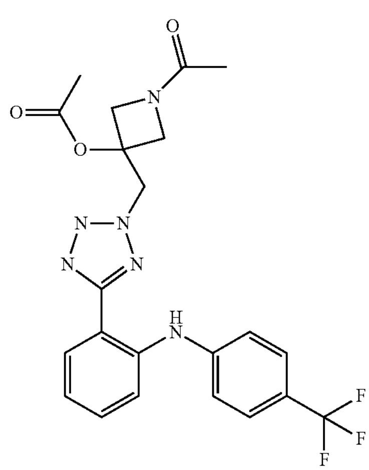 [SMILES: CC(=O)OC1(CN2N=C(c3ccccc3Nc3ccc(C(F)(F)F)cc3)NN2)CN(C(C)=O)C1] | [1-acetyl-3-[[5-[2-[4-(trifluoromethyl)anilino]phenyl]tetrazol-2-yl]methyl]azetidin-3-yl]acetate |

TABLE 1-continued

| Compound No. | Structure | Name |
|---|---|---|
| 163 | 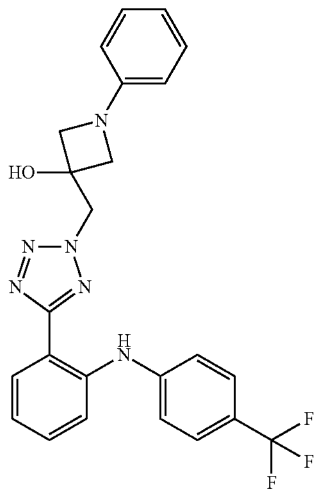 [SMILES: OC1(Cn2nnc(-c3ccccc3Nc3ccc(C(F)(F)F)cc3)n2)CN(c2ccccc2)C1] | 1-phenyl-3-[[5-[2-[4-(trifluoromethyl)anilino]phenyl]tetrazol-2-yl]methyl]azetidin-3-ol |
| 164 | 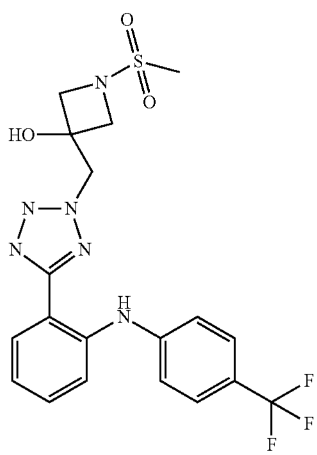 [SMILES: CS(=O)(=O)N1CC(O)(CN2N=C(c3ccccc3Nc3ccc(C(F)(F)F)cc3)NN2)C1] | 1-methylsulfonyl-3-[[5-[2-[4-(trifluoromethyl)anilino]phenyl]tetrazol-2-yl]methyl]azetidin-3-ol |
| 165 | 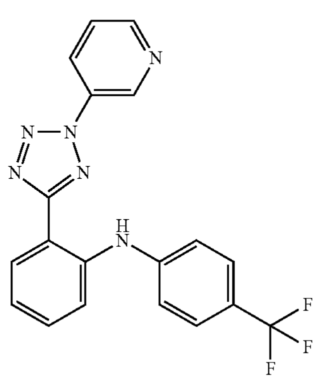 [SMILES: FC(F)(F)c1ccc(Nc2ccccc2-c2nnn(-c3cccnc3)n2)cc1] | 2-[2-(3-pyridyl)tetrazol-5-yl]-N-[4-(trifluoromethyl)phenyl]aniline |

TABLE 1-continued
| Compound No. | Structure | Name |
|---|---|---|
| 166 | 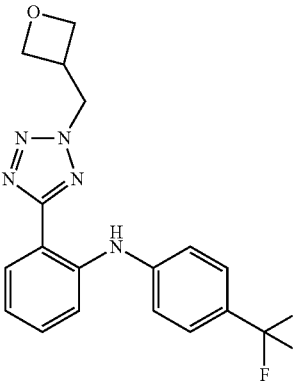 | 2-(2-(oxetan-3-ylmethyl)-2H-tetrazol-5-yl)-N-(4-(trifluoromethyl)phenyl)aniline |
| 167 | 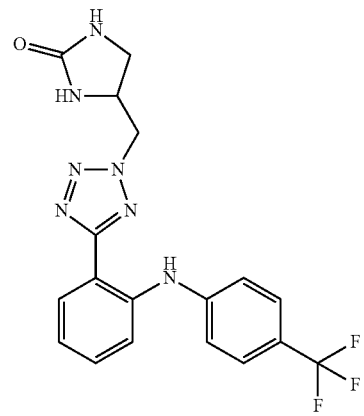 [SMILES: O=C1NCC(Cn2nnc(-c3ccccc3Nc3ccc(C(F)(F)F)cc3)n2)N1] | 4-((5-(2-((4-(trifluoromethyl)phenyl)amino)phenyl)-2H-tetrazol-2-yl)methyl)imidazolidin-2-one |
| 168 | 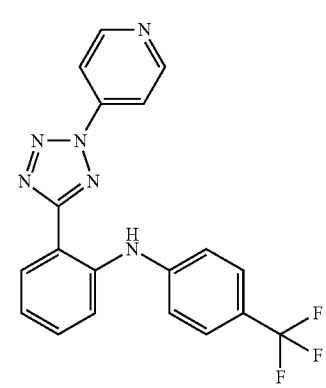 | 2-[2-(4-pyridyl)tetrazol-5-yl]-N-[4-(trifluoromethyl)phenyl]aniline |
| 169 | 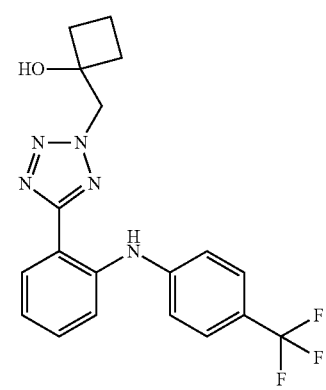 [SMILES: OC1(Cn2nnc(-c3ccccc3Nc3ccc(C(F)(F)F)cc3)n2)CCC1] | 1-((5-(2-((4-(Trifluoromethyl)phenyl)amino)phenyl)-2H-tetrazol-2-yl)methyl)cyclobutanol |

TABLE 1-continued

| Compound No. | Structure | Name |
|---|---|---|
| 170 | 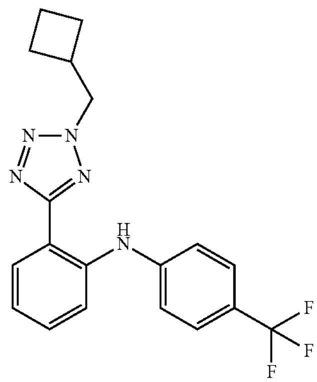 [SMILES: FC(F)(F)c1ccc(Nc2ccccc2-c2nnn(CC3CCC3)n2)cc1] | 2-(2-(Cyclobutylmethyl)-2H-tetrazol-5-yl)-N-(4-(trifluoromethyl)phenyl)aniline |
| 171 | 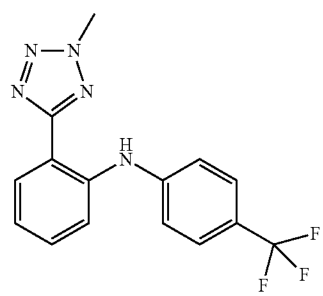 [SMILES: Cn1nnc(-c2ccccc2Nc2ccc(C(F)(F)F)cc2)n1] | 2-(2-methyltetrazol-5-yl)-N-[4-(trifluoromethyl)phenyl]aniline |
| 172 | 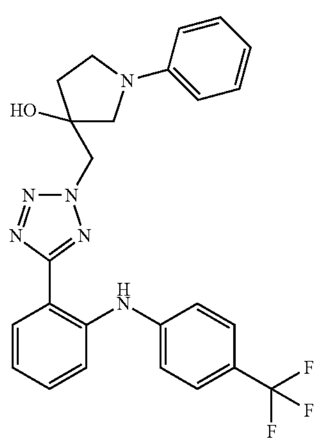 [SMILES: OC1(Cn2nnc(-c3ccccc3Nc3ccc(C(F)(F)F)cc3)n2)CCN(c2ccccc2)C1] | 1-phenyl-3-((5-(2-((4-(trifluoromethyl)phenyl)amino)phenyl)-2H-tetrazol-2-yl)methyl)pyrrolidin-3-ol |
| 173 | 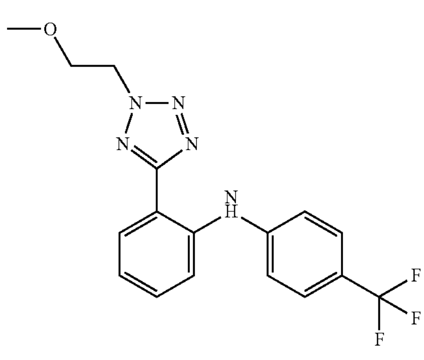 [SMILES: COCCn1nnc(-c2ccccc2Nc2ccc(C(F)(F)F)cc2)n1] | 2-(2-(2-methoxyethyl)-2H-tetrazol-5-yl)-N-(4-(trifluoromethyl)phenyl)aniline |

TABLE 1-continued

| Compound No. | Structure | Name |
|---|---|---|
| 174 | 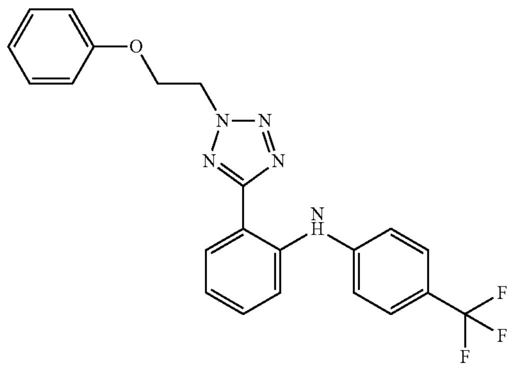 [SMILES: FC(F)(F)c1ccc(Nc2ccccc2-c2nnn(CCOc3ccccc3)n2)cc1] | 2-(2-(2-phenoxyethyl)-2H-tetrazol-5-yl)-N-(4-(trifluoromethyl)phenyl)aniline |
| 175 | 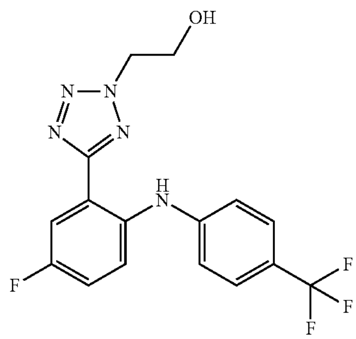 [SMILES: OCCn1nnc(-c2cc(F)ccc2Nc2ccc(C(F)(F)F)cc2)n1] | 2-[5-[5-fluoro-2-[4-(trifluoromethyl)anilino]phenyl]tetrazol-2-yl]ethanol |
| 176 | 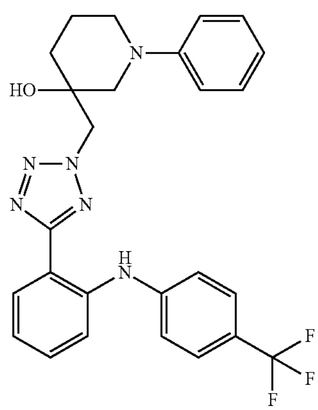 [SMILES: OC1(Cn2nnc(-c3ccccc3Nc3ccc(C(F)(F)F)cc3)n2)CCCN(c2ccccc2)C1] | 1-phenyl-3-((5-(2-((4-(trifluoromethyl)phenyl)amino)phenyl)-2H-tetrazol-2-yl)methyl)piperidin-3-ol |
| 177 | 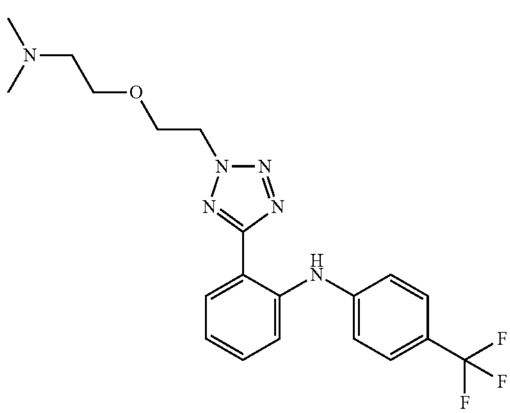 [SMILES: CN(C)CCOCCn1nnc(-c2ccccc2Nc2ccc(C(F)(F)F)cc2)n1] | 2-(2-(2-(2-(dimethylamino)ethoxy)ethyl)-2H-tetrazol-5-yl)-N-(4-(trifluoromethyl)phenyl)aniline |

TABLE 1-continued

| Compound No. | Structure | Name |
|---|---|---|
| 178 | 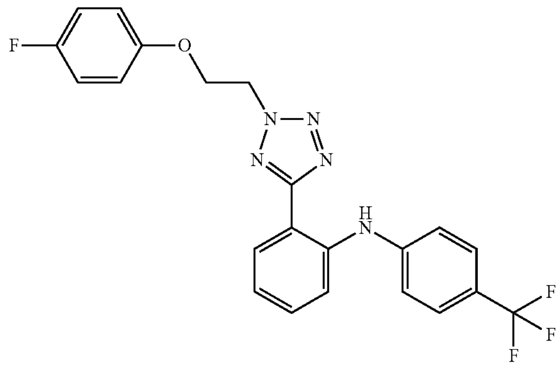 [SMILES: Fc1ccc(OCCn2nnc(-c3ccccc3Nc3ccc(C(F)(F)F)cc3)n2)cc1] | 2-[2-[2-(4-fluorophenoxy)ethyl]tetrazol-5-yl]-N-[4-(trifluoromethyl)phenyl]aniline |
| 179 | 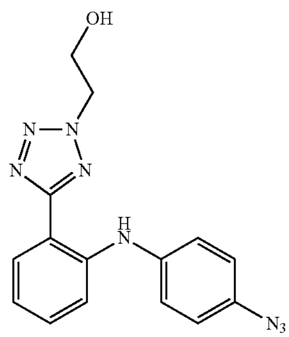 [SMILES: [N-]=[N+]=Nc1ccc(Nc2ccccc2-c2nnn(CCO)n2)cc1] | 2-[5-[2-(4-azidoanilino)phenyl]tetrazol-2-yl]ethanol |
| 180 | 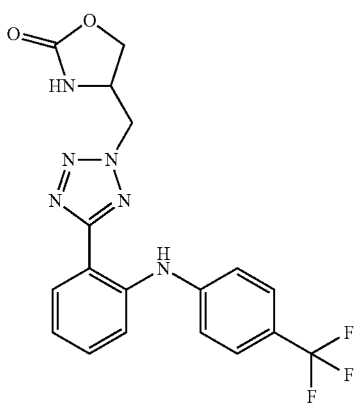 [SMILES: O=C1NC(Cn2nnc(-c3ccccc3Nc3ccc(C(F)(F)F)cc3)n2)CO1] | 4-((5-(2-((4-(trifluoromethyl)phenyl)amino)phenyl)-2H-tetrazol-2-yl)methyl)oxazolidin-2-one |
| 181 | 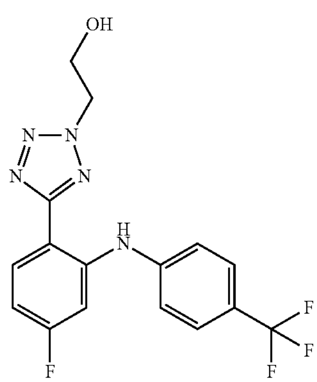 [SMILES: OCCn1nnc(-c2ccc(F)cc2Nc2ccc(C(F)(F)F)cc2)n1] | 2-[5-[4-fluoro-2-[4-(trifluoromethyl)anilino]phenyl]tetrazol-2-yl]ethanol |

TABLE 1-continued

| Compound No. | Structure | Name |
|---|---|---|
| 182 | 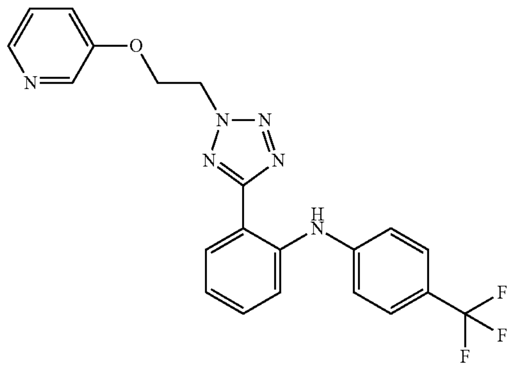 [SMILES: FC(F)(F)c1ccc(Nc2ccccc2-c2nnn(CCOc3cccnc3)n2)cc1] | 2-[2-[2-(3-pyridyloxy)ethyl]tetrazol-5-yl]-N-[4-(trifluoromethyl)phenyl]aniline |
| 183 | 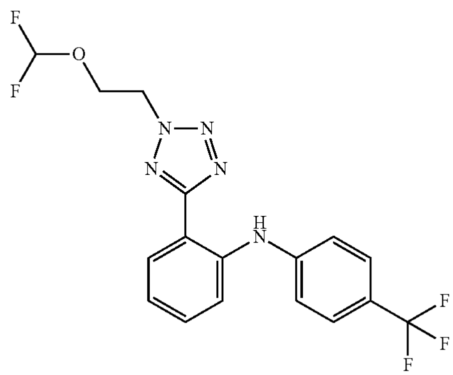 [SMILES: FC(F)OCCn1nnc(-c2ccccc2Nc2ccc(C(F)(F)F)cc2)n1] | 2-(2-(2-(difluoromethoxy)ethyl)-2H-tetrazol-5-yl)-N-(4-(trifluoromethyl)phenyl)aniline |
| 184 | 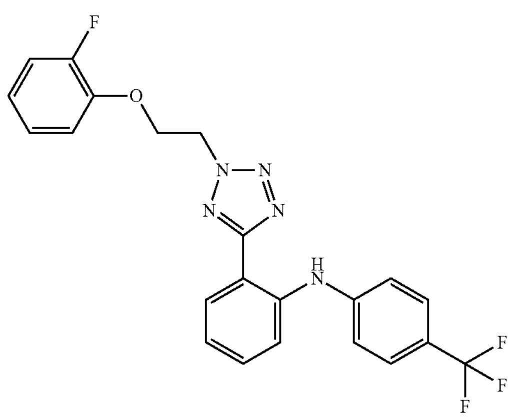 [SMILES: Fc1ccccc1OCCn1nnc(-c2ccccc2Nc2ccc(C(F)(F)F)cc2)n1] | 2-[2-[2-(2-fluorophenoxy)ethyl]tetrazol-5-yl]-N-[4-(trifluoromethyl)phenyl]aniline |
| 185 | 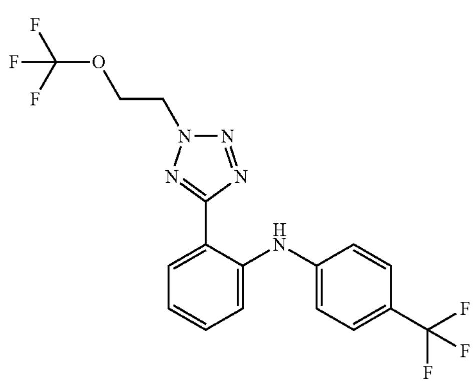 [SMILES: FC(F)(F)OCCn1nnc(-c2ccccc2Nc2ccc(C(F)(F)F)cc2)n1] | 2-(2-(2-(trifluoromethoxy)ethyl)-2H-tetrazol-5-yl)-N-(4-(trifluoromethyl)phenyl)aniline |

TABLE 1-continued

| Compound No. | Structure | Name |
|---|---|---|
| 186 | 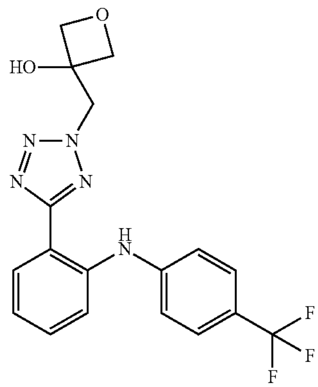 [SMILES: OC1(Cn2nnc(-c3ccccc3Nc3ccc(C(F)(F)F)cc3)n2)COC1] | 3-((5-(2-((4-(trifluoromethyl)phenyl)amino)phenyl)-2H-tetrazol-2-yl)methyl)oxetan-3-ol |
| 187 | 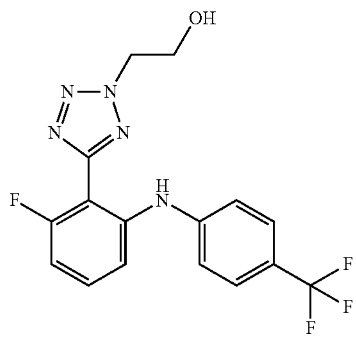 [SMILES: OCCn1nnc(-c2c(F)cccc2Nc2ccc(C(F)(F)F)cc2)n1] | 2-(5-(2-fluoro-6-((4-(trifluoromethyl)phenyl)amino)phenyl)-2H-tetrazol-2-yl)ethan-1-ol |
| 188 | 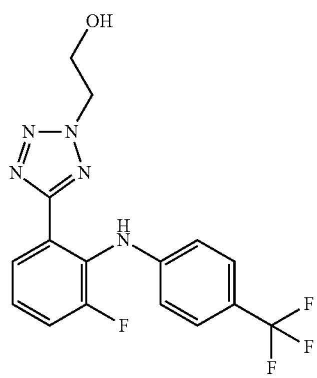 [SMILES: OCCn1nnc(-c2cccc(F)c2Nc2ccc(C(F)(F)F)cc2)n1] | 2-(5-(3-fluoro-2-((4-(trifluoromethyl)phenyl)amino)phenyl)-2H-tetrazol-2-yl)ethanol |
| 189 | 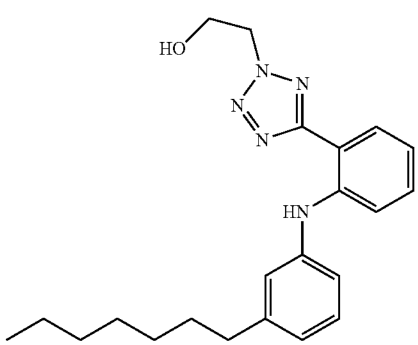 [SMILES: CCCCCCCc1cccc(Nc2ccccc2-c2nnn(CCO)n2)c1] | 2-(5-(2-((3-heptylphenyl)amino)phenyl)-2H-tetrazol-2-yl)ethan-1-ol |

TABLE 1-continued

| Compound No. | Structure | Name |
|---|---|---|
| 190 | 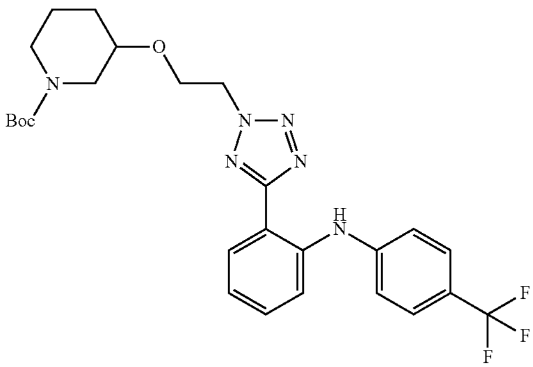 [SMILES: CC(C)(C)OC(=O)N1CCCC(OCCn2nnc(-c3ccccc3Nc3ccc(C(F)(F)F)cc3)n2)C1] | tert-butyl 3-(2-(5-(2-((4-(trifluoromethyl)phenyl)amino)phenyl)-2H-tetrazol-2-yl)ethoxy)piperidine-1-carboxylate |
| 191 | 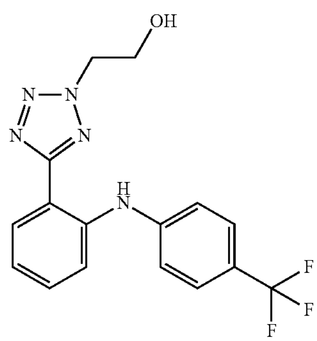 [SMILES: OCCn1nnc(-c2ccccc2Nc2ccc(C(F)(F)F)cc2)n1] | 2-(4-(2-((4-(trifluoromethyl)phenyl)amino)phenyl)-1H-1,2,3-triazol-1-yl)ethan-1-ol |
| 192 | 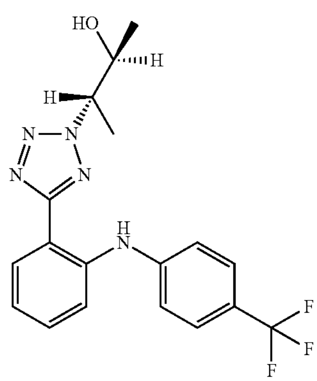 [SMILES: C[C@H](O)[C@H](C)n1nnc(-c2ccccc2Nc2ccc(C(F)(F)F)cc2)n1] | (2S,3S)-3-(5-(2-((4-(trifluoromethyl)phenyl)amino)phenyl)-2H-tetrazol-2-yl)butan-2-ol |
| 193 | 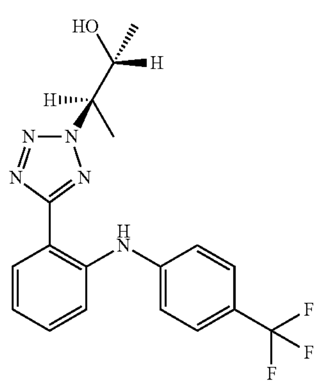 [SMILES: C[C@H]([C@@H](C)O)n1nnc(-c2ccccc2Nc2ccc(C(F)(F)F)cc2)n1] | (2R,3R)-3-(5-(2-((4-(trifluoromethyl)phenyl)amino)phenyl)-2H-tetrazol-2-yl)butan-2-ol |

TABLE 1-continued

| Compound No. | Structure | Name |
|---|---|---|
| 194 | 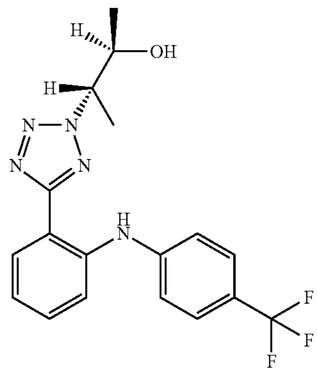 [SMILES: C[C@@H](O)[C@H](C)n1nnc(-c2ccccc2Nc2ccc(C(F)(F)F)cc2)n1] | (2R,3S)-3-(5-(2-((4-(trifluoromethyl)phenyl)amino)phenyl)-2H-tetrazol-2-yl)butan-2-ol |
| 195 | 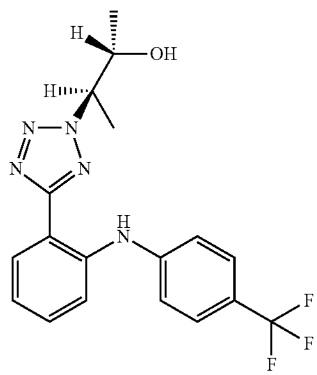 [SMILES: C[C@H](O)[C@@H](C)n1nnc(-c2ccccc2Nc2ccc(C(F)(F)F)cc2)n1] | (2S,3R)-3-(5-(2-((4-(trifluoromethyl)phenyl)amino)phenyl)-2H-tetrazol-2-yl)butan-2-ol |
| 196 | 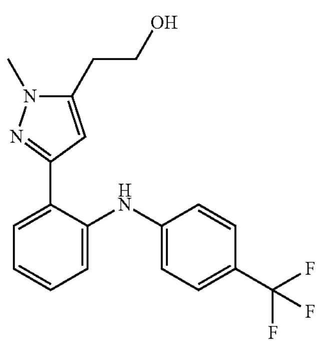 [SMILES: Cn1nc(-c2ccccc2Nc2ccc(C(F)(F)F)cc2)cc1CCO] | 2-(1-methyl-3-(2-((4-(trifluoromethyl)phenyl)amino)phenyl)-1H-pyrazol-5-yl)ethan-1-ol |
| 197 | 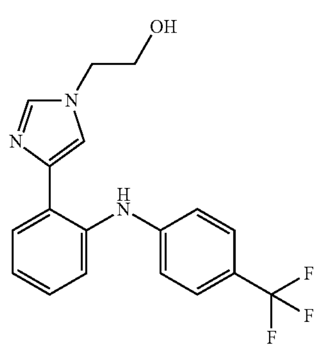 [SMILES: OCCn1cnc(-c2ccccc2Nc2ccc(C(F)(F)F)cc2)c1] | 2-(4-(2-((4-(trifluoromethyl)phenyl)amino)phenyl)-1H-imidazol-1-yl)ethan-1-ol |

TABLE 1-continued
| Compound No. | Structure | Name |
|---|---|---|
| 198 | 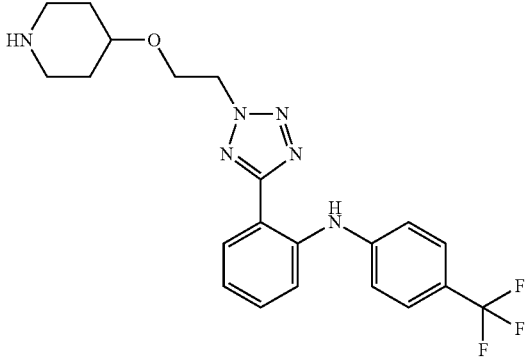 [SMILES: FC(F)(F)c1ccc(Nc2ccccc2-c2nnn(CCOC3CCNCC3)n2)cc1] | 2-(2-(2-(piperidin-4-yloxy)ethyl)-2H-tetrazol-5-yl)-N-(4-(trifluoromethyl)phenyl)aniline |
| 199 | 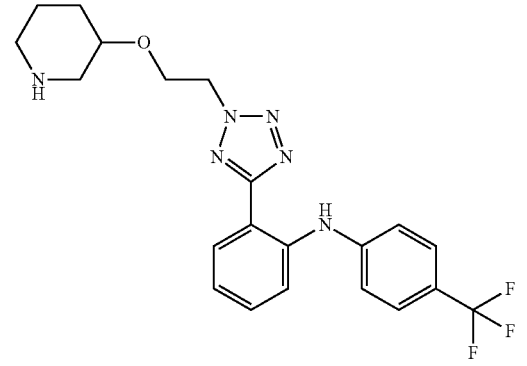 [SMILES: FC(F)(F)c1ccc(Nc2ccccc2-c2nnn(CCOC3CCCNC3)n2)cc1] | 2-(2-(2-(piperidin-3-yloxy)ethyl)-2H-tetrazol-5-yl)-N-(4-(trifluoromethyl)phenyl)aniline |
| 200 | 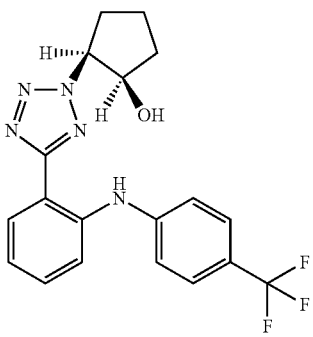 [SMILES: O[C@@H]1CCC[C@@H]1n1nnc(-c2ccccc2Nc2ccc(C(F)(F)F)cc2)n1] | (1R,2S)-2-(5-(2-((4-(trifluoromethyl)phenyl)amino)phenyl)-2H-tetrazol-2-yl)cyclopentan-1-ol |
| 201 | 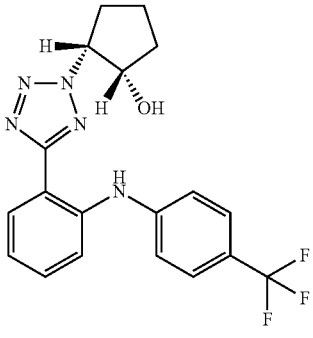 [SMILES: O[C@H]1CCC[C@H]1n1nnc(-c2ccccc2Nc2ccc(C(F)(F)F)cc2)n1] | (1S,2R)-2-(5-(2-((4-(trifluoromethyl)phenyl)amino)phenyl)-2H-tetrazol-2-yl)cyclopentan-1-ol |

TABLE 1-continued

| Compound No. | Structure | Name |
|---|---|---|
| 202 | 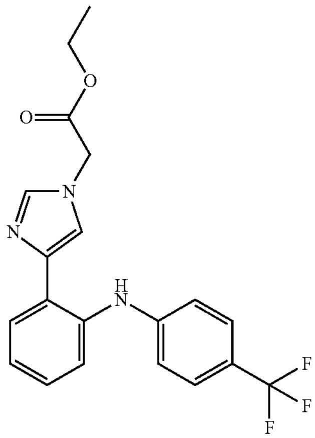 [SMILES: CCOC(=O)Cn1cnc(-c2ccccc2Nc2ccc(C(F)(F)F)cc2)c1] | ethyl 2-(4-(2-((4-(trifluoromethyl)phenyl)amino)phenyl)-1H-imidazol-1-yl)acetate |
| 203 | 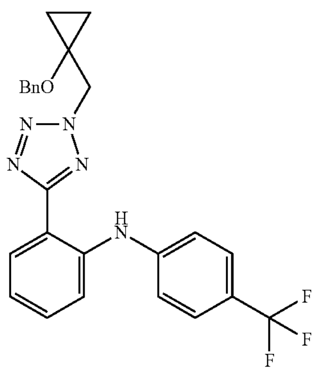 [SMILES: FC(F)(F)c1ccc(Nc2ccccc2-c2nnn(CC3(OCc4ccccc4)CC3)n2)cc1] | 2-(2-((1-(benzyloxy)cyclopropyl)methyl)-2H-tetrazol-5-yl)-N-(4-(trifluoromethyl)phenyl)aniline |
| 204 | 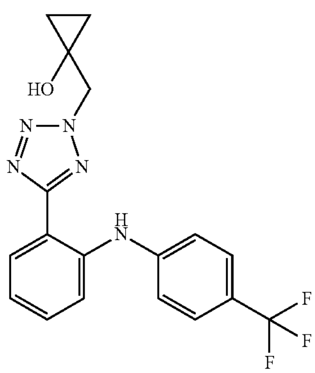 [SMILES: OC1(Cn2nnc(-c3ccccc3Nc3ccc(C(F)(F)F)cc3)n2)CC1] | 1-((5-(2-((4-(trifluoromethyl)phenyl)amino)phenyl)-2H-tetrazol-2-yl)methyl)cyclopropan-1-ol |
| 205 | 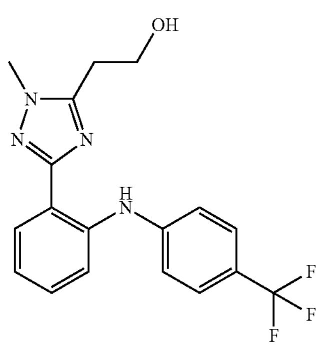 [SMILES: Cn1nc(-c2ccccc2Nc2ccc(C(F)(F)F)cc2)nc1CCO] | 2-(1-methyl-3-(2-((4-(trifluoromethyl)phenyl)amino)phenyl)-1H-1,2,4-triazol-5-yl)ethan-1-ol |

TABLE 1-continued

| Compound No. | Structure | Name |
|---|---|---|
| 206 | 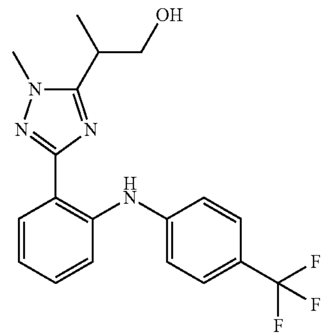 [SMILES: CC(CO)c1nc(-c2ccccc2Nc2ccc(C(F)(F)F)cc2)nn1C] | 2-(1-methyl-3-(2-((4-(trifluoromethyl)phenyl)amino)phenyl)-1H-1,2,4-triazol-5-yl)propan-1-ol |
| 207 | 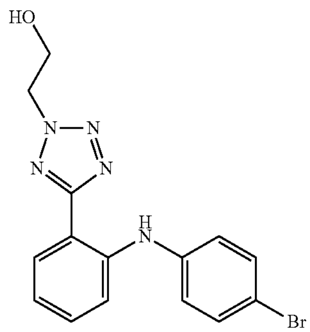 [SMILES: OCCn1nnc(-c2ccccc2Nc2ccc(Br)cc2)n1] | 2-(5-(2-((4-bromophenyl)amino)phenyl)-2H-tetrazol-2-yl)ethan-1-ol |
| 208 | 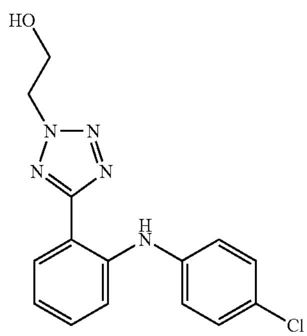 [SMILES: OCCn1nnc(-c2ccccc2Nc2ccc(Cl)cc2)n1] | 2-(5-(2-((4-chlorophenyl)amino)phenyl)-2H-tetrazol-2-yl)ethan-1-ol |
| 209 | 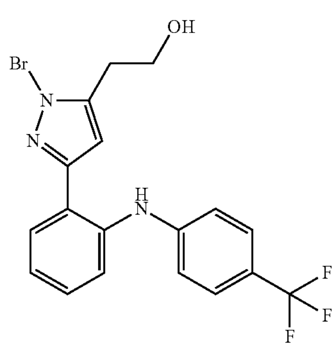 [SMILES: OCCc1cc(-c2ccccc2Nc2ccc(C(F)(F)F)cc2)nn1Br] | 2-(1-benzyl-3-(2-((4-(trifluoromethyl)phenyl)amino)phenyl)-1H-pyrazol-5-yl)ethan-1-ol |

TABLE 1-continued

| Compound No. | Structure | Name |
|---|---|---|
| 210 | 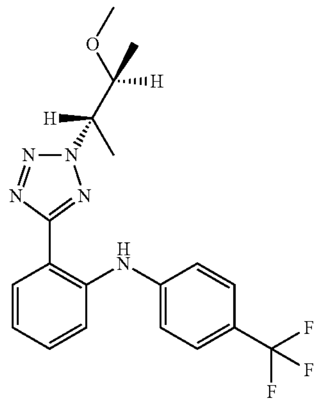 [SMILES: CO[C@@H](C)[C@H](C)n1nnc(-c2ccccc2Nc2ccc(C(F)(F)F)cc2)n1] | 2-(2-((2S,3S)-3-methoxybutan-2-yl)-2H-tetrazol-5-yl)-N-(4-(trifluoromethyl)phenyl)aniline |
| 211 | 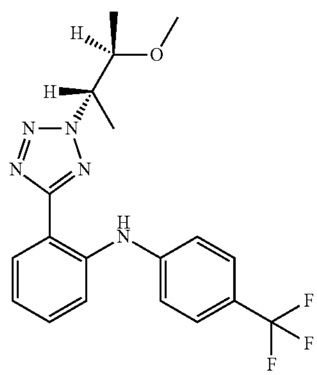 [SMILES: CO[C@H](C)[C@H](C)n1nnc(-c2ccccc2Nc2ccc(C(F)(F)F)cc2)n1] | 2-(2-((2S,3R)-3-methoxybutan-2-yl)-2H-tetrazol-5-yl)-N-(4-(trifluoromethyl)phenyl)aniline |
| 212 | 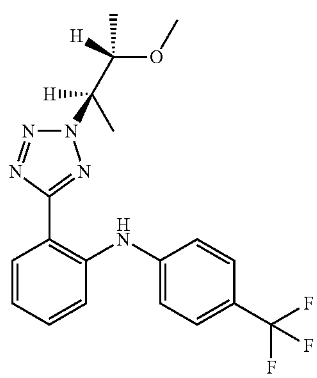 [SMILES: CO[C@@H](C)[C@@H](C)n1nnc(-c2ccccc2Nc2ccc(C(F)(F)F)cc2)n1] | 2-(2-((2R,3S)-3-methoxybutan-2-yl)-2H-tetrazol-5-yl)-N-(4-(trifluoromethyl)phenyl)aniline |
| 213 | 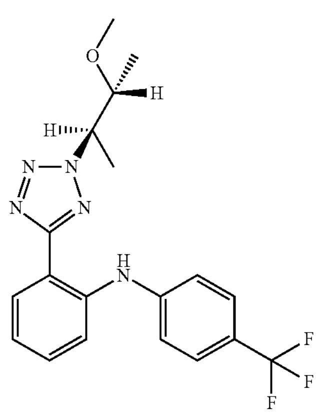 [SMILES: CO[C@H](C)[C@@H](C)n1nnc(-c2ccccc2Nc2ccc(C(F)(F)F)cc2)n1] | 2-(2-((2R,3R)-3-methoxybutan-2-yl)-2H-tetrazol-5-yl)-N-(4-(trifluoromethyl)phenyl)aniline |

TABLE 1-continued

| Compound No. | Structure | Name |
|---|---|---|
| 214 | 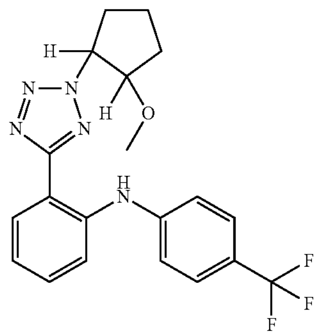 [SMILES: COC1CCCC1n1nnc(-c2ccccc2Nc2ccc(C(F)(F)F)cc2)n1] | 2-(2-(2-methoxycyclopentyl)-2H-tetrazol-5-yl)-N-(4-(trifluoromethyl)phenyl)aniline |
| 215 | 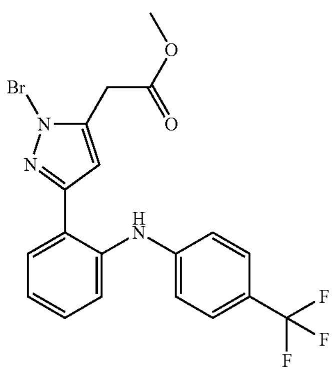 [SMILES: COC(=O)Cc1cc(-c2ccccc2Nc2ccc(C(F)(F)F)cc2)nn1Br] | methyl 2-(1-benzyl-3-(2-((4-(trifluoromethyl)phenyl)amino)phenyl)-1H-pyrazol-5-yl)acetate |
| 216 | 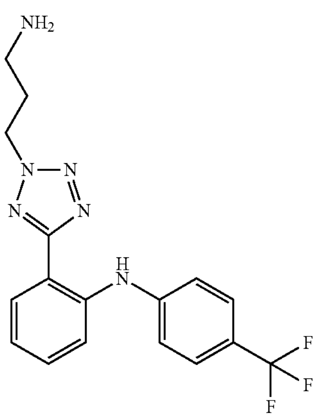 [SMILES: NCCCn1nnc(-c2ccccc2Nc2ccc(C(F)(F)F)cc2)n1] | 2-(2-(3-aminopropyl)-2H-tetrazol-5-yl)-N-(4-(trifluoromethyl)phenyl)aniline |
| 217 | 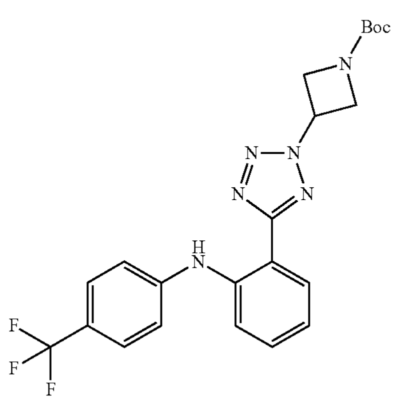 [SMILES: CC(C)(C)OC(=O)N1CC(n2nnc(-c3ccccc3Nc3ccc(C(F)(F)F)cc3)n2)C1] | tert-butyl 3-(5-(2-((4-(trifluoromethyl)phenyl)amino)phenyl)-2H-tetrazol-2-yl)azetidine-1-carboxylate |

TABLE 1-continued

| Compound No. | Structure | Name |
|---|---|---|
| 218 | 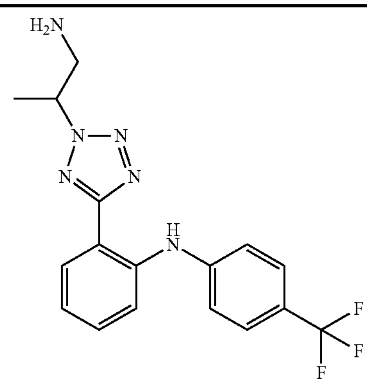 | 2-(2-(1-aminopropan-2-yl)-2H-tetrazol-5-yl)-N-(4-(trifluoromethyl)phenyl)aniline |
| 219 | 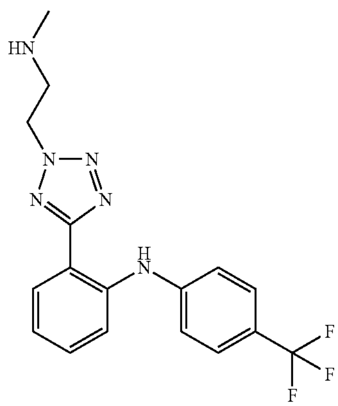 [SMILES: CNCCn1nnc(-c2ccccc2Nc2ccc(C(F)(F)F)cc2)n1] | 2-(2-(2-(methylamino)ethyl)-2H-tetrazol-5-yl)-N-(4-(trifluoromethyl)phenyl)aniline |
| 220 | 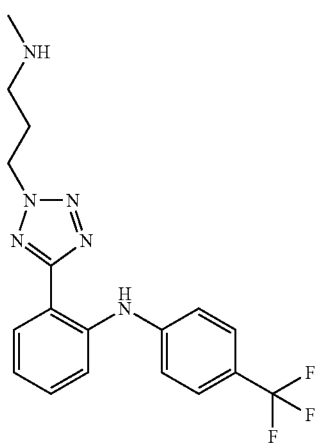 [SMILES: CNCCCn1nnc(-c2ccccc2Nc2ccc(C(F)(F)F)cc2)n1] | 2-(2-(3-(methylamino)propyl)-2H-tetrazol-5-yl)-N-(4-(trifluoromethyl)phenyl)aniline |
| 221 | 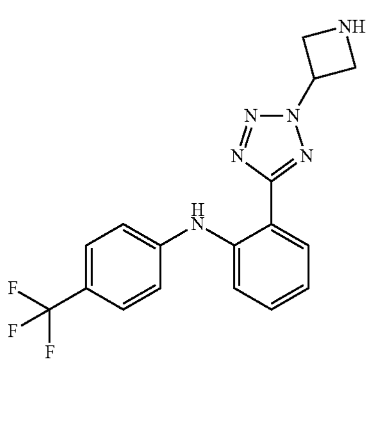 [SMILES: FC(F)(F)c1ccc(Nc2ccccc2-c2nnn(C3CNC3)n2)cc1] | 2-(2-(azetidin-3-yl)-2H-tetrazol-5-yl)-N-(4-(trifluoromethyl)phenyl)aniline |

TABLE 1-continued

| Compound No. | Structure | Name |
|---|---|---|
| 222 | 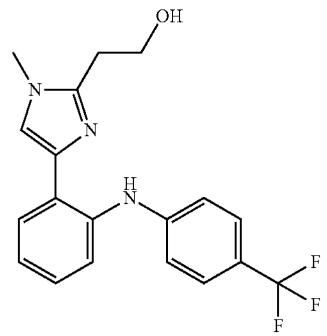 [SMILES: Cn1cc(-c2ccccc2Nc2ccc(C(F)(F)F)cc2)nc1CCO] | 2-(1-methyl-4-(2-((4-(trifluoromethyl)phenyl)amino)phenyl)-1H-imidazol-2-yl)ethan-1-ol |
| 223 | 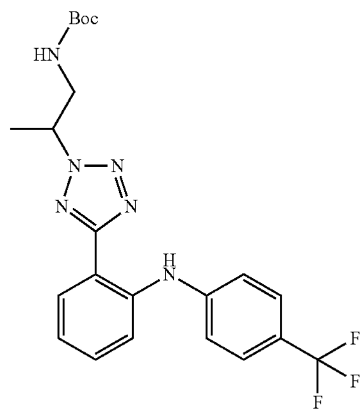 [SMILES: CC(CNC(=O)OC(C)(C)C)n1nnc(-c2ccccc2Nc2ccc(C(F)(F)F)cc2)n1] | tert-butyl (2-(5-(2-((4-(trifluoromethyl)phenyl)amino)phenyl)-2H-tetrazol-2-yl)propyl)carbamate |
| 224 | 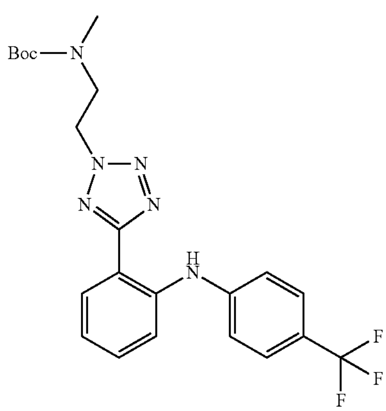 [SMILES: CN(CCn1nnc(-c2ccccc2Nc2ccc(C(F)(F)F)cc2)n1)C(=O)OC(C)(C)C] | tert-butyl methyl(2-(5-(2-((4-(trifluoromethyl)phenyl)amino)phenyl)-2H-tetrazol-2-yl)ethyl)carbamate |
| 225 | 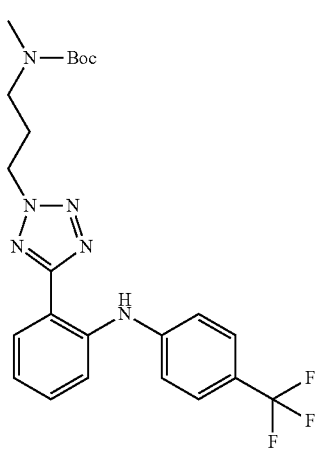 [SMILES: CN(CCCn1nnc(-c2ccccc2Nc2ccc(C(F)(F)F)cc2)n1)C(=O)OC(C)(C)C] | tert-butyl methyl(3-(5-(2-((4-(trifluoromethyl)phenyl)amino)phenyl)-2H-tetrazol-2-yl)propyl)carbamate |

TABLE 1-continued

| Compound No. | Structure | Name |
|---|---|---|
| 226 | 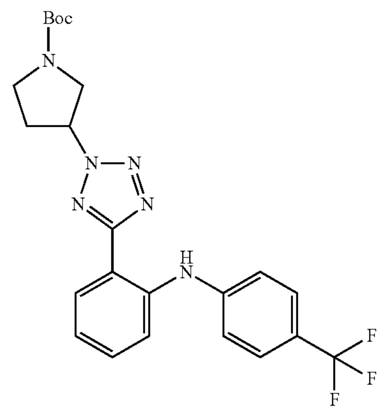 [SMILES: CC(C)(C)OC(=O)N1CCC(n2nnc(-c3ccccc3Nc3ccc(C(F)(F)F)cc3)n2)C1] | tert-butyl 3-(5-(2-((4-(trifluoromethyl)phenyl)amino)phenyl)-2H-tetrazol-2-yl)pyrrolidine-1-carboxylate |
| 227 | 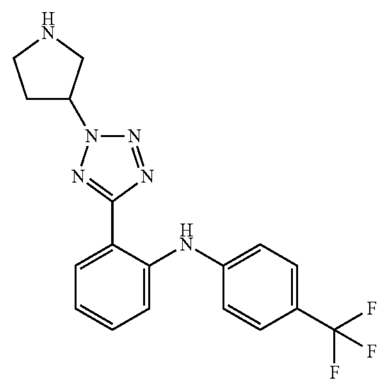 [SMILES: FC(F)(F)c1ccc(Nc2ccccc2-c2nnn(C3CCNC3)n2)cc1] | 2-(2-(pyrrolidin-3-yl)-2H-tetrazol-5-yl)-N-(4-(trifluoromethyl)phenyl)aniline |
| 228 | 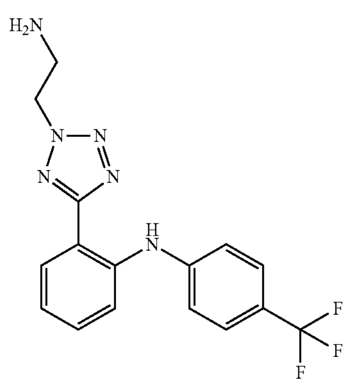 [SMILES: NCCn1nnc(-c2ccccc2Nc2ccc(C(F)(F)F)cc2)n1] | 2-(2-(2-aminoethyl)-2H-tetrazol-5-yl)-N-(4-(trifluoromethyl)phenyl)aniline |
| 229 | 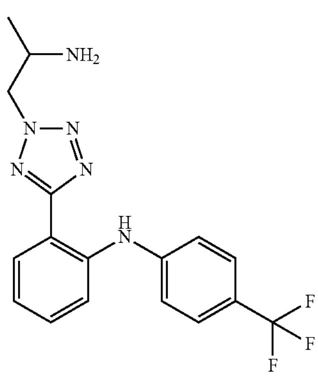 [SMILES: CC(N)Cn1nnc(-c2ccccc2Nc2ccc(C(F)(F)F)cc2)n1] | 2-(2-(2-aminopropyl)-2H-tetrazol-5-yl)-N-(4-(trifluoromethyl)phenyl)aniline |

TABLE 1-continued

| Compound No. | Structure | Name |
|---|---|---|
| 230 | 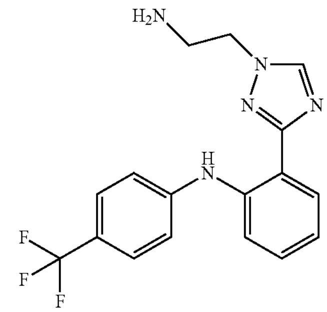 [SMILES: NCCn1cnc(-c2ccccc2Nc2ccc(C(F)(F)F)cc2)n1] | 2-(1-(2-aminoethyl)-1H-1,2,4-triazol-3-yl)-N-(4-(trifluoromethyl)phenyl)aniline |
| 231 | 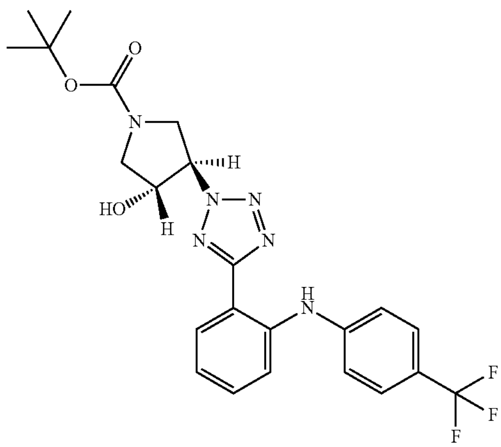 [SMILES: CC(C)(C)OC(=O)N1C[C@@H](O)[C@H](n2nnc(-c3ccccc3Nc3ccc(C(F)(F)F)cc3)n2)C1] | tert-butyl (3R,4R)-3-hydroxy-4-(5-(2-((4-(trifluoromethyl)phenyl)amino)phenyl)-2H-tetrazol-2-yl)pyrrolidine-1-carboxylate |
| 232 | 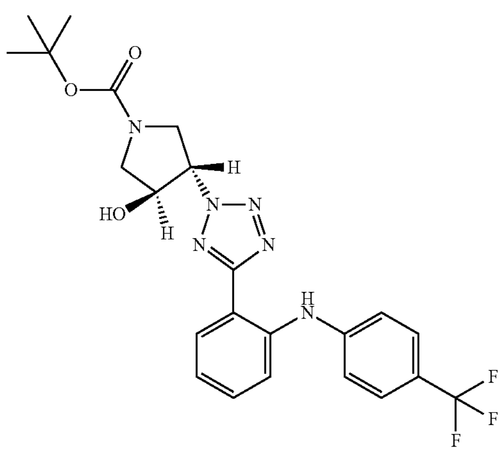 [SMILES: CC(C)(C)OC(=O)N1C[C@H](O)[C@@H](n2nnc(-c3ccccc3Nc3ccc(C(F)(F)F)cc3)n2)C1] | tert-butyl (3S,4S)-3-hydroxy-4-(5-(2-((4-(trifluoromethyl)phenyl)amino)phenyl)-2H-tetrazol-2-yl)pyrrolidine-1-carboxylate |
| 233 | 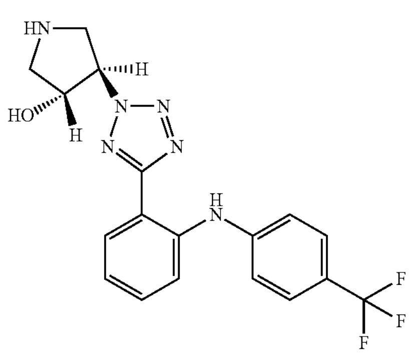 [SMILES: O[C@@H]1CNC[C@H]1n1nnc(-c2ccccc2Nc2ccc(C(F)(F)F)cc2)n1] | (3R,4R)-4-(5-(2-((4-(trifluoromethyl)phenyl)amino)phenyl)-2H-tetrazol-2-yl)pyrrolidin-3-ol |

TABLE 1-continued

| Compound No. | Structure | Name |
|---|---|---|
| 234 | 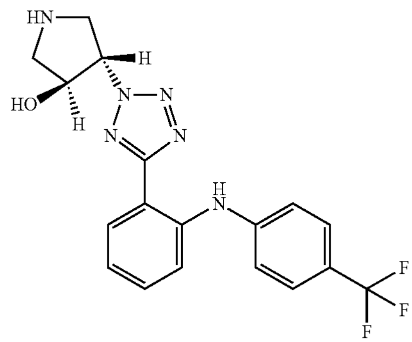 [SMILES: O[C@H]1CNC[C@@H]1n1nnc(-c2ccccc2Nc2ccc(C(F)(F)F)cc2)n1] | (3S,4S)-4-(5-(2-((4-(trifluoromethyl)phenyl)amino)phenyl)-2H-tetrazol-2-yl)pyrrolidin-3-ol |
| 235 | 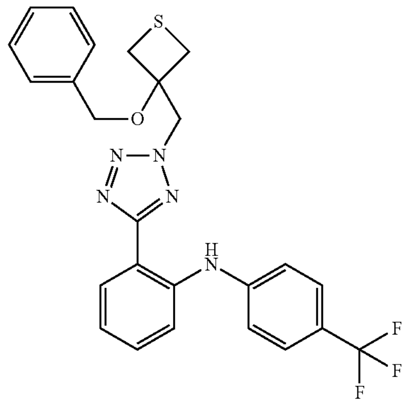 [SMILES: FC(F)(F)c1ccc(Nc2ccccc2-c2nnn(CC3(OCc4ccccc4)CSC3)n2)cc1] | 2-(2-((3-(benzyloxy)thietan-3-yl)methyl)-2H-tetrazol-5-yl)-N-(4-(trifluoromethyl)phenyl)aniline |
| 236 | 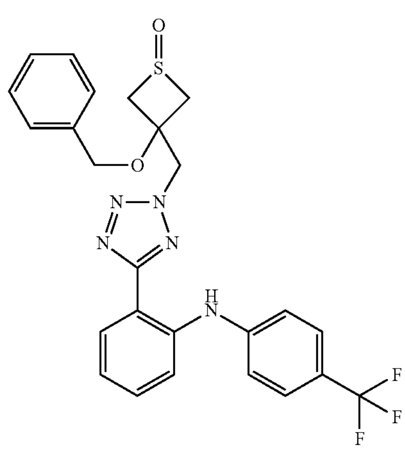 [SMILES: O=S1CC(Cn2nnc(-c3ccccc3Nc3ccc(C(F)(F)F)cc3)n2)(OCc2ccccc2)C1] | 3-(benzyloxy)-3-((5-(2-((4-(trifluoromethyl)phenyl)amino)phenyl)-2H-tetrazol-2-yl)methyl)thietane-1-oxide |

TABLE 1-continued

| Compound No. | Structure | Name |
|---|---|---|
| 237 | 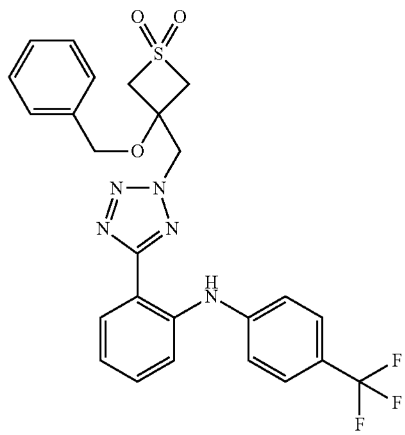 [SMILES: O=S1(=O)CC(Cn2nnc(-c3ccccc3Nc3ccc(C(F)(F)F)cc3)n2)(OCc2ccccc2)C1] | 3-(benzyloxy)-3-((5-(2-((4-(trifluoromethyl)phenyl)amino)phenyl)-2H-tetrazol-2-yl)methyl)thietane-1,1-dioxide |
| 238 | 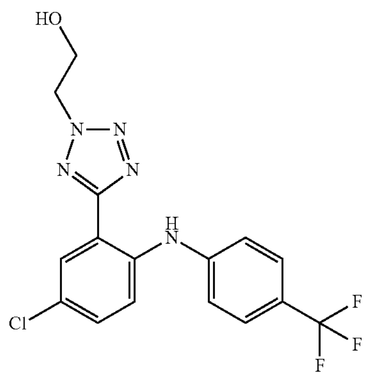 [SMILES: OCCn1nnc(-c2cc(Cl)ccc2Nc2ccc(C(F)(F)F)cc2)n1] | 2-(5-(5-chloro-2-((4-(trifluoromethyl)phenyl)amino)phenyl)-2H-tetrazol-2-yl)ethanol |
| 239 | 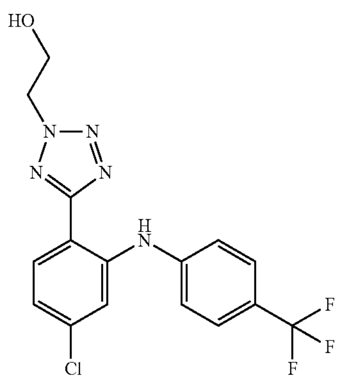 [SMILES: OCCn1nnc(-c2ccc(Cl)cc2Nc2ccc(C(F)(F)F)cc2)n1] | 2-(5-(4-chloro-2-((4-(trifluoromethyl)phenyl)amino)phenyl)-2H-tetrazol-2-yl)ethanol |
| 240 | 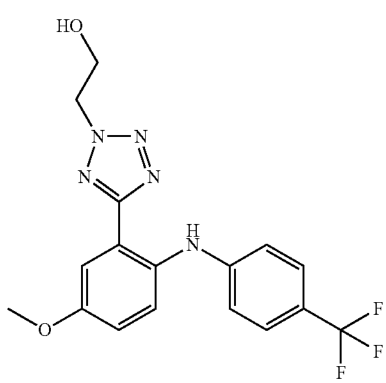 [SMILES: COc1ccc(Nc2ccc(C(F)(F)F)cc2)c(-c2nnn(CCO)n2)c1] | 2-[5-[5-methoxy-2-[4-(trifluoromethyl)anilino]phenyl]tetrazol-2-yl]ethanol |

TABLE 1-continued

| Compound No. | Structure | Name |
|---|---|---|
| 241 | 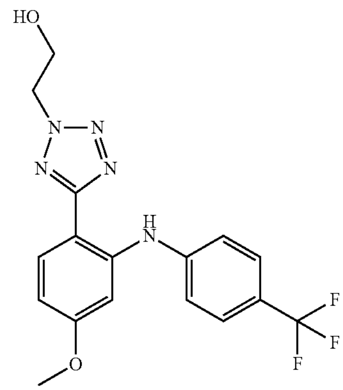 [SMILES: COc1ccc(-c2nnn(CCO)n2)c(Nc2ccc(C(F)(F)F)cc2)c1] | 2-[5-[4-methoxy-2-[4-(trifluoromethyl)anilino]phenyl]tetrazol-2-yl]ethanol |
| 242 | 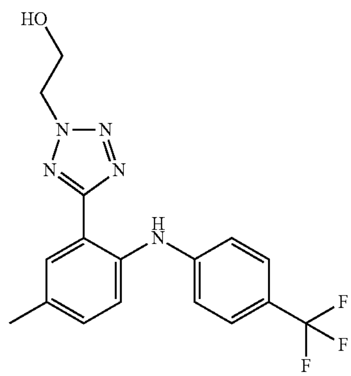 [SMILES: Cc1ccc(Nc2ccc(C(F)(F)F)cc2)c(-c2nnn(CCO)n2)c1] | 2-(5-(5-methyl-2-((4-(trifluoromethyl)phenyl)amino)phenyl)-2H-tetrazol-2-yl)ethanol |
| 243 | 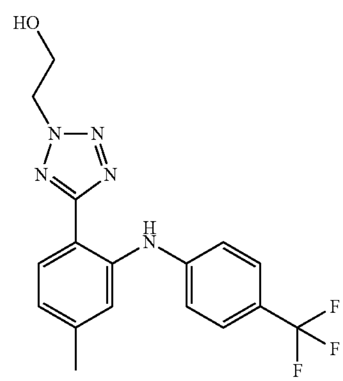 [SMILES: Cc1ccc(-c2nnn(CCO)n2)c(Nc2ccc(C(F)(F)F)cc2)c1] | 2-(5-(4-methyl-2-((4-(trifluoromethyl)phenyl)amino)phenyl)-2H-tetrazol-2-yl)ethanol |
| 244 | 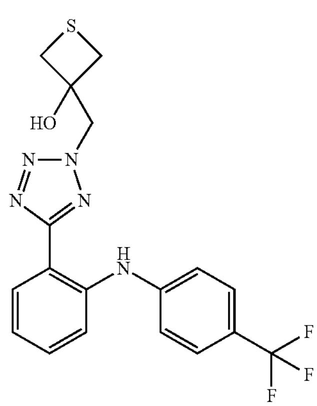 [SMILES: OC1(Cn2nnc(-c3ccccc3Nc3ccc(C(F)(F)F)cc3)n2)CSC1] | 3-[[5-[2-[4-(trifluoromethyl)anilino]phenyl]tetrazol-2-yl]methyl]thietan-3-ol |

TABLE 1-continued

| Compound No. | Structure | Name |
|---|---|---|
| 245 | 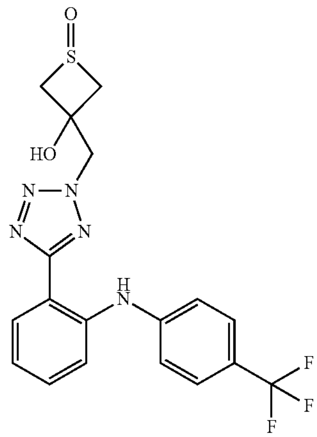 [SMILES: O=S1CC(O)(Cn2nnc(-c3ccccc3Nc3ccc(C(F)(F)F)cc3)n2)C1] | 1-oxo-3-[[5-[2-[4-(trifluoromethyl)anilino]phenyl]tetrazol-2-yl]methyl]thietan-3-ol |
| 246 | 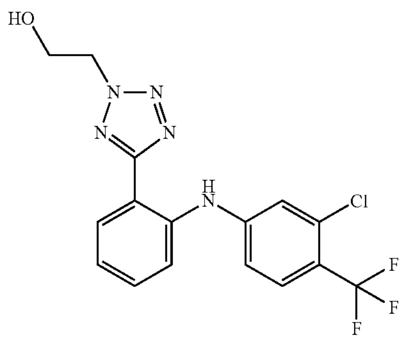 [SMILES: OCCn1nnc(-c2ccccc2Nc2ccc(C(F)(F)F)c(Cl)c2)n1] | 2-(5-(2-((3-chloro-4-(trifluoromethyl)phenyl)amino)phenyl)-2H-tetrazol-2-yl)ethanol |
| 247 | 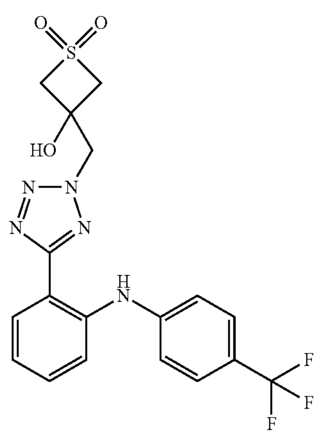 [SMILES: O=S1(=O)CC(O)(Cn2nnc(-c3ccccc3Nc3ccc(C(F)(F)F)cc3)n2)C1] | 1,1-dioxo-3-[[5-[2-[4-(trifluoromethyl)anilino]phenyl]tetrazol-2-yl]methyl]thietan-3-ol |
| 248 | 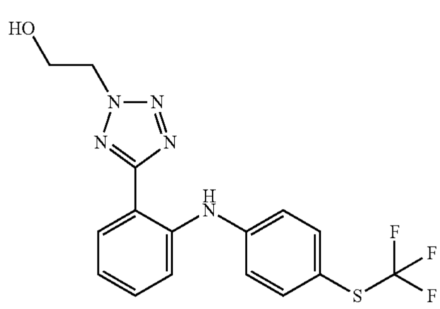 [SMILES: OCCn1nnc(-c2ccccc2Nc2ccc(SC(F)(F)F)cc2)n1] | 2-(5-(2-((4-((trifluoromethyl)thio)phenyl)amino)phenyl)-2H-tetrazol-2-yl)ethanol |

TABLE 1-continued

| Compound No. | Structure | Name |
|---|---|---|
| 249 | 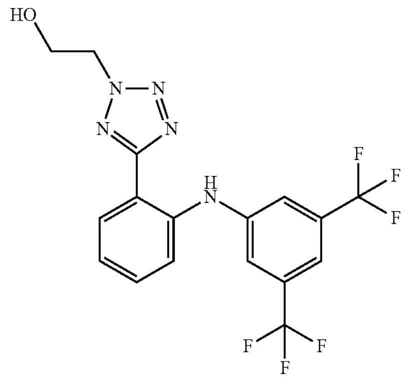 [SMILES: OCCn1nnc(-c2ccccc2Nc2cc(C(F)(F)F)cc(C(F)(F)F)c2)n1] | 2-[5-[2-[3,5-bis(trifluoromethyl)anilino]phenyl]tetrazol-2-yl]ethanol |
| 250 | 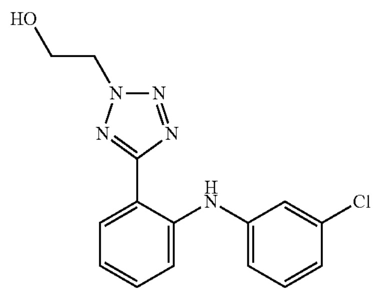 [SMILES: OCCn1nnc(-c2ccccc2Nc2cccc(Cl)c2)n1] | 2-(5-(2-((3-chlorophenyl)amino)phenyl)-2H-tetrazol-2-yl)ethanol |
| 251 | 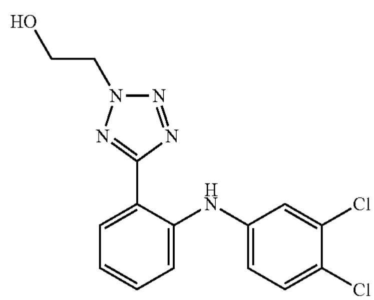 [SMILES: OCCn1nnc(-c2ccccc2Nc2ccc(Cl)c(Cl)c2)n1] | 2-(5-(2-((3,4-dichlorophenyl)amino)phenyl)-2H-tetrazol-2-yl)ethanol |
| 252 | 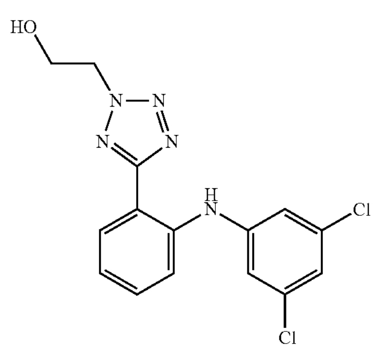 [SMILES: OCCn1nnc(-c2ccccc2Nc2cc(Cl)cc(Cl)c2)n1] | 2-(5-(2-((3,5-dichlorophenyl)amino)phenyl)-2H-tetrazol-2-yl)ethanol |

TABLE 1-continued

| Compound No. | Structure | Name |
|---|---|---|
| 253 | 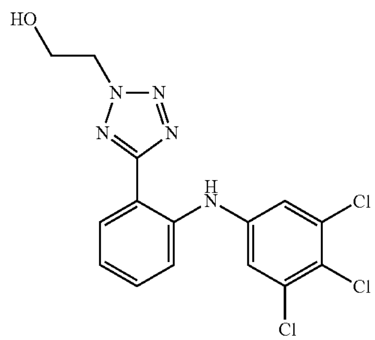 [SMILES: OCCn1nnc(-c2ccccc2Nc2cc(Cl)c(Cl)c(Cl)c2)n1] | 2-(5-(2-((3,4,5-trichlorophenyl)amino)phenyl)-2H-tetrazol-2-yl)ethanol |
| 254 | 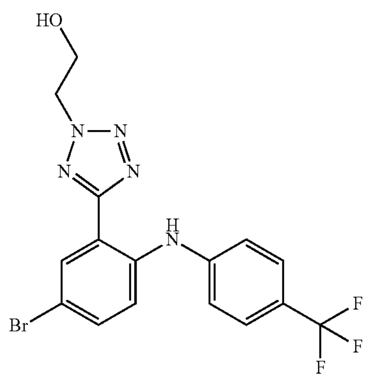 [SMILES: OCCn1nnc(-c2cc(Br)ccc2Nc2ccc(C(F)(F)F)cc2)n1] | 2-[5-[5-bromo-2-[4-(trifluoromethyl)anilino]phenyl]tetrazol-2-yl]ethanol |
| 255 | 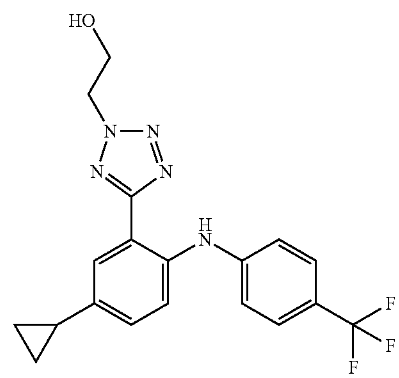 [SMILES: OCCn1nnc(-c2cc(C3CC3)ccc2Nc2ccc(C(F)(F)F)cc2)n1] | 2-(5-(5-cyclopropyl-2-((4-(trifluoromethyl)phenyl)amino)phenyl)-2H-tetrazol-2-yl)ethanol |
| 256 | 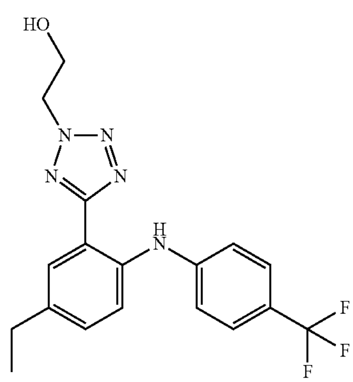 [SMILES: CCc1ccc(Nc2ccc(C(F)(F)F)cc2)c(-c2nnn(CCO)n2)c1] | 2-[5-[5-ethyl-2-[4-(trifluoromethyl)anilino]phenyl]tetrazol-2-yl]ethanol |

TABLE 1-continued

| Compound No. | Structure | Name |
|---|---|---|
| 257 | 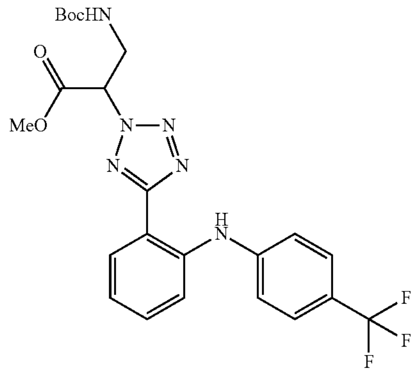 [SMILES: COC(=O)C(CNC(=O)OC(C)(C)C)n1nnc(-c2ccccc2Nc2ccc(C(F)(F)F)cc2)n1] | methyl 3-((tert-butoxycarbonyl)amino)-2-(5-(2-((4-(trifluoromethyl)phenyl)amino)phenyl)-2H-tetrazol-2-yl)propanoate |
| 258 | 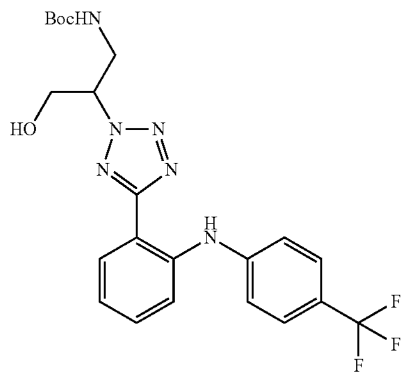 [SMILES: CC(C)(C)OC(=O)NCC(CO)n1nnc(-c2ccccc2Nc2ccc(C(F)(F)F)cc2)n1] | tert-butyl (3-hydroxy-2-(5-(2-((4-(trifluoromethyl)phenyl)amino)phenyl)-2H-tetrazol-2-yl)propyl)carbamate |
| 259 | 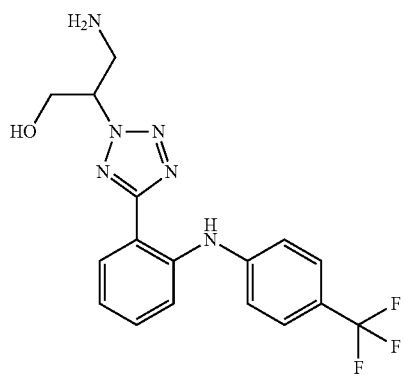 [SMILES: NCC(CO)n1nnc(-c2ccccc2Nc2ccc(C(F)(F)F)cc2)n1] | 3-amino-2-(5-(2-((4-(trifluoromethyl)phenyl)amino)phenyl)-2H-tetrazol-2-yl)propan-1-ol |
| 260 | 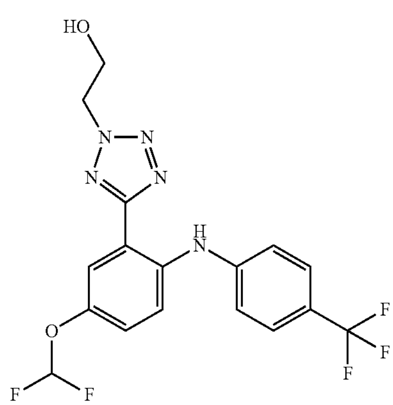 [SMILES: OCCn1nnc(-c2cc(OC(F)F)ccc2Nc2ccc(C(F)(F)F)cc2)n1] | 2-(5-(5-(difluoromethoxy)-2-((4-(trifluoromethyl)phenyl)amino)phenyl)-2H-tetrazol-2-yl)ethanol |

TABLE 1-continued

| Compound No. | Structure | Name |
|---|---|---|
| 261 | 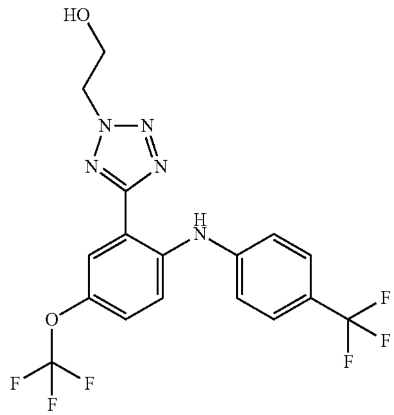 [SMILES: OCCn1nnc(-c2cc(OC(F)(F)F)ccc2Nc2ccc(C(F)(F)F)cc2)n1] | 2-(5-(5-(trifluoromethoxy)-2-((4-(trifluoromethyl)phenyl)amino)phenyl)-2H-tetrazol-2-yl)ethanol |
| 262 | 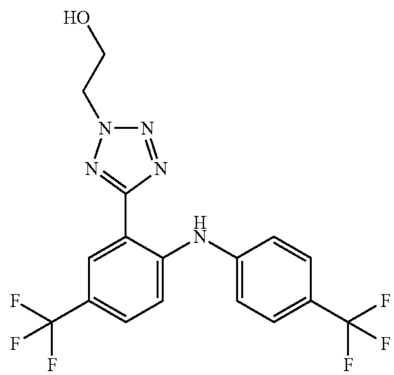 [SMILES: OCCn1nnc(-c2cc(C(F)(F)F)ccc2Nc2ccc(C(F)(F)F)cc2)n1] | 2-(5-(5-(trifluoromethyl)-2-((4-(trifluoromethyl)phenyl)amino)phenyl)-2H-tetrazol-2-yl)ethanol |
| 263 | 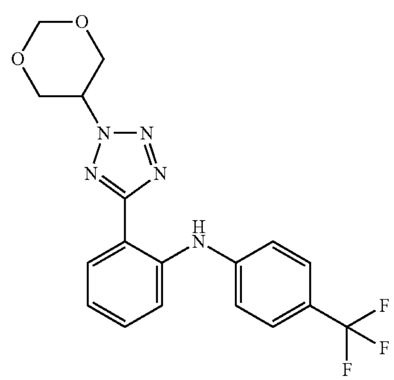 [SMILES: FC(F)(F)c1ccc(Nc2ccccc2-c2nnn(C3COCOC3)n2)cc1] | 2-(2-(1,3-dioxan-5-yl)-2H-tetrazol-5-yl)-N-(4-(trifluoromethyl)phenyl)aniline |
| 264 | 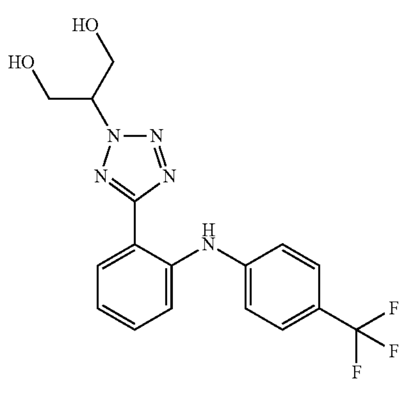 [SMILES: OCC(CO)n1nnc(-c2ccccc2Nc2ccc(C(F)(F)F)cc2)n1] | 3-(5-(2-((4-(trifluoromethyl)phenyl)amino)phenyl)-2H-tetrazol-2-yl)propane-1,3-diol |

TABLE 1-continued

| Compound No. | Structure | Name |
|---|---|---|
| 265 | 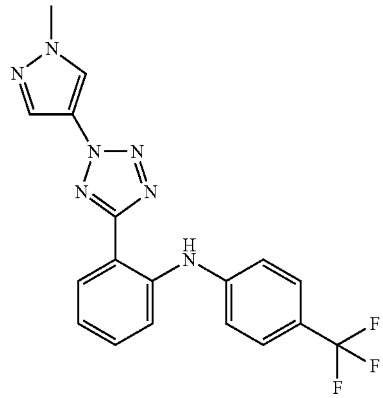 [SMILES: Cn1cc(-n2nnc(-c3ccccc3Nc3ccc(C(F)(F)F)cc3)n2)cn1] | 2-(2-(1-methyl-1H-pyrazol-4-yl)-2H-tetrazol-5-yl)-N-(4-(trifluoromethyl)phenyl)aniline |
| 266 | 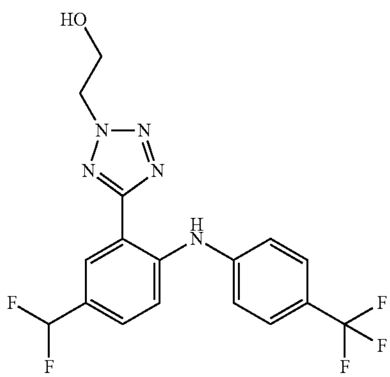 [SMILES: OCCn1nnc(-c2cc(C(F)F)ccc2Nc2ccc(C(F)(F)F)cc2)n1] | 2-[5-[5-(difluoromethyl)-2-[4-(trifluoromethyl)anilino]phenyl]tetrazol-2-yl]ethanol |

TABLE 2

| Structure | Name |
|---|---|
| 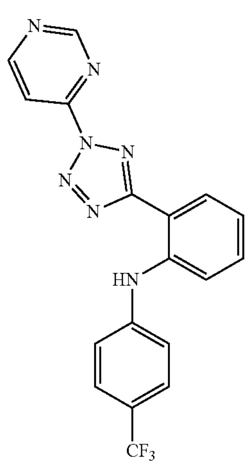 [SMILES: FC(F)(F)c1ccc(Nc2ccccc2-c2nnn(-c3ccncn3)n2)cc1] | 2-(2-(pyrimidin-4-yl)-2H-tetrazol-5-yl)-N-(4-(trifluoromethyl)phenyl)aniline |

TABLE 2-continued

| Structure | Name |
|---|---|
| 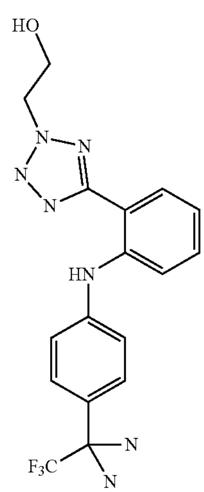 [SMILES: NC(N)(c1ccc(Nc2ccccc2C2=NN(CCO)NN2)cc1)C(F)(F)F] | 2-(5-(2-((4-(3-(trifluoromethyl)-3H-diazirin-3-yl)phenyl)amino)phenyl)-2H-tetrazol-2-yl)ethan-1-ol |

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some instances, specific and analogous reactants are identified through the indices of known chemicals prepared by the Chemical Abstract Service of the American Chemical Society, which are available in most public and university libraries, as well as through on-line databases (the American Chemical Society, Washington, D.C., is contacted for more details). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds disclosed herein are prepared as described in the Examples section.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. In some embodiments, examples of isotopes that are incorporated into compounds of the disclosure include isotopes of hydrogen, carbon, nitrogen, oxygen, phosphorous, sulfur, fluorine, and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the metabolites, pharmaceutically acceptable salts, esters, prodrugs, solvates, hydrates or derivatives thereof which contain the aforementioned isotopes and/or other isotopes of other atoms are within the scope of this disclosure. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In some embodiments, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e. g., two, three or four) amino acid residues is covalently joined through an amide or ester bond to a free amino, hydroxy, or carboxylic acid group of compounds of the present disclosure. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, metal salts and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including but not limited to ether, amine, and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, sulfonate esters, sulfate esters and disulfide containing esters; ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to, the following groups and combinations of groups:

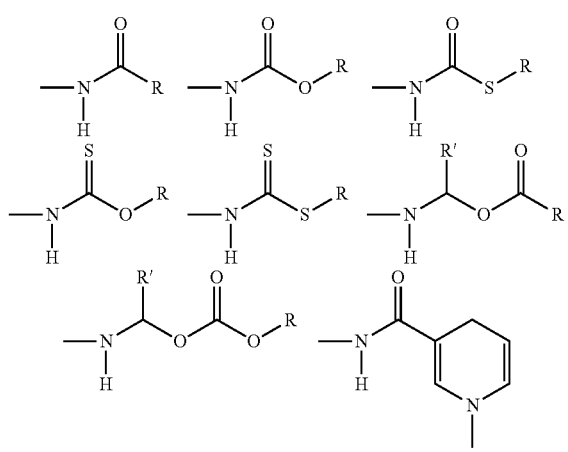

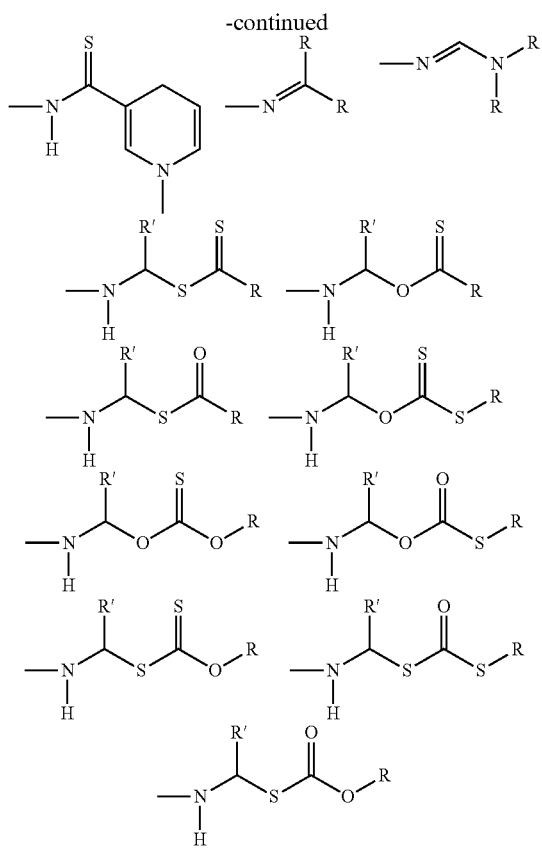

as well as sulfonamides and phosphonamides.

In certain instances, sites on any aromatic ring portions are susceptible to various metabolic reactions, therefore incorporation of appropriate substituents on the aromatic ring structures, reduce, minimize, or eliminate this metabolic pathway.

Metabolites

In some embodiments, compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds described herein are metabolized upon administration to an organism in need to produce a metabolite that is then used to produce a desired effect, including a desired therapeutic effect.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one compound described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (II), or a pharmaceutically acceptable salt thereof.

One embodiment provides a pharmaceutical composition comprising a pharmaceutically acceptable carrier and a compound of Formula (III), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof. Another embodiment provides a pharmaceutical composition consisting essentially of a pharmaceutically acceptable carrier and a compound of Formula (II), or a pharmaceutically acceptable salt thereof. Another embodiment provides a pharmaceutical composition consisting essentially of a pharmaceutically acceptable carrier and a compound of Formula (III), or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

In some instances, exemplary pharmaceutical compositions are used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets in some instances, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the compositions also comprise buffering agents in some embodiments. Solid compositions of a similar type are also employed as fillers in soft and hard-filled gelatin capsules using such excipients as lactose or milk sugars, as well as high molecular weight polyethylene glycols and the like.

In some instances, a tablet is made by compression or molding, optionally with one or more accessory ingredients. Compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets are made by molding in a suitable machine a mixture of the subject composition moistened with an inert liquid diluent. Tablets, and other solid dosage forms, such as dragees, capsules, pills and granules, are optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms contain optionally inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, optionally contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component is optionally mixed under sterile conditions with a pharmaceutically acceptable carrier, and with any preservatives, buffers, or propellants which are required in some embodiments.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. Sprays additionally contain customary propellants, such as chlorofluorohydrocarbons and volatile unsubstituted hydrocarbons, such as butane and propane.

Compositions and compounds disclosed herein are alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are used because they minimize exposing the agent to shear, which result in degradation of the compounds contained in the subject compositions in some embodiments. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which optionally contain antioxidants, buffers, bacteriostats, solutes which render the formulation isotonic with the blood of the intended recipient or suspending or thickening agents.

Examples of suitable aqueous and non-aqueous carriers employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. In some embodiments, proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

In some embodiments, the dose of the composition comprising at least one compound as described herein differ, depending upon the patient's (e.g., human) condition, that is, stage of the disease, general health status, age, and other factors that a person skilled in the medical art will use to determine dose.

In some instances, pharmaceutical compositions are administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

In some embodiments, oral doses typically range from about 1.0 mg to about 1000 mg, one to four times, or more, per day.

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional co-activator with PDZ-binding motif (TAZ; also known as WWTR1) (FIG. 1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST1/2 (homologues of Hippo/Hpo in *Drosophila*), Lats1/2 (homologues of Warts/Wts), and their adaptor proteins Sav1 (homologue of Salvador/Sav) and Mob (MOBKL1A and MOBKL1B; homologues of Mats), respectively (FIG. 1). In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] consensus motifs. YAP comprises five [HXRXXS] consensus motifs, wherein X denotes any amino acid residue. In some instances, Lats1/2 phosphorylates YAP at one or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ primes both proteins for further phosphorylation events by CK1δ/ε in the degradation motif, which then signals for interaction with the β-TRCP E3 ubiquitin ligase, leading to polyubiquitination and degradation of YAP.

In some instances, Lats1/2 phosphorylates TAZ at the [HXRXXS] consensus motifs. TAZ comprises four [HXRXXS] consensus motifs, wherein X denotes any amino acid residues. In some instances, Lats1/2 phosphorylates TAZ at one or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cytoplasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes SCF$^{\beta-TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g. Cdc4), Skp1, a bridging protein, and RBX1 which contains a small RING Finger domain which interacts with E2-ubiquitin conjugating enzyme. In some cases, the F-box family comprises more than 40 members, in which exemplary members include F-box/WD repeat-containing protein 1A (FBXW1A, βTrCP1, Fbxw1, hsSlimb, plkappaBalpha-E3 receptor subunit) and S-phase kinase-associated proteins 2 (SKP2). In some embodiments, the SCF complex (e.g. SCP$^{\beta TrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, UBA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE2I, UBE2I1, UBE2J2, UBE2K, UBE2L3, UBE2L6, UBE2M, UBE2N, UBE2O, UBE2Q1, UBE2Q2, UBE2R1, UBE2R2, UBE2S, UBE2T, UBE2U, UBE2V1, UBE2V2, UBE2Z, ATG2, BIRC5, and UFC1. In some embodiments, the ubiquitinated YAP/TAZ further undergoes the degradation process through the 26S proteasome.

In some embodiments, the Hippo pathway is regulated upstream by several different families of regulators (FIG. 1). In some instances, the Hippo pathway is regulated by the G-protein and its coupled receptors, the Crumbs complex, regulators upstream of the MST kinases, and the adherens junction.

YAP/TAZ Interaction with TEAD

In some embodiments, un-phosphorylated and/or dephosphorylated YAP/TAZ accumulates in the nucleus. Within the nucleus, YAP/TAZ interacts with the TEAD family of transcription factors (e.g. TEAD1, TEAD2, TEAD3, or TEAD4) to activate genes involved in anti-apoptosis and proliferation, such as for example CTFG, Cyr61, and FGF 1.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

YAP/TAZ Regulation Mediated by G-Proteins/GPCRs

Figure 2:
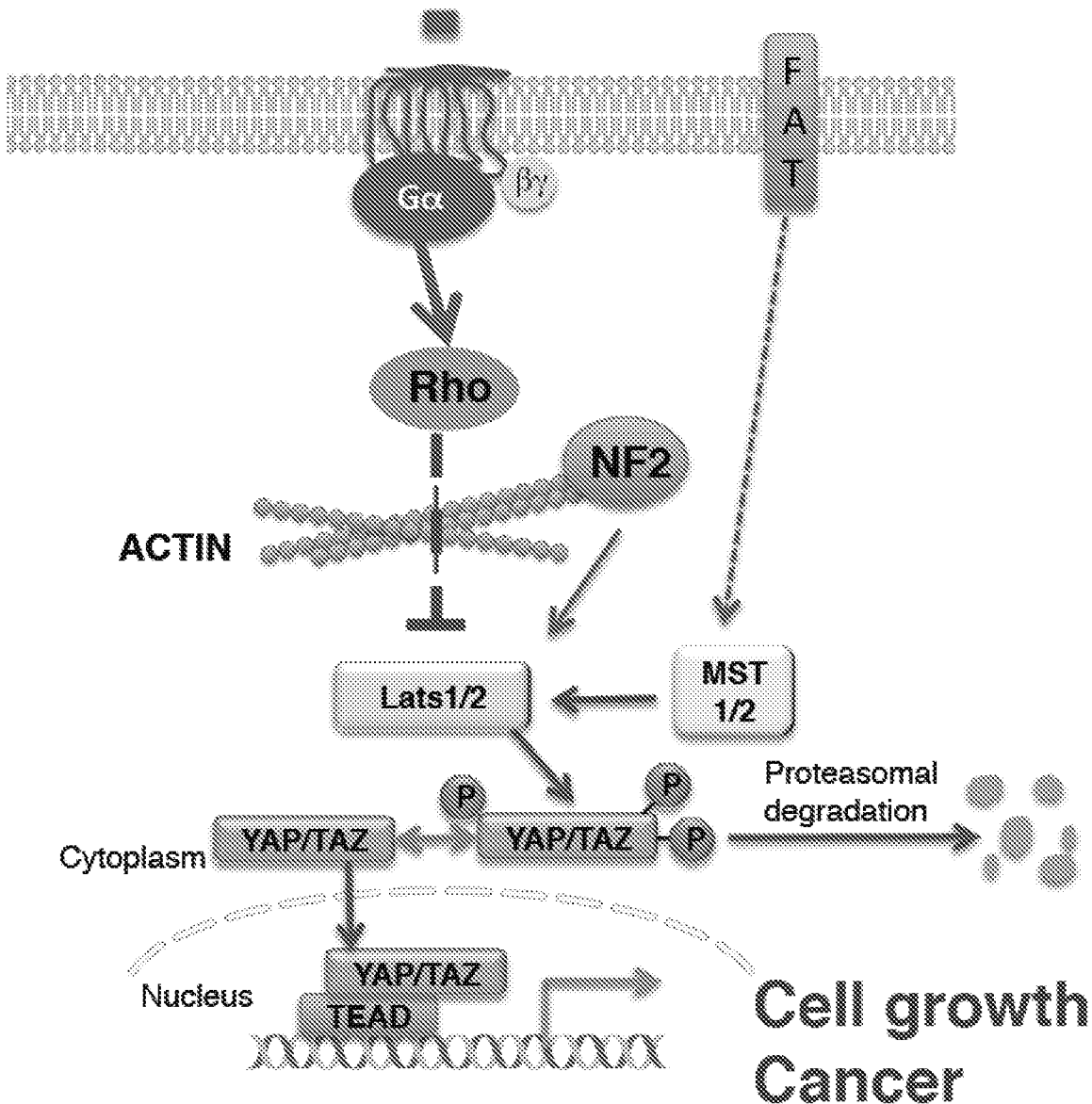
FIG. 2 illustrates a schematic representation of the Hippo signaling pathway regulated by G alpha proteins.

In some embodiments, the Hippo pathway is regulated by the G protein-coupled receptor (GPCR) and G protein (also known as guanine nucleotide-binding proteins) family of proteins (FIG. 2). G proteins are molecular switches that transmit extracellular stimuli into the cell through GPCRs. In some instances, there are two classes of G proteins: monomeric small GTPases; and heterotrimeric G protein complexes. In some instances, the latter class of complexes comprise of alpha ($G_\alpha$), beta ($G_\beta$), and gamma ($G_\gamma$) subunits. In some cases, there are several classes of $G_\alpha$ subunits: $G_{q/11}\alpha$, $G_{12/13}\alpha$, $G_{i/o}\alpha$ (G inhibitory, G other), and $G_s\alpha$ (G stimulatory).

In some instances, $G_i\alpha$ (G inhibitory), $G_o\alpha$ (G other), $G_{q/11}\alpha$, and $G_{12/13}\alpha$ coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s\alpha$, in some embodiments, induces Lats1/2 activity, thereby promoting YAP/TAZ degradation.

$G_q$ Family $G_q\alpha$ (also known as $G_{q/11}$ protein), participates in the inositol trisphosphate (IP$_3$) signal transduction pathway and calcium (Ca$^{2+}$) release from intracellular storage through the activation of phospholipase C (PLC). The activated PLC hydrolyzes phosphatidylinositol 4,5-bisphosphate (PIP$_2$) to diacyl glycerol (DAG) and IP$_3$. In some instances, IP$_3$ then diffuses through the cytoplasm into the ER or the sarcoplasmic reticulum (SR) in the case of muscle cells, and then binds to inositol trisphosphate receptor (InsP3R), which is a Ca$^{2+}$ channel. In some cases, the binding triggers the opening of the Ca$^{2+}$ channel, and thereby increases the release of Ca$^{2+}$ into the cytoplasm.

In some embodiments, the GPCRs that interact with $G_q\alpha$ include, but are not limited to, 5-hydroxytryptamine receptor (5-HT receptor) types 5-HT$_2$ and 5-HT$_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors M$_1$, M$_3$, and M$_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q\alpha$ genes have been associated with cancer. Indeed, studies have shown that mutations in $G_q\alpha$ promote uveal melanoma (UM) tumorigenesis. In some instances, about 80% of UM cases have been detected to contain a mutation in GNAQ and/or GNA11.

In some instances, mutations or modifications of the $G_q\alpha$ genes have been associated with congenital diseases. In some instances, mutations of $G_q\alpha$ have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

$G_{12/13}$ Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g. Rho family such as Cdc42), which is involved in cell differentiation, proliferation, cytoskeletal organization, vesicle trafficking, and nuclear transport.

In some embodiments, the GPCRs that interact with $G_{12/13}\alpha$ include, but are not limited to, purinergic receptors (e.g. P2Y$_1$, P2Y$_2$, P2Y$_4$, P2Y$_6$); muscarinic acetylcholine receptors M1 and M3; receptors for thrombin [protease-activated receptor (PAR)-1, PAR-2]; thromboxane (TXA2); sphingosine 1-phosphate (e.g. S1P$_2$, S1P$_3$, S1P$_4$ and S1P$_5$); lysophosphatidic acid (e.g. LPA$_1$, LPA$_2$, LPA$_3$); angiotensin II (AT1); serotonin (5-HT$_{2c}$ and 5-HT$_4$); somatostatin (sst$_5$); endothelin (ET$_A$ and ET$_B$); cholecystokinin (CCK$_1$); V$_{1a}$ vasopressin receptors; D$_5$ dopamine receptors; fMLP formyl peptide receptors; GAL$_2$ galanin receptors; EP$_3$ prostanoid receptors; $A_1$ adenosine receptors; $\alpha_1$ adrenergic receptors; $BB_2$ bombesin receptors; $B_2$ bradykinin receptors; calcium-sensing receptors; KSHV-ORF74 chemokine receptors; $NK_1$ tachykinin receptors; and thyroid-stimulating hormone (TSH) receptors.

In some instances, $G_{12/13}\alpha$ is further subdivided into $G_{12}$ and $G_{13}$ types which are encoded by GNA12 and GNA13, respectively.

$G_{i/o}$ Family $G_{i/o}\alpha$ (G inhibitory, G other) (also known as $G_i/G_0$ or $G_i$ protein) that suppresses the production of 3',5'-cyclic AMP (cAMP) from adenosine triphosphate (ATP) through an inhibition of adenylate cyclase activity, which converts ATP to cAMP.

In some embodiments, the GPCRs that interact with $G_i\alpha$ include, but are not limited to, 5-hydroxytryptamine receptor (5-HT receptor) types $5-HT_1$ and $5-HT_5$; muscarinic acetylcholine receptors such as $M_2$ and $M_4$; adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as $\delta$, $\kappa$, $\mu$, and nociceptin receptors; prostaglandin receptors such as prostaglandin E receptor 1 ($EP_1$) prostaglandin E receptor 3 ($EP_3$), prostaglandin F receptor (FP), and thromboxane receptor (TP); somatostatin receptors sst1, sst2, sst3, sst4, and sst5; and trace amine-associated receptor 8.

In some instances, there are several types of $G_i\alpha$: $G_i\alpha1$, $G_i\alpha2$, $G_i\alpha3$, $G_i\alpha4$, $G_o\alpha$, $G_t$, $G_{gust}$, and $G_z$. $G_i\alpha1$ is encoded by GNAI1. $G_i\alpha2$ is encoded by GNAI2. $G_i\alpha3$ is encoded by GNAI3. $G_o\alpha$, the $a_o$ subunit, is encoded by GNAO1. $G_t$ is encoded by GNAT1 and GNAT2. $G_{gust}$ is encoded by GNATS. $G_z$ is encoded by GNAZ.

$G_s$ Family $G_s\alpha$ (also known as G stimulatory, $G_s$ alpha subunit, or $G_s$ protein) activates the cAMP-dependent pathway through the activation of adenylate cyclase, which convers adenosine triphosphate (ATP) to 3',5'-cyclic AMP (cAMP) and pyrophosphate. In some embodiments, the GPCRs that interact with $G_s\alpha$ include, but are not limited to, 5-hydroxytryptamine receptor (5-HT receptor) types $5-HT_4$, $5-HT_6$, and $5-HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $\beta_1$, $\beta_2$, and $\beta_3$; calcitonin receptor; calcitonin gene-related peptide receptor; corticotropin-releasing hormone receptor; dopamine receptor $D_1$-like family receptors such as $D_1$ and $D_5$; follicle-stimulating hormone receptor (FSH-receptor); gastric inhibitory polypeptide receptor; glucagon receptor; histamine $H_2$ receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein α-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

In some embodiments, the compounds described herein are inhibitors of transcriptional coactivator with PDZ binding motif/Yes-associated protein transcriptional coactivator (TAZ/YAP). In some embodiments, the compounds described herein increase the phosphorylation of transcriptional coactivator with PDZ binding motif/Yes-associated protein transcriptional coactivator (TAZ/YAP) or decrease the dephosphorylation of transcriptional coactivator with PDZ binding motif/Yes-associated protein transcriptional coactivator (TAZ/YAP). In some embodiments, the compounds increase the ubiquitination of transcriptional coactivator with PDZ binding motif/Yes-associated protein transcriptional coactivator (TAZ/YAP) or decrease the deubiquitination of transcriptional coactivator with PDZ binding motif/Yes-associated protein transcriptional coactivator (TAZ/YAP).

In some embodiments, the compounds disclosed herein are inhibitors of one or more of the proteins encompassed by, or related to, the Hippo pathway. In some instances, the one or more proteins comprise a protein shown in FIGS. 1 and/or 2. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha1$, $G_i\alpha2$, $G_i\alpha3$, $G_i\alpha4$, $G_o\alpha$, $G_t$, $G_{gust}$, and $G_z$. In some embodiments, an inhibitor of the Hippo pathway is an inhibitor of $G_q$. In some embodiments, an inhibitor of the Hippo pathway is an inhibitor of $G_{q/11}$. In some embodiments, an inhibitor of the Hippo pathway is an inhibitor of $G_{q/14}$. In some embodiments, an inhibitor of the Hippo pathway is an inhibitor of $G_{q/15}$. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha1$. In some embodiments, an inhibitor of the Hippo pathway is an inhibitor of $G_i\alpha2$. In some embodiments, an inhibitor of the Hippo pathway is an inhibitor of $G_i\alpha3$. In some embodiments, an inhibitor of the Hippo pathway is an inhibitor of $G_i\alpha4$. In some embodiments, an inhibitor of the Hippo pathway is an inhibitor of $G_o\alpha$. In some embodiments, an inhibitor of the Hippo pathway is an inhibitor of $G_t$. In some embodiments, an inhibitor of the Hippo pathway is an inhibitor of $G_{qust}$. In some embodiments, an inhibitor of the Hippo pathway is an inhibitor of $G_z$.

In some embodiments, an inhibitor of the Hippo pathway is an inhibitor of a core protein of the Hippo pathway. In some embodiments, an inhibitor of the Hippo pathway is an inhibitor of Sav1. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g. 26S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

Further embodiments provided herein include combinations of one or more of the particular embodiments set forth above.

Diseases

Cancer

In some embodiments, the compounds disclosed herein are useful for treating cancer. In some embodiments, the cancer is mediated by activation of transcriptional coactivator with PDZ binding motif/Yes-associated protein transcription coactivator (TAZ/YAP). In some embodiments, the cancer is mediated by modulation of the interaction of YAP/TAZ with TEAD. In some embodiments, the cancer is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the cancer is a solid tumor. In some instances, the cancer is a hematologic malignancy. In some instances, the solid tumor is a sarcoma or carcinoma. In some instances, the solid tumor is a sarcoma. In some instances, the solid tumor is a carcinoma.

Exemplary sarcoma includes, but is not limited to, alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, and telangiectatic osteosarcoma.

Exemplary carcinoma includes, but is not limited to, adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer. In some instances, the liver cancer is primary liver cancer.

In some instances, the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the cancer is uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the cancer is uveal melanoma, mesothelioma, esophageal cancer, or liver cancer. In some cases, the cancer is uveal melanoma. In some cases, the cancer is mesothelioma. In some cases, the cancer is esophageal cancer. In some cases, the cancer is liver cancer. In some cases, the cancer is primary liver cancer.

In some instances, the cancer is a hematologic malignancy. In some embodiments, a hematologic malignancy is a leukemia, a lymphoma, a myeloma, a non-Hodgkin's lymphoma, a Hodgkin's lymphoma, a T-cell malignancy, or a B-cell malignancy. In some instances, a hematologic malignancy is a T-cell malignancy. Exemplary T-cell malignancy includes, but is not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, and treatment-related T-cell lymphomas.

In some instances, a hematologic malignancy is a B-cell malignancy. Exemplary B-cell malignancy includes, but is not limited to, chronic lymphocytic leukemia (CLL), small lymphocytic lymphoma (SLL), high risk CLL, and a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a relapsed or refractory cancer. In some embodiments, the relapsed or refractory cancer is a relapsed or refractory solid tumor. In some embodiments, the relapsed or refractory solid tumor is a relapsed or refractory sarcoma or a relapsed or refractory carcinoma. In some embodiments, the relapsed or refractory carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the relapsed or refractory cancer is selected from relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the relapsed or refractory cancer is relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the relapsed or refractory cancer is relapsed or refractory uveal melanoma, mesothelioma, esophageal cancer, or liver cancer. In some cases, the relapsed or refractory cancer is relapsed or refractory uveal melanoma. In some cases, the relapsed or refractory cancer is relapsed or refractory mesothelioma. In some cases, the relapsed or refractory cancer is relapsed or refractory esophageal cancer. In some cases, the relapsed or refractory cancer is relapsed or refractory liver cancer. In some cases, the relapsed or refractory cancer is relapsed or refractory primary liver cancer.

In some instances, the relapsed or refractory cancer is a relapsed or refractory hematologic malignancy. In some embodiments, a relapsed or refractory hematologic malignancy is a relapsed or refractory leukemia, a relapsed or refractory lymphoma, a relapsed or refractory myeloma, a relapsed or refractory non-Hodgkin's lymphoma, a relapsed or refractory Hodgkin's lymphoma, a relapsed or refractory T-cell malignancy, or a relapsed or refractory B-cell malignancy. In some instances, a relapsed or refractory hematologic malignancy is a relapsed or refractory T-cell malignancy. In some instances, a relapsed or refractory hematologic malignancy is a relapsed or refractory B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a metastasized cancer. In some instances, the metastasized cancer is a metastasized solid tumor. In some instances, the metastasized solid tumor is a metastasized sarcoma or a metastasized carcinoma. In some embodiments, the metastasized carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the metastasized cancer is metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the metastasized cancer is metastasized uveal melanoma, mesothelioma, esophageal cancer, or liver cancer. In some cases, the metastasized cancer is metastasized uveal melanoma. In some cases, the metastasized cancer is metastasized mesothelioma. In some cases, the metastasized cancer is metastasized esophageal cancer. In some cases, the metastasized cancer is metastasized liver cancer. In some cases, the metastasized cancer is metastasized primary liver cancer.

In some instances, the metastasized cancer is a metastasized hematologic malignancy. In some embodiments, the metastasized hematologic malignancy is a metastasized leukemia, a metastasized lymphoma, a metastasized myeloma, a metastasized non-Hodgkin's lymphoma, a metastasized Hodgkin's lymphoma, a metastasized T-cell malignancy, or a metastasized B-cell malignancy. In some instances, a metastasized hematologic malignancy is a metastasized T-cell malignancy. In some instances, a metastasized hematologic malignancy is a metastasized B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Congenital Diseases

In some embodiments, the compounds disclosed herein are useful for treating a congenital disease. In some embodiments, the congenital disease is mediated by activation of transcriptional coactivator with PDZ binding motif/Yes-associated protein transcription coactivator (TAZ/YAP). In some embodiments, the congenital disease is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the congenital disease is the result of a genetic abnormality, an intrauterine environment, errors related to morphogenesis, infection, epigenetic modifications on a parental germline, or a chromosomal abnormality. Exemplary congenital diseases include, but are not limited to, Sturge-Weber Syndrome, Port-Wine stain, Holt-Oram syndrome, abdominal wall defects, Becker muscular dystrophy (BMD), biotinidase deficiency, Charcot-Marie-Tooth (CMT), cleft lip, cleft palate, congenital adrenal hyperplasia, congenital heart defects, congenital hypothyroidism, congenital muscular dystrophy, cystic fibrosis, Down syndrome, Duchenne muscular dystrophy, Fragile X syndrome, Friedreich's ataxia, galactosemia, hemoglobinopathies, Krabbe disease, limb-girdle muscular dystrophy, medium chain acyl-CoA dehydrogenase definiency, myasthenia gravis, neural tube defects, phenylketonuria, Pompe disease, severe combined immunie deficiency (SCID), Stickler syndrome (or hereditary progressive arthro-ophthalmopathy), spinal muscular atrophy, and trisomy 18. In some embodiments, the congenital disease is Sturge-Weber Syndrome or Port-Wine stain. In some embodiments, the congenital disease is Sturge-Weber Syndrome. In some embodiments, the congenital disease is Port-Wine stain.

EXAMPLES

These examples are provided for illustrative purposes only and not to limit the scope of the claims provided herein.

List of Abbreviations

As used above, and throughout the disclosure, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DBA dibenzylideneacetone
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
eq equivalent(s)
Et ethyl
$Et_2O$ diethyl ether
EtOH ethanol
EtOAc ethyl acetate
HPLC high performance liquid chromatography
LAH lithium aluminum anhydride
LCMS liquid chromatography mass spectrometry
Me methyl
MeOH methanol
MS mass spectroscopy
NMM N-methyl-morpholine
NMP N-methyl-pyrrolidin-2-one
NMR nuclear magnetic resonance
RP-HPLC reverse phase-high pressure liquid chromatography
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times were approximate and were Example 1: ethyl 2-[5-[2-[3-(trifluoromethyl)anilino]phenyl]tetrazol-2-yl]acetate (Compound 1)

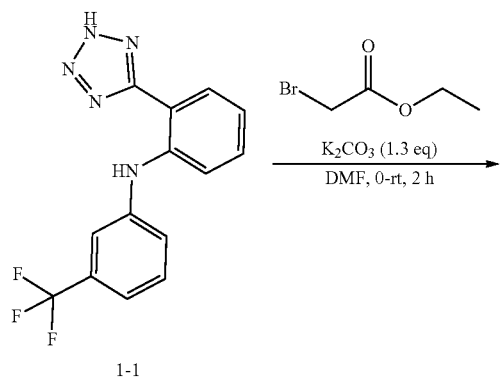

Example 2: 2-[5-[2-[3-(trifluoromethyl)anilino]phenyl]tetrazol-2-yl]acetic Acid (Compound 2)

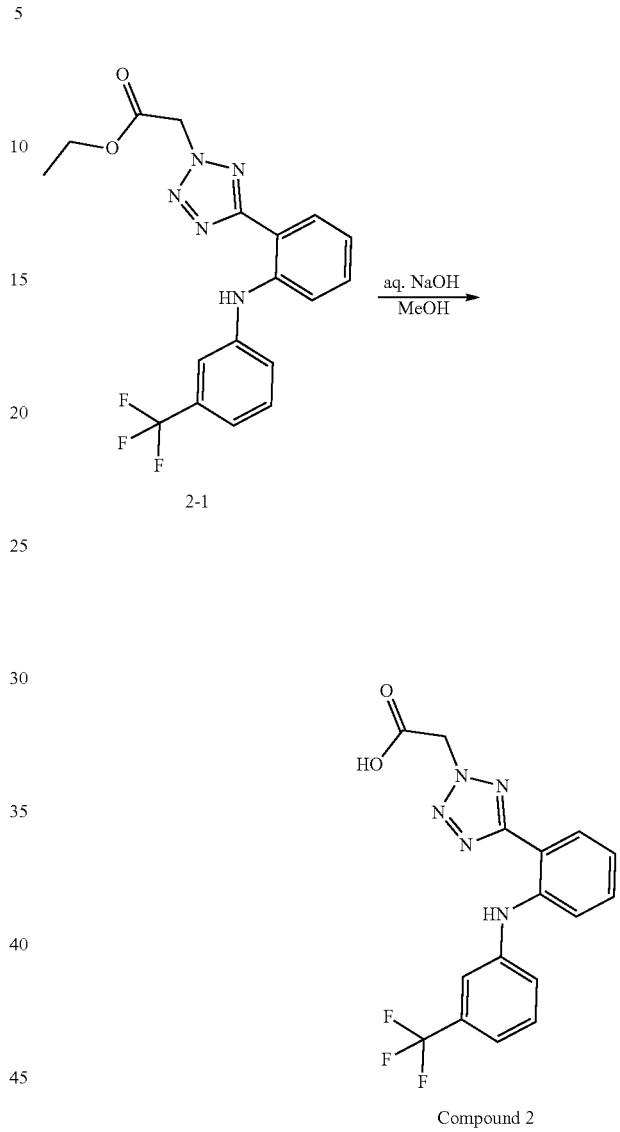

To a mixture of 1-1 (140 mg, 0.459 mmol, 1.00 eq) and K₂CO₃ (84 mg, 0.610 mmol, 1.33 eq) in DMF (14 mL) and CH₃CN (2 mL) was stirred at 0° C. for 5 min. The mixture was added ethyl 2-bromoacetate (80 mg, 0.482 mmol, 1.05 eq), then warmed to 28° C. and stirred for 2 h. LCMS showed the starting material and one peak with the desired MS was detected. The reaction mixture was stirred for an additional 1 h. TLC indicated the starting material was consumed completely. The reaction mixture was concentrated under reduced pressure to remove solvent. The residue was purified by flash silica gel chromatography to provide the title compound (140 mg, 0.322 mmol, 70.2% yield). LCMS (ESI): RT=0.900 min, mass calcd. for $C_{18}H_{16}F_3N_5O_2$ 391.13, m/z found 392.0[M+H]⁺. ¹HNMR (400 MHz, CHLOROFORM-d) δ 8.89 (s, 1H), 8.23 (dd, J=7.60, 1.40 Hz, 1H), 7.50-7.35 (m, 5H), 7.27-7.23 (m, 1H), 7.03-6.99 (m, 1H), 5.50 (s, 2H), 4.34-4.29 (m, 2H), 1.31 (t, J=7.20 Hz, 3H).

To a mixture of 2-1 (20 mg, 46 umol, 1.00 eq) in MeOH (1 mL) and H₂O (1 mL) was added NaOH (12 mg, 0.312 mmol, 6.79 eq) in one portion at 28° C. The mixture was stirred at 45° C. for 30 min. LCMS showed that compound 2-1 was consumed completely. The reaction mixture was concentrated under reduced pressure to remove MeOH. The residue was adjusted to pH 1 by adding HCl (1M), and filtered under reduced pressure to give a residue. LCMS and ¹H NMR confirmed the title compound (4.89 mg, 13.46 umol, 29.27% yield). LCMS (ESI): RT=0.805 min, mass calcd. for $C_{16}H_{12}F_3N_5O_2$ 363.09, m/z found 363.9[M+H]⁺. ¹H NMR (400 MHz, CHLOROFORM-d) δ8.83 (br s, 1H), 8.22 (d, J=7.20 Hz, 1H), 7.49 (s, 1H), 7.43-7.34 (m, 4H), 7.27-7.26 (m, 1H), 7.01 (t, J=7.60 Hz, 1H), 5.55 (s, 2H).

Example 3: 2-[5-[2-[3-(trifluoromethyl)anilino]phenyl]tetrazol-2-yl]ethanol (Compound 3)

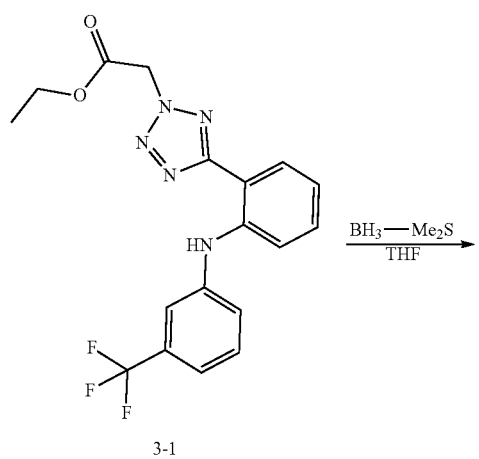

Example 4: ethyl 3-[5-[2-[3-(trifluoromethyl)anilino]phenyl]tetrazol-2-yl]propanoate (Compound 4)

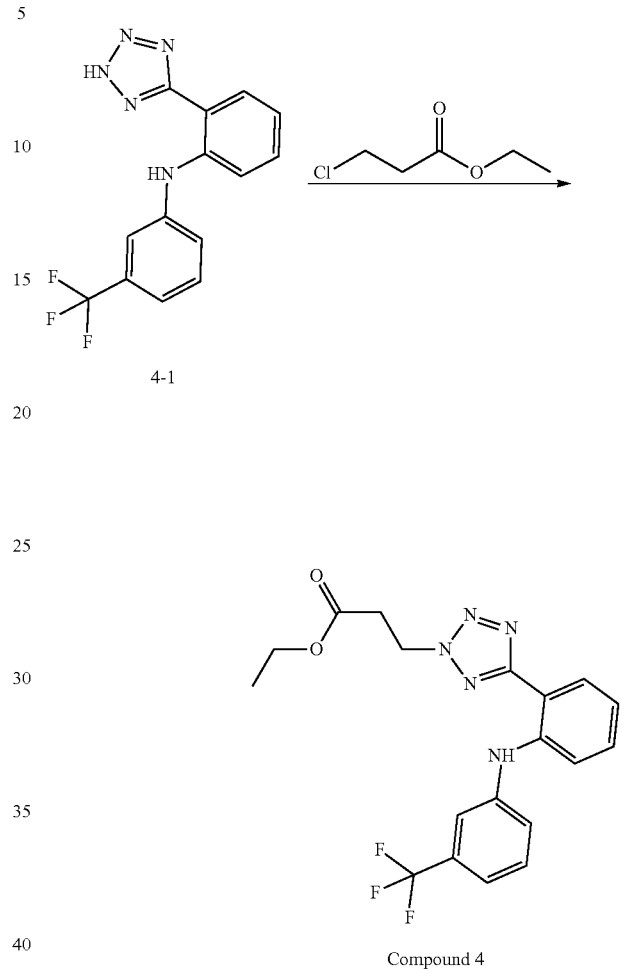

To a mixture of 3-1 (40 mg, 0.102 mmol, 1.00 eq) in THF (5 mL) was added $BH_3$-$Me_2S$ (10 M, 0.15 mL, 15.00 eq) in one portion at 0° C. under $N_2$. The mixture was stirred at 0° C. for 5 min, then heated to 60° C. and stirred for 2 h. LCMS indicated the starting material remained, and one small peak with the desired MS was detected. The reaction mixture was stirred an additional 2 h. LCMS showed 24% of compound 3-1 remained. Several new peaks were shown on LCMS and 52% of the desired compound was detected. The reaction mixture was continued by stirring for 1.5 h. LCMS indicated the starting material was consumed completely and one main peak with the desired mass was detected. TLC (Petroleum ether:Ethyl acetate=5:1) showed one spot had formed. The reaction mixture was quenched with MeOH (5 mL), and then concentrated under reduced pressure to give a residue. The residue was purified by flash silica gel chromatography to provide the title compound (11.10 mg, 30.82 umol, 30.2% yield). LCMS (ESI): RT=0.807 min, mass calcd. for $C_{16}H_{14}F_3N_5O$ 349.12, m/z found 349.9[M+H]$^+$. $^1$HNMR (400 MHz, DMSO-$d_6$) δ 8.74 (s, 1H), 8.05 (d, J=7.60 Hz, 1H), 7.51-7.42 (m, 5H), 7.23 (d, J=7.20 Hz, 1H), 7.14-7.10 (m, 1H), 5.07 (t, J=5.60 Hz, 1H), 4.78 (t, J=5.20 Hz, 2H), 3.97-3.93 (m, 2H).

Compound 4-1 (55 mg, 0.18 mmol, 1.00 eq), ethyl 3-chloropropanoate (74 mg, 0.541 mmol, 3.00 eq) and $K_2CO_3$ (77 mg, 0.559 mmol, 3.10 eq) were taken up into a microwave tube in DMF (3.5 mL). The sealed tube was heated at 130° C. for 30 min under microwave. LCMS showed compound 4-1 remained and one peak with the desired MS was detected. TLC (Ethyl acetate:Petroleum ether=5:1) indicated one new spot had formed. The reaction mixture was diluted with water (30 mL) and extracted with EtOAc (20 mL*6). The combined organic layers were dried with anhydrous $Na_2SO_4$, filtered and concentrated under vacuum. The residue was purified by flash silica gel chromatography to provide the title compound (18.00 mg, 44 umol, 12.2% yield). LCMS (ESI): RT=1.297 min, mass calcd. for $C_{19}H_{18}F_3N_5O_2$ 405.14, m/z found 406.1[M+H]$^+$. $^1$H NMR (400 MHz, CHLOROFORM-d) δ 8.94 (s, 1H), 8.30-8.19 (m, 1H), 7.50 (s, 1H), 7.44-7.36 (m, 4H), 7.27-7.25 (m, 1H), 7.02-7.00 (m, 1H), 5.01 (t, J=6.8, 2H), 4.22-4.16 (m, 2H), 3.15 (t, J=6.8 Hz, 2H), 1.25 (t, J=7.2 Hz, 3H).

Example 5: 2-[2-(2-methoxyethyl)tetrazol-5-yl]-N-[3-(trifluoromethyl)phenyl]aniline (Compound 5)

Example 6: 2-[5-[2-[3-(trifluoromethyl)anilino]phenyl]tetrazol-2-yl]acetamide (Compound 6)

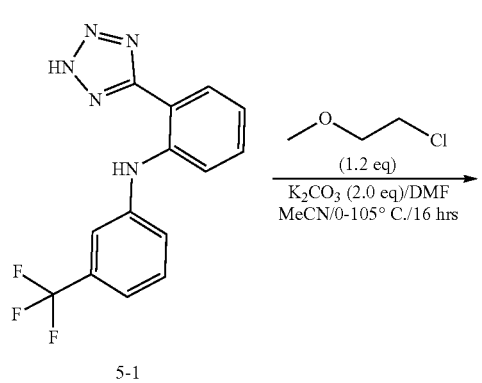

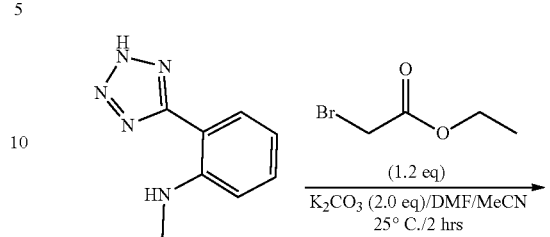

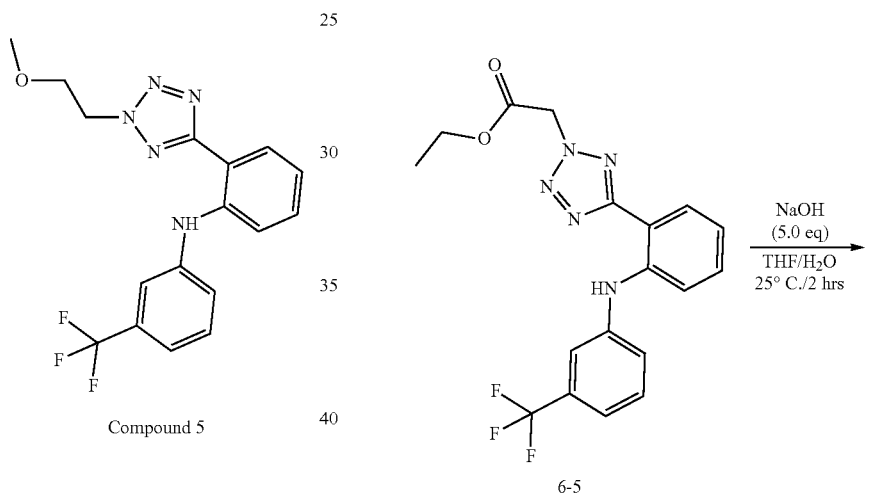

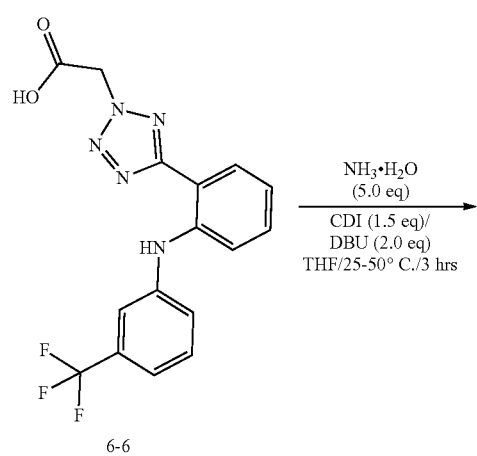

To a solution of 5-1 (50.0 mg, 0.16 mmol, 1.0 eq) in DMF (5.0 mL) and MeCN (0.6 mL) was added K$_2$CO$_3$ (45.3 mg, 0.33 mmol, 2.0 eq) at 0° C. The reaction mixture was stirred at 0° C. for 5 min and 1-chloro-2-methoxy-ethane (18.6 mg, 0.20 mmol, 17.9 uL, 1.20 eq) was added. The reaction mixture was warmed to 25° C. and stirred at 105° C. for 16 hrs. LCMS showed that 5-1 was consumed completely and the desired product was detected. The reaction mixture was diluted with H$_2$O (100 mL), extracted with DCM (3*20 mL). The combined organic layers were washed with brine (3*20 mL), dried over Na$_2$SO$_4$ and filtered. The filtrate was concentrated under reduced pressure. The residue was purified by prep-HPLC to obtain the title compound (4.08 mg, 11.23 umol, 6.86% yield). LCMS (ESI): RT=0.913 min, mass calc. for C$_{17}$H$_{16}$F$_3$N$_5$O 363.13, m/z found 364.0 [M+H]+. $^1$HNMR (400 MHz, DMSO-d$_6$) δ 8.75-8.65 (s, 1H), 8.10-8.00 (d, J=7.7 Hz, 1H), 7.50-7.43 (m, 3H), 7.42-7.30 (br. d, J=4.9 Hz, 1H), 7.26-7.16 (br. d, J=7.5 Hz, 1H), 7.15-7.05 (t, J=6.7 Hz, 1H), 4.95-4.85 (t, J=5.1 Hz, 2H), 3.95-3.85 (t, J=5.1 Hz, 2H), 3.25-3.15 (s, 3H).

-continued

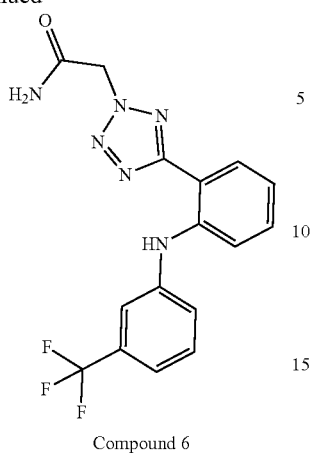

Compound 6

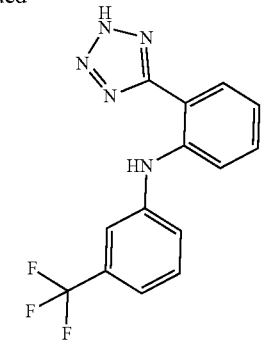

6-4

Step 1: 2-[3-(trifluoromethyl)anilino]benzamide

To a suspension of 6-1 (2.00 g, 7.11 mmol, 1.0 eq) in THF (100.0 mL) was added CDI (1.73 g, 10.67 mmol, 1.5 eq). After stirring at 50° C. for 0.5 hr, the reaction mixture was cooled to 25° C. and DBU (1.73 g, 11.38 mmol, 1.71 mL, 1.6 eq), NH3·H$_2$O (1.99 g, 14.22 mmol, 2.19 mL, 2.0 eq) was added. The reaction mixture was stirred at 50° C. for another 3 hrs. LCMS showed that the desired product was detected. TLC showed that 6-1 was consumed completely and a new spot had formed. The reaction mixture was diluted with H$_2$O (150 mL), extracted with EtOAc (3*50 mL). The combined organic layers were washed with brine (3*50 mL), dried over Na$_2$SO$_4$ and filtered. The filtrate was concentrated under reduced pressure. The residue was purified by flash silica gel to obtain 6-2 (1.40 g, 5.00 mmol, 70.3% yield).

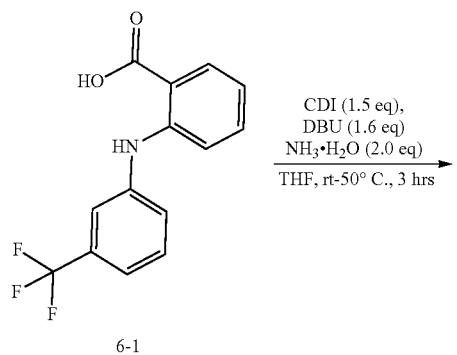

6-1

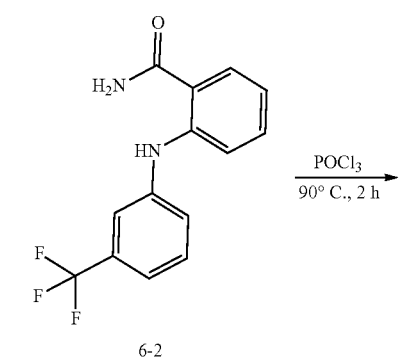

6-2

Step 2: 2-[3-(trifluoromethyl)anilino]benzonitrile 6-2 (1.40 g, 5.00 mmol, 1.00 eq) was added to POCl$_3$ (16.50 g, 107.61 mmol, 10.0 mL, 21.52 eq). The reaction mixture was stirred at 90° C. for 2 hrs. TLC showed that 6-2 was consumed completely and a new spot had formed. The reaction mixture was dropwise added to 150 mL water at 25° C. and stirred vigorously until heat was not given out from the system. Then, the reaction mixture was extracted with EtOAc (3*50 mL) and the combined organic layers were washed with brine (3*50 mL), dried over Na$_2$SO$_4$ and filtered. The filtrate was concentrated under reduced pressure. The residue was purified by flash silica gel chromatography to obtain 6-3 (1.29 g, 4.92 mmol, 98.4% yield).

Step 3: 2-(2H-tetrazol-5-yl)-N-[3-(trifluoromethyl) phenyl]aniline

To a solution of 6-3 (1.09 g, 4.16 mmol, 1.00 eq) in DMF (8.0 mL) was added NaN$_3$ (351.57 mg, 5.41 mmol, 1.30 eq) and NH$_4$Cl (289.27 mg, 5.41 mmol, 189.07 uL, 1.30 eq). The reaction mixture was stirred at 127° C. for 16 hrs. LCMS showed that 6-3 was consumed completely and the desired product was detected. The reaction mixture was quenched by addition of saturated aq. Na$_2$CO$_3$ to adjust the pH to 9, and extracted with EtOAc (3*20 mL). The combined organic layers were washed with brine (3*20 mL), dried over Na$_2$SO$_4$ and filtered. The filtrate was concentrated under reduced pressure, and a residue was formed. The aqueous layer was quenched by aq. NaClO (200 mL) and

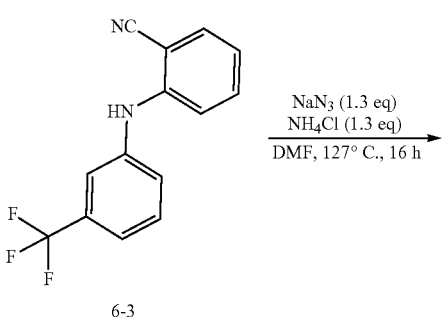

6-3 stewed for 16 hrs. The residue was purified by flash silica gel chromatography to obtain 6-4 (500.0 mg, 1.64 mmol, 39.4% yield).

Step 4: ethyl 2-[5-[2-[3-(trifluoromethyl)anilino]phenyl]tetrazol-2-yl]acetate To a solution of 6-4 (150.0 mg, 0.49 mmol, 1.0 eq), K$_2$CO$_3$ (135.8 mg, 0.98 mmol, 2.0 eq) in MeCN (0.6 mL) and DMF (5.0 mL) was added ethyl 2-bromoacetate (98.5 mg, 0.59 mmol, 65.2 uL, 1.20 eq) at 0° C., and stirred for 5 min. The reaction mixture was then stirred at 25° C. for an additional 2 hrs. LCMS showed that the 6-4 was consumed and the desired product was detected. The reaction mixture was diluted with H$_2$O (30 mL), extracted with EtOAc (3*15 mL). The combined organic layers were washed with brine (3*15 mL), dried over Na$_2$SO$_4$ and filtered. The filtrate was concentrated under reduced pressure. The residue was used to next step without purification. 6-5 (200.0 mg, crude) was obtained as colorless oil.

Step 5: 2-[5-[2-[3-(trifluoromethyl)anilino]phenyl]tetrazol-2-yl]acetic acid To a solution of 6-5 (200.0 mg, 0.51 mmol, 1.00 eq) in THF (5.0 mL) was added the solution of NaOH (102.2 mg, 2.56 mmol, 5.00 eq) in H$_2$O (2.6 mL). The reaction mixture was stirred at 25° C. for 2 hrs. LCMS showed that the 6-5 was consumed and the desired product was detected. The reaction mixture was evaporated to remove THF, 20 mL H$_2$O was added, and 1N HCl was added to adjust the pH to 1; forming a suspension. Then, the suspension was extracted with EtOAc (3*15 mL), and the combined organic layers were washed with brine (3*15 mL), dried over Na$_2$SO$_4$ and filtered. The filtrate was concentrated under reduced pressure. The residue (6-6) was used in the next step without purification (210.0 mg, crude).

Step 6: 2-[5-[2-[3-(trifluoromethyl)anilino]phenyl]tetrazol-2-yl]acetamide

To a suspension of 6-6 (100.0 mg, 0.28 mmol, 1.0 eq) in THF (5.0 mL) was added CDI (67.0 mg, 0.41 mmol, 1.5 eq). After stirring at 50° C. for 0.5 hr, the reaction mixture was cooled to 25° C. and DBU (83.8 mg, 0.55 mmol, 83.0 uL, 2.0 eq), NH$_3$.H$_2$O (77.2 mg, 0.55 mmol, 84.8 uL, 2.0 eq) was added. The reaction mixture was stirred at 50° C. for another 3 hrs. LCMS showed that the desired product was detected. The reaction mixture was diluted with H$_2$O (150 mL), extracted with EtOAc (3*50 mL). The combined organic layers were washed with brine (3*50 mL), dried over Na$_2$SO$_4$ and filtered. The filtrate was concentrated under reduced pressure. The residue was purified by prep-HPLC to obtain Compound 6 (13.23 mg, 35.42 umol, 12.87% yield). LCMS (ESI): RT=0.799 min, mass cal.cd for C$_{16}$H$_{13}$F$_3$N$_6$O 362.11, m/z found 363.0 [M+H]$^+$. $^1$HNMR (400 MHz, DMSO-d$_6$) δ 8.75-8.65 (s, 1H), 8.10-8.00 (d, J=7.5 Hz, 1H), 7.90-7.80 (br. s, 1H), 7.60-7.50 (br. s, 1H), 7.52-7.41 (m, 5H), 7.30-7.20 (d, J=7.7 Hz, 1H), 7.15-7.05 (t, J=6.7 Hz, 1H), 5.60-5.50 (s, 2H).

Example 7: ethyl 2-[5-[2-(4-fluoroanilino)phenyl]tetrazol-2-yl]acetate (Compound 7)

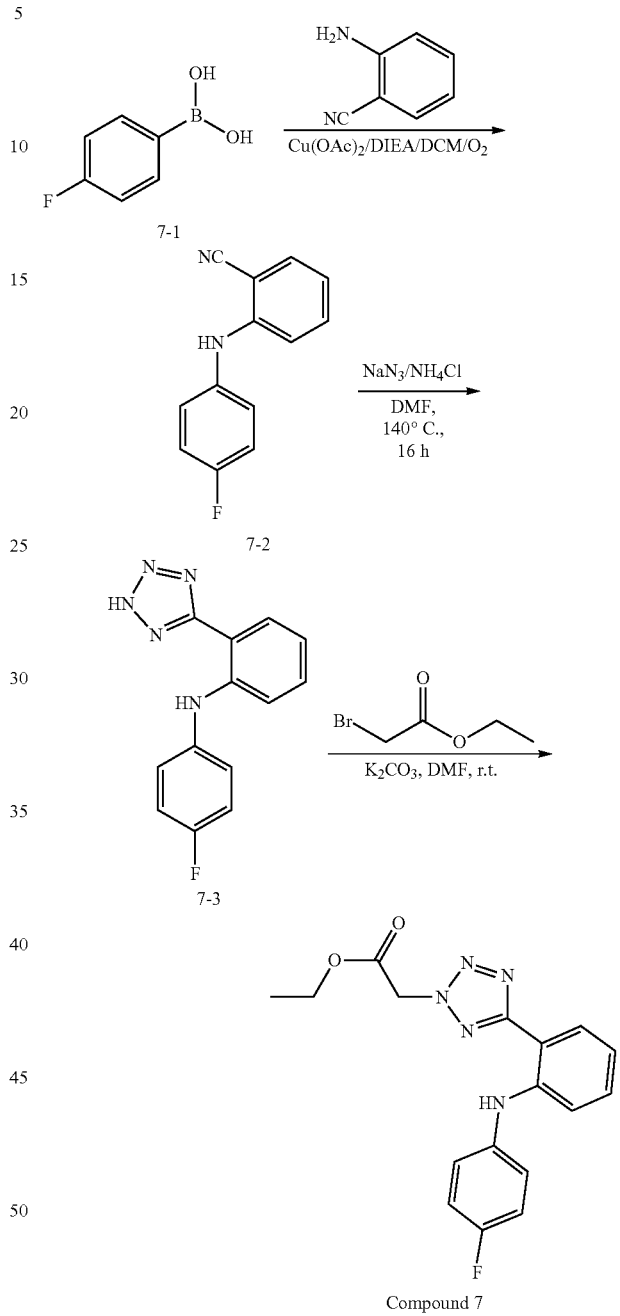

Step 1: 2-(4-fluoroanilino)benzonitrile

To a solution of 7-1 (500.0 mg, 3.6 mmol, 1.0 eq) and 2-aminobenzonitrile (422.2 mg, 3.6 mmol, 1.00 eq) in DCM (10.0 mL) was added Cu(OAc)$_2$ (649.1 mg, 3.6 mmol, 1.0 eq) and DIPEA (748.19 uL, 4.28 mmol, 1.2 eq). The mixture was stirred at 20-30° C. for 16 hour under O$_2$ atmosphere. The reaction was monitored by LC-MS. The reaction mixture was filtered through a Celite pad and washed with DCM (30 mL). The filtrate was concentrated to give a residue. The residue was purified by flash column chromatography to obtain 7-2 (400.0 mg, 1.9 mmol, 52.8% yield). LCMS (ESI): RT=0.783 min, mass calc. for $C_{13}H_9FN_2$ 212.07, m/z found 212.8 [M+H]$^+$; $^1$HNMR (400 MHz, CDCl$_3$) δ (ppm): 7.55-7.46 (m, 1H) 7.37-7.33 (m, 1H) 7.22-7.14 (m, 2H) 7.13-7.04 (m, 2H) 7.01-6.99 (m, 1H) 6.87-6.69 (m, 1H) 6.23 (s, 1H).

Step 2: N-(4-fluorophenyl)-2-(2H-tetrazol-5-yl)aniline

To a solution of 7-2 (100.0 mg, 0.47 mmol, 1.0 eq) in DMF (5.0 mL) was added NH$_4$Cl (65.6 mg, 1.22 mmol, 3.0 eq) and NaN$_3$ (80.0 mg, 1.22 mmol, 3.0 eq). The mixture was stirred at 120° C. for 16 h under an N$_2$ atmosphere. TLC showed a trace of reactant remained and one new spot had formed. The reaction mixture was poured into sat. aq. NaHCO$_3$ (5 mL) and extracted with EtOAc (5 mL*3). The combined organic layers were washed with brine (10 mL), dried over Na$_2$SO$_4$ and filtered. The filtrate was concentrated to give a residue. The residue was used in the next step directly without further purification to obtain 7-3 (120.00 mg, crude). LCMS (ESI): RT=0.768 min, mass calc. for $C_{13}H_{10}FN_5$ 255.09, m/z found 255.9 [M+$^{1-1}$]$^+$.

Step 3: ethyl 2-[5-[2-(4-fluoroanilino)phenyl]tetrazol-2-yl]acetate

To a solution of 7-3 (120.0 mg, 0.47 mmol, 1.0 eq) in DMF (5.0 mL) was added K$_2$CO$_3$ (130.0 mg, 0.94 mmol, 2.0 eq) and ethyl 2-bromoacetate (78.5 mg, 0.47 mmol, 52.0 uL, 1.00 eq). The mixture was stirred at 20-30° C. for 5 hours to give a brown solution. LCMS indicated the starting material was consumed completely and one main peak with the desired MS was detected on LCMS. The reaction mixture was poured into water (10 mL) and extracted with EtOAc (5 mL*3). The combined organic layer was washed with brine (10 mL), dried over Na$_2$SO$_4$ and filtered. The filtrate was concentrated to give a residue. The residue was purified by prep-HPLC to obtain Compound 7 (25.98 mg, 68.8 umol, 14.6% yield, HCl). LCMS (ESI): RT=0.883 min, mass calc. for $C_{17}H_{16}FN_5O_2$ 341.13, m/z found 341.9 [M+H]$^+$; $^1$HNMR (400 MHz, DMSO-d$_6$) δ ppm 8.55 (s, 1H) 8.09-8.06 (m, 1H) 7.40-7.33 (m, 1H) 7.30-7.25 (m, 2H) 7.23-7.16 (m, 3H) 6.99-6.95 (m, 1H) 5.94 (s, 2H) 4.22 (q, J=7.19 Hz, 2H) 1.23 (t, J=7.03 Hz, 3H).

Example 8: 2-[5-[2-(4-fluoroanilino)phenyl]tetrazol-2-yl]ethanol (Compound 8)

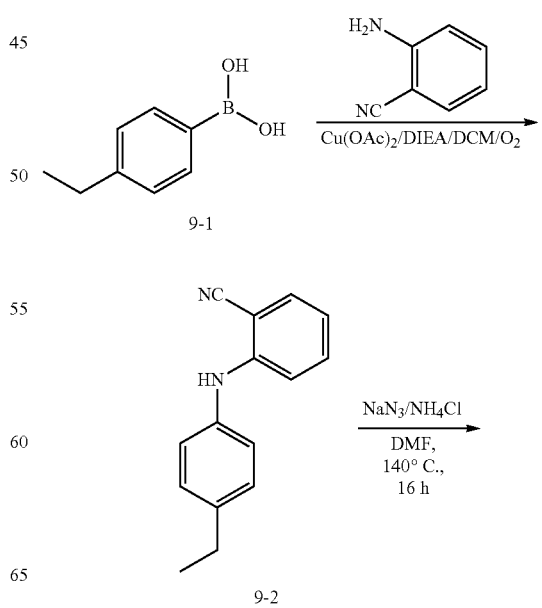

8-1

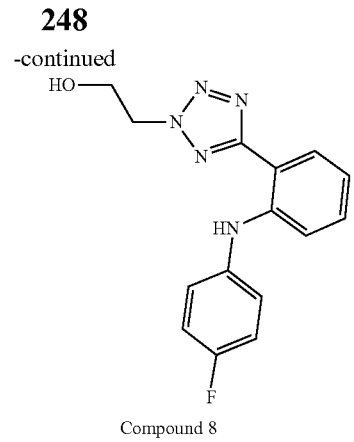

Compound 8

To a solution of 8-1 (150.0 mg, 0.59 mmol, 1.0 eq) in DMF (3.00 mL) was added K$_2$CO$_3$ (162.4 mg, 1.18 mmol, 2.0 eq) and 2-bromoethanol (88.13 mg, 0.71 mmol, 50.0 uL, 1.2 eq) and was stirred for 4 h at 80° C. LC-MS showed 8-1 was consumed completely and ~50% of the desired MS was detected. The reaction mixture was filtered and washed with DCM (10 mL). The filtrate was concentrated to give a residue. The residue was purified by prep-HPLC (TFA). The resulting eluent was concentrated to give a residue, and the residue was lyophilized to give the title compound (18.79 mg, 45.46 umol, 7.74% yield, TFA). (LCMS (ESI): RT=1.998 min, mass calc. for $C_{15}H_{14}FN_5O$ 299.12, m/z found 300.1 [M+H]$^+$; $^1$HNMR (400 MHz, DMSO-d$_6$) δ ppm 8.64 (s, 1H) 8.06 (d, J=7.40 Hz, 1H) 7.39-7.32 (m, 1H) 7.30-7.15 (m, 6H) 6.96 (t, J=7.40 Hz, 1H) 5.13 (s, 1H) 4.80 (t, J=5.02 Hz, 2H) 3.97 (d, J=4.52 Hz, 2H).

Example 9: 2-[5-[2-(4-ethylanilino)phenyl]tetrazol-2-yl]ethanol (Compound 9)

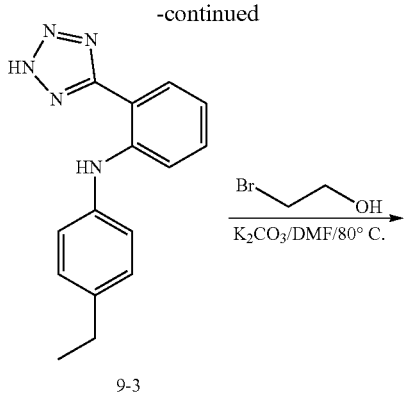

9-3

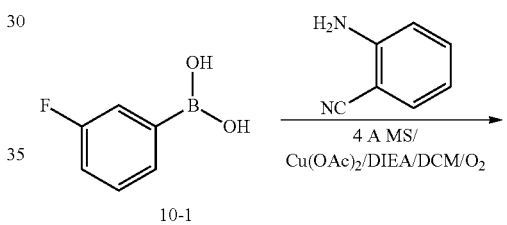

Compound 9

Step 1: 2-(4-ethylanilino)benzonitrile

To a solution of 9-1 (761.3 mg, 5.08 mmol, 1.2 eq) and 2-aminobenzonitrile (500.0 mg, 4.23 mmol, 1.0 eq) in DCM (20.00 mL) was added Cu(OAc)$_2$ (768.7 mg, 4.23 mmol, 1.0 eq) and DIPEA (820.0 mg, 6.35 mmol, 1.1 mL, 1.5 eq). The mixture was stirred at 20-30° C. for 40 hours under O$_2$ atmosphere. The reaction was monitored by LC-MS. The reaction mixture was filtered through a Celite pad and washed with DCM (30 mL). The filtrate was concentrated to give a residue. The residue was purified by flash column chromatography to obtain 9-2 (410.0 mg, 1.84 mmol, 43.6% yield) was obtained as a white solid. $^1$HNMR (400 MHz, CDCl$_3$) δ ppm 7.49-7.47 (m, 1H) 7.37-7.30 (m, 1H) 7.17-7.23 (m, 2H) 7.15-7.08 (m, 3H) 6.82-6.78 (m, 1H) 2.65 (q, J=7.5 Hz, 2H) 1.28-1.22 (t, J=7.5 Hz, 3H).

Step 2: N-(4-ethylphenyl)-2-(2H-tetrazol-5-yl)aniline

To a solution of 9-2 (410.0 mg, 1.84 mmol, 1.0 eq) in DMF (5.00 mL) was added NH$_4$Cl (295.3 mg, 5.52 mmol, 3.0 eq) and NaN$_3$ (358.9 mg, 5.52 mmol, 3.00 eq). The mixture was stirred at 140° C. for 16 h under an N$_2$ atmosphere. The reaction was monitored by LC-MS, and TLC showed that the starting materials were consumed completely. The reaction mixture was poured into sat. aq. NaHCO$_3$ (5 mL) and extracted with EtOAc (5 mL*3). The combined organic layers were washed with brine (10 mL), dried over Na$_2$SO$_4$ and filtered. The filtration was concentrated to give a residue. The residue 9-3 (500.0 mg, crude) was used in next step directly without further purification. LCMS (ESI): RT=0.837 min, mass calc. for C$_{15}$H$_{15}$N$_5$ 265.13, m/z found 265.9 [M+H]$^+$.

Step 3: 2-[5-[2-(4-ethylanilino)phenyl]tetrazol-2-yl]ethanol

To a solution of 9-3 (200.0 mg, 0.75 mmol, 1.0 eq) in DMF (3.0 mL) was added K$_2$CO$_3$ (208.4 mg, 1.5 mmol, 2.0 eq) and 2-bromoethanol (113.0 mg, 0.90 mmol, 1.2 eq). The mixture was stirred at 80° C. for 2 hours to give a brown solution. The reaction was monitored by LC-MS. The reaction mixture was poured into water (10 mL) and extracted with EtOAc (5 mL*3). The combined organic layers were washed with brine (10 mL), dried over Na$_2$SO$_4$ and filtered. The filtrate was concentrated to give a residue. The residue was purified by prep-HPLC (TFA). The eluent was concentrated to give a residue, and the residue was lyophilized to give Compound 9 (43.54 mg, 0.10 mmol, 13.6% yield, TFA). LCMS (ESI): RT=2.207 min, mass calc. for C$_{17}$H$_{19}$N$_5$O 309.16, m/z found 310.0 [M+H]$^+$; $^1$HNMR (400 MHz, DMSO-d$_6$) δ ppm 8.68 (s, 1H) 8.07 (d, J=7.28 Hz, 1H) 7.41-7.25 (m, 2H) 7.18 (s, 4H) 6.93 (t, J=6.78 Hz, 1H) 4.80 (s, 2H) 3.98 (s, 2H) 2.65-2.53 (m, 2H) 1.18 (t, J=7.28 Hz, 3H).

Example 10: 2-(5-(2-((3-fluorophenyl)amino)phenyl)-2H-tetrazol-2-yl)ethanol (Compound 10)

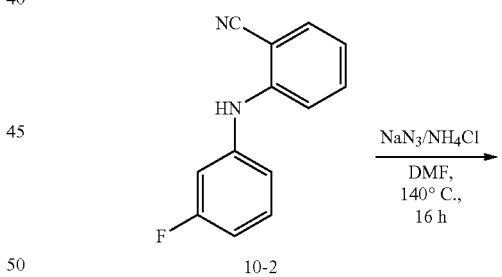

10-1

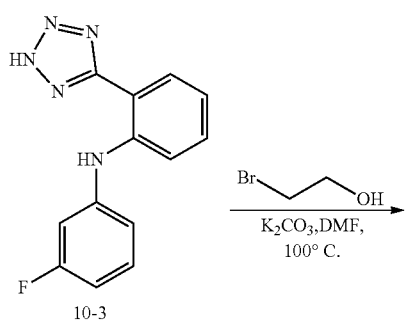

10-2

10-3

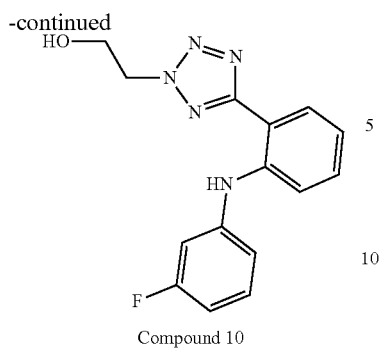

Compound 10

Step 1: 2-((3-fluorophenyl)amino)benzonitrile

To the solution of 2-aminobenzonitrile (422 mg, 4.0 mmol, 1.0 eq) in DCM (10 mL) was added 10-1 (500 mg, 4.0 mmol, 1.0 eq), Cu(OAc)$_2$ (648 mg, 4.0 mmol, 1.0 eq) and DIEA (554 mg, 4 mmol, 748 uL, 1.2 eq). The mixture was stirred at 30° C. for 16 hr. The reaction was monitored by TLC. The reaction solution was concentrated under reduced pressure. The residue was purified by column chromatography (SiO$_2$) to give compound 10-2 (343 mg, 1.6 mmol, 45% yield).

Step 2: N-(3-fluorophenyl)-2-(2H-tetrazol-5-yl)aniline

To the solution of 10-2 (343 mg, 1.6 mmol, 1.0 eq) in DMF (2 mL) was added NaN$_3$ (316 mg, 4.9 mmol, 3.0 eq) and NH$_4$Cl (260 mg, 4.9 mmol, 3.0 eq). The mixture was stirred at 140° C. for 16 hr under N$_2$ atmosphere. The reaction was monitored by LCMS. The reaction solution was poured into HCl aqueous (1M, 20 mL). An insoluble solid appeared. The mixture was filtered and the solid was washed with H$_2$O (20 mL*2) to give 10-3 (357 mg, 1.4 mmol, 86% yield).

Step 3: 2-(5-(2-((3-fluorophenyl)amino)phenyl)-2H-tetrazol-2-yl)ethanol

To the solution of 10-3 (157 mg, 0.6 mmol, 1.0 eq) in DMF (5 mL) was added 2-bromoethanol (92 mg, 0.7 mmol, 52 uL, 1.2 eq) and K$_2$CO$_3$ (128 mg, 0.9 mmol, 1.5 eq). The mixture was stirred at 100° C. for 16 hr. The reaction was monitored by LCMS. The reaction solution was concentrated under reduced pressure. The residue was purified by Prep-HPLC to give Compound 10 (29.13 mg, 95.4 umol, 15.5% yield). LCMS (ESI): RT=1.152 min, mass calc. for C$_{15}$H$_{14}$FN$_5$O 299.12, m/z found 300.0 [M+H]$^+$, $^1$HNMR (400 MHz, DMSO-d$_6$) δ 8.72 (s, 1H), 8.10-8.03 (m, 1H), 7.50-7.42 (m, 2H), 7.34-7.28 (m, 1H), 7.12-7.06 (m, 1H), 7.04-6.97 (m, 2H), 6.78-6.70 (m, 1H), 5.08 (t, J=5.5 Hz, 1H), 4.80 (t, J=5.3 Hz, 2H), 3.97 (q, J=5.3 Hz, 2H).

Example 11: 2-(5-(2-((4-(Trifluoromethoxy)phenyl)amino)phenyl)-2H-tetrazol-2-yl)ethanol (Compound 11)

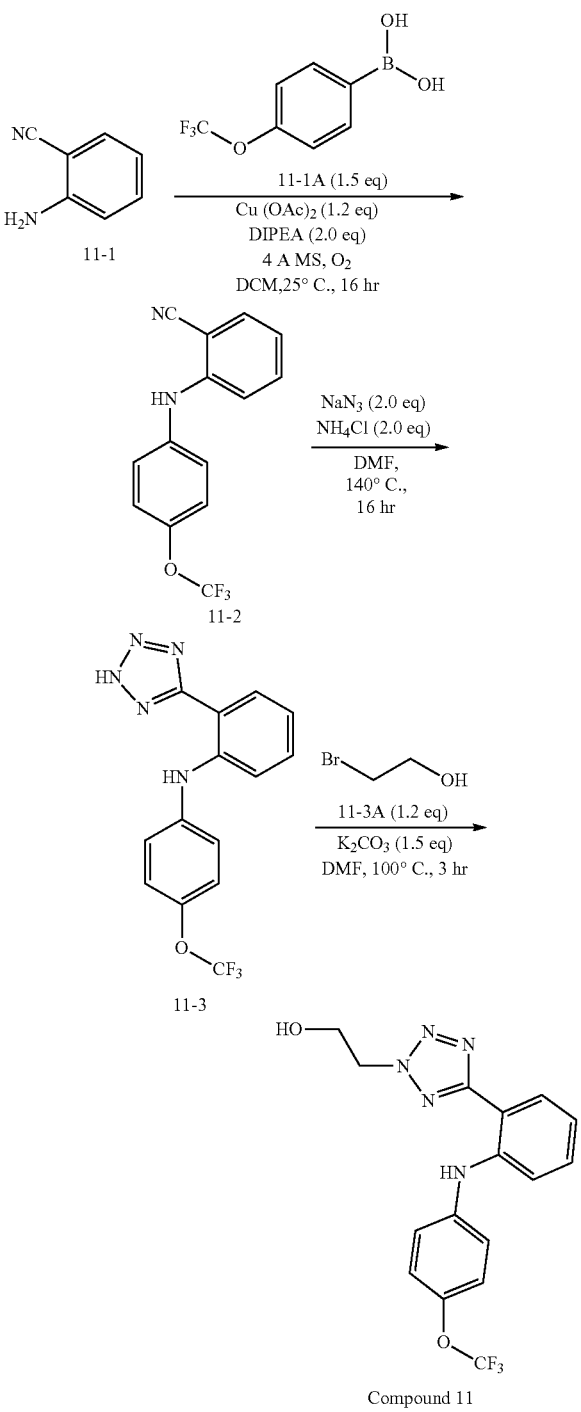

Compound 11

Step 1: 2-((4-(Trifluoromethoxy)phenyl)amino)benzonitrile

To a solution of 11-1 (500 mg, 4.23 mmol, 1.0 eq), 11-1A (1.3 g, 6.4 mmol, 1.5 eq), Cu(OAc)$_2$ (922 mg, 5.08 mmol, 1.2 eq), DIPEA (1.1 g, 8.5 mmol, 2.0 eq) in DCM (10 mL)

was added 4 A MS (200 mg). The reaction mixture was stirred at 25° C. for 16 hours under O$_2$. The reaction mixture was concentrated under reduced pressure. The mixture was diluted with water (30 mL) and the resultant mixture was extracted with DCM (50 mL*3). The combined organic layers were dried over Na$_2$SO$_4$, filtered and concentrated to dryness under reduced pressure. The residue was purified by column chromatography over silica gel to afford 11-2 (850 mg, 72% yield). LCMS (ESI): RT=0.862 min, mass calc. for C$_{14}$H$_9$F$_3$N$_2$O 278.07, m/z found 278.8 [M+H]$^+$.

Step 2: 2-(2H-Tetrazol-5-yl)-N-(4-(trifluoromethoxy)phenyl)aniline

A solution of 11-2 (300 mg, 1.08 mmol, 1.0 eq), NH$_4$Cl (116 mg, 2.16 mmol, 2.0 eq) and NaN$_3$ (140 mg, 2.16 mmol, 2.0 eq) in DMF (4 mL) was stirred at 140° C. for 16 hours. The reaction mixture was acidified with HCl (1M) to pH 2. The mixture was diluted with water (30 mL) and the resultant mixture was extracted with DCM (EtOAc mL*3). The combined organic layers were dried over Na$_2$SO$_4$, filtered and concentrated to dryness under reduced pressure. The residue was purified by column chromatography over silica gel to afford 11-3 (210 mg, 59% yield). LCMS (ESI): RT=1.215 min, mass calc. for C$_{14}$H$_{10}$F$_3$N$_5$O 321.08, m/z found 321.9 [M+H]$^+$, $^1$HNMR (400 MHz, DMSO-d$_6$) δ 9.09 (s, 1H), 7.89 (d, J=7.8 Hz, 1H), 7.48-7.41 (m, 2H), 7.33-7.25 (m, 4H), 7.11-7.04 (m, 1H).

Step 3: 2-(5-(2-((4-(Trifluoromethoxy)phenyl) amino)phenyl)-2H-tetrazol-2-yl)ethanol To a solution of 11-3 (100 mg, 0.311 mmol, 1.0 eq) and 11-3A (47 mg, 0.37 mmol, 1.2 eq) in DMF (3 mL) was added K$_2$CO$_3$ (65 mg, 0.47 mmol, 1.5 eq). The reaction mixture was stirred at 100° C. for 3 hours. The reaction mixture was concentrated under reduced pressure. The mixture was diluted with water (10 mL) and the resultant mixture was extracted with DCM (30 mL*2). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely to obtain Compound 11 (37.94 mg, 33% yield). LCMS (ESI): RT=2.259 min, mass calc. for C$_{16}$H$_{14}$F$_3$N$_5$O$_2$ 365.11, m/z found 366.0 [M+H]$^+$, $^1$HNMR (400 MHz, DMSO-d$_6$) δ 8.72 (s, 1H), 8.07 (d, J=7.5 Hz, 1H), 7.45-7.39 (m, 2H), 7.33-7.26 (m, 4H), 7.08-7.04 (m, 1H), 5.15-5.02 (m, 1H), 4.80 (t, J=5.3 Hz, 2H), 3.97 (t, J=5.1 Hz, 2H)

Example 12: 2-[5-[2-(4-methoxyanilino)phenyl] tetrazol-2-yl]ethanol (Compound 12)

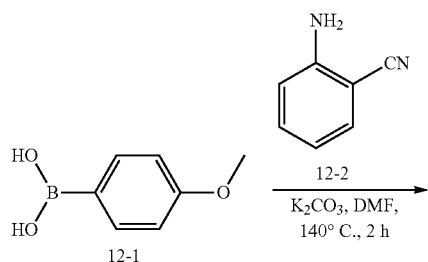

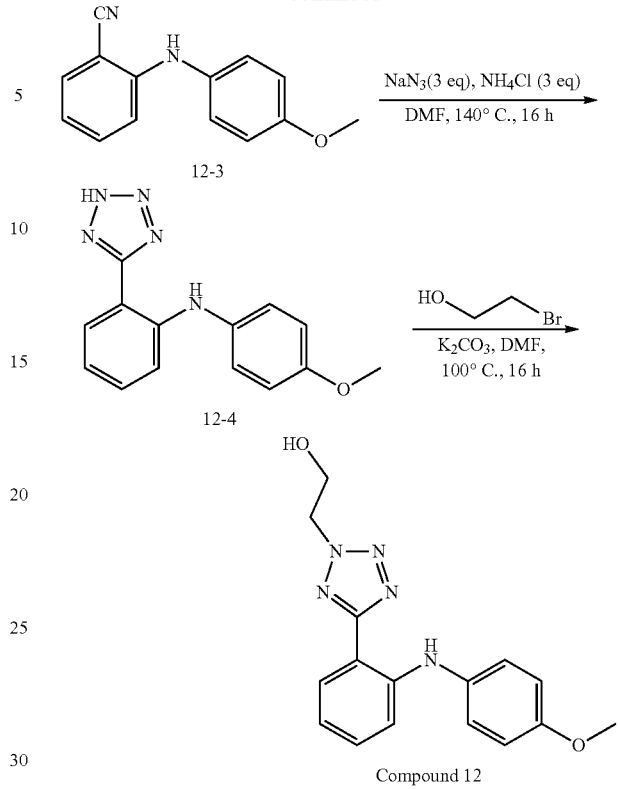

Step 1: 2-(4-methoxyanilino)benzonitrile

To a solution of 12-1 (700 mg, 4.61 mmol, 1.0 eq) and 12-2 (545 mg, 4.61 mmol, 1.0 eq) in DCM (10 mL) was added DIEA (714 mg, 5.53 mmol, 965 uL, 1.2 eq), Cu(OAc)$_2$ (837 mg, 4.61 mmol, 1.0 eq) and 4 A MS (500 mg, 4.61 mmol, 1.0 eq). The resulting mixture was stirred at 30° C. for 16 hr under O$_2$. LCMS and TLC (Petroleum ether:Ethyl acetate=10/1) showed the desired compound was found and the starting material remained. The mixture was concentrated in vacuo to give a crude product. The crude product was purified by column chromatography (silica) to give 12-3 (380 mg, 1.57 mmol, 34% yield). LCMS (ESI): RT=0.790 min, mass calc. for C$_{14}$H$_{12}$N$_2$O 224.09, m/z found 224.8 [M+H]$^+$; $^1$HNMR (400 MHz, CHLOROFORM-d) δ 7.48 (dd, J=1.5, 7.8 Hz, 1H), 7.33 (ddd, J=1.5, 7.4, 8.7 Hz, 1H), 7.20-7.14 (m, 2H), 6.97-6.90 (m, 3H), 6.81-6.75 (m, 1H), 6.21 (br s, 1H).

Step 2: N-(4-methoxyphenyl)-2-(2H-tetrazol-5-yl) aniline

To a solution of 12-3 (200 mg, 0.825 mmol, 1.0 eq) and NH$_4$Cl (132 mg, 2.47 mmol, 87 uL, 3.0 eq) in DMF (2 mL) was added NaN$_3$ (161 mg, 2.47 mmol, 3.0 eq). The resulting mixture was stirred at 140° C. for 16 hr. The reaction was monitored by LCMS. The reaction mixture was poured into cold water (10 mL), HCl (1N, 1 mL) and then extracted by ethyl acetate (3×10 mL). The combined organic layers were washed with brine (10 mL*2) dried over Na$_2$SO$_4$, concentrated under reduced pressure to give 12-4 (300 mg, crude), and the compound was directly used without further purification. LCMS (ESI): RT=0.762 min, mass calc. for C$_{14}$H$_{13}$N$_5$O 267.11, m/z found 267.9 [M+H]$^+$.

Step 3: 2-[5-[2-(4-methoxyanilino)phenyl]tetrazol-2-yl]ethanol

To a solution of 12-4 (100 mg, 0.322 mmol, 1.0 eq) and 2-bromoethanol (60 mg, 0.483 mmol, 34 uL, 1.5 eq) in DMF (2 mL) was added K$_2$CO$_3$ (89 mg, 0.644 mmol, 2.0 eq). The resulting mixture was stirred at 100° C. for 1 hour. The reaction was monitored by LCMS. The mixture was concentrated in vacuo to give a crude product. The crude product was purified by HPLC to give Compound 12 (40 mg, 0.128 mmol, 40% yield). LCMS (ESI): RT=2.023 min, mass calc. for C$_{16}$H$_{17}$N$_5$O$_2$ 311.14, m/z found 312.0 [M+H]$^+$; $^1$HNMR (400 MHz, DMSO-d$_6$) δ 8.59 (s, 1H), 8.08 (dd, J=1.5, 7.9 Hz, 1H), 7.34-7.28 (m, 1H), 7.22 (d, J=8.8 Hz, 2H), 7.08 (d, J=8.4 Hz, 1H), 6.98 (d, J=8.8 Hz, 2H), 6.89 (t, J=7.4 Hz, 1H), 5.11 (t, J=5.5 Hz, 1H), 4.82 (t, J=5.3 Hz, 2H), 3.99 (q, J=5.4 Hz, 2H), 3.78 (s, 3H).

Example 13: 3-[5-[2-[3-(trifluoromethyl)anilino]phenyl]tetrazol-2-yl]propan-1-ol (Compound 13)

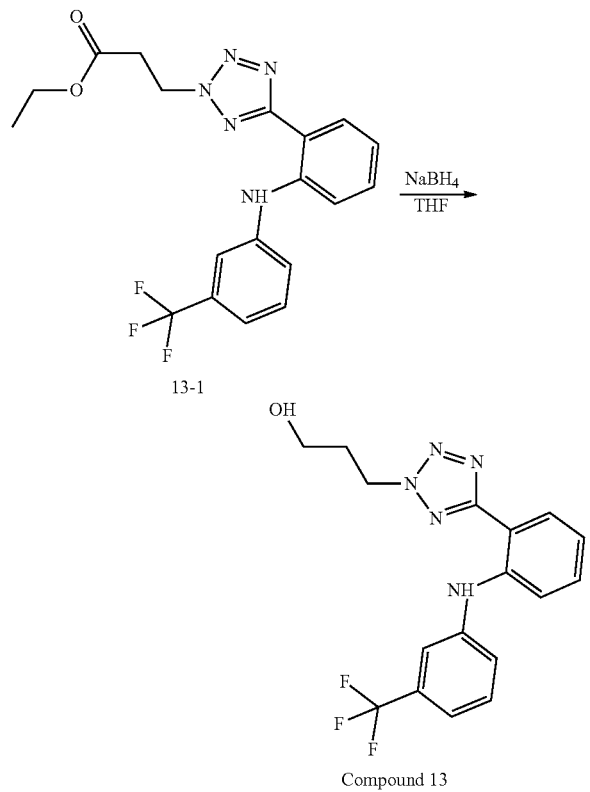

Compound 13

To a mixture of 13-1 (12.0 mg, 30 umol, 1.00 eq) in THF (2 mL) was added NaBH$_4$ (4.5 mg, 118 umol, 4.00 eq) at 28° C. under N$_2$. The mixture was heated to 60° C. and stirred for 3 h. LCMS showed the starting material was remained and one main peak with the desired MS was detected. The reaction mixture was quenched by addition H$_2$O (10 mL) at 0° C. and concentrated under reduced pressure to remove solvent. The residue was purified by prep-HPLC to provide the title compound (4.43 mg, 11.8 umol, 39.9% yield). LCMS (ESI): RT=1.226 min, mass calcd. for C$_{17}$H$_{16}$F$_3$N$_5$O, 363.13 m/z found 364.0[M+H]$^+$. $^1$HNMR (400 MHz, CHLOROFORM-d) δ 9.01 (s, 1H), 8.20 (dd, J=7.60, 1.20 Hz, 1H), 7.50 (s, 1H), 7.46-7.40 (m, 3H), 7.39-7.33 (m, 1H), 7.26-7.22 (m, 1H), 7.04-6.98 (m, 1H), 4.89 (t, J=6.80 Hz, 2H), 3.77 (t, J=5.60 Hz, 2H), 2.33 (quin, J=6.30 Hz, 2H), 1.72 (br s, 1H).

Example 14: tert-butyl N-[2-[5-[2-[3-(trifluoromethyl)anilino]phenyl]tetrazol-2-yl]ethyl]carbamate (Compound 14)

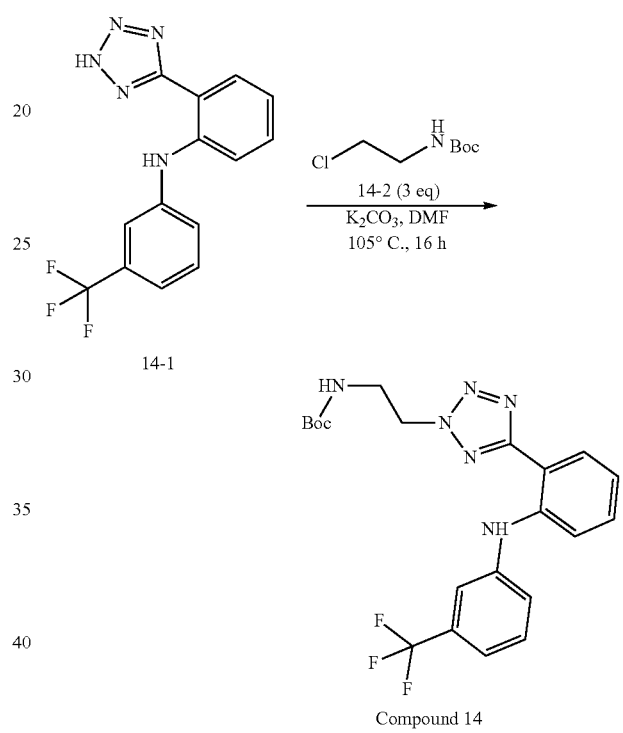

Compound 14

A mixture of 14-1 (160 mg, 0.524 mmol, 1.00 eq) and K$_2$CO$_3$ (254 mg, 1.83 mmol, 3.50 eq) in DMF (8 mL) was stirred at 28° C. for 5 min. To the mixture was added 14-2 (282 mg, 1.57 mmol, 3.00 eq), and then the mixture was heated to 105° C. and stirred for 18 h. LCMS showed the starting material was consumed completely and one main peak with the desired MS was detected. TLC indicated one new spot had formed. The reaction mixture was diluted with water (20 mL) and extracted with EtOAc (20 mL*6). The combined organic layers were dried with anhydrous Na$_2$SO$_4$, filtered and concentrated under vacuum. The residue was purified by flash silica gel chromatography to provide the title compound (115 mg, 0.250 mmol, 47.7% yield). LCMS (ESI): RT=1.357 min, mass calcd. for C$_{21}$H$_{23}$F$_3$N$_6$O$_2$, 448.18 m/z found 393.0[M+H-56]$^+$. $^1$HNMR (400 MHz, CHLOROFORM-d) δ8.94 (s, 1H), 8.20 (dd, J=7.60, 1.20 Hz, 1H), 7.51 (s, 1H), 7.47-7.41 (m, 3H), 7.39-7.34 (m, 1H), 7.26-7.23 (m, 1H), 7.01 (t, J=7.4 Hz, 1H), 4.90-4.77 (m, 3H), 3.87-3.78 (m, 2H), 1.42 (s, 9H).

Example 15: 2-[2-(2-aminoethyl)tetrazol-5-yl]-N-[3-(trifluoromethyl)phenyl]aniline (Compound 15)

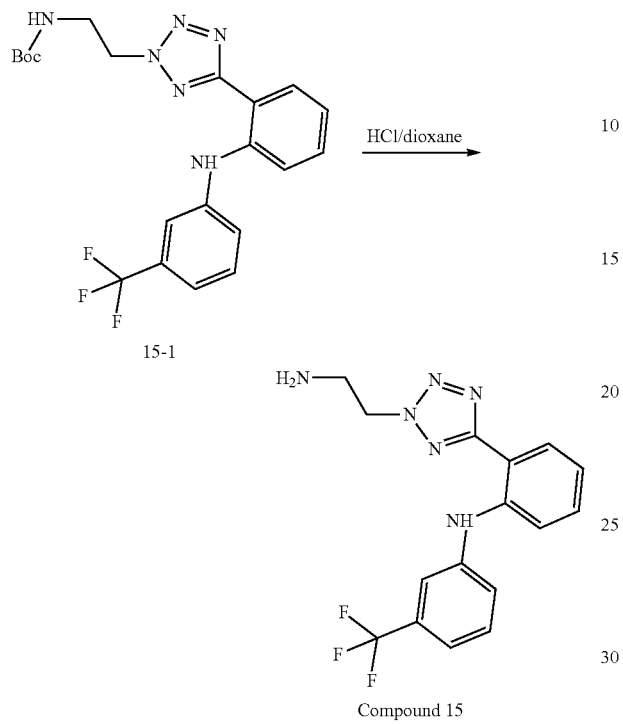

Compound 15-1 (100 mg, 0.223 mmol, 1.00 eq) in HCl/dioxane (4 M, 2 mL, 35.87 eq) was stirred at 28° C. for 2 h. LCMS showed the starting material was consumed completely and one main peak with the desired MS was detected. The reaction mixture was concentrated under reduced pressure to remove solvent. The residue was purified by prep-HPLC (HCl condition) to provide the title compound (45 mg, 0.115 mmol, 51.4% yield, HCl). LCMS (ESI): RT=0.705 min, mass calcd. for $C_{16}H_{15}F_3N_6$, 348.13 m/z found 348.9[M+H]$^+$. $^1$HNMR (400 MHz, DMSO-d$_6$) δ 8.71 (s, 1H), 8.33 (br s, 3H), 8.04 (d, J=7.20 Hz, 1H), 7.53-7.42 (m, 5H), 7.22 (d, J=7.20 Hz, 1H), 7.18-7.11 (m, 1H), 5.05 (t, J=6.00 Hz, 2H), 3.54-3.44 (m, 2H).

Example 16: 2-[5-[2-(2-ethylanilino)phenyl]tetrazol-2-yl]ethanol (Compound 16)

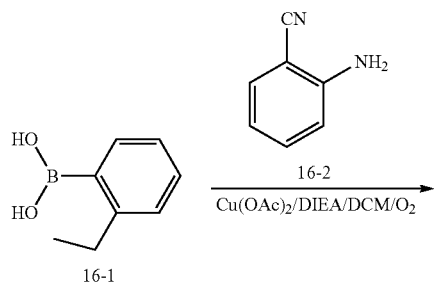

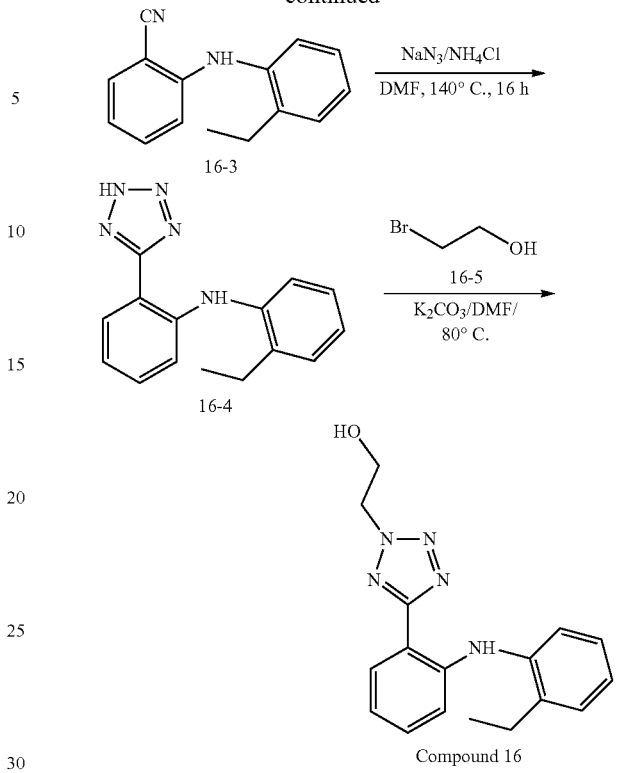

Step 1: 2-(2-ethylanilino)benzonitrile

To a solution of 16-2 (500.0 mg, 4.23 mmol, 1.0 eq) and 16-1 (634.4 mg, 4.23 mmol, 1.0 eq) in DCM (10.0 mL) was added DIEA (656.0 mg, 5.1 mmol, 886.5 uL, 1.2 eq) and Cu(OAc)$_2$ (768.3 mg, 4.23 mmol, 1.0 eq). The mixture was stirred at 30° C. for 16 hour under O$_2$ atmosphere. LCMS showed the desired compound was formed. TLC (30% ethyl acetate in petroleum ether, Rf=0.6) showed a new spot had appeared. The reaction was filtered through celatom and concentrated under reduced pressure to give a residue. The crude product was purified by column chromatography over silica gel to give 16-3 (280.0 mg, 1.26 mmol, 29.8% yield) a colourless oil. LCMS (ESI): RT=0.857 min, mass calc. for $C_{15}H_{14}N_2$ 222.12, m/z found 222.9 [M+H]$^+$; $^1$HNMR (400 MHz, DMSO-d$_6$) δ 7.86 (s, 1H), 7.57 (dd, J=1.5, 7.8 Hz, 1H), 7.41-7.34 (m, 1H), 7.23-7.14 (m, 3H), 7.11-7.06 (m, 1H), 6.85-6.79 (m, 1H), 6.53 (d, J=8.5 Hz, 1H), 2.55-2.52 (m, 2H), 1.11 (d, J=1.5 Hz, 3H).

Step 2: 2-ethyl-N-[2-(2H-tetrazol-5-yl)phenyl]aniline

To a solution of 16-3 (280.0 mg, 1.26 mmol, 1.0 eq) in DMF (10.0 mL) was added NH$_4$Cl (202.4 mg, 3.78 mmol, 0.13 mL, 3.0 eq) and NaN$_3$ (819.1 mg, 12.6 mmol, 10.0 eq). The mixture was stirred at 140° C. for 16 hour under an N$_2$ atmosphere. LCMS showed the desired compound had formed. The reaction mixture was poured into sat. aq. NaHCO$_3$ (5 mL) and extracted with EtOAc (5 mL*2). The combined organic layer was washed with brine (10 mL), dried over Na$_2$SO$_4$ and filtered. The solvent was removed under reduced pressure to afford 16-4 (300.0 mg, 1.13 mmol, 89.7% yield), which was directly used without further purification. LCMS (ESI): RT=0.819 min, mass calc. for $C_{15}H_{15}N_5$ 265.13, m/z found 265.9 [M+H]+.

Step 3: 2-[5-[2-(2-ethylanilino)phenyl]tetrazol-2-yl]ethanol

To a solution of 16-4 (100.0 mg, 0.38 mmol, 1.0 eq) in DMF (5.0 mL) was added $K_2CO_3$ (78.1 mg, 0.57 mmol, 1.5 eq) and 16-5 (56.5 mg, 0.45 mmol, 32.1 uL, 1.2 eq). The mixture was stirred at 100° C. for 3 hours under an $N_2$ atmosphere. LCMS showed the desired compound had formed. The reaction was filtered to give a crude product. The crude product was purified by prep-HPLC to give Compound 16 (21.11 mg, 32.77 umol, 68.7% yield). LCMS (ESI): RT=0.832 min, mass calc. for $C_{17}H_{19}N_5O$ 309.16, m/z found 309.9 [M+H]+; 1HNMR (400 MHz, DMSO-$d_6$) δ 8.66 (s, 1H), 8.11 (dd, J=1.5, 8.0 Hz, 1H), 7.35-7.28 (m, 3H), 7.25-7.19 (m, 1H), 7.13-7.07 (m, 1H), 7.03 (d, J=8.3 Hz, 1H), 6.94-6.87 (m, 1H), 5.11 (br s, 1H), 4.81 (t, J=5.1 Hz, 2H), 3.98 (t, J=5.1 Hz, 2H), 2.65 (q, J=7.5 Hz, 2H), 1.19 (t, J=7.5 Hz, 3H).

Example 17: 2-[5-[2-(3-ethylanilino)phenyl]tetrazol-2-yl]ethanol (Compound 17)

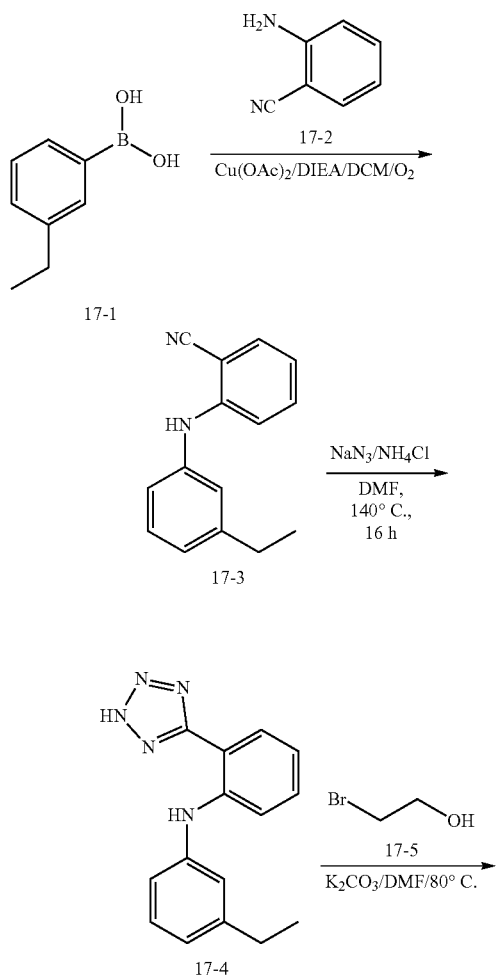

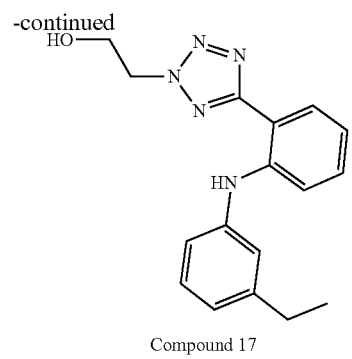

Compound 17

Step 1: 2-(3-ethylanilino)benzonitrile

To a solution of 17-2 (500.0 mg, 4.23 mmol, 1.0 eq) and 17-1 (634.43 mg, 4.23 mmol, 1.0 eq) in DCM (10.0 mL) was added DIEA (656.0 mg, 5.1 mmol, 0.89 mL, 1.2 eq) and $Cu(OAc)_2$ (768.3 mg, 4.23 mmol, 1.0 eq). The mixture was stirred at 30° C. for 16 hour under $O_2$ atmosphere. LCMS showed the desired compound was formed. TLC (30% ethyl acetate in petroleum ether, Rf=0.6) showed a new spot. The reaction was filtered through celatom and concentrated under reduced pressure to give a residue. The crude product was purified by column chromatography over silica gel to provide 17-3 (450.0 mg, 2.02 mmol, 47.9% yield). LCMS (ESI): RT=0.867 min, mass calc. for $C_{15}H_{14}N_2$ 222.12, m/z found 222.9 [M+H]+; 1HNMR (400 MHz, DMSO-$d_6$) δ 8.36 (s, 1H), 7.65 (dd, J=1.5, 7.8 Hz, 1H), 7.51-7.46 (m, 1H), 7.25-7.17 (m, 2H), 7.00-6.92 (m, 3H), 6.83 (d, J=7.8 Hz, 1H), 2.59-2.53 (m, 2H), 1.17 (t, J=7.5 Hz, 3H).

Step 2: N-(3-ethylphenyl)-2-(2H-tetrazol-5-yl)aniline

To a solution of 17-3 (300.0 mg, 1.35 mmol, 1.0 eq) in DMF (10.0 mL) was added $NH_4Cl$ (216.6 mg, 4.05 mmol, 0.14 mL, 3.0 eq) and $NaN_3$ (263.3 mg, 4.05 mmol, 3.0 eq). The mixture was stirred at 140° C. for 16 hour under an $N_2$ atmosphere. LCMS showed the desired compound was formed. The reaction mixture was poured into sat. aq. $NaHCO_3$ (5 mL) and extracted with EtOAc (5 mL*2). The combined organic layer was washed with brine (10 mL), dried over $Na_2SO_4$, and filtered. The solvent was removed under reduced pressure to afford 17-4 (300.0 mg, 1.13 mmol, 83.8% yield), which was directly used without further purification. LCMS (ESI): RT=0.826 min, mass calc. for $C_{15}H_{15}N_5$ 265.13, m/z found 265.9 [M+H]+.

Step 3: 2-[5-[2-(3-ethylanilino)phenyl]tetrazol-2-yl]ethanol

To a solution of 17-4 (100.0 mg, 0.38 mmol, 1.0 eq) in DMF (5.0 mL) was added $K_2CO_3$ (78.1 mg, 0.57 mmol, 1.5 eq) and 2-bromoethanol (56.5 mg, 0.45 mmol, 32.1 uL, 1.2 eq). The mixture was stirred at 100° C. for 3 hours under an $N_2$ atmosphere. LCMS showed the desired compound was formed. The reaction was filtered to give a crude product. The crude product was purified by prep-HPLC to give Compound 17 (19.79 mg, 63.97 umol, 16.97% yield). LCMS (ESI): RT=0.846 min, mass calc. for $C_{17}H_{19}N_5O$ 309.16, m/z found 309.9 [M+H]+; 1HNMR (400 MHz, DMSO-$d_6$) δ 8.69 (s, 1H), 8.06 (d, J=7.5 Hz, 1H), 7.39-7.35 (m, 2H), 7.24 (t, J=7.7 Hz, 1H), 7.08-7.03 (m, 2H), 6.99-

6.94 (m, 1H), 6.87 (d, J=7.5 Hz, 1H), 5.10 (br s, 1H), 4.80 (t, J=5.1 Hz, 2H), 3.97 (br s, 2H), 2.58 (q, J=7.5 Hz, 2H), 1.18 (t, J=7.5 Hz, 3H).

Example 18: Ethyl 2-[4-[2-[3-(trifluoromethyl)anilino]phenyl]triazol-1-yl]acetate (Compound 18)

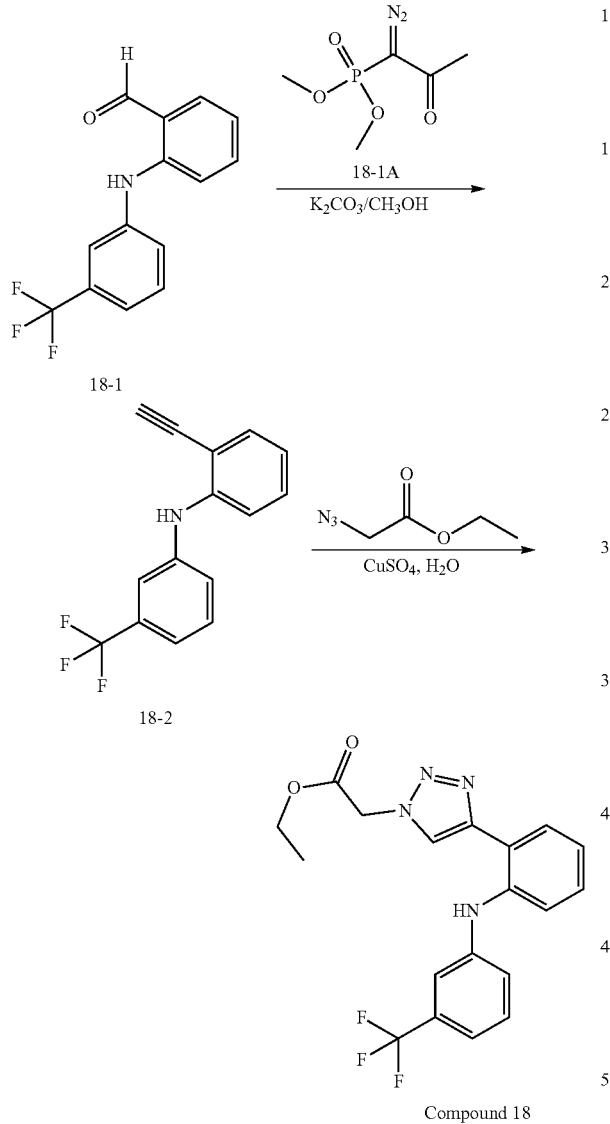

Compound 18

Step 1: 2-ethynyl-N-[3-(trifluoromethyl)phenyl]aniline

To a solution of 18-1 (150.0 mg, 0.57 mmol, 1.0 eq) in MeOH (3.00 mL) was added $K_2CO_3$ (156.3 mg, 1.1 mmol, 2.0 eq) and 18-1A (108.7 mg, 0.57 mmol, 1.0 eq). The mixture was stirred at 20-30° C. for 16 hour to give a yellow solution. The reaction was monitored by LC-MS and TLC. The reaction mixture was concentrated to give a residue. The residue was purified by flash column chromatography to provide 18-2 (70.0 mg, 0.13 mmol, 23.69% yield) as a light yellow oil. LCMS (ESI): RT=2.706 min, mass calc. for $C_{15}H_{10}F_3N$ 261.08, m/z found 261.9 $[M+H]^+$.

Step 2: Ethyl 2-[4-[2-[3-(trifluoromethyl)anilino]phenyl]triazol-1-yl]acetate

To a suspension of ethyl 2-azidoacetate (41.5 mg, 0.32 mmol, 45.1 uL, 1.2 eq) and 18-2 (70.0 mg, 0.27 mmol, 1.0 eq) in $H_2O$ (2.00 mL) was added $CuSO_4.5H_2O$ (669.04 ug, 2.68 umol, 0.01 eq). The mixture was stirred at 100° C. for 6 hour. The reaction was monitored by LC-MS. The reaction mixture was extracted with DCM (5 mL*3). The combined organic layer was washed with brine (10 mL), dried over $Na_2SO_4$ and filtered The filtrate was concentrated to give a residue. The residue was purified by prep-HPLC to give Compound 18 (50.0 mg, 0.13 mmol, 47.8% yield). LCMS (ESI): RT=2.323 min, mass calc. for $C_{19}H_{17}F_3N_4O_2$ 390.13, m/z found 391.0 $[M+H]^+$; $^1$HNMR (400 MHz, $CDCl_3$) δ (ppm): 7.57-7.55 (m, 1H), 7.28-7.24 (m, 2H), 7.13-7.10 (m, 1H), 3.95-3.88 (m, 2H), 3.06-3.00 (m, 2H). LCMS (ESI): RT=0.856 min, mass calc. for $C_{33}H_{40}N_4O_5S_2$ 636.24, m/z found 637.1 $[M+H]^+$; $^1$HNMR (400 MHz, $CDCl_3$) δ (ppm) 9.19 (s, 1H), 7.89 (s, 1H), 7.47-7.45 (m, 1H), 7.40-7.34 (m, 2H), 7.29-7.28 (m, 2H), 7.23-7.18 (m, 1H), 7.13-7.05 (m, 1H), 6.92-6.85 (m, 1H), 5.15 (s, 2H), 4.23 (q, J=7.3 Hz, 2H), 1.25 (t, J=7.2 Hz, 3H)

Example 19: 2-(5-(2-((3-methoxyphenyl)amino)phenyl)-2H-tetrazol-2-yl)ethan-1-ol (Compound 19)

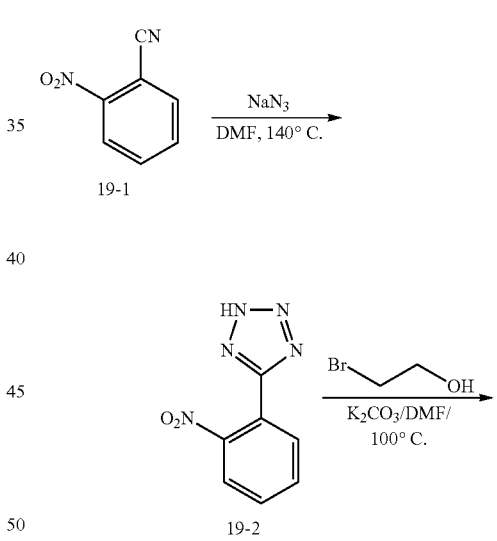

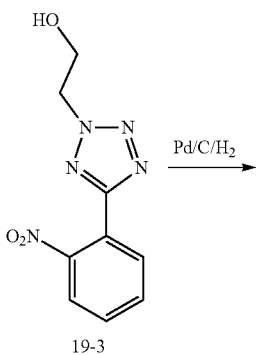

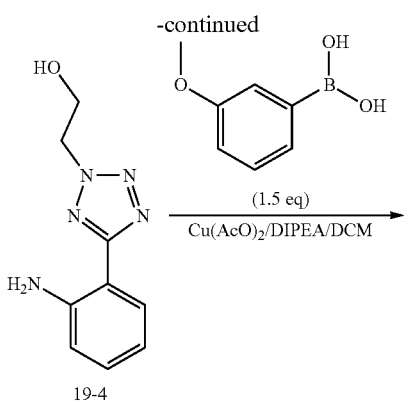

19-4

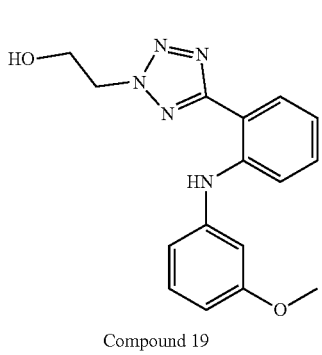

Compound 19

Step 1: 5-(2-nitrophenyl)-2H-tetrazole

To a solution of 19-1 (400.0 mg, 2.7 mmol, 1.0 eq), sodium azide (1.1 g, 16.2 mmol, 6.0 eq) in DMF (4.0 mL) was added NH$_4$Cl (866.5 mg, 16.2 mmol, 6.00 eq). The mixture was stirred at 140° C. for 16 hour under N$_2$ atmosphere. The reaction was monitored by LC-MS. The reaction mixture was poured into 1N HCl (20 mL) and extracted with EtOAc (10 ml*3). The combined organic layers were washed with brine (10 mL), dried over Na$_2$SO$_4$, and filtered. The filtrate was concentrated to give 19-2 (550.0 mg, crude) as a yellow oil. The crude product was used in next step directly without further purification. $^1$HNMR (400 MHz, CDCl$_3$) δ (ppm): 8.00 (d, J=8.0 Hz, 1H), 7.98-7.95 (m, 1H), 7.90 (dd, J=1.3, 7.8 Hz, 1H), 7.71 (dt, J=1.3, 7.5 Hz, 1H), 7.67-7.61 (m, 1H).

Step 2: 2-[5-(2-nitrophenyl)tetrazol-2-yl]ethanol

To a solution of 19-2 (250.0 mg, 1.31 mmol, 1.0 eq) in DMF (3.0 mL) was added K$_2$CO$_3$ (271.58 mg, 2.0 mmol, 1.5 eq) and 2-bromoethanol (196.5 mg, 1.6 mmol, 111.6 uL, 1.20 eq). The mixture was stirred at 100° C. for 16 hours to give a brown suspension. The reaction was monitored by LC-MS. The reaction mixture was poured into water (5 mL) and extracted with EtOAc (5 mL*3). The combined organic layers were dried over Na$_2$SO$_4$, and filtered. The filtrate was concentrated to give a residue. The residue was purified by flash column chromatography to give 19-3 (150.0 mg, 0.64 mmol, 48.7% yield) was obtained as a light yellow oil. $^1$HNMR (400 MHz, CDCl$_3$) δ (ppm): 8.03 (dd, J=1.4, 7.7 Hz, 1H), 7.92 (dd, J=1.3, 8.0 Hz, 1H), 7.75 (dt, J=1.3, 7.5 Hz, 1H), 7.71-7.65 (m, 1H), 4.88-4.83 (m, 2H), 4.29-4.22 (m, 2H), 2.30 (t, J=6.4 Hz, 1H).

Step 3: 2-[5-(2-aminophenyl)tetrazol-2-yl]ethanol

To a solution of 19-3 (150.0 mg, 0.64 mmol, 1.0 eq) in MeOH (5.0 mL) was added Pd/C (10%, 20 mg) under N$_2$.

The suspension was degassed under vacuum and purged with H$_2$ several times. The mixture was stirred under H$_2$ (15 psi) at 20-30° C. for 3 hours. LCMS showed the starting material was consumed completely and one main peak with the desired MS was detected. The reaction mixture was filtered and the filtrate was concentrated to give crude product 19-4 (140.0 mg, crude). The crude product was use in next step directly without further purification. LCMS (ESI): RT=0.538 min, mass calc. for C$_9$H$_{11}$N$_5$O 205.10, m/z found 205.8 [M+H]$^+$.

Step 4: 2-(5-(2-((3-methoxyphenyl)amino)phenyl)-2H-tetrazol-2-yl)ethan-1-ol

To a solution of (3-methoxyphenyl)boronic acid (155.5 mg, 1.0 mmol, 1.5 eq) and 19-4 (140.0 mg, 0.68 mmol, 1.0 eq) in DCM (20.0 mL) was added Cu(OAc)$_2$ (136.3 mg, 0.75 mmol, 1.10 eq) and DIPEA (132.3 mg, 1.0 mmol, 178.7 uL, 1.5 eq). The mixture was stirred at 20-30° C. for 60 hr under O$_2$ atmosphere. The reaction was monitored by LCMS. The reaction mixture was filtered through a Celite pad and washed with DCM (30 mL). The filtrate was concentrated to give a residue. The residue was purified by flash column chromatography to provide Compound 19 (45.31 mg, 0.15 mmol, 21.3% yield). LCMS (ESI): RT=1.982 min, mass calc. for C$_{16}$H$_{17}$N$_5$O$_2$ 311.14, m/z found 311.9 [M+H]$^+$; $^1$HNMR (400 MHz, CDCl$_3$) δ (ppm): 8.75 (s, 1H), 8.09 (dd, J=1.6, 7.9 Hz, 1H), 7.38 (d, J=7.8 Hz, 1H), 7.29-7.08 (m, 1H), 6.89-6.83 (m, 1H), 6.81-6.73 (m, 2H), 6.53 (dd, J=2.0, 8.0 Hz, 1H), 4.82-4.71 (m, 2H), 4.18 (q, J=5.3 Hz, 2H), 3.77-3.67 (m, 3H), 2.24 (br t, J=6.0 Hz, 1H).

Example 20: 2-[2-[2-(3-methoxyphenoxy)ethyl]tetrazol-5-yl]-N-(3-methoxyphenyl)aniline (Compound 20)

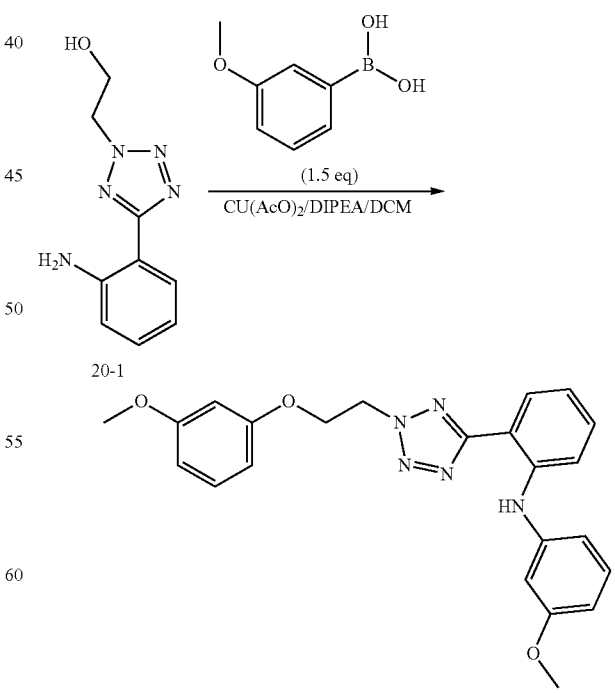

Compound 20

To a solution of (3-methoxyphenyl)boronic acid (155.5 mg, 1.0 mmol, 1.5 eq) and 20-1 (140.0 mg, 0.68 mmol, 1.0 eq) in DCM (20.0 mL) was added Cu(OAc)$_2$ (136.3 mg, 0.75 mmol, 1.10 eq) and DIPEA (132.3 mg, 1.0 mmol, 178.7 uL, 1.5 eq). The mixture was stirred at 20-30° C. for 60 hr under O$_2$ atmosphere. The reaction was monitored by LCMS. The reaction mixture was filtered through a Celite pad and washed with DCM (30 mL). The filtrate was concentrated to give a residue. The residue was purified by flash column chromatography (EtOAc/petroleum ether=0~20%) to give Compound 20 (45.11 mg, 0.11 mmol, 15.8% yield). LCMS (ESI): RT=2.489 min, mass calc. for C$_{23}$H$_{23}$N$_5$O$_3$ 417.18, m/z found 418.1 [M+H]$^+$; $^1$HNMR (400 MHz, CDCl$_3$) δ (ppm): 8.74 (s, 1H), 8.12 (dd, J=1.5, 7.8 Hz, 1H), 7.37 (d, J=8.3 Hz, 1H), 7.26-7.20 (m, 1H), 7.15 (t, J=8.0 Hz, 1H), 7.08 (t, J=8.3 Hz, 1H), 6.88-6.82 (m, 1H), 6.80-6.72 (m, 2H), 6.52 (dd, J=2.0, 8.0 Hz, 1H), 6.46 (dd, J=2.3, 8.3 Hz, 1H), 6.40 (dd, J=2.0, 8.0 Hz, 1H), 6.37-6.34 (m, 1H), 4.99 (t, J=5.5 Hz, 2H), 4.50 (t, J=5.4 Hz, 2H), 3.73 (s, 3H), 3.67 (s, 3H).

Example 21: 2-[5-[2-(2-methoxyanilino)phenyl]tetrazol-2-yl]ethanol (Compound 21)

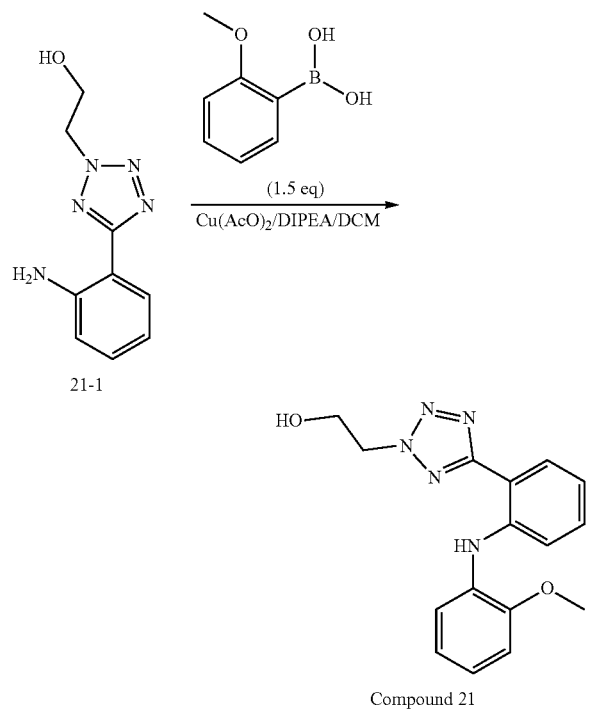

Compound 21

To a solution of (2-methoxyphenyl)boronic acid (74.1 mg, 0.49 mmol, 1.0 eq) and 21-1 (100.0 mg, 0.49 mmol, 1.0 eq) in DCM (20.0 mL) was added Cu(OAc)$_2$ (97.36 mg, 536.01 umol, 1.10 eq) and DIPEA (94.5 mg, 0.73 mmol, 127.7 uL, 1.5 eq). The mixture was stirred at 20-30° C. for 60 hr under O$_2$ atmosphere. TLC showed most of reactant remained, and one new spot had formed. The reaction mixture was filtered through a Celite pad and washed with DCM (30 mL). The filtrate was concentrated to give a residue. The residue was purified by flash column chromatography and then by prep-HPLC). The resulting eluent was concentrated to remove the organic solvent and the residue was lyophilized to give the title compound (4.23 mg, 13.59 umol, 2.8% yield). LCMS (ESI): RT=2.013 min, mass calc. for C$_{16}$H$_{17}$N$_5$O$_2$ 311.14, m/z found 312.0 [M+H]$^+$; $^1$HNMR (400 MHz, CDCl$_3$) δ ppm: 8.67 (s, 1H), 8.14-8.12 (m, 1H), 7.44-7.33 (m, 2H), 7.28-7.21 (m, 1H), 6.94-6.81 (m, 4H), 4.78-4.72 (m, 2H), 4.16-4.15 (m, 2H), 3.85 (s, 3H), 2.57 (s, 1H).

Example 22: 2-[4-[2-[3-(trifluoromethyl)anilino]phenyl]triazol-1-yl]ethanol (Compound 22)

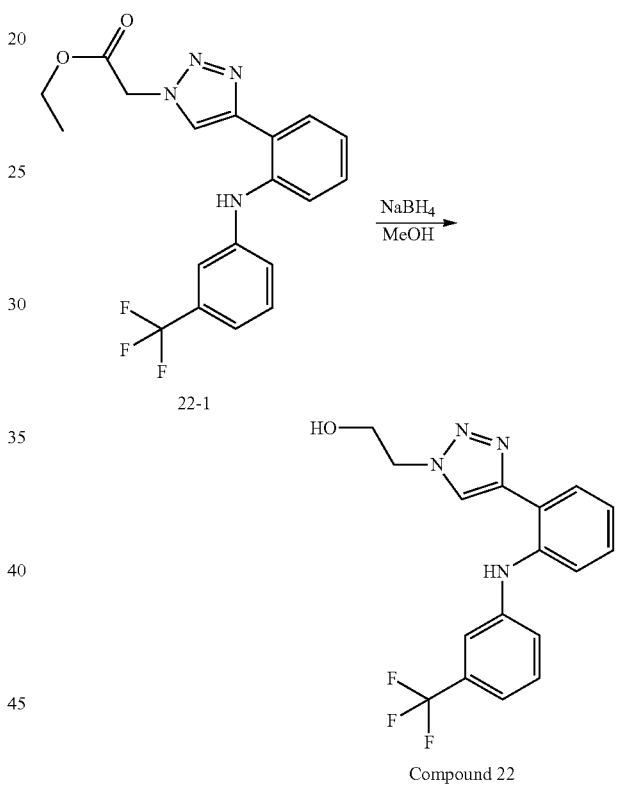

Compound 22

To a solution of 22-1 (40.0 mg, 0.10 mmol, 1.0 eq) in MeOH (5.0 mL) was added NaBH$_4$ (38.8 mg, 1.0 mmol, 10.0 eq) at 0° C. The mixture was stirred at 0-30° C. for 2 hour. LC-MS showed reactant was consumed completely and one main peak with the desired MS was detected. The reaction was quenched by adding water (1 mL). The mixture was purified by prep-HPLC. The resulting eluent was concentrated to remove the organic solvent and the residue was lyophilized to give the title compound (5.74 mg, 16.48 umol, 16.1% yield). LCMS (ESI): RT=2.068 min, mass calc. for C$_{17}$H$_{15}$F$_3$N$_4$O 348.12, m/z found 349.1 [M+H]$^+$; $^1$HNMR (400 MHz, CDCl$_3$) δ (ppm): 9.24 (s, 1H), 7.86 (s, 1H), 7.44-7.37 (m, 1H), 7.40-7.34 (m, 2H), 7.31-7.26 (m, 2H), 7.20-7.17 (m, 1H), 7.09-7.08 (m, 1H), 6.92-6.86 (m, 1H), 4.44-4.53 (m, 2H), 3.99-4.09 (m, 2H).

Example 23: 2-(5-(2-((4-(Trifluoromethyl)phenyl)amino)phenyl)-2H-tetrazol-2-yl)ethanol (Compound 23)

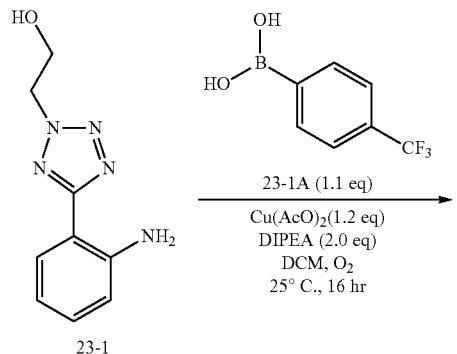

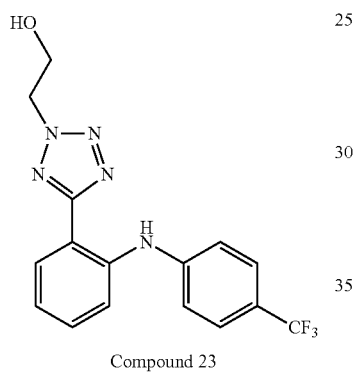

Compound 23

To a solution of 23-1 (100 mg, 0.487 mmol, 1.0 eq), 23-1A (110 mg, 0.536 mmol, 1.1 eq), Cu(OAc)$_2$ (106 mg, 0.585 umol, 1.2 eq), DIPEA (126 mg, 0.975 mmol, 2.0 eq) in DCM (5 mL) was added 4 A MS (50 mg). The reaction mixture was stirred at 25° C. for 16 hours under O$_2$. The reaction mixture was concentrated under reduced pressure. The mixture was diluted with water (30 mL) and the resultant mixture was extracted with DCM (50 mL*3). The combined organic layers were dried over Na$_2$SO$_4$, filtered, and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely to provide the title compound (80.94 mg, 47% yield). LCMS (ESI): RT=2.232 min, mass calc. for C$_{16}$H$_{14}$F$_3$N$_5$O 349.12, m/z found 349.9 [M+H]$^+$, $^1$HNMR (400 MHz, DMSO-d$_6$) δ 8.82 (s, 1H), 8.06 (dd, J=1.5, 7.8 Hz, 1H), 7.60-7.53 (m, 3H), 7.52-7.47 (m, 1H), 7.25 (d, J=8.5 Hz, 2H), 7.21-7.16 (m, 1H), 5.11-5.03 (m, 1H), 4.77 (t, J=5.3 Hz, 2H), 4.00-3.90 (m, 2H).

Example 24: 2-(5-(2-((3-(Trifluoromethoxy)phenyl)amino)phenyl)-2H-tetrazol-2-yl)ethanol (Compound 24)

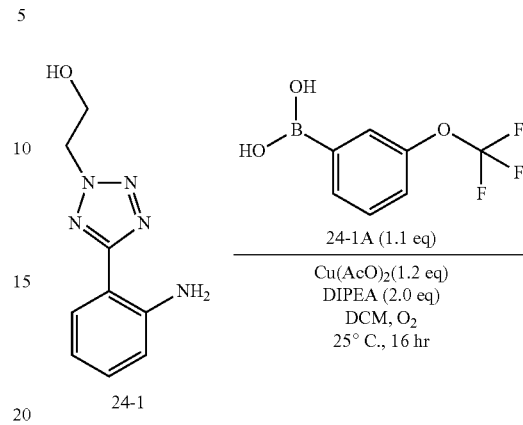

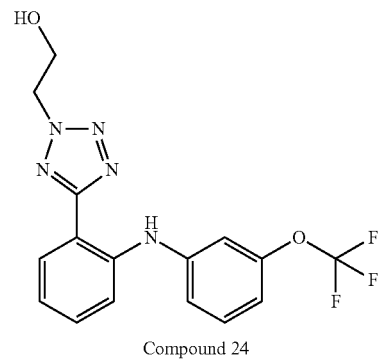

Compound 24

To a solution of 24-1 (100 mg, 0.487 mmol, 1.0 eq), 24-1a (110 mg, 0.536 mmol, 1.1 eq), Cu(OAc)$_2$ (106 mg, 0.585 umol, 1.2 eq), DIPEA (126 mg, 0.975 mmol, 2.0 eq) in DCM (5 mL) was added 4 A MS (50 mg). The reaction mixture was stirred at 25° C. for 16 hours under O$_2$. The reaction mixture was concentrated under reduced pressure. The mixture was diluted with water (30 mL) and the resultant mixture was extracted with DCM (50 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely to provide the title compound (77.97 mg, 44% yield). LCMS (ESI): RT=2.251 min, mass calc. for C$_{16}$H$_{14}$F$_3$N$_5$O$_2$ 365.11, m/z found 366.0 [M+H]$^+$, $^1$HNMR (400 MHz, DMSO-d$_6$) δ 8.73 (s, 1H), 8.06 (d, J=7.5 Hz, 1H), 7.49-7.42 (m, 2H), 7.41-7.35 (m, 1H), 7.17 (dd, J=1.8, 8.0 Hz, 1H), 7.14-7.08 (m, 2H), 6.87 (d, J=8.0 Hz, 1H), 5.08 (t, J=5.6 Hz, 1H), 4.78 (t, J=5.3 Hz, 2H), 3.96 (q, J=5.4 Hz, 2H).

Example 25: 2-[5-[2-(3,4-difluoroanilino)phenyl]tetrazol-2-yl]ethanol (Compound 25)

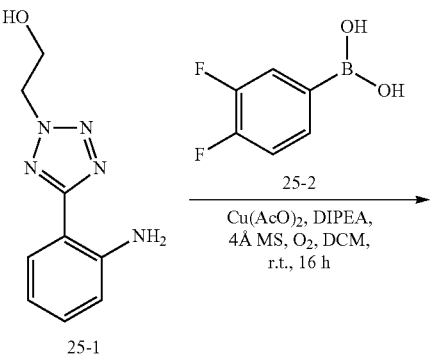

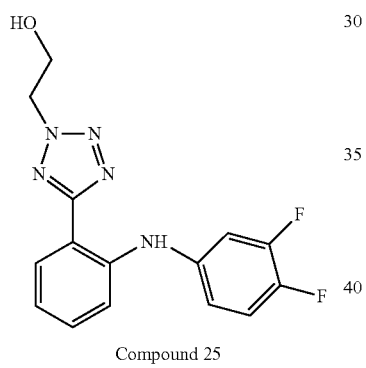

Compound 25

To a solution of 25-1 (100 mg, 0.487 mmol, 1.0 eq) and 25-2 (77 mg, 0.487 mmol, 1.0 eq) in DCM (10 mL) was added DIPEA (76 mg, 0.585 mmol, 102 uL, 1.2 eq), Cu(OAc)$_2$ (89 mg, 0.487 mmol, 1.0 eq) and 4 A MS (100 mg). The resulting mixture was stirred at 30° C. for 16 hr under O$_2$. The reaction was monitored by LCMS and TLC (Petroleum ether:Ethyl acetate=10/1). The mixture was concentrated in vacuo to give a crude product. The crude product was purified by column chromatography (silica) to give the title compound (110 mg, 0.347 mmol, 71% yield). LCMS (ESI): RT=0.809 min, mass calc. for $C_{15}H_{13}F_2N_5O$ 317.11, m/z found 317.9 [M+H]$^+$; $^1$HNMR (400 MHz, DMSO-d$_6$) δ 8.65 (s, 1H), 8.06 (dd, J=1.3, 7.8 Hz, 1H), 7.45-7.31 (m, 3H), 7.26 (ddd, J=2.5, 7.2, 12.7 Hz, 1H), 7.09-6.99 (m, 2H), 5.08 (t, J=5.6 Hz, 1H), 4.80 (t, J=5.1 Hz, 2H), 3.97 (q, J=5.5 Hz, 2H).

Example 26: 2-[5-[2-[2-(trifluoromethoxy)anilino]phenyl]tetrazol-2-yl]ethanol (Compound 26)

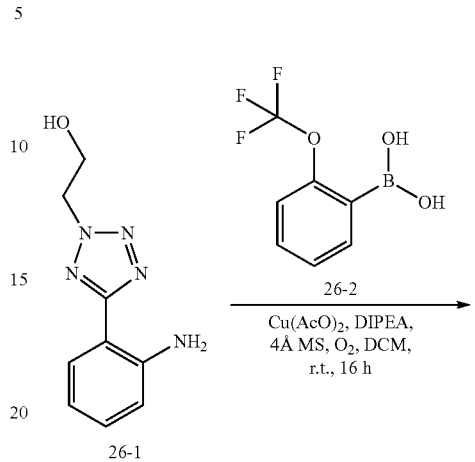

Compound 26

To a solution of 26-1 (100 mg, 0.487 mmol, 1.0 eq) and 26-2 (100 mg, 0.487 mmol, 1.0 eq) in DCM (10 mL) was added DIEA (76 mg, 0.585 mmol, 102 uL, 1.2 eq), Cu(OAc)$_2$ (89 mg, 0.487 mmol, 1.0 eq) and 4 A MS (100 mg). The resulting mixture was stirred at 30° C. for 16 hr under O$_2$. The reaction was monitored by LCMS and TLC (Petroleum ether:Ethyl acetate=10/1). The mixture was concentrated in vacuo to give a crude product. The crude product was purified by column chromatography (silica) to give the title compound (40 mg, 0.110 mmol, 22% yield). LCMS (ESI): RT=0.845 min, mass calc. for $C_{16}H_{14}F_3N_5O_2$ 365.11, m/z found 365.9 [M+H]$^+$; $^1$HNMR (400 MHz, DMSO-d$_6$) δ 9.07 (s, 1H), 8.14 (d, J=7.5 Hz, 1H), 7.58 (dd, J=1.3, 8.3 Hz, 1H), 7.49-7.41 (m, 3H), 7.40-7.33 (m, 1H), 7.15-7.05 (m, 2H), 5.10 (t, J=5.6 Hz, 1H), 4.79 (t, J=5.3 Hz, 2H), 3.98 (q, J=5.4 Hz, 2H).

Example 27: 2-(5-(2-((2,3-difluorophenyl)amino)phenyl)-2H-tetrazol-2-yl)ethan-1-ol (Compound 27)

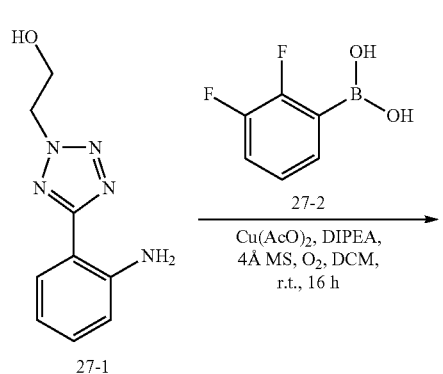

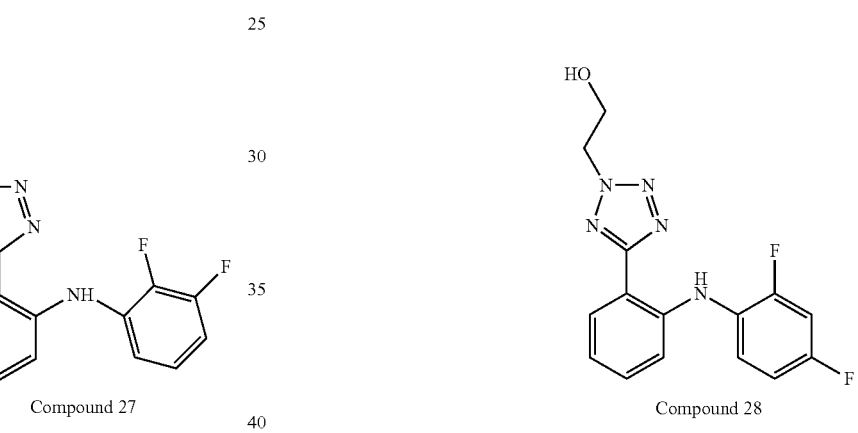

To a solution of 27-1 (50.0 mg, 0.24 mmol, 1.0 eq) and 27-2 (38.5 mg, 0.24 mmol, 1.0 eq) in DCM (5.0 mL) was added DIEA (37.8 mg, 0.29 mmol, 51.1 uL, 1.2 eq) and Cu(OAc)$_2$ (44.3 mg, 0.24 mmol, 1.0 eq). The mixture was stirred at 30° C. for 16 hour under O$_2$ atmosphere. LCMS showed the desired compound was formed. TLC (30% ethyl acetate in petroleum ether, Rf=0.6) showed a new spot appeared. The reaction was filtered through celatom and concentrated under reduced pressure to give a residue. The crude product was purified by column chromatography over silica gel. The crude product was purified by prep-HPLC to obtain the title compound (2.24 mg, 7.06 umol, 2.90% yield). LCMS (ESI): RT=0.795 min, mass calc. for C$_{15}$H$_{13}$F$_2$N$_5$O 317.11, m/z found 317.9 [M+H]$^+$; $^1$HNMR (400 MHz, DMSO-d$_6$) δ 8.85 (s, 1H), 8.11 (dd, J=1.4, 7.9 Hz, 1H), 7.47-7.41 (m, 1H), 7.31 (d, J=8.5 Hz, 1H), 7.27-7.22 (m, 1H), 7.17-7.01 (m, 3H), 5.10 (t, J=5.5 Hz, 1H), 4.80 (t, J=5.3 Hz, 2H), 3.97 (q, J=5.4 Hz, 2H).

Example 28: 2-(5-(2-((2,4-difluorophenyl)amino)phenyl)-2H-tetrazol-2-yl)ethan-1-ol (Compound 28)

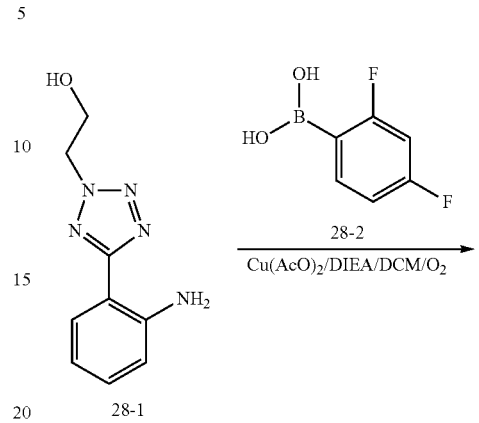

To a solution of 28-1 (50.0 mg, 0.24 mmol, 1.0 eq) and 28-2 (38.5 mg, 0.24 mmol, 1.0 eq) in DCM (10.0 mL) was added DIEA (37.8 mg, 0.29 mmol, 51.1 uL, 1.2 eq) and Cu(OAc)$_2$ (44.3 mg, 0.24 mmol, 1.0 eq). The mixture was stirred at 30° C. for 16 hour under O$_2$ atmosphere. LCMS showed the desired compound was formed. TLC (30% ethyl acetate in petroleum ether, Rf=0.6) showed residual starting material and a new spot. The reaction was filtered through celatom and concentrated under reduced pressure to give a residue. The crude product was purified by column chromatography over silica gel. The crude product was purified by prep-HPLC to give the title compound (5.76 mg, 18.15 umol, 7.45% yield). LCMS (ESI): RT=0.791 min, mass calc. for C$_{15}$H$_{13}$F$_2$N$_5$O 317.11, m/z found 317.9 [M+H]$^+$; $^1$HNMR (400 MHz, DMSO-d$_6$) δ 8.63 (s, 1H), 8.09 (dd, J=1.3, 7.8 Hz, 1H), 7.50 (dt, J=6.1, 9.1 Hz, 1H), 7.43-7.33 (m, 2H), 7.13-7.07 (m, 1H), 7.04-6.96 (m, 2H), 5.11 (t, J=5.6 Hz, 1H), 4.81 (t, J=5.1 Hz, 2H), 3.98 (q, J=5.4 Hz, 2H).

Example 29: N-[2-[5-[2-[3-(trifluoromethyl)anilino]phenyl]tetrazol-2-yl]ethyl]methane sulfonamide (Compound 29)

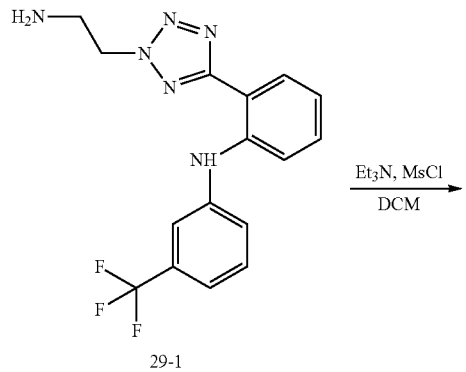

Example 30: N-[2-[5-[2-[3-(trifluoromethyl)anilino]phenyl]tetrazol-2-yl]ethyl]acetamide (Compound 30)

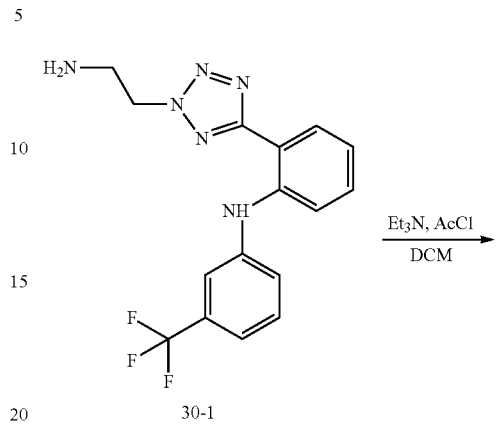

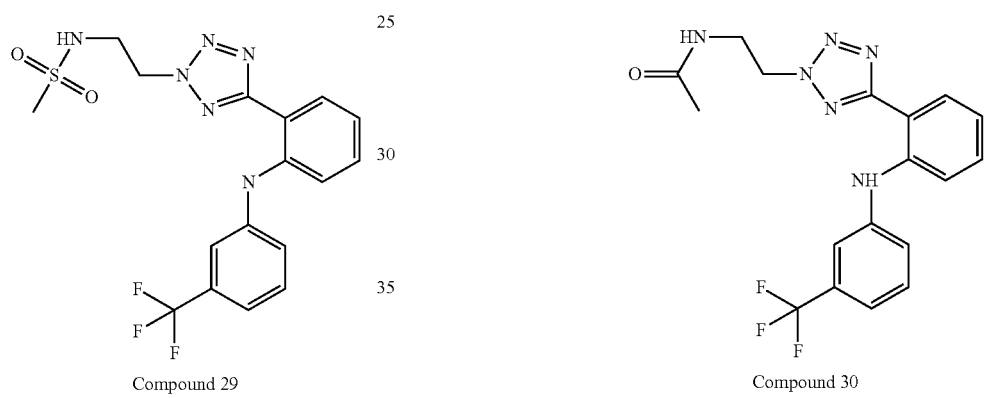

Compound 29

Compound 30

To a mixture of 29-1 (15 mg, 39 umol, 1.00 eq, HCl) and Et$_3$N (12 mg, 0.117 mmol, 16 uL, 3.00 eq) in DCM (2 mL) was added MSCl (6.7 mg, 59 umol, 5 uL, 1.50 eq) in one portion at 28° C. The mixture was stirred at 28° C. for 2 h. LCMS showed 29-1 was consumed completely and one main peak with the desired MS was detected. The reaction mixture was concentrated under reduced pressure to remove solvent. The residue was diluted with water (6 mL) and extracted with EtOAc (8 mL*6). The combined organic layers were dried with anhydrous Na$_2$SO$_4$, filtered, and concentrated under vacuum. The residue was purified by prep-HPLC (basic condition) to provide the title compound (4.57 mg, 9.9 umol, 25.3% yield). LCMS (ESI): RT=0.852 min, mass calcd. for C$_{17}$H$_{17}$F$_3$N$_6$O$_2$S, 426.11 m/z found 426.9[M+H]$^+$. $^1$HNMR (400 MHz, CHLOROFORM-d) δ 8.89 (s, 1H), 8.18 (dd, J=7.60, 1.4 Hz, 1H), 7.50 (s, 1H), 7.44-7.42 (m, 3H), 7.40-7.35 (m, 1H), 7.27-7.26 (m, 1H), 7.04-7.00 (m, 1H), 4.93-4.90 (m, 3H), 3.83 (t, J=5.20 Hz, 2H), 2.98 (s, 3H).

To a mixture of 30-1 (20 mg, 52 umol, 1.00 eq, HCl) and Et$_3$N (21 mg, 0.208 mmol, 28 uL, 4.00 eq) in DCM (2 mL) was added AcCl (16 mg, 0.208 mmol, 15 uL, 4.00 eq) in one portion at 28° C. The mixture was stirred at 28° C. for 2 h. LCMS showed 30-1 was consumed completely and one main peak with the desired MS was detected. The reaction mixture was concentrated under reduced pressure to remove solvent. The residue was diluted with water (6 mL) and extracted with EtOAc (8 mL*6). The combined organic layers were dried with anhydrous Na$_2$SO$_4$, filtered and concentrated under vacuum. The residue was purified by prep-HPLC (basic condition) to provide the title compound (13.95 mg, 35.7 umol, 68.8% yield). LCMS (ESI): RT=0.835 min, mass calcd. for C$_{18}$H$_{17}$F$_3$N$_6$O, 390.14 m/z found 391.0[M+H]$^+$. $^1$HNMR (400 MHz, CHLOROFORM-d) δ8.93 (s, 1H), 8.19 (dd, J=7.60, 1.40 Hz, 1H), 7.50 (s, 1H), 7.45-7.43 (m, 3H), 7.40-7.36 (m, 1H), 7.27-7.26 (m, 1H), 7.02 (t, J=7.60 Hz, 1H), 5.87 (br s, 1H), 4.87-4.84 (m, 2H), 3.96-3.92 (m, 2H), 1.99 (s, 3H).

Example 31: 2-[5-[2-[4-(difluoromethylsulfanyl)anilino]phenyl]tetrazol-2-yl]ethanol (Compound 31)

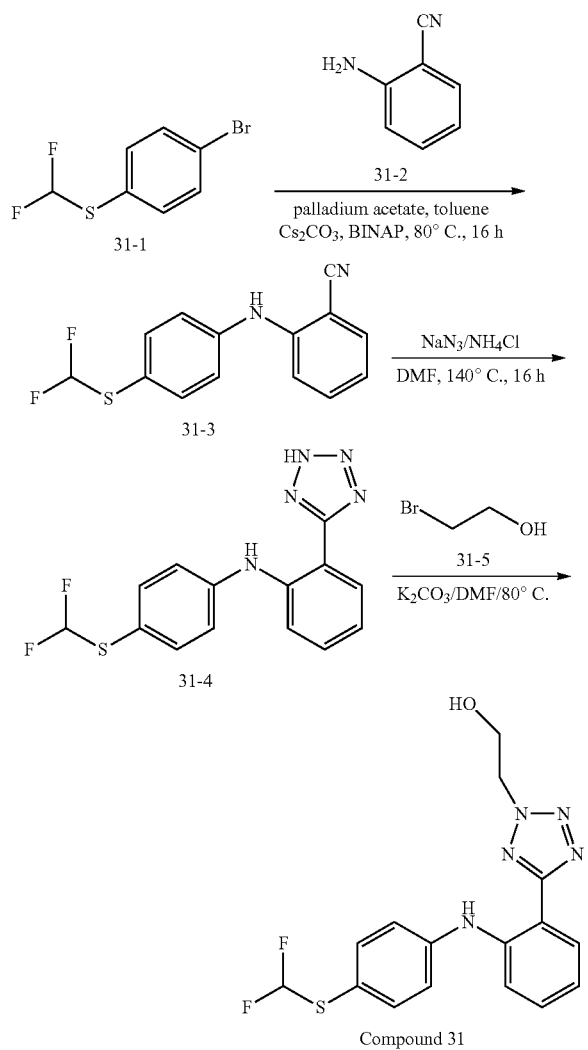

Step 1: 2-[4-(difluoromethylsulfanyl)anilino]benzonitrile

To a solution of 31-1 (400.0 mg, 1.7 mmol, 1.0 eq), 31-2 (197.7 mg, 1.7 mmol, 1.0 eq) and $Cs_2CO_3$ (545.1 mg, 1.7 mmol, 1.0 eq) in toluene (300.0 mL) was added BINAP (104.18 mg, 167.31 umol, 0.10 eq) and palladium acetate (37.56 mg, 167.31 umol, 0.10 eq). The resulting mixture was stirred at 100° C. under $N_2$ for 15 hours. LCMS showed the desired compound was formed and the starting material was consumed completely. The reaction mixture was concentrated. The residue crude product was dissolved with $CH_2Cl_2$ (500 ml) and washed with water (2×100 mL). After drying the organic layer over anhydrous $Na_2SO_4$, the solvent was removed under reduced pressure to afford the crude product. The crude product was purified by column chromatography over silica gel to give 31-3 (100.0 mg, 0.36 mmol, 21.7% yield). LCMS (ESI): RT=0.832 min, mass calc. for $C_{14}H_{10}F_2N_2S$ 276.05, m/z found 276.8 $[M+H]^+$.

Step 2: N-[4-(difluoromethylsulfanyl)phenyl]-2-(2H-tetrazol-5-yl)aniline

To a solution of 31-3 (100.0 mg, 0.36 mmol, 1.0 eq) in DMF (10.0 mL) was added $NH_4Cl$ (58.1 mg, 1.1 mmol, 38.0 uL, 3.0 eq) and $NaN_3$ (235.3 mg, 3.6 mmol, 10.0 eq). The mixture was stirred at 140° C. for 16 hour under $N_2$ atmosphere. LCMS showed the desired compound was formed. The reaction mixture was poured into sat. aq. $NaHCO_3$ (5 mL) and extracted with EtOAc (5 mL*2). The combined organic layer was washed with brine (10 mL), dried over $Na_2SO_4$, and filtered. The solvent was removed under reduced pressure to afford 31-4 (100.0 mg, 0.31 mmol, 86.5% yield) as a yellow oil, which was directly used without further purification. LCMS (ESI): RT=0.796 min, mass calc. for $C_{14}H_{11}F_2N_5S$ 319.07, m/z found 319.9 $[M+H]^+$.

Step 3: 2-[5-[2-[4-(difluoromethylsulfanyl)anilino]phenyl]tetrazol-2-yl]ethanol To a solution of 31-4 (100.0 mg, 0.31 mmol, 1.0 eq) in DMF (5.0 mL) was added $K_2CO_3$ (64.9 mg, 0.47 mmol, 1.5 eq) and 31-5 (47.0 mg, 0.38 mmol, 26.7 uL, 1.2 eq). The mixture was stirred at 100° C. for 3 hours under $N_2$ atmosphere. LCMS showed the desired compound was formed. The reaction was filtered to give a crude product. The crude product was purified by prep-HPLC to give Compound 31 (10.94 mg, 30.11 umol, 9.61% yield). LCMS (ESI): RT=0.832 min, mass calc. for $C_{16}H_{15}F_2N_5OS$ 363.10, m/z found 363.9 $[M+H]^+$; $^1$HNMR (400 MHz, DMSO-$d_6$) δ 8.76 (s, 1H), 8.06 (dd, J=1.3, 7.8 Hz, 1H), 7.53-7.43 (m, 5H), 7.34 (s, 1H), 7.22 (d, J=8.8 Hz, 2H), 7.15-7.09 (m, 1H), 5.08 (t, J=5.6 Hz, 1H), 4.78 (t, J=5.3 Hz, 2H), 3.95 (q, J=5.5 Hz, 2H).

Example 32: 2-(5-(2-((3,5-difluorophenyl)amino)phenyl)-2H-tetrazol-2-yl)ethan-1-ol (Compound 32)

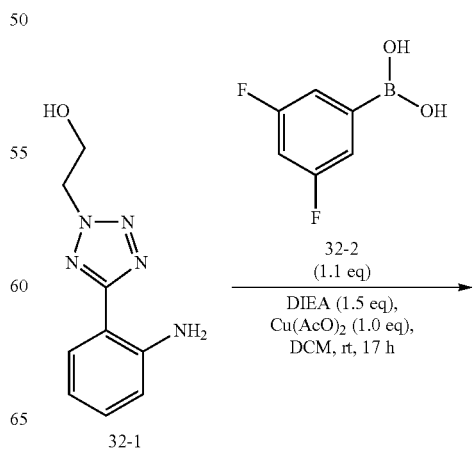

-continued

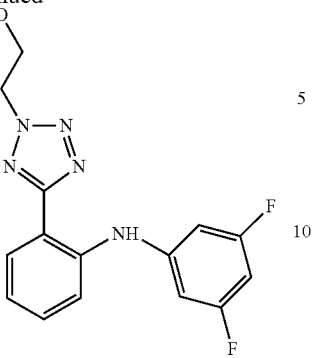

Compound 32

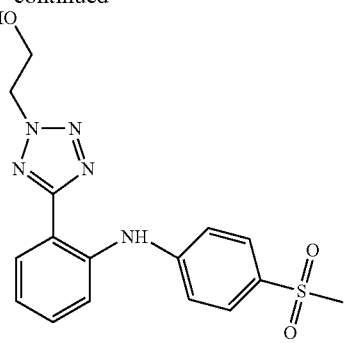

Compound 33

To a mixture of 32-1 (100.0 mg, 487.3 umol, 1.00 eq), 32-2 (84.6 mg, 536.0 umol, 1.10 eq) and Cu(OAc)$_2$ (88.5 mg, 487.3 umol, 1.00 eq) in DCM (6.0 mL), was added DIEA (94.7 mg, 732.9 umol, 128 uL, 1.50 eq). The mixture was degassed under vacuum and purged with O$_2$ 3 times. The resulting mixture was stirred at 26° C. under O$_2$ (15 Psi) for 17 h. LCMS detected about 71% of the desired compound, and about 6% starting material remained. The mixture was filtered, and the solid was washed with DCM (5 mL*2). The filtrate was concentrated under vacuum. The residue was purified by silica gel chromatography to provide the title compound (101.42 mg, 319.6 umol, 65.6% yield). LCMS (ESI): RT=0.818 min, mass calc. for $C_{15}H_{13}F_2N_5O$ 317.11, m/z found 317.9 [M+H]$^+$. $^1$HNMR (400 MHz, DMSO-d$_6$) δ ppm 8.73 (s, 1H) 8.04 (dd, J=7.8, 1.3 Hz, 1H) 7.45-7.56 (m, 2H) 7.15-7.23 (m, 1H) 6.71-6.80 (m, 2H) 6.63 (tt, J=9.4, 2.3 Hz, 1H) 5.07 (t, J=5.7 Hz, 1H) 4.78 (t, J=5.3 Hz, 2H) 3.95 (q, J=5.5 Hz, 2H).

Example 33: 2-(5-(2-((4-(methylsulfonyl)phenyl)amino)phenyl)-2H-tetrazol-2-yl)ethanol (Compound 33)

To a mixture of 33-1 (100.0 mg, 487.3 umol, 1.00 eq), 33-2 (102.3 mg, 511.6 umol, 1.05 eq) and Cu(OAc)$_2$ (88.5 mg, 487.3 umol, 1.00 eq) in DCM (6.0 mL), was added DIEA (94.5 mg, 730.9 umol, 128 uL, 1.50 eq). The mixture was degassed under vacuum and purged with O$_2$ for 3 times. The resulting mixture was stirred at 26° C. under O$_2$ (15 Psi) for 17 h. LCMS detected about 68% of the desired compound, and about 23% starting material remained. The mixture was filtered, and the solid was washed with DCM (5 mL*2). The filtrate was concentrated under vacuum. The residue was purified by prep-HPLC (acidic HCl condition) to provide the title compound (69.93 mg, 194.6 umol, 39.9% yield). LCMS (ESI): RT=0.977 min, mass calc. for $C_{16}H_{17}N_5O_3S$ 359.11, m/z found 382.0 [M+Na]$^+$. $^1$HNMR (400 MHz, DMSO-d$_6$) δ ppm 8.89 (s, 1H) 8.06 (dd, J=7.8, 1.3 Hz, 1H) 7.72 (d, J=8.8 Hz, 2H) 7.55-7.59 (m, 1H) 7.49-7.55 (m, 1H) 7.22-7.27 (m, 1H) 7.19 (d, J=8.8 Hz, 2H) 5.05 (t, J=5.8 Hz, 1H) 4.75 (t, J=5.3 Hz, 2H) 3.93 (q, J=5.5 Hz, 2H) 3.11 (s, 3H).

Example 34: 2-(5-(2-((2,5-difluorophenyl)amino)phenyl)-2H-tetrazol-2-yl)ethanol (Compound 34)

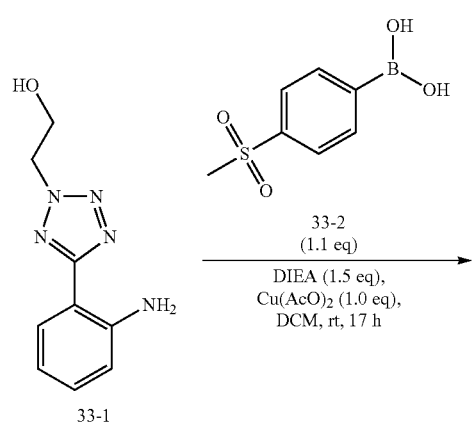

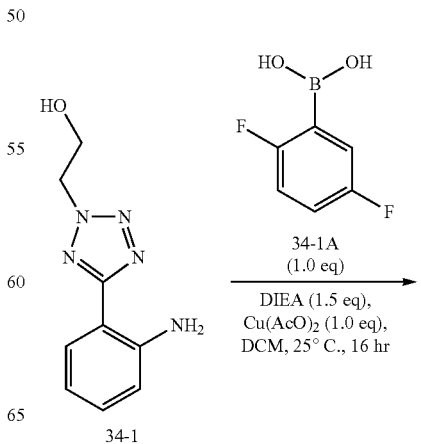

279

-continued

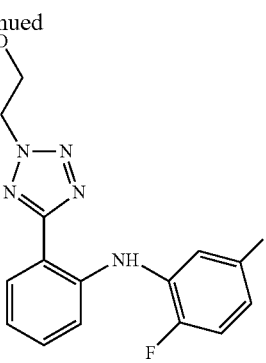

Compound 34

To the solution of 34-1A (100 mg, 0.6 mmol, 1.0 eq) in DCM (10 mL) was added compound 34-1 (130 mg, 0.6 mmol, 1.0 eq), DIPEA (123 mg, 1.0 mmol, 166 uL, 1.5 eq), Cu(OAc)$_2$ (115 mg, 0.6 mmol, 1.0 eq). The mixture was stirred at 25° C. for 16 hr under O$_2$ atmosphere. The reaction was monitored by LCMS. The reaction solution was washed with H$_2$O (10 mL). The organic layer was filtered and concentrated under reduced pressure. The residue was purified by Prep-HPLC to give the title compound (5.97 mg, 18.3 umol, 2.88% yield). LCMS (ESI): RT=1.150 min, mass calc. for C$_{15}$H$_{13}$F$_2$N$_5$O 317.11, m/z found 317.9 [M+H]$^+$, $^1$HNMR (400 MHz, CHLOROFORM-d) δ 8.89 (s, 1H), 8.29-8.15 (m, 1H), 7.51-7.38 (m, 2H), 7.23-7.11 (m, 1H), 7.11-7.03 (m, 2H), 6.64-6.57 (m, 1H), 4.89-4.83 (m, 2H), 4.33-4.23 (m, 2H), 2.32 (br, 1H).

Example 35: 2-(5-(2-((3-(methylsulfonyl)phenyl)amino)phenyl)-2H-tetrazol-2-yl)ethanol (Compound 35)

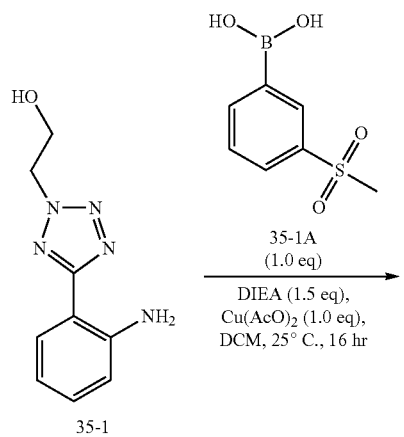

280

-continued

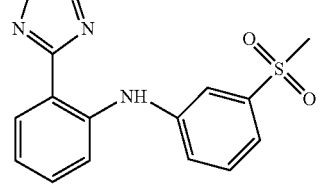

Compound 35

To the solution of 35-1 (103 mg, 0.5 mmol, 1.0 eq) in DCM (10 mL) was added 35-1A (100 mg, 0.5 mmol, 1.0 eq), DIPEA (97 mg, 0.7 mmol, 131 uL, 1.5 eq), Cu(OAc)$_2$ (91 mg, 0.5 mmol, 1.0 eq). The mixture was stirred at 25° C. for 16 hr under O$_2$ atmosphere. The reaction was monitored by LCMS. The reaction solution was washed with H$_2$O (10 mL). The organic layer was filtered and concentrated under reduced pressure. The residue was purified by Prep-HPLC to provide the title compound (44.72 mg, 117.0 umol, 23.4% yield). LCMS (ESI): RT=0.999 min, mass calc. for C$_{16}$H$_{17}$N$_5$O$_3$S 359.11, m/z found 382.0 [M+Na]$^+$, $^1$HNMR (400 MHz, CHLOROFORM-d) δ 9.02 (s, 1H), 8.22-8.14 (m, 1H), 7.78-7.73 (m, 1H), 7.52-7.43 (m, 4H), 7.40-7.34 (m, 1H), 7.06-7.00 (m, 1H), 4.88-4.81 (m, 2H), 4.25 (q, J=5.4 Hz, 2H), 3.06 (s, 3H), 2.63 (t, J=6.0 Hz, 1H).

Example 36: 2-(5-(2-((2-fluorophenyl)amino)phenyl)-2H-tetrazol-2-yl)ethanol (Compound 36)

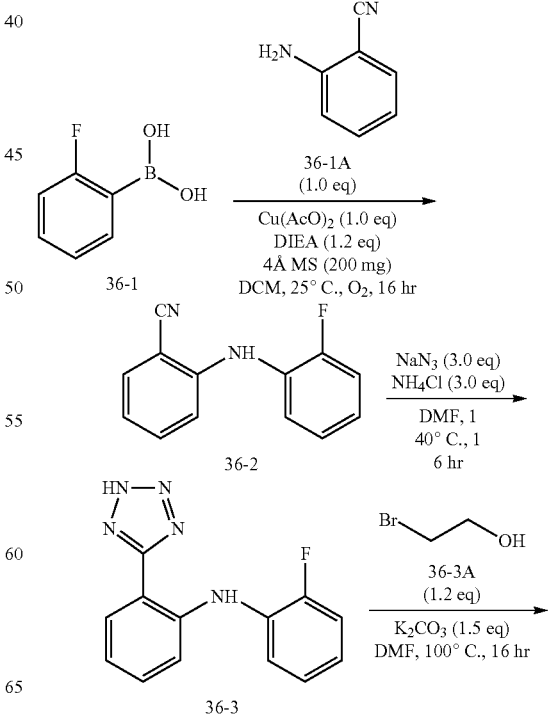

-continued

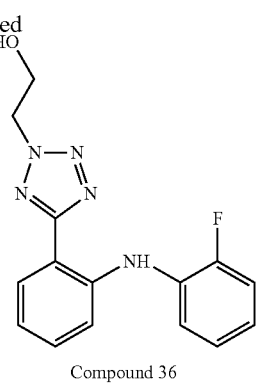

Compound 36

Step 1: 2-((2-fluorophenyl)amino)benzonitrile

To the solution of 36-1 (500 mg, 3.6 mmol, 1.0 eq) in DCM (10 mL) was added 36-1A (422 mg, 3.6 mmol, 1.0 eq), Cu(OAc)$_2$ (648 mg, 3.6 mmol, 1.0 eq) and DIEA (554 mg, 4.3 mmol, 748 uL, 1.2 eq), 4 A MS (200 mg). The mixture was stirred at 30° C. for 16 hr. The reaction was monitored by TLC. The reaction solution was concentrated under reduced pressure. The residue was purified by column chromatography (SiO$_2$) to give 36-2 (73 mg, 0.3 mmol, 9.6% yield).

Step 2: N-(2-(2H-tetrazol-5-yl)phenyl)-2-fluoroaniline

To the solution of 36-2 (73 mg, 0.3 mmol, 1.0 eq) in DMF (2 mL) was added NaN$_3$ (67 mg, 1.0 mmol, 3.0 eq) and NH$_4$Cl (55 mg, 1.0 mmol, 3.0 eq). The mixture was stirred at 140° C. for 16 hr under N$_2$ atmosphere. The reaction was monitored by LCMS. The reaction solution was poured into aqueous HCl (1M, 20 mL). An insoluble solid appeared and the mixture was filtered. The solid was washed with H$_2$O (20 mL*2) to give 36-3 (68 mg, crude).

Step 3: 2-(5-(2-((2-fluorophenyl)amino)phenyl)-2H-tetrazol-2-yl)ethanol

To the solution of 36-3A (40 mg, 0.3 mmol, 23 uL, 1.2 eq) in DMF (5 mL) was added 36-3 (68 mg, 0.3 mmol, 1.0 eq) and K$_2$CO$_3$ (55 mg, 0.4 mmol, 1.5 eq). The mixture was stirred at 100° C. for 16 hr. The reaction was monitored by LCMS. The reaction solution was concentrated under reduced pressure. The residue was purified by Prep-HPLC to give Compound 36 (29.79 mg, 97.5 umol, 36.6% yield). LCMS (ESI): RT=1.129 min, mass calc. for C$_{15}$H$_{14}$FN$_5$O 299.12, m/z found 299.9 [M+H]$^+$, $^1$HNMR (400 MHz, CHLOROFORM-d) δ 8.75 (s, 1H), 8.22-8.17 (m, 1H), 7.46 (dt, J=1.5, 8.2 Hz, 1H), 7.38-7.26 (m, 2H), 7.18-6.91 (m, 4H), 4.86-4.79 (m, 2H), 4.28-4.20 (m, 2H).

Example 37: 2-[5-[2-(2,6-difluoroanilino)phenyl]tetrazol-2-yl]ethanol (Compound 37)

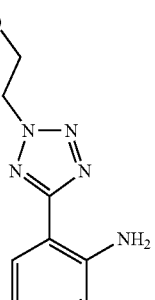

37-1

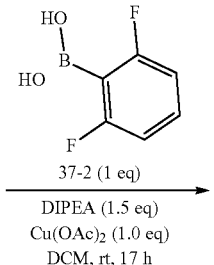

37-2 (1 eq)

DIPEA (1.5 eq)
Cu(OAc)$_2$ (1.0 eq)
DCM, rt, 17 h

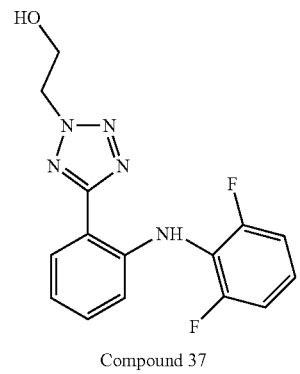

Compound 37

To a solution of 37-2 (100 mg, 0.633 mmol, 1.00 eq), DIEA (123 mg, 0.950 mmol, 0.16 mL, 1.50 eq), Cu(OAc)$_2$ (115 mg, 0.633 mmol, 1.00 eq) in DCM (7 mL) was added 37-1 (125 mg, 0.609 mmol, 0.96 eq). The mixture was stirred at 25° C. for 16 h under O$_2$ atmosphere. The reaction was monitored by LCMS. To the reaction mixture was added additional 37-2 (100 mg, 0.633 mmol, 1.00 eq) and continued stirred 4 h. LCMS indicated the amount of the desired compound was increased. The reaction mixture was continued stirred 18 h. LCMS showed no obvious changed. The reaction mixture was filtered and washed with EtOAc (5 mL*6), and then concentrated under vacuum. The residue was purified by flash silica gel chromatography and then purified by prep-HPLC (basic condition) to obtain the title compound (2.27 mg, 7.15 umol, 1.1% yield). LCMS (ESI): RT=0.784 min, mass calcd. for C$_{15}$H$_{13}$F$_2$N$_5$O, 317.11 m/z found 317.9[M+H]$^+$. $^1$HNMR (400 MHz, CHLOROFORM-d) δ8.56 (s, 1H), 8.21 (dd, J=1.60, 8.00 Hz, 1H), 7.35-7.28 (m, 1H), 7.18-7.11 (m, 1H), 7.05-6.93 (m, 3H), 6.75-6.71 (m, 1H), 4.90-4.85 (m, 2H), 4.30-4.25 (m, 2H), 2.36-2.32 (m, 1H).

Example 38: 2-[5-[2-(2-methylsulfonylanilino)phenyl]tetrazol-2-yl]ethanol (Compound 38)

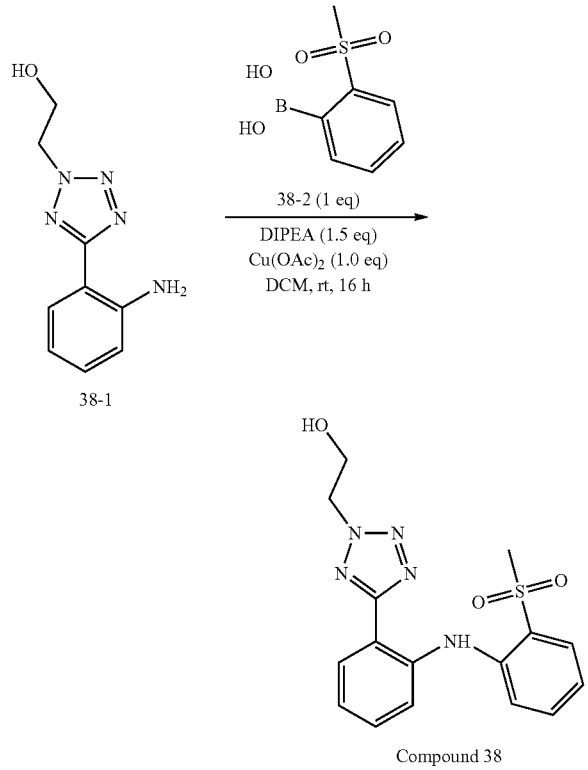

Compound 38

To the solution of 38-2 (91 mg, 0.455 mmol, 1.00 eq), DIPEA (88 mg, 682.43 umol, 0.12 mL, 1.50 eq), Cu(OAc)₂ (83 mg, 0.455 mmol, 1.00 eq) in DCM (7 mL) was added compound 38-1 (100 mg, 487.28 umol, 1.07 eq). The mixture was stirred at 25° C. for 16 hr under O₂ atmosphere. The reaction was monitored by LCMS and TLC. The reaction mixture was concentrated under reduced pressure to remove solvent. The residue was diluted with water (8 mL) and extracted with EtOAc (10 mL*6). The combined organic layers were washed with brine (5 mL), dried with anhydrous Na₂SO₄, filtered, and concentrated under vacuum. The residue was purified by flash silica gel chromatography and then purified by prep-HLC (basic condition) to obtain the title compound (28.03 mg, 77.21 umol, 16.97% yield). LCMS (ESI): RT=0.728 min, mass calcd. for $C_{16}H_{17}N_5O_3S$, 359.11 m/z found 360.0[M+H]⁺. ¹H NMR (400 MHz, CHLOROFORM-d) δ9.26 (s, 1H), 8.35 (dd, J=8.00, 1.60 Hz, 1H), 7.98 (dd, J=8.40, 1.20 Hz, 1H), 7.56-7.45 (m, 3H), 7.43-7.35 (m, 1H), 7.22-7.14 (m, 1H), 7.13-7.07 (m, 1H), 4.86-4.81 (m, 2H), 4.30-4.20 (m, 2H), 3.15 (s, 3H), 2.99 (t, J=6.40 Hz, 1H).

Example 39: 2-(3-(2-((3-(trifluoromethyl)phenyl)amino)phenyl)-1H-1,2,4-triazol-1-yl)ethanol (Compound 39)

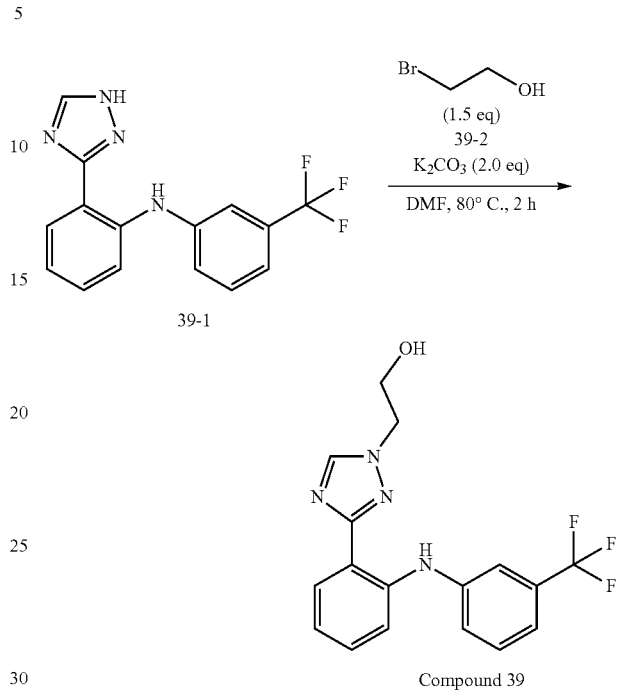

Compound 39

To a mixture of 39-1 (35.0 mg, 0.1 mmol, 1.00 eq) and K₂CO₃ (31.8 mg, 0.2 mmol, 2.00 eq) in DMF (3.0 mL), was added 39-2 (21.6 mg, 0.1 mmol, 1.50 eq). The resulting mixture was stirred at 80° C. under N₂ for 2 h. LCMS showed the reaction was complete. The mixture was filtered, and the solid was washed with DMF (1 mL). The filtrate was purified by prep-HPLC (acidic HCl condition) to provide the title compound (6.88 mg, 16.6 umol, 14.5% yield, HCl). LCMS (ESI): RT=1.174 min, mass calc. for $C_{17}H_{15}F_3N_4O$ 348.12, m/z found 349.1 [M+H]⁺. ¹HNMR (400 MHz, DMSO-d₆) δ 8.68 (s, 1H), 8.10 (dd, J=1.5, 7.8 Hz, 1H), 7.46-7.54 (m, 2H), 7.44 (s, 1H), 7.39-7.42 (m, 1H), 7.31-7.37 (m, 1H), 7.24 (d, J=7.0 Hz, 1H), 6.97-7.03 (m, 1H), 4.31 (t, J=5.3 Hz, 2H), 3.80 (t, J=5.3 Hz, 2H).

Example 40: 2-[2-(3-pyridylmethyl)tetrazol-5-yl]-N-[4-(trifluoromethyl)phenyl]aniline (Compound 40)

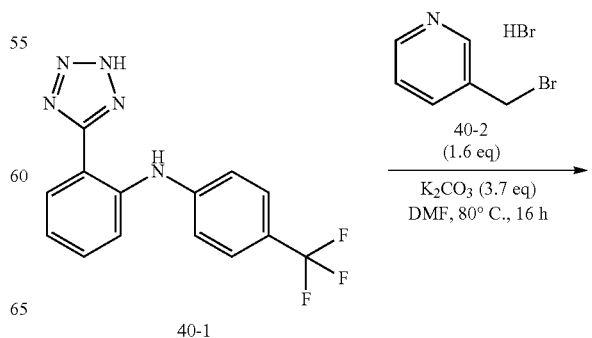

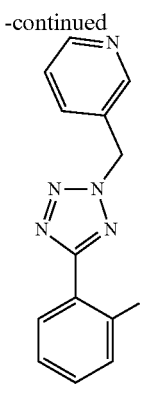

Compound 40

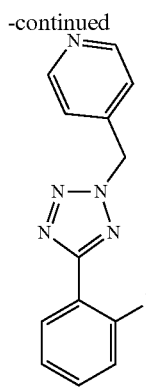

Compound 41

To a mixture of 40-1 (60 mg, 0.197 mmol, 1.00 eq) and 40-2 (80 mg, 0.316 mmol, 1.61 eq, HBr) in DMF (2 mL) was added K$_2$CO$_3$ (100 mg, 0.723 mmol, 3.68 eq) in one portion at 25° C. The mixture was stirred at 80° C. for 16 h. LCMS showed the starting material was consumed completely. TLC showed one new spot was formed. The reaction mixture was diluted with water (15 mL) and extracted with EtOAc (20 mL*3). The combined organic layers were dried with anhydrous Na$_2$SO$_4$, filtered, and concentrated under vacuum. The residue was purified by flash silica gel chromatography to obtain the title compound (36.35 mg, 90 umol, 46.2% yield). LCMS (ESI): RT=0.797 min, mass calcd. for C$_{20}$H$_{15}$F$_3$N$_6$, 396.13 m/z found 377.0[M+H−20]$^+$. $^1$HNMR (400 MHz, DMSO-d$_6$) δ8.74-8.67 (m, 2H), 8.58 (dd, J=4.80, 1.60 Hz, 1H), 8.04-7.95 (m, 1H), 7.84-7.77 (m, 1H), 7.54-7.47 (m, 4H), 7.44-7.39 (m, 1H), 7.23-7.16 (m, 1H), 7.12 (d, J=8.80 Hz, 2H), 6.06 (s, 2H).

Example 41: 2-[2-(4-pyridylmethyl)tetrazol-5-yl]-N-[4-(trifluoromethyl)phenyl]aniline (Compound 41)

To a mixture of 41-1 (60 mg, 0.197 mmol, 1.00 eq) and 41-2 (80 mg, 0.316 mmol, 1.61 eq, HBr) in DMF (2.5 mL) was added K$_2$CO$_3$ (100 mg, 0.723 mmol, 3.68 eq) in one portion at 25° C. The mixture was stirred at 80° C. for 16 h. The reaction was monitored by LCMS. The reaction mixture was diluted with water (15 mL) and extracted with EtOAc (20 mL*3). The combined organic layers were dried with anhydrous Na$_2$SO$_4$, filtered and concentrated under vacuum. The residue was purified by flash silica gel chromatography to provide the title compound (31.32 mg, 75 umol, 38.2% yield). LCMS (ESI): RT=1.126 min, mass calcd. for C$_{20}$H$_{15}$F$_3$N$_6$, 396.13 m/z found 397.0[M+H]$^+$ and 377.0[M+H−20]$^+$. $^1$HNMR (400 MHz, DMSO-d$_6$) δ8.71 (s, 1H), 8.61-8.53 (m, 2H), 8.03-7.97 (m, 1H), 7.56-7.48 (m, 4H), 7.32-7.26 (m, 2H), 7.24-7.17 (m, 1H), 7.11 (d, J=8.50 Hz, 2H), 6.09 (s, 2H).

Example 42: N-methyl-2-[5-[2-[4-(trifluoromethyl)anilino]phenyl]tetrazol-2-yl]acetamide (Compound 42)

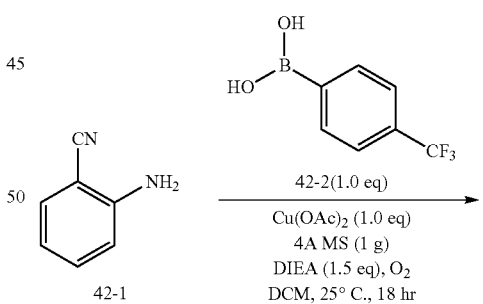

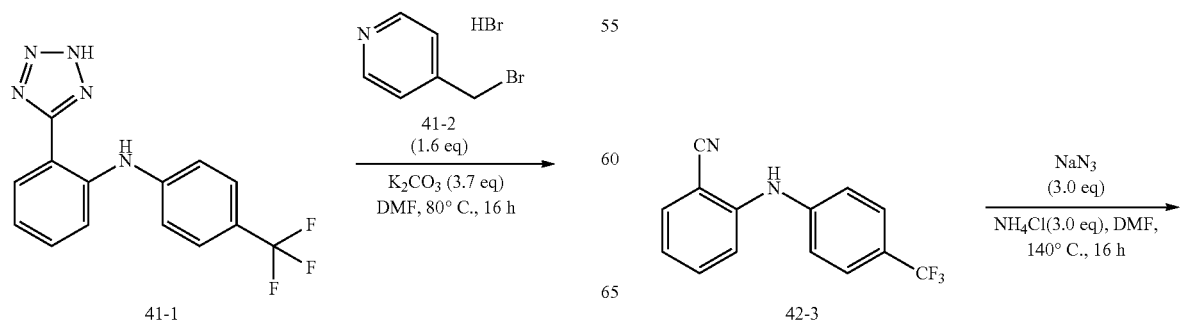

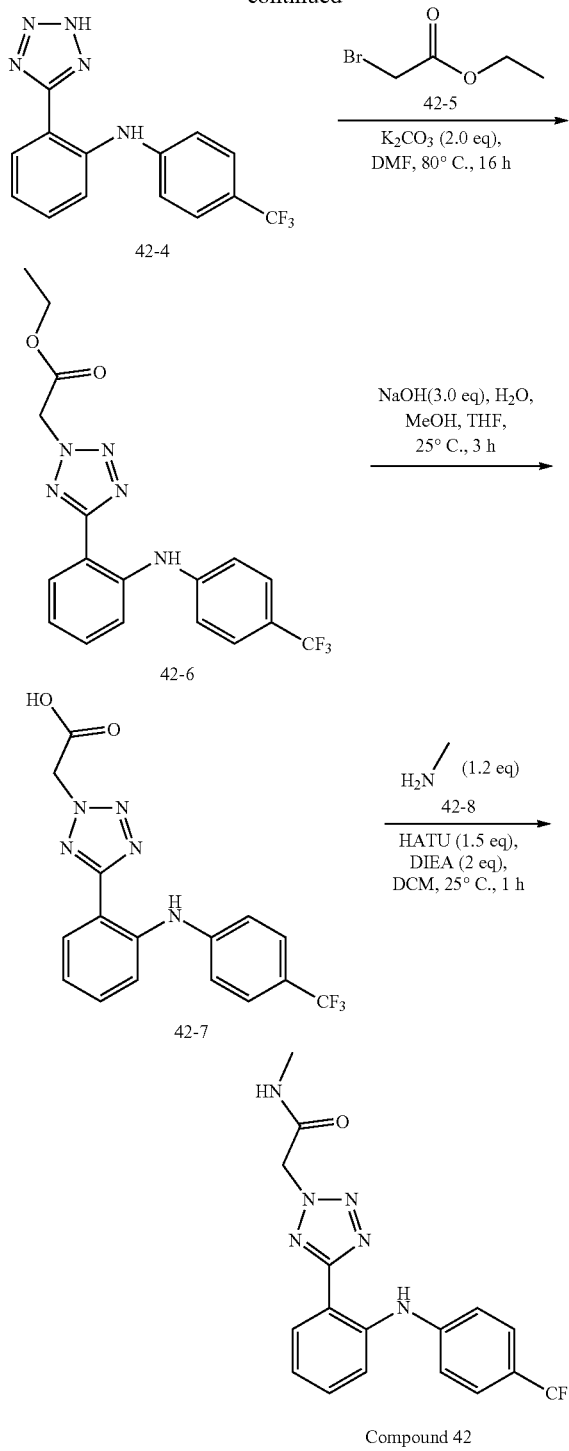

Compound 42 filtered through celite and concentrated under reduced pressure to give a residue. The crude product was purified by column chromatography over silica gel to give 42-3 (1.0 g, 3.7 mmol, 36.8% yield) as a colourless oil. LCMS (ESI): RT=0.817 min, mass calc. for $C_{14}H_9F_3N_2$ 262.07 m/z found 262.8 [M+H]$^+$.

Step 2: 2-(2H-tetrazol-5-yl)-N-[4-(trifluoromethyl)phenyl]aniline

To a solution of 42-3 (1.0 g, 3.8 mmol, 1.0 eq) in DMF (10.0 mL) was added NH$_4$Cl (611.9 mg, 11.4 mmol, 0.4 mL, 3.0 eq) and NaN$_3$ (743.1 mg, 11.4 mmol, 3.0 eq). The mixture was stirred at 140° C. for 16 hour under an N$_2$ atmosphere. LCMS showed the desired compound was formed. The reaction mixture was poured into sat. aq. NaHCO$_3$ (5 mL) and extracted with EtOAc (5 mL*2). The combined organic layers were washed with brine (10 mL), dried over Na$_2$SO$_4$ and filtered. The solvent was removed under reduced pressure to afford the crude compound 42-4 (1.1 g, 3.6 mmol, 94.6% yield). LCMS (ESI): RT=0.806 min, mass calc. for $C_{14}H_{10}F_3N_5$ 305.09, m/z found 305.9 [M+H]$^+$.

Step 3: ethyl 2-[5-[2-[4-(trifluoromethyl)anilino]phenyl]tetrazol-2-yl]acetate

To a solution of 42-4 (500.0 mg, 1.6 mmol, 1.0 eq) in DMF (5.0 mL) was added K$_2$CO$_3$ (339.6 mg, 2.5 mmol, 1.5 eq) and 42-5 (273.5 mg, 1.6 mmol, 0.18 mL, 1.0 eq). The mixture was stirred at 80° C. for 16 hour under an N$_2$ atmosphere. LCMS showed the desired compound was formed. TLC (Petroleum ether:Ethyl acetate=3/1) showed the starting material was consumed completely. The reaction mixture was concentrated to give the crude product. The crude product was purified by column chromatography over silica gel to give 42-6 (480.0 mg, 1.2 mmol, 72.5% yield). LCMS (ESI): RT=0.886 min, mass calc. for $C_{18}H_{16}F_3N_5O_2$, 391.13 m/z found 392.0 [M+H]$^+$.

Step 4: 2-[5-[2-[4-(trifluoromethyl)anilino]phenyl]tetrazol-2-yl]acetic acid

To a solution of 42-6 (480.0 mg, 1.2 mmol, 1.0 eq) in H$_2$O (2.0 mL) and MeOH (4.0 mL) was added NaOH (147.2 mg, 36.8 mmol, 29.9 eq). The resulting mixture was stirred at 25° C. for 4 hours. LCMS showed the desired compound was formed. TLC (Petroleum ether:Ethyl acetate=3/1) showed the starting material was consumed and a new spot appeared. The reaction solvent was removed under reduced pressure and water (5 mL) was added. The reaction was acidified by adding 1M HCl (10 mL) to precipitate a solid. The mixture was was washed with EtOAc (20 mL×2). The combined organic layers were concentrated to give crude 42-7 (400.0 mg, 1.1 mmol, 89.5% yield). LCMS (ESI): RT=0.826 min, mass calc. for $C_{16}H_{12}F_3N_5O_2$ 363.09 m/z found 363.9 [M+H]$^+$.

Step 5: N-methyl-2-[5-[2-[4-(trifluoromethyl)anilino]phenyl]tetrazol-2-yl]acetamide To a solution of 42-7 (50.0 mg, 0.14 mmol, 1.0 eq) and 42-8 (4.3 mg, 0.14 mmol, 1.0 eq) in DCM (5.0 mL) was added HATU (52.3 mg, 0.14 mmol, 1.0 eq) and DIEA (53.4 mg, 0.41 mmol, 72.1 uL, 3.0 eq). The resulting mixture was stirred at 20° C. for 1 hour. LCMS showed the desired compound was formed. The reaction mixture was concen- Step 1: 2-[4-(trifluoromethyl)anilino]benzonitrile To a solution of 42-1 (1.2 g, 10.2 mmol, 1.0 eq) and 42-2 (2.9 g, 15.2 mmol, 1.5 eq) in DCM (20.0 mL) was added DIEA (1.6 g, 12.2 mmol, 2.13 mL, 1.2 eq) and Cu(OAc)$_2$ (1.9 g, 10.2 mmol, 1.0 eq). The mixture was stirred at 25° C. for 16 hour under O$_2$ atmosphere. LCMS showed the desired compound was formed. TLC (30% ethyl acetate in petroleum ether, Rf=0.6) showed a new spot. The reaction was

Example 43: N,N-dimethyl-2-[5-[2-[4-(trifluoromethyl)anilino]phenyl]tetrazol-2-yl]acetamide (Compound 43)

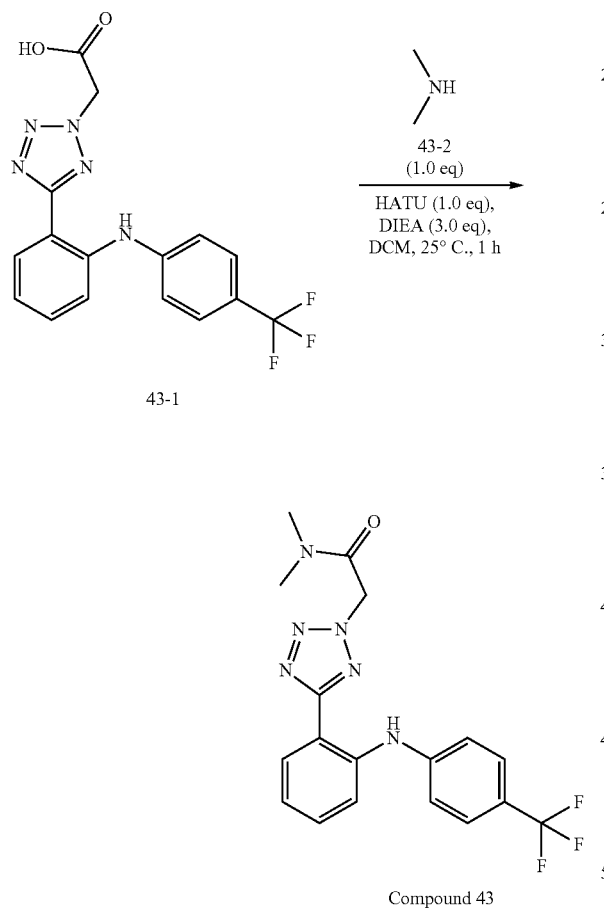

Compound 43

To a solution of 43-1 (50.0 mg, 0.14 mmol, 1.0 eq) and 43-2 (6.2 mg, 0.14 mmol, 7.0 uL, 1.0 eq) in DCM (5.0 mL) was added HATU (52.3 mg, 0.14 mmol, 1.0 eq) and DIEA (53.4 mg, 0.41 mmol, 72.1 uL, 3.0 eq). The resulting mixture was stirred at 20° C. for 1 hour. LCMS showed the desired compound was formed. The reaction mixture was concentrated under reduced pressure to give a residue. The crude product was purified by prep-HPLC to give the title compound (14.31 mg, 35.93 umol, 26.10% yield). LCMS (ESI): RT=0.830 min, mass calc. for $C_{18}H_{17}F_3N_6O$ 390.14, m/z found 391.0 [M+H]$^+$; $^1$HNMR (400 MHz, DMSO-d$_6$) δ 8.82 (s, 1H), 8.08-8.03 (m, 1H), 7.56 (t, J=9.2 Hz, 3H), 7.51-7.46 (m, 1H), 7.27 (d, J=8.3 Hz, 2H), 7.18 (t, J=7.2 Hz, 1H), 5.95 (s, 2H), 3.08 (s, 3H), 2.87 (s, 3H).

Example 44: N,N-diethyl-2-[5-[2-[4-(trifluoromethyl)anilino]phenyl]tetrazol-2-yl]acetamide (Compound 44)

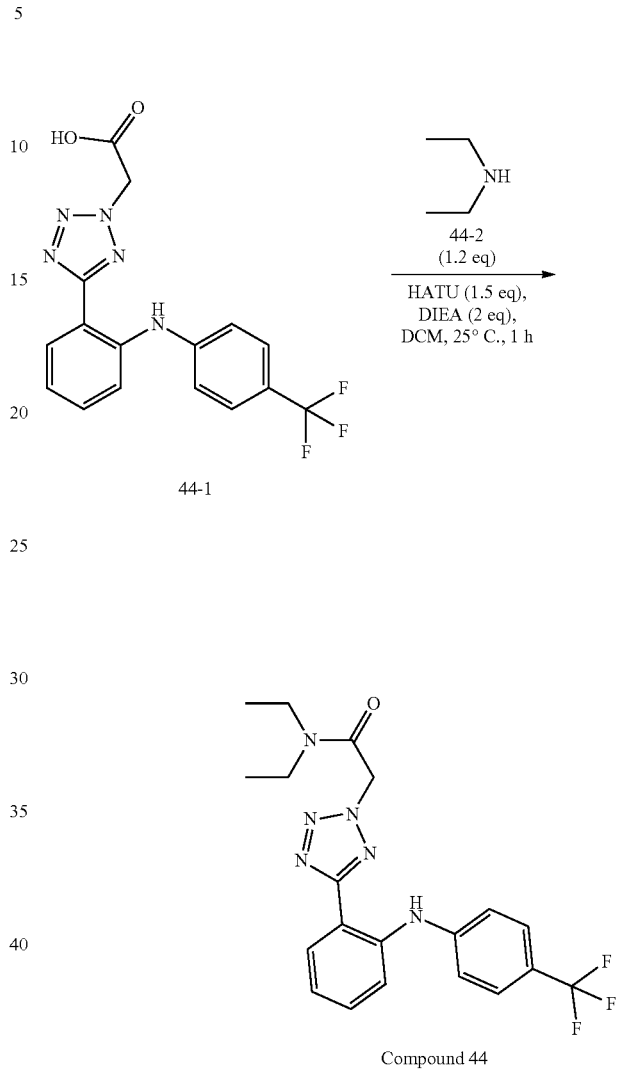

Compound 44

To a solution of 44-1 (50.0 mg, 0.14 mmol, 1.0 eq) and 44-2 (10.1 mg, 0.14 mmol, 14.2 uL, 1.0 eq) in DCM (5.0 mL) was added HATU (52.3 mg, 0.14 mmol, 1.0 eq) and DIEA (53.4 mg, 0.41 mmol, 72.1 uL, 3.0 eq). The resulting mixture was stirred at 20° C. for 1 hour. LCMS showed the desired compound was formed. The reaction mixture was concentrated under reduced pressure to give a residue. The crude product was purified by prep-HPLC to give the title compound (4.44 mg, 10.61 umol, 7.71% yield). LCMS (ESI): RT=0.886 min, mass calc. for $C_{20}H_{21}F_3N_6O$ 418.17, m/z found 441.1 [M+23]$^+$; $^1$HNMR (400 MHz, DMSO-d$_6$) δ 8.83 (s, 1H), 8.06 (dd, J=1.0, 7.8 Hz, 1H), 7.56 (t, J=8.4 Hz, 3H), 7.51-7.46 (m, 1H), 7.26 (m, J=8.5 Hz, 2H), 7.18 (t, J=7.3 Hz, 1H), 5.93 (s, 2H), 3.42 (q, J=7.0 Hz, 2H), 3.30 (q, J=7.0 Hz, 2H), 1.21 (t, J=7.0 Hz, 3H), 1.04 (t, J=7.0 Hz, 3H).

--- trated under reduced pressure to give a residue. The crude product was purified by prep-HPLC to give Compound 42 (8.24 mg, 20.36 umol, 14.80% yield). LCMS (ESI): RT=0.814 min, mass calc. for $C_{17}H_{15}F_3N_6O$ 376.13, m/z found 377.0 [M+H]$^+$; $^1$HNMR (400 MHz, DMSO-d$_6$) δ=8.78 (s, 1H), 8.37 (br d, J=4.3 Hz, 1H), 8.04 (dd, J=1.3, 7.8 Hz, 1H), 7.56 (t, J=7.7 Hz, 3H), 7.52-7.46 (m, 1H), 7.24 (d, J=8.5 Hz, 2H), 7.21-7.15 (m, 1H), 5.51 (s, 2H), 2.66 (d, J=4.5 Hz, 3H).

Example 45: 1-pyrrolidin-1-yl-2-[5-[2-[4-(trifluoromethyl)anilino]phenyl]tetrazol-2-yl]ethanone (Compound 45)

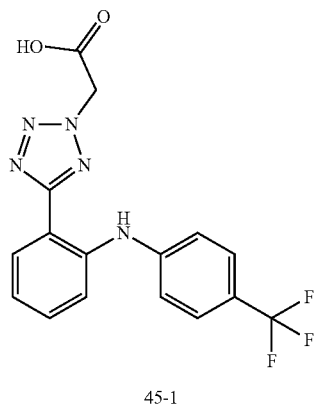
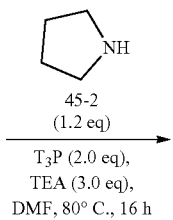

Example 46: N-methyl-2-[5-[2-[4-(trifluoromethoxy)anilino]phenyl]tetrazol-2-yl]acetamide (Compound 46)

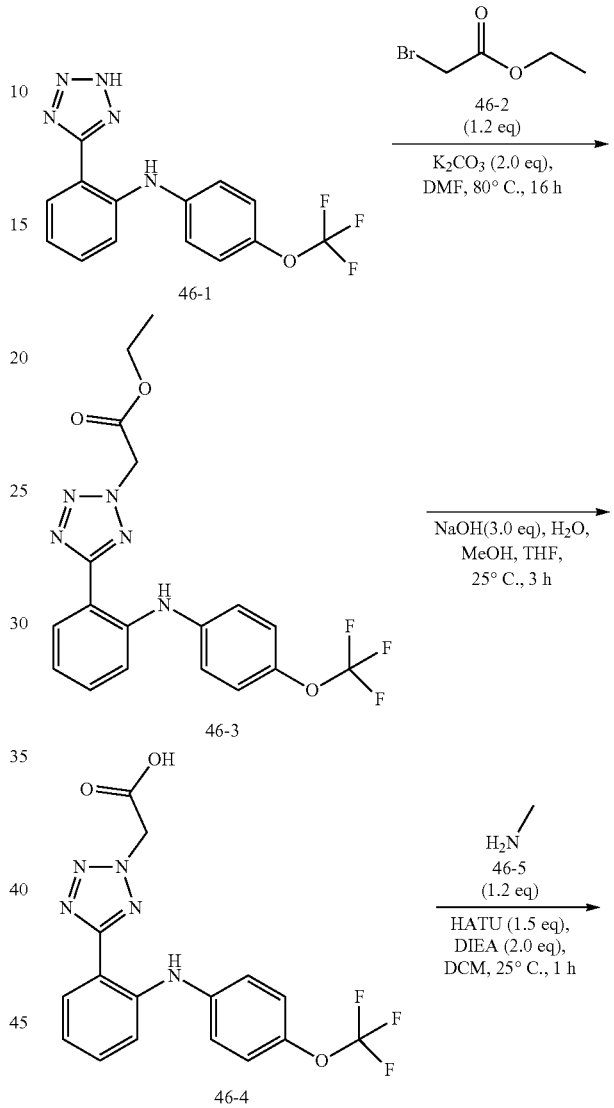

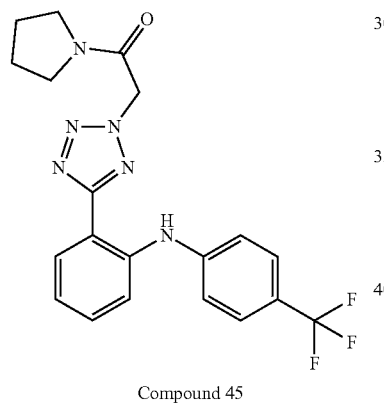

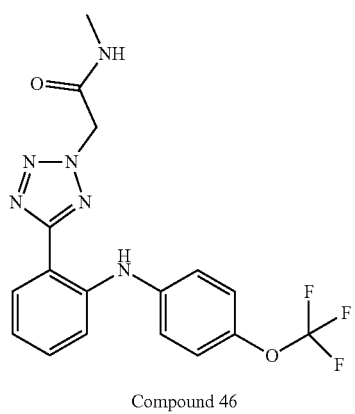

To a solution of 45-1 (30.0 mg, 82.6 umol, 1.0 eq) and 45-2 (5.9 mg, 82.6 umol, 6.9 uL, 1.0 eq) in DMF (2.0 mL) was added TEA (33.4 mg, 0.33 mmol, 45.8 uL, 4.0 eq) and T₃P (52.6 mg, 82.6 umol, 49.1 uL, 50% purity, 1.0 eq). The resulting mixture was stirred at 80° C. for 16 hours. LCMS showed the desired compound was formed. The reaction mixture was concentrated under reduced pressure to give a residue. The crude product was purified by prep-HPLC to give the title compound (8.34 mg, 19.83 umol, 24.01% yield). LCMS (ESI): RT=0.855 min, mass calc. for $C_{20}H_{19}F_3N_6O$ 416.16, m/z found 439.0 [M+23]⁺; ¹HNMR (400 MHz, CDCl₃-d) δ 8.97 (s, 1H), 8.22 (dd, J=1.5, 7.8 Hz, 1H), 7.53 (t, J=8.0 Hz, 3H), 7.40-7.34 (m, 1H), 7.30 (d, J=8.5 Hz, 2H), 7.03 (t, J=7.7 Hz, 1H), 5.50 (s, 2H), 3.57 (q, J=6.4 Hz, 4H), 2.13-2.05 (m, 2H), 1.98-1.90 (m, 2H).

293
Step 1: ethyl 2-[5-[2-[4-(trifluoromethoxy)anilino]phenyl]tetrazol-2-yl]acetate To a solution of 46-1 (600.0 mg, 1.9 mmol, 1.0 eq) in DMF (5.0 mL) was added $K_2CO_3$ (387.2 mg, 2.8 mmol, 1.5 eq) and 46-2 (374.8 mg, 2.2 mmol, 0.25 mL, 1.2 eq). The mixture was stirred at 80° C. for 16 hour under $N_2$ atmosphere. LCMS showed the desired compound was formed. TLC (Petroleum ether:Ethyl acetate=3/1) showed the starting material was consumed completely. The reaction was filtered to give a crude product. The crude product was purified by column chromatography over silica gel to give 46-3 (620.0 mg, 1.5 mmol, 81.4% yield). LCMS (ESI): RT=0.897 min, mass calc. for $C_{18}H_{16}F_3N_5O_3$ 407.12, m/z found 408.0 $[M+H]^+$.

Step 2: 2-[5-[2-[4-(trifluoromethoxy)anilino]phenyl]tetrazol-2-yl]acetic acid

To a solution of 46-3 (620.0 mg, 1.5 mmol, 1.0 eq) in $H_2O$ (2.0 mL) MeOH (4.0 mL) was added NaOH (243.2 mg, 6.1 mmol, 4.0 eq). The resulting mixture was stirred at 20° C. for 4 hours. LCMS showed the desired compound was formed. TLC (Petroleum ether:Ethyl acetate=3/1) showed the starting material was consumed and a new spot appeared. The reaction solvent was removed under reduced pressure and water (5 mL) was added. The reaction was acidified by adding 1M HCl (10 mL) and solid precipitated. The mixture was washed with EtOAc (20 mL×2). The combined organic layers were concentrated to give crude 46-4 (250.0 mg, 0.66 mmol, 43.4% yield). LCMS (ESI): RT=0.806 min, mass calc. for $C_{16}H_{12}F_3N_5O_3$ 379.09, m/z found 379.9 $[M+H]^+$.

Step 3: N-methyl-2-[5-[2-[4-(trifluoromethoxy)anilino]phenyl]tetrazol-2-yl]acetamide To a solution of 46-4 (40.0 mg, 0.11 mmol, 1.0 eq) and compound 5 (4.9 mg, 0.16 mmol, 1.5 eq) in DCM (5.0 mL) was added HATU (40.1 mg, 0.11 mmol, 1.0 eq) and DIEA (40.9 mg, 0.32 mmol, 55.3 uL, 3.0 eq). The resulting mixture was stirred at 20° C. for 1 hour. LCMS showed the desired compound was formed. The reaction mixture was concentrated under reduced pressure to give a residue. The residue was purified by prep-HPLC to give Compound 46 (2.38 mg, 6.07 umol, 5.75% yield). LCMS (ESI): RT=0.830 min, mass calc. for $C_{17}H_{15}F_3N_6O_2$ 392.12, m/z found 393.0 $[M+H]^+$; $^1$HNMR (400 MHz, $CDCl_3$-d) δ 8.77 (s, 1H), 8.20 (d, J=8.0 Hz, 1H), 7.37 (s, 2H), 7.29 (br s, 2H), 7.23-7.17 (m, 2H), 6.98 (br t, J=6.7 Hz, 1H), 5.86 (br s, 1H), 5.43 (s, 2H), 2.88 (d, J=4.8 Hz, 3H).

294
Example 47: N,N-dimethyl-2-[5-[2-[4-(trifluoromethoxy)anilino]phenyl]tetrazol-2-yl]acetamide (Compound 47)

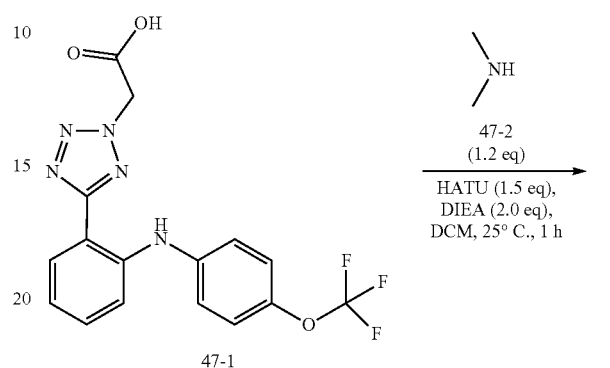

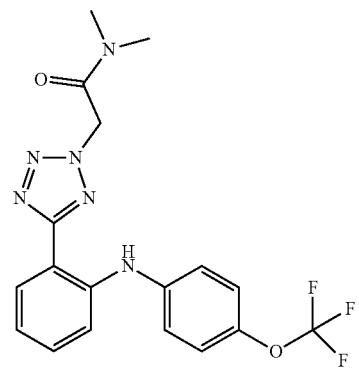

Compound 47

To a solution of 47-1 (40.0 mg, 0.11 mmol, 1.0 eq) and 47-2 (4.8 mg, 0.11 mmol, 5.3 uL, 1.0 eq) in DCM (5.0 mL) was added HATU (40.1 mg, 0.11 mmol, 1.0 eq) and DIEA (40.9 mg, 0.32 mmol, 55.3 uL, 3.0 eq). The resulting mixture was stirred at 20° C. for 1 hour. LCMS showed the desired compound was formed. The reaction mixture was concentrated under reduced pressure to give a residue. The residue was purified by prep-HPLC to give the title compound (2.49 mg, 6.13 umol, 5.81% yield). LCMS (ESI): RT=0.853 min, mass calc. for $C_{18}H_{17}F_3N_6O_2$ 406.14, m/z found 407.0 $[M+H]^+$; $^1$HNMR (400 MHz, $CDCl_3$-d) δ 8.82 (s, 1H), 8.22 (d, J=7.8 Hz, 1H), 7.39-7.31 (m, 2H), 7.30-7.27 (m, 2H), 7.22-7.16 (m, 2H), 6.96 (t, J=7.3 Hz, 1H), 5.59 (s, 2H), 3.17 (s, 3H), 3.06 (s, 3H).

Example 48: N,N-diethyl-2-[5-[2-[4-(trifluoromethoxy)anilino]phenyl]tetrazol-2-yl]acetamide (Compound 48)

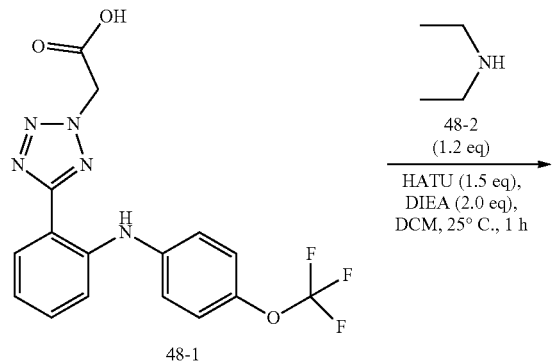

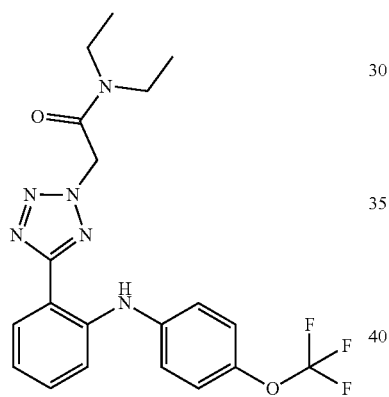

Compound 48

To a solution of 48-1 (40.0 mg, 0.11 mmol, 1.0 eq) and 48-2 (7.7 mg, 0.11 mmol, 10.9 uL, 1.0 eq) in DCM (5.0 mL) was added HATU (40.1 mg, 0.11 mmol, 1.0 eq) and DIEA (40.9 mg, 0.32 mmol, 55.3 uL, 3.0 eq). The resulting mixture was stirred at 20° C. for 1 hour. LCMS showed the desired compound was formed. The reaction mixture was concentrated under reduced pressure to give a residue. The residue was purified by prep-HPLC to give the title compound (4.44 mg, 10.61 umol, 7.71% yield). LCMS (ESI): RT=0.906 min, mass calc. for $C_{20}H_{21}F_3N_6O_2$ 434.17, m/z found 435.1 [M+H]$^+$; $^1$HNMR (400 MHz, CDCl$_3$-d) δ 8.83 (s, 1H), 8.22 (dd, J=1.1, 7.9 Hz, 1H), 7.39-7.31 (m, 2H), 7.31-7.27 (m, 2H), 7.21-7.17 (m, 2H), 7.01-6.92 (m, 1H), 5.57 (s, 2H), 3.46 (t, J=7.2, 9.7 Hz, 4H), 1.34 (t, J=7.2 Hz, 3H), 1.19 (t, J=7.2 Hz, 3H).

Example 49: 1-(pyrrolidin-1-yl)-2-(5-(2-((4-(trifluoromethoxy)phenyl)amino)phenyl)-2H-tetrazol-2-yl)ethan-1-one (Compound 49)

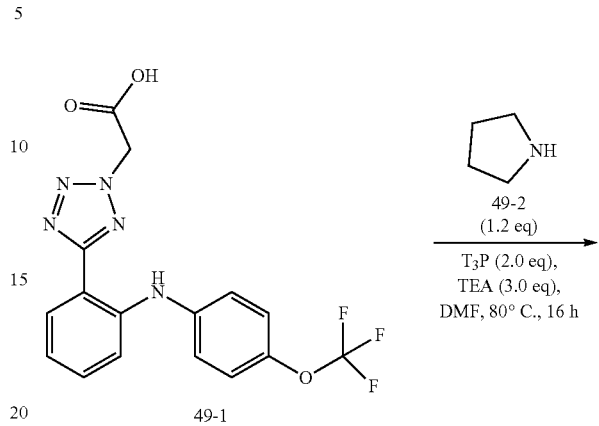

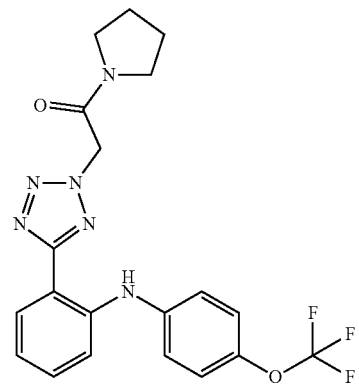

Compound 49

To a solution of 49-1 (50.0 mg, 0.13 mmol, 1.0 eq) and 49-2 (14.1 mg, 0.20 mmol, 16.5 uL, 1.5 eq) in DMF (2.0 mL) was added TEA (53.4 mg, 0.52 mmol, 73.1 uL, 4.0 eq) and T$_3$P (83.9 mg, 0.13 mmol, 78.4 uL, 50% purity, 1.0 eq). The resulting mixture was stirred at 80° C. for 16 hour. LCMS showed the desired compound was formed. The reaction mixture was concentrated under reduced pressure to give a residue. The crude product was purified by prep-HPLC to give the title compound (11.54 mg, 26.69 umol, 20.24% yield). LCMS (ESI): RT=0.873 min, mass calc. for $C_{20}H_{19}F_3N_6O_2$ 432.15, m/z found 433.0 [M+H]$^+$; $^1$HNMR (400 MHz, CDCl$_3$-d) δ 8.82 (s, 1H), 8.22 (d, J=8.0 Hz, 1H), 7.38-7.30 (m, 2H), 7.30-7.27 (m, 2H), 7.21-7.15 (m, 2H), 6.95 (t, J=7.5 Hz, 1H), 5.49 (s, 2H), 3.56 (q, J=6.9 Hz, 4H), 2.08 (t, J=6.6 Hz, 2H), 1.94 (t, J=6.7 Hz, 2H).

Example 50: 2-[2-[2-(dimethylamino)ethyl]tetrazol-5-yl]-N-[4-(trifluoromethyl)phenyl]aniline (Compound 50)

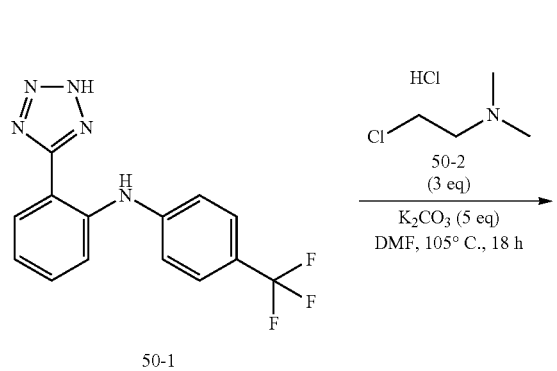

Compound 50

Example 51: 2-[2-(3-pyridylmethyl)tetrazol-5-yl]-N-[4-(trifluoromethoxy)phenyl]aniline (Compound 51)

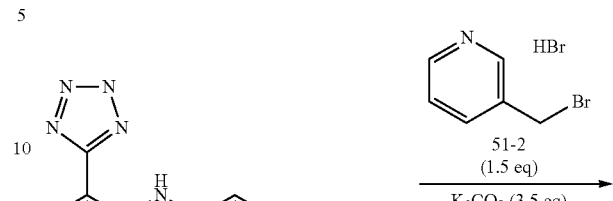

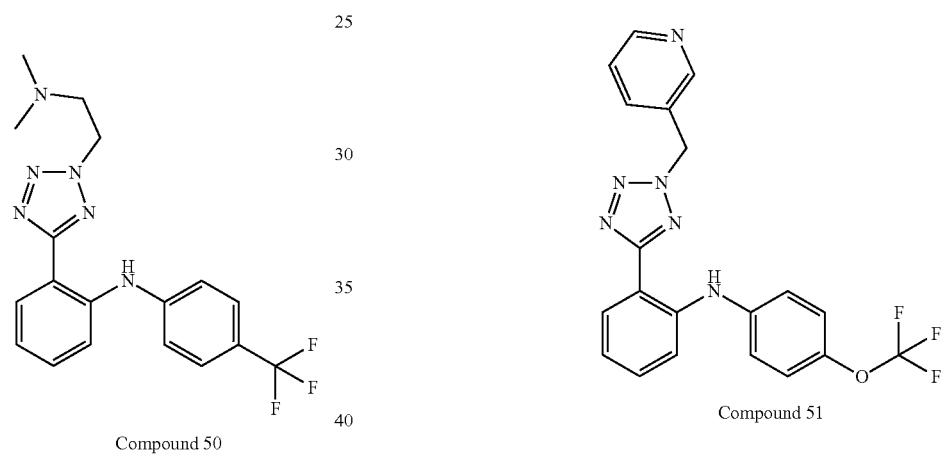

Compound 51

To a mixture of 50-1 (100 mg, 0.327 mmol, 1.00 eq) and 50-2 (141 mg, 0.979 mmol, 2.99 eq, HCl) in DMF (5 mL) was added $K_2CO_3$ (226 mg, 1.63 mmol, 4.99 eq) in one portion at 25° C. The mixture was stirred at 105° C. for 18 h. LCMS showed the starting material was consumed completely and one main peak with the desired MS was detected. TLC showed many new spots were formed. The reaction mixture was diluted with water (15 mL) and extracted with EtOAc (20 mL*3). The combined organic layers were dried with anhydrous $Na_2SO_4$, filtered, and concentrated under vacuum. The residue was purified by flash silica gel chromatography to provide the title compound (40.12 mg, 106.6 umol, 32.5% yield). LCMS (ESI): RT=1.023 min, mass calc. for $C_{18}H_{19}F_3N_6$ 376.16, m/z found 377.1[M+H]$^+$ and 357.1 [M+H−20]$^+$. $^1$HNMR (400 MHz, DMSO-d$_6$) δ 8.82 (s, 1H), 8.08-7.99 (m, 1H), 7.57-7.46 (m, 4H), 7.23-7.13 (m, 3H), 4.82 (t, J=6.00 Hz, 2H), 2.81 (t, J=6.00 Hz, 2H), 2.14 (s, 6H).

To a mixture of 51-1 (60 mg, 0.186 mmol, 1.00 eq) and 51-2 (85 mg, 0.336 mmol, 1.80 eq, HBr) in DMF (3 mL) was added $K_2CO_3$ (100 mg, 0.723 mmol, 3.87 eq) in one portion at 25° C. The mixture was stirred at 80° C. for 3.5 h. LCMS showed the starting material was consumed completely and one main peak with the desired MS was detected. TLC showed one new spot was formed. The reaction mixture was extracted with EtOAc (40 mL) and washed with brine (30 mL*4). The organic layer was dried with anhydrous $Na_2SO_4$, filtered, and concentrated under vacuum. The residue was purified by flash silica gel chromatography to provide the title compound (35.20 mg, 85.4 umol, 45.7% yield). LCMS (ESI): RT=1.174 min, mass calc. for $C_{20}H_{15}F_3N_6O$ 412.13, m/z found 413.1[M+H]$^+$. $^1$HNMR (400 MHz, DMSO-d$_6$) δ8.73 (d, J=2.00 Hz, 1H), 8.63-8.55 (m, 2H), 8.00 (dd, J=8.00, 1.20 Hz, 1H), 7.89-7.82 (m, 1H), 7.47-7.35 (m, 3H), 7.30-7.16 (m, 4H), 7.09-7.01 (m, 1H), 6.09 (s, 2H).

Example 52: 2-[2-(2-pyridylmethyl)tetrazol-5-yl]-N-[4-(trifluoromethyl)phenyl]aniline (Compound 52)

Example 53: 2-[2-(4-pyridylmethyl)tetrazol-5-yl]-N-[4-(trifluoromethoxy)phenyl]aniline (Compound 53)

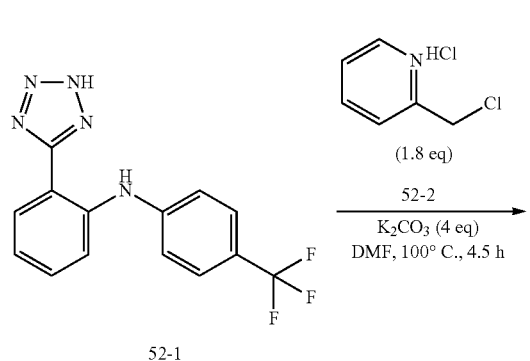

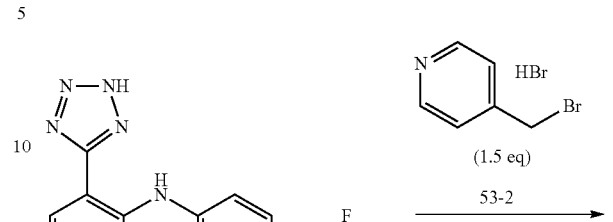

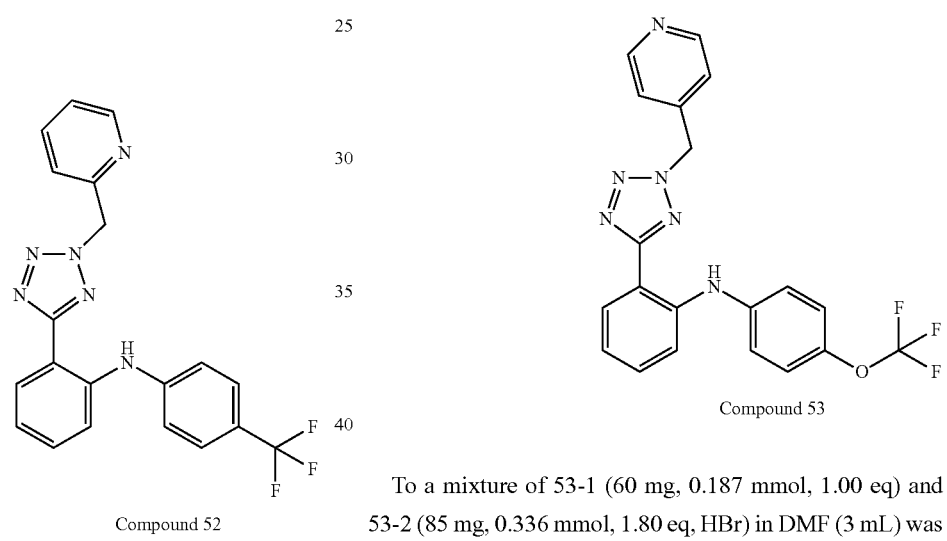

To a mixture of 52-1 (60 mg, 0.197 mmol, 1.00 eq) and 52-2 (60 mg, 366 mmol, 1.86 eq, HCl) in DMF (3 mL) was added K$_2$CO$_3$ (110 mg, 0.796 mmol, 4.05 eq) in one portion at 25° C. The mixture was stirred at 100° C. for 4.5 h. The reaction was monitored by LCMS and TLC. The reaction mixture was diluted with water (15 mL) and extracted with EtOAc (20 mL*3). The combined organic layers were dried with anhydrous Na$_2$SO$_4$, filtered, and concentrated under vacuum. The residue was purified by flash silica gel chromatography to provide the title compound (48.77 mg, 123.0 umol, 62.6% yield). LCMS (ESI): RT=1.294 min, mass calc. for C$_{20}$H$_{15}$F$_3$N$_6$ 396.13, m/z found 397.0[M+H]$^+$ and 377.0 [M+H−20]$^+$. $^1$HNMR (400 MHz, DMSO-d$_6$) δ 8.77 (s, 1H), 8.51 (d, J=4.00 Hz, 1H), 8.06-7.97 (m, 1H), 7.88-7.81 (m, 1H), 7.56-7.36 (m, 6H), 7.21-7.10 (m, 3H), 6.11 (s, 2H).

To a mixture of 53-1 (60 mg, 0.187 mmol, 1.00 eq) and 53-2 (85 mg, 0.336 mmol, 1.80 eq, HBr) in DMF (3 mL) was added K$_2$CO$_3$ (100 mg, 0.723 mmol, 3.87 eq) in one portion at 25° C. The mixture was stirred at 80° C. for 3.5 h. LCMS showed the starting material was consumed completely and one main peak with the desired MS was detected. TLC showed one new spot was formed. The reaction mixture was extracted with EtOAc (40 mL) and washed with brine (30 mL*4). The organic layer was dried with anhydrous Na$_2$SO$_4$, filtered, and concentrated under vacuum. The residue was purified by flash silica gel chromatography and then by prep-HPLC (basic condition) to provide the title compound (11.77 mg, 28.5 umol, 15.3% yield). LCMS (ESI): RT=1.120 min, mass calc. for C$_{20}$H$_{15}$F$_3$N$_6$O 412.13, m/z found 413.0[M+H]$^+$. $^1$HNMR (400 MHz, DMSO-d$_6$) δ8.65-8.55 (m, 3H), 8.01 (d, J=8.00 Hz, 1H), 7.47-7.37 (m, 2H), 7.33 (br d, J=5.20 Hz, 2H), 7.30-7.24 (m, 2H), 7.23-7.17 (m, 2H), 7.06 (t, J=6.80 Hz, 1H), 6.12 (s, 2H).

Example 54: 2-(2-(pyridin-2-ylmethyl)-2H-tetrazol-5-yl)-N-(4-(trifluoromethoxy)phenyl)aniline (Compound 54)

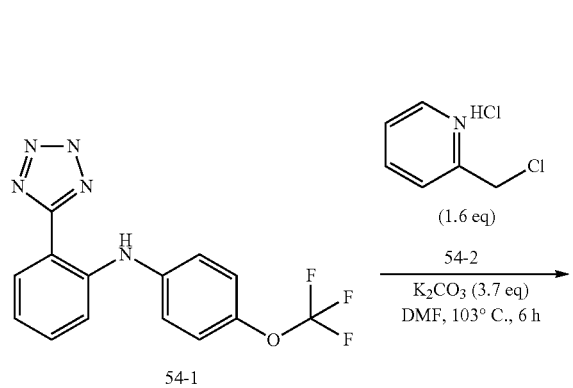

54-1

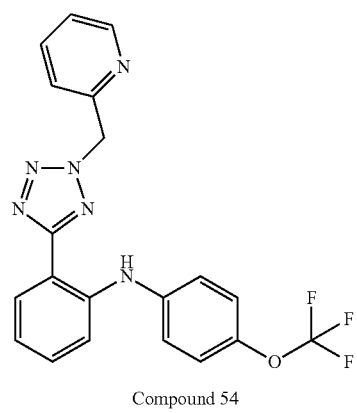

Compound 54

To a mixture of 54-1 (60 mg, 0.187 mmol, 1.00 eq) and 54-2 (60 mg, 0.366 mmol, 1.96 eq, HCl) in DMF (3 mL) was added $K_2CO_3$ (105 mg, 0.760 mmol, 4.07 eq) in one portion at 25° C. The mixture was stirred at 103° C. for 6 h. LCMS showed the starting material was consumed completely and one main peak with the desired MS was detected. The reaction mixture was extracted with EtOAc (40 mL) and washed with brine (30 mL*4). The organic layer was dried with anhydrous $Na_2SO_4$, filtered, and concentrated under vacuum. The residue was purified by prep-HPLC (basic condition) to provide the title compound (42.39 mg, 0.102 mmol, 54.5% yield). LCMS (ESI): RT=1.295 min, mass calc. for $C_{20}H_{15}F_3N_6O$ 412.13, m/z found 413.0[M+H]$^+$. $^1$HNMR (400 MHz, DMSO-d$_6$) δ8.66 (s, 1H), 8.52 (br d, J=3.60 Hz, 1H), 8.02 (d, J=8.00 Hz, 1H), 7.86 (t, J=7.60 Hz, 1H), 7.47 (d, J=7.60 Hz, 1H), 7.44-7.35 (m, 3H), 7.31-7.20 (m, 4H), 7.04 (t, J=6.80 Hz, 1H), 6.15 (s, 2H).

Example 55: 2-[2-[2-(dimethylamino)ethyl]tetrazol-5-yl]-N-[4-(trifluoromethoxy)phenyl]aniline (Compound 55)

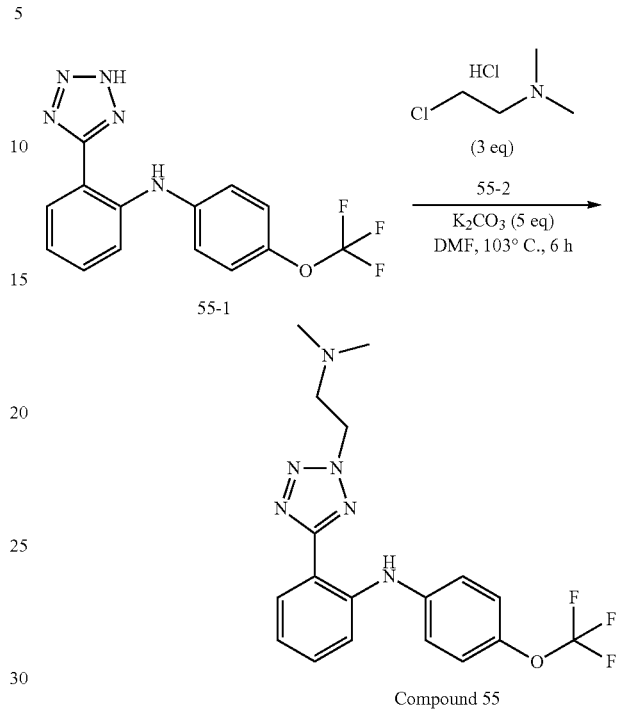

Compound 55

To a mixture of 55-1 (100 mg, 0.311 mmol, 1.00 eq) and 55-2 (135 mg, 0.934 mmol, 3.00 eq, HCl) in DMF (5 mL) was added $K_2CO_3$ (215 mg, 1.56 mmol, 5.00 eq) in one portion at 25° C. The mixture was stirred at 103° C. for 6 h. LCMS showed the starting material was consumed completely and one main peak with the desired MS was detected. The reaction mixture was extracted with EtOAc (40 mL) and washed with brine (30 mL*4). The organic layer was dried with anhydrous $Na_2SO_4$, filtered, and concentrated under vacuum. The residue was purified by prep-HPLC (basic condition) to provide the title compound (67.62 mg, 0.171 mmol, 54.8% yield). LCMS (ESI): RT=1.038 min, mass calc. for $C_{18}H_{19}F_3N_6O$ 392.16, m/z found 393.4[M+H]$^+$. $^1$HNMR (400 MHz, DMSO-d$_6$) δ8.71 (s, 1H), 8.05 (d, J=7.60 Hz, 1H), 7.45-7.37 (m, 2H), 7.32-7.23 (m, 4H), 7.06 (t, J=6.80 Hz, 1H), 4.85 (t, J=6.00 Hz, 2H), 2.86 (t, J=6.00 Hz, 2H), 2.16 (s, 6H).

Example 56: 2-[4-[2-[3-(trifluoromethyl)anilino]phenyl]pyrazol-1-yl]ethanol (Compound 56)

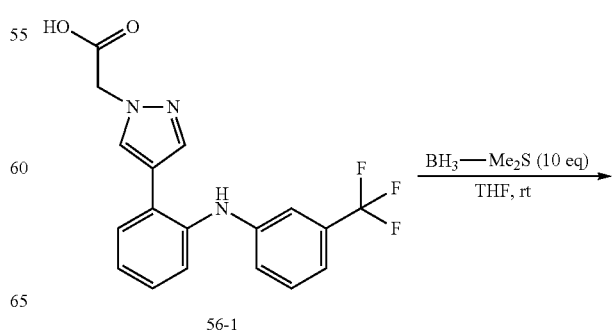

56-1

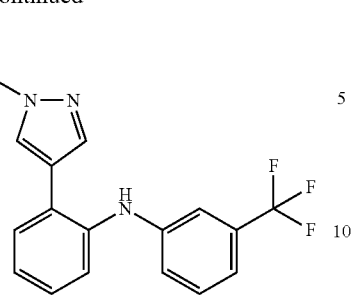

Compound 56

To a solution of 56-1 (50 mg, 0.14 mmol, 1.00 eq) in THF (3 mL) was added BH$_3$-Me$_2$S (10 M, 138.38 uL, 10.00 eq) and the resulting mixture was stirred at 25° C. for 16 hr. LCMS showed that the desired MS signal was detected. The reaction was quenched by MeOH (10 mL) slowly and concentrated. The crude product was purified by CombiFlash to give the title compound (12 mg, 28.68 umol, 20.72% yield). LCMS (ESI): RT=0.781 min, mass calc. for C$_{18}$H$_{16}$F$_3$N$_3$O 347.12, m/z found 347.9 [M+H]$^+$. $^1$HNMR (400 MHz, CHLOROFORM-d) δ7.71 (s, 1H), 7.62 (s, 1H), 7.40-7.20 (m, 1H), 7.16 (s, 1H), 7.15-7.00 (m, 4H), 5.71 (brs, 1H), 4.30-4.20 (m, 2H), 4.10-3.95 (m, 2H).

Example 57: 2-[4-[2-[3-(trifluoromethyl)anilino]phenyl]pyrazol-1-yl]ethanol (Compound 57)

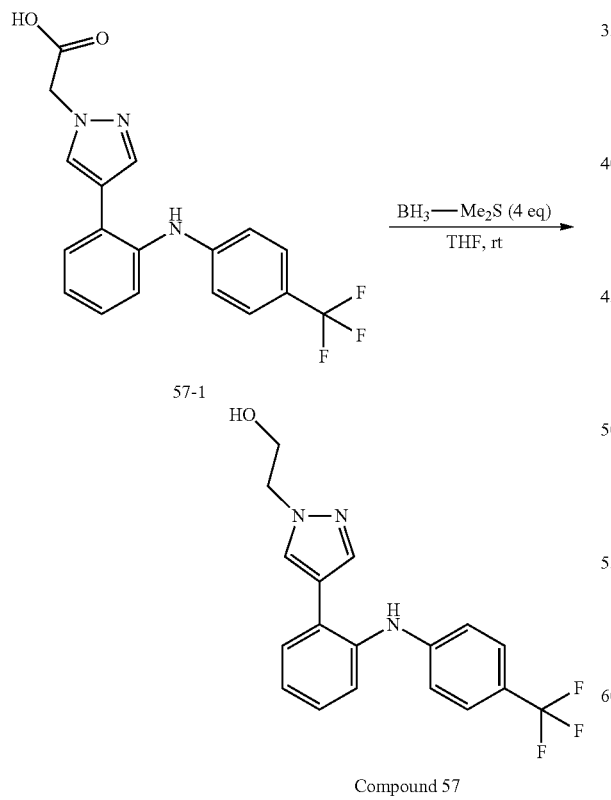

the resulting mixture was stirred at 30° C. for 16 hr. LCMS showed that the desired MS signal was detected. The reaction was quenched by MeOH (10 mL) slowly and concentrated. The crude product was purified by CombiFlash to give the title compound (15.00 mg, 39.30 umol, 71.00% yield). LCMS (ESI): RT=0.786 min, mass calc. for C$_{18}$H$_{16}$F$_3$N$_3$O 347.12, m/z found 347.9 [M+H]$^+$. $^1$HNMR (400 MHz, CHLOROFORM-d) δ7.70 (s, 1H), 7.60 (s, 1H), 7.40-7.30 (m, 4H), 7.28-7.20 (m, 1H), 7.16 (s, 1H), 7.03-6.80 (m, 2H), 5.76 (brs, 1H), 4.30-4.20 (m, 2H), 4.10-3.95 (m, 2H).

Example 58: ethyl 2-(4-(2-((3-(trifluoromethyl)phenyl)amino)phenyl)-1H-pyrazol-1-yl)acetate (Compound 58) and 2-(4-(2-((3-(trifluoromethyl)phenyl)amino)phenyl)-1H-pyrazol-1-yl)acetic Acid (Compound 59)

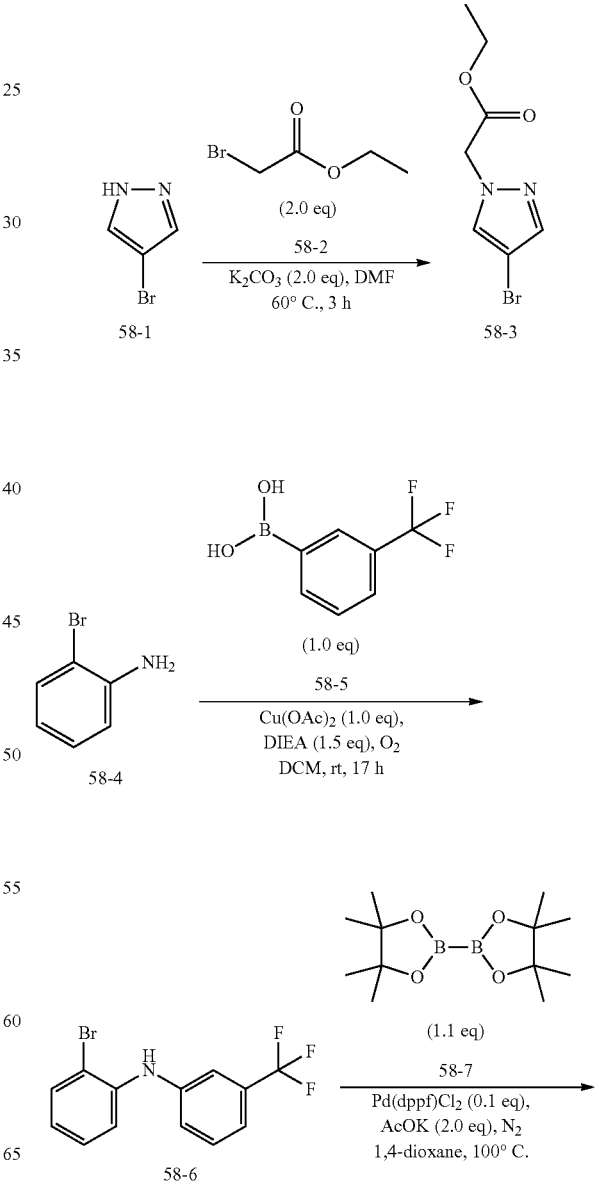

To a solution of 57-1 (20 mg, 55.35 umol, 1.00 eq) in THF (2 mL) was added BH$_3$-Me$_2$S (10 M, 22.14 uL, 4.00 eq) and -continued

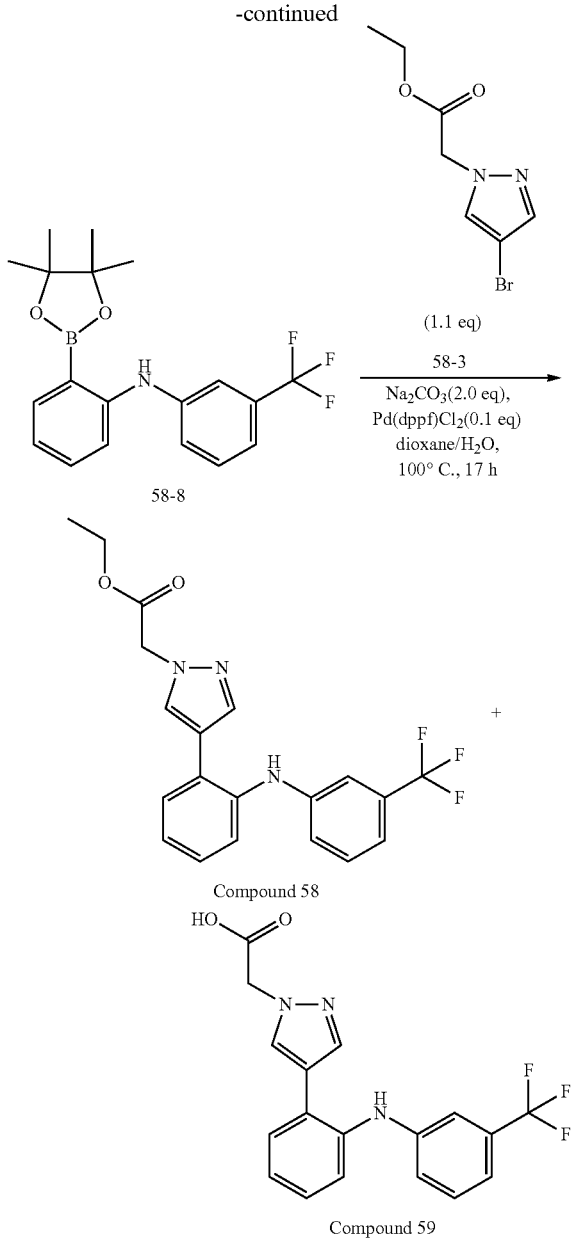

Step 1: ethyl 2-(4-bromo-1H-pyrazol-1-yl)acetate

To a mixture of 58-1 (1.0 g, 6.8 mmol, 1.00 eq) and $K_2CO_3$ (1.9 g, 13.6 mmol, 2.00 eq) in DMF (10.0 mL), was added 58-2 (2.3 g, 13.6 mmol, 1.5 mL, 2.00 eq). The resulting mixture was stirred at 26° C. for 2 h. LCMS showed the starting material remained. The mixture was stirred at 26° C. for an additional 17 h. TLC showed the starting material remained. The mixture was stirred at 60° C. for an additional 3 h. LCMS showed the reaction was complete. The mixture was diluted with EtOAc (40 mL), and washed with water (40 mL*5). The organic layer was dried over anhydrous $Na_2SO_4$, and concentrated under vacuum. The residue was purified by silica gel chromatography to provide 58-3 (1.8 g, 4.3 mmol, 62.5% yield) as a light yellow oil.

Step 2: 2-bromo-N-(3-(trifluoromethyl)phenyl)aniline

To a mixture of 58-4 (4.5 g, 26.3 mmol, 1.00 eq), 58-5 (5.0 g, 26.3 mmol, 1.00 eq) and $Cu(OAc)_2$ (4.8 g, 26.3 mmol, 1.00 eq) in DCM (100.0 mL), was added DIEA (5.1 g, 39.5 mmol, 6.9 mL, 1.50 eq). The mixture was degassed under vacuum and purged with $O_2$ 3 times. The resulting mixture was stirred at 26° C. under $O_2$ (15 Psi) for 17 h. The reaction was monitored by LCMS. The mixture was filtered, and the solid was washed with DCM (10 mL*3). The filtrate was washed with water (100 mL). The combined organic washings were dried over anhydrous $Na_2SO_4$, and concentrated under vacuum. The residue was purified by silica gel chromatography to provide 58-6 (4.25 g, 11.8 mmol, 44.9% yield). $^1$HNMR (400 MHz, CHLOROFORM-d) δ 7.58 (dd, J=1.3, 8.0 Hz, 1H), 7.44-7.39 (m, 1H), 7.37 (s, 1H), 7.30 (d, J=1.5 Hz, 1H), 7.28 (d, J=1.5 Hz, 1H), 7.27-7.20 (m, 2H), 6.84 (ddd, J=1.6, 7.2, 8.0 Hz, 1H), 6.16 (s, 1H).

Step 3: 2-(4,4,5,5-tetramethyl-1,3,2-dioxaborolan-2-yl)-N-(3-(trifluoromethyl)phenyl)aniline To a mixture of 58-6 (1.0 g, 3.2 mmol, 1.00 eq), 58-7 (882.7 mg, 3.5 mmol, 1.10 eq) and $Pd(dppf)Cl_2$ (231.2 mg, 0.3 mmol, 0.10 eq) in dioxane (20.0 mL), was added AcOK (620.2 mg, 6.3 mmol, 2.00 eq). The mixture was degassed under vacuum and purged with $N_2$ 3 times. The resulting mixture was stirred at 100° C. under $N_2$ for 17 h. LCMS showed the reaction was complete. The mixture was concentrated under vacuum. The residue was purified by silica gel chromatography to provide 58-8 (900.0 mg, crude).

Step 4: ethyl 2-(4-(2-((3-(trifluoromethyl)phenyl)amino)phenyl)-1H-pyrazol-1-yl)acetate and 2-(4-(2-((3-(trifluoromethyl)phenyl)amino)phenyl)-1H-pyrazol-1-yl)acetic acid To a mixture of 58-8 (200.0 mg, 0.6 mmol, 1.00 eq), 58-3 (154.0 mg, 0.7 mmol, 1.20 eq) and $Na_2CO_3$ (116.7 mg, 1.1 mmol, 2.00 eq) in dioxane (4.0 mL) and $H_2O$ (0.5 mL), was added $Pd(dppf)Cl_2$ (40.3 mg, 55.1 umol, 0.10 eq). The mixture was degassed under vacuum and purged with $N_2$ 3 times. The resulting mixture was stirred at 100° C. for 17 h. LCMS showed the reaction was complete. The mixture was concentrated under vacuum. The residue was purified by silica gel chromatography to afford the crude products. The crude products were purified by prep-HPLC (acidic HCl condition) to provide Compound 58 and Compound 59.

Compound 58: 2.31 mg, 4.4 umol, 0.8% yield, HCl. LCMS (ESI): RT=0.852 min, mass calc. for $C_{20}H_{18}F_3N_3O_2$ 389.14, m/z found 390.0 [M+H]$^+$. $^1$HNMR (400 MHz, CHLOROFORM-d) δ 7.74 (s, 1H), 7.66 (s, 1H), 7.41 (dd, J=1.5, 7.5 Hz, 1H), 7.38-7.31 (m, 2H), 7.29-7.24 (m, 1H), 7.20 (s, 1H), 7.15-7.06 (m, 3H), 5.78 (s, 1H), 4.94 (s, 2H), 4.26 (q, J=7.0 Hz, 2H), 1.30 (t, J=7.2 Hz, 3H).

Compound 59: 52.51 mg, 0.1 mmol, 24.0% yield, HCl. LCMS (ESI): RT=0.783 min, mass calc. for $C_{18}H_{14}F_3N_3O_2$ 361.10, m/z found 361.9 [M+H]$^+$. $^1$HNMR (400 MHz, METHANOL-d$_4$) δ 7.81 (s, 1H), 7.65 (s, 1H), 7.49 (d, J=7.5 Hz, 1H), 7.34-7.27 (m, 2H), 7.26-7.21 (m, 1H), 7.15-7.10 (m, 1H), 7.09-7.06 (m, 2H), 6.97 (d, J=7.8 Hz, 1H), 4.77 (s, 2H).

Example 59: ethyl 2-(4-(2-((4-(trifluoromethyl)phenyl)amino)phenyl)-1H-pyrazol-1-yl)acetate (Compound 60) and 2-(4-(2-((4-(trifluoromethyl)phenyl)amino)phenyl)-1H-pyrazol-1-yl)acetic Acid (Compound 61)

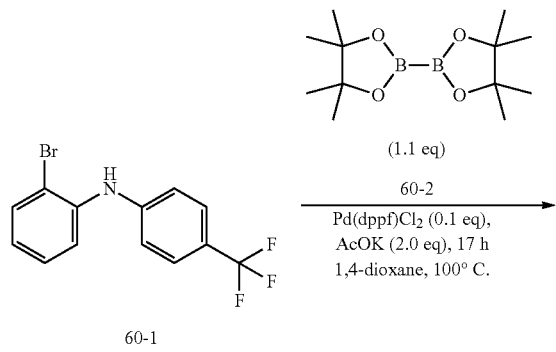

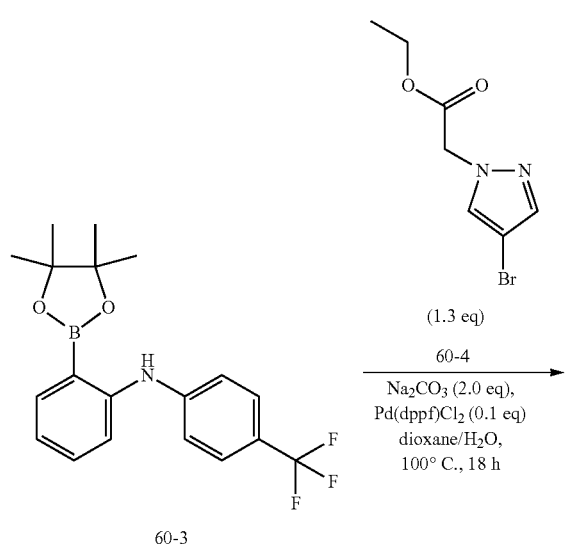

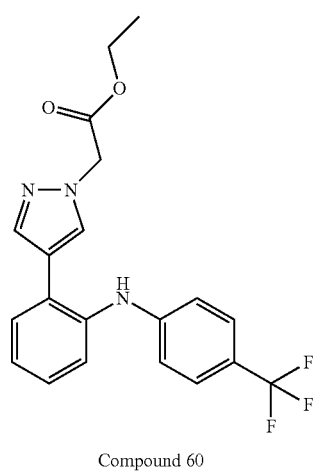

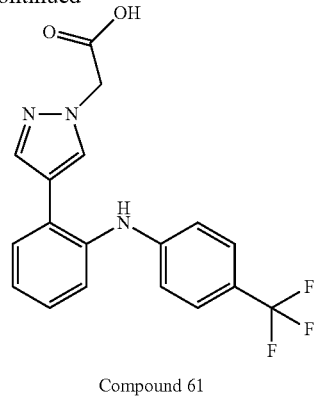

Compound 61

Step 1: 2-(4,4,5,5-tetramethyl-1,3,2-dioxaborolan-2-yl)-N-(4-(trifluoromethyl)phenyl)aniline To a mixture of 60-1 (2.0 g, 6.3 mmol, 1.00 eq), 60-2 (1.8 g, 7.0 mmol, 1.10 eq) and Pd(dppf)Cl$_2$ (462.9 mg, 0.6 mmol, 0.10 eq) in 1,4-dioxane (20.0 mL), was added AcOK (1.2 g, 12.7 mmol, 2.00 eq). The mixture was degassed under vacuum and purged with N$_2$ 3 times. The resulting mixture was stirred at 100° C. under N$_2$ for 17 h. LCMS showed the reaction was complete. The mixture was concentrated under vacuum. The residue was purified by silica gel chromatography to provide 60-3 (1.70 g, crude).

Step 2: ethyl 2-(4-(2-((4-(trifluoromethyl)phenyl)amino)phenyl)-1H-pyrazol-1-yl)acetate and 2-(4-(2-((4-(trifluoromethyl)phenyl)amino)phenyl)-1H-pyrazol-1-yl)acetic acid To a mixture of 60-3 (300.0 mg, 0.8 mmol, 1.00 eq), 60-4 (250.3 mg, 1.1 mmol, 1.30 eq) and Na$_2$CO$_3$ (175.1 mg, 1.7 mmol, 2.00 eq) in 1,4-dioxane (4.0 mL) and H$_2$O (0.5 mL), was added Pd(dppf)Cl$_2$ (60.4 mg, 82.6 umol, 0.10 eq). The mixture was degassed under vacuum and purged with N$_2$ 3 times. The resulting mixture was stirred at 100° C. under N$_2$ for 18 h. LCMS showed the reaction was complete. The mixture was diluted with water (30 mL), acidified with 2 M aqueous HCl to pH 6. The mixture was extracted with DCM (30 mL*4). The combined organic layers were dried over anhydrous Na$_2$SO$_4$, and concentrated under vacuum. The residue was purified by prep-HPLC (acidic HCl condition) to provide Compound 60 and Compound 61.

Compound 60: 37.81 mg, 88.8 umol, 10.8% yield, HCl salt. LCMS (ESI): RT=0.861 min, mass calc. for C$_{20}$H$_{18}$F$_3$N$_3$O$_2$ 389.14, m/z found 390.0 [M+H]$^+$. $^1$HNMR (400 MHz, CHLOROFORM-d) δ 7.73 (s, 1H), 7.65 (s, 1H), 7.49-7.38 (m, 4H), 7.31-7.27 (m, 1H), 7.18-7.11 (m, 1H), 6.98 (d, J=8.3 Hz, 2H), 5.78 (s, 1H), 4.93 (s, 2H), 4.26 (q, J=7.1 Hz, 2H), 1.30 (t, J=7.0 Hz, 3H).

Compound 61: 22.17 mg, 55.7 umol, 6.8% yield, HCl salt. LCMS (ESI): RT=0.779 min, mass calc. for C$_{18}$H$_{14}$F$_3$N$_3$O$_2$ 361.10, m/z found 362.0 [M+H]$^+$. $^1$HNMR (400 MHz, METHANOL-d$_4$) δ 7.88 (s, 1H), 7.73 (s, 1H), 7.55 (dd, J=1.0, 7.5 Hz, 1H), 7.39-7.33 (m, 3H), 7.28 (dt, J=1.5, 7.7 Hz, 1H), 7.23-7.17 (m, 1H), 6.84 (d, J=8.5 Hz, 2H), 4.96 (s, 2H).

Example 60: 2-(2-(3-(dimethylamino)propyl)-2H-tetrazol-5-yl)-N-(4-(trifluoromethyl)phenyl) Aniline (Compound 62)

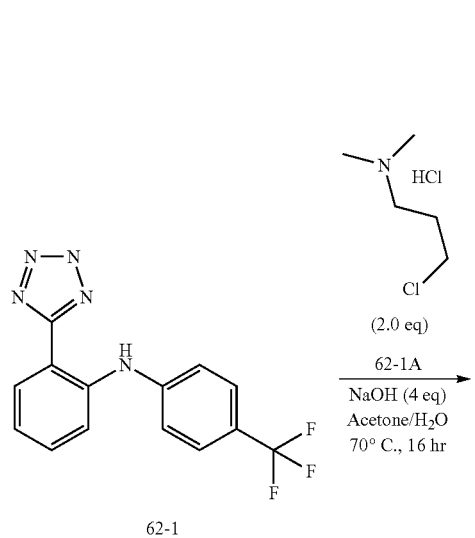

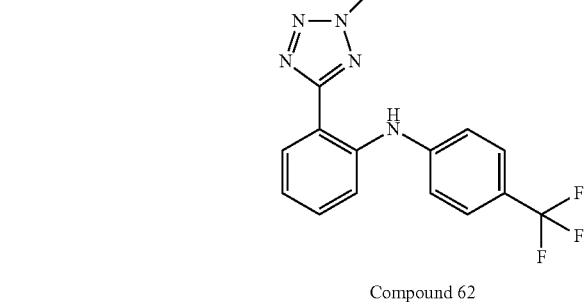

To the solution of 62-1 (100 mg, 0.3 mmol, 1.0 eq) in acetone (1 mL) was added 62-1A (103 mg, 0.7 mmol, 2.0 eq, HCl). Then NaOH (52 mg, 1.3 mmol, 4.0 eq) in H$_2$O (1.00 mL) was added to the mixture. The solution was stirred at 70° C. for 16 hr. The reaction was monitored by LCMS. The residue was purified by Prep-HPLC to give the title compound (9.22 mg, 21.6 umol, 6.6% yield, HCl salt). LCMS (ESI): RT=1.048 min, mass calc. for C$_{19}$H$_{21}$F$_3$N$_6$ 390.18, m/z found 391.1 [M+H]$^+$, $^1$HNMR (400 MHz, CHLOROFORM-d) δ 8.97 (s, 1H), 8.22-8.15 (m 1H), 7.57-7.49 (m, 3H), 7.42-7.35 (m, 1H), 7.30 (d, J=8.5 Hz, 2H), 7.05 (t, J=7.7 Hz, 1H), 4.87 (t, J=6.5 Hz, 2H), 2.90-2.77 (m, 2H), 2.62-2.49 (m, 8H).

Example 61: 2-(2-(3-(dimethylamino)propyl)-2H-tetrazol-5-yl)-N-(4-(trifluoromethoxy)phenyl) Aniline (Compound 63)

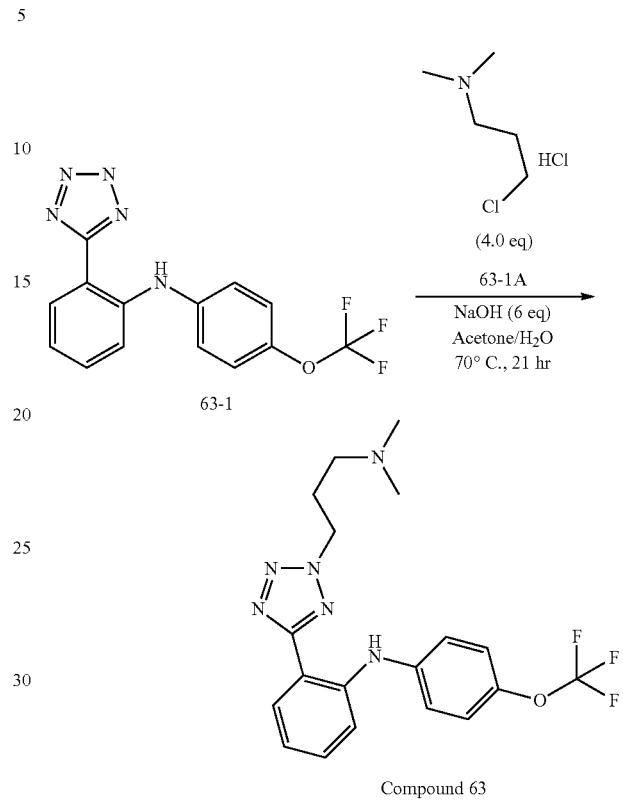

To the solution of 63-1 (100 mg, 0.3 mmol, 1.0 eq) in acetone (1 mL) was added 63-1A (197 mg, 1.3 mmol, 4.0 eq, HCl salt). Then a solution of NaOH (50 mg, 1.3 mmol, 4.0 eq) in H$_2$O (1 mL) was added to the mixture. The solution was stirred at 70° C. for 21 hr. The reaction was monitored by LCMS. The residue was purified by Prep-HPLC to provide the title compound (13.83 mg, 31.2 umol, 10.0% yield, HCl salt). LCMS (ESI): RT=1.062 min, mass calc. for C$_{19}$H$_{21}$F$_3$N$_6$O 406.17, m/z found 407.1 [M+H]$^+$, $^1$HNMR (400 MHz, CHLOROFORM-d) δ 12.70 (s, 1H), 8.14 (d, J=7.3 Hz, 1H), 7.39-7.25 (m, 4H), 7.18 (d, J=7.8 Hz, 2H), 6.96 (t, J=6.7 Hz, 1H), 4.93 (s, 2H), 3.38-2.36 (m, 10H).

Example 62: 2-(2-(2-morpholinoethyl)-2H-tetrazol-5-yl)-N-(4-(trifluoromethoxy)phenyl)aniline (Compound 64)

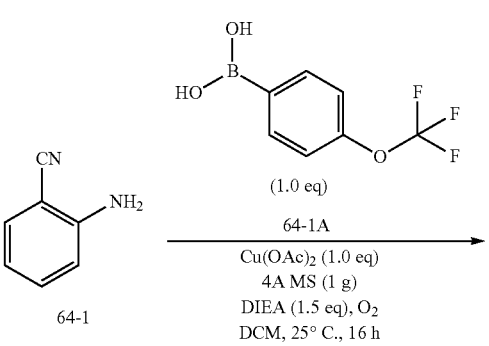

-continued

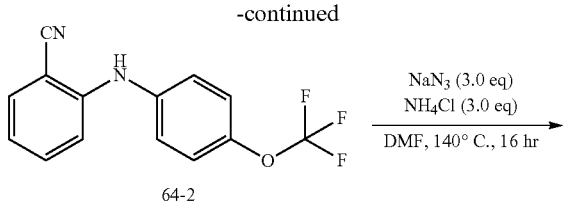

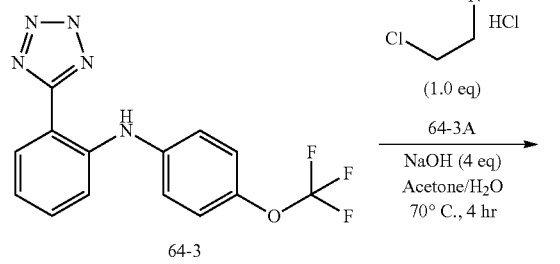

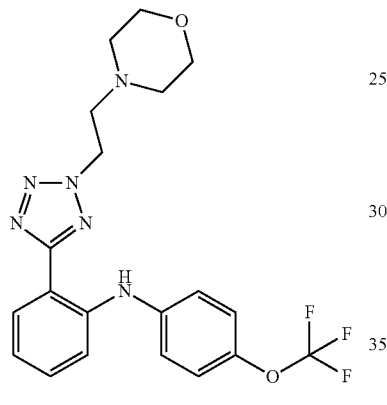

Compound 64

Step 1: 2-((4-(trifluoromethoxy)phenyl)amino)benzonitrile

To the solution of 64-1 (2.0 g, 17.0 mmol, 1.0 eq) in DCM (70 mL) was added 64-1A (3.5 g, 17.0 mmol, 1.0 eq), Cu(OAc)₂ (3.1 g, 17.0 mmol, 1.0 eq) and DIEA (3.3 g, 25.5 mmol, 4.5 mL, 1.5 eq). The mixture was stirred at 25° C. for 16 hr under O₂ atmosphere. The reaction was monitored by TLC. The reaction was concentrated under reduced pressure. The residue was purified by column chromatography (SiO₂) to give 64-2 (1.4 g, 5.0 mmol, 29.6% yield).

Step 2: 2-(2H-tetrazol-5-yl)-N-(4-(trifluoromethoxy)phenyl)aniline

To the solution of 64-2 (1.4 g, 5.0 mmol, 1.0 eq) in DMF (10 mL) was added NH₄Cl (807 mg, 15.1 mmol, 3.0 eq) and NaN₃ (1.0 g, 15.7 mmol, 3.0 eq). The mixture was stirred at 140° C. for 16 hr. The reaction was monitored by LCMS. The reaction solution was poured into aqueous HCl (1M, 50 mL). An insoluble solid appeared. The mixture was filtered and the solid was washed with H₂O (30 mL) to give compound 64-3 (1.6 g, 5.0 mmol, 99.0% yield).

Step 3: 2-(2-(2-morpholinoethyl)-2H-tetrazol-5-yl)-N-(4-(trifluoromethoxy)phenyl)aniline To the solution of 64-3 (100 mg, 0.3 mmol, 1.0 eq) in acetone (1 mL) was added 64-3A (58 mg, 0.3 mmol, 1.0 eq, HCl). Then NaOH (50 mg, 1.3 mmol, 4.0 eq) in H₂O (1 mL) was added to the mixture. The solution was stirred at 70° C. for 4 hr. The reaction was monitored by LCMS. The reaction solution was concentrated under reduced pressure. The residue was purified by Prep-HPLC to give Compound 64 (19.13 mg, 40.22 umol, 12.92% yield, HCl salt). LCMS (ESI): RT=1.062 min, mass calc. for C₂₀H₂₁F₃N₆O₂ 434.17, m/z found 435.1 [M+H]⁺, ¹HNMR (400 MHz, CHLOROFORM-d) δ 8.92 (s, 1H), 8.25-8.18 (m, 1H), 7.40-7.23 (m, 4H), 7.23-7.17 (m, 2H), 6.97 (t, J=7.1 Hz, 1H), 4.82 (t, J=6.5 Hz, 2H), 3.71-3.61 (m, 4H), 3.06 (t, J=6.5 Hz, 2H), 2.59-2.50 (m, 4H).

Example 63: 2-(2-(3-morpholinopropyl)-2H-tetrazol-5-yl)-N-(4-(trifluoromethyl)phenyl)aniline (Compound 65)

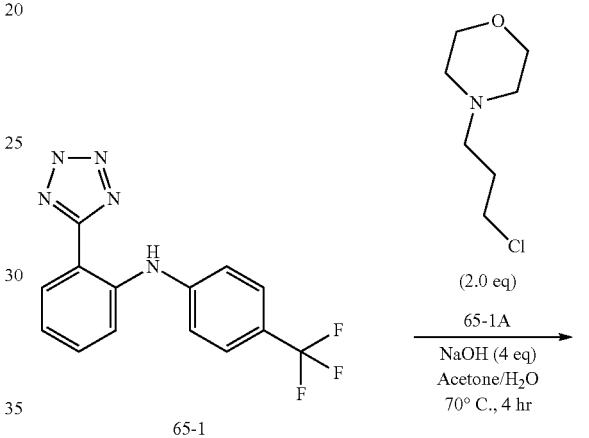

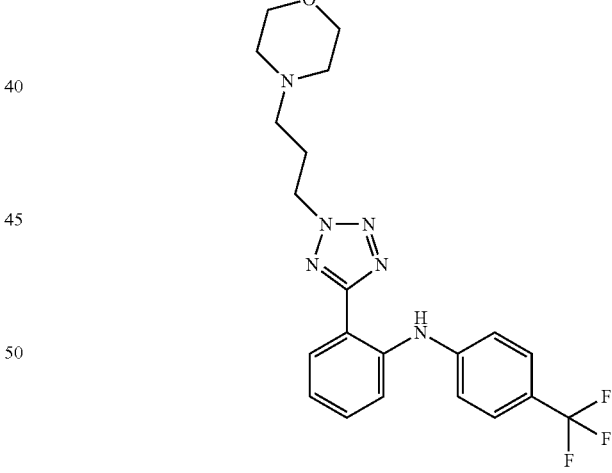

Compound 65

To the solution of 65-1 (100 mg, 0.3 mmol, 1.0 eq) in acetone (1 mL) was added 65-1A (107 mg, 0.7 mmol, 2.0 eq). Then NaOH (52 mg, 1.3 mmol, 4.0 eq) in H₂O (1 mL) was added to the mixture. The solution was stirred at 70° C. for 4 hr. The residue was purified by Prep-HPLC to give the title compound (34.91 mg, 74.5 umol, 22.7% yield, HCl salt). LCMS (ESI): RT=1.050 min, mass calc. for C₂₁H₂₃F₃N₆O 432.19, m/z found 433.1 [M+H]⁺, ¹HNMR (400 MHz, CHLOROFORM-d) δ 9.02 (s, 1H), 8.23-8.15 (m, 1H), 7.60-7.44 (m, 3H), 7.38 (t, J=7.1 Hz, 1H), 7.33-

7.25 (m, 2H), 7.04 (t, J=7.4 Hz, 1H), 4.92-4.68 (m, 2H), 3.85-3.65 (m, 4H), 2.80-2.22 (m, 8H).

Example 64: ethyl 2-(3,5-dimethyl-4-(2-((4-(trifluoromethyl)phenyl)amino)phenyl)-1H-pyrazol-1-yl)acetate (Compound 66) and 2-(3,5-dimethyl-4-(2-((4-(trifluoromethyl) phenyl)amino)phenyl)-1H-pyrazol-1-yl)acetic Acid (Compound 67)

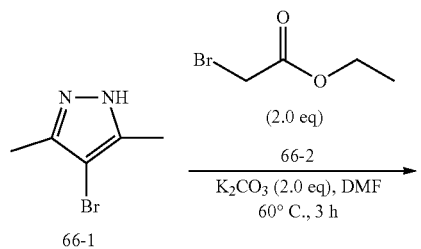

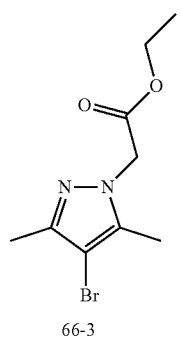

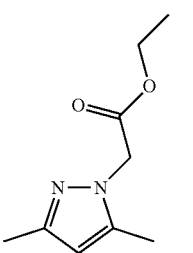

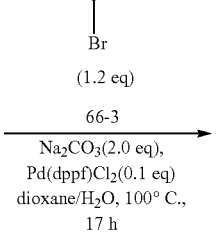

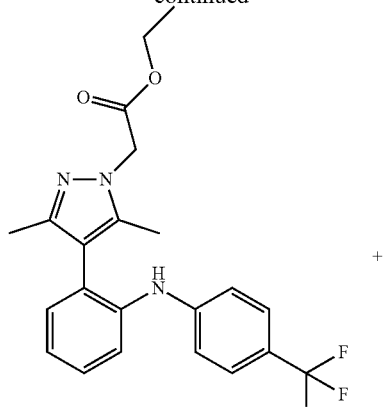

Compound 66

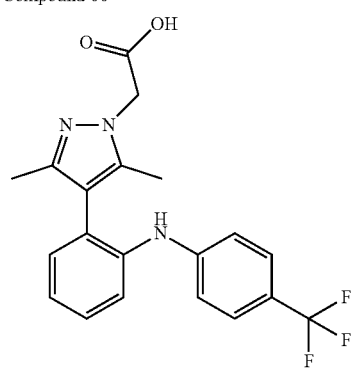

Compound 67

Step 1: ethyl 2-(4-bromo-3,5-dimethyl-1H-pyrazol-1-yl)acetate

To a mixture of 66-1 (1.0 g, 5.7 mmol, 1.00 eq) and K₂CO₃ (1.6 g, 11.4 mmol, 2.00 eq) in DMF (10.0 mL), was added 66-2 (1.9 g, 11.4 mmol, 1.3 mL, 2.00 eq). The resulting mixture was stirred at 60° C. for 3 h. LCMS showed the reaction was complete. The mixture was diluted with EtOAc (40 mL), washed with water (40 mL*5). The combined organic layers were dried over anhydrous Na₂SO₄, and concentrated under vacuum. 66-3 (1.5 g, crude) was obtained.

Step 2: 2-(3,5-dimethyl-4-(2-((4-(trifluoromethyl) phenyl)amino)phenyl)-1H-pyrazol-1-yl)acetate To a mixture of 66-3 (258.8 mg, 1.0 mmol, 1.20 eq), 66-4 (300.0 mg, 0.8 mmol, 1.00 eq) and Na₂CO₃ (175.1 mg, 1.7 mmol, 2.00 eq) in 1,4-dioxane (4.0 mL) and H₂O (0.5 mL), was added Pd(dppf)Cl₂ (60.4 mg, 82.6 umol, 0.10 eq). The mixture was degassed under vacuum and purged with N₂ 3 times. The resulting mixture was stirred at 100° C. under N₂ for 17 h. LCMS showed the reaction was complete. The mixture was concentrated under vacuum. The residue was purified by silica gel chromatography to afford Compound 66 (0.3 g) and Compound 67 (0.4 g).

Crude Compound 66 was purified by prep-HPLC (acidic_HCl condition): 87.22 mg, 177.87 umol, 21.53% yield, 2HCl salt. LCMS (ESI): RT=1.277 min, mass calc. for $C_{22}H_{22}F_3N_3O_2$ 417.17, m/z found 418.1 [M+H]⁺. ¹HNMR (400 MHz, CHLOROFORM-d) δ 7.66 (s, 3H), 7.53 (t, J=6.5

Hz, 1H), 7.46 (s, 1H), 7.43-7.23 (m, 3H), 5.94 (s, 1H), 5.18 (s, 2H), 4.46 (d, J=5.8 Hz, 2H), 2.37 (s, 3H), 2.28 (s, 3H), 1.55-1.44 (m, 3H).

Crude Compound 67 was purified by prep-HPLC (acidic_TFA condition): 52.68 mg, 104.7 umol, 12.7% yield, TFA salt. LCMS (ESI): RT=1.172 min, mass calc. for $C_{20}H_{18}F_3N_3O_2$ 389.14, m/z found 390.0 $[M+H]^+$. $^1$HNMR (400 MHz, METHANOL-$d_4$) δ 7.48-7.42 (m, 1H), 7.39 (d, J=6.8 Hz, 2H), 7.36-7.29 (m, 1H), 7.23-7.17 (m, 1H), 7.12 (dd, J=3.3, 6.0 Hz, 1H), 7.07-7.00 (m, 2H), 4.82 (s, 2H), 2.06 (s, 6H).

Example 65: 2-(2-(2-morpholinoethyl)-2H-tetrazol-5-yl)-N-(4-(trifluoromethyl)phenyl)aniline (Compound 68)

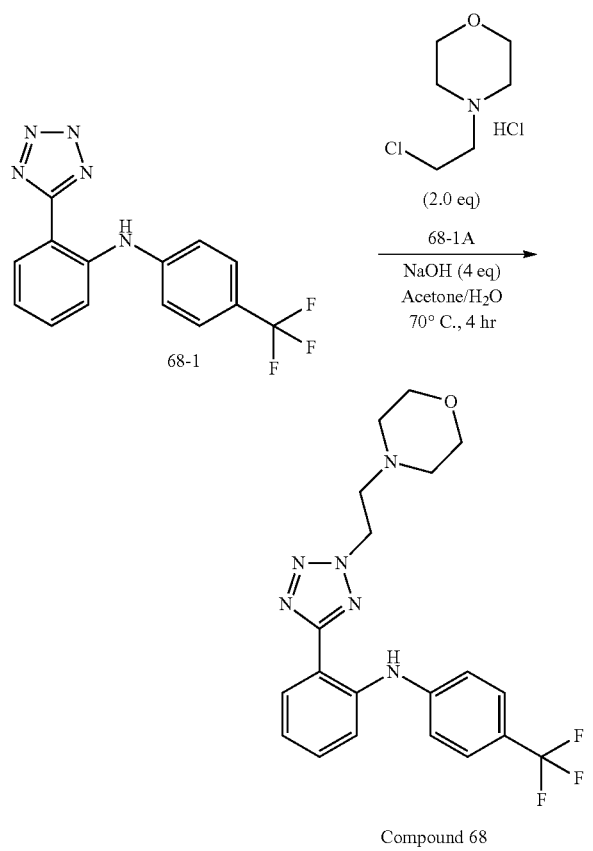

Compound 68

To the solution of 68-1 (100 mg, 0.3 mmol, 1.0 eq) in acetone (1 mL) was added 68-1A (122 mg, 0.7 mmol, 2.00 eq, HCl salt). Then NaOH (52 mg, 1.3 mmol, 4.0 eq) in H$_2$O (1 mL) was added to the mixture. The solution was stirred at 70° C. for 4 hr. The reaction was monitored by LCMS. The residue was purified by Prep-HPLC to give the title compound (33.76 mg, 72.0 umol, 22.0% yield, HCl salt). LCMS (ESI): RT=1.041 min, mass calc. for $C_{20}H_{21}F_3N_6O$ 418.17, m/z found 419.1 $[M+H]^+$, $^1$HNMR (400 MHz, CHLOROFORM-d) δ 9.08 (s, 1H), 8.21 (d, J=7.8 Hz, 1H), 7.59-7.50 (m, 3H), 7.41-7.26 (m, 3H), 7.05 (t, J=7.4 Hz, 1H), 4.82 (t, J=6.3 Hz, 2H), 3.71-3.60 (m, 4H), 3.05 (t, J=6.4 Hz, 2H), 2.59-2.49 (m, 4H).

Example 66: 2-(5-(2-((4-(trifluoromethyl)phenyl)amino)pyridin-3-yl)-2H-tetrazol-2-yl)ethanol (Compound 69)

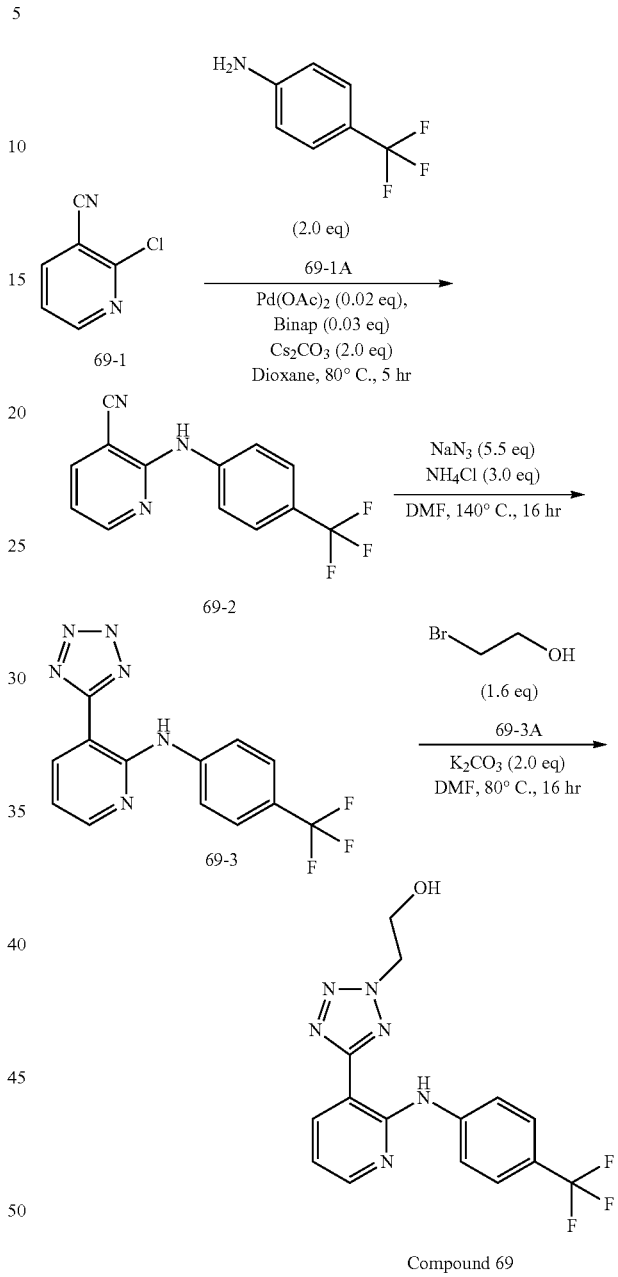

Compound 69

Step 1: 2-((4-(trifluoromethyl)phenyl)amino)nicotinonitrile

To the solution of 69-1 (500 mg, 3.6 mmol, 1.0 eq) in dioxane (15 mL) was added 69-1A (1.2 g, 7.2 mmol, 0.9 mL, 2.0 eq), Pd(OAc)$_2$ (16 mg, 72 umol, 0.02 eq), BINAP (67 mg, 0.1 mmol, 0.03 eq), Cs$_2$CO$_3$ (2.4 g, 7.2 mmol, 2.0 eq). The mixture was stirred at 80° C. for 5 hr under N$_2$ atmosphere. The reaction was monitored by LCMS. The reaction solution was concentrated under reduced pressure. The residue was purified by column chromatography (SiO$_2$) to give the yellow solid. The solid was dissolved in MeOH (4 mL). The solution was poured into H₂O (10 mL). The insoluble solid disappeared. The mixture was filtered. The solid was dried under reduced pressure to give 69-2 (960 mg, crude) as a yellow solid.

Step 2: 3-(2H-tetrazol-5-yl)-N-(4-(trifluoromethyl)phenyl)pyridin-2-amine

To the solution of 69-2 (200 mg, 0.8 mmol, 1.0 eq) in DMF (2 mL) was added NaN₃ (270 mg, 4.2 mmol, 5.5 eq) and NH₄Cl (122 mg, 2.3 mmol, 3.0 eq). The mixture was stirred at 140° C. for 16 hr. The reaction was monitored with LCMS. The reaction solution was poured into HCl aqueous (1M, 15 mL). The insoluble solid appeared. The mixture was filtered. The solid was washed with H₂O (20 mL) to give 69-3 (130 mg, 0.4 mmol, 56% yield).

Step 3: 2-(5-(2-((4-(trifluoromethyl)phenyl)amino)pyridin-3-yl)-2H-tetrazol-2-yl)ethanol To the solution of 69-3 (130 mg, 0.4 mmol, 1.0 eq) in DMF (2 mL) was added 69-3A (85 mg, 0.7 mmol, 48 uL, 1.6 eq) and K₂CO₃ (117 mg, 0.8 mmol, 2.0 eq). The mixture was stirred at 80° C. for 16 hr. The reaction was monitored by LCMS. The residue was purified by Prep-HPLC to give Compound 69 (15.50 mg, 44.3 umol, 10.4% yield). LCMS (ESI): RT=3.142 min, mass calcd. for C₁₅H₁₃F₃N₆O 350.11, m/z found 350.9 [M+H]⁺, ¹HNMR (400 MHz, DMSO-d₆) δ9.95 (s, 1H), 8.48-8.40 (m, 2H), 7.99 (d, J=8.5 Hz, 2H), 7.67 (d, J=8.5 Hz, 2H), 7.15-7.07 (m, 1H), 4.86 (t, J=5.1 Hz, 2H), 4.01 (t, J=5.1 Hz, 2H).

Example 67: 2-(2-(3-morpholinopropyl)-2H-tetrazol-5-yl)-N-(4-(trifluoromethoxy)phenyl) Aniline (Compound 70)

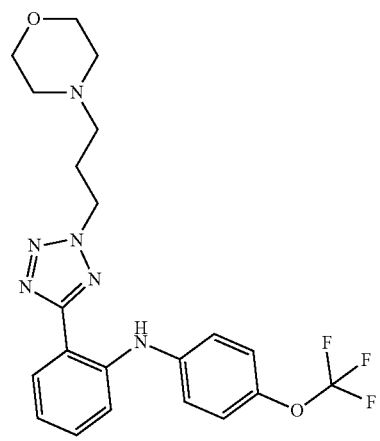

Compound 70

To the solution of 70-1 (100 mg, 0.3 mmol, 1.0 eq) in acetone (1 mL) was added 70-1A (102 mg, 0.6 mmol, 2.0 eq). Then the solution of NaOH (50 mg, 1.3 mmol, 4.0 eq) in H₂O (1 mL) was added to the mixture. The solution was stirred at 70° C. for 21 hr. The reaction was monitored by LCMS. The residue was purified by Prep-HPLC to give the title compound (31.14 mg, 61.7 umol, 19.8% yield, HCl). LCMS (ESI): RT=1.070 min, mass calcd. for C₂H₂₃F₃N₆O₂ 418.17, m/z found 448.18 [M+H]⁺, ¹HNMR (400 MHz, CHLOROFORM-d) δ 13.20 (s, 1H), 8.13 (d, J=7.0 Hz, 1H), 7.39-7.14 (m, 6H), 7.00-6.91 (m, 1H), 5.06-4.75 (m, 2H), 4.37-3.81 (m, 4H), 3.62-2.60 (m, 8H).

Example 68: ethyl 2-(3,5-dimethyl-4-(2-((3-(trifluoromethyl)phenyl)amino)phenyl)-1H-pyrazol-1-yl)acetate (Compound 71) and 2-(3,5-dimethyl-4-(2-((3-(trifluoromethyl) phenyl)amino)phenyl)-1H-pyrazol-1-yl)acetic Acid (Compound 72)

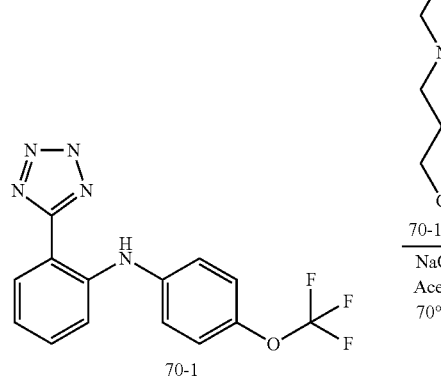

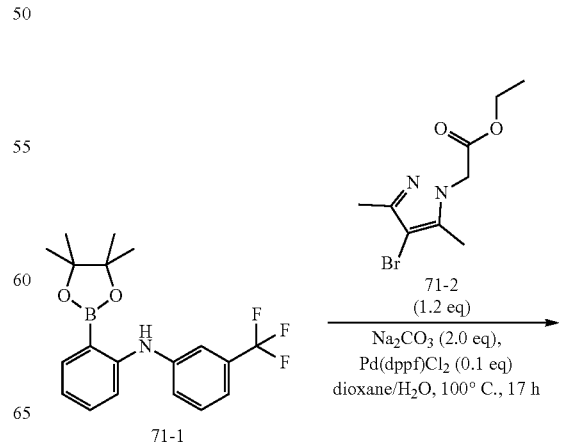

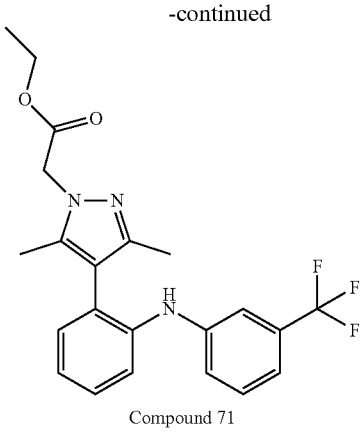

Compound 71

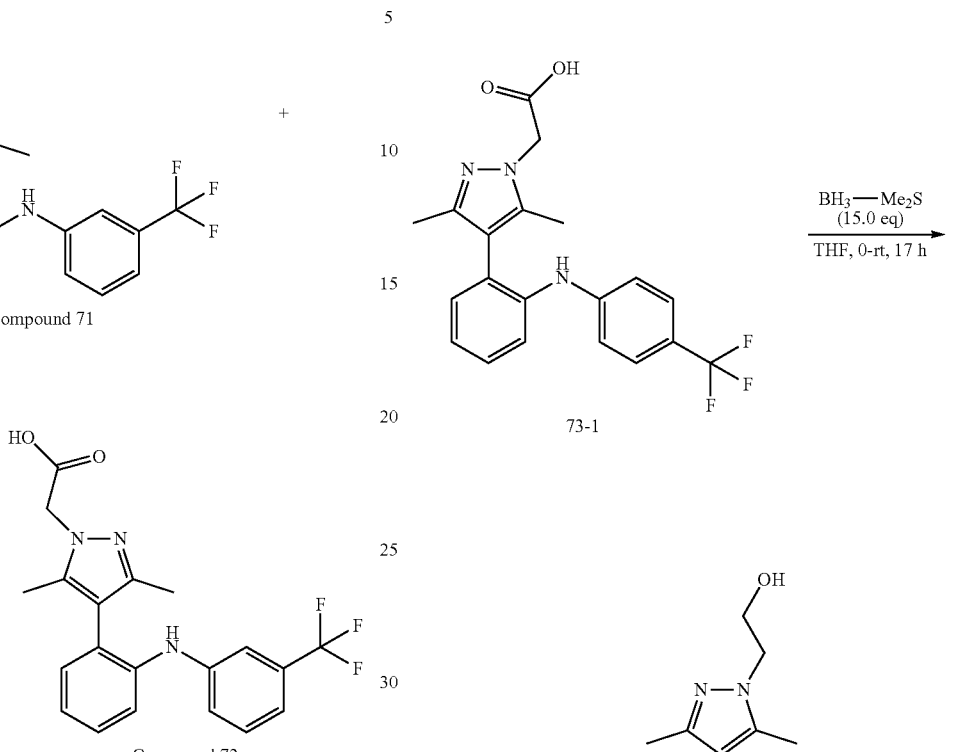

Compound 72

To a mixture of 71-1 (200.0 mg, 0.6 mmol, 1.00 eq), 72-2 (172.6 mg, 0.7 mmol, 1.20 eq) and Na₂CO₃ (116.7 mg, 1.1 mmol, 2.00 eq) in dioxane (4.0 mL) and H₂O (0.5 mL), was added Pd(dppf)Cl₂ (40.3 mg, 55.1 umol, 0.10 eq). The mixture was degassed under vacuum and purged with N₂ 3 times. The resulting mixture was stirred at 100° C. under N₂ for 17 h. LCMS showed the reaction was complete. The mixture was concentrated under vacuum. The residue was purified by silica gel chromatography to give Compound 71 and Compound 72.

Compound 71: 8.63 mg, 18.8 umol, 3.4% yield, HCl salt. LCMS (ESI): RT=1.267 min, mass calc. for $C_{22}H_{22}F_3N_3O_2$ 417.17, m/z found 418.5 [M+H]⁺. ¹HNMR (400 MHz, CHLOROFORM-d) δ 7.45-7.24 (m, 5H), 7.22-7.01 (m, 3H), 5.81 (s, 1H), 5.08 (s, 2H), 4.26 (d, J=6.5 Hz, 2H), 2.21 (s, 3H), 2.12 (s, 3H), 1.31 (t, J=6.0 Hz, 3H).

Compound 72: 46.98 mg, 110.3 umol, 20.0% yield, HCl salt. LCMS (ESI): RT=1.166 min, mass calc. for $C_{20}H_{18}F_3N_3O_2$ 389.14, m/z found 390.0 [M+H]⁺. ¹HNMR (400 MHz, METHANOL-d₄) δ 7.46-7.39 (m, 2H), 7.35-7.29 (m, 1H), 7.28-7.25 (m, 1H), 7.21-7.12 (m, 2H), 7.08-7.01 (m, 2H), 5.13 (d, J=3.3 Hz, 2H), 2.25 (s, 3H), 2.22 (s, 3H).

Example 69: 2-(3,5-dimethyl-4-(2-((4-(trifluoromethyl)phenyl)amino)phenyl)-1H-pyrazol-1-yl)ethanol (Compound 73)

To a mixture of 73-1 (40.0 mg, 0.1 mmol, 1.00 eq) in THF (5.0 mL), was added BH₃-Me₂S (10 M, 0.2 mL, 15.00 eq) at 0° C. The resulting mixture was stirred at 26° C. for 17 h. LCMS showed the reaction was complete. The mixture was quenched with MeOH (5 mL). The mixture was concentrated under vacuum. The residue was diluted with water (10 mL), extracted with DCM (10 mL*3). The combined organic layers were dried over anhydrous Na₂SO₄, and concentrated under vacuum. The residue was purified by prep-HPLC (acidic_HCl condition). The desired compound was combined with the previous batch and lyophilized to provide the title compound (25.59 mg, 68.17 umol, 66.36% yield). LCMS (ESI): RT=1.147 min, mass calc. for $C_{20}H_{20}F_3N_3O$ 375.16, m/z found 376.1 [M+H]⁺. ¹HNMR (400 MHz, DMSO-d₆) δ 7.92 (s, 1H), 7.42 (d, J=8.8 Hz, 2H), 7.40-7.30 (m, 2H), 7.23-7.18 (m, 1H), 7.16-7.08 (m, 1H), 6.98 (d, J=8.5 Hz, 2H), 4.09 (q, J=4.5 Hz, 2H), 3.66 (t, J=5.6 Hz, 3H), 2.05 (s, 3H), 2.03 (s, 3H).

Example 70: 2-(3,5-dimethyl-4-(2-((3-(trifluoromethyl)phenyl)amino)phenyl)-1H-pyrazol-1-yl)ethanol (Compound 74)

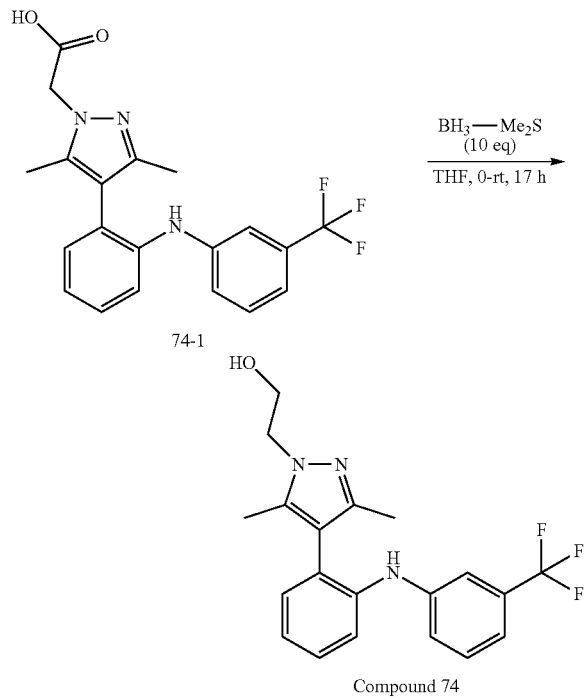

To a mixture of 74-1 (40.0 mg, 0.1 mmol, 1.00 eq) in THF (5.0 mL), was added BH₃-Me₂S (10 M, 102.7 uL, 10.00 eq) at 0° C. The resulting mixture was stirred at 22° C. for 17 h. LCMS showed the reaction was complete. The mixture was quenched with MeOH (5 mL), and concentrated under vacuum. The residue was diluted with water (15 mL), and extracted with DCM (15 mL*3). The combined organic layers were dried over anhydrous Na₂SO₄, and concentrated under vacuum. The residue was purified by prep-HPLC (acidic_HCl condition) to provide the title compound (15.22 mg, 37.0 umol, 36.0% yield, HCl salt). LCMS (ESI): RT=0.777 min, mass calc. for $C_{20}H_{20}F_3N_3O$ 375.16, m/z found 376.1 [M+H]⁺. ¹HNMR (400 MHz, DMSO-d₆) δ 7.86 (s, 1H), 7.37-7.31 (m, 3H), 7.20 (d, J=7.8 Hz, 2H), 7.14 (s, 1H), 7.12-7.07 (m, 1H), 7.01 (d, J=7.5 Hz, 1H), 4.16 (d, J=2.3 Hz, 2H), 3.69 (t, J=5.4 Hz, 2H), 2.10 (s, 3H), 2.08 (s, 3H).

Example 71: 2-(5-(2-((4-(trifluoromethoxy)phenyl)amino)pyridin-3-yl)-2H-tetrazol-2-yl)ethanol (Compound 75)

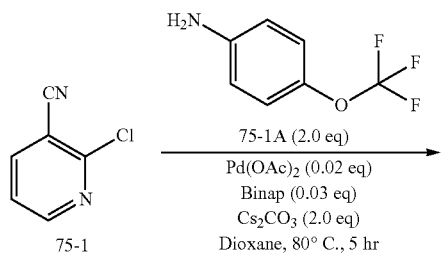

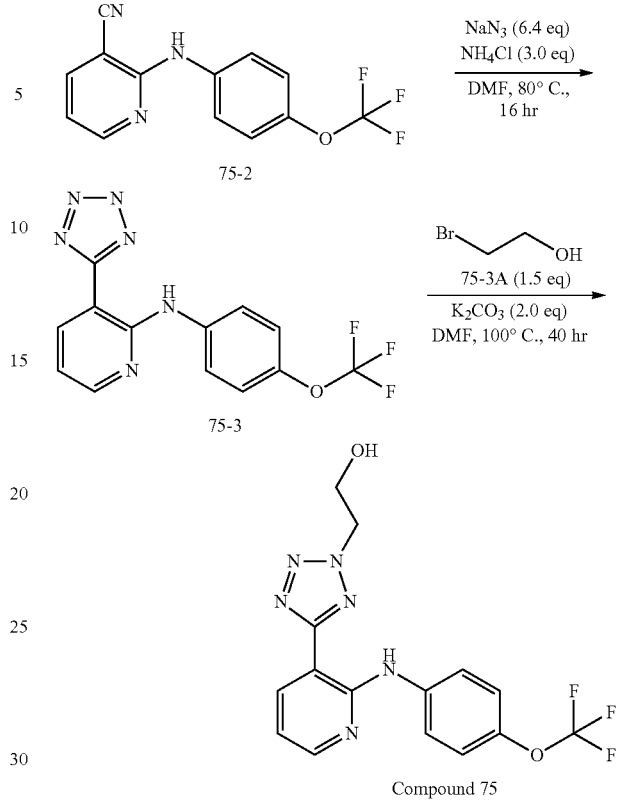

Step 1: 2-((4-(trifluoromethoxy)phenyl)amino)nicotinonitrile

To the solution of 75-1 (500 mg, 3.6 mmol, 1.0 eq) in dioxane (15 mL) was added 75-1A (1.28 g, 7.2 mmol, 976 uL, 2.0 eq), Pd(OAc)₂ (16 mg, 72 umol, 0.02 eq), BINAP (67 mg, 0.1 mmol, 0.03 eq), Cs₂CO₃ (2.35 g, 7.2 mmol, 2.0 eq). The mixture was stirred at 80° C. for 5 hr under N₂ atmosphere. The reaction was monitored by LCMS. The reaction solution was concentrated under reduced pressure. The residue was purified by column chromatography (SiO₂) to give a yellow solid. The solid was dissolved in MeOH (4 mL). The solution was poured into H₂O (10 mL). The insoluble solid disappeared. The mixture was filtered. The solid was dried under reduced pressure to give 75-2 (560 mg, 2.0 mmol, 56% yield).

Step 2: 3-(2H-tetrazol-5-yl)-N-(4-(trifluoromethoxy)phenyl)pyridin-2-amine

To the solution of 75-2 (200 mg, 0.7 mmol, 1.0 eq) in DMF (2 mL) was added NaN₃ (300 mg, 4.6 mmol, 6.4 eq) and NH₄Cl (115 mg, 2.2 mmol, 75 uL, 3.0 eq). The mixture was stirred at 140° C. for 16 hr. The reaction was monitored by LCMS. The reaction solution was poured into aqueous HCl (1M, 15 mL). The mixture was extracted with EtOAc (15 mL*4). The combined organic layers were dried with Na₂SO₄, and concentrated under reduced pressure to give 75-3 (231 mg, 0.7 mmol, 100.00% yield) in DMF as a yellow solution.

Step 3: 2-(5-(2-((4-(trifluoromethoxy)phenyl)amino)pyridin-3-yl)-2H-tetrazol-2-yl)ethanol To the solution of 75-3 (230 mg, 0.7 mmol, 1.0 eq) in DMF (2 mL) was added 75-3A (134 mg, 1.1 mmol, 76 uL, 1.5 eq) and K$_2$CO$_3$ (197 mg, 1.4 mmol, 2.0 eq). The mixture was stirred at 100° C. for 40 hr. The reaction was monitored by LCMS. LCMS showed that most of the starting material was remaining, and only a small amount of the desired MS was observed. The reaction time was prolonged. LCMS showed that the starting material was consumed and the main peak was the desired MS. The residue was purified by Prep-HPLC to give Compound 75 (63.60 mg, 173.63 umol, 24.33% yield). LCMS (ESI): RT=1.118 min, mass calc. for C$_{15}$H$_{13}$F$_3$N$_6$O$_2$ 366.11, m/z found 367.0 [M+H]$^+$, $^1$HNMR (400 MHz, DMSO-d$_6$) δ 9.76 (s, 1H), 8.49-8.43 (m, 1H), 8.39-8.35 (m, 1H), 7.87 (d, J=9.0 Hz, 2H), 7.35 (d, J=8.5 Hz, 2H), 7.09-7.01 (m, 1H), 4.86 (t, J=5.1 Hz, 2H), 4.02-3.99 (m, 2H).

Example 72: ethyl 2-[3-methyl-4-[2-[4-(trifluoromethyl)anilino]phenyl]pyrazol-1-yl]acetate (Compound 76)

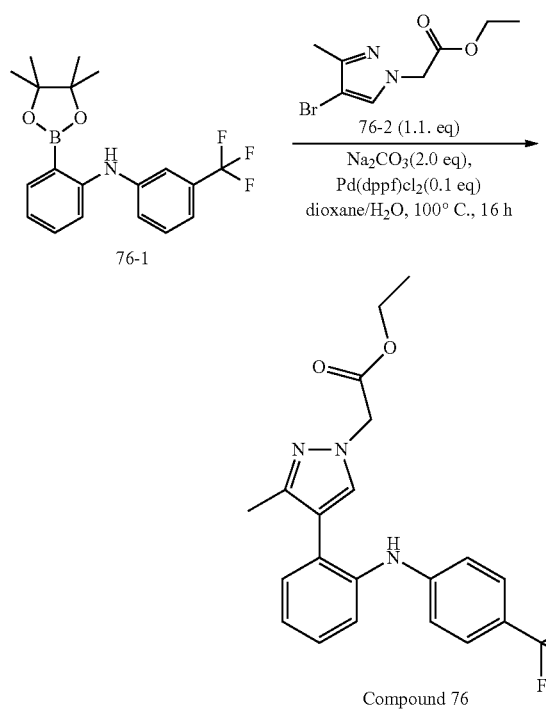

Compound 76

To a solution of 76-1 (400.0 mg, 1.1 mmol, 1.0 eq) and 76-2 (326.2 mg, 1.3 mmol, 1.2 eq) in dioxane (5.0 mL) was added H$_2$O (500.00 uL) Pd(dppf)Cl$_2$ (80.49 mg, 0.11 mmol, 0.1 eq) and Na$_2$CO$_3$ (233.2 mg, 2.2 mmol, 2.0 eq). The mixture was stirred at 100° C. for 16 hour under N$_2$ atmosphere. LCMS showed the desired compound was formed. TLC (5% ethyl acetate in petroleum ether) showed the starting material remained and new spots appeared. The reaction was filtered through celite and concentrated under reduced pressure to give a residue. The crude product was purified by column chromatography over silica gel and further purified by prep-HPLC to obtain the title compound (7.08 mg, 17.20 umol, 1.56% yield). LCMS (ESI): RT=0.874 min, mass calc. for C$_{21}$H$_{20}$F$_3$N$_3$O$_2$ 403.15, m/z found 404.1 [M+H]$^+$; $^1$HNMR (400 MHz, CDCl$_3$-d) δ 7.49-7.42 (m, 4H), 7.33-7.27 (m, 2H), 7.09-7.03 (m, 3H), 5.80 (s, 1H), 4.86 (s, 2H), 4.26 (q, J=7.0 Hz, 2H), 2.17 (s, 3H), 1.30 (t, J=7.0 Hz, 3H).

Example 73: ethyl 2-[5-methyl-4-[2-[4-(trifluoromethyl)anilino]phenyl]pyrazol-1-yl]acetate (Compound 77)

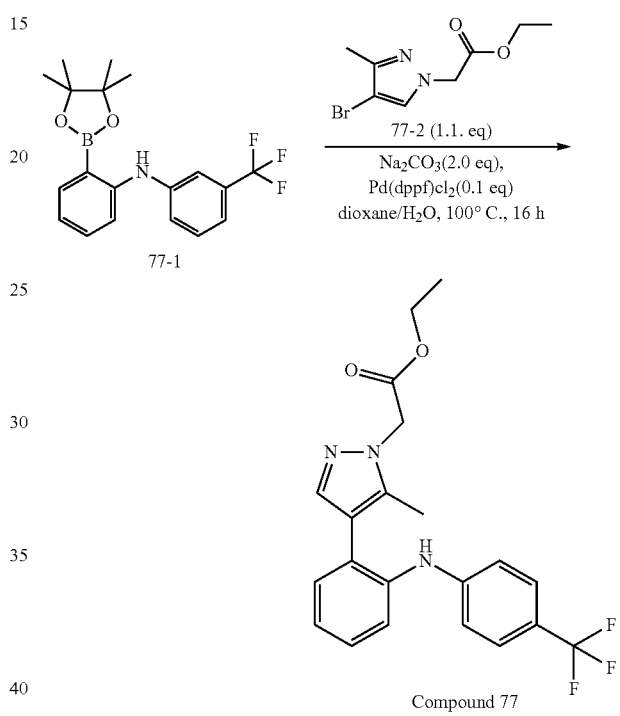

Compound 77

To a solution of 77-1 (400.0 mg, 1.1 mmol, 1.0 eq) and 77-2 (326.2 mg, 1.3 mmol, 1.2 eq) in dioxane (5.0 mL) was added H$_2$O (500.00 uL) Pd(dppf)Cl$_2$ (80.49 mg, 0.11 mmol, 0.1 eq) and Na$_2$CO$_3$ (233.2 mg, 2.2 mmol, 2.0 eq). The mixture was stirred at 100° C. for 16 hour under N$_2$ atmosphere. LCMS showed the desired compound was formed and TLC was used to monitor the reaction. The reaction was filtered through celite and concentrated under reduced pressure to give a residue. The crude product was purified by column chromatography over silica gel and further purified by prep-HPLC and then prep-SFC to obtain the title compound (2.93 mg, 7.26 umol, 0.66% yield). LCMS (ESI): RT=0.876 min, mass calc. for C$_{21}$H$_{20}$F$_3$N$_3$O$_2$ 403.15, m/z found 404.0 [M+H]$^+$; $^1$HNMR (400 MHz, CDCl$_3$-d) δ 7.52 (s, 1H), 7.46 (dd, J=3.1, 8.4 Hz, 3H), 7.33-7.27 (m, 1H), 7.24 (d, J=1.5 Hz, 1H), 7.10-7.03 (m, 3H), 5.80 (s, 1H), 4.90 (s, 2H), 4.26 (q, J=7.3 Hz, 2H), 2.11 (s, 3H), 1.30 (t, J=7.2 Hz, 3H).

Example 74: 2-[5-[4-[4-(trifluoromethyl)anilino]-3-pyridyl]tetrazol-2-yl]ethanol (Compound 78)

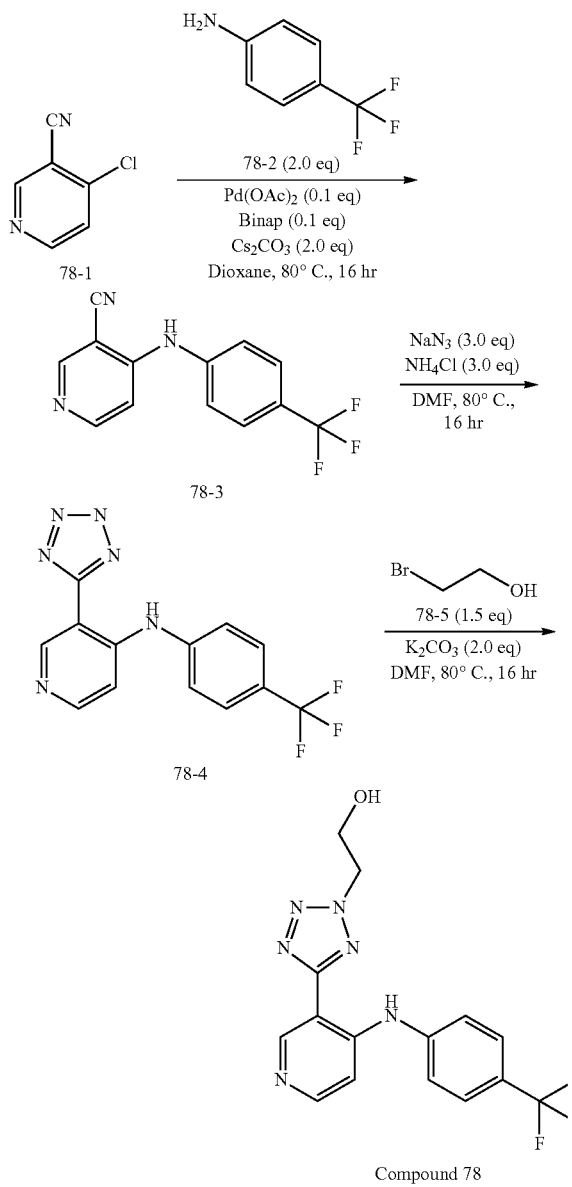

Compound 78

Step 1: 4-[4-(trifluoromethyl)anilino]pyridine-3-carbonitrile

To a solution of 78-1 (500.0 mg, 3.6 mmol, 1.0 eq), 78-2 (581.5 mg, 3.6 mmol, 0.45 mL, 1.0 eq) and $Cs_2CO_3$ (1.2 g, 3.6 mmol, 1.0 eq) in dioxane (10.0 mL) was added BINAP (224.7 mg, 0.36 mmol, 0.1 eq) and palladium acetate (81.0 mg, 0.36 mmol, 0.1 eq). The resulting mixture was stirred at 100° C. under $N_2$ for 15 hour. LCMS showed the desired compound was formed and the starting material was consumed completely. TLC (30% ethyl acetate in petroleum ether, Rf=0.4) showed the starting material was consumed and a new spot appeared. The reaction mixture was concentrated. The crude residue was dissolved in $CH_2Cl_2$ (25 ml) and washed with water (2×15 mL). After drying over anhydrous $Na_2SO_4$, the solvent was removed under reduced pressure to afford the crude product. The crude product was purified by column chromatography over silica gel to provide 78-3 (620.0 mg, 2.4 mmol, 65.3% yield). LCMS (ESI): RT=0.575 min, mass calc. for $C_{13}H_8F_3N_3$ 263.07, m/z found 263.8 $[M+H]^+$.

Step 2: 3-(2H-tetrazol-5-yl)-N-[4-(trifluoromethyl)phenyl]pyridin-4-amine

To a solution of 78-3 (620.0 mg, 2.4 mmol, 1.0 eq) in DMF (15.0 mL) was added $NH_4Cl$ (378.7 mg, 7.1 mmol, 0.25 mL, 3.0 eq) and $NaN_3$ (460.3 mg, 7.1 mmol, 3.0 eq). The mixture was stirred at 140° C. for 16 hour under an $N_2$ atmosphere. LCMS showed the desired compound was formed. The reaction mixture was poured into sat. aq. $NaHCO_3$ (5 mL) and extracted with EtOAc (5 mL*2). The combined organic layer was washed with brine (10 mL), dried over $Na_2SO_4$, and filtered. The solvent was removed under reduced pressure to afford crude 78-4 (500.0 mg, 1.6 mmol, 69.1% yield). LCMS (ESI): RT=0.647 min, mass calc. for $C_{13}H_9F_3N_6$ 306.08, m/z found 306.8 $[M+H]^+$.

Step 3: 2-[5-[4-[4-(trifluoromethyl)anilino]-3-pyridyl]tetrazol-2-yl]ethanol To a solution of 78-4 (100.0 mg, 0.33 mmol, 1.0 eq) in DMF (5.0 mL) was added $K_2CO_3$ (90.3 mg, 0.65 mmol, 2.0 eq) and 78-5 (48.9 mg, 0.39 mmol, 27.8 uL, 1.2 eq). The mixture was stirred at 100° C. for 3 hour under an $N_2$ atmosphere. LCMS showed the desired compound was formed. The reaction was filtered to give a crude product. The crude product was purified by prep-HPLC to give Compound 78 (16.50 mg, 47.10 umol, 14.43% yield). LCMS (ESI): RT=0.631 min, mass calc. for $C_{15}H_{13}F_3N_6O$ 350.10, m/z found 350.9 $[M+H]^+$; $^1$HNMR (400 MHz, $CDCl_3$-d) δ 9.61 (s, 1H), 9.03 (s, 1H), 8.08 (d, J=6.0 Hz, 1H), 7.58 (d, J=8.5 Hz, 2H), 7.29 (d, J=8.3 Hz, 2H), 7.12 (d, J=6.0 Hz, 1H), 4.91-4.86 (m, 2H), 4.38-4.33 (m, 2H).

Example 75: 2-[5-[4-[4-(trifluoromethoxy)anilino]-3-pyridyl]tetrazol-2-yl]ethanol (Compound 79)

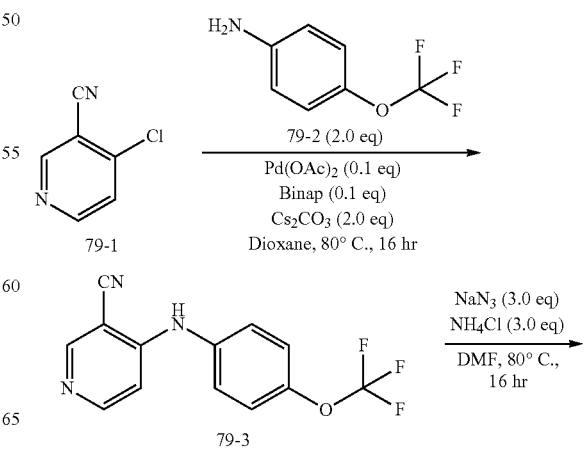

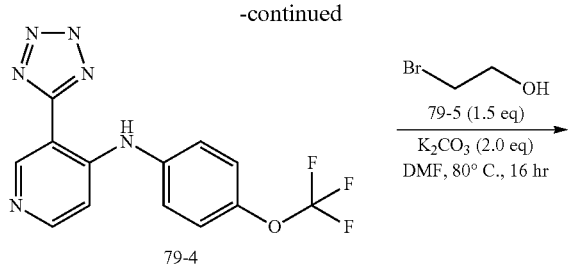

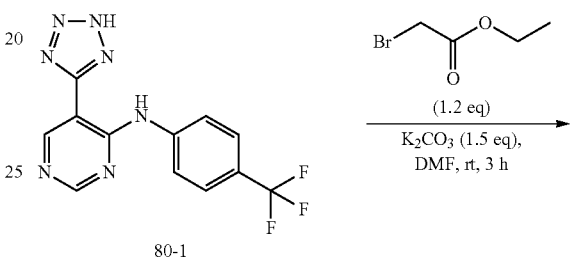

Step 1: 4-[4-(trifluoromethoxy)anilino]pyridine-3-carbonitrile

To a solution of 79-1 (300.0 mg, 2.2 mmol, 1.0 eq), 79-2 (384.4 mg, 2.2 mmol, 0.29 mL, 1.0 eq) and palladium acetate (48.7 mg, 0.22 mmol, 0.1 eq) in dioxane (8.0 mL) was added BINAP (135.1 mg, 0.22 mmol, 0.1 eq) and $Cs_2CO_3$ (707.0 mg, 2.2 mmol, 1.0 eq). The resulting mixture was stirred at 100° C. under $N_2$ for 15 hour. LCMS showed the desired compound was formed and the starting material was consumed completely. TLC (30% ethyl acetate in petroleum ether, Rf=0.4) showed the starting material was consumed and a new spot appeared. The reaction mixture was concentrated. The crude product residue was dissolved in $CH_2Cl_2$ (25 ml) and washed with water (2×15 mL). After drying over anhydrous $Na_2SO_4$, the solvent was removed under reduced pressure to afford the crude product. The crude product was purified by column chromatography over silica gel to give 79-3 (400.0 mg, 1.4 mmol, 65.9% yield). LCMS (ESI): RT=0.573 min, mass calc. for $C_{13}H_8F_3N_3O$ 279.06, m/z found 279.9 [M+H]+.

Step 2: 3-(2H-tetrazol-5-yl)-N-[4-(trifluoromethoxy)phenyl]pyridin-4-amine

To a solution of 79-3 (400.0 mg, 1.4 mmol, 1.0 eq) in DMF (10.0 mL) was added $NH_4Cl$ (229.9 mg, 4.3 mmol, 0.15 mL, 3.0 eq) and $NaN_3$ (464.8 mg, 7.2 mmol, 5.0 eq). The mixture was stirred at 140° C. for 16 hour under an $N_2$ atmosphere. LCMS showed the desired compound was formed. The reaction mixture was poured into sat. aq. $NaHCO_3$ (5 mL) and extracted with EtOAc (5 mL*2). The combined organic layer was washed with brine (10 mL), dried over $Na_2SO_4$, and filtered. The solvent was removed under reduced pressure to afford the crude 79-4 (300.0 mg, 0.93 mmol, 65.1% yield). LCMS (ESI): RT=0.661 min, mass calc. for $C_{13}H_9F_3N_6O$ 322.08, m/z found 322.9 [M+H]+.

Step 3: 2-[5-[4-[4-(trifluoromethoxy)anilino]-3-pyridyl]tetrazol-2-yl]ethanol To a solution of 79-4 (100.0 mg, 0.31 mmol, 1.0 eq) in DMF (5.0 mL) was added $K_2CO_3$ (85.8 mg, 0.62 mmol, 2.0 eq) and 79-5 (46.5 mg, 0.37 mmol, 26.4 uL, 1.2 eq). The mixture was stirred at 100° C. for 3 hour under an $N_2$ atmosphere. LCMS showed the desired compound was formed. The reaction was filtered to give a crude product. The crude product was purified by prep-HPLC to give Compound 79 (6.03 mg, 16.46 umol, 5.30% yield). LCMS (ESI): RT=0.644 min, mass calc. for $C_{15}H_{13}F_3N_6O_2$ 366.11, m/z found 367.0 [M+H]+; 1HNMR (400 MHz, $CDCl_3$-d) δ 9.40 (s, 1H), 9.05 (s, 1H), 8.08 (d, J=6.0 Hz, 1H), 7.25 (d, J=3.5 Hz, 4H), 6.97 (d, J=6.0 Hz, 1H), 4.91-4.86 (m, 2H), 4.36-4.32 (m, 2H).

Example 76: ethyl 2-[5-[4-[4-(trifluoromethyl)anilino]pyrimidin-5-yl]tetrazol-2-yl]acetate (Compound 80)

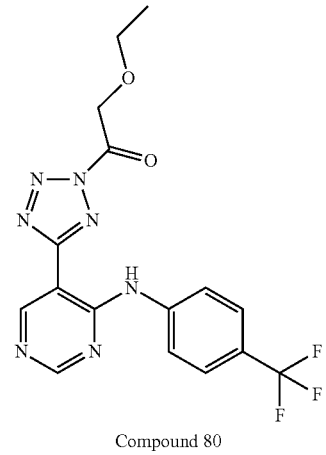

Compound 80

To a solution of 80-1 (50 mg, 0.16 mmol, 1.00 eq) and $K_2CO_3$ (33.7 mg, 0.24 mmol, 1.50 eq) in DMF (2 mL) was added ethyl 2-bromoacetate (32.6 mg, 0.20 mmol, 21.60 uL, 1.20 eq). The resulting mixture was stirred at 25° C. for 1 hr. LCMS showed that ~40% of the desired MS signal was detected. To the reaction was added water (5 mL), and the mixture was extracted with EtOAc (2*10 mL). The combined organic extracts were washed with brine (2*10 mL), dried over $Na_2SO_4$, and concentrated. The residue was purified by CombiFlash to give the title compound (23 mg, 52.04 umol, 31.98% yield). LCMS (ESI): RT=2.074 min, mass calc. for $C_{16}H_{14}N_7O_2F_3$ 393.12, m/z found 394.0 [M+H]+; 1HNMR (400 MHz, DMSO) δ 9.93 (s, 1H), 9.17 (s, 1H), 8.88 (s, 1H), 8.04 (d, J=8.4 Hz, 1H), 7.78 (d, J=8.4 Hz, 1H), 6.06 (s, 2H), 4.26 (q, J=7.2 Hz, 2H), 1.26 (t, J=6.8 Hz, 3H).

Example 77: ethyl 2-(5-(2-((4-(trifluoromethyl)phenyl)amino)phenyl)-2H-tetrazol-2-yl)acetate (Compound 81)

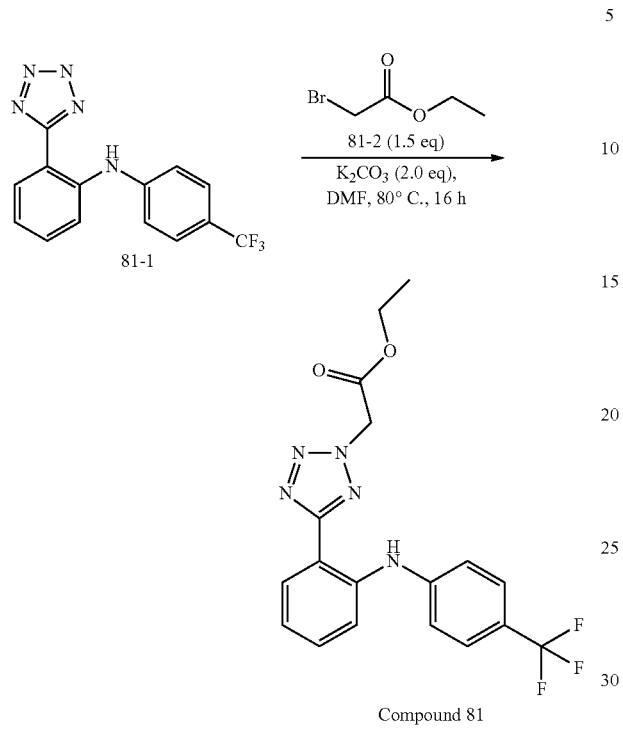

Compound 81

To a solution of 81-1 (50.0 mg, 0.16 mmol, 1.0 eq) in DMF (5.0 mL) was added K₂CO₃ (34.0 mg, 0.25 mmol, 1.5 eq) and 81-2 (32.8 mg, 0.20 mmol, 21.7 uL, 1.2 eq). The mixture was stirred at 80° C. for 16 hour under an N₂ atmosphere. LCMS showed the desired compound was formed. The reaction was filtered to give a crude product. The crude product was purified by prep-HPLC to give the title compound (8.03 mg, 19.90 umol, 12.15% yield). LCMS (ESI): RT=0.926 min, mass calc. for C₁₈H₁₆F₃N₅O₂ 391.13, m/z found 392.1 [M+H]⁺; ¹HNMR (400 MHz, DMSO-d₆) δ 8.75 (s, 1H), 8.05 (dd, J=1.1, 7.7 Hz, 1H), 7.59-7.47 (m, 4H), 7.26-7.17 (m, 3H), 5.90 (s, 2H), 4.20 (q, J=7.2 Hz, 2H), 1.21 (t, J=7.2 Hz, 3H).

Example 78: 2-[5-[2-[4-(trifluoromethyl)anilino]phenyl]tetrazol-2-yl]acetic acid (Compound 82)

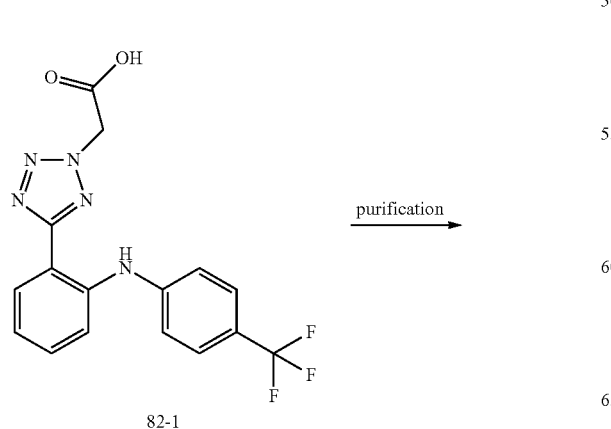

82-1 purification →

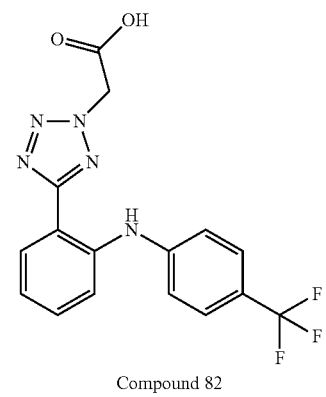

Compound 82

A solution of 82-1 (10.0 mg, 27.5 umol, 1.0 eq) in DMF (2.0 mL). LCMS showed the desired compound was formed. The reaction was filtered to give a crude product. The crude product was purified by prep-HPLC to give the title compound (2.78 mg, 7.65 umol, 27.79% yield). LCMS (ESI): RT=0.836 min, mass calc. for C₁₆H₁₂F₃N₅O₂ 363.09, m/z found 364.0 [M+H]⁺; ¹HNMR (400 MHz, DMSO-d₆) δ 8.79 (s, 1H), 8.06 (dd, J=1.3, 7.8 Hz, 1H), 7.59-7.53 (m, 3H), 7.52-7.47 (m, 1H), 7.25 (d, J=8.5 Hz, 2H), 7.21-7.16 (m, 1H), 5.77 (s, 2H).

Example 79: 2-[3-methyl-4-[2-[4-(trifluoromethyl)anilino]phenyl]pyrazol-1-yl]ethanol (Compound 83)

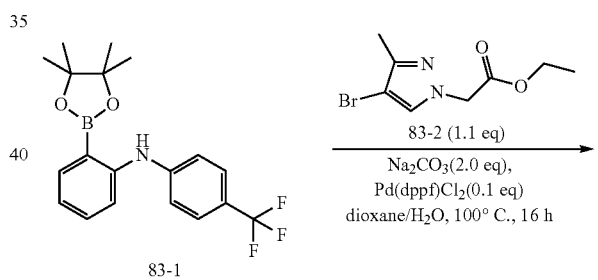

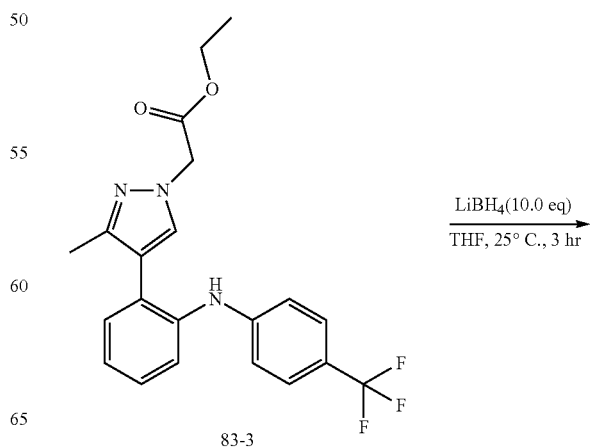

83-3

331
-continued

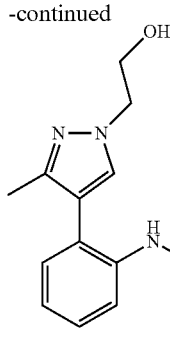

Compound 83

Step 1: ethyl 2-[3-methyl-4-[2-[4-(trifluoromethyl)anilino]phenyl]pyrazol-1-yl]acetate To a solution of 83-1 (400.0 mg, 1.1 mmol, 1.0 eq) and 83-2 (326.6 mg, 1.3 mmol, 1.2 eq) in dioxane (5.0 mL) was added H$_2$O (0.5 mL), Pd(dppf)Cl$_2$ (80.6 mg, 0.11 mmol, 0.1 eq) and Na$_2$CO$_3$ (233.5 mg, 2.2 mmol, 2.0 eq). The mixture was stirred at 100° C. for 16 hour under N$_2$ atmosphere. LCMS showed the desired compound was formed. TLC (5% ethyl acetate in petroleum ether) showed the starting material remained and new spots appeared. The reaction was filtered through celite and concentrated under reduced pressure to give a residue. The crude product was purified by column chromatography over silica gel to give 83-3 (150.0 mg, 0.37 mmol, 33.8% yield). LCMS (ESI): RT=0.843 min, mass calc. for C$_{21}$H$_{20}$F$_3$N$_3$O$_2$ 403.15, m/z found 404.0 [M+H]$^+$.

Step 2: 2-[3-methyl-4-[2-[4-(trifluoromethyl)anilino]phenyl]pyrazol-1-yl]ethanol To a solution of 83-3 (150.0 mg, 0.37 mmol, 1.0 eq) in THF (4.0 mL) was added LiBH$_4$ (81.0 mg, 3.7 mmol, 10.0 eq). The resulting mixture was stirred at 20° C. for 3 hours. LCMS showed the desired compound was found and the starting material was consumed completely. The reaction mixture was treated dropwise with aq. NH$_4$Cl (5 mL) and extracted with EtOAc (5 mL*2). The combined organic layers were washed with brine (10 mL), dried over Na$_2$SO$_4$, and filtered. The solvent was removed under reduced pressure to afford the crude product. The crude product was purified by prep-HPLC and then purified by prep-SFC to give Compound 83 (8.89 mg, 24.60 umol, 6.62% yield). LCMS (ESI): RT=0.795 min, mass calc. for C$_{19}$H$_{18}$F$_3$N$_3$O 361.14, m/z found 362.1 [M+H]$^+$; $^1$HNMR (400 MHz, DMSO-d$_6$) δ 7.86 (s, 1H), 7.62 (s, 1H), 7.41 (d, J=8.5 Hz, 2H), 7.36-7.32 (m, 1H), 7.30-7.24 (m, 2H), 7.16-7.10 (m, 1H), 6.93 (d, J=8.5 Hz, 2H), 4.80 (t, J=5.5 Hz, 1H), 4.01 (t, J=5.8 Hz, 2H), 3.67 (q, J=5.7 Hz, 2H), 2.04 (s, 3H).

332

Example 80: 2-[5-methyl-4-[2-[4-(trifluoromethyl)anilino]phenyl]pyrazol-1-yl]ethanol (Compound 84)

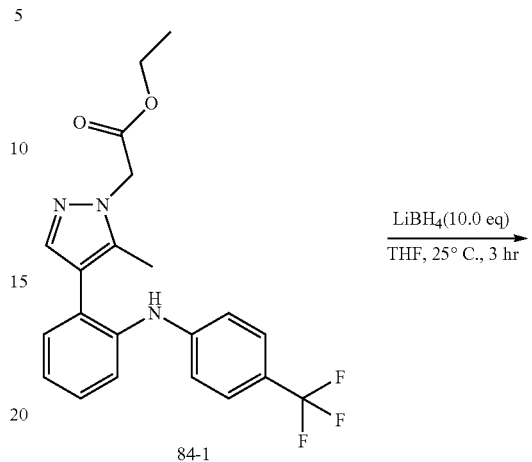

84-1

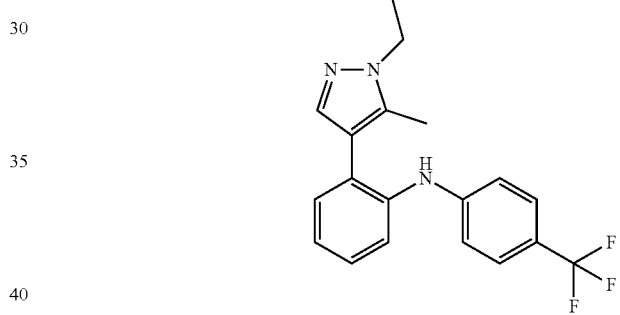

Compound 84

To a solution of 84-1 (150.0 mg, 0.37 mmol, 1.0 eq) in THF (4.0 mL) was added LiBH$_4$ (81.0 mg, 3.7 mmol, 10.0 eq). The resulting mixture was stirred at 20° C. for 3 hours. LCMS showed the desired compound was found and the starting material was consumed completely. The reaction mixture was treated dropwise with aq. NH$_4$Cl (5 mL) and extracted with EtOAc (5 mL*2). The combined organic layers were washed with brine (10 mL), dried over Na$_2$SO$_4$, and filtered. The solvent was removed under reduced pressure to afford the crude product. The crude product was purified by prep-HPLC and then purified by prep-SFC to give the title compound (7.51 mg, 20.78 umol, 5.59% yield). LCMS (ESI): RT=0.799 min, mass calc. for C$_{19}$H$_{18}$F$_3$N$_3$O 361.14, m/z found 362.1 [M+H]$^+$; $^1$HNMR (400 MHz, DMSO-d$_6$) δ 7.88 (s, 1H), 7.41 (d, J=8.5 Hz, 2H), 7.38-7.33 (m, 2H), 7.32-7.28 (m, 1H), 7.26 (d, J=7.8 Hz, 1H), 7.19-7.13 (m, 1H), 6.92 (d, J=8.5 Hz, 2H), 4.84 (t, J=5.6 Hz, 1H), 4.05 (t, J=5.9 Hz, 2H), 3.66 (q, J=5.8 Hz, 2H), 2.11 (s, 3H).

333

Example 81: N-methylsulfonyl-2-[5-[2-[4-(trifluoromethyl)anilino]phenyl]tetrazol-2-yl]acetamide (Compound 85)

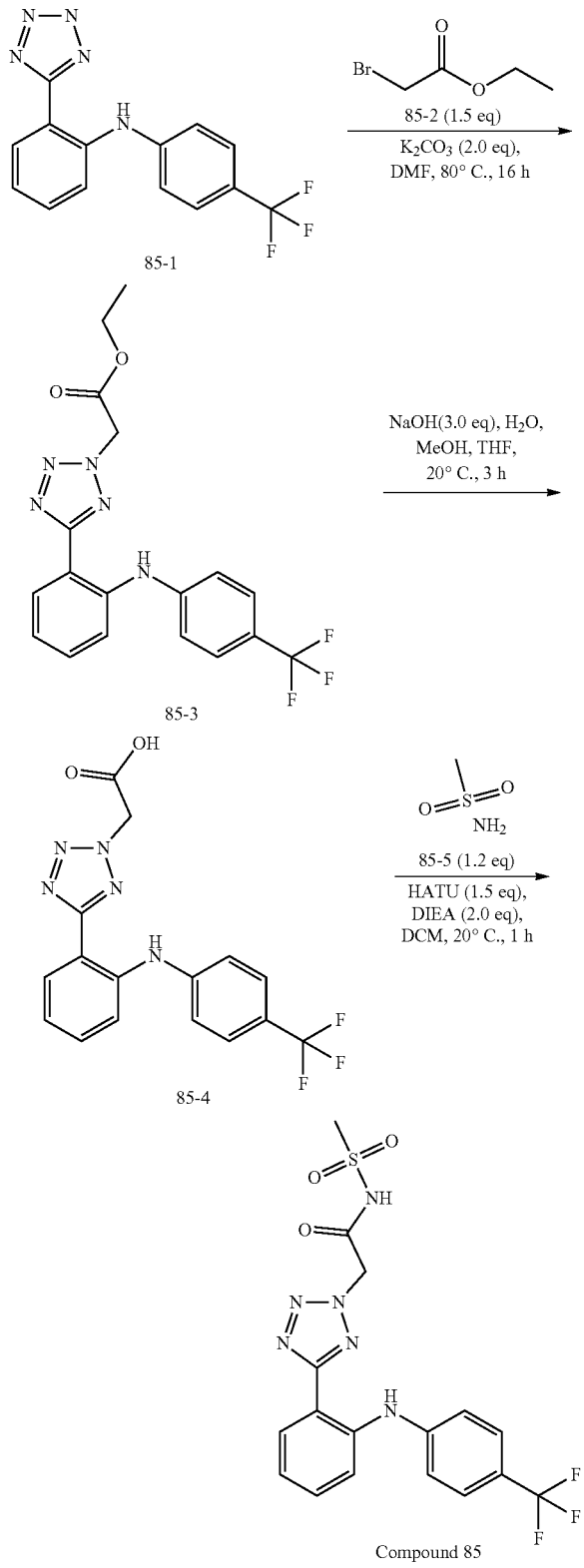

334

Step 1: ethyl 2-[5-[2-[4-(trifluoromethyl)anilino]phenyl]tetrazol-2-yl]acetate To a solution of 85-1 (400.0 mg, 1.3 mmol, 1.0 eq) in DMF (5.0 mL) was added $K_2CO_3$ (362.1 mg, 2.6 mmol, 2.0 eq) and 85-2 (437.5 mg, 2.6 mmol, 0.29 mL, 2.0 eq). The mixture was stirred at 80° C. for 16 hours under an under an $N_2$ atmosphere. LCMS showed the desired compound was formed. TLC (Petroleum ether:Ethyl acetate=3/1) showed a new spot, and the starting material was consumed completely. The reaction mixture was concentrated to give the crude product. The crude product was purified by column chromatography over silica gel to give 85-3 (350.00 mg, 894.34 umol, 68.27% yield). LCMS (ESI): RT=0.914 min, mass calc. for $C_{18}H_{16}F_3N_5O_2$ 391.13, m/z found 392.1 $[M+H]^+$.

Step 2: 2-[5-[2-[4-(trifluoromethyl)anilino]phenyl]tetrazol-2-yl]acetic acid To a solution of 85-3 (350.0 mg, 0.89 mmol, 1.0 eq) in $H_2O$ (2.0 mL) and MeOH (4.0 mL) was added NaOH (107.0 mg, 26.8 mmol, 29.9 eq). The resulting mixture was stirred at 25° C. for 4 hr. LCMS showed the desired compound was formed. TLC (Petroleum ether:Ethyl acetate=3/1) showed the starting material was consumed and a new spot appeared. The reaction solvent was removed under reduced pressure and water (5 mL) was added. The reaction was acidified by adding 1M HCl (10 mL) to precipitate a solid. The solid was washed with EtOAc (20 mL×2). The combined organic layers were concentrated to give 85-4 (200.0 mg, 0.55 mmol, 61.6% yield). LCMS (ESI): RT=0.831 min, mass calc. for $C_{16}H_{12}F_3N_5O_2$ 363.09, m/z found 363.9 $[M+H]^+$.

Step 3: N-methylsulfonyl-2-[5-[2-[4-(trifluoromethyl)anilino]phenyl]tetrazol-2-yl]acetamide To a solution of 85-4 (30.0 mg, 82.6 umol, 1.0 eq) and 85-5 (11.8 mg, 0.12 mmol, 1.5 eq) in DCM (5.0 mL) was added HATU (31.4 mg, 82.6 umol, 1.0 eq) and DIEA (32.0 mg, 0.25 mmol, 43.3 uL, 3.0 eq). The resulting mixture was stirred at 20° C. for 1 hour. LCMS showed the desired compound was formed. The reaction mixture was concentrated under reduced pressure to give a residue. The crude product was purified by prep-HPLC to give Compound 85 (5.07 mg, 11.51 umol, 13.94% yield). LCMS (ESI): RT=0.826 min, mass calc. for $C_{17}H_{15}F_3N_6O_3S$ 440.09, m/z found 441.0 $[M+H]^+$; $^1$HNMR (400 MHz, DMSO-$d_6$) δ 8.89 (s, 1H), 8.08 (dd, J=1.3, 7.7 Hz, 1H), 7.56 (t, J=8.0 Hz, 3H), 7.50-7.44 (m, 1H), 7.29 (d, J=8.4 Hz, 2H), 7.18-7.14 (m, 1H), 7.05 (d, J=18.7 Hz, 1H), 5.29 (s, 2H), 2.80 (s, 3H).

Example 82: 2-(5-(4-((4-(trifluoromethyl)phenyl) amino)pyrimidin-5-yl)-2H-tetrazol-2-yl)ethan-1-ol (Compound 86)

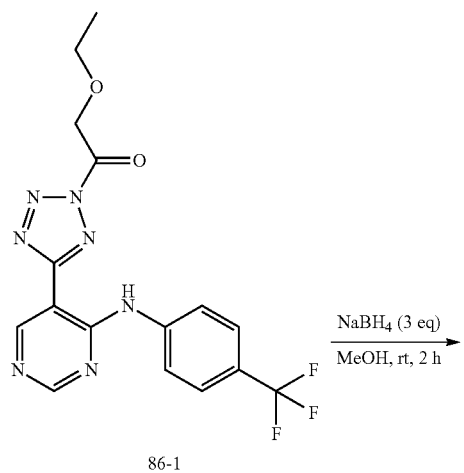

86-1

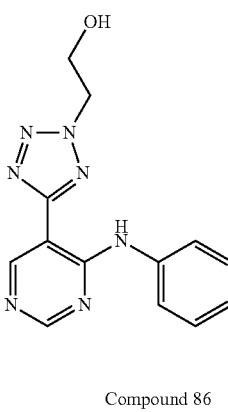

Compound 86

To a solution of 86-1 (20 mg, 50.85 umol, 1.00 eq) in MeOH (1 mL) was added NaBH$_4$ (5.77 mg, 0.15 mmol, 3.00 eq). The resulting mixture was stirred at 25° C. for 2 hr. LCMS showed that desired MS signal was detected. The reaction was diluted with EtOAc (10 mL) and washed with water (2*5 mL). The organic layer was dried over Na$_2$SO$_4$ and concentrated. The residue was purified by Prep-HPLC (HCl condition) to give Compound 86 (4.84 mg, 13.78 umol, 27.09% yield). LCMS (ESI): RT=1.874 min, mass calc. for C$_{14}$H$_{12}$N$_7$OF$_3$ 351.12, m/z found 351.9 [M+H]$^+$; $^1$HNMR (400 MHz, DMSO) δ 10.20 (s, 1H), 9.17 (s, 1H), 8.93 (s, 1H), 8.00 (d, J=8.4 Hz, 1H), 7.79 (d, J=8.4 Hz, 1H), 4.89 (t, J=5.2 Hz, 2H), 4.02 (t. J=5.2 Hz, 2H).

Example 83: 2-(3-methyl-4-(2-((3-(trifluoromethyl)phenyl)amino)phenyl)-1H-pyrazol-1-yl)acetic Acid (Compound 87) and 2-(5-methyl-4-(2-((3-(trifluoromethyl)phenyl)amino)phenyl)-1H-pyrazol-1-yl) acetic Acid (Compound 88)

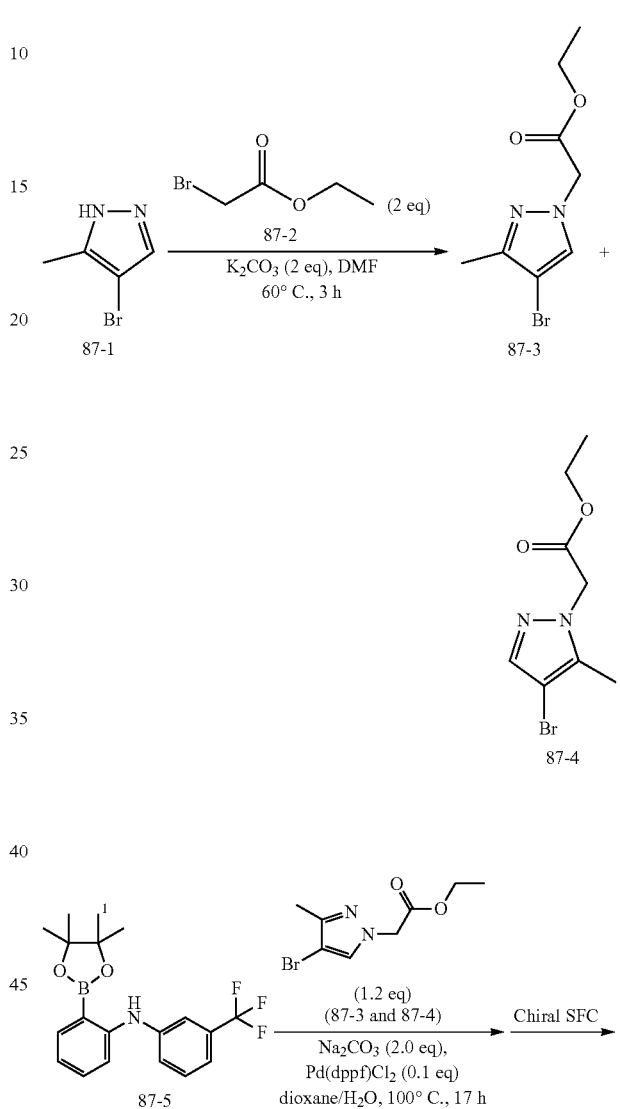

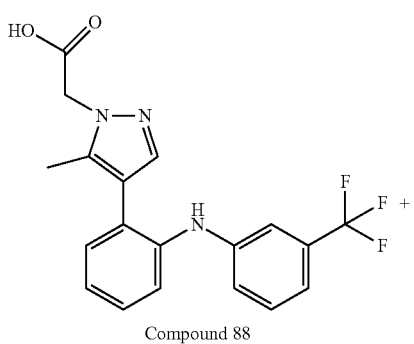

Compound 88

337

-continued

Compound 87

Step 1: ethyl 2-(4-bromo-3-methyl-1H-pyrazol-1-yl)acetate and ethyl 2-(4-bromo-5-methyl-1H-pyrazol-1-yl)acetate To a mixture 87-1 (1.0 g, 6.2 mmol, 1.00 eq) and K$_2$CO$_3$ (1.7 g, 12.4 mmol, 2.00 eq) in DMF (10.0 mL), was added 87-2 (2.1 g, 12.4 mmol, 1.4 mL, 2.00 eq). The resulting mixture was stirred at 60° C. for 3 h. LCMS showed the reaction was complete. The mixture was diluted with EtOAc (40 mL), washed with water (40 mL*5). The organic layer was dried over anhydrous Na$_2$SO$_4$, and concentrated under vacuum. A mixture of 87-3 and 87-4 (1.6 g, crude) was obtained.

Step 2: 2-(5-methyl-4-(2-((3-(trifluoromethyl)phenyl)amino)phenyl)-1H-pyrazol-1-yl)acetic acid and 2-(3-methyl-4-(2-((3-(trifluoromethyl)phenyl)amino)phenyl)-1H-pyrazol-1-yl)acetic Acid To a mixture of 87-3 and 87-4 (409.2 mg, 1.7 mmol, 1.20 eq), 5 (500.0 mg, 1.4 mmol, 1.00 eq), and Na$_2$CO$_3$ (292.5 mg, 2.8 mmol, 2.00 eq) in dioxane (8.0 mL) and H$_2$O (1.0 mL), was added Pd(dppf)Cl$_2$ (101.0 mg, 0.1 mmol, 0.10 eq). The mixture was degassed under vacuum and purged with N$_2$ 3 times. The resulting mixture was stirred at 100° C. under N$_2$ for 17 h. LCMS showed the reaction was complete. The mixture was concentrated under vacuum. The residue was purified by silica gel chromatography to afford the crude product, which was then purified by prep-HPLC (acidic_HCl condition). The mixture of Compound 87 and Compound 88 was separated by chiral SFC.

Compound 87: 27.43 mg, 66.50 umol, 41.6% yield. LCMS (ESI): RT=0.794 min, mass calc. for C$_{19}$H$_{16}$F$_3$N$_3$O$_2$ 375.12, m/z found 376.0 [M+H]$^+$. $^1$HNMR (400 MHz, DMSO-d$_6$) δ 7.67 (d, J=2.3 Hz, 2H), 7.34-7.22 (m, 4H), 7.15-7.07 (m, 3H), 6.96 (br d, J=7.3 Hz, 1H), 4.70 (s, 2H), 2.03 (s, 3H).

Compound 88: 12.33 mg, 29.57 umol, 18.5% yield. LCMS (ESI): RT=0.803 min, mass calc. for C$_{19}$H$_{16}$F$_3$N$_3$O$_2$ 375.12, m/z found 376.0 [M+H]$^+$. $^1$H NMR (400 MHz, DMSO-d$_6$) δ 7.68 (s, 1H), 7.36-7.31 (m, 1H), 7.31-7.26 (m, 2H), 7.24 (d, J=6.8 Hz, 1H), 7.15-7.08 (m, 2H), 7.06 (s, 1H), 6.95 (d, J=7.5 Hz, 1H), 4.72 (s, 2H), 2.07 (s, 3H).

338

Example 84: ethyl 2-(3-methyl-4-(2-((3-(trifluoromethyl)phenyl)amino)phenyl)-1H-pyrazol-1-yl)acetate (Compound 89) and ethyl 2-(5-methyl-4-(2-((3-(trifluoromethyl)phenyl)amino) phenyl)-1H-pyrazol-1-yl)acetate (Compound 90)

Compound 90

Compound 89

To a mixture of 89-1 (400.0 mg, 1.1 mmol, 1.00 eq), Pd(dppf)Cl$_2$ (80.5 mg, 0.1 mmol, 0.10 eq) and Na$_2$CO$_3$ (233.2 mg, 2.2 mmol, 2.00 eq) in H$_2$O (1.0 mL) and THF (8.0 mL), was added the mixture of 89-2 and 89-3 (326.2 mg, 1.3 mmol, 1.20 eq). The mixture was degassed under vacuum and purged with N$_2$ 3 times. The resulting mixture was stirred at 70° C. under N$_2$ for 17 h. LCMS showed the reaction was complete. The mixture was concentrated under vacuum. The residue was purified by prep-HPLC (acidic_HCl condition). The mixture of Compound 89 and Compound 90 (100 mg) was obtained, which was separated by chiral SFC.

Compound 89: 33.39 mg, 78.6 umol, 31.7% yield. LCMS (ESI): RT=0.878 min, mass calc. for C$_{21}$H$_{20}$F$_3$N$_3$O$_2$ 403.15, m/z found 404.1 [M+H]$^+$. $^1$HNMR (400 MHz, CHLOROFORM-d) δ 7.47 (s, 1H), 7.42-7.38 (m, 1H), 7.38-7.33 (m, 1H), 7.33-7.26 (m, 3H), 7.22 (d, J=8.0 Hz, 1H), 7.15 (d, J=7.8 Hz, 1H), 7.05 (dt, J=1.0, 7.4 Hz, 1H), 5.79 (s, 1H), 4.89 (s, 2H), 4.28 (q, J=7.3 Hz, 2H), 2.21 (s, 3H), 1.33 (t, J=7.2 Hz, 3H).

Compound 90: 17.10 mg, 39.0 umol, 15.7% yield. LCMS (ESI): RT=1.375 min, mass calc. for $C_{21}H_{20}F_3N_3O_2$ 403.15, m/z found 404.5 [M+H]$^+$. $^1$HNMR (400 MHz, CHLOROFORM-d) δ 7.54 (s, 1H), 7.39 (d, J=8.0 Hz, 1H), 7.36-7.27 (m, 3H), 7.26-7.18 (m, 2H), 7.13 (d, J=7.8 Hz, 1H), 7.04 (dt, J=1.1, 7.5 Hz, 1H), 5.77 (s, 1H), 4.91 (s, 2H), 4.26 (q, J=7.3 Hz, 2H), 2.14 (s, 3H), 1.30 (t, J=7.0 Hz, 3H).

Example 85: 2-(3-methyl-4-(2-((3-(trifluoromethyl)phenyl)amino)phenyl)-1H-pyrazol-1-yl)ethanol (Compound 91)

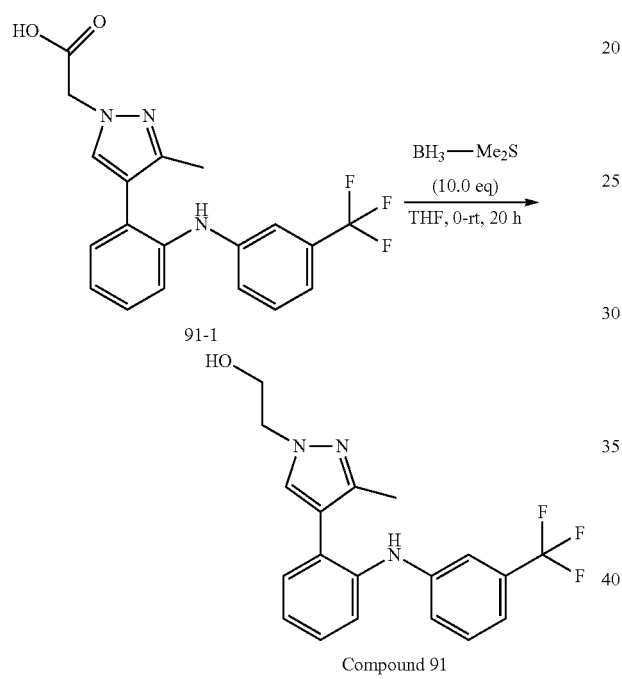

To a mixture of 91-1 (22.0 mg, 58.6 umol, 1.00 eq) in THF (3.0 mL), was added BH$_3$-Me$_2$S (10 M, 58.6 uL, 10.00 eq) at 0° C. The resulting mixture was stirred at 20° C. for 20 h. LCMS showed the reaction was complete. The mixture was quenched with MeOH (5 mL), and concentrated under vacuum. The residue was diluted with saturated aqueous NH$_4$Cl (15 mL), and extracted with DCM (15 mL*3). The combined organic layers were dried over anhydrous Na$_2$SO$_4$, and concentrated under vacuum. The residue was purified by prep-HPLC (acidic_HCl condition) to provide the title compound (12.72 mg, 31.0 umol, 52.9% yield, HCl salt). LCMS (ESI): RT=1.229 min, mass calc. for $C_{19}H_{18}F_3N_3O$ 361.14, m/z found 362.1 [M+H]$^+$. $^1$HNMR (400 MHz, DMSO-d$_6$) δ 7.70 (s, 1H), 7.66 (s, 1H), 7.35-7.23 (m, 4H), 7.13-7.07 (m, 2H), 7.05 (s, 1H), 6.96 (d, J=7.8 Hz, 1H), 4.02 (t, J=5.8 Hz, 2H), 3.66 (t, J=5.8 Hz, 2H), 2.05 (s, 3H).

Example 86: N-[2-[5-[2-[4-(trifluoromethyl)anilino]phenyl]tetrazol-2-yl]ethyl]acetamide (Compound 92)

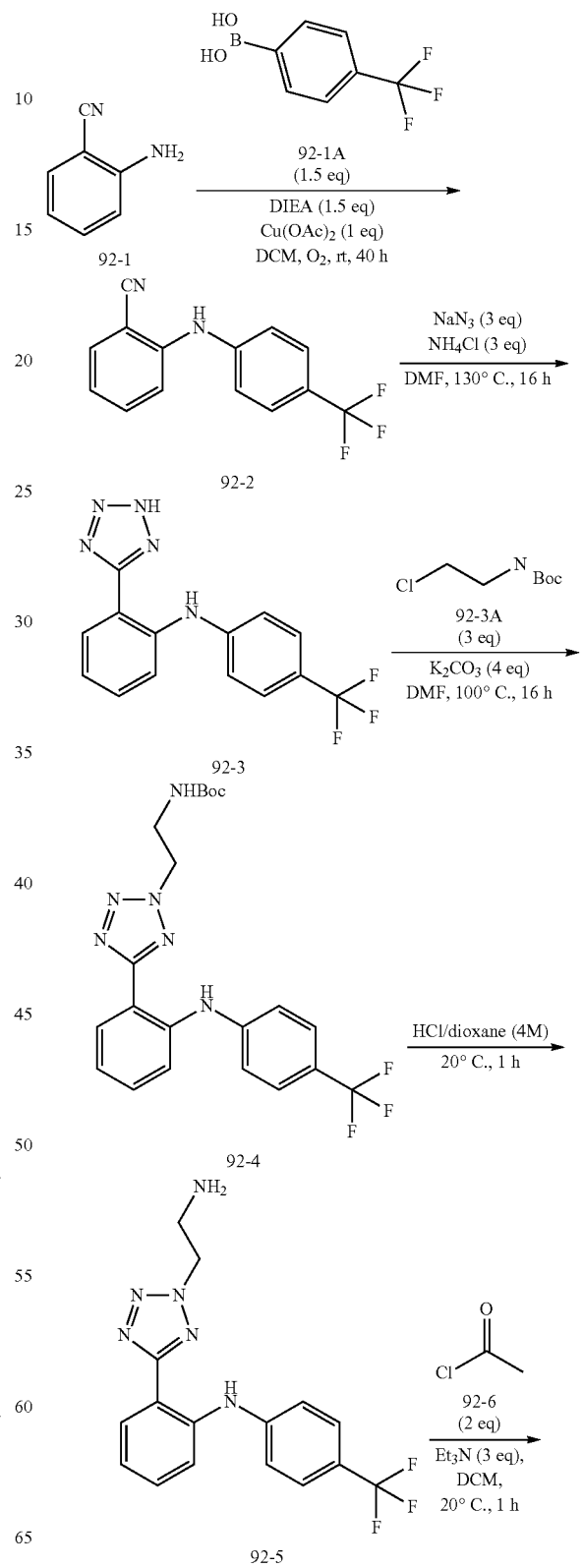

-continued

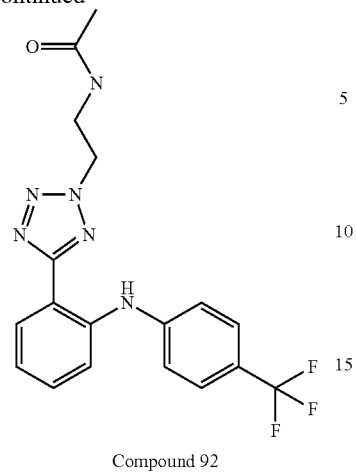

Compound 92

Step 1: 2-[4-(trifluoromethyl)anilino]benzonitrile

To the solution of 92-1 (3.20 g, 27.09 mmol, 1.00 eq), DIEA (5.18 g, 40.08 mmol, 7 mL, 1.48 eq), Cu(OAc)$_2$ (5.07 g, 27.91 mmol, 1.03 eq) in DCM (50 mL) was added 92-1A (6.00 g, 31.59 mmol, 1.17 eq). The mixture was stirred at 20° C. for 20 hour under an O$_2$ atmosphere. LCMS showed 52% of reactant 92-1 remained. Several new peaks were detected with LCMS and 27% of the desired compound was detected. The reaction mixture was continued with stirring for 2.5 h. LCMS showed no obvious changes. To the reaction mixture was added additional 92-1A (2.00 g, 10.53 mmol, 0.39 eq) and stirring continued for 1 h. LCMS indicated one small new peak was found. The reaction mixture was stirred an additional 16 h. LCMS showed no obvious changes. The reaction mixture was filtered and concentrated under vacuum. TLC indicated reactant 92-1 remained, and many new spots were formed. The residue was purified by flash silica gel chromatography to provide 92-2 (1.10 g, 3.82 mmol, 14.09% yield). LCMS (ESI): RT=0.843 min, mass calc. for $C_{14}H_9F_3N_2$ 262.07, m/z found 262.8[M+H]$^+$.

Step 2: 2-(2H-tetrazol-5-yl)-N-[4-(trifluoromethyl)phenyl]aniline

To a mixture of 92-2 (370 mg, 1.41 mmol, 1.00 eq) and NaN$_3$ (275 mg, 4.23 mmol, 3.00 eq) in DMF (10 mL) was added NH$_4$Cl (226 mg, 4.23 mmol, 3.00 eq) in one portion at 25° C. under N$_2$. The mixture was heated to 130° C. for 16 h. TLC indicated 92-2 was consumed completely and one major new spot with high polarity was detected. The reaction mixture was treated dropwise with aq. HCl (0.8 M) to give a suspension, filtered, and the solid was dried under reduced pressure to provide 92-3 (1.20 g, 3.85 mmol, 90.9% yield). LCMS (ESI): RT=0.810 min, mass calc. for $C_{14}H_{10}F_3N_5$ 305.09, m/z found 305.9[M+H]$^+$.

Step 3: tert-butyl N-[2-[5-[2-[4-(trifluoromethyl)anilino]phenyl]tetrazol-2-yl]ethyl]carbamate To a mixture of 92-3 (200 mg, 0.586 mmol, 1.00 eq, HCl) and K$_2$CO$_3$ (324 mg, 2.34 mmol, 4.00 eq) in DMF (6 mL) was stirred at 20° C. for 5 min. The mixture was added 92-3A (315 mg, 1.76 mmol, 3.00 eq), then heated to 105° C. and stirred for 16 hours. LCMS showed 92-3 remained and one peak with the desired MS was detected. TLC (Petroleum ether:Ethyl acetate=3:1) indicated one new spot was formed. The reaction mixture was diluted with EtOAc (35 mL) and washed with brine (20 mL*4). The combined organic layers were dried with anhydrous Na$_2$SO$_4$, filtered, and concentrated under vacuum. The residue was purified by flash silica gel chromatography to provide 92-4 (190 mg, 0.424 mmol, 72.4% yield). LCMS (ESI): RT=0.923 min, mass calcd. for $C_{21}H_{23}F_3N_6O_2$ 448.18, m/z found 449.3[M+H]$^+$ and 471.1 [M+23]$^+$.

Step 4: 2-[2-(2-aminoethyl)tetrazol-5-yl]-N-[4-(trifluoromethyl)phenyl]aniline To a mixture of 92-4 (190 mg, 0.423 mmol, 1.00 eq) was added HCl/dioxane (4 M, 5.00 mL, 47.20 eq) in one portion at 20° C. under N$_2$. The mixture was stirred at 20° C. for 1 h. LCMS showed the starting material was consumed completely and one main peak with MS was detected. The reaction mixture was concentrated under reduced pressure to remove solvent to provide 92-5 (160.00 mg, crude, HCl salt) which was used in the next step without further purification.

Step 5: N-[2-[5-[2-[4-(trifluoromethyl)anilino]phenyl]tetrazol-2-yl]ethyl]acetamide To a mixture of 92-5 (50 mg, 0.144 mmol, 1.00 eq) and Et$_3$N (44 mg, 0.431 mmol, 60 uL, 3.00 eq) in DCM (2 mL) was added 92-6 (23 mg, 0.287 mmol, 21 uL, 2.00 eq) in one portion at 20° C. under N$_2$. The mixture was stirred at 20° C. for 1 h. LCMS showed the compound 92-5 was consumed completely and one main peak with the desired MS was detected. The reaction mixture was concentrated under reduced pressure to remove solvent and the resulting residue was purified by prep-HPLC (basic condition) to provide Compound 92 (19.23 mg, 48.8 umol, 34% yield). LCMS (ESI): RT=1.265 min, mass calcd. for $C_{18}H_{17}F_3N_6O$ 390.14, m/z found 371.1[M+H−20]$^+$ and 413.1[M+23]$^+$. $^1$HNMR (400 MHz, CHLOROFORM-d) δ8.98 (s, 1H), 8.19 (dd, J=7.60, 1.60 Hz, 1H), 7.58-7.51 (m, 3H), 7.43-7.36 (m, 1H), 7.31 (d, J=8.40 Hz, 2H), 7.10-7.03 (m, 1H), 5.82 (br s, 1H), 4.89-4.82 (m, 2H), 3.99-3.87 (m, 2H), 1.98 (s, 3H).

Example 87: N-[2-[5-[2-[4-(trifluoromethyl)anilino]phenyl]tetrazol-2-yl]ethyl]methane Sulfonamide (Compound 93)

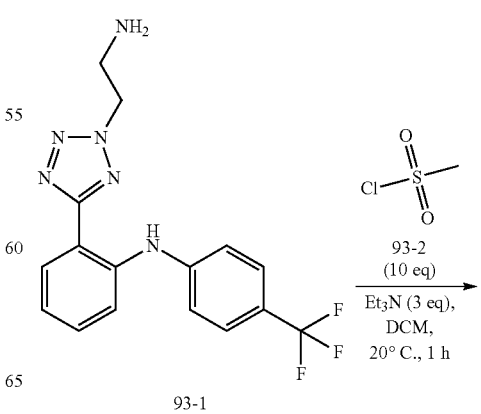

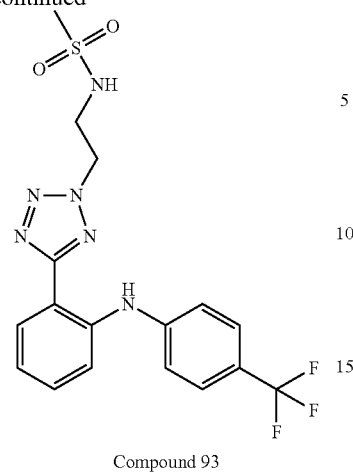

Compound 93

To a mixture of 93-1 (50 mg, 0.143 mmol, 1.00 eq) and Et₃N (44 mg, 0.431 mmol, 60 uL, 3.00 eq) in DCM (4 mL) was added 93-2 (170 mg, 1.48 mmol, 114 uL, 10 eq) in one portion at 20° C. under N₂. The mixture was stirred at 20° C. for 1 h. LCMS showed reactant 93-1 was consumed completely and one main peak with the desired MS was detected. The reaction mixture was concentrated under reduced pressure to remove solvent and the resulting residue was purified by prep-HPLC (basic condition) to provide the title compound (9.83 mg, 23 umol, 16.1% yield). LCMS (ESI): RT=1.290 min, mass calcd. for $C_{17}H_{17}F_3N_6O_2S$ 426.11, m/z found 427.1[M+H]⁺ and 449.1[M+23]⁺. ¹HNMR (400 MHz, CHLOROFORM-d) δ8.93 (s, 1H), 8.18 (dd, J=7.60, 1.20 Hz, 1H), 7.59-7.49 (m, 3H), 7.44-7.35 (m, 1H), 7.31 (d, J=8.40 Hz, 2H), 7.06 (t, J=7.20 Hz, 1H), 4.98-4.80 (m, 3H), 3.93-3.82 (m, 2H), 2.98 (s, 3H).

Example 88: ethyl 2-[5-[4-[4-(trifluoromethoxy) anilino]pyrimidin-5-yl]tetrazol-2-yl]acetate (Compound 94)

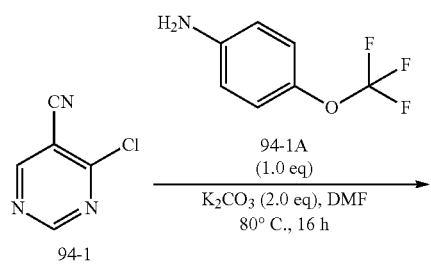

94-1

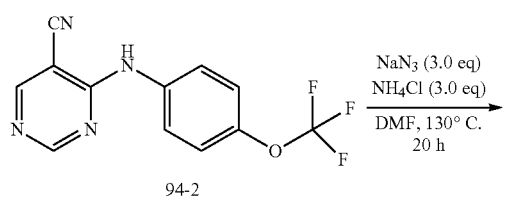

94-2

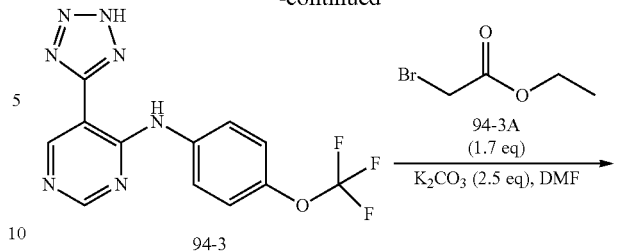

94-3

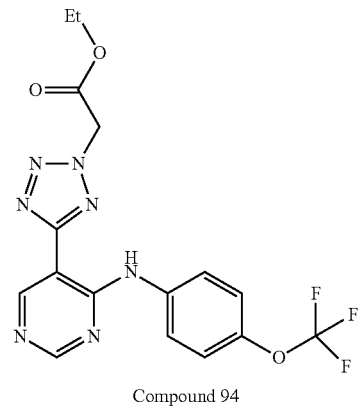

Compound 94

Step 1: 4-[4-(trifluoromethoxy)anilino]pyrimidine-5-carbonitrile

To a mixture of 94-1A (253 mg, 1.43 mmol, 193 uL, 1.00 eq) and 94-1 (200 mg, 1.43 mmol, 1.00 eq) in DMF (4 mL) was added K₂CO₃ (395 mg, 2.86 mmol, 2.00 eq) in one portion at 25° C. The mixture was stirred at 80° C. for 6 h. LCMS showed 94-1 was consumed completely. Several new peaks were detected on LCMS and 57% of the desired compound was detected. The reaction mixture was extracted with EtOAc (40 mL) and washed with brine (30 mL*4). The combined organic layers were dried with anhydrous Na₂SO₄, filtered, and concentrated under vacuum. TLC showed many new spots were formed. The residue was purified by flash silica gel chromatography to provide 94-2 (150 mg, 0.524 mmol, 36.7% yield). LCMS (ESI): RT=1.154 min, mass calcd. for $C_{12}H_7F_3N_4O$ 280.06, m/z found 280.9[M+H]⁺.

Step 2: 5-(2H-tetrazol-5-yl)-N-[4-(trifluoromethoxy)phenyl]pyrimidin-4-amine

To a mixture of 94-2 (150 mg, 0.512 mmol, 1.00 eq) and NaN₃ (50 mg, 0.769 mmol, 1.50 eq) in DMF (4.5 mL) was added NH₄Cl (41 mg, 0.768 mmol, 1.50 eq) in one portion at 20° C. under N₂. The mixture was heated to 130° C. for 16 h. LCMS showed the starting material was consumed completely and one main peak with the desired MS was detected. The reaction mixture was diluted with EtOAc (60 mL) and washed with brine (50 mL*5). The organic phase was dried with anhydrous Na₂SO₄, filtered and concentrated under vacuum to provide 94-3 (160 mg, 0.480 mmol, 93.8% yield), which was used next step without further purification.

Step 3: ethyl 2-[5-[4-[4-(trifluoromethoxy)anilino]pyrimidin-5-yl]tetrazol-2-yl]acetate To a mixture of 94-3 (80 mg, 0.248 mmol, 1.00 eq) and K₂CO₃ (86 mg, 0.619 mmol, 2.50 eq) in DMF (2 mL) was added 94-3A (73 mg, 0.438 mmol, 49 uL, 1.77 eq) in one portion at 20° C. under N₂. The mixture was stirred at 20° C. for 2 h. LCMS showed the starting material was remained and one peak with the desired MS was detected. The reaction mixture was diluted with EtOAc (60 mL) and washed with brine (50 mL*5). The organic phase was dried with anhydrous Na₂SO₄, filtered and concentrated under vacuum. HPLC showed 42% of desired product was found. The residue was purified by prep-HPLC (HCl condition) to provide Compound 94 (26.00 mg, 59 umol, 23.9% yield). LCMS (ESI): RT=1.198 min, mass calcd. for $C_{16}H_{14}F_3N_7O_3$ 409.11, m/z found 410.1[M+H]⁺. ¹HNMR (400 MHz, CHLOROFORM-d) M1.10 (br s, 1H), 9.24 (br s, 1H), 8.86 (br s, 1H), 7.77 (br d, J=8.40 Hz, 2H), 7.37 (br d, J=7.60 Hz, 2H), 5.60 (br s, 2H), 4.42-4.32 (m, 2H), 1.37 (t, J=7.20 Hz, 3H).

Example 89: N-tert-butyl-2-[5-[2-[4-(trifluoromethyl)anilino]phenyl]tetrazol-2-yl]acetamide (Compound 95)

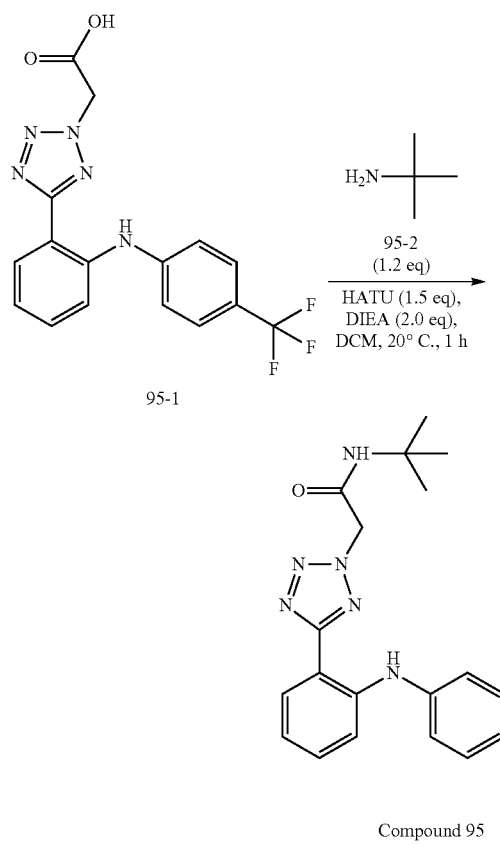

Compound 95

To a solution of 95-1 (30.0 mg, 82.6 umol, 1.0 eq) and 95-2 (9.1 mg, 0.12 mmol, 12.9 uL, 1.5 eq) in DCM (5.0 mL) was added HATU (31.4 mg, 82.6 umol, 1.0 eq) and DIEA (32.0 mg, 0.25 mmol, 43.3 uL, 3.0 eq). The resulting mixture was stirred at 20° C. for 1 hour. LCMS showed the desired compound was formed. TLC (Petroleum ether:Ethyl acetate=3/1) showed new spot appeared and the starting material was consumed completely. The reaction mixture was concentrated under reduced pressure to give a residue. The crude product was purified by column chromatography over silica gel and then further purified by prep-HPLC to give Compound 95 (20.27 mg, 48.45 umol, 58.66% yield). LCMS (ESI): RT=0.902 min, mass calc. for $C_{20}H_{21}F_3N_6O$ 418.17, m/z found 419.2 [M+H]⁺; ¹HNMR (400 MHz, DMSO-d₆) δ 8.79 (s, 1H), 8.17 (s, 1H), 8.04 (dd, J=1.4, 7.9 Hz, 1H), 7.59-7.53 (m, 3H), 7.52-7.46 (m, 1H), 7.24 (d, J=8.5 Hz, 2H), 7.21-7.15 (m, 1H), 5.45 (s, 2H), 1.28 (s, 9H).

Example 90: 2-(5-methyl-4-(2-((3-(trifluoromethyl)phenyl)amino)phenyl)-1H-pyrazol-1-yl)ethanol (Compound 96)

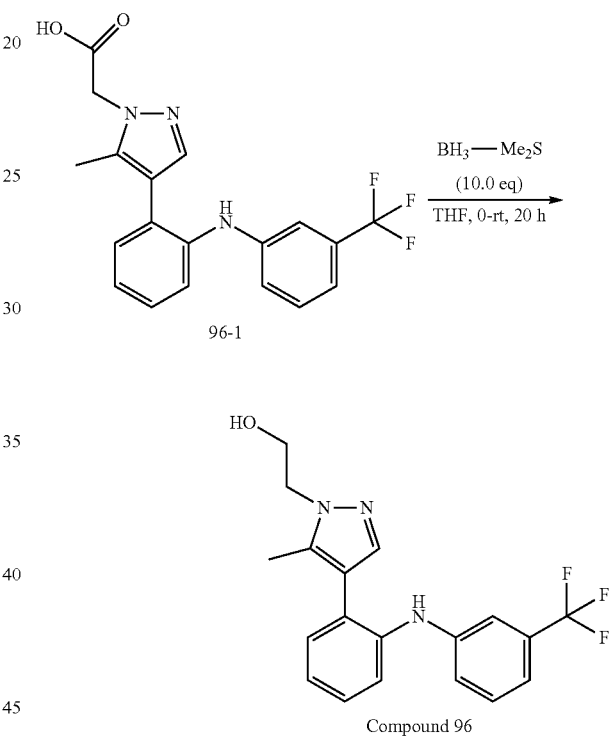

Compound 96

To a mixture of 96-1 (10.0 mg, 26.6 umol, 1.00 eq) in THF (3.0 mL), was added BH₃-Me₂S (10 M, 26.6 uL, 10.00 eq) at 0° C. The resulting mixture was stirred at 20° C. for 20 h. LCMS showed the reaction was complete. The mixture was quenched with MeOH (5 mL), and concentrated under vacuum. The residue was diluted with saturated NH₄Cl aqueous (15 mL), and extracted with DCM (15 mL*3). The combined organic layers were dried over anhydrous Na₂SO₄, and concentrated under vacuum. The residue was purified by prep-HPLC (acidic_HCl condition) to provide the title compound (3.90 mg, 9.6 umol, 36.1% yield, HCl salt). LCMS (ESI): RT=1.239 min, mass calc. for $C_{19}H_{18}F_3N_3O$ 361.14, m/z found 362.1 [M+H]⁺. ¹HNMR (400 MHz, DMSO-d₆) δ 7.70 (s, 1H), 7.46 (s, 1H), 7.34-7.25 (m, 3H), 7.23 (d, J=7.0 Hz, 1H), 7.13-7.08 (m, 2H), 7.04 (s, 1H), 6.96 (d, J=7.5 Hz, 1H), 4.06 (t, J=5.9 Hz, 2H), 3.68-3.63 (m, 2H), 2.12 (s, 3H).

Example 91: N-tert-butyl-1-(5-(2-((4-(trifluoromethyl)phenyl)amino)phenyl)-2H-tetrazol-2-yl)methanesulfonamide (Compound 97)

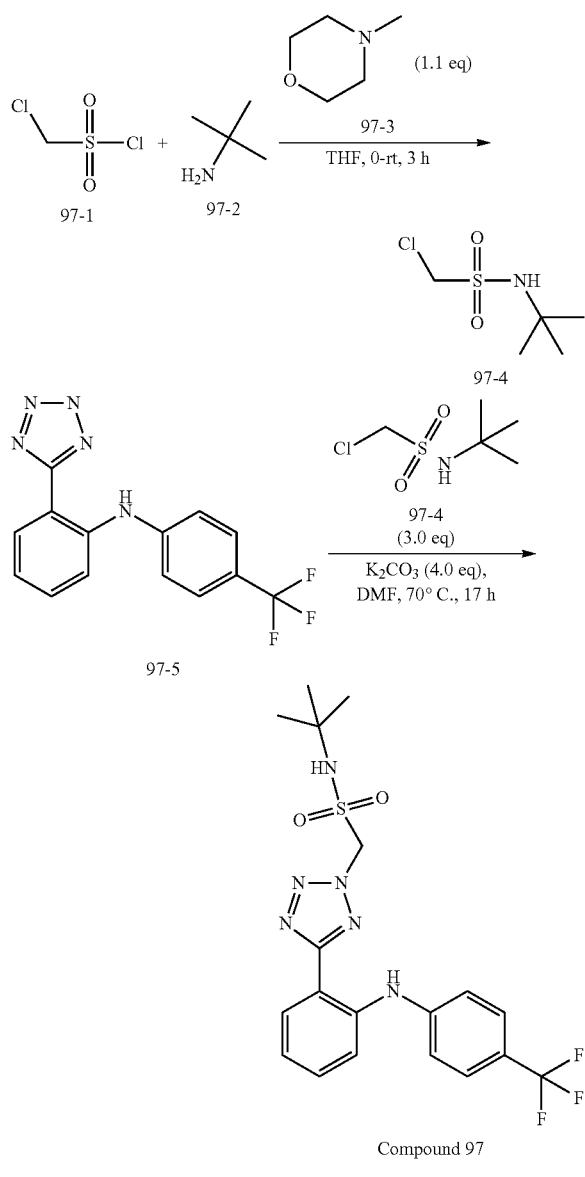

Step 1: N-tert-butyl-1-chloromethanesulfonamide 97-2 (258.0 mg, 3.5 mmol, 1.05 eq) and 97-3 (373.9 mg, 3.7 mmol, 1.10 eq) were dissolved in THF (7 mL), and a solution of 97-1 (500.0 mg, 3.4 mmol, 1.00 eq) in THF (3 mL) was added dropwise at 0° C. The resulting mixture was stirred at 0° C. for 0.5 h, then 20° C. for 2.5 h. TLC detected a new spot. The mixture was diluted with EtOAc (30 mL), washed with 1 M aqueous HCl (20 mL), water (30 mL), and brine (30 mL). The organic layer was dried over anhydrous $Na_2SO_4$, and concentrated under vacuum. 97-4 (460.0 mg, 2.5 mmol, 73.7% yield) was obtained as light yellow oil. $^1$HNMR (400 MHz, CHLOROFORM-d) δ 4.57 (s, 1H), 4.48 (s, 2H), 1.41 (s, 9H).

Step 2: N-tert-butyl-1-(5-(2-((4-(trifluoromethyl)phenyl)amino)phenyl)-2H-tetrazol-2-yl)methanesulfonamide To a mixture of 97-5 (50.0 mg, 0.2 mmol, 1.00 eq) and $K_2CO_3$ (90.6 mg, 0.7 mmol, 4.00 eq) in DMF (3.0 mL), was added 97-4 (91.2 mg, 0.5 mmol, 3.00 eq). The resulting mixture was stirred at 70° C. for 17 h. The reaction was monitored by LCMS. The mixture was filtered, and the solid was washed with DMF (1 mL). The filtrate was checked by HPLC and purified by prep-HPLC (basic condition) to provide Compound 97 (16.04 mg, 35.3 umol, 21.6% yield). LCMS (ESI): RT=1.403 min, mass calc. for $C_{19}H_{21}F_3N_6O_2S$ 454.14, m/z found 455.1 [M+H]$^+$. $^1$HNMR (400 MHz, DMSO-$d_6$) δ 8.70 (s, 1H), 8.09 (dd, J=1.4, 7.9 Hz, 1H), 7.61-7.55 (m, 3H), 7.54-7.46 (m, 2H), 7.26 (d, J=8.5 Hz, 2H), 7.23-7.17 (m, 1H), 6.20 (s, 2H), 1.26 (s, 9H).

Example 92: 3-(5-(2-((4-(trifluoromethyl)phenyl)amino)phenyl)-2H-tetrazol-2-yl)propan-1-ol (Compound 98)

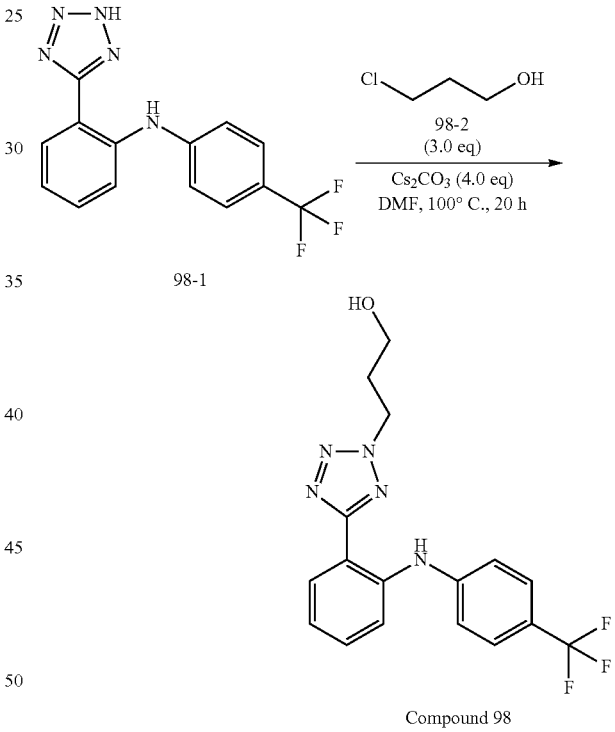

To a mixture of 98-1 (50.0 mg, 0.2 mmol, 1.00 eq) and $Cs_2CO_3$ (213.5 mg, 0.7 mmol, 4.00 eq) in DMF (3.0 mL), was added 98-2 (46.5 mg, 0.5 mmol, 3.00 eq). The resulting mixture was stirred at 100° C. for 20 h. The reaction was monitored by LCMS. The mixture was filtered, and the solid was washed with DMF (1 mL). The filtrate was checked by HPLC and purified by prep-HPLC (basic condition) to provide the title compound (6.70 mg, 18.4 umol, 11.3% yield). LCMS (ESI): RT=1.329 min, mass calc. for $C_{17}H_{16}F_3N_5O$ 363.13, m/z found 364.1 [M+H]$^+$. $^1$HNMR (400 MHz, CHLOROFORM-d) δ 9.06 (s, 1H), 8.20 (dd, J=1.4, 7.9 Hz, 1H), 7.54 (dd, J=2.8, 8.5 Hz, 3H), 7.42-7.35 (m, 1H), 7.30 (d, J=8.5 Hz, 2H), 7.08-7.00 (m, 1H), 4.88 (t, J=6.8 Hz, 2H), 3.76 (t, J=5.9 Hz, 2H), 2.35-2.29 (m, 2H).

349

Example 93: 2-[2-(sulfamoylamino)ethyl]-5-[2-[4-(trifluoromethyl)anilino]phenyl]tetrazole (Compound 99)

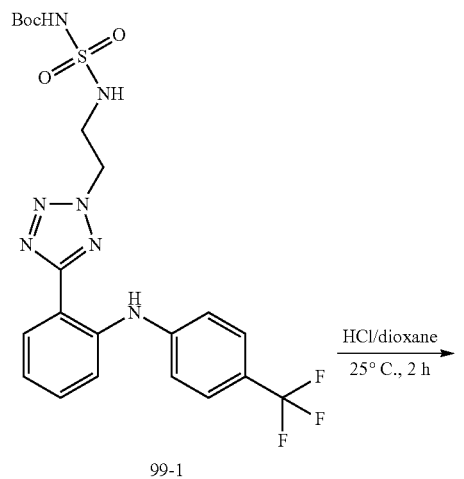

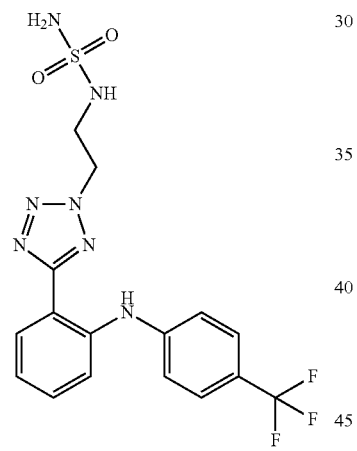

A solution of 99-1 (100 mg, 0.190 mmol, 1.0 eq) in HCl/dioxane (3 mL) was stirred at 25° C. for 1 hour. LCMS showed 85% of the desired compound was formed and the starting material was consumed completely. The reaction mixture was concentrated under reduced pressure to give a residue. The residue product was purified by HPLC to give the title compound (20 mg, 0.044 mmol, 23% yield). LCMS (ESI): RT=2.299 min, mass calc. for $C_{16}H_{16}F_3N_7O_2S$ 427.10, m/z found 450.0 [M+23]$^+$; $^1$HNMR (400 MHz, DMSO-$d_6$) δ 8.74 (s, 1H), 8.06 (d, J=7.5 Hz, 1H), 7.57 (d, J=8.0 Hz, 3H), 7.53-7.45 (m, 1H), 7.26 (d, J=8.0 Hz, 2H), 7.18 (t, J=7.3 Hz, 1H), 6.89 (s, 1H), 6.72 (s, 2H), 4.86 (s, 2H), 3.53 (d, J=5.3 Hz, 2H).

350

Example 94: tert-butyl (N-(2-(5-(2-((4-(trifluoromethyl)phenyl)amino)phenyl)-2H-tetrazol-2-yl)ethyl)sulfamoyl)carbamate (Compound 100)

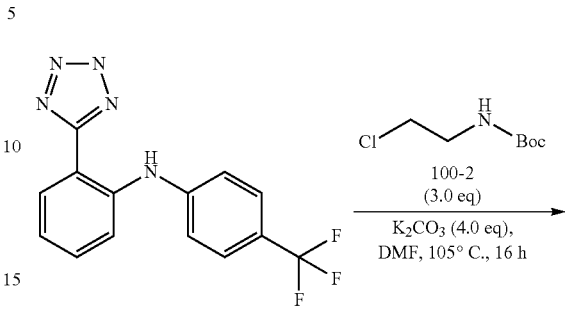

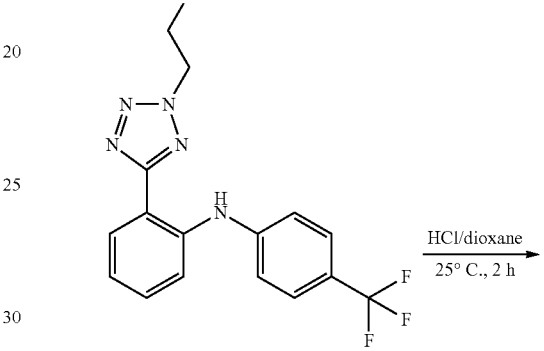

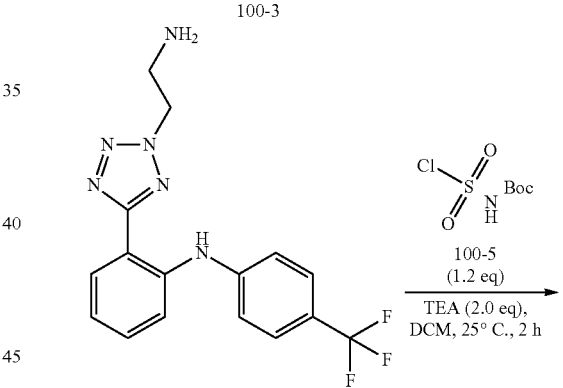

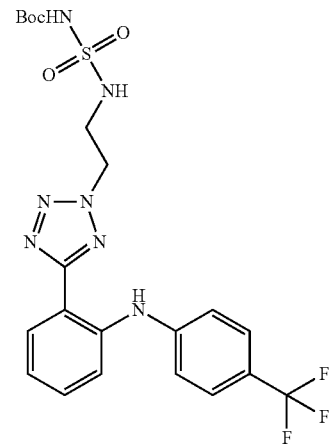

Step 1: tert-butyl N-[2-[5-[2-[4-(trifluoromethyl)anilino]phenyl]tetrazol-2-yl]ethyl]carbamate To a stirred mixture of 100-1 (100 mg, 0.293 mmol, 1.0 eq, HCl) and 100-2 (158 mg, 0.878 mmol, 3.0 eq) in DMF (3 mL) was added $K_2CO_3$ (162 mg, 1.17 mmol, 4.0 eq). The mixture was heated to 105° C. for 16 hr. LCMS showed 87% desired compound was formed and the starting material was consumed completely. The mixture was cooled. Water (10 mL) was added and the mixture extracted with ethyl acetate (3×10 mL). The combined organics were dried over magnesium sulfate, filtered, and concentrated to give a residue. The residue was purified by flash column chromatography to afford 100-3 (120 mg, 0.268 mmol, 91% yield). LCMS (ESI): RT=0.934 min, mass calc. for $C_{21}H_{23}F_3N_6O_2$ 448.18, m/z found 393.1 [M+H−56]$^+$; $^1$HNMR (400 MHz, DMSO-$d_6$) δ 8.73 (s, 1H), 8.04 (d, J=7.5 Hz, 1H), 7.61-7.53 (m, 4H), 7.51-7.46 (m, 1H), 7.26 (d, J=8.5 Hz, 2H), 7.18 (t, J=7.4 Hz, 1H), 7.03 (t, J=6.0 Hz, 1H), 4.76 (t, J=5.5 Hz, 2H), 3.56-3.47 (m, 2H), 1.27 (s, 9H).

Step 2: 2-[2-(2-aminoethyl)tetrazol-5-yl]-N-[4-(trifluoromethyl)phenyl]aniline A solution of 100-3 (120 mg, 0.268 mmol, 1.0 eq) in HCl/dioxane (4.0 mL) was stirred at 25° C. for 2 hour. LCMS showed 94% of the desired compound was formed and the starting material was consumed completely. The mixture was concentrated to give 100-4 (100 mg, 0.244 mmol, 91% yield, HCl) as a light yellow oil. The residue was directly used without further purification. LCMS (ESI): RT=0.713 min, mass calc. for $C_{16}H_{15}F_3N_6$ 348.13, m/z found 328.9 [M+H−20]$^+$; $^1$HNMR (400 MHz, DMSO-$d_6$) δ 8.76 (s, 1H), 8.16 (s, 2H), 8.07 (d, J=7.8 Hz, 1H), 7.58 (d, J=8.3 Hz, 3H), 7.54-7.48 (m, 1H), 7.27 (d, J=8.5 Hz, 2H), 7.21 (t, J=8.0 Hz, 1H), 5.02 (t, J=5.6 Hz, 2H), 3.50 (s, 2H).

Step 3: tert-butylN-[2-[5-[2-[4-(trifluoromethyl)anilino]phenyl]tetrazol-2-yl]ethylsulfamoyl]carbamate To a solution of 100-4 (40 mg, 0.115 mmol, 1.0 eq) and TEA (23 mg, 0.230 mmol, 32 uL, 2.0 eq) in DCM (2 mL) was added 100-5 (30 mg, 0.138 mmol, 1.2 eq). The resulting mixture was stirred at 25° C. for 1 hour. LCMS showed 90% desired compound was formed and the starting material was consumed completely. Water (2 ml) was added and the mixture extracted with DCM (3×3 mL). The combined organic layers were dried over $Na_2SO_4$, filtered, and concentrated under reduced pressure to give a residue. The residue was purified by HPLC to give Compound 100 (18 mg, 0.034 mmol, 30% yield). LCMS (ESI): RT=2.613 min, mass calc. for $C_{21}H_{24}F_3N_7O_4S$ 527.16, m/z found 472.1[M+H−56]$^+$; $^1$HNMR (400 MHz, DMSO-$d_6$) δ 8.74 (s, 1H), 8.06 (d, J=6.8 Hz, 1H), 7.64-7.42 (m, 4H), 7.35-7.04 (m, 5H), 4.83 (s, 2H), 3.49-3.43 (m, 2H), 1.28 (s, 9H). $^1$HNMR (400 MHz, CHLOROFORM-d) δ 8.92 (s, 1H), 8.20 (d, J=7.8 Hz, 1H), 7.59-7.49 (m, 3H), 7.39 (t, J=7.4 Hz, 1H), 7.30 (d, J=8.5 Hz, 2H), 7.05 (t, J=7.4 Hz, 1H), 4.92 (t, J=5.5 Hz, 2H), 3.84 (t, J=5.6 Hz, 2H), 1.44 (s, 9H).

Example 95: (5-(2-((4-(trifluoromethyl)phenyl)amino)phenyl)-2H-tetrazol-2-yl)methane sulfonamide (Compound 101)

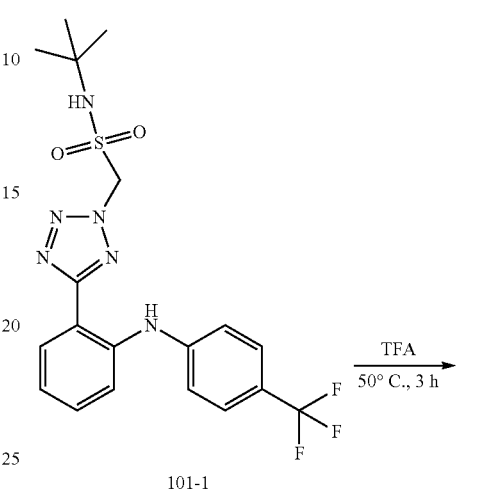

101-1

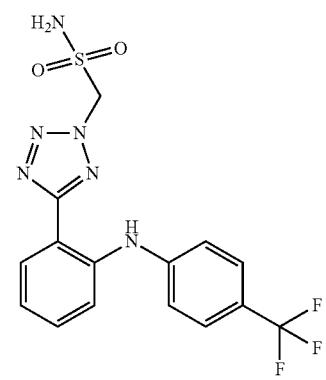

Compound 101

A mixture of 101-1 (30.0 mg, 66.0 umol, 1.00 eq) in TFA (4.6 g, 40.5 mmol, 3.0 mL, 613.8 eq) was stirred at 50° C. for 3 h. LCMS showed the reaction was complete. The mixture was concentrated under vacuum. The residue was checked by HPLC and purified by prep-HPLC (acidic_HCl condition) to provide the title compound (1.91 mg, 4.2 umol, 6.3% yield, HCl). LCMS (ESI): RT=1.253 min, mass calc. for $C_{15}H_{13}F_3N_6O_2S$ 398.08, m/z found 399.0 [M+H]$^+$. $^1$HNMR (400 MHz, DMSO-$d_6$) δ 8.68 (s, 1H), 8.10 (dd, J=1.5, 7.8 Hz, 1H), 7.61-7.48 (m, 6H), 7.25 (d, J=8.5 Hz, 2H), 7.20 (dt, J=1.1, 7.5 Hz, 1H), 6.18 (s, 2H).

Example 96: 2-[5-[2-[4-(trifluoromethyl)anilino]phenyl]tetrazol-2-yl]acetamide (Compound 102)

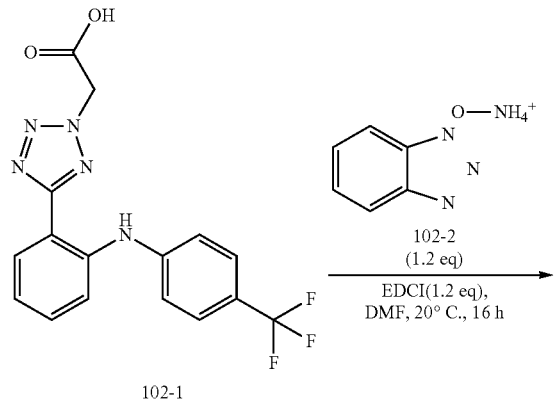

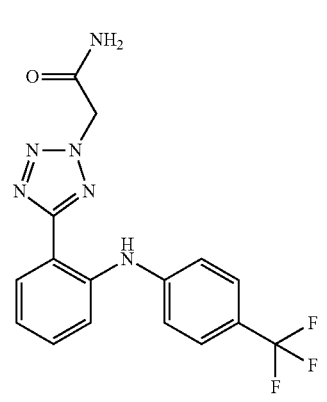

Compound 102

To a solution of 102-1 (30.0 mg, 82.6 umol, 1.0 eq) and 102-2 (12.6 mg, 82.6 umol, 1.0 eq) in DCM (5.0 mL) was added EDCI (17.4 mg, 90.8 umol, 1.1 eq). The resulting mixture was stirred at 20° C. for 16 hours. LCMS showed the desired compound was formed. The reaction mixture was concentrated under reduced pressure to give a residue. The crude product was purified by prep-HPLC to give the title compound (7.81 mg, 21.56 umol, 26.10% yield). LCMS (ESI): RT=0.800 min, mass calc. for $C_{16}H_{13}F_3N_6O$ 362.11, m/z found 363.0 [M+H]$^+$; $^1$HNMR (400 MHz, DMSO-d$_6$) δ 8.79 (s, 1H), 8.05 (d, J=7.8 Hz, 1H), 7.85 (s, 1H), 7.56 (t, J=7.9 Hz, 4H), 7.51-7.46 (m, 1H), 7.25 (d, J=8.5 Hz, 2H), 7.18 (t, J=7.4 Hz, 1H), 5.51 (s, 2H).

Example 97: 2-[5-[4-[4-(trifluoromethoxy)anilino]pyrimidin-5-yl]tetrazol-2-yl]ethanol (Compound 103)

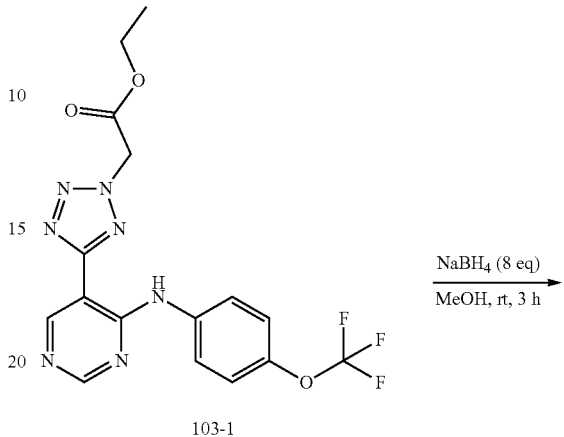

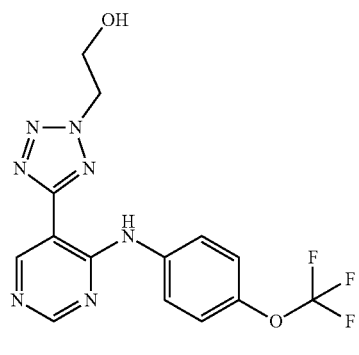

Compound 103

To a mixture of 103-1 (20 mg, 35 umol, 1.00 eq) in MeOH (2 mL) was stirred at 0° C. for 5 min. To the reaction mixture was added NaBH$_4$ (5.3 mg, 0.141 mmol, 4.00 eq) and the mixture stirred at 20° C. for 2 h. LCMS showed the starting material remained and no desired product MS was detected. To the reaction mixture was added additional NaBH$_4$ (5.3 mg, 0.141 mmol, 4.00 eq) and stirring continued for 1 h. LCMS showed 48% of starting material was remaining and 47% of desired product was detected. The reaction mixture was quenched by addition water (5 mL), and then concentrated under reduced pressure to remove MeOH and extracted with EtOAc (5 mL*3). The combined organic layers were dried with anhydrous Na$_2$SO$_4$, filtered, and concentrated under reduced pressure to give a residue. The residue was purified by prep-HPLC (HCl condition) to obtain the title compound (2.09 mg, 5.7 umol, 16.2% yield). LCMS (ESI): RT=2.571 min, mass calcd. for $C_{14}H_{12}F_3N_7O_2$ 367.10, m/z found 368.0[M+H]$^+$. $^1$H NMR (400 MHz, DMSO-d$_6$) δ10.10 (s, 1H), 9.02 (br s, 1H), 10.04-8.67 (m, 1H), 7.84 (d, J=8.80 Hz, 2H), 7.44 (br d, J=8.80 Hz, 2H), 4.88 (t, J=5.20 Hz, 2H), 4.02 (t, J=5.20 Hz, 2H).

Example 98: 1-tert-butyl-3-[2-[5-[2-[4-(trifluoromethyl)anilino]phenyl]tetrazol-2-yl]ethyl]urea (Compound 104)

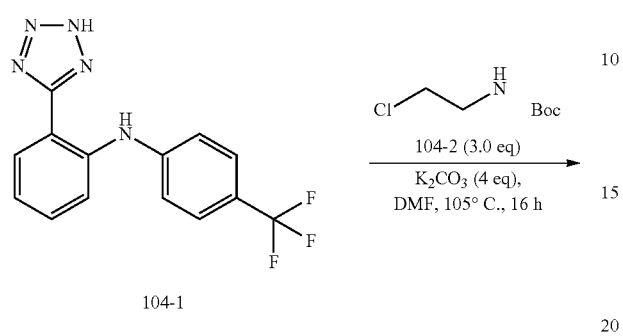

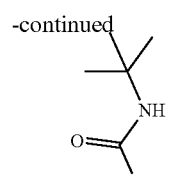
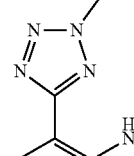
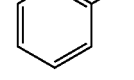

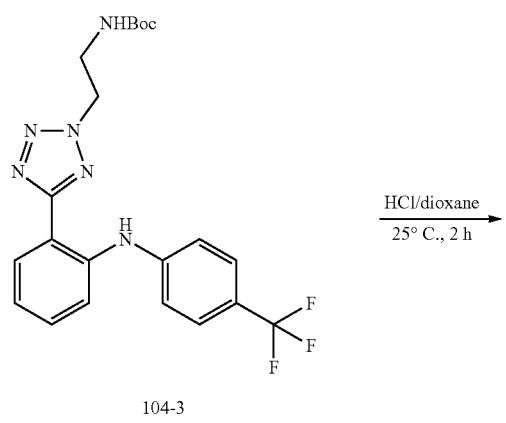

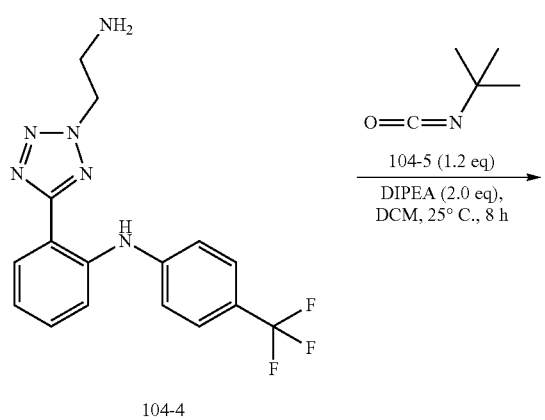

Step 1: tert-butyl N-[2-[5-[2-[4-(trifluoromethyl)anilino]phenyl]tetrazol-2-yl]ethyl]carbamate To a stirred mixture of 104-1 (300 mg, 0.878 mmol, 1.0 eq, HCl) and 104-2 (473 mg, 2.63 mmol, 3.0 eq) in DMF (6 mL) was added $K_2CO_3$ (485 mg, 3.51 mmol, 4.0 eq). The mixture was heated to 105° C. for 16 hr. LCMS showed 75% of the desired compound was formed and the starting material was consumed completely. The mixture was cooled. Water (15 mL) was added and the mixture extracted with ethyl acetate (3×15 mL). The combined organics were dried over magnesium sulfate, filtered, and concentrated to give a residue. The residue was purified by flash column chromatography to afford 104-3 (350 mg, 0.741 mmol, 84% yield). LCMS (ESI): RT=1.438 min, mass calc. for $C_{21}H_{23}F_3N_6O_2$ 448.18, m/z found 390.0 [M+H−56]$^+$.

Step 2: 2-[2-(2-aminoethyl)tetrazol-5-yl]-N-[4-(trifluoromethyl)phenyl]aniline

A solution of 104-3 (350 mg, 0.780 mmol, 1.0 eq) in HCl/dioxane (7 mL) was stirred at 25° C. for 2 hour. LCMS showed 94% of the desired compound was found and the starting material was consumed completely. The mixture was concentrated to give compound 104-4 (280 mg, 0.756 mmol, 97% yield) as a light yellow oil. The oil was directly used without further purification. LCMS (ESI): RT=0.702 min, mass calc. for $C_{16}H_{15}F_3N_6$ 348.13, m/z found 328.9 [M+H−20]$^+$.

Step 3: 1-tert-butyl-3-[2-[5-[2-[4-(trifluoromethyl)anilino]phenyl]tetrazol-2-yl]ethyl]urea To a solution of 104-4 (80 mg, 0.208 mmol, 1.0 eq, HCl) and DIPEA (54 mg, 0.416 mmol, 73 uL, 2.0 eq) in DCM (6 mL) was added compound 5 (25 mg, 0.249 mmol, 29 uL, 1.2 eq). The resulting mixture was stirred at 25° C. for 8 hour. LCMS showed 92% of the desired compound was found and the starting material was consumed completely. The reaction mixture was concentrated under reduced pressure to give a residue. The residue was purified by flash column chromatography to give Compound 104 (50 mg, 0.112 mmol, 54% yield). LCMS (ESI): RT=2.605 min, mass calc. for $C_{21}H_{24}F_3N_7O$ 447.20, m/z found 470.2 [M+23]$^+$; $^1$HNMR (400 MHz, CHLOROFORM-d) δ 8.96 (s, 1H), 8.17 (dd, J=1.5, 7.9 Hz, 1H), 7.55-7.46 (m, 3H), 7.40-7.33 (m, 1H), 7.28 (d, J=8.4 Hz, 2H), 7.07-6.98 (m, 1H), 4.84-4.76 (m, 2H), 4.49-4.31 (m, 1H), 4.11 (s, 1H), 3.88-3.79 (m, 2H), 1.27 (s, 9H).

Example 99: 1-[5-[2-[4-(trifluoromethyl)anilino]phenyl]tetrazol-2-yl]propan-2-ol (Compound 105)

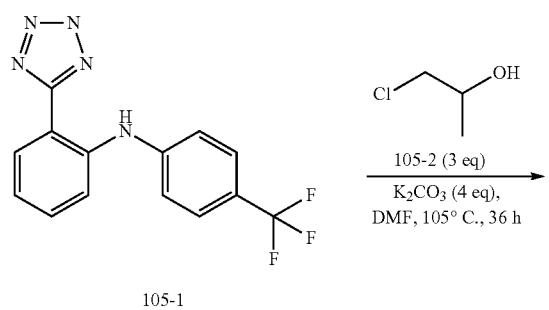

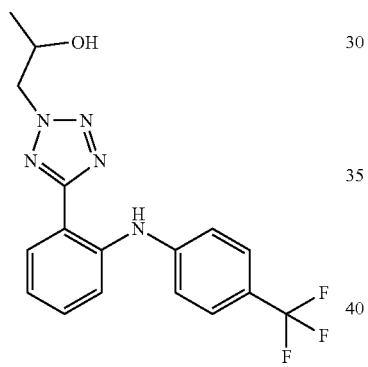

Compound 105

To a stirred solution of 105-1 (100 mg, 0.293 mmol, 1.0 eq, HCl) and $K_2CO_3$ (162 mg, 1.17 mmol, 4.0 eq) in DMF (3 mL) was 105-2 (83 mg, 0.878 mmol, 3.0 eq). The resulting mixture was heated to 105° C. for 36 hours. LCMS showed 56% of the desired compound was found and 39% of the starting material remained. The mixture was cooled. Water (10 mL) was added and the mixture extracted with ethyl acetate (3×10 mL). The combined organics were dried over $Na_2SO_4$, filtered, and concentrated to give a residue. The residue was purified by HPLC to give the title compound (40 mg, 0.107 mmol, 36% yield). LCMS (ESI): RT=2.485 min, mass calc. for $C_{17}H_{16}F_3N_5O$ 363.13, m/z found 364.2 [M+H]$^+$; $^1$HNMR (400 MHz, CHLOROFORM-d) δ 9.03 (s, 1H), 8.23-8.14 (m, 1H), 7.53 (dd, J=3.5, 8.3 Hz, 3H), 7.42-7.34 (m, 1H), 7.29 (d, J=8.5 Hz, 2H), 7.04 (t, J=7.5 Hz, 1H), 4.78-4.70 (m, 1H), 4.70-4.62 (m, 1H), 4.54-4.42 (m, 1H), 2.50 (d, J=4.8 Hz, 1H), 1.37 (d, J=6.3 Hz, 3H).

Example 100: 1-[5-[2-[4-(trifluoromethyl)anilino]phenyl]tetrazol-2-yl]propan-2-ol (Compound 106)

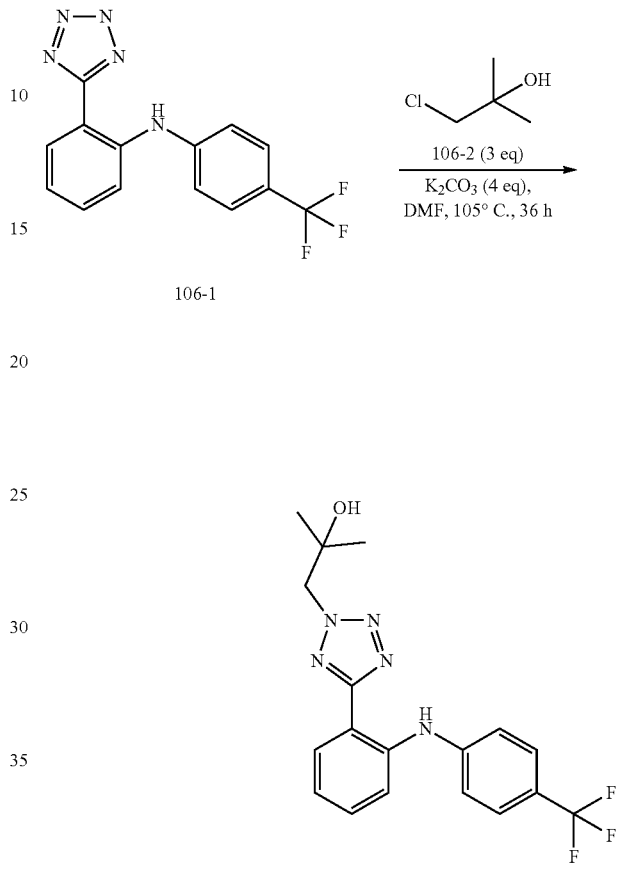

Compound 106

To a stirred solution of 106-1 (100 mg, 0.293 mmol, 1.0 eq, HCl) and $K_2CO_3$ (162 mg, 1.17 mmol, 4.0 eq) in DMF (3 mL) was added 106-2 (95 mg, 0.878 mmol, 90 uL, 3.0 eq). The resulting mixture was heated to 105° C. for 36 hours. LCMS showed 55% of the desired compound was found and 44% of the starting material remained. The mixture was cooled. Water (10 mL) was added and the mixture extracted with ethyl acetate (3×10 mL). The combined organics were dried over $Na_2SO_4$, filtered, and concentrated to give a residue. The residue was purified by purified by HPLC to give the title compound (25.00 mg, 66.25 umol, 22.64% yield). LCMS (ESI): RT=2.536 min, mass calc. for $C_{18}H_{18}F_3N_5O$ 377.15, m/z found 378.0 [M+H]$^+$; $^1$HNMR (400 MHz, CHLOROFORM-d) δ 9.06 (s, 1H), 8.20 (dd, J=1.4, 7.9 Hz, 1H), 7.54 (d, J=8.5 Hz, 3H), 7.42-7.35 (m, 1H), 7.29 (d, J=8.3 Hz, 2H), 7.08-7.00 (m, 1H), 4.71 (s, 2H), 2.64 (s, 1H), 1.32 (s, 6H).

Example 101: 2-[5-[2-[4-(trifluoromethyl)anilino]phenyl]tetrazol-2-yl]ethyl N-tert-butylcarbamate (Compound 107)

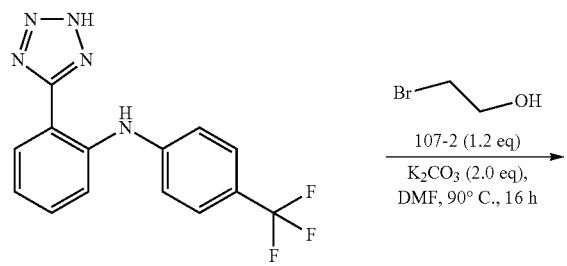

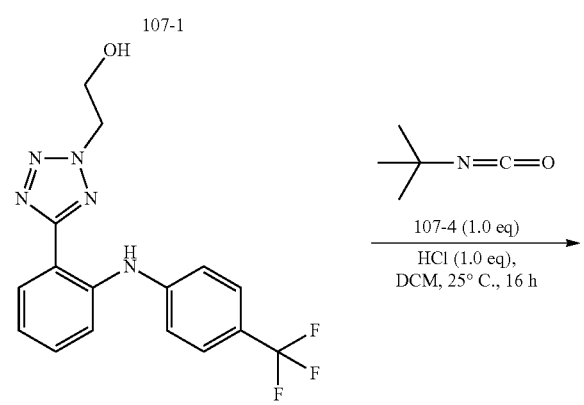

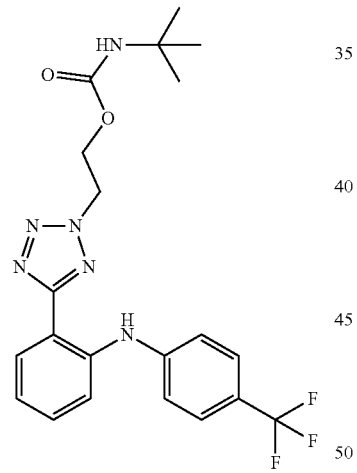

Compound 107

Step 1: 2-[5-[2-[4-(trifluoromethyl)anilino]phenyl]tetrazol-2-yl]ethanol

To a stirred solution of 107-1 (300 mg, 0.878 mmol, 1.0 eq, HCl salt) and K₂CO₃ (121 mg, 0.878 mmol, 1.0 eq) in DMF (6 mL) was added 107-2 (165 mg, 1.32 mmol, 94 uL, 1.5 eq). The resulting mixture was heated to 80° C. for 16 hour. LCMS showed 86% of the desired compound was found and the starting material was consumed completely. The mixture was cooled. Water (15 mL) was added and the mixture extracted with ethyl acetate (3×15 mL). The combined organics were dried over magnesium sulfate, filtered and concentrated to give a residue. The residue was purified by flash column chromatography to afford 107-3 (300 mg, 0.764 mmol, 87% yield) as a light yellow oil. LCMS (ESI): RT=1.288 min, mass calc. for $C_{16}H_{14}F_3N_5O$ 349.12, m/z found 349.9 [M+H]⁺.

Step 2: 2-[5-[2-[4-(trifluoromethyl)anilino]phenyl]tetrazol-2-yl]ethyl N-tert-butylcarbamate To a solution of 107-3 (100 mg, 0.258 mmol, 1.0 eq) and 107-4 (31 mg, 0.309 mmol, 36 uL, 1.2 eq) in DCM (4 mL) was added HCl (0.3 M, 9 uL, 1.0 eq). The mixture was stirred at 30° C. for 16 hours. LCMS showed 33% of the desired compound was found and 60% of the starting material remained. Water (8 ml) was added and the mixture extracted by DCM (3×10 mL). The combined organic layers were dried over Na₂SO₄, filtered, and concentrated under reduced pressure to give a residue. The residue was purified by flash column chromatography to give Compound 107 (30 mg, 67 mmol, 26% yield). LCMS (ESI): RT=2.286 min, mass calc. for $C_{21}H_{23}F_3N_6O_2$ 448.18, m/z found 449.0 [M+H]⁺; ¹HNMR (400 MHz, CHLOROFORM-d) δ 9.00 (s, 1H), 8.19 (d, J=7.9 Hz, 1H), 7.52 (dd, J=3.2, 8.5 Hz, 3H), 7.36 (t, J=7.8 Hz, 1H), 7.29 (d, J=8.4 Hz, 2H), 7.03 (t, J=7.5 Hz, 1H), 4.90 (s, 2H), 4.59 (s, 3H), 1.24 (s, 9H).

Example 102: 2-[5-[2-[4-(trifluoromethyl)anilino]phenyl]tetrazol-2-yl]ethylurea (Compound 108)

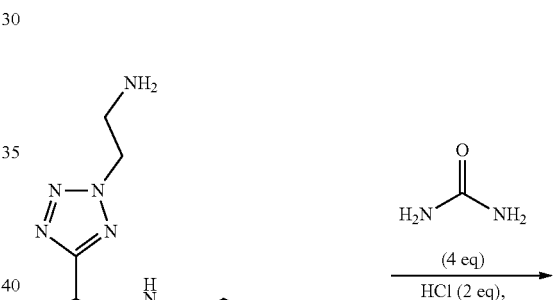

108-1

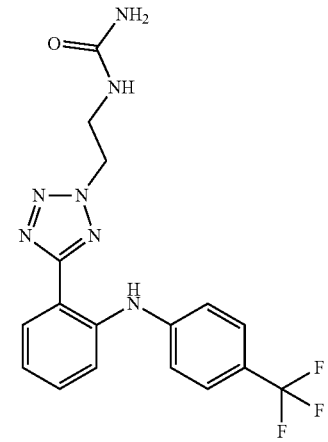

Compound 108

To a stirred solution of 108-1 (50 mg, 0.130 mmol, 1.0 eq, HCl) and urea (31 mg, 0.520 mmol, 28 uL, 4.0 eq) in H$_2$O (1.0 mL) was added HCl (9 mg, 0.260 mmol, 9 uL, 2.0 eq). The mixture was heated to 100° C. for 3 hour. LCMS showed 47% of the desired compound was found and the starting material was consumed completely. The mixture was cooled and extracted with DCM (3×4 mL). The combined organics were dried over Na$_2$SO$_4$, filtered, and concentrated to give a residue. The residue was purified by HPLC to give the title compound (23 mg, 59 mmol, 45% yield). LCMS (ESI): RT=2.222 min, mass calc. for C$_{17}$H$_{16}$F$_3$N$_7$O 391.14, m/z found 414.0[M+23]$^+$; $^1$HNMR (400 MHz, DMSO-d$_6$) δ 8.70 (s, 1H), 8.01 (dd, J=1.3, 7.7 Hz, 1H), 7.57-7.49 (m, 3H), 7.48-7.41 (m, 1H), 7.24 (d, J=8.6 Hz, 2H), 7.14 (t, J=7.1 Hz, 1H), 6.09 (t, J=6.0 Hz, 1H), 5.53 (s, 2H), 4.70 (t, J=5.6 Hz, 2H), 3.54 (q, J=6.0 Hz, 2H).

Example 103: N-(3-(5-(2-((4-(trifluoromethyl)phenyl)amino)phenyl)-2H-tetrazol-2-yl)propyl)methanesulfonamide (Compound 109)

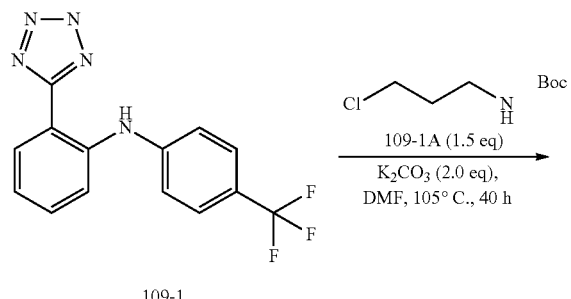

109-1

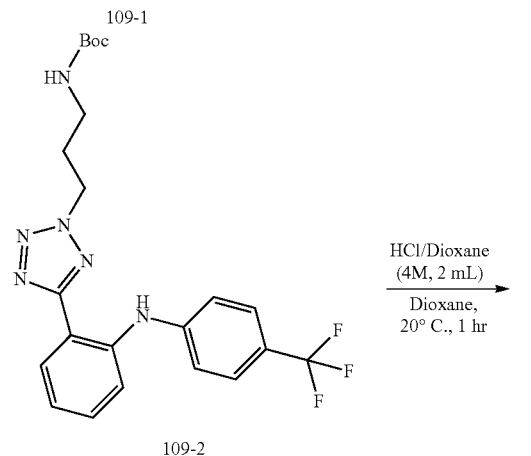

109-2

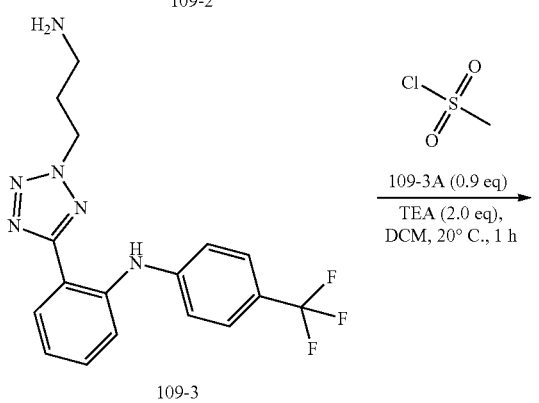

109-3

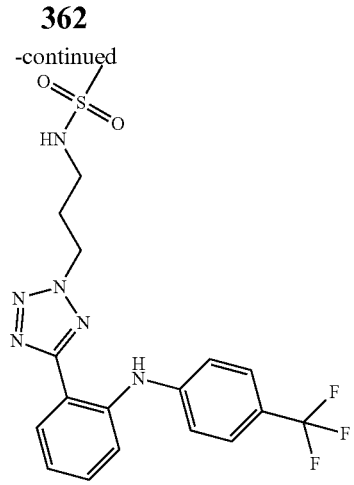

Compound 109

Step 1: tert-butyl (3-(5-(2-((4-(trifluoromethyl)phenyl)amino)phenyl)-2H-tetrazol-2-yl)propyl)carbamate To the solution of 109-1 (50 mg, 0.2 mmol, 1.0 eq) in DMF (5 mL) was added 109-1A (48 mg, 0.2 mmol, 1.5 eq) and K$_2$CO$_3$ (45. mg, 0.3 mmol, 2.0 eq). The mixture was stirred at 105° C. for 40 hr. The reaction was monitored by LCMS. The reaction solution was concentrated under reduced pressure. The residue was purified by column chromatography (SiO$_2$) to give 109-2 (99 mg, 0.2 mmol, 92.80% yield).

Step 2: 2-(2-(3-aminopropyl)-2H-tetrazol-5-yl)-N-(4-(trifluoromethyl)phenyl)aniline To a solution of 109-2 (99 mg, 0.2 mmol, 1.0 eq) in dioxane (3 mL) was added HCl/dioxane (4 M, 2.00 mL, 37 eq). The mixture was stirred at 20° C. for 1 hr. The reaction was monitored by LCMS. The reaction solution was concentrated under reduced pressure to give 109-3 (121 mg, crude, HCl) as yellow oil.

Step 3: N-(3-(5-(2-((4-(trifluoromethyl)phenyl)amino)phenyl)-2H-tetrazol-2-yl)propyl)methane Sulfonamide To a solution of 109-3 (121 mg, 0.3 mmol, 1.0 eq, HCl salt) in DCM (5 mL) was added TEA (610 mg, 0.6 mmol, 84 uL, 2.0 eq). The mixture was stirred for 5 min at 20° C., then MsCl (30 mg, 0.3 mmol, 20 uL, 0.9 eq) was added to the solution and followed by stirring for 1 hr at 20° C. The reaction was monitored by LCMS. The reaction solution was added dropwise into H$_2$O (15 mL). The mixture was extracted with DCM (10 mL*3). The combined organic layers were concentrated under reduced pressure. The residue was purified by Prep-HPLC to give Compound 109 (15.39 mg, 35.0 umol, 11.5% yield). LCMS (ESI): RT=1.308 min, mass calc. for C$_{18}$H$_{19}$F$_3$N$_6$O$_2$S 440.12, m/z found 463.0 [M+Na]$^+$, $^1$HNMR (400 MHz, DMSO-d$_6$) δ 8.76 (s, 1H), 8.07-8.01 (m, 1H), 7.57-7.47 (m, 4H), 7.25-7.13 (m, 4H), 4.80 (t, J=7.0 Hz, 2H), 3.08-3.00 (m, 2H), 2.90 (s, 3H), 2.20-2.10 (m, 2H).

Example 104: 4-[2-[2-(2-ureidoethyl)tetrazol-5-yl]anilino]benzoic Acid (Compound 110)

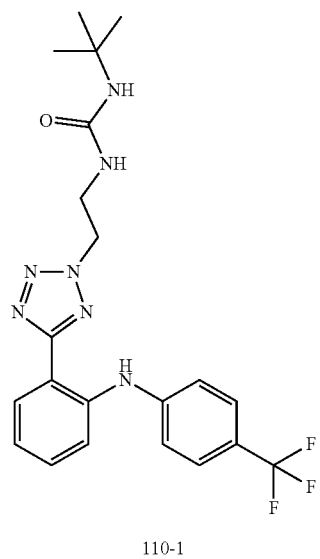

A solution of compound 110-1 (26 mg, 0.058 mmol, 1.0 eq) in TFA (1 mL) was stirred at 50° C. for 2 hour. The reaction was monitored by LCMS. The reaction mixture was concentrated under reduced pressure to give a residue. The residue product was purified by HPLC to give the title compound (4 mg, 0.011 mmol, 19% yield). LCMS (ESI): RT=1.692 min, mass calc. for $C_{17}H_{17}N_7O_3$ 367.14, m/z found 389.9 [M+23]$^+$; $^1$HNMR (400 MHz, DMSO-d$_6$) δ 12.82-12.01 (m, 1H), 8.80 (s, 1H), 8.06 (d, J=6.8 Hz, 1H), 7.83 (d, J=8.8 Hz, 2H), 7.61-7.54 (m, 1H), 7.53-7.44 (m, 1H), 7.25-7.13 (m, 3H), 6.19-6.07 (m, 1H), 5.57 (s, 2H), 4.75 (t, J=5.5 Hz, 2H), 3.68-3.52 (m, 2H).

Example 105: N-[3-[5-[2-[4-(trifluoromethyl)anilino]phenyl]tetrazol-2-yl]propyl]acetamide (Compound 111) and N-acetyl-N-[3-[5-[2-[4-(trifluoromethyl)anilino]phenyl]tetrazol-2-yl]propyl]acetamide (Compound 112)

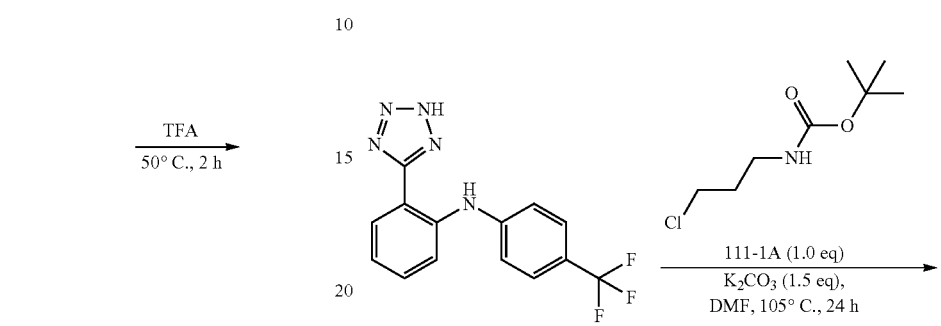

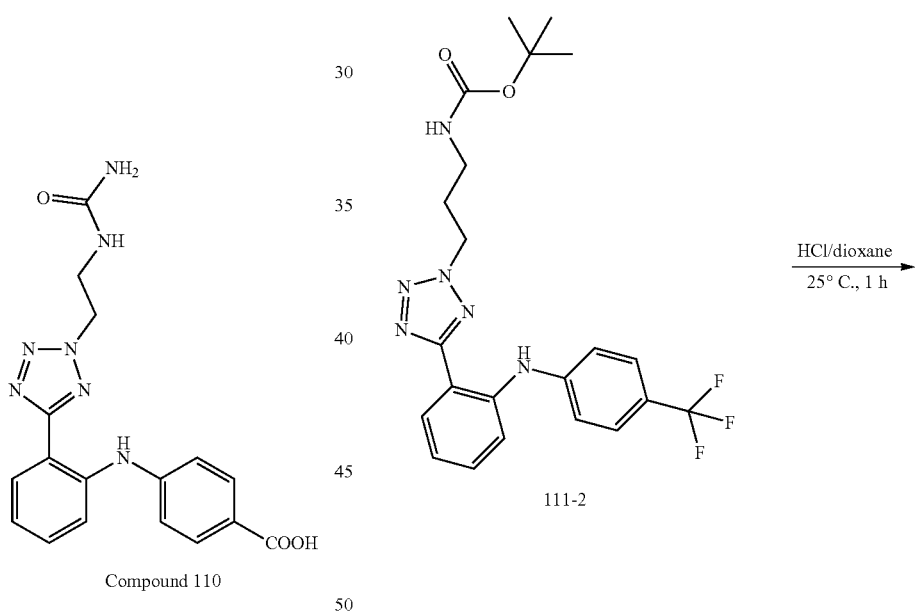

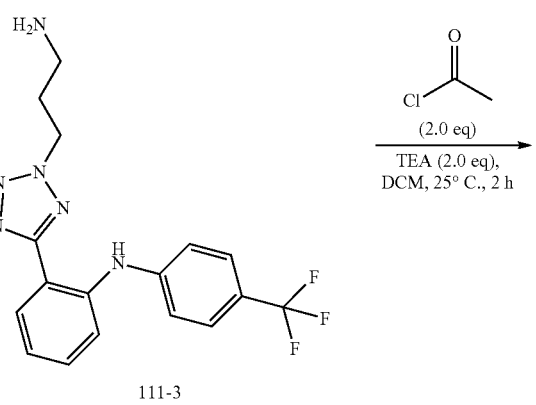

365

-continued

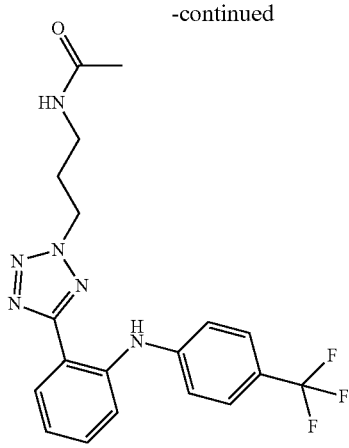

Compound 111

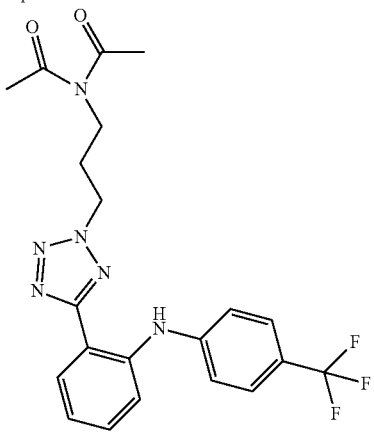

Compound 112

Step 1: tert-butyl N-[3-[5-[2-[4-(trifluoromethyl)anilino]phenyl]tetrazol-2-yl]propyl]carbamate To a solution of 111-1 (50.0 mg, 0.3 mmol, 1.0 eq) in DMF (2.0 mL) was added $K_2CO_3$ (53.5 mg, 0.4 mmol, 1.5 eq) and 111-1A (94.5 mg, 0.3 mmol, 1.2 eq). The mixture was stirred at 105° C. for 24 h. LC-MS showed 40% of 111-1 remained. Several new peaks were detected on LC-MS and 54% of the desired compound was detected. The reaction mixture was diluted with $H_2O$ (10 mL) and extracted with EtOAc (10 mL*3). The combined organic layers were washed with brine (10 mL*3), dried over $Na_2SO_4$, filtered, and concentrated under reduced pressure to give a residue. The residue was purified by column chromatography to provide 111-2 (110.0 mg, 237.85 umol, 92% yield). LCMS (ESI): RT=0.940 min, mass calc. for $C_{22}H_{25}F_3N_6O$ 462.20, m/z found 407.1 [M−tBu+H]$^+$.

Step 2: 2-[2-(3-aminopropyl)tetrazol-5-yl]-N-[4-(trifluoromethyl)phenyl]aniline To a solution of 111-2 (110.0 mg, 0.2 mmol, 1.0 eq) in dioxane (1.0 mL) was added HCl/dioxane (3.0 mL). The mixture was stirred at 25° C. for 1 h. LC-MS showed 111-2

366 was consumed completely and 97% of the desired compound was detected. The reaction mixture was concentrated under reduced pressure to give 111-3 (100.0 mg, crude). LCMS (ESI): RT=0.713 min, mass calc. for $C_{17}H_{17}F_3N_6$ 362.15, m/z found 342.9 [M−F+H]$^+$.

Step 3: N-[3-[5-[2-[4-(trifluoromethyl)anilino]phenyl]tetrazol-2-yl]propyl]acetamide and N-acetyl-N-[3-[5-[2-[4-(trifluoromethyl)anilino]phenyl]tetrazol-2-yl]propyl]acetamide To a solution of 111-3 (90.0 mg, 0.2 mmol, 1.0 eq) in DCM (5.0 mL) was added TEA (50.2 mg, 0.5 mmol, 68.8 uL, 2.0 eq) and acetyl chloride (29.2 mg, 0.4 mmol, 26.6 uL, 1.5 eq). The mixture was stirred at 25° C. for 3 h. LC-MS showed 111-3 was consumed completely. Several new peaks were shown on LC-MS, and 51% of Compound 111 and 36% of Compound 112 was detected. The residue was purified by prep-HPLC to give Compound 111 (18.68 mg, 46.19 umol, 18% yield) and Compound 112 (6.81 mg, 15.10 umol, 6% yield).

Compound 111: LCMS (ESI): RT=1.772 min, mass calc. for $C_{19}H_{19}F_3N_6O$ 404.16, m/z found 427.0 [M+Na]$^+$; (400 MHz, DCCl$_3$) δ (ppm) 9.00 (s, 1H), 8.19-8.17 (m, J=1.4, 7.9 Hz, 1H), 7.55-7.51 (m, J=5.0, 8.0 Hz, 3H), 7.41-7.35 (m, 1H), 7.30 (d, J=8.3 Hz, 2H), 7.05 (t, J=7.5 Hz, 1H), 5.76 (s, 1H), 4.77 (t, J=6.8 Hz, 2H), 3.35 (q, J=6.5 Hz, 2H), 2.31 (quin, J=6.7 Hz, 2H), 1.99 (s, 3H).

Compound 112: LCMS (ESI): RT=1.363 min, mass calc. for $C_{21}H_{21}F_3N_6O_2$ 446.42, m/z found 469.0 [M+Na]$^+$; (400 MHz, DCCl$_3$) δ (ppm) 8.43 (s, 1H), 7.63 (s, 2H), 7.54-7.44 (m, 2H), 7.40 (s, 1H), 7.31 (s, 2H), 6.32 (s, 1H), 4.76-4.60 (m, 2H), 3.01 (s, 1H), 2.75 (s, 1H), 2.27-2.06 (m, 2H), 1.97 (s, 6H).

Example 106: 2-[5-[2-[4-(trifluoromethyl)anilino]phenyl]tetrazol-2-yl]ethanehydroxamic acid (Compound 113)

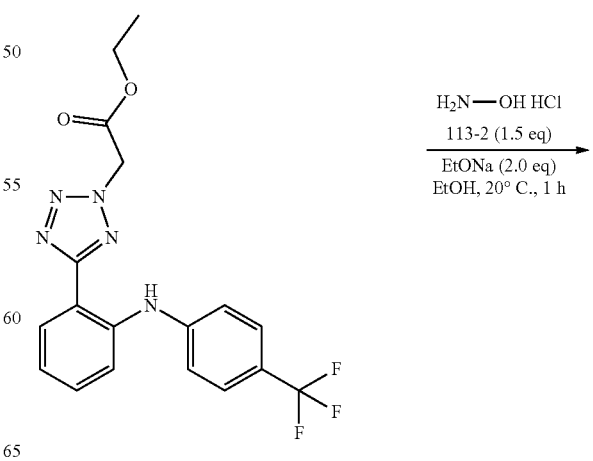

113-1

-continued

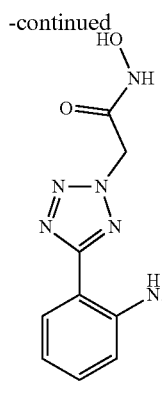

Compound 113

To a solution of 113-1 (50.0 mg, 0.13 mmol, 1.0 eq) and 113-2 (13.3 mg, 0.19 mmol, 1.5 eq, HCl) in EtOH (3.0 mL) was added EtONa (17.4 mg, 0.26 mmol, 2.0 eq). The resulting mixture was stirred at 20° C. for 1 hour. LCMS showed the desired compound was formed. The reaction was acidified by adding 1M HCl (3 mL) and filtered to give a crude product. The crude product was purified by prep-HPLC to give the title compound (15.66 mg, 41.39 umol, 32.40% yield). LCMS (ESI): RT=0.787 min, mass calc. for $C_{16}H_{13}F_3N_6O_2$ 378.11, m/z found 379.0[M+H]$^+$; $^1$HNMR (400 MHz, DMSO-$d_6$) δ 11.13 (s, 1H), 9.31 (s, 1H), 8.79 (s, 1H), 8.04 (dd, J=1.3, 8.0 Hz, 1H), 7.59-7.54 (m, 3H), 7.52-7.47 (m, 1H), 7.26 (d, J=8.3 Hz, 2H), 7.18 (t, J=7.4 Hz, 1H), 5.44 (s, 2H).

Example 107: 3-(5-(2-((4-(trifluoromethyl)phenyl) amino)phenyl)-2H-tetrazol-2-yl)propane-1,2-diol (Compound 114)

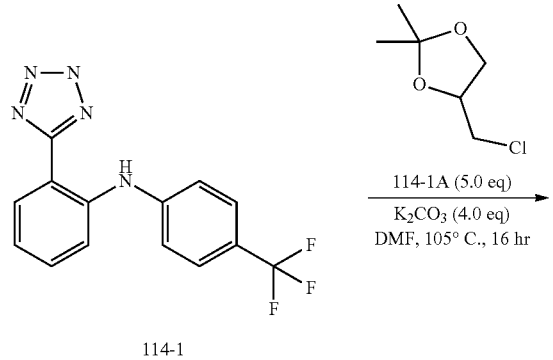

-continued

114-2

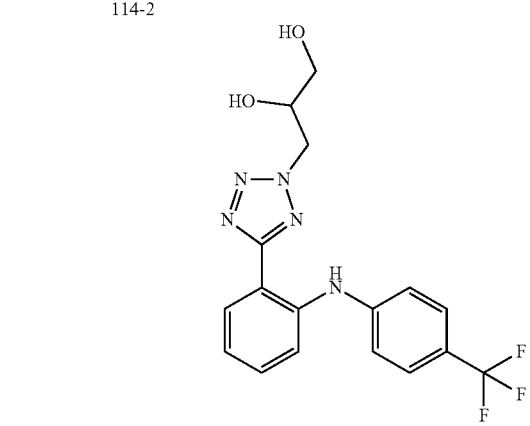

Compound 114

Step 1: 2-(2-((2,2-dimethyl-1,3-dioxolan-4-yl) methyl)-2H-tetrazol-5-yl)-N-(4-(trifluoromethyl) phenyl)aniline To the solution of 114-1 (300 mg, 1.0 mmol, 1.0 eq) in DMF (5 mL) was added 114-1A (740 mg, 5.0 mmol, 698 uL, 5.0 eq) and K$_2$CO$_3$ (543 mg, 3.9 mmol, 4.0 eq). The solution was stirred for 16 hr at 105° C. The reaction was monitored by LCMS. The reaction solution was concentrated under reduced pressure. The residue was purified by column chromatography (SiO$_2$) to give 114-2 (41 mg, 98 umol, 10% yield).

Step 2: 3-(5-(2-((4-(trifluoromethyl)phenyl)amino) phenyl)-2H-tetrazol-2-yl)propane-1,2-diol To the solution of 114-2 (20 mg, 48 umol, 1.0 eq) in MeOH (4 mL) was added HCl (20 mg, 0.6 mmol, 20 uL, 12 eq). The mixture was stirred at 20° C. for 2 hr. The reaction was monitored by LCMS. The reaction solution was concentrated under reduced pressure. The residue was purified by Prep-HPLC to give Compound 114 (7.86 mg, 20.7 umol, 43.45% yield). LCMS (ESI): RT=0.803 min, mass calc. for $C_{17}H_{16}F_3N_5O_2$ 379.13, m/z found 380.0 [M+H]$^+$, $^1$HNMR (400 MHz, CHLOROFORM-d) δ 8.18 (d, J=7.5 Hz, 1H), 7.59-7.50 (m, 3H), 7.39 (t, J=7.3 Hz, 1H), 7.32-7.28 (m, 2H), 7.05 (t, J=7.4 Hz, 1H), 4.93-4.77 (m, 2H), 4.47-4.35 (m, 1H), 3.92-3.65 (m, 2H).

Example 108: 2-(2-((2,2-dimethyl-1,3-dioxolan-4-yl)methyl)-2H-tetrazol-5-yl)-N-(4-(trifluoromethyl)phenyl)aniline (Compound 115)

Example 109: ethyl 2-[5-[2-[4-(trifluoromethyl)anilino]phenyl]tetrazol-2-yl]propanoate (Compound 116)

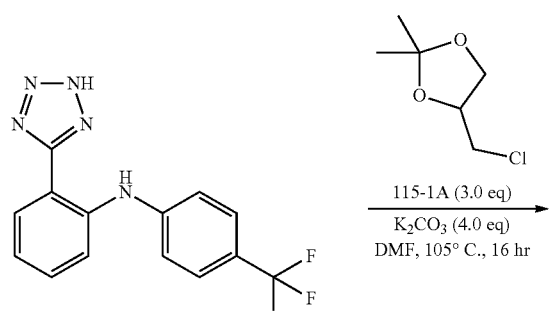

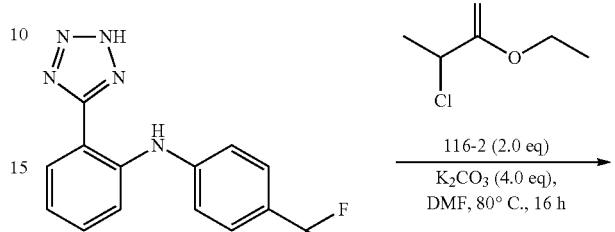

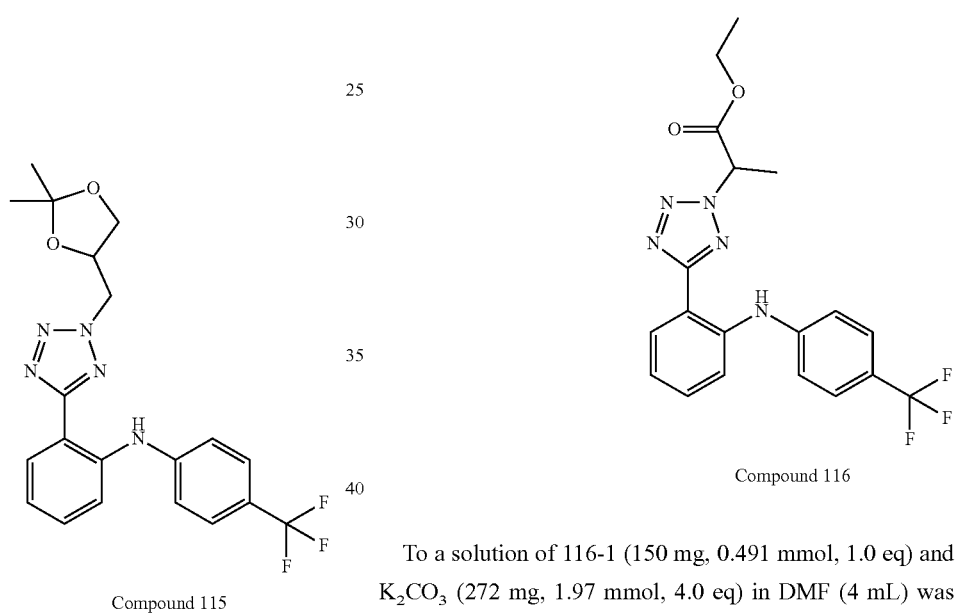

To the solution of 115-1 (100 mg, 0.3 mmol, 1.0 eq) in DMF (5 mL) was added 115-1A (148 mg, 1.0 mmol, 140 uL, 3.0 eq) and $K_2CO_3$ (181 mg, 1.3 mmol, 4.0 eq). The solution was stirred for 16 hr at 105° C. The reaction was monitored by LCMS. The reaction solution was concentrated under reduced pressure. The residue was purified by column chromatography ($SiO_2$) and then purified by Prep-HPLC to give the title compound (8.51 mg, 20.3 umol, 6.2% yield). LCMS (ESI): RT=0.939 min, mass calc. for $C_{20}H_{20}F_3N_5O_2$ 419.16, m/z found 420.0 [M+H]$^+$, $^1$HNMR (400 MHz, CHLOROFORM-d) δ 9.01 (s, 1H), 8.22-8.17 (m, 1H), 7.57-7.50 (m, 3H), 7.38 (t, J=7.8 Hz, 1H), 7.32-7.26 (m, 2H), 7.04 (t, J=7.2 Hz, 1H), 4.89-4.77 (m, 1H), 4.77-4.66 (m, 2H), 4.20-4.14 (m, 1H), 4.07-4.00 (m, 1H), 1.43 (s, 3H), 1.35 (s, 3H).

To a solution of 116-1 (150 mg, 0.491 mmol, 1.0 eq) and $K_2CO_3$ (272 mg, 1.97 mmol, 4.0 eq) in DMF (4 mL) was 116-2 (120 mg, 0.983 mmol, 106 uL, 2.0 eq). The resulting mixture was stirred at 100° C. for 16 hours. LCMS showed 79% desired compound was found and the starting material was consumed completely. Water (10 mL) was added and the mixture extracted with ethyl acetate (3×10 mL). The combined organics were dried over $Na_2SO_4$, filtered, and concentrated to give a residue. The residue was purified by flash column chromatography to afford the product (180 mg, 0.404 mmol, 82% yield). 80 mg of the product was purified by HPLC to give the title compound (28.39 mg). LCMS (ESI): RT=0.956 min, mass calc. for $C_{19}H_{18}F_3N_5O_2$ 405.14, m/z found 406.1 [M+H]$^+$; $^1$HNMR (400 MHz, CHLOROFORM-d) δ 9.02 (s, 1H), 8.23 (dd, J=1.3, 7.8 Hz, 1H), 7.54 (d, J=8.5 Hz, 3H), 7.44-7.35 (m, 1H), 7.29 (d, J=8.3 Hz, 2H), 7.05 (t, J=7.5 Hz, 1H), 5.70 (q, J=7.4 Hz, 1H), 4.25 (q, J=7.3 Hz, 2H), 2.05 (d, J=7.3 Hz, 3H), 1.25 (t, J=7.2 Hz, 3H).

Example 110: 2-[2-(2-fluoroethyl)tetrazol-5-yl]-N-[4-(trifluoromethyl)phenyl]aniline (Compound 117)

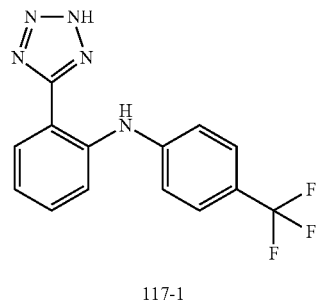

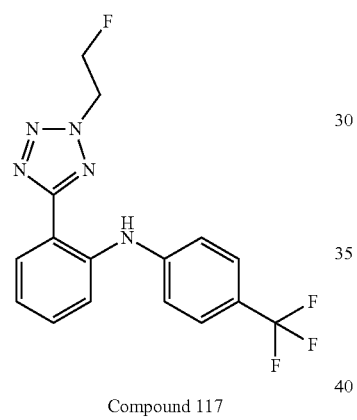

Compound 117

To a stirred solution of 117-1 (50 mg, 0.146 mmol, 1.0 eq, HCl) and K$_2$CO$_3$ (51 mg, 0.366 mmol, 2.5 eq) in DMF (2 mL) was added 117-2 (19 mg, 0.146 mmol, 1.0 eq). The resulting mixture was heated to 80° C. for 16 hours. LCMS showed 39% desired compound was formed and the starting material was consumed completely. The mixture was cooled. Water (10 mL) was added and the mixture extracted with ethyl acetate (3×10 mL). The combined organics were dried over Na$_2$SO$_4$, filtered and concentrated to give a residue. The residue was purified by purified by HPLC to give the title compound (15 mg, 42.7 umol, 29% yield). LCMS (ESI): RT=2.716 min, mass calc. for C$_{16}$H$_{13}$F$_4$N$_5$ 351.11, m/z found 352.0 [M+H]$^+$; $^1$HNMR (400 MHz, CHLOROFORM-d) δ 9.01 (s, 1H), 8.21 (dd, J=1.4, 7.9 Hz, 1H), 7.54 (dd, J=2.5, 8.5 Hz, 3H), 7.43-7.34 (m, 1H), 7.30 (d, J=8.5 Hz, 2H), 7.09-7.00 (m, 1H), 5.11-5.01 (m, 2H), 5.01-4.93 (m, 2H).

Example 111: N-[[5-[2-[4-(trifluoromethyl)anilino]phenyl]tetrazol-2-yl]methylsulfonyl]acetamide (Compound 118)

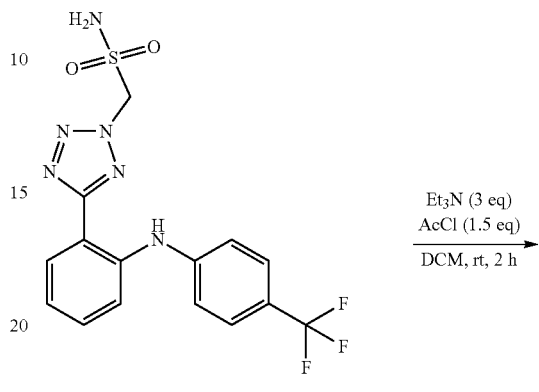

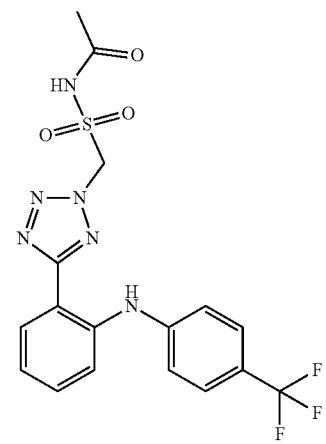

Compound 118

To a solution of 118-1 (100 mg, 0.25 mmol, 1.00 eq) and Et$_3$N (76 mg, 0.75 mmol, 0.1 mL, 3.00 eq) in DCM (5 mL) was added acetyl chloride (29.6 mg, 0.38 mmol, 26.87 uL, 1.50 eq). The reaction was stirred at 25° C. for 16 hr. LCMS showed that the desired MS signal was detected. The reaction was then concentrated. The reaction was purified by Prep.HPLC (HCl condition) to give the initial title compound (10 mg) and was then further re-purified by Prep.HPLC (basic conditions) to give the title compound (2.30 mg, 5.22 umol, 2.08% yield). $^1$HNMR and LCMS confirmed that desired product was obtained. LCMS (ESI): RT=0.843 min, mass calcd. for C$_{17}$H$_{15}$F$_3$N$_6$O$_3$S, 440.09 m/z found 441.0[M+H]$^+$. $^1$HNMR (400 MHz, DMSO-d$_6$) δ8.87 (s, 1H), 8.08 (d, J=8.8 Hz, 1H), 7.70-7.60 (m, 3H), 7.55-7.45 (m, 1H), 7.31 (d, J=8.0 Hz, 2H), 7.18 (d, J=8.0 Hz, 1H), 7.15 (br, 1H), 5.99 (s, 2H), 1.71 (s, 3H).

Example 112: 2-(2-(tetrahydrofuran-3-yl)-2H-tetrazol-5-yl)-N-(4-(trifluoromethyl)phenyl) Aniline (Compound 119)

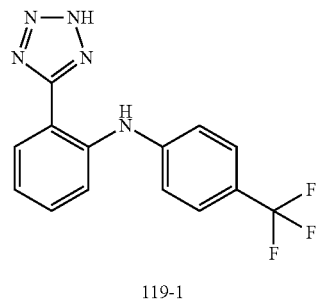 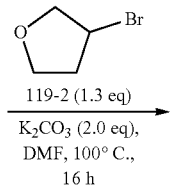

119-1

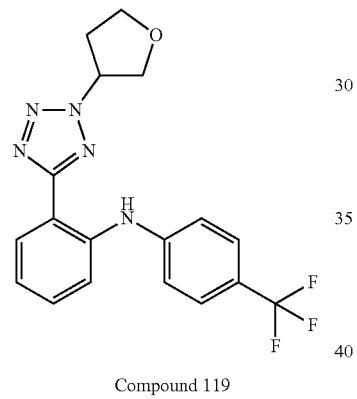

Compound 119

To a solution of 119-1 (50 mg, 0.16 mmol, 1.00 eq) and 119-2 (32.2 mg, 0.21 mmol, 1.30 eq) in DMF (3 mL) was added K$_2$CO$_3$ (45.3 mg, 0.33 mmol, 2.00 eq). The reaction was heated to 100° C. for 16 hr. LCMS showed that ~80% of desired MS signal was detected. The reaction was diluted with EtOAc (20 mL) and washed with brine (2*10 mL). The organic layer was dried over Na$_2$SO$_4$ and concentrated. The crude product was purified by Prep.HPLC (acidic conditions) to give the title compound (17.36 mg, 46.25 umol, 28.24% yield). $^1$HNMR and LCMS confirmed that the desired product was obtained. LCMS (ESI): RT=0.910 min, mass calc. for C$_{18}$H$_{16}$F$_3$N$_5$O 375.13, m/z found 376.0[M+H]$^+$; $^1$HNMR (400 MHz, CDCl$_3$) δ 9.05 (s, 1H), 8.21 (dd, J=8.0, 1.6 Hz, 1H), 7.60-7.50 (m, 3H), 7.40-7.35 (m, 1H), 7.29 (d, J=8.4 Hz, 2H), 7.05 (t, J=8.0 Hz, 1H), 5.65-5.50 (m, 1H), 4.40-4.25 (m, 3H), 4.15-4.00 (m, 1H), 2.80-2.65 (m, 1H), 2.65-2.50 (m, 1H).

Example 113: 2-(2-tetrahydropyran-3-yltetrazol-5-yl)-N-[4-(trifluoromethyl)phenyl]aniline (Compound 120)

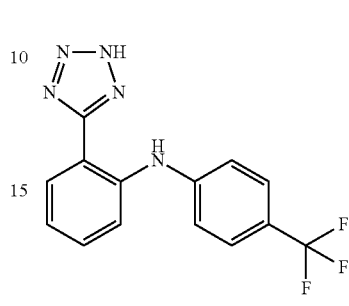 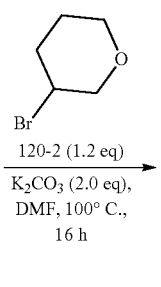

120-1

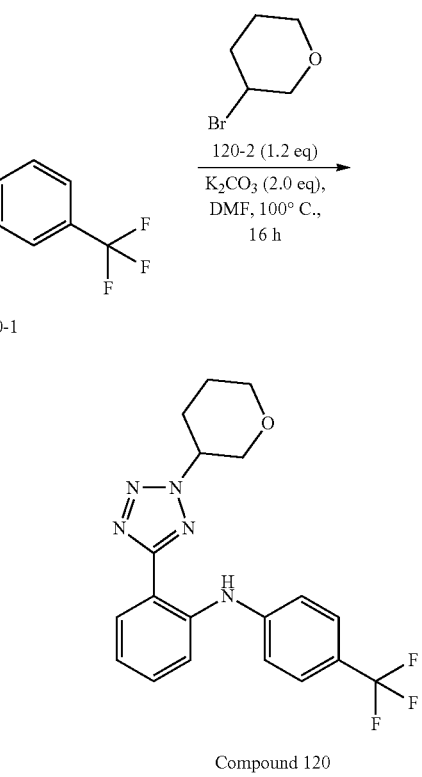

Compound 120

To a solution of 120-1 (50 mg, 0.16 mmol, 1.00 eq) and 120-2 (35 mg, 0.21 mmol, 1.30 eq) in DMF (3 mL) was added K$_2$CO$_3$ (45.37 mg, 0.33 mmol, 2.00 eq). The reaction was heated at 100° C. for 16 hr. LCMS showed that only starting material was present. The reaction was heated to 150° C. for 1 hr under microwave conditions. LCMS showed that about 20% of the desired MS signal was detected. The reaction was continued with stirring at 150° C. for 3 hr. LCMS showed that 30% of the desired MS signal was detected. The reaction was diluted with EtOAc (20 mL) and washed with brine (2*10 mL). The organic layer was dried over Na$_2$SO$_4$ and concentrated. The residue was purified by Prep.HPLC (base) to give the title compound (8.72 mg, 22.40 umol, 13.67% yield). LCMS (ESI): RT=0.946 min, mass calc. for C$_{19}$H$_{18}$F$_3$N$_5$O 389.15, m/z found 390.1 [M+H]$^+$; $^1$HNMR (400 MHz, CDCl$_3$-d) δ 9.08 (s, 1H), 8.20 (d, J=8.4 Hz, 1H), 7.65-7.50 (m, 3H), 7.40-7.35 (m, 1H), 7.30 (d, J=7.6 Hz, 2H), 7.05 (t, J=8.0 Hz, 1H), 5.00-4.85 (m, 1H), 4.35-4.25 (m, 1H), 4.05-3.90 (m, 2H), 3.70-3.55 (m, 1H), 2.50-2.35 (m, 2H), 2.05-1.90 (m, 2H).

Example 114: 1-cyclopropyl-2-[5-[2-[4-(trifluoromethyl)anilino]phenyl]tetrazol-2-yl]ethanone (Compound 121)

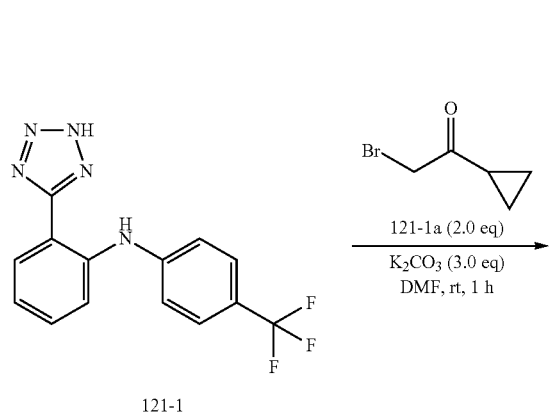

121-1

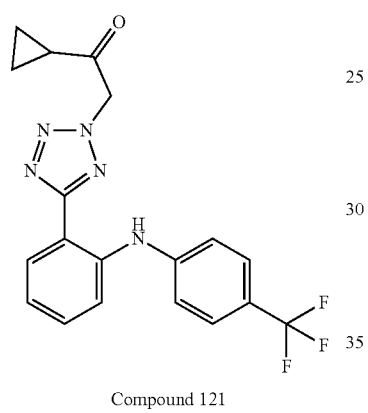

Compound 121

To a mixture of 121-1 (60 mg, 0.197 mmol, 1.00 eq) and 121-1a (64 mg, 0.393 mmol, 2.00 eq) in DMF (2 mL) was added K₂CO₃ (82 mg, 0.590 mmol, 3.00 eq) in one portion at 10° C. under N₂. The mixture was stirred at 10° C. for 1 hour. TLC showed the starting material was consumed completely and many new spot were formed. LCMS showed one main peak with the desired MS was detected. The reaction mixture was diluted with H₂O (20 mL) and extracted with EtOAc (20 mL*3). The combined organic layers were washed with brine (40 mL*3), dried with anhydrous Na₂SO₄, filtered, and concentrated under vacuum. The residue was purified by prep-HPLC (basic condition) to provide the title compound (36.66 mg, 94 umol, 48.2% yield). LCMS (ESI): RT=0.920 min, mass calcd. for $C_{19}H_{16}F_3N_5O$ 387.13, m/z found 388.0[M+H]⁺. ¹HNMR (400 MHz, CHLOROFORM-d) δ8.97 (s, 1H), 8.21 (dd, J=7.60, 1.20 Hz, 1H), 7.57-7.51 (m, 3H), 7.42-7.35 (m, 1H), 7.30 (d, J=8.80 Hz, 2H), 7.04 (t, J=7.60 Hz, 1H), 5.69 (s, 2H), 1.97-1.88 (m, 1H), 1.26 (t, J=4.00 Hz, 2H), 1.1-1.07 (m, 2H).

Example 115: 2-(2-tetrahydropyran-4-yltetrazol-5-yl)-N-[4-(trifluoromethyl)phenyl]aniline (Compound 122)

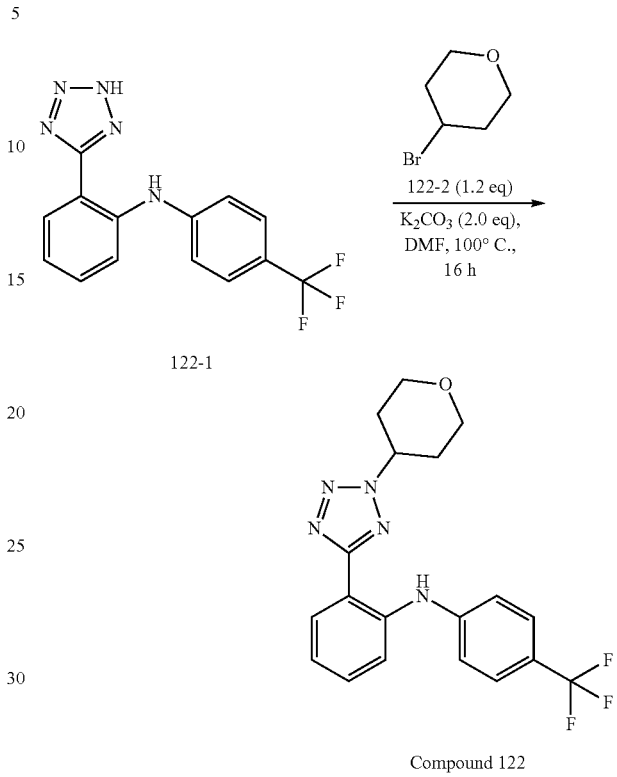

To a solution of 122-1 (50.0 mg, 0.16 mmol, 1.0 eq) in DMF (5.0 mL) was added K₂CO₃ (45.23 mg, 0.33 mmol, 2.0 eq) and 122-2 (32.4 mg, 0.120 mmol, 1.2 eq). The mixture was stirred at 100° C. for 24 hours under an N₂ atmosphere. LCMS showed the desired compound was formed. The reaction was filtered to give a crude product. The crude product was purified by prep-HPLC to give the title compound (27.33 mg, 70.19 umol, 42.85% yield). LCMS (ESI): RT=0.932 min, mass calc. for $C_{19}H_{18}F_3N_5O$ 389.15, m/z found 390.0[M+H]⁺; ¹HNMR (400 MHz, CDCl₃-d) δ 9.08 (s, 1H), 8.21 (dd, J=1.4, 7.9 Hz, 1H), 7.54 (d, J=8.5 Hz, 3H), 7.41-7.35 (m, 1H), 7.29 (d, J=8.5 Hz, 2H), 7.05 (t, J=7.3 Hz, 1H), 5.07-4.95 (m, 1H), 4.16 (td, J=3.3, 12.0 Hz, 2H), 3.64 (dt, J=2.3, 11.5 Hz, 2H), 2.46-2.24 (m, 4H).

Example 116: 2-[2-(oxetan-3-yl)tetrazol-5-yl]-N-[4-(trifluoromethyl)phenyl]aniline (Compound 123)

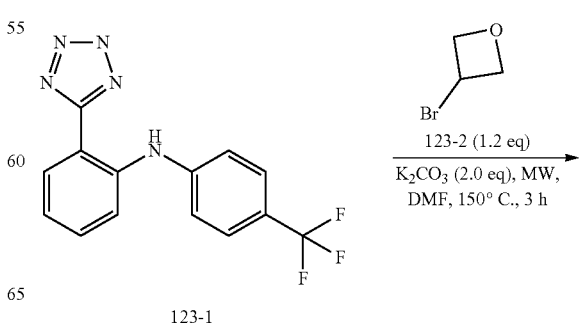

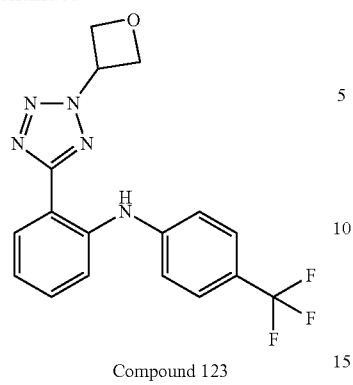

Compound 123

123-1 (50.0 mg, 0.16 mmol, 1.0 eq), 123-2 (26.9 mg, 0.20 mmol, 1.2 eq) and K₂CO₃ (45.3 mg, 0.33 mmol, 2.0 eq) were taken up into a microwave tube in DMF (2.0 mL). The sealed tube was heated at 150° C. for 3 hours under microwave conditions. LCMS showed the desired compound was formed. The reaction was filtered to give a crude product. The crude product was purified by prep-HPLC to give the title compound (2.57 mg, 6.46 umol, 3.94% yield, HCl). LCMS (ESI): RT=0.890 min, mass calc. for $C_{17}H_{14}F_3N_5O$ 361.12, m/z found 362.0[M+H]⁺; ¹HNMR (400 MHz, CDCl₃-d) δ 9.01 (s, 1H), 8.25 (dd, J=1.5, 7.9 Hz, 1H), 7.55 (d, J=8.4 Hz, 3H), 7.41 (dt, J=1.5, 7.8 Hz, 1H), 7.31 (d, J=8.6 Hz, 2H), 7.10-7.05 (m, 1H), 6.15-6.07 (m, 1H), 5.31-5.25 (m, 2H), 5.24-5.19 (m, 2H).

Example 117: 2-[5-[2-[4-(trifluoromethyl)anilino]phenyl]tetrazol-2-yl]ethyl carbamate (Compound 124)

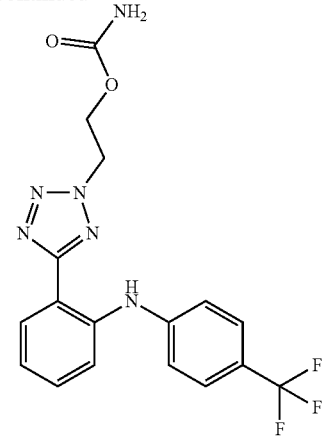

Compound 124

To a stirred solution of 124-1 (50 mg, 0.143 mmol, 1.0 eq) in DMA (100 uL) was added 124-1a (69 mg, 1.15 mmol, 8.0 eq). The resulting mixture was heated to 165° C. for 5 hour. LCMS and TLC (Petroleum ether:Ethyl acetate=3/1) showed the desired compound was formed and the starting material remained. The mixture was cooled. Water (15 mL) was added and the mixture extracted with ethyl acetate (3×15 mL). The combined organics were dried over magnesium sulfate, filtered and concentrated to give a residue. The residue was purified by HPLC to give the title compound (10 mg, 25.49 umol, 18% yield). LCMS (ESI): RT=0.834 min, mass calc. for $C_{17}H_{15}F_3N_6O_2$ 392.12, m/z found 393.1[M+H]⁺; ¹HNMR (400 MHz, CHLOROFORM-d) δ 9.00 (s, 1H), 8.21 (dd, J=1.4, 7.9 Hz, 1H), 7.53 (dd, J=3.5, 8.3 Hz, 3H), 7.38 (t, J=7.2 Hz, 1H), 7.30 (d, J=8.5 Hz, 2H), 7.05 (t, J=7.2 Hz, 1H), 4.96 (t, J=5.1 Hz, 2H), 4.76-4.51 (m, 4H).

Example 118: 2-[5-[2-[4-(trifluoromethyl)anilino]phenyl]tetrazol-2-yl]propan-1-ol (Compound 125)

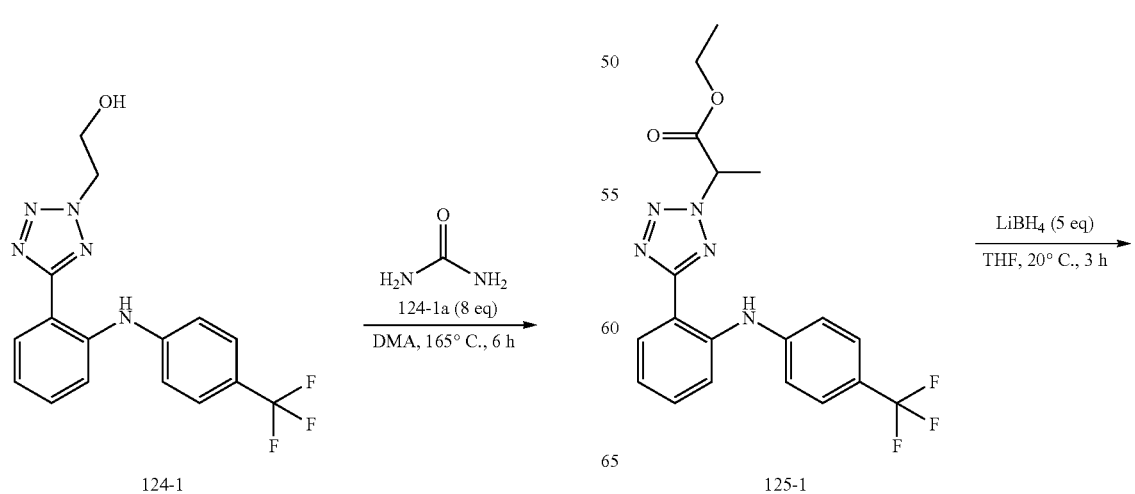

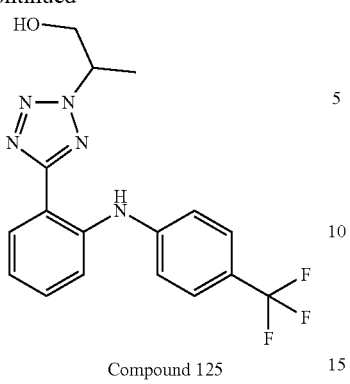

Compound 125

To a solution of 125-1 (100 mg, 0.247 mmol, 1.0 eq) in THF (3 mL) was added LiBH$_4$ (27 mg, 1.23 mmol, 5.0 eq) at 0° C. under N$_2$. The resulting mixture was stirred at 20° C. for 3 hours. LCMS showed the desired compound was found and the starting material was consumed completely. The reaction mixture was treated dropwise with aq. NH$_4$Cl (5 mL) and extracted with EtOAc (5 mL*2). The combined organic layers were washed with brine (10 mL), dried over Na$_2$SO$_4$, and filtered. The solvent was removed under reduced pressure to afford the crude product. The crude product was purified by HPLC to give the title compound (73 mg, 0.201 mmol, 81% yield). LCMS (ESI): RT=0.876 min, mass calc. for C$_{17}$H$_{16}$F$_3$N$_5$O 363.13, m/z found 364.0 [M+H]$^+$; $^1$HNMR (400 MHz, CHLOROFORM-d) δ 9.11 (s, 1H), 8.21 (dd, J=1.4, 7.9 Hz, 1H), 7.56 (d, J=8.5 Hz, 3H), 7.44-7.36 (m, 1H), 7.31 (d, J=8.5 Hz, 2H), 7.07 (t, J=7.2 Hz, 1H), 5.20-5.08 (m, 1H), 4.24-4.09 (m, 2H), 2.24 (t, J=6.7 Hz, 1H), 1.75 (d, J=7.0 Hz, 3H).

Example 119: 2-[2-(3-fluoropropyl)tetrazol-5-yl]-N-[4-(trifluoromethyl)phenyl]aniline (Compound 126)

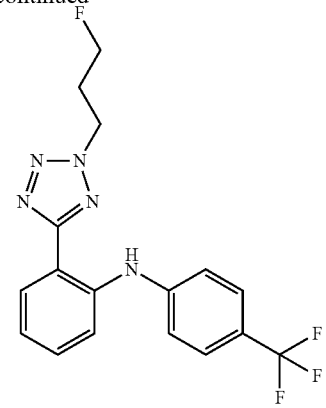

Compound 126

To a stirred solution of 126-1 (60 mg, 0.176 mmol, 1.0 eq, HCl salt) and K$_2$CO$_3$ (61 mg, 0.439 mmol, 2.5 eq) in DMF (2 mL) was added 126-2 (37 mg, 0.263 mmol, 1.5 eq). The resulting mixture was heated to 80° C. for 6 hours. LCMS showed 93% of the desired compound was formed and the starting material was consumed completely. The mixture was cooled. Water (10 mL) was added and the mixture extracted with ethyl acetate (3×10 mL). The combined organics were dried over Na$_2$SO$_4$, filtered and concentrated to give a residue. The residue was purified by purified by HPLC to give the title compound (55 mg, 0.151 mmol, 86% yield). LCMS (ESI): RT=0.927 min, mass calc. for C$_{17}$H$_{15}$F$_4$N$_5$ 365.13, m/z found 366.0 [M+H]$^+$; $^1$HNMR (400 MHz, CHLOROFORM-d) δ 9.03 (s, 1H), 8.20 (d, J=7.5 Hz, 1H), 7.60-7.48 (m, 3H), 7.38 (t, J=7.5 Hz, 1H), 7.30 (d, J=8.3 Hz, 2H), 7.05 (t, J=7.5 Hz, 1H), 4.88 (t, J=6.9 Hz, 2H), 4.64 (t, J=5.4 Hz, 1H), 4.52 (t, J=5.5 Hz, 1H), 2.58-2.40 (m, 2H).

Example 120: 1-cyclopropyl-2-[5-[2-[4-(trifluoromethyl)anilino]phenyl]tetrazol-2-yl]ethanol (Compound 127)

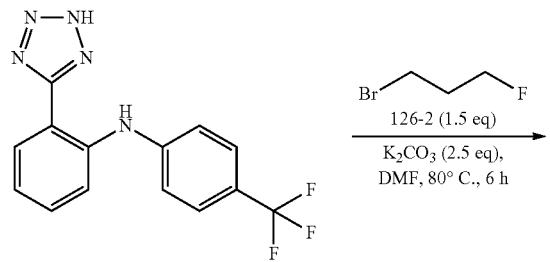

126-1

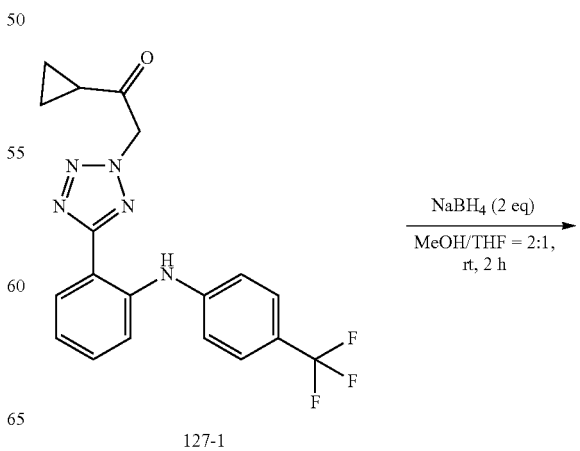

127-1

381
-continued

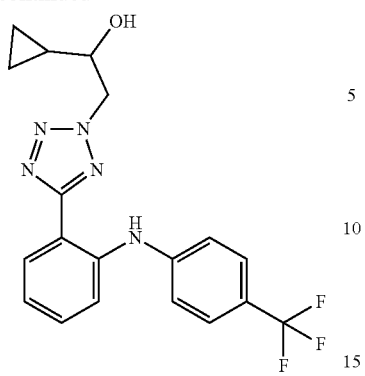

Compound 127

382
-continued

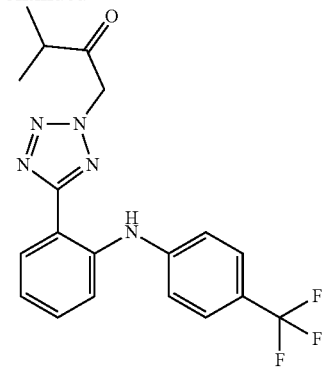

Compound 128

To a mixture of 127-1 (32 mg, 83 umol, 1.00 eq) in MeOH (2 mL) and THF (1 mL) was added NaBH$_4$ (6.3 mg, 0.165 mmol, 2.00 eq) in one portion at 15° C. under N$_2$. The mixture was stirred at 15° C. for 2 h. LCMS showed the compound 127-1 was consumed completely and one main peak with the desired MS was detected. The reaction mixture was quenched by addition water (5 mL) at 15° C., and then extracted with DCM (10 mL*3). The combined organic layers were dried with anhydrous Na$_2$SO$_4$, filtered, and concentrated under vacuum to provide the title compound (22.92 mg, 58.86 umol, 71.3% yield). LCMS (ESI): RT=0.897 min, mass calcd. for C$_{19}$H$_{18}$F$_3$N$_5$O 389.15, m/z found 390.0[M+H]$^+$. $^1$HNMR (400 MHz, DMSO-d$_6$) δ8.81 (s, 1H), 8.04 (dd, J=8.00 Hz, J=1.20 Hz, 1H), 7.59-7.52 (m, 3H), 7.52-7.46 (m, 1H), 7.26-7.16 (m, 3H), 5.16 (d, J=5.60 Hz, 1H), 4.82-4.69 (m, 2H), 3.57-3.45 (m, 1H), 0.98-0.84 (m, 1H), 0.45-0.34 (m, 2H), 0.34-0.26 (m, 1H), 0.19-0.10 (m, 1H).

Example 121: 3-methyl-1-[5-[2-[4-(trifluoromethyl)anilino]phenyl]tetrazol-2-yl]butan-2-one (Compound 128)

To a mixture of 128-1 (60 mg, 0.197 mmol, 1.00 eq) and 128-1a (65 mg, 0.393 mmol, 2.00 eq) in DMF (2 mL) was added K$_2$CO$_3$ (82 mg, 0.590 mmol, 3.00 eq) in one portion at 15° C. under N$_2$. The mixture was stirred at 15° C. for 1 hour. TLC showed the starting material was consumed completely and many new spots were formed. The reaction mixture was diluted with EtOAc (40 mL) and washed with brine (40 mL*3), dried with anhydrous Na$_2$SO$_4$, filtered, and concentrated under vacuum. LCMS showed 69% of desired product was formed. The residue was purified by prep-HPLC (basic condition) to provide the title compound (22.00 mg, 56.5 umol, 28.8% yield). LCMS (ESI): RT=0.910 min, mass calcd. for C$_{19}$H$_{18}$F$_3$N$_5$O 389.15, m/z found 390.0[M+H]$^+$. $^1$HNMR (400 MHz, CHLOROFORM-d) δ8.96 (s, 1H), 8.24-8.15 (m, 1H), 7.53 (br t, J=6.40 Hz, 3H), 7.42-7.37 (m, 1H), 7.30 (br d, J=8.40 Hz, 2H), 7.03 (t, J=7.60 Hz, 1H), 5.61 (s, 2H), 2.85-2.72 (m, 1H), 1.26 (d, J=6.80 Hz, 7H).

Example 122: 2-(2-(1-methoxypropan-2-yl)-2H-tetrazol-5-yl)-N-(4-(trifluoromethyl)phenyl) Aniline (Compound 129)

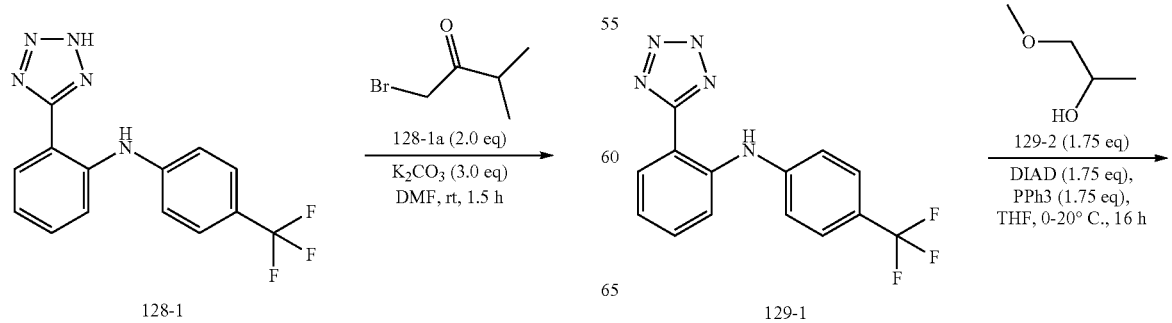

383

-continued

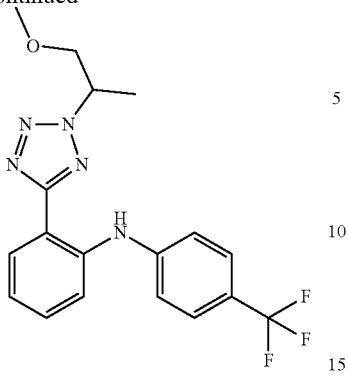

Compound 129

A solution of 129-1 (100 mg, 0.292 mmol, 1.0 eq, HCl) in anhydrous THF (3 mL) and DCM (1.5 mL) was cooled at 0° C. under $N_2$. To this mixture were added 129-2 (46 mg, 0.512 mmol, 50 uL, 1.75 eq), $PPh_3$ (134 mg, 0.512 mmol, 1.75 eq), and DIAD (103 mg, 0.512 mmol, 100 uL, 1.75 eq) and the mixture was stirred for 5 min and then warmed to 20° C. and stirred 16 h. LCMS showed 44% of the desired compound was formed and 17% of the starting material was remaining. The solution was concentrated under reduced pressure to give a residue. The residue was purified by prep-HPLC to give the title compound (45 mg, 0.109 mmol, 37% yield, HCl salt). LCMS (ESI): RT=0.908 min, mass calc. for $C_{18}H_{18}F_3N_5O$ 377.15, m/z found 378.0 [M+H]$^+$; $^1$HNMR (400 MHz, CHLOROFORM-d) δ 9.14 (s, 1H), 8.22 (d, J=7.8 Hz, 1H), 7.53 (d, J=8.5 Hz, 3H), 7.41-7.34 (m, 1H), 7.29 (d, J=8.5 Hz, 2H), 7.04 (t, J=7.4 Hz, 1H), 5.22 (dd, J=7.2, 12.2 Hz, 1H), 3.95 (dd, J=8.0, 10.0 Hz, 1H), 3.80 (dd, J=4.8, 10.3 Hz, 1H), 3.34 (s, 3H), 1.70 (d, J=7.0 Hz, 3H).

Example 123: 1-phenyl-2-[5-[2-[4-(trifluoromethyl)anilino]phenyl]tetrazol-2-yl]ethanone (Compound 130)

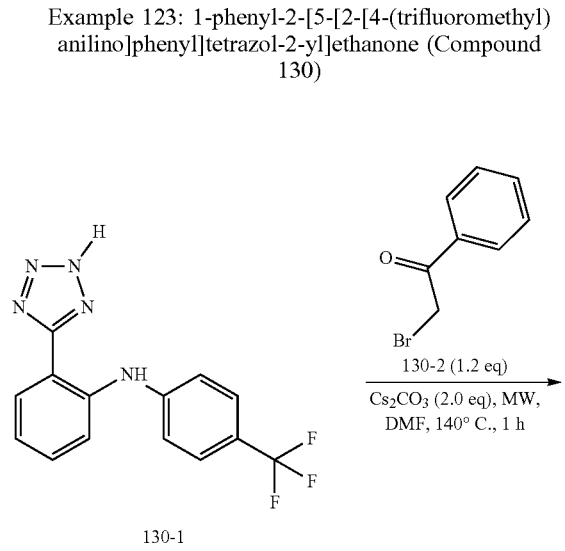

130-1

384

-continued

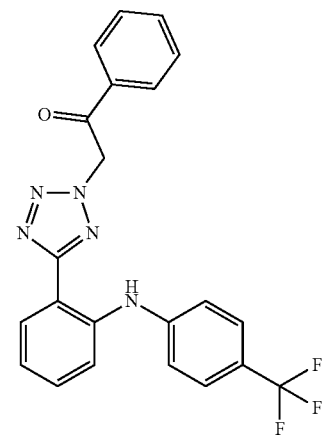

Compound 130

130-1 (30.0 mg, 98.3 umol, 1.0 eq), 130-2 (46.9 mg, 0.12 mmol, 1.2 eq) and $Cs_2CO_3$ (64.0 mg, 0.20 mmol, 2.0 eq) were taken up into a microwave tube in DMF (3.0 mL). The sealed tube was heated at 150° C. for 1 hour under microwave conditions. LCMS showed the desired compound was formed. The reaction was filtered to give a crude product. The crude product was purified by column chromatography over silica gel and then further purified by prep-HPLC to give the title compound (2.21 mg, 5.22 umol, 5.31% yield). LCMS (ESI): RT=0.929 min, mass calc. for $C_{22}H_{16}F_3N_5O$ 423.13, m/z found 424.1[M+H]$^+$; $^1$HNMR (400 MHz, CDCl$_3$-d) δ 8.98 (s, 1H), 8.24 (dd, J=1.4, 7.9 Hz, 1H), 8.06-8.00 (m, 2H), 7.75-7.69 (m, 1H), 7.62-7.56 (m, 2H), 7.54 (d, J=8.5 Hz, 3H), 7.38 (t, J=7.8 Hz, 1H), 7.31 (d, J=8.5 Hz, 2H), 7.05 (t, J=7.5 Hz, 1H), 6.20 (s, 2H).

Example 124: 1,1,1-trifluoro-3-[5-[2-[4-(trifluoromethyl)anilino]phenyl]tetrazol-2-yl]propan-2-ol (Compound 131)

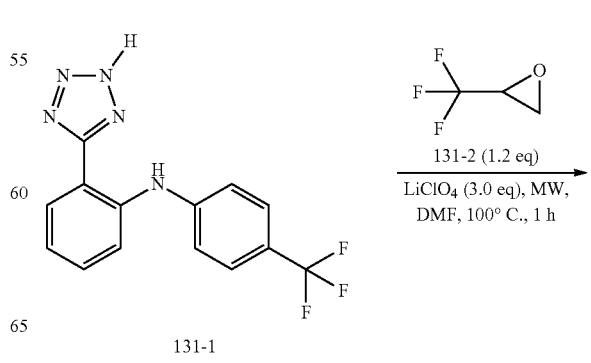

131-1

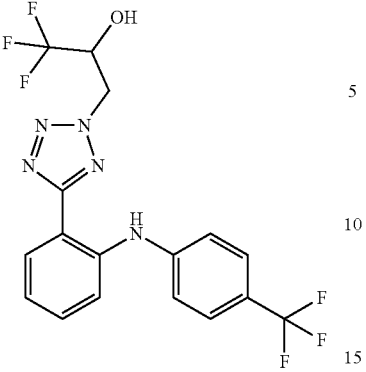

Compound 131

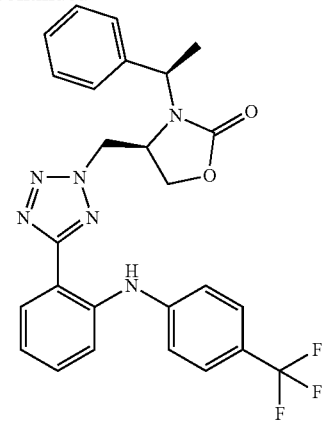

Compound 132

131-1 (30.0 mg, 98.3 umol, 1.0 eq), 131-2 (33.0 mg, 0.29 mmol, 3.0 eq) and LiClO$_4$ (31.4 mg, 0.29 mmol, 12.9 uL, 3.0 eq) were taken up into a microwave tube in DMF (5.0 mL). The sealed tube was heated at 100° C. for 1 hour under microwave conditions. LCMS showed the desired compound was formed. The reaction was filtered to give a crude product. The product was purified by prep-HPLC to give the title compound (21.07 mg, 50.49 umol, 51.37% yield). LCMS (ESI): RT=0.884 min, mass calc. for $C_{17}H_{13}F_6N_5O$ 417.10, m/z found 418.0[M+H]$^+$; $^1$HNMR (400 MHz, DMSO-d$_6$) δ 8.77 (s, 1H), 8.08 (dd, J=1.1, 7.9 Hz, 1H), 7.60-7.53 (m, 3H), 7.53-7.47 (m, 1H), 7.25 (d, J=8.5 Hz, 2H), 7.19 (t, J=7.0 Hz, 1H), 6.94 (d, J=6.3 Hz, 1H), 5.10-5.02 (m, 1H), 4.97-4.89 (m, 1H), 4.76 (s, 1H).

Example 125: (4R)-3-[(1R)-1-phenylethyl]-4-[[5-[2-[4-(trifluoromethyl)anilino]phenyl]tetrazol-2-yl]methyl]oxazolidin-2-one (Compound 132)

To a solution of 132-2a (53 mg, 0.219 mmol, 1.5 eq) and Cs$_2$CO$_3$ (143 mg, 0.439 mmol, 3.0 eq) in DMF (2.0 mL) was added 132-1 (50 mg, 0.146 mmol, 1.0 eq, HCl). The resulting mixture was stirred at 100° C. for 32 hours. LCMS showed 14% desired compound was formed and the starting material remained. The reaction mixture was poured into water (5 mL) and stirred for 5 min. The aqueous phase was extracted with ethyl acetate (5 mL*3). The combined organic layers were washed with brine (5 mL*2), dried with anhydrous Na$_2$SO$_4$, filtered, and concentrated under vacuum to give a residue. The residue was purified by HPLC to give the title compound (11.0 mg, 21.63 umol, 15% yield). LCMS (ESI): RT=0.932 min, mass calc. for $C_{26}H_{23}F_3N_6O_2$ 508.18, m/z found 531.1 [M+23]$^+$; $^1$HNMR (400 MHz, CHLOROFORM-d) δ 8.82 (d, J=16.1 Hz, 1H), 8.12 (t, J=7.2 Hz, 1H), 7.52 (dd, J=8.2, 13.2 Hz, 4H), 7.59-7.47 (m, 1H), 7.46-7.32 (m, 5H), 7.29 (s, 1H), 7.03 (t, J=7.5 Hz, 1H), 5.29 (m, J=6.8 Hz, 1H), 4.88-4.70 (m, 1H), 4.44-4.35 (m, 1H), 4.34-4.30 (m, 1H), 4.27-4.18 (m, 1H), 4.16-4.08 (m, 0.5H), 4.05-3.95 (m, 0.5H), 1.79 (t, J=8.0 Hz, 3H).

Example 126: 1-[[5-[2-[4-(trifluoromethyl)anilino]phenyl]tetrazol-2-yl]methyl]cyclohexanol (Compound 133)

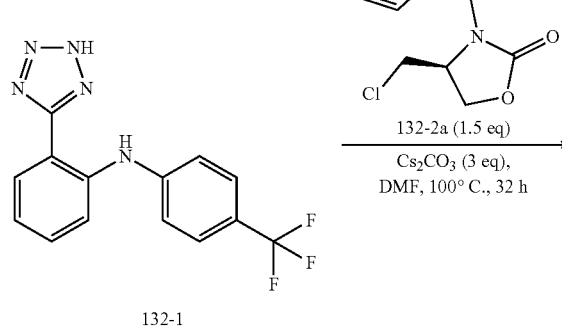

132-1

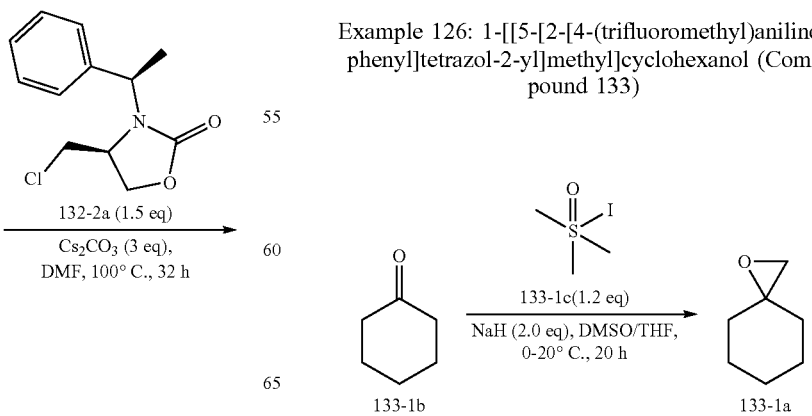

132-2a (1.5 eq)

Cs$_2$CO$_3$ (3 eq), DMF, 100° C., 32 h

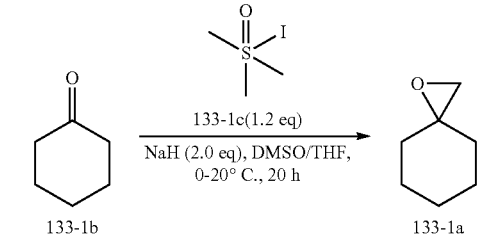

133-1b    133-1c(1.2 eq)   NaH (2.0 eq), DMSO/THF, 0-20° C., 20 h    133-1a

-continued

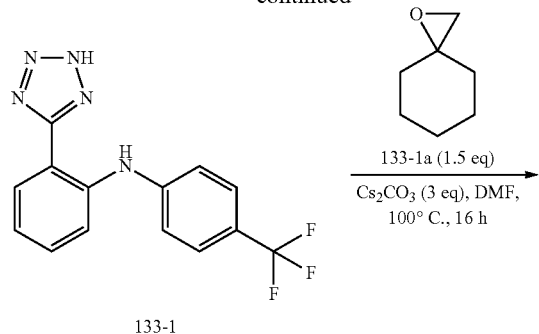

Compound 133

Step 1: 1-oxaspiro[2.5]octane

To a solution of 133-1b (500 mg, 5.09 mmol, 526 uL, 1.0 eq) in DME (15 mL) was added t-BuOK (571 mg, 5.09 mmol, 1.0 eq) and 133-1c (1.12 g, 5.09 mmol, 1.0 eq). Then the mixture was stirred at 80° C. for 16 hr. TLC (Petroleum ether:Ethyl acetate=10/1, Rf=0.6) showed the starting material was consumed completely. The mixture was quenched with H$_2$O (20 mL) and extracted with DCM (40 mL×3). The combined organic layers were washed with brine, dried over Na$_2$SO$_4$ and concentrated under reduced pressure to give 133-1a (220 mg, 1.96 mmol, 39% yield) as an oil. The oil was directly used without further purification.

Step 2: 1-[[5-[2-[4-(trifluoromethyl)anilino]phenyl]tetrazol-2-yl]methyl]cyclohexanol To a stirred solution of 133-1 (100 mg, 0.293 mmol, 1.0 eq, HCl) and Cs$_2$CO$_3$ (286 mg, 0.878 mmol, 3.0 eq) in DMF (2 mL) was added 133-1a (66 mg, 0.585 mmol, 2.0 eq). The resulting mixture was stirred at 100° C. for 16 hours. LCMS showed 19% of the desired compound was formed and 75% the starting material remained. The mixture was cooled. The reaction mixture was poured into water (10 mL) and stirred for 5 min. The aqueous phase was extracted with ethyl acetate (10 mL*3). The combined organic phases were dried with anhydrous Na$_2$SO$_4$, filtered, and concentrated under vacuum to give a residue. The residue was purified by HPLC to give Compound 133 (17 mg, 41 umol, 14% yield). LCMS (ESI): RT=0.922 min, mass calc. for C$_{21}$H$_{22}$F$_3$N$_5$O 417.18, m/z found 418.1[M+H]$^+$; $^1$HNMR (400 MHz, DMSO-d$_6$) δ 8.78 (s, 1H), 8.02 (d, J=8.2 Hz, 1H), 7.52 (d, J=8.4 Hz, 3H), 7.49-7.43 (m, 1H), 7.21-7.10 (m, 3H), 4.67-4.55 (m, 3H), 1.56-1.30 (m, 10H).

Example 127: tert-butyl 4-hydroxy-4-[[5-[2-[4-(trifluoromethyl)anilino]phenyl]tetrazol-2-yl]methyl]piperidine-1-carboxylate (Compound 134)

Compound 134

Step 1: tert-butyl 1-oxa-6-azaspiro[2.5]octane-6-carboxylate t-BuOK (1.35 g, 12.05 mmol, 1.20 eq) and DMSO (11 mL) were charged to a reaction vessel and the mixture cooled to around 20° C. with stirring. Trimethylsulfoxonium iodide (2.43 g, 11.04 mmol, 1.10 eq) was added in portions over a period of 10 min, maintaining the reaction temperature between 20~25° C. On completion of the addition, the mixture was maintained at this temperature for 1 hr. DME (3 mL) was added to the reaction flask and the solution cooled to 0-5° C. A pre-cooled solution of 134-1 (2 g, 10.04 mmol, 1.00 eq) in a mixture of DME (3 mL) and DMSO (1 ml) was transferred into the reaction mixture over a period of 15 min, maintaining the reaction temperature between 0~5° C. On completion of the addition, the reaction mixture was held at this temperature for a further 1.5 hr. TLC (EtOAc:PE=1:10) showed that starting material was consumed completely. The reaction was diluted with EtOAc (80 mL) and washed with brine (3*30 mL). The combined organic layers were dried over $Na_2SO_4$ and concentrated to give 134-2 (1.80 g, 8.44 mmol, 84.06% yield). $^1$H NMR (400 MHz, CHLOROFORM-d) δ3.82-3.55 (m, 2H), 3.50-3.30 (m, 2H), 2.69 (s, 2H), 1.80-1.70 (m, 2H), 1.55-1.40 (m, 11H).

Step 2: tert-butyl 4-hydroxy-4-[[5-[2-[4-(trifluoromethyl)anilino]phenyl]tetrazol-2-yl]methyl]piperidine-1-carboxylate To a solution of 134-3 (50 mg, 0.16 mmol, 1.00 eq) and $K_2CO_3$ (90.6 mg, 0.66 mmol, 4.00 eq) in DMF (4.00 mL) was added 134-2 (52.4 mg, 0.25 mmol, 1.50 eq). The reaction was heated to 120° C. for 16 hr. LCMS showed that the desired MS signal was detected. The reaction was diluted with EtOAc (30 mL) and washed with brine (2*20 mL). The organic layer was dried over $Na_2SO_4$ and concentrated. The crude product was purified by CombiFlash to give Compound 134 (40 mg, 76.37 umol, 46.63% yield). LCMS (ESI): RT=0.933 min, mass calc. for $C_{25}H_{29}F_3N_6O_3$ 518.23, m/z found 541.1 [M+Na]$^+$. $^1$HNMR (400 MHz, CHLOROFORM-d) δ 8.78 (s, 1H), 8.06 (d, J=7.6 Hz, 1H), 7.58-7.51 (m, 4H), 7.40 (t, J=7.5 Hz, 1H), 7.31-7.15 (m, 3H), 4.97 (s, 1H), 4.71 (s, 2H), 3.75-3.60 (m, 2H), 3.15-2.80 (m, 2H), 1.60-1.50 (m, 4H), 1.39 (s, 9H).

Example 128: 4-[[5-[2-[4-(trifluoromethyl)anilino]phenyl]tetrazol-2-yl]methyl]piperidin-4-ol (Compound 135)

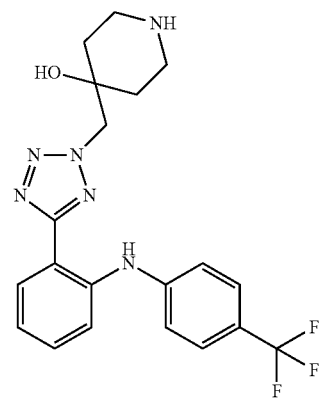

Compound 135

To a solution of 135-1 (37 mg, 71.36 umol, 1.00 eq) in dioxane (3 mL) was added HCl/dioxane (4 M, 462.59 uL, 25.93 eq) at 15° C. The reaction was stirred at 15° C. for 1 hr. LCMS showed that only the desired product was detected. The reaction was concentrated to afford the title compound (27.97 mg, 56.36 umol, 78.98% yield, 2HCl salt). LCMS (ESI): RT=0.727 min, mass calc. for $C_{20}H_{21}F_3N_6O$ 418.16, m/z found 419.1 [M+H]$^+$. $^1$HNMR (400 MHz, DMSO-d$_6$) δ 8.80 (s, 1H), 8.73 (br, 1H), 8.55 (br, 1H), 8.05 (d, J=7.2 Hz, 1H), 7.59-7.50 (m, 4H), 7.31-7.18 (m, 3H), 5.39 (s, 1H), 4.78 (s, 2H), 4.49 (s, 1H), 3.20-3.10 (m, 2H), 3.11-2.95 (m, 2H), 1.90-1.75 (m, 2H), 1.75-1.65 (m, 2H).

Example 129: 5-((5-(2-((4-(trifluoromethyl)phenyl)amino)phenyl)-2H-tetrazol-2-yl)methyl)oxazolidin-2-one (Compound 136)

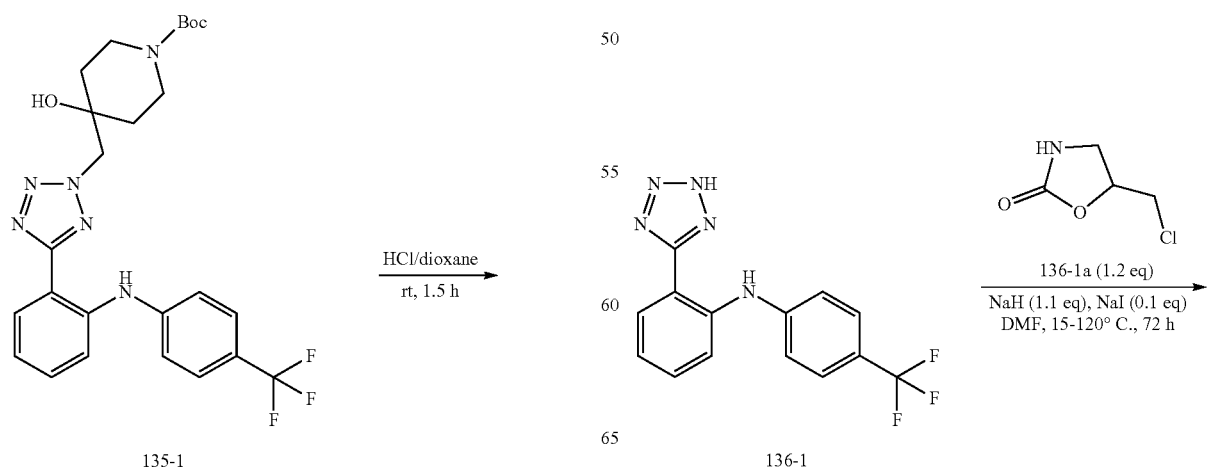

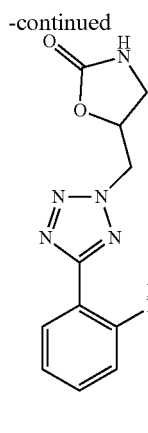

Compound 136

To a solution of 136-1 (30.00 mg, 98.28 umol, 1.00 eq) and NaI (1.47 mg, 9.83 umol, 0.10 eq) in DMF (500.00 uL) was added NaH (4.32 mg, 108.10 umol, 60% purity, 1.10 eq) at 0° C. After stirring for 10 min, 136-1a (15.99 mg, 117.93 umol, 1.20 eq) was added and then the resulting mixture was stirred at 15° C. for 16 h. TLC showed most of starting material remained. Then the mixture was stirred at 80° C. for 20 h. LCMS showed most of starting material remained, and one peak with the desired mass was detected. Then the mixture was stirred at 120° C. for 16 h. LCMS still showed around 23% of the starting material remained and around 68% of desired product was formed. Then the mixture was continuously stirred at 120° C. for another 20 h. LCMS showed the reaction had no further improvement. TLC showed most of material was consumed and mainly one new spot was formed. The mixture was purified by prep-HPLC to give the title compound (20.00 mg, 49.46 umol, 25.16% yield of two batches). LCMS (ESI): RT=1.674 min, mass calc. for $C_{18}H_{15}F_3N_6O_2$ 404.12, m/z found 404.90 [M+1]$^+$; $^1$HNMR (400 MHz, DMSO-$d_6$) δ 8.74 (s, 1H), 8.11-8.03 (m, 1H), 7.66-7.47 (m, 5H), 7.29-7.15 (m, 3H), 5.18-5.02 (m, 3H), 3.72-3.63 (m, 1H), 3.38 (m, J=5.0 Hz, 1H).

Example 130: 2-(2-pyrimidin-5-yltetrazol-5-yl)-N-[4-(trifluoromethyl)phenyl]aniline (Compound 137)

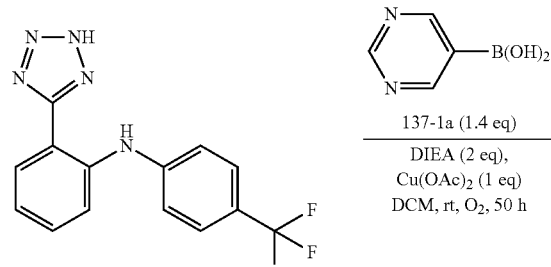

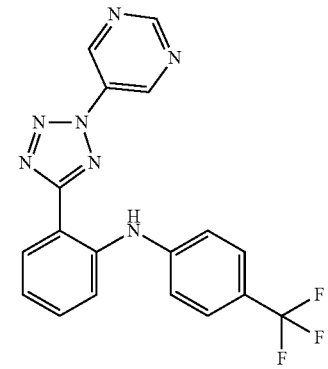

Compound 137

To a mixture of 137-1 (50 mg, 0.164 mmol, 1.00 eq) and 137-1a (28 mg, 0.229 mmol, 1.40 eq) in DCM (2 mL) was added Cu(OAc)$_2$ (30 mg, 0.164 mmol, 1.00 eq) and DIPEA (42 mg, 0.327 mmol, 60 uL, 2.00 eq) in one portion at 15° C. under O$_2$. The mixture was stirred at 15° C. for 50 h. LCMS showed the starting material was consumed completely and one peak with the desired MS was detected. The reaction mixture was filtered and concentrated under vacuum. The residue was purified by prep-HPLC (basic condition) to provide the title compound (2.03 mg, 5.3 umol, 3.2% yield). LCMS (ESI): RT=0.740 min, mass calcd. for $C_{18}H_{12}F_3N_7$ 383.11, m/z found 384.0[M+H]$^+$. $^1$H NMR (400 MHz, CHLOROFORM-d) δ8.60-8.17 (m, 1H), 8.00 (br s, 1H), 7.62-7.54 (m, 1H), 7.51-7.39 (m, 3H), 7.39-7.33 (m, 1H), 7.15-7.00 (m, 2H).

Example 131: 4-[[5-[2-[4-(trifluoromethyl)anilino]phenyl]tetrazol-2-yl]methyl]tetrahydropyran-4-ol (Compound 138)

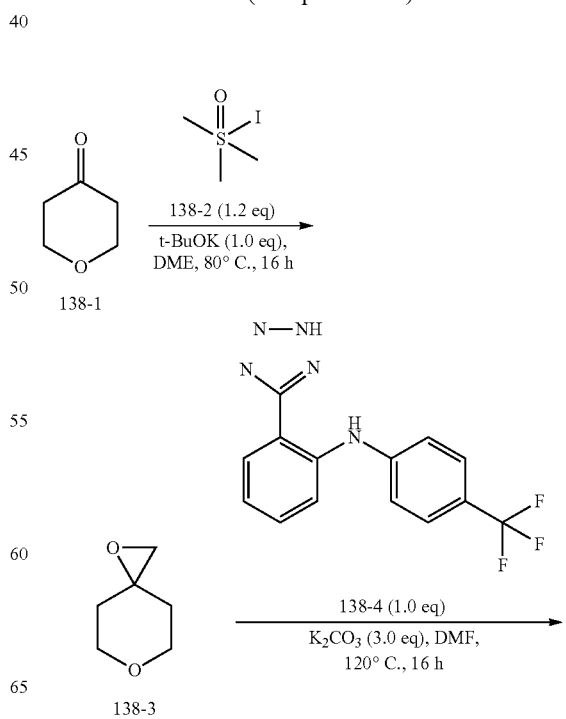

-continued

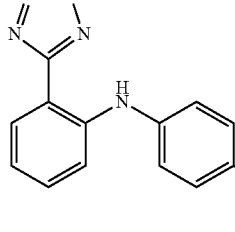

Compound 138

Step 1: 1,6-dioxaspiro[2.5]octane

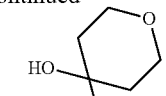

To a solution of 138-1 (300.0 mg, 3.0 mmol, 0.28 mL, 1.0 eq) in DME (4.0 mL) was added t-BuOK (370.3 mg, 3.3 mmol, 1.1 eq) and 138-2 (726.2 mg, 3.3 mmol, 1.1 eq). The mixture was stirred at 80° C. for 16 hour under $N_2$ atmosphere. TLC (Petroleum ether:Ethyl acetate=10/1) showed a new spot appeared. The reaction was filtered and concentrated under reduced pressure to give a crude product. The crude product was diluted with water (5 mL) and washed with EtOAc (10 mL×2). The combined organic layers were concentrated to give crude 138-3 (300.0 mg, 1.8 mmol, 61.3% yield) as a yellow oil. $^1$HNMR (400 MHz, CDCl$_3$-d) δ 3.89-3.79 (m, 4H), 2.70 (s, 2H), 1.88 (ddd, J=4.6, 8.4, 13.3 Hz, 2H), 1.54 (td, J=4.5, 13.4 Hz, 2H).

Step 2: 4-[[5-[2-[4-(trifluoromethyl)anilino]phenyl]tetrazol-2-yl]methyl]tetrahydropyran-4-ol To a solution of 138-4 (30.0 mg, 98.3 umol, 1.0 eq) in DMF (5.0 mL) was added $K_2CO_3$ (27.2 mg, 0.20 mmol, 2.0 eq) and 138-3 (13.5 mg, 0.12 mmol, 1.2 eq). The mixture was stirred at 120° C. for 16 hour under an $N_2$ atmosphere. LCMS showed the desired compound was formed. The reaction was filtered to give a crude product. The crude product was purified by prep-HPLC to give Compound 138 (5.80 mg, 13.83 umol, 14.07% yield). LCMS (ESI): RT=0.697 min, mass calc. for $C_{20}H_{20}F_3N_5O_2$ 419.16, m/z found 420.1 [M+H]$^+$; $^1$HNMR (400 MHz, CDCl$_3$-d) δ 9.03 (s, 1H), 8.18 (dd, J=1.1, 7.9 Hz, 1H), 7.58-7.51 (m, 3H), 7.44-7.36 (m, 1H), 7.30 (d, J=8.5 Hz, 2H), 7.06 (t, J=7.5 Hz, 1H), 4.75 (s, 2H), 3.84-3.76 (m, 4H), 2.70 (s, 1H), 1.82 (ddd, J=6.5, 9.9, 13.7 Hz, 2H), 1.45 (d, J=12.0 Hz, 2H).

Example 132: 1-(5-(2-((4-(trifluoromethyl)phenyl)amino)phenyl)-2H-tetrazol-2-yl)butan-2-ol (Compound 139)

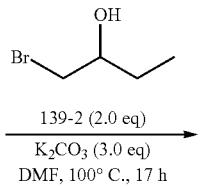

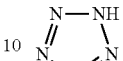

139-1

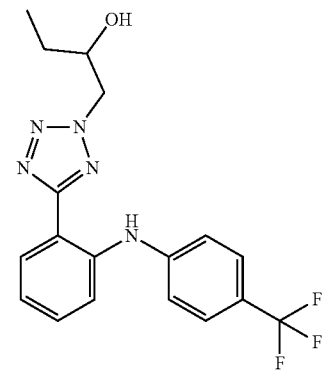

Compound 139

To a mixture of 139-1 (50.0 mg, 0.2 mmol, 1.00 eq) and $K_2CO_3$ (67.9 mg, 0.5 mmol, 3.00 eq) in DMF (3.0 mL), was added 139-2 (50.1 mg, 0.3 mmol, 2.00 eq). The resulting mixture was stirred at 100° C. under $N_2$ for 17 h. LCMS showed the reaction was complete. The mixture was filtered, and the solid was washed with 1 mL DMF. The filtrate was purified by prep-HPLC (basic condition) to obtain the title compound (15.88 mg, 41.7 umol, 25.4% yield). LCMS (ESI): RT=0.885 min, mass calc. for $C_{18}H_{18}F_3N_5O$ 377.15, m/z found 378.0 [M+H]$^+$. $^1$HNMR (400 MHz, DMSO-d$_6$) δ 8.87-8.79 (m, 1H), 8.09-8.02 (m, 1H), 7.59-7.45 (m, 4H), 7.25-7.12 (m, 3H), 5.17-4.79 (m, 1H), 4.75-4.56 (m, 2H), 4.00-3.78 (m, 1H), 1.99-1.32 (m, 2H), 1.00-0.61 (m, 3H).

Example 133: 2-[2-(2-pyridyl)tetrazol-5-yl]-N-[4-(trifluoromethyl)phenyl]aniline (Compound 140)

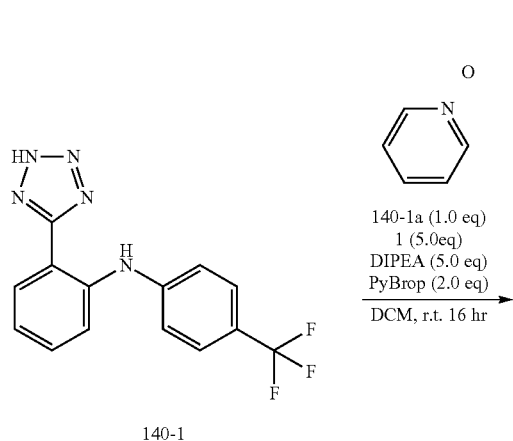

Example 134: 3-methyl-1-[5-[2-[4-(trifluoromethyl)anilino]phenyl]tetrazol-2-yl]butan-2-ol (Compound 141)

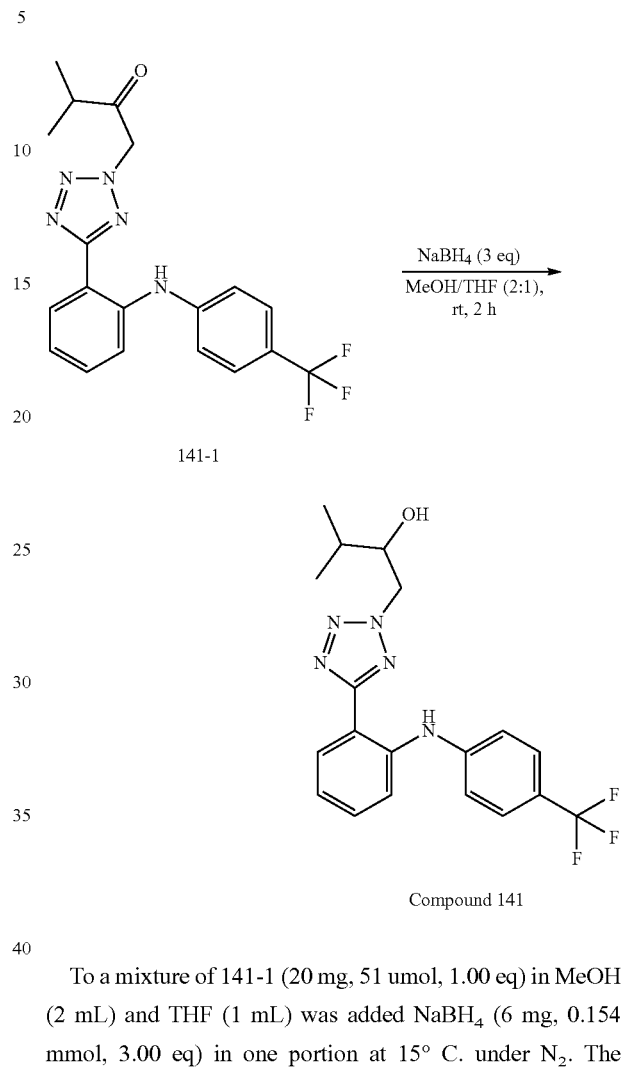

To a solution of 140-1a (15.0 mg, 0.16 mmol, 1.0 eq), 140-1 (240.7 mg, 0.79 mmol, 5.0 eq) and DIEA (101.9 mg, 0.79 mmol, 137.7 uL, 5.0 eq) in DCM (5.0 mL) was added PyBrop (147.1 mg, 0.32 mmol, 2.0 eq). The mixture was stirred at 10-15° C. for 16 hour. LC-MS showed most of 140-1 and one peak with an MS of 354.9 and 404.9. The combined reaction mixture was concentrated to give a residue. The residue was pre-purified by flash column chromatography to give crude product (150 mg), which was re-purified by prep-HPLC to give the title compound (102.06 mg, 0.24 mmol, HCl salt). LCMS (ESI): RT=1.381 min, mass calc. for $C_{19}H_{13}F_3N_6$ 382.12, m/z found 404.9 [M+Na]$^+$; $^1$HNMR (400 MHz, DMSO-d6) δ 8.76-8.63 (m, 2H), 8.22-8.14 (m, 1H), 8.14-8.06 (m, 2H), 7.67 (dd, J=5.0, 6.5 Hz, 1H), 7.59-7.44 (m, 4H), 7.26-7.13 (m, 3H).

To a mixture of 141-1 (20 mg, 51 umol, 1.00 eq) in MeOH (2 mL) and THF (1 mL) was added NaBH$_4$ (6 mg, 0.154 mmol, 3.00 eq) in one portion at 15° C. under N$_2$. The mixture was stirred at 15° C. for 2 h. LCMS showed the 141-1 was consumed completely and one main peak with the desired MS was detected. The reaction mixture was quenched by addition of water (5 mL) at 15° C. and concentrated under reduced pressure to remove MeOH and THF. The residue was extracted with DCM (10 mL*3). The combined organic layers were dried with anhydrous Na$_2$SO$_4$, filtered, and concentrated under vacuum. The residue was purified by prep-HPLC (basic condition) to provide the title compound (5.07 mg, 13 umol, 25.2% yield). LCMS (ESI): RT=0.916 min, mass calc. for $C_{19}H_{20}F_3N_5O$ 391.16, m/z found 392.1[M+H]$^+$. $^1$HNMR (400 MHz, CHLOROFORM-d) δ9.07 (s, 1H), 8.19 (d, J=7.60 Hz, 1H), 7.60-7.50 (m, 3H), 7.39 (t, J=7.80 Hz, 1H), 7.30 (br d, J=8.40 Hz, 2H), 7.05 (t, J=7.60 Hz, 1H), 4.84-4.69 (m, 2H), 4.09-4.01 (m, 1H), 2.39 (d, J=4.80 Hz, 1H), 1.89-1.78 (m, 1H).

Example 135: 3-[[5-[2-[4-(trifluoromethyl)anilino]phenyl]tetrazol-2-yl]methyl]tetra hydropyran-3-ol (Compound 142)

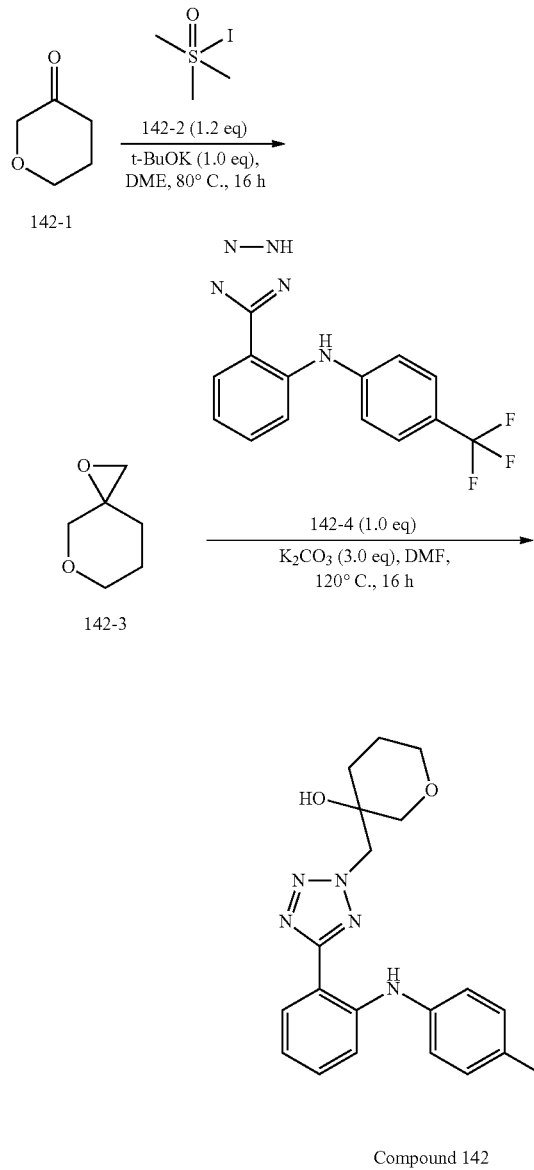

Step 1: 1,7-dioxaspiro[2.5]octane

To a solution of 142-1 (200.0 mg, 2.0 mmol, 1.0 eq) in DME (4.0 mL) was added t-BuOK (224.4 mg, 2.0 mmol, 1.0 eq) and 142-2 (484.2 mg, 2.2 mmol, 1.1 eq). The mixture was stirred at 80° C. for 16 hour under an $N_2$ atmosphere. TLC (Petroleum ether:Ethyl acetate=3/1) showed a new spot appeared. The reaction was filtered and concentrated under reduced pressure to give a crude product. The crude product was diluted with water (5 mL) and washed with EtOAc (10 mL×2). The combined organic layers were concentrated to give crude 142-3 (60.0 mg, 0.53 mmol, 26.3% yield) as a yellow oil.

Step 2: 3-[[5-[2-[4-(trifluoromethyl)anilino]phenyl]tetrazol-2-yl]methyl]tetrahydropyran-3-ol To a solution of 142-4 (30.0 mg, 98.3 umol, 1.0 eq) in DMF (5.0 mL) was added $K_2CO_3$ (27.2 mg, 0.20 mmol, 2.0 eq) and 142-3 (11.2 mg, 98.3 umol, 1.0 eq). The mixture was stirred at 120° C. for 16 hours under an $N_2$ atmosphere. LCMS showed the desired compound was formed. The reaction was filtered to give a crude product. The crude product was purified by prep-HPLC to give Compound 142 (6.22 mg, 14.83 umol, 15.09% yield). LCMS (ESI): RT=0.843 min, mass calc. for $C_{20}H_{20}F_3N_5O_2$ 419.16, m/z found 420.0 [M+H]$^+$; $^1$HNMR (400 MHz, CDCl$_3$-d) δ 9.05 (s, 1H), 8.20 (dd, J=1.4, 7.9 Hz, 1H), 7.54 (d, J=8.3 Hz, 3H), 7.42-7.36 (m, 1H), 7.30 (d, J=8.5 Hz, 2H), 7.05 (t, J=7.2 Hz, 1H), 4.94 (d, J=14.1 Hz, 1H), 4.77 (d, J=14.1 Hz, 1H), 3.70 (d, J=2.8 Hz, 2H), 3.65-3.60 (m, 1H), 3.55-3.50 (m, 1H), 2.93 (s, 1H), 1.87-1.62 (m, 4H).

Example 136: 1-phenyl-2-[5-[2-[4-(trifluoromethyl)anilino]phenyl]tetrazol-2-yl]ethanol (Compound 143)

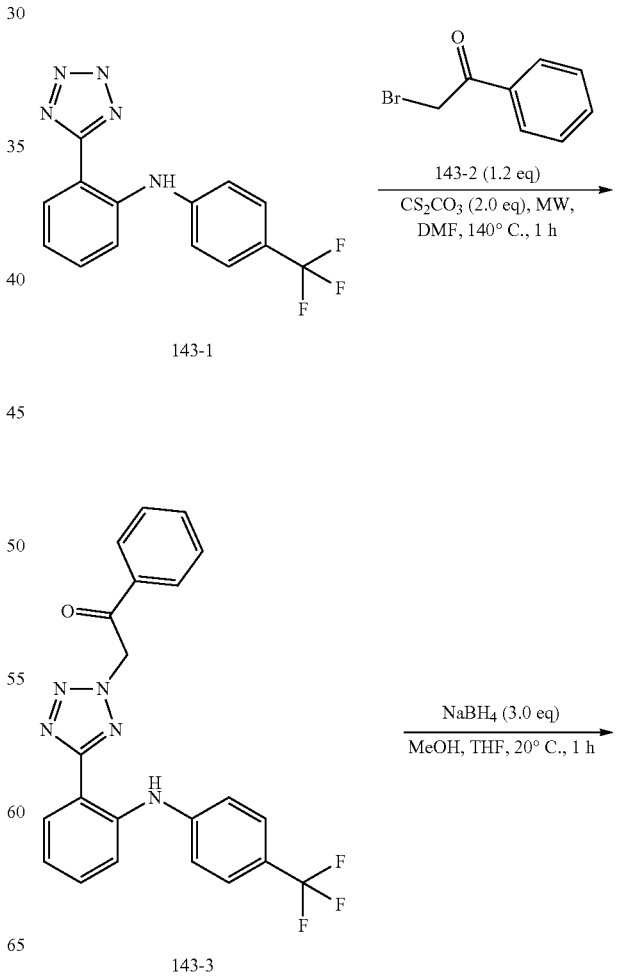

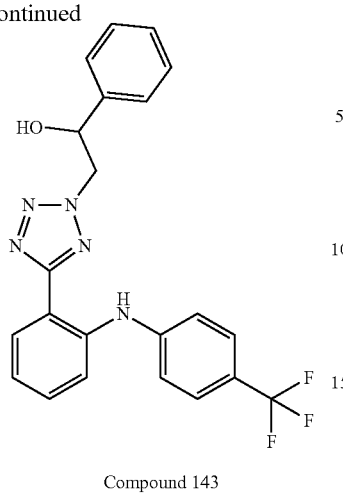

Compound 143

Step 1: 1-phenyl-2-[5-[2-[4-(trifluoromethyl)anilino]phenyl]tetrazol-2-yl]ethanone 143-1 (200.0 mg, 0.66 mmol, 1.0 eq), 143-2 (391.2 mg, 0.98 mmol, 1.5 eq) and $Cs_2CO_3$ (426.9 mg, 1.3 mmol, 2.0 eq) were taken up into a microwave tube in DMF (3.0 mL). The sealed tube was heated at 150° C. for 1 hour under microwave conditions. LCMS showed the desired compound was formed. TLC (Petroleum ether:Ethyl acetate=3/1) showed new spots had appeared. The reaction was filtered and concentrated under reduced pressure to give a crude product. The crude product was purified by column chromatography over silica gel to give 143-3 (150.0 mg, 0.26 mmol, 39.5% yield). LCMS (ESI): RT=0.912 min, mass calc. for $C_{22}H_{16}F_3N_5O$ 423.13, m/z found 424.0 $[M+H]^+$.

Step 2: 1-phenyl-2-[5-[2-[4-(trifluoromethyl)anilino]phenyl]tetrazol-2-yl]ethanol To a solution of 143-3 (150.0 mg, 0.26 mmol, 1.0 eq) in THF (3.0 mL) and MeOH (3.0 mL) was added $NaBH_4$ (29.4 mg, 0.78 mmol, 3.0 eq). The resulting mixture was stirred at 20° C. for 1 hour. LCMS showed the desired compound was formed and the starting material was consumed completely. The reaction mixture was treated dropwise with aq. $NH_4Cl$ (5 mL) and extracted with EtOAc (5 mL*2). The combined organic layers were washed with brine (10 mL), dried over $Na_2SO_4$, and filtered. The solvent was removed under reduced pressure to afford the crude product. The product was purified by prep-HPLC to give Compound 143 (73.20 mg, 172.07 umol, 66.53% yield). LCMS (ESI): RT=0.897 min, mass calc. for $C_{22}H_{18}F_3N_5O$ 425.15, m/z found 426.0 $[M+H]^+$; $^1$HNMR (400 MHz, $CDCl_3$-d) δ 9.00 (s, 1H), 8.20 (dd, J=1.4, 7.9 Hz, 1H), 7.57-7.51 (m, 3H), 7.49-7.45 (m, 2H), 7.44-7.35 (m, 4H), 7.29 (d, J=8.5 Hz, 2H), 7.08-7.03 (m, 1H), 5.40 (d, J=7.5 Hz, 1H), 4.98-4.83 (m, 2H), 2.84 (s, 1H).

Example 137: tert-butyl 3-hydroxy-3-((5-(2-((4-(trifluoromethyl)phenyl)amino)phenyl)-2H-tetrazol-2-yl)methyl)pyrrolidine-1-carboxylate (Compound 144)

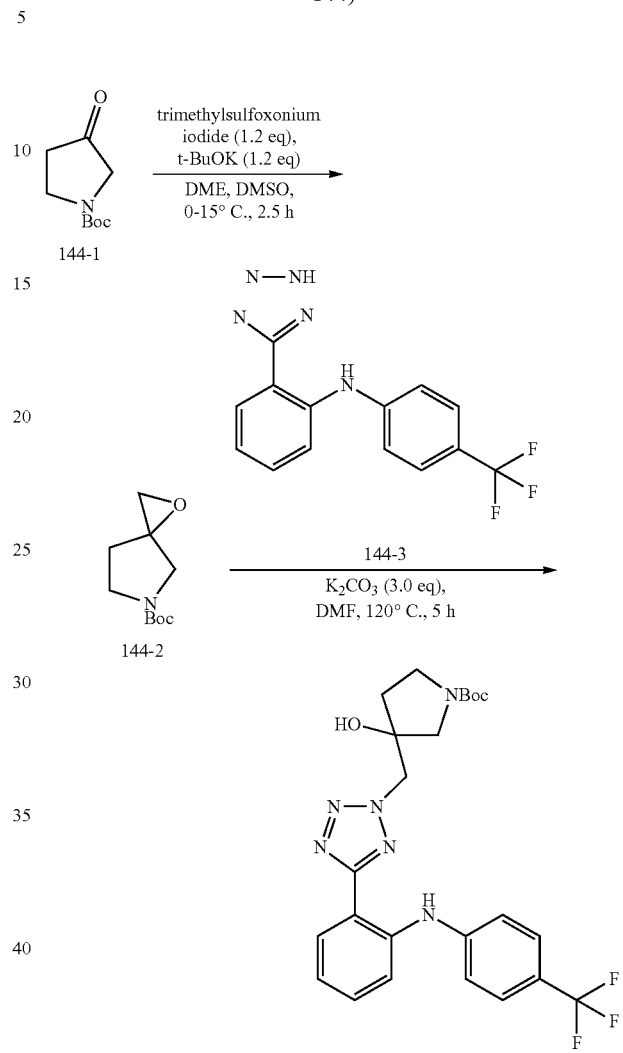

Compound 144

Step 1: tert-butyl 1-oxa-5-azaspiro[2.4]heptane-5-carboxylate

To a mixture of t-BuOK (727.1 mg, 6.5 mmol, 1.20 eq) in DMSO (10 mL), was added trimethylsulfoxonium iodine (1.4 g, 6.5 mmol, 1.20 eq) by portions. The mixture was stirred at 15° C. for 0.5 h. DME (5 mL) was added, and the mixture was cooled to 0° C. A solution of 144-1 (1.0 g, 5.4 mmol, 1.00 eq) in DMSO (2 mL) and DME (4 mL) was added dropwise at 0° C. The resulting mixture was stirred at 0° C. for 2 h. TLC showed the reaction was complete. The mixture was diluted with water (20 mL), and extracted with DCM (20 mL*3). The combined organic layers were dried over anhydrous $Na_2SO_4$, and concentrated under vacuum. The residue was purified by silica gel chromatography to provide 144-2 (200.0 mg, 1.0 mmol, 18.6% yield). $^1$HNMR (400 MHz, CHLOROFORM-d) δ 3.72-3.49 (m, 3H), 3.26 (t, J=11.4 Hz, 1H), 2.93 (s, 2H), 2.26-2.24 (m, 1H), 1.88-1.78 (m, 1H), 1.46 (s, 9H).

401

Step 2: tert-butyl 3-hydroxy-3-((5-(2-((4-(trifluoromethyl)phenyl)amino)phenyl)-2H-tetrazol-2-yl)methyl)pyrrolidine-1-carboxylate To a mixture of 144-3 (70.0 mg, 0.2 mmol, 1.00 eq) and $K_2CO_3$ (95.1 mg, 0.7 mmol, 3.00 eq) in DMF (3.0 mL), was added 144-2 (45.7 mg, 0.2 mmol, 1.00 eq). The resulting mixture was stirred at 120° C. under $N_2$ for 5 h. LCMS showed about 67% of the desired compound, and 28% starting material remained. The mixture was combined with a previous batch, and filtered. The filtrate was checked by HPLC. The filtrate was purified by prep-HPLC (basic condition) to obtain Compound 144 (37.19 mg, 73.7 umol, 32.2% yield). LCMS (ESI): RT=0.906 min, mass calc. for $C_{24}H_{27}F_3N_6O_3$ 504.21, m/z found 527.1 [M+Na]$^+$. $^1$HNMR (400 MHz, CHLOROFORM-d) δ 9.00 (s, 1H), 8.24-8.11 (m, 1H), 7.58-7.51 (m, 3H), 7.40 (t, J=7.5 Hz, 1H), 7.31 (d, J=8.3 Hz, 2H), 7.05 (t, J=7.5 Hz, 1H), 4.90 (s, 2H), 3.66-3.42 (m, 4H), 2.87 (s, 1H), 2.08-1.93 (m, 2H), 1.46 (s, 9H).

Example 138: 1-(methylsulfonyl)-3-((5-(2-((4-(trifluoromethyl)phenyl)amino)phenyl)-2H-tetrazol-2-yl)methyl)piperidin-3-ol (Compound 145)

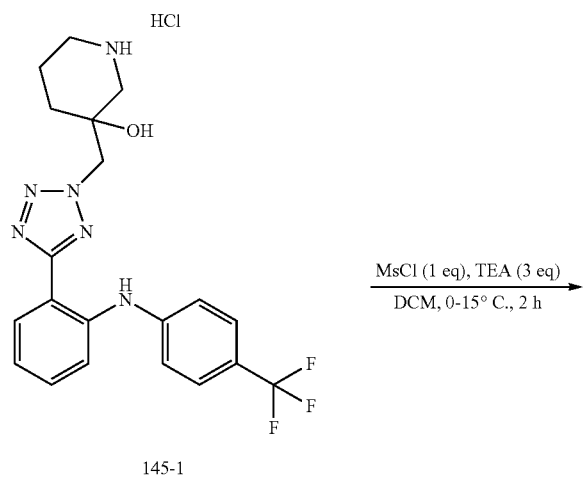

402

Step 1: 1-(methylsulfonyl)-34(5-(2-((4-(trifluoromethyl)phenyl)amino)phenyl)-2H-tetrazol-2-yl)methyl)piperidin-3-ol To a mixture of 145-1 (30.00 mg, 65.95 umol, 1.00 eq, HCl salt) in DCM (1.00 mL) was added $Et_3N$ (20.02 mg, 197.85 umol, 27.42 uL, 3.00 eq) in one portion at 0° C. The mixture was stirred at 0° C. for 10 min, and MsCl (7.55 mg, 65.95 umol, 5.10 uL, 1.00 eq) was added and the reaction stirred for 1 hour at 15° C. The mixture became a yellow solution. LCMS showed 23% of the starting material remained and 71% of desired product was formed. Then, another batch of MsCl (4 mg) was added and the resulting solution was continuously stirred at 15° C. for another 16 h. LCMS showed only a trace of starting material remained and 93% of the desired product was formed. The solution was quenched with 2 drops of water and concentrated to give a residue, which was purified by prep HPLC to give the title compound (14.00 mg, 28.20 umol, 42.75% yield). LCMS (ESI): RT=1.8 min, mass calc. for $C_{21}H_{23}F_3N_6O_3S$ 496.15, m/z found 497.00 [M+1]$^+$; $^1$HNMR (400 MHz, DMSO-$d_6$) δ 8.78 (s, 1H), 8.09 (d, J=7.5 Hz, 1H), 7.63-7.46 (m, 4H), 7.31-7.15 (m, 3H), 5.32 (s, 1H), 4.86-4.73 (m, 2H), 3.25 (d, J=12.0 Hz, 1H), 3.20-3.03 (m, 3H), 2.90 (s, 3H), 1.76 (m, 1H), 1.70-1.45 (m, 3H).

Example 139: 1-[4-hydroxy-4-[[5-[2-[4-(trifluoromethyl)anilino]phenyl]tetrazol-2-yl]methyl]-1-piperidyl]ethanone (Compound 146)

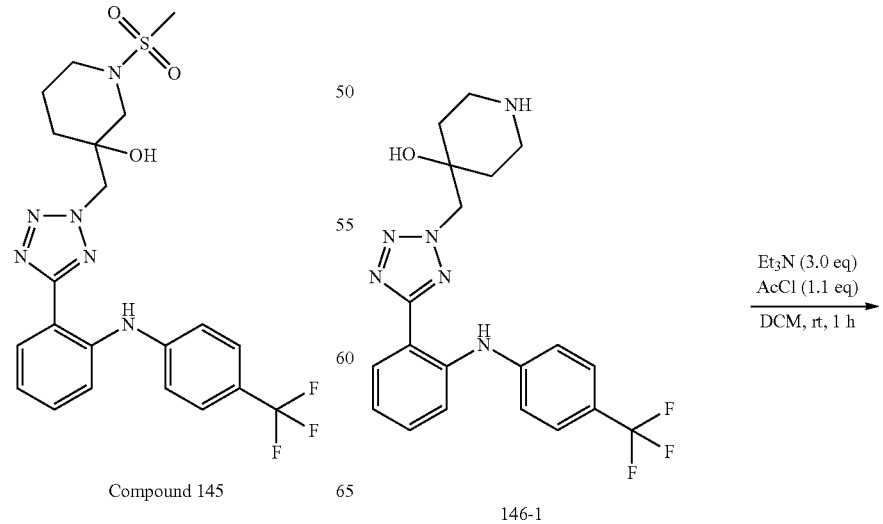

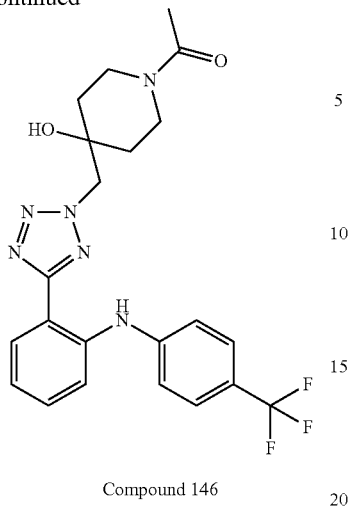

Compound 146

To a solution of 146-1 (40 mg, 95.60 umol, 1.00 eq) and Et₃N (29 mg, 0.29 mmol, 39.75 uL, 3.00 eq) in DCM (2 mL) was added AcCl (4.73 mg, 95.60 umol, 1.00 eq). The reaction was stirred at 25° C. for 1 hr. LCMS showed that the desired MS signal was detected. The reaction was concentrated. The crude product was purified by Prep-HPLC (acidic conditions) to give the title compound (11.22 mg, 23.39 umol, 24.47% yield). LCMS (ESI): RT=0.808 min, mass calc. for $C_{22}H_{23}F_3N_6O_2$ 460.17, m/z found 483.2 [M+Na]⁺. ¹HNMR (400 MHz, DMSO-$d_6$) δ 8.80 (s, 1H), 8.05 (d, J=7.2 Hz, 1H), 7.59-7.47 (m, 4H), 7.25-7.15 (m, 3H), 5.06 (br, 1H), 4.71 (s, 2H), 4.20-4.05 (m, 1H), 3.65-3.55 (m, 1H), 3.33-3.23 (m, 1H), 2.90-2.75 (m, 1H), 1.97 (s, 3H), 1.75-1.55 (m, 1H), 1.55-1.45 (m, 3H).

Example 140: tert-butyl 3-hydroxy-34(5-(2-((4-(trifluoromethyl)phenyl)amino)phenyl)-2H-tetrazol-2-yl)methyl)piperidine-1-carboxylate (Compound 147)

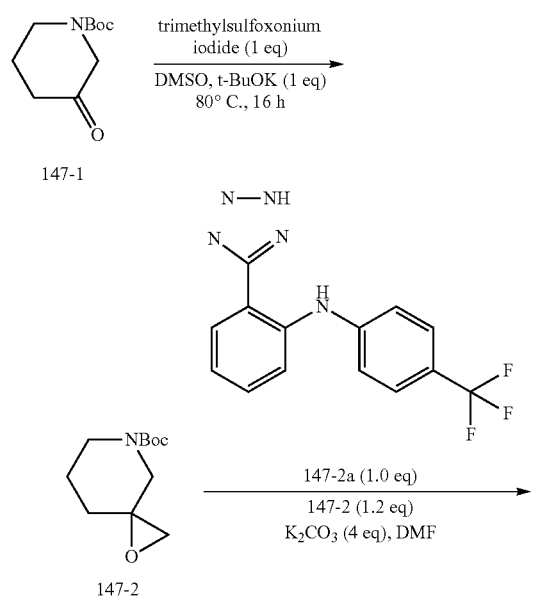

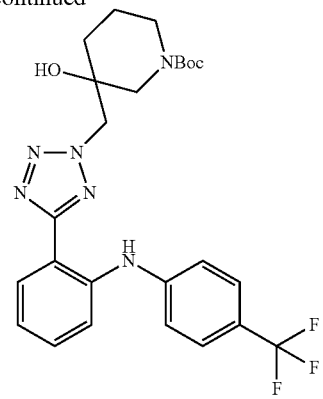

Compound 147

Step 1: tert-butyl 1-oxa-5-azaspiro[2.5]octane-5-carboxylate

To the solution of 147-1 (2.00 g, 10.04 mmol, 1.00 eq) in DME (40.00 mL) was added t-BuOK (1.13 g, 10.04 mmol, 1.00 eq) and trimethylsulfoxonium iodide (2.21 g, 10.04 mmol, 1.00 eq). Then the mixture was stirred at 80° C. for 16 hr. TLC showed some material remained and new spots were formed. The mixture was quenched with H₂O (20 mL) and extracted with EtOAc (40 mL×3). The combined organic layers were washed with brine (20 mL), dried over Na₂SO₄, filtered, and concentrated under reduced pressure to give a residue. The residue was purified by column chromatography to give 147-2 (770.00 mg, 3.61 mmol, 35.96% yield) as a colorless oil. ¹HNMR (400 MHz, CHLOROFORM-d) δ 3.50-3.40 (m, 3H), 3.39-3.31 (m, 1H), 2.76 (br s, 1H), 2.66 (d, J=4.5 Hz, 1H), 1.89-1.78 (m, 1H), 1.77-1.62 (m, 3H), 1.45 (s, 9H).

Step 2: tert-butyl 3-hydroxy-34(5-(2-((4-(trifluoromethyl)phenyl)amino)phenyl)-2H-tetrazol-2-yl)methyl)piperidine-1-carboxylate 147-2a (50.00 mg, 163.79 umol, 1.00 eq), 147-2 (61.92 mg, 290.34 umol, 1.77 eq) and K₂CO₃ (90.55 mg, 655.16 umol, 4.00 eq) were taken up into a microwave tube in DMF (2.00 mL). The sealed tube was heated at 100° C. for 30 min under microwave conditions. Then the sealed tube was heated at 150° C. for 2.5 h under microwave conditions. The crude LCMS showed the desired product MS value was detected. The reaction mixture was combined with another batch, and the mixture was filtered and concentrated under reduced pressure to give a residue. The residue was purified by prep-HPLC to give compound Compound 147 (19.00 mg, 36.64 umol, 11.19% yield). LCMS (ESI): RT=2.132 min, mass calc. for $C_{25}H_{29}F_3N_6O_3$ 518.53, m/z found 541.00 [M+23]⁺; ¹HNMR (400 MHz, DMSO-$d_6$) δ 1.17-1.71 (m, 13H), 3.12 (br s, 1H), 3.20-3.31 (m, 1H), 3.39-3.54 (m, 2H), 4.70 (s, 2H), 5.06 (s, 1H), 7.13-7.31 (m, 3H), 7.44-7.67 (m, 4H), 8.07 (d, J=7.28 Hz, 1H), 8.81 (br s, 1H).

Example 141: tert-butyl 3-hydroxy-3-[[5-[2-[4-(trifluoromethyl)anilino]phenyl]tetrazol-2-yl]methyl]azetidine-1-carboxylate (Compound 148)

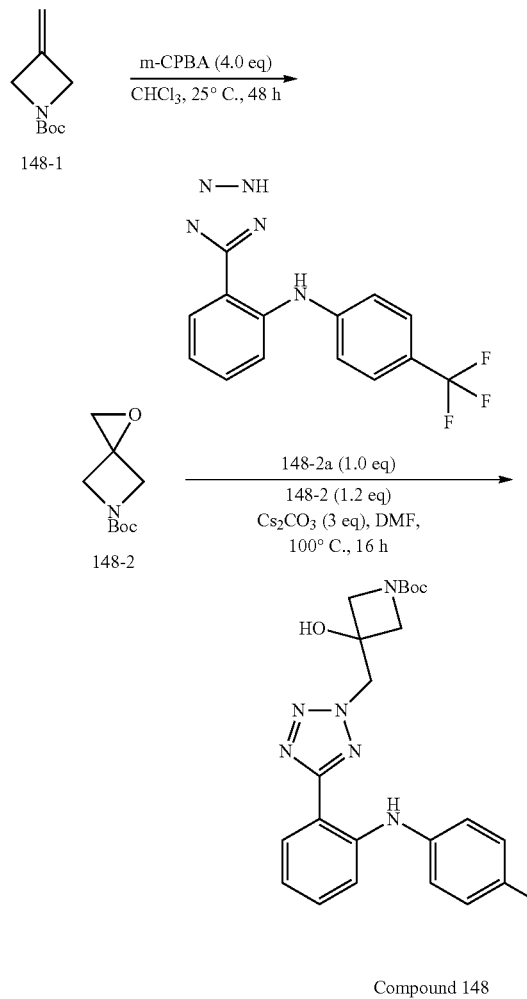

Step 1: tert-butyl 1-oxa-5-azaspiro[2.3]hexane-5-carboxylate

To a solution of 148-1 (1.0 g, 5.9 mmol, 1.0 eq) in CHCl₃ (20.0 mL) was added m-CPBA (4.1 g, 23.6 mmol, 4.0 eq). The mixture was stirred at 25° C. for 48 hours. TLC indicated 148-1 was consumed completely and one new spot formed. The reaction mixture was quenched by addition aq. Na₂SO₃ and aq. NaHCO₃ (50 mL, 1:1), then extracted with DCM (30 mL*3). The combined organic layers were washed with brine (20 mL*3), dried over Na₂SO₄, filtered, and concentrated under reduced pressure to give a residue. The residue was purified by column chromatography to give 148-2 (500.0 mg, 2.7 mmol, 45% yield) as a colorless oil. ¹HNMR (400 MHz, DCCl₃) δ (ppm) 4.29-4.23 (m, 2H), 4.23-4.17 (m, 2H), 2.86 (s, 2H), 1.46 (s, 9H).

Step 2: tert-butyl 3-hydroxy-3-[[5-[2-[4-(trifluoromethyl)anilino]phenyl]tetrazol-2-yl]methyl]azetidine-1-carboxylate To a solution of 148-2a (100.0 mg, 0.3 mmol, 1.0 eq) in DMF (3.0 mL) was added K₂CO₃ (181.1 mg, 1.3 mmol, 4.0 eq) and 148-2 (72.8 mg, 0.4 mmol, 1.2 eq). The mixture was stirred at 150° C. under microwave conditions for 1 hour. LC-MS showed 36% of 148-2 remained. Several new peaks were shown on LC-MS and 36% of the desired compound was detected. The reaction mixture was diluted with H₂O (10 mL) and extracted with EtOAc (10 mL*3). The combined organic layers were washed with brine (20 mL), dried over Na₂SO₄, filtered, and concentrated under reduced pressure to give a residue. The residue was purified by column chromatography to give Compound 148 (60.0 mg, 122.33 umol, 37% yield). LCMS (ESI): RT=0.910 min, mass calc. for C₂₃H₂₅F₃N₆O₃ 490.19, m/z found 513.1 [M+Na]⁺; ¹HNMR (400 MHz, DCCl₃) δ (ppm) 8.98 (s, 1H), 8.17-8.15 (m, J=1.3, 8.0 Hz, 1H), 7.56-7.52 (m, J=4.4, 8.2 Hz, 3H), 7.40 (t, J=7.8 Hz, 1H), 7.30 (d, J=8.3 Hz, 2H), 7.27 (s, 1H), 7.06 (t, J=7.5 Hz, 1H), 5.00 (s, 2H), 4.09 (d, J=9.8 Hz, 2H), 3.97 (d, J=9.8 Hz, 2H), 3.46 (s, 1H), 1.45 (s, 9H).

Example 142: 1-methylsulfonyl-4-[[5-[2-[4-(trifluoromethyl)anilino]phenyl]tetrazol-2-yl]methyl]piperidin-4-ol (Compound 149)

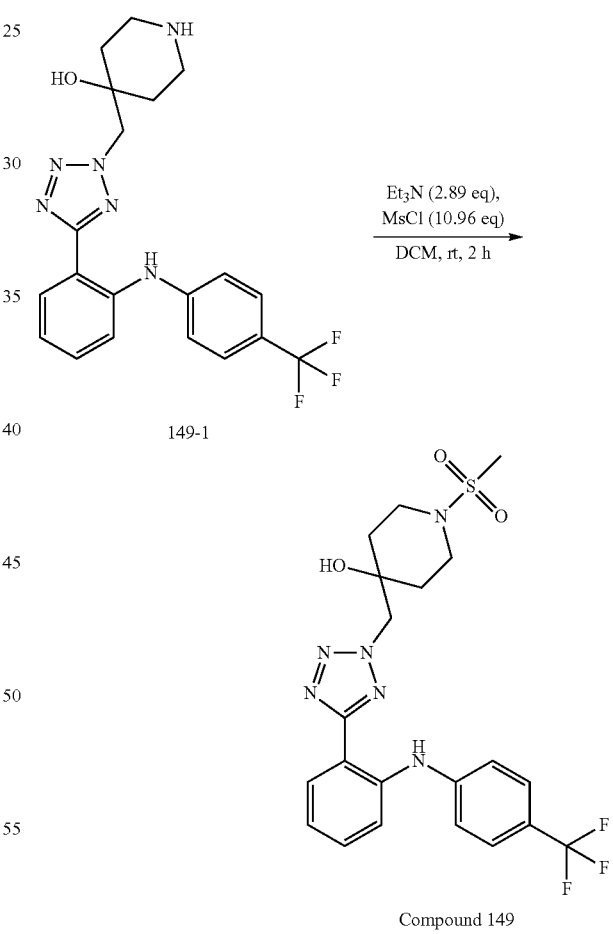

To a mixture of 149-1 (40 mg, 95.6 umol, 1.00 eq) and Et₃N (28 mg, 0.277 mmol, 38 uL, 2.89 eq) in DCM (3 mL) was added MsCl (120 mg, 1.05 mmol, 81 uL, 10.96 eq) in one portion at 15° C. under N₂. The mixture was stirred at 15° C. for 1 h. LCMS showed the starting material was nearly consumed, and one main peak with the desired MS was detected. The reaction mixture was concentrated under reduced pressure to remove the solvent. The residue was purified by prep-HPLC (basic condition) to provide the title compound (15.90 mg, 31.38 umol, 32.8% yield). LCMS (ESI): RT=0.844 min, mass calcd. for $C_{21}H_{23}F_3N_6O_3S$ 496.15, m/z found 519.1[M+23]+. 1HNMR (400 MHz, CHLOROFORM-d) δ9.00 (s, 1H), 8.17 (d, J=6.80 Hz, 1H), 7.59-7.52 (m, 3H), 7.41 (t, J=8.00 Hz, 1H), 7.30 (d, J=8.80 Hz, 2H), 7.06 (t, J=7.20 Hz, 1H), 4.76 (s, 2H), 3.68 (br d, J=11.20 Hz, 2H), 3.11-3.01 (m, 2H), 2.81 (s, 4H), 1.92-1.82 (m, 2H), 1.62 (br s, 1H).

Example 143: 1-phenyl-4-[[5-[2-[4-(trifluoromethyl) anilino]phenyl]tetrazol-2-yl]methyl]piperidin-4-ol (Compound 150)

was detected. The residue was purified by prep-HPLC to provide the title compound (10.24 mg, 20.3 umol, 10.0% yield). LCMS (ESI): RT=0.806 min, mass calcd. for $C_{26}H_{25}F_3N_6O$ 494.20, m/z found 495.2[M+23]+. 1HNMR (400 MHz, DMSO-$d_6$) δ8.80 (s, 1H), 8.07 (d, J=8.00 Hz, 1H), 7.61-7.47 (m, 4H), 7.26-7.14 (m, 5H), 6.92 (d, J=8.00 Hz, 2H), 6.74 (t, J=7.40 Hz, 1H), 4.93 (s, 1H), 4.74 (s, 2H), 3.44 (br d, J=12.00 Hz, 2H), 2.98 (br t, J=11.20 Hz, 2H), 1.82-1.69 (m, 2H), 1.59 (br d, J=12.40 Hz, 2H).

Example 144: 3-[[5-[2-[4-(trifluoromethyl)anilino] phenyl]tetrazol-2-yl]methyl]tetrahydro furan-3-ol (Compound 151)

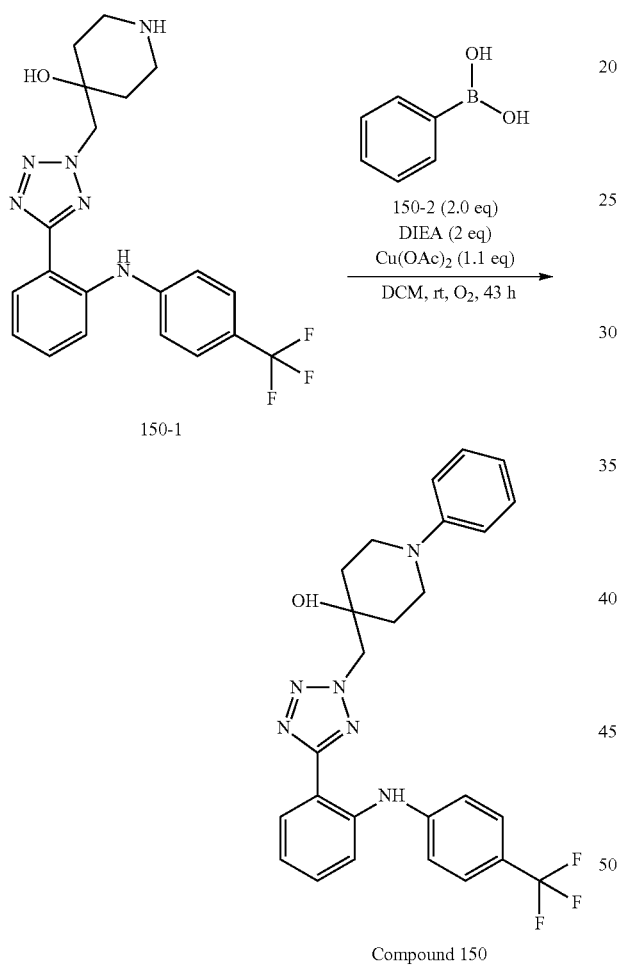

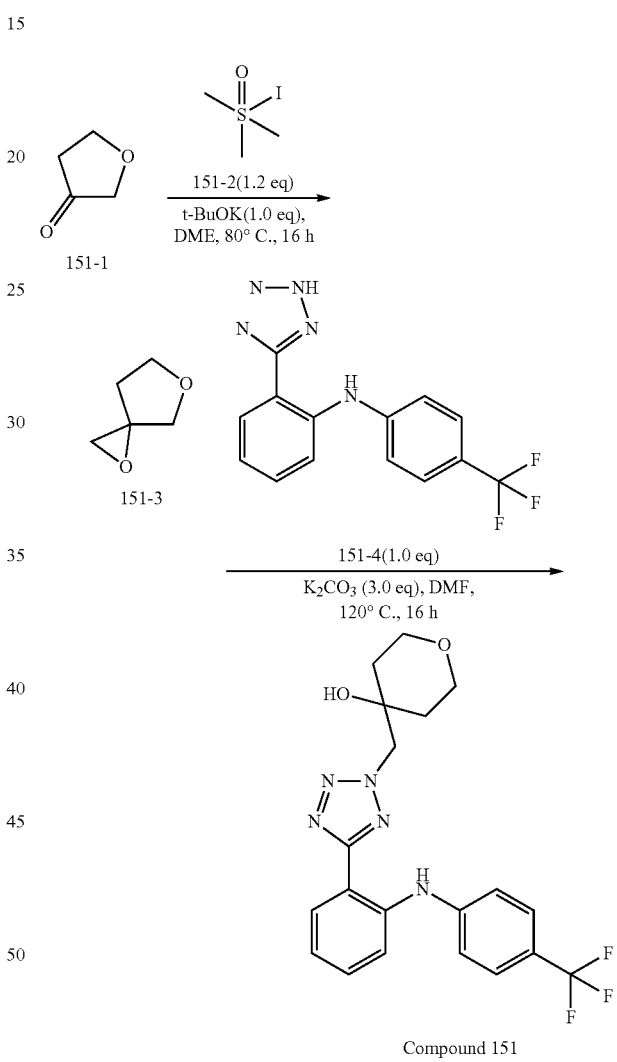

To a mixture of 150-1 (100 mg, 0.204 mmol, 1.00 eq, 2HCl) and 150-2 (50 mg, 0.407 mmol, 2.00 eq) in DCM (2 mL) was added Cu(OAc)₂ (37 mg, 0.204 mmol, 1.00 eq) in one portion at 15° C. under O₂. The mixture was stirred at 15° C. for 27 h. LCMS showed 38% of 150-1 remained. Several new peaks were detected on LCMS and 30% of the desired compound was detected. The reaction mixture was stirred an additional 16 h. The reaction mixture was filtered and concentrated under reduced pressure to give a residue. LCMS showed 41% of 150-1 remained. Several new peaks were detected on LCMS and 47% of the desired compound was detected. HPLC indicated 52% of the desired compound Step 1: 1,6-dioxaspiro[2.4]heptane Compound t-BuOK (782.0 mg, 6.9 mmol, 1.2 eq) were added in DMSO (10.0 mL) and the mixture cooled to around 20° C. with stirring. 151-2 (1.3 g, 5.8 mmol, 1.0 eq) was added in portions over a period of 15 min, maintaining the reaction temperature between 20-25° C. On completion of the addition, the mixture was maintained at this temperature until a yellow solution was obtained (1 h). DME (2.0 mL) was added to the reaction flask and the solution cooled to 0-5° C. A pre-cooled solution of 151-1 (500.0 mg, 5.8 mmol, 1.0 eq) in a mixture of DME (2.0 mL) and DMSO (1.0 mL) was transferred into the reaction mixture over a period of around 45 min, maintaining the reaction temperature between 0-5° C. On completion of the addition, the reaction mixture was held at this temperature for a further 1 h. TLC (Petroleum ether:Ethyl acetate=10/1) showed no new spots. The product was directly used as a solution in DMSO without further purification. 151-3 (500.0 mg, 5.0 mmol, 85.9% yield) was obtained in DMSO (11.0 mL).

Step 2: 3-[[5-[2-[4-(trifluoromethyl)anilino]phenyl]tetrazol-2-yl]methyl]tetrahydrofuran-3-ol To a solution of 151-4 (30.0 mg, 98.3 umol, 1.0 eq) in DMF (5.0 mL) was added K₂CO₃ (27.2 mg, 0.20 mmol, 2.0 eq) and 151-3 (9.8 mg, 98.3 umol, 1.0 eq). The mixture was stirred at 120° C. for 16 hours under an N₂ atmosphere. LCMS showed the desired compound was formed. The reaction was filtered to give a crude product. The crude product was purified by prep-HPLC to give Compound 151 (6.93 mg, 17.10 umol, 17.39% yield). LCMS (ESI): RT=0.849 min, mass calc. for $C_{19}H_{18}F_3N_5O_2$ 405.14, m/z found 406.1 [M+H]⁺; ¹HNMR (400 MHz, CDCl₃-d) δ 9.02 (s, 1H), 8.18 (d, J=6.8 Hz, 1H), 7.55 (dd, J=2.3, 8.5 Hz, 3H), 7.40 (t, J=7.8 Hz, 1H), 7.30 (d, J=8.5 Hz, 2H), 7.06 (t, J=7.7 Hz, 1H), 5.02-4.84 (m, 2H), 4.11-3.98 (m, 2H), 3.93 (d, J=9.8 Hz, 1H), 3.79 (d, J=9.8 Hz, 1H), 2.95 (s, 1H), 2.18-2.09 (m, 1H), 2.07-2.00 (m, 1H).

Example 145: 1-((5-(2-((4-(Trifluoromethyl)phenyl)amino)phenyl)-2H-tetrazol-2-yl)methyl)cyclopentanol (Compound 152)

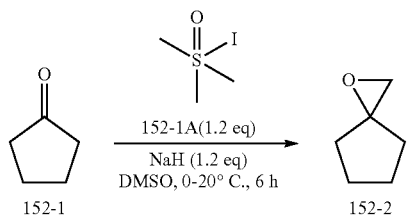

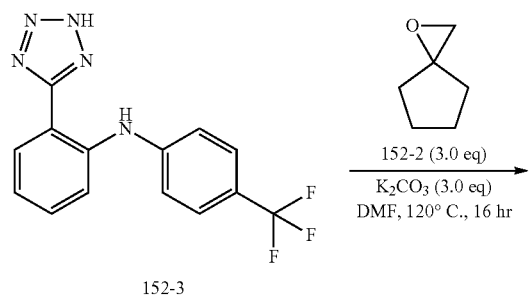

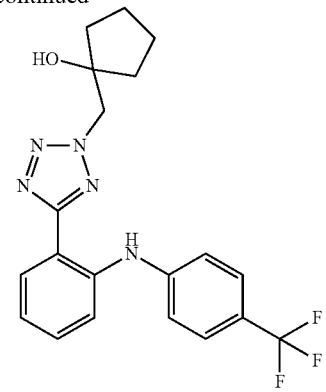

Compound 152

Step 1: 1-Oxaspiro[2.4]heptane

NaH (571 mg, 14.3 mmol, 60% purity, 1.2 eq) was added to a solution of compound 152-1A (3.1 g, 14 mmol, 1.2 eq) in DMSO (20 mL) at 0° C. The reaction mixture was stirred at 20° C. for 1 hour. 152-1 (1.0 g, 12 mmol, 1.0 eq) in DMSO (4 mL) was added dropwise. The reaction mixture was stirred at 20° C. for 5 hours. The reaction was quenched by addition of water (30 mL) and then extracted with Et₂O (80 mL). The organic extract was washed with water (2*30 mL), dried over Na₂SO₄, filtered, and concentrated to dryness under reduced pressure to obtain the title compound (700 mg, crude) as yellow oil. ¹HNMR (400 MHz, CDCl₃-d) δ 2.84 (s, 2H), 1.91-1.82 (m, 4H), 1.74-1.62 (m, 4H).

Step 2: 1-((5-(2-((4-(Trifluoromethyl)phenyl)amino)phenyl)-2H-tetrazol-2-yl)methyl) Cyclopentanol To a solution of 152-3 (100 mg, 0.328 mmol, 1.0 eq) and 152-2 (96 mg, 0.98 mmol, 3.0 eq) in DMF (4 mL) was added K₂CO₃ (136 mg, 0.983 mmol, 3.0 eq). The reaction mixture was stirred at 120° C. for 16 hours. The reaction mixture was concentrated under reduced pressure. The mixture was diluted with water (10 mL) and the resultant mixture was extracted with DCM (30 mL*3). The combined organic layers were dried over Na₂SO₄, filtered, and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely to obtain Compound 152 (18.81 mg, 14% yield). LCMS (ESI): RT=0.727 min, mass calc. for $C_{20}H_{20}F_3N_5O$ 403.16, m/z found 404.1 [M+H]⁺, ¹HNMR (400 MHz, DMSO-d₆) δ 8.83 (s, 1H), 8.07 (d, J=7.3 Hz, 1H), 7.56 (d, J=8.5 Hz, 3H), 7.53-7.46 (m, 1H), 7.25-7.17 (m, 3H), 4.82-4.72 (m, 3H), 1.79-1.64 (m, 4H), 1.63-1.50 (m, 4H).

Example 146: 3-((5-(2-((4-(trifluoromethyl)phenyl)amino)phenyl)-2H-tetrazol-2-yl)methyl)pyrrolidin-3-ol (Compound 153)

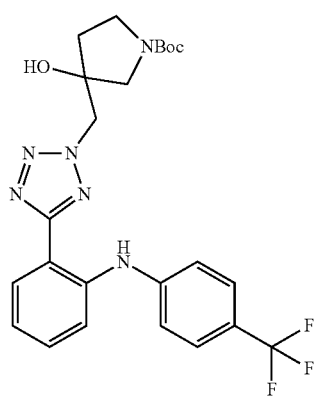

153-1

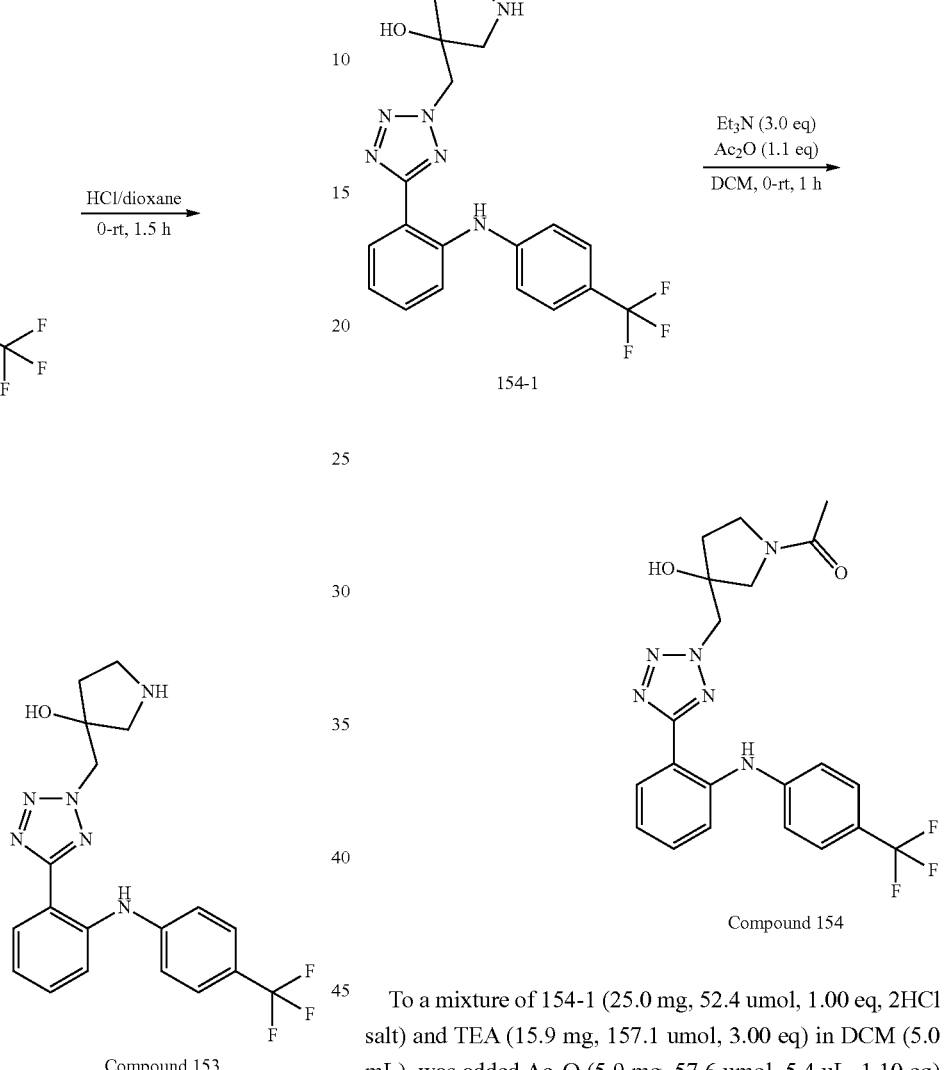

Compound 153

To a mixture of 153-1 (35.0 mg, 69.4 umol, 1.00 eq) in dioxane (2.0 mL), was added HCl/dioxane (4 M, 3.0 mL, 172.96 eq) at 0° C. The mixture was stirred at 15° C. for 1.5 h. LCMS showed the reaction was complete. The mixture was concentrated under vacuum to provide the title compound (27.78 mg, 55.3 umol, 79.7% yield, 2HCl salt). LCMS (ESI): RT=0.722 min, mass calc. for $C_{19}H_{19}F_3N_6O$ 404.16, m/z found 405.0 [M+H]$^+$. $^1$HNMR (400 MHz, DMSO-$d_6$) δ 9.22 (s, 2H), 8.77 (s, 1H), 8.06 (d, J=7.8 Hz, 1H), 7.59-7.54 (m, 3H), 7.54-7.48 (m, 1H), 7.25-7.18 (m, 3H), 5.74 (s, 1H), 5.02 (s, 2H), 4.47 (s, 1H), 3.44-3.41 (m, 1H), 3.31-3.21 (m, 2H), 3.19 (d, J=12.0 Hz, 1H), 2.19-2.08 (m, 1H), 2.01-1.95 (m, 1H).

Example 147: 1-(3-hydroxy-3-((5-(2-((4-(trifluoromethyl)phenyl)amino)phenyl)-2H-tetrazol-2-yl)methyl)pyrrolidin-1-yl)ethanone (Compound 154)

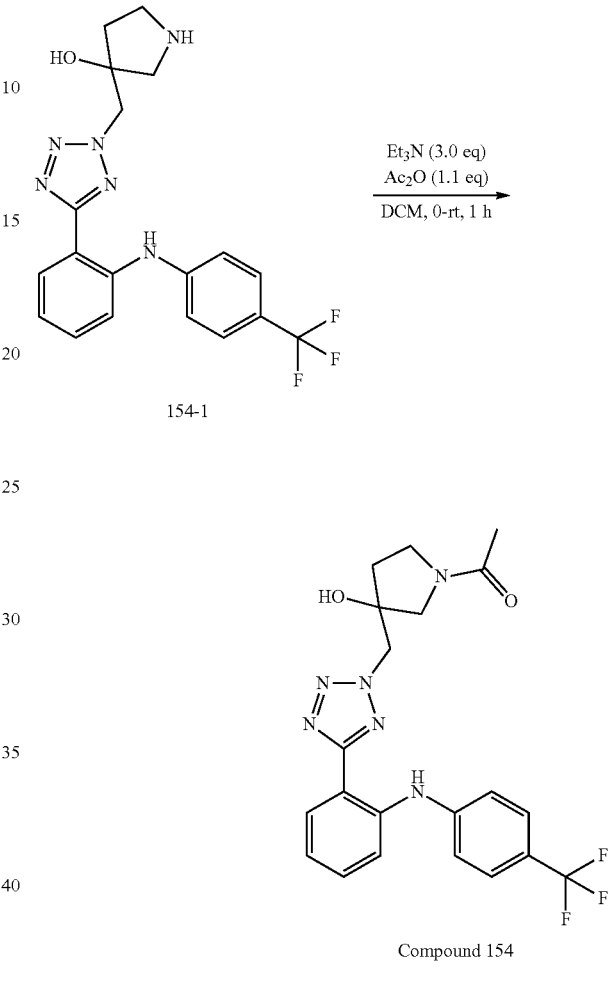

To a mixture of 154-1 (25.0 mg, 52.4 umol, 1.00 eq, 2HCl salt) and TEA (15.9 mg, 157.1 umol, 3.00 eq) in DCM (5.0 mL), was added Ac$_2$O (5.9 mg, 57.6 umol, 5.4 uL, 1.10 eq) at 0° C. The resulting mixture was stirred at 15° C. for 1 h. LCMS showed the reaction was complete. The mixture was diluted with water (10 mL), and extracted with DCM (10 mL*3). The organic layer was dried over anhydrous Na$_2$SO$_4$, concentrated under vacuum. The residue was purified by prep-HPLC (acidic conditions) to provide the title compound (10.78 mg, 22.9 umol, 43.8% yield). LCMS (ESI): RT=0.804 min, mass calc. for $C_{21}H_{21}F_3N_6O_2$ 446.17, m/z found 469.1 [M+Na]$^+$. $^1$HNMR (400 MHz, DMSO-$d_6$) δ 8.77 (d, J=11.3 Hz, 1H), 8.07 (d, J=7.8 Hz, 1H), 7.56 (d, J=8.3 Hz, 3H), 7.53-7.47 (m, 1H), 7.28-7.17 (m, 3H), 4.92 (d, J=3.5 Hz, 2H), 3.70 (d, J=10.8 Hz, 1H), 3.39 (d, J=11.0 Hz, 2H), 3.33-3.23 (m, 1H), 2.16-1.97 (m, 1H), 1.95-1.80 (m, 4H).

Example 148: 1-(3-hydroxy-3-((5-(2-((4-(trifluoromethyl) phenyl) amino) phenyl)-2H-tetrazol-2-yl) methyl) piperidin-1-yl) Ethanone (Compound 155)

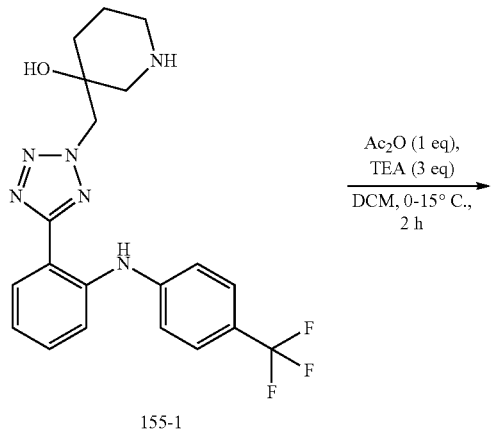

155-1

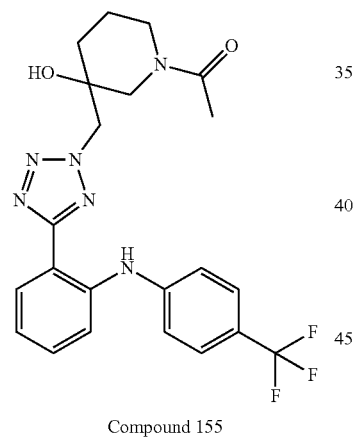

Compound 155

To a mixture of compound 155-1 (30.00 mg, 65.95 umol, 1.00 eq, HCl) and TEA (20.02 mg, 197.85 umol, 27.42 uL, 3.00 eq) in DCM (1.00 mL) was added Ac$_2$O (6.73 mg, 65.95 umol, 6.18 uL, 1.00 eq) in one portion stirred at 0° C. for 15 min. The mixture was stirred at 15° C. for 70 h. The crude LCMS showed the desired compound was detected. The reaction mixture was concentrated under reduced pressure to give a residue. The residue was purified by prep-HPLC to give the title compound (7.14 mg, 15.51 umol, 23.51% yield). LCMS (ESI): RT=0.818 min, mass calc. for C$_{22}$H$_{23}$F$_3$N$_6$O$_2$ 460.45, m/z found 483.1 [M+23]$^+$; $^1$HNMR (400 MHz, CHLOROFORM-d) δ 1.66 (s, 1H), 1.72-2.03 (m, 4H), 2.15 (s, 4H), 3.28 (s, 2H), 3.61 (s, 1H), 3.89-4.19 (m, 1H), 4.78 (s, 2H), 7.04 (t, J=7.28 Hz, 1H), 7.30 (d, J=8.28 Hz, 2H), 7.38 (t, J=7.65 Hz, 1H), 7.53 (d, J=8.28 Hz, 3H), 8.19 (d, J=7.78 Hz, 1H).

Example 149: 3-((5-(2-((4-(trifluoromethyl) phenyl) amino) phenyl)-2H-tetrazol-2-yl) methyl) piperidin-3-ol (Compound 156)

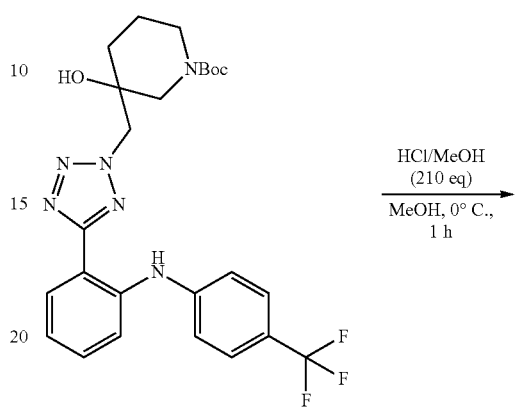

156-1

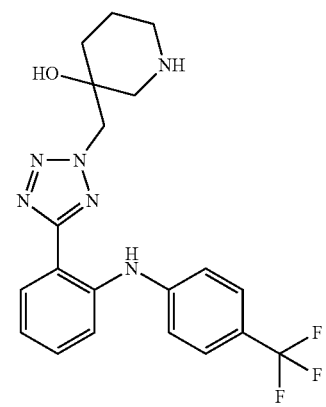

Compound 156

To a mixture of compound 156-1 (16.00 mg, 30.86 umol, 1.00 eq) in MeOH (2.00 mL) was added HCl/MeOH (4 M, 1.62 mL, 210.00 eq) at 0° C., The mixture was stirred at 15° C. for 23 hr. The crude LCMS showed the desired product was detected. The reaction mixture was concentrated under reduced pressure to give a residue. The residue was purified by prep-HPLC to give the title compound (2.17 mg, 5.03 umol, 16.30% yield). LCMS (ESI): RT=0.743 min, mass calc. for C$_{20}$H$_{21}$F$_3$N$_6$O 418.42, m/z found 419.2 [M+1]$^+$; $^1$HNMR (400 MHz, DMSO-d$_6$) δ 1.38-1.63 (m, 4H), 2.57-2.67 (m, 4H), 2.76 (d, J=12.05 Hz, 1H), 4.67-4.96 (m, 3H), 7.12-7.28 (m, 3H), 7.43-7.67 (m, 4H), 8.06 (d, J=6.78 Hz, 1H), 8.82 (br s, 1H).

Example 150: 3-[[5-[2-[4-(trifluoromethyl)anilino]phenyl]tetrazol-2-yl]methyl]azetidin-3-ol (Compound 157)

Example 151: (R)-4-((5-(2-((4-(trifluoromethyl)phenyl)amino)phenyl)-2H-tetrazol-2-yl)methyl)oxazolidin-2-one (Compound 158)

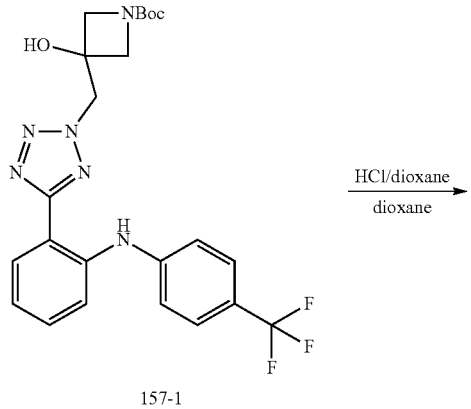

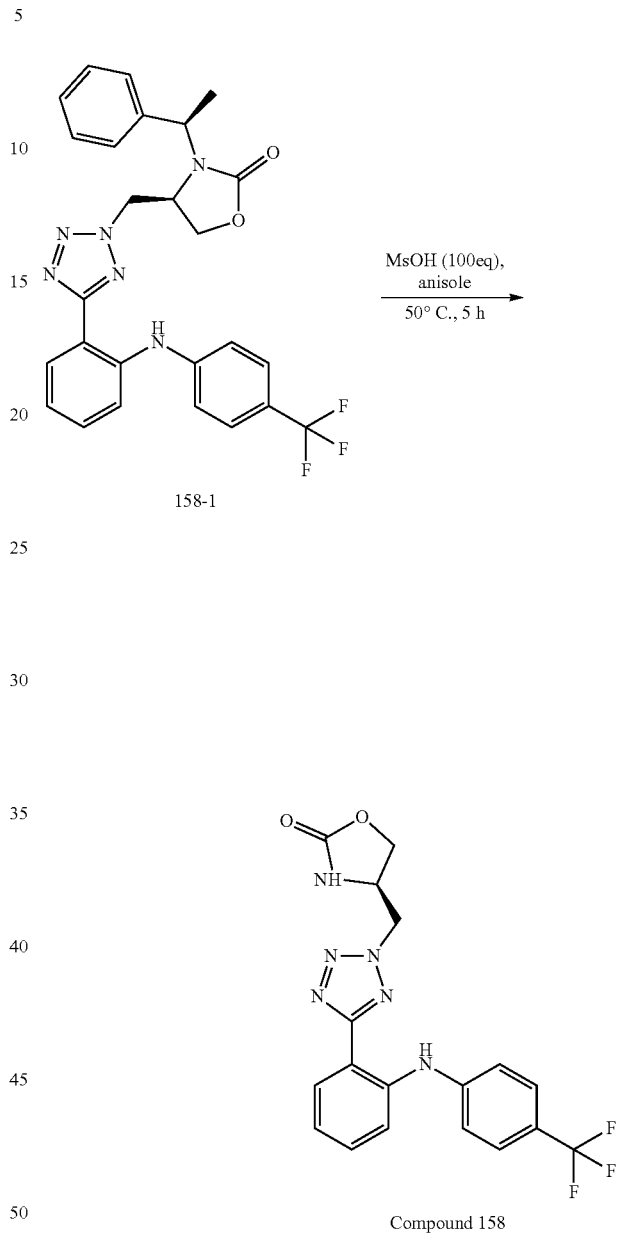

To a solution of 157-1 (20.0 mg, 40.78 umol, 1.0 eq) in dioxane (0.5 mL) was added HCl/dioxane (1.0 mL). The mixture was stirred at 25° C. for 0.1 h. LC-MS showed 157-1 was consumed completely. Several new peaks were detected on LC-MS and 81% of the desired compound was detected. The pH of the reaction mixture was adjusted with aq. NaHCO$_3$ to 7-8, and then extracted with EtOAc (10 mL*3). The combined organic layers were washed with brine (20 mL), dried over Na$_2$SO$_4$, filtered, and concentrated under reduced pressure to give a residue. The residue was purified by prep-HPLC to give the title compound (2.70 mg, 6.92 umol, 17% yield). LCMS (ESI): RT=0.738 min, mass calc. for C$_{18}$H$_{17}$F$_3$N$_6$O$_3$ 390.14, m/z found 371.2 [M−F]$^+$; $^1$HNMR (400 MHz, DCCl$_3$) δ (ppm) 8.80 (s, 1H), 8.06 (d, J=7.5 Hz, 1H), 7.60-7.52 (m, 3H), 7.52-7.45 (m, 1H), 7.26-7.15 (m, 3H), 5.85 (s, 1H), 4.96 (s, 2H), 3.51 (d, J=7.5 Hz, 2H), 3.43 (d, J=7.8 Hz, 2H).

A mixture of 158-1 (13 mg, 26 umol, 1.0 eq) and MsOH (246 mg, 2.56 mmol, 182 uL, 100.0 eq) in anisole (260 mg, 2.4 mmol, 260 uL, 94 eq) was stirred at 50° C. for 16 hours. LCMS showed 12% of the desired compound was formed and the starting material was consumed completely. The mixture was combined with another batch and concentrated under vacuum to give a residue. The residue was purified by prep-HPLC to give the title compound (9 mg, 20 umol, 78% yield, HCl salt). LCMS (ESI): RT=0.838 min, mass calc. for C$_{18}$H$_{15}$F$_3$N$_6$O$_2$ 404.12, m/z found 427.0 [M+23]$^+$; $^1$HNMR (400 MHz, DMSO-d$_6$) δ 8.69 (s, 1H), 8.07 (d, J=7.5 Hz, 1H), 7.97 (s, 1H), 7.57 (d, J=8.5 Hz, 3H), 7.54-7.47 (m, 1H), 7.28-7.16 (m, 3H), 4.89 (d, J=5.0 Hz, 2H), 4.50-4.36 (m, 2H), 4.25 (dd, J=3.6, 8.2 Hz, 1H).

Example 152: 1-(methylsulfonyl)-3-((5-(2-((4-(trifluoromethyl)phenyl)amino)phenyl)-2H-tetrazol-2-yl)methyl)pyrrolidin-3-ol (Compound 159)

Example 153: [1-methylsulfonyl-3-[[5-[2-[4-(trifluoromethyl)anilino]phenyl]tetrazol-2-yl]methyl]azetidin-3-yl]methanesulfonate (Compound 160)

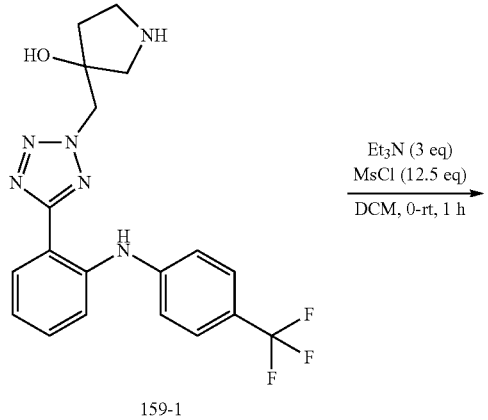

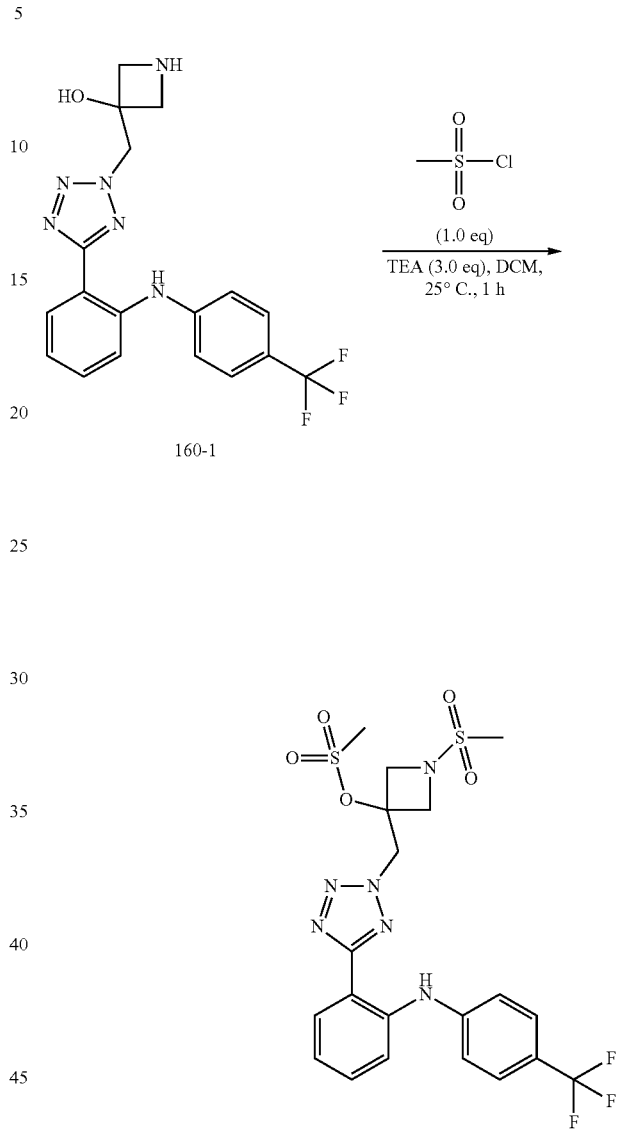

To a mixture of 159-1 (30.0 mg, 62.9 umol, 1.00 eq, 2HCl) and TEA (19.1 mg, 0.2 mmol, 3.00 eq) in DCM (5.0 mL), was added MSCl (90.0 mg, 0.8 mmol, 60.8 uL, 12.50 eq) at 0° C. The resulting mixture was stirred at 15° C. for 1 h. LCMS and HPLC showed the reaction was completed. The mixture was diluted with water (10 mL), and extracted with DCM (10 mL*3). The organic layer was dried over anhydrous $Na_2SO_4$, and concentrated under vacuum. The residue was purified by prep-HPLC (acidic_HCl condition) to provide the title compound (7.32 mg, 15.2 umol, 24.1% yield). LCMS (ESI): RT=0.837 min, mass calc. for $C_{20}H_{21}F_3N_6O_3S$ 482.13, m/z found 483.1 [M+H]$^+$. $^1$HNMR (400 MHz, DMSO-$d_6$) δ 8.76 (s, 1H), 8.07 (dd, J=1.3, 7.8 Hz, 1H), 7.59-7.54 (m, 3H), 7.53-7.47 (m, 1H), 7.25-7.17 (m, 3H), 5.40 (s, 1H), 4.95 (s, 2H), 3.57 (d, J=11.0 Hz, 1H), 3.44-3.40 (m, 1H), 3.33-3.28 (m, 2H), 2.86 (s, 3H), 2.16-2.08 (m, 1H), 1.90 (dd, J=6.4, 12.7 Hz, 1H).

To a solution of 160-1 (70.0 mg, 0.2 mmol, 1.00 eq) in DCM (3.0 mL) was added TEA (54.4 mg, 0.5 mmol, 74.5 uL, 3.0 eq) and methanesulfonyl chloride (120.0 mg, 1.0 mmol, 81.0 uL, 5.8 eq). The mixture was stirred at 25° C. for 1 hour. LC-MS showed 160-1 was consumed completely and one main peak with the desired MS was detected. The residue was purified by prep-HPLC to give the title compound (5.59 mg, 10.3 umol, 5.7% yield). LCMS (ESI): RT=0.836 min, mass calc. for $C_{20}H_{21}F_3N_6O_5S_2$ 546.10, m/z found 569.1 [M+Na]$^+$; $^1$HNMR (400 MHz, DMSO-$d_6$) δ (ppm) 8.68 (s, 1H), 8.08 (d, J=7.5 Hz, 1H), 7.60-7.48 (m, 4H), 7.28-7.13 (m, 3H), 5.49 (s, 2H), 4.32 (s, 4H), 3.33 (s, 3H), 3.14 (s, 3H).

Example 154: 1-[3-hydroxy-3-[[5-[2-[4-(trifluoromethyl)anilino]phenyl]tetrazol-2-yl]methyl]azetidin-1-yl]ethanone (Compound 161)

Example 155: [1-acetyl-3-[[5-[2-[4-(trifluoromethyl)anilino]phenyl]tetrazol-2-yl]methyl]azetidin-3-yl] acetate (Compound 162)

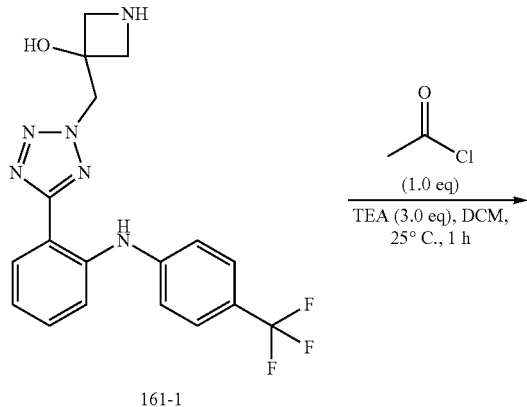

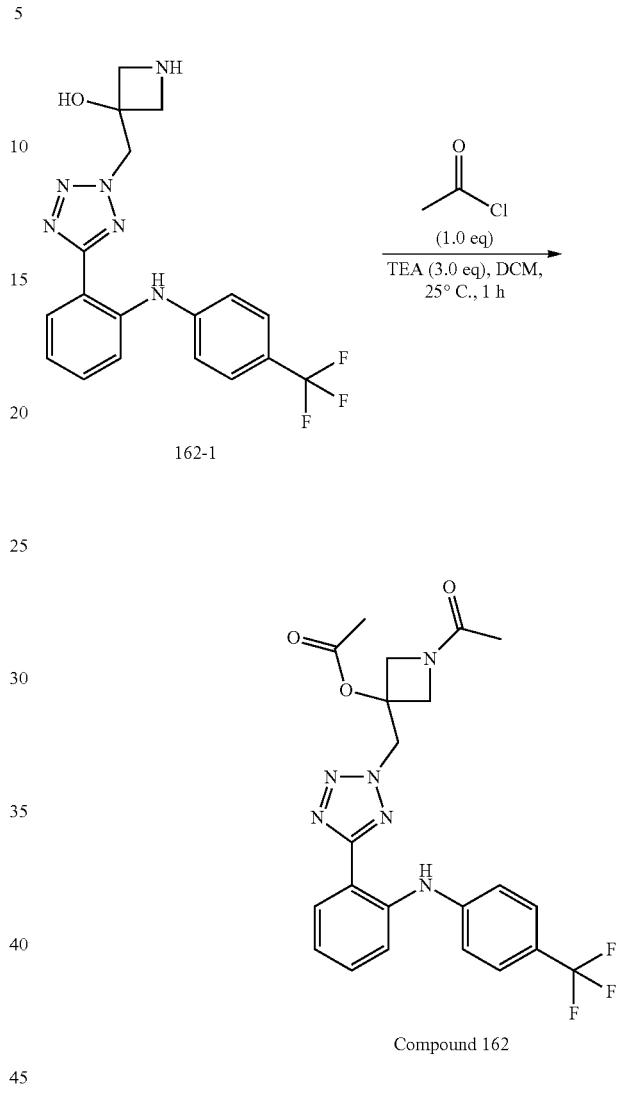

To a solution of 161-1 (60.0 mg, 0.2 mmol, 1.0 eq) in DCM (2.0 mL) was added TEA (46.6 mg, 0.5 mmol, 63.9 uL, 3.0 eq) and acetyl chloride (12.0 mg, 0.2 mmol, 10.9 uL, 1.0 eq) at 0° C. The mixture was stirred at 25° C. for 1 hour. LC-MS showed 22% of 161-1 remained. Several new peaks were detected on LC-MS and 34% of the desired compound was detected. The residue was purified by prep-HPLC to give the title compound (7.73 mg, 17.88 umol, 11% yield). LCMS (ESI): RT=0.821 min, mass calc. for $C_{20}H_{19}F_3N_6O_2$ 432.15, m/z found 455.1 [M+Na]$^+$; (400 MHz, DMSO-$d_6$) δ (ppm) 8.75 (s, 1H), 8.07 (d, J=7.8 Hz, 1H), 7.56 (d, J=8.3 Hz, 3H), 7.53-7.46 (m, 1H), 7.26-7.18 (m, 3H), 6.25 (s, 1H), 5.03 (s, 2H), 4.42 (d, J=9.0 Hz, 1H), 4.14 (d, J=10.3 Hz, 1H), 3.95 (d, J=9.3 Hz, 1H), 3.68 (d, J=10.0 Hz, 1H), 1.77 (s, 3H).

To a solution of 162-1 (60.0 mg, 0.2 Mmol, 1.0 eq) in DCM (2.0 mL) was added TEA (46.6 mg, 0.5 mmol, 63.9 uL, 3.0 eq) and acetyl chloride (12.0 mg, 0.2 mmol, 10.9 uL, 1.0 eq) at 0° C. The mixture was stirred at 25° C. for 1 hour. LC-MS showed 22% of 162-1 remained. Several new peaks were detected on LC-MS and 34% of the desired compound was detected. The reaction mixture was purified by prep-HPLC to give the title compound (3.52 mg, 7.42 umol, 5% yield). LCMS (ESI): RT=0.872 min, mass calc. for $C_{22}H_{21}F_3N_6O_3$ 474.16, m/z found 497.1 [M+Na]$^+$; $^1$HNMR (400 MHz, DMSO-$d_6$) δ (ppm) 8.70 (s, 1H), 8.05 (d, J=7.5 Hz, 1H), 7.58-7.51 (m, 4H), 7.23 (t, J=7.7 Hz, 1H), 7.17 (d, J=8.5 Hz, 2H), 5.47-5.35 (m, 2H), 4.50 (d, J=10.3 Hz, 1H), 4.26-4.22 (m, J=5.4, 10.2 Hz, 2H), 3.90 (d, J=11.0 Hz, 1H), 1.93 (s, 3H), 1.79 (s, 3H).

Example 156: 1-phenyl-3-[[5-[2-[4-(trifluoromethyl)anilino]phenyl]tetrazol-2-yl]methyl]azetidin-3-ol (Compound 163)

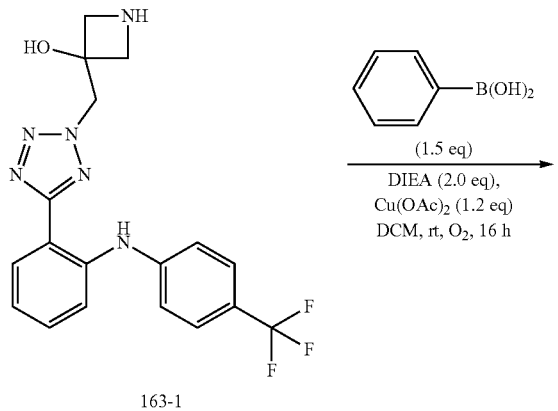

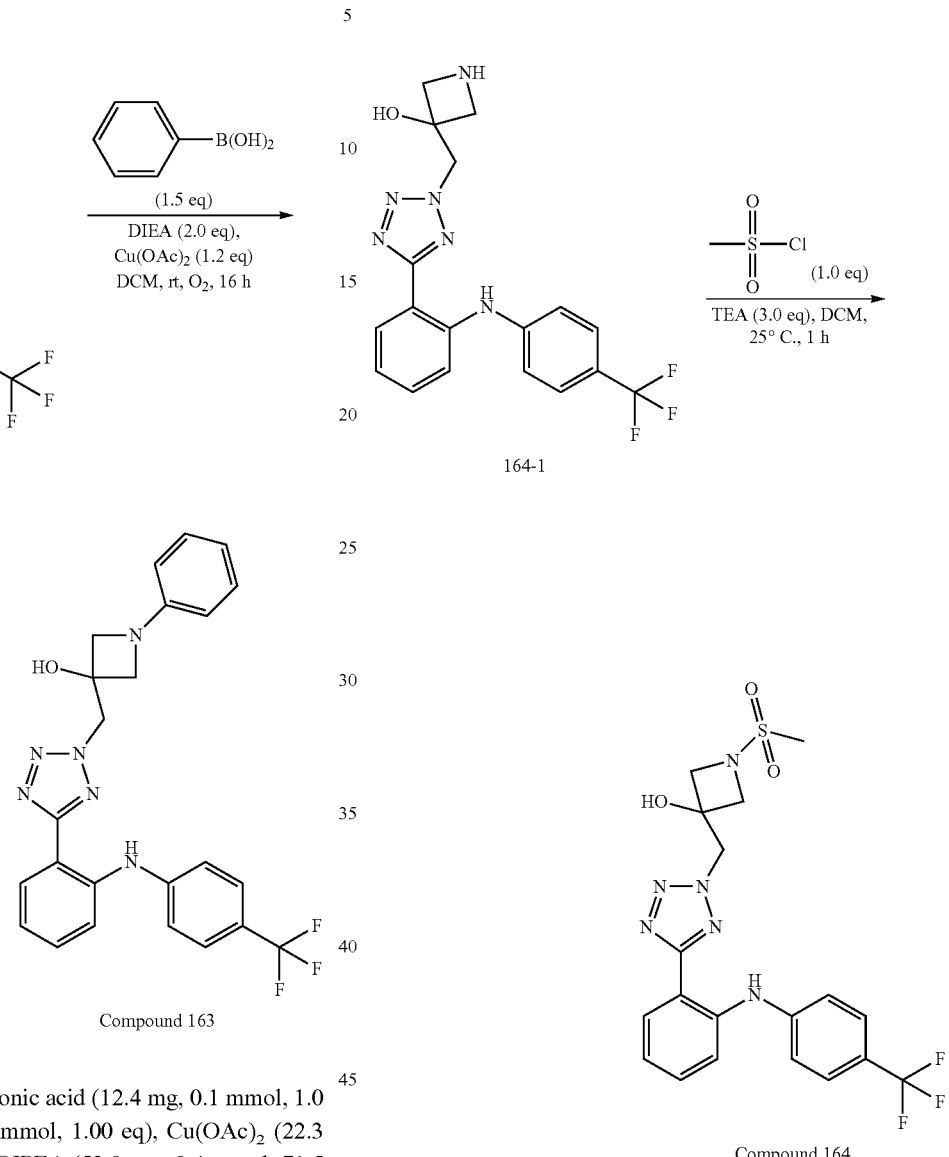

A mixture of phenylboronic acid (12.4 mg, 0.1 mmol, 1.0 eq), 163-1 (40.0 mg, 0.1 mmol, 1.00 eq), Cu(OAc)$_2$ (22.3 mg, 0.1 mmol, 1.20 eq), DIPEA (52.9 mg, 0.4 mmol, 71.5 uL, 4.0 eq) in DCM (2.0 mL) was degassed and purged with O$_2$ 3 times, and then the mixture was stirred at 40° C. for 16 hr under an O$_2$ (15 psi) atmosphere. LC-MS showed 163-1 was consumed completely and 24% of the desired compound was detected. The reaction mixture was washed with brine (10 mL*3), dried over Na$_2$SO$_4$, filtered, and concentrated under reduced pressure to give a residue. The residue was purified by prep-TLC to give the title compound (6.86 mg, 14.41 umol, 14% yield). LCMS (ESI): RT=0.907 min, mass calc. for C$_{24}$H$_{21}$F$_3$N$_6$O$_3$ 466.17, m/z found 467.0 [M+H]$^+$; $^1$HNMR (400 MHz, DMSO-d$_6$) δ (ppm) 8.77 (s, 1H), 8.09 (d, J=6.8 Hz, 1H), 7.63-7.54 (m, 3H), 7.53-7.48 (m, 1H), 7.26-7.20 (m, 3H), 7.17 (t, J=7.8 Hz, 2H), 6.70 (t, J=7.2 Hz, 1H), 6.44 (d, J=7.8 Hz, 2H), 6.16 (s, 1H), 5.07 (s, 2H), 4.16 (d, J=8.0 Hz, 2H), 3.61 (d, J=8.0 Hz, 2H).

Example 157: 1-methylsulfonyl-3-[[5-[2-[4-(trifluoromethyl)anilino]phenyl]tetrazol-2-yl]methyl]azetidin-3-ol (Compound 164)

To a solution of 164-1 (40.0 mg, 0.1 mmol, 1.00 eq) in DCM (2.0 mL) was added TEA (25.9 mg, 0.3 mmol, 35.5 uL, 2.5 eq) and methanesulfonyl chloride (11.7 mg, 0.1 mmol, 7.9 uL, 1.0 eq) at 0° C. The mixture was stirred at 25° C. for 0.5 hour. LC-MS showed 164-1 was consumed completely. Several new peaks were shown on LC-MS and 44% of the desired compound was detected. The residue was purified by prep-HPLC to provide the title compound (2.2 mg, 4.62 umol, 4% yield). LCMS (ESI): RT=0.796 min, mass calc. for C$_{19}$H$_{19}$F$_3$N$_6$O$_3$S 468.12, m/z found 491.1 [M+Na]$^+$; $^1$HNMR (400 MHz, DMSO-d$_6$) 8.76 (s, 1H), 8.08 (d, J=7.0 Hz, 1H), 7.60-7.46 (m, 4H), 7.26-7.17 (m, 3H), 6.40 (s, 1H), 5.04 (s, 2H), 4.11 (d, J=8.8 Hz, 2H), 3.81 (d, J=8.8 Hz, 2H), 3.03 (s, 3H).

Example 158: 2-[2-(3-pyridyl)tetrazol-5-yl]-N-[4-(trifluoromethyl)phenyl]aniline (Compound 165)

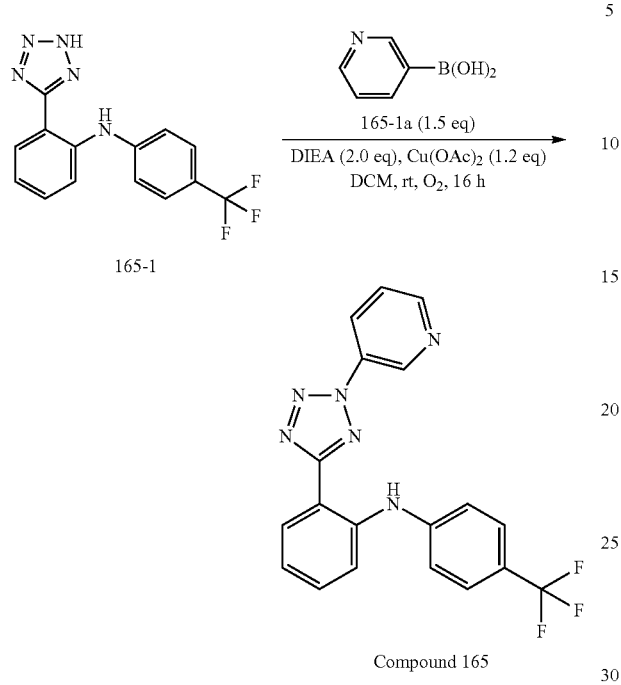

Compound 165

A mixture of 165-1 (100.0 mg, 0.3 mmol, 1.0 eq), 3-pyridylboronic acid 165-1a (60.4 mg, 0.5 mmol, 1.5 eq), DIPEA (84.6 mg, 0.6 mmol, 0.1 mL, 2.0 eq) and Cu(OAc)$_2$ (89.2 mg, 0.5 mmol, 1.5 eq) in DCM (2.0 mL) was degassed and purged with O$_2$ 3 times, and then the mixture was stirred at 40° C. for 72 hour under an O$_2$ (15 psi) atmosphere. LC-MS showed 165-1 was consumed completely. Several new peaks were detected on LC-MS and 30% of the desired compound was detected. The reaction mixture was purified by prep-HPLC to give the title compound (3.99 mg, 10.44 umol, 3.19% yield). LCMS (ESI): RT=0.931 min, mass calc. for C$_{19}$H$_{13}$F$_3$N$_6$O 382.12, m/z found 381.1 [M−H]$^−$; $^1$HNMR (400 MHz, DMSO-d$_6$) δ (ppm) 9.34 (s, 1H), 8.82 (d, J=4.3 Hz, 1H), 8.72 (s, 1H), 8.54 (d, J=8.3 Hz, 1H), 8.16 (d, J=7.8 Hz, 1H), 7.79-7.54 (m, J=4.8, 8.3 Hz, 1H), 7.62-7.49 (m, 4H), 7.29-7.19 (m, 3H).

Example 159: 2-(2-(oxetan-3-ylmethyl)-2H-tetrazol-5-yl)-N-(4-(trifluoromethyl) phenyl) Aniline (Compound 166)

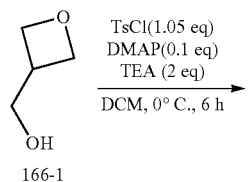

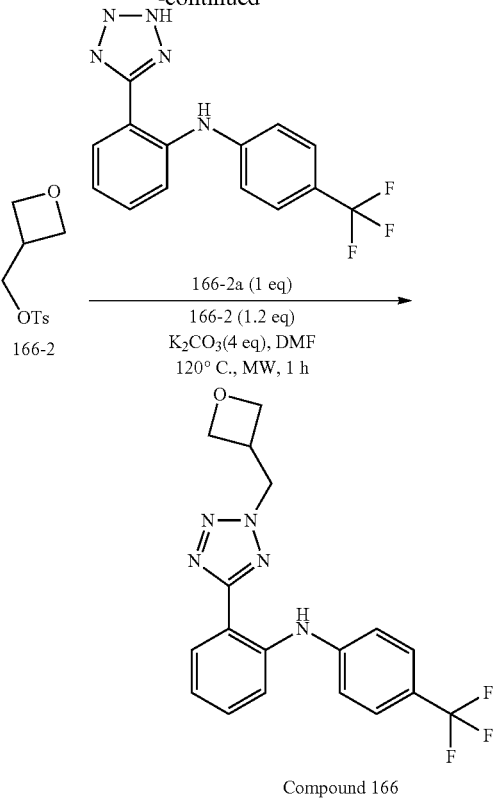

Compound 166

Step 1: oxetan-3-ylmethyl 4-methylbenzenesulfonate

A mixture of 166-1 (200.00 mg, 2.27 mmol, 1.00 eq), TEA (459.38 mg, 4.54 mmol, 629.29 uL, 2.00 eq) and DMAP (27.73 mg, 227.00 umol, 0.10 eq) in DCM (10.00 mL) was stirred at 0° C. for 5 min under N$_2$. Then 4-methylbenzenesulfonyl chloride (454.39 mg, 2.38 mmol, 1.05 eq) was added, and the mixture was stirred at 0° C. for 1 h. The crude LCMS showed no desired product MS value was detected, and the mixture was stirred at 0° C. for an additional 5 h. TLC(PE:EtOAc=2:1 UV) indicated 166-1 was consumed completely and one new spot formed. The reaction mixture was diluted with DCM (20 mL), washed with brine (20 mL), and then extracted with DCM (25 mL*3). The combined organic layers were dried over Na$_2$SO$_4$, filtered, and concentrated under reduced pressure to give a residue. The residue was purified by flash silica gel chromatography to give 166-2 (0.25 g, 1.02 mmol, 45.00% yield).

Step 2: 2-(2-(oxetan-3-ylmethyl)-2H-tetrazol-5-yl)-N-(4-(trifluoromethyl) phenyl) Aniline 166-2 (100.00 mg, 412.73 umol, 1.20 eq), 166-2a (104.99 mg, 343.94 umol, 1.00 eq) and K$_2$CO$_3$ (190.14 mg, 1.38 mmol, 4.00 eq) were taken up into a microwave tube in DMF (4.00 mL). The sealed tube was heated at 120° C. for 1 h under microwave conditions. The crude LCMS showed the desired product MS value was detected. The reaction mixture was combined with another batch, and the reaction mixture was quenched by addition of water (30 mL) and extracted with EtOAc (25 mL*3). The combined organic layers were washed with brine (20 mL*2), dried over Na$_2$SO$_4$, filtered, and concentrated under reduced pressure to give a residue. The residue was purified by flash silica gel chromatography to give the product, which was diluted with MeOH (5 mL) and water (5 mL). Most of MeOH was removed under reduced pressure, and the remaining aqueous layer was lyophilized to give provide Compound 166 (0.13253 g, 353.09 umol, 68.44% yield). LCMS (ESI): RT=0.847 min, mass calc. for C$_{18}$H$_{16}$F$_3$N$_5$O 375.35, m/z found 376.1 [M+1]$^+$; $^1$HNMR (400 MHz, DMSO-d$_6$) δ 3.49-3.62 (m, 1H), 4.47 (t, J=6.15 Hz, 2H), 4.67 (dd, J=7.65, 6.40 Hz, 2H), 5.06 (d, J=7.28 Hz, 2H), 7.13-7.24 (m, 3H), 7.46-7.58 (m, 4H), 8.03 (d, J=7.53 Hz, 1H), 8.72 (br, s, 1H).

Example 160: 4-((5-(2-((4-(trifluoromethyl)phenyl)amino)phenyl)-2H-tetrazol-2-yl)methyl)imidazolidin-2-one (Compound 167)

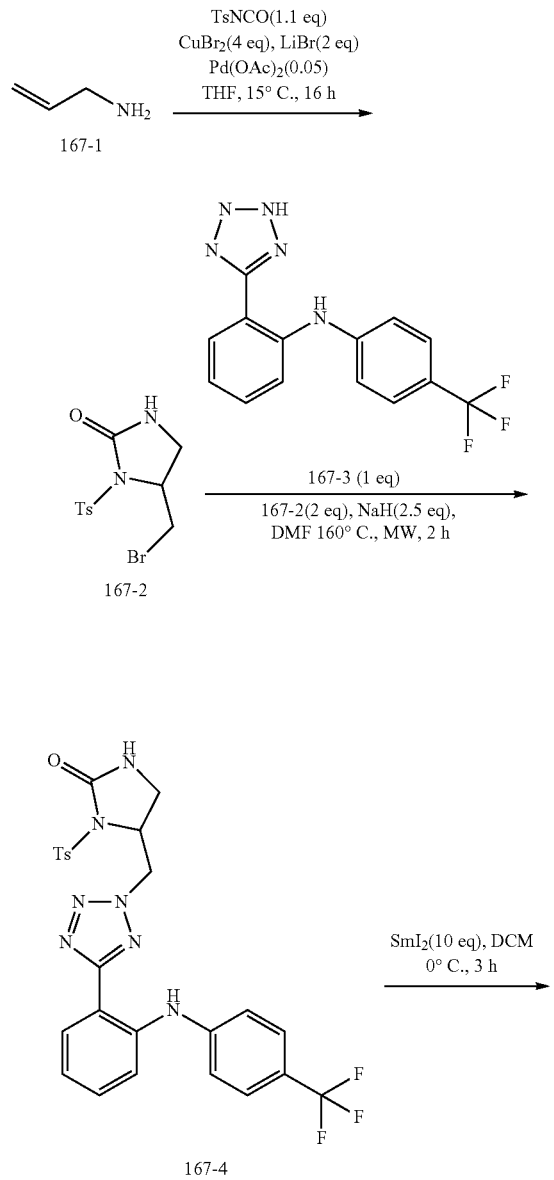

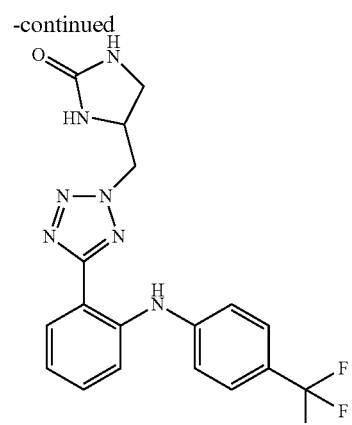

Compound 167

Step 1: 5-(bromomethyl)-1-tosylimidazolidin-2-one

Prop-2-en-1-amine 167-1 (1.30 g, 22.77 mmol, 1.71 mL, 1.00 eq) was reacted with 4-methyl-N-(oxomethylene)benzenesulfonamide (4.94 g, 25.05 mmol, 3.80 mL, 1.10 eq) in THF (110.00 mL) for 10 min at 5° C. under N$_2$; then, LiBr (3.96 g, 45.54 mmol, 1.14 mL, 2.00 eq), CuBr$_2$ (20.34 g, 91.08 mmol, 4.26 mL, 4.00 eq) and Pd(OAc)$_2$ (255.60 mg, 1.14 mmol, 0.05 eq) were added and the reaction was stirred at 15° C. for 16 hr. TLC showed new spots were formed. The dark colored mixture was filtered via a pad of celite and washed with EtOAc (150 mL). The filtrate was washed with brine (50 mL) four times, dried over Na$_2$SO$_4$ and concentrated under reduced pressure to give a residue. The residue was dissolved in 5 mL of methanol and then diluted with a mix solution of PE:EtOAc=1:1(80 mL), forming solids. The resulting mixture was filtered and the solids washed with DCM (50 mL). The filter cake was collected to give an isomeric byproduct (2.8 g) as a light yellow solid, as confirmed by $^1$HNMR. The filtrate was concentrated to give crude 167-2, which was purified by prep-HPLC to give 167-2 (750.00 mg, 2.25 mmol, 9.89% yield). $^1$HNMR (400 MHz, CHLOROFORM-d) δ 7.94 (d, J=8.5 Hz, 2H), 7.34 (d, J=8.5 Hz, 2H), 5.10 (br s, 1H), 4.66-4.54 (m, 1H), 3.83 (dd, J=3.0, 10.5 Hz, 1H), 3.70-3.58 (m, 2H), 3.42 (dd, J=4.0, 9.0 Hz, 1H), 2.45 (s, 3H).

Step 2: 1-tosyl-54(5-(2-((4-(trifluoromethyl)phenyl)amino)phenyl)-2H-tetrazol-2-yl)methyl)imidazolidin-2-one To a solution of 167-3 in DMF (4.00 mL) was added NaH (29.26 mg, 731.60 umol, 60% purity, 2.50 eq) at 0° C. After stirring for 10 min, 167-2 (117.01 mg, 351.17 umol, 1.20 eq) was added and then the resulting mixture was stirred at 160° C. for 1 h under microwave conditions. The yellow mixture became a dark colored mixture. LCMS detected 47% of 167-3 remained and 5% of the desired product was detected. Another 100 mg of 167-2 (117.01 mg, 351.17 umol, 1.20 eq) was added and then the resulting mixture was stirred at 160° C. for another 1 h under microwave conditions. LCMS detected 65% of the desired product. The resulting dark mixture was combined with another batch and concentrated to give a dark residue. The residue was purified by column chromatography (SiO$_2$) to give 167-4 (190.00 mg, crude) as a yellow gum. LCMS (ESI): RT=0.904 min, mass calc. for C$_{25}$H$_{22}$F$_3$N$_7$O$_3$S 557.15, m/z found 580.10 [M+23]$^+$;

¹HNMR (400 MHz, CHLOROFORM-d) δ 8.87 (s, 1H), 8.11 (d, J=6.5 Hz, 1H), 8.03-7.97 (m, 4H), 7.58-7.48 (m, 3H), 7.37-7.29 (m, 5H), 7.02 (t, J=7.5 Hz, 1H), 5.25-5.08 (m, 2H), 5.00-4.87 (m, 1H), 4.81-4.75 (m, 1H), 3.64-3.54 (m, 1H), 3.51-3.42 (m, 1H), 2.44 (s, 3H).

Step 3: 4-((5-(2-((4-(trifluoromethyl)phenyl)amino)phenyl)-2H-tetrazol-2-yl)methyl)imidazolidin-2-one To a colorless solution of 167-4 (135.00 mg, 242.13 umol, 1.00 eq) in THF (10.00 mL) was added diiodosamarium (0.1 M, 24.21 mL, 10.00 eq) at 0° C. and the resulting blue solution was stirred at 0° C. for 1 hr. LCMS showed 56% of the desired product was formed and 8% of the starting material remained. Then the solution was stirred at 0° C. for another 2 h. LCMS showed the starting material was consumed completely and 87% of the desired product was formed. The solution was combined with another batch for workup and quenched with saturated aq. $K_2CO_3$ (15 mL) and separated. The separated aqueous layer was extracted with DCM (15 mL*3). The combined organic layers were dried by anhydrous $Na_2SO_4$, filtered, and concentrated a residue which was purified by prep-HPLC to give Compound 167 (0.01025 g, 24.88 umol, 10.27% yield). LCMS (ESI): RT=0.766 min, mass calc. for $C_{18}H_{16}F_3N_7O$ 403.14, m/z found 426.0 [M+23]⁺.

¹HNMR (400 MHz, DMSO-$d_6$) δ 8.67 (br s, 1H), 8.02 (d, J=7.1 Hz, 1H), 7.64-7.41 (m, 4H), 7.37-7.07 (m, 3H), 6.53 (br s, 1H), 4.74 (br s, 2H), 4.14 (br s, 1H), 3.40-3.37 (m, 1H), 3.39-3.31 (m, 1H), 3.40-3.31 (m, 1H), 3.26-3.11 (m, 1H), 3.24-3.10 (m, 1H), 3.24-3.10 (m, 1H), 3.18 (br s, 1H).

¹HNMR (400 MHz, CHLOROFORM-d) δ 8.15 (d, J=7.5 Hz, 1H), 7.52 (t, J=7.9 Hz, 3H), 7.38 (t, J=7.5 Hz, 1H), 7.29 (d, J=8.3 Hz, 1H), 7.32-7.27 (m, 1H), 7.04 (t, J=7.3 Hz, 1H), 6.02-5.32 (m, 1H), 5.30 (s, 1H), 5.83-5.22 (m, 1H), 4.81 (br s, 2H), 4.44 (br s, 1H), 3.77 (br s, 1H), 3.49 (s, 1H), 2.17 (s, 1H).

Example 161: 2-[2-(4-pyridyl)tetrazol-5-yl]-N-[4-(trifluoromethyl)phenyl]aniline (Compound 168)

A mixture of 168-1 (200.0 mg, 0.6 mmol, 1.0 eq), 168-1a (120.80 mg, 0.9 mmol, 1.5 eq), Cu(OAc)₂ (178.5 mg, 0.9 mmol, 1.5 eq) and DIPEA (169.3 mg, 1.3 mmol, 0.2 mL, 2.0 eq) in DCM (5.0 mL) was degassed and purged with O₂ 3 times, and the mixture was stirred at 40° C. for 72 hours under an O₂ (15 psi) atmosphere. LC-MS detected 62% of 168-1 remained. Several new peaks were detected on LC-MS and 17% of the desired compound was detected. The reaction mixture was washed with brine (10 mL*3), dried over Na₂SO₄, filtered, and concentrated under reduced pressure to give a residue. The residue was purified by prep-TLC to give the title compound (3.14 mg, 8.21 umol, 1% yield). LCMS (ESI): RT=0.870 min, mass calc. for $C_{19}H_{13}F_3N_6$ 382.12, m/z found 381.1298 [M–H]⁻; ¹HNMR (400 MHz, DCCl₃) δ (ppm) 8.95 (s, 2H), 8.35-8.33 (m, J=1.4, 7.9 Hz, 1H), 8.15 (s, 2H), 7.62-7.55 (m, 3H), 7.45 (t, J=7.2 Hz, 1H), 7.34 (d, J=8.3 Hz, 2H), 7.11 (t, J=7.7 Hz, 1H).

Example 162: 1-((5-(2-((4-(Trifluoromethyl)phenyl)amino)phenyl)-2H-tetrazol-2-yl)methyl)cyclobutanol (Compound 169)

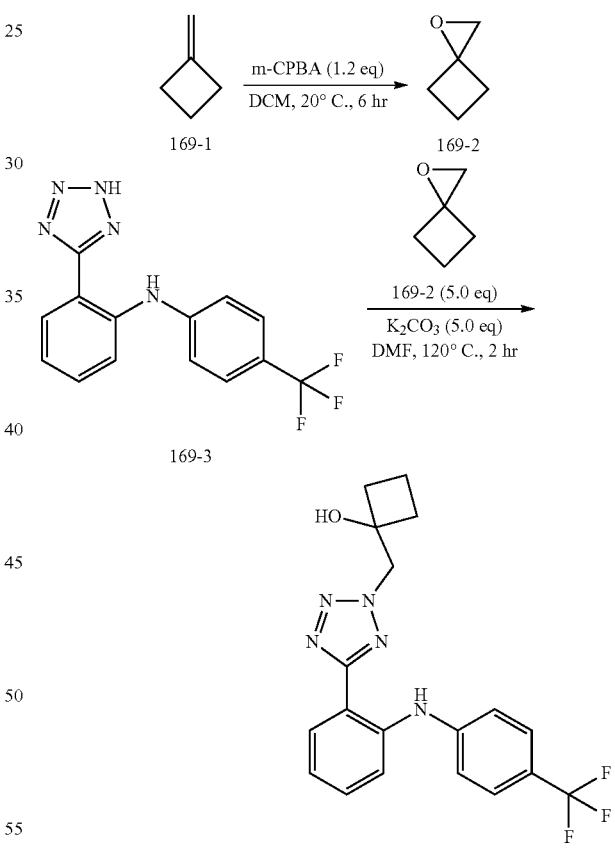

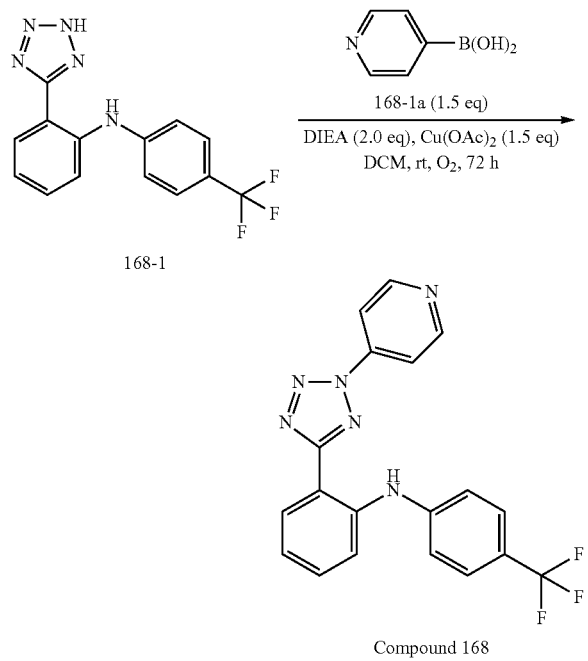

Compound 168

Step 1: 1-Oxaspiro[2.3]hexane

To a solution of 169-1 (980 mg, 14.4 mmol, 1.0 eq) in DCM (20 mL) was added m-CPBA (3.5 g, 17 mmol, 85% purity, 1.2 eq). The reaction mixture was stirred at 20° C. for 6 hours. The reaction mixture was filtered and the filtrate was washed with NaOH (0.25 M, 10 mL), and water (10 mL). The organic layer was dried over Na₂SO₄, filtered, and concentrated to dryness under reduced pressure at 10° C. to obtain 169-2 (600 mg, crude). ¹HNMR (400 MHz, CDCl₃-d) δ 2.72 (s, 2H), 2.60-2.47 (m, 2H), 2.34-2.24 (m, 2H), 1.93-1.76 (m, 2H).

Step 2: 1-((5-(2-((4-(Trifluoromethyl)phenyl)amino)phenyl)-2H-tetrazol-2-yl)methyl)cyclobutanol To a solution of 169-3 (50 mg, 0.16 mmol, 1.0 eq) and 169-2 (69 mg, 0.82 mmol, 5.0 eq) in DMF (2 mL) was added K₂CO₃ (113 mg, 0.819 mmol, 5.0 eq). The reaction mixture was stirred at 120° C. for 2 hours. The mixture was diluted with water (10 mL) and the resultant mixture was extracted with EtOAc (30 mL*3). The combined organic layers were dried over Na₂SO₄, filtered, and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely to obtain Compound 169 (28.70 mg, 45% yield). LCMS (ESI): RT=0.864 min, mass calc. for $C_{19}H_{18}F_3N_5O$ 389.15, m/z found 390.0 [M+H]⁺, ¹HNMR (400 MHz, CDCl₃-d) δ 9.07 (s, 1H), 8.18 (dd, J=1.4, 7.9 Hz, 1H), 7.54 (d, J=8.3 Hz, 3H), 7.42-7.36 (m, 1H), 7.30 (d, J=8.5 Hz, 2H), 7.08-7.02 (m, 1H), 4.86 (s, 2H), 3.01 (s, 1H), 2.29-2.14 (m, 4H), 1.99-1.87 (m, 1H), 1.80-1.67 (m, 1H).

Example 163: 2-(2-(Cyclobutylmethyl)-2H-tetrazol-5-yl)-N-(4-(trifluoromethyl)phenyl)aniline (Compound 170)

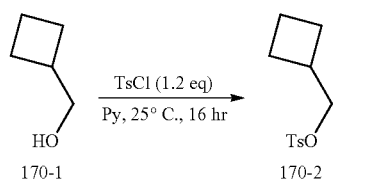

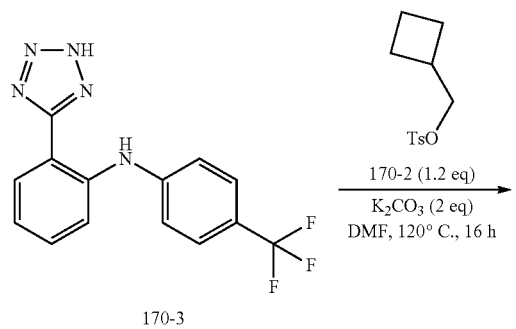

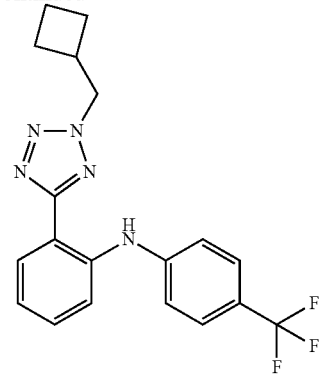

Compound 170

Step 1: Cyclobutylmethyl 4-methylbenzenesulfonate

To a solution of 170-1 (500 mg, 5.81 mmol, 1.0 eq) in pyridine (5 mL) was added TsCl (1.3 g, 7.0 mmol, 1.2 eq). The reaction mixture was stirred at 25° C. for 16 hours. The reaction mixture was concentrated under reduced pressure. The mixture was diluted with water (10 mL) and the resultant mixture was extracted with DCM (3 mL*3). The combined organic layers were dried over Na₂SO₄, filtered, and concentrated to dryness under reduced pressure to obtain the 170-2 (1.2 g, 86% yield) as a white solid. ¹HNMR (400 MHz, CDCl₃-d) δ 7.79 (d, J=8.3 Hz, 2H), 7.34 (d, J=8.0 Hz, 2H), 3.98 (d, J=6.8 Hz, 2H), 2.67-2.55 (m, 1H), 2.45 (s, 3H), 2.06-1.96 (m, 2H), 1.95-1.77 (m, 2H), 1.76-1.65 (m, 2H).

Step 2: 2-(2-(Cyclobutylmethyl)-2H-tetrazol-5-yl)-N-(4-(trifluoromethyl)phenyl)aniline To a solution of 170-3 (50 mg, 0.16 mmol, 1.0 eq) and 170-2 (47 mg, 0.20 mmol, 1.2 eq) in DMF (2 mL) was added K₂CO₃ (45 mg, 0.33 mmol, 2.0 eq). The reaction mixture was stirred at 120° C. for 16 hours. The mixture was diluted with water (10 mL) and the resultant mixture was extracted with EtOAc (30 mL*3). The combined organic layers were dried over Na₂SO₄, filtered, and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely to provide Compound 170 (21.72 mg, 36% yield). LCMS (ESI): RT=0.976 min, mass calc. for $C_{19}H_{18}F_3N_5$ 373.15, m/z found 374.0 [M+H]⁺, ¹HNMR (400 MHz, CDCl₃-d) δ 9.08 (s, 1H), 8.21 (dd, J=1.4, 7.9 Hz, 1H), 7.53 (dd, J=2.4, 8.4 Hz, 3H), 7.40-7.34 (m, 1H), 7.30 (d, J=8.5 Hz, 2H), 7.08-7.01 (m, 1H), 4.70 (d, J=7.5 Hz, 2H), 3.10-2.95 (m, 1H), 2.20-2.12 (m, 2H), 2.04-1.88 (m, 4H).

Example 164: 2-(2-methyltetrazol-5-yl)-N-[4-(trifluoromethyl)phenyl]aniline (Compound 171)

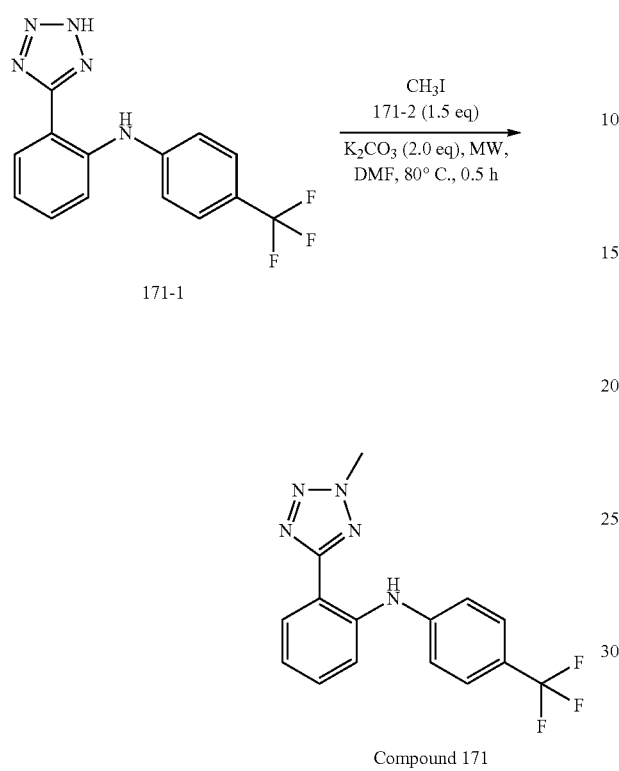

171-1 (50.0 mg, 0.16 mmol, 1.0 eq), methyl iodide 171-2 (34.9 mg, 0.25 mmol, 15.3 uL, 1.5 eq) and K$_2$CO$_3$ (45.3 mg, 0.33 mmol, 2.0 eq) were taken up into a microwave tube in DMF (2.0 mL). The sealed tube was heated at 100° C. for 0.5 hr under microwave conditions. LCMS showed the desired compound was formed. The reaction was filtered to give a crude product. The crude product was purified by prep-HPLC to give the title compound (4.90 mg, 15.35 umol, 9.37% yield). LCMS (ESI): RT=0.859 min, mass calc. for C$_{15}$H$_{12}$F$_3$N$_5$ 319.10, m/z found 319.9 [M+H]$^+$; $^1$HNMR (400 MHz, CDCl$_3$-d) δ 9.02 (s, 1H), 8.20 (dd, J=1.4, 7.9 Hz, 1H), 7.54 (t, J=7.4 Hz, 3H), 7.41-7.35 (m, 1H), 7.31 (d, J=8.5 Hz, 2H), 7.08-7.02 (m, 1H), 4.45 (s, 3H).

Example 165: 1-phenyl-34(5-(2-((4-(trifluoromethyl)phenyl)amino)phenyl)-2H-tetrazol-2-yl)methyl)pyrrolidin-3-ol (Compound 172)

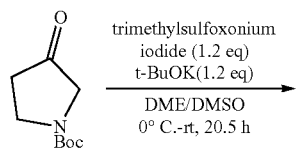

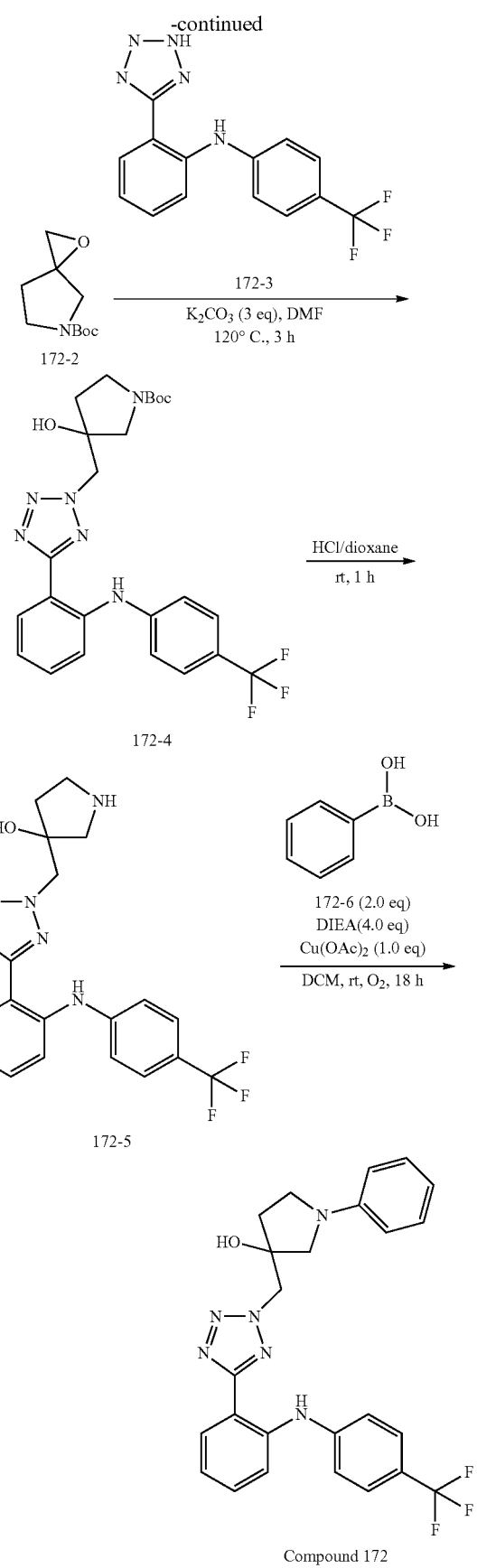

Step 1: tert-butyl 1-oxa-5-azaspiro[2.4]heptane-5-carboxylate

To a mixture of t-BuOK (727.0 mg, 6.5 mmol, 1.20 eq) in DMSO (10 mL), was added trimethylsulfoxonium iodide (1.43 g, 6.5 mmol, 1.20 eq) by portions at 0° C. The mixture was stirred at 15° C. for 0.5 h. DME (5 mL) was added, and the mixture was cooled to 0° C. A solution of 172-1 (1.0 g, 5.4 mmol, 1.00 eq) in DMSO (2 mL) and DME (4 mL) was added dropwise at 0° C. The resulting mixture was stirred at 0° C. for 3 h, 15° C. for 17 h. TLC showed two new spots with lower polarity, and the starting material remained. The mixture was diluted with water (20 mL), and extracted with DCM (20 mL*3). The combined organic layers were dried over anhydrous Na$_2$SO$_4$, and concentrated under vacuum. The residue was purified by silica gel chromatography to provide 172-2 (0.22 g, 1.1 mmol, 20.5% yield). $^1$HNMR (400 MHz, CHLOROFORM-d) δ 3.73-3.52 (m, 3H), 3.28 (t, J=11.3 Hz, 1H), 2.94 (s, 2H), 2.34-2.21 (m, 1H), 1.85 (ddd, J=3.9, 7.5, 13.5 Hz, 1H), 1.47 (s, 9H).

Step 2: tert-butyl 3-hydroxy-34(5-(2-((4-(trifluoromethyl)phenyl)amino)phenyl)-2H-tetrazol-2-yl)methyl)pyrrolidine-1-carboxylate To a mixture of 172-3 (0.3 g, 1.0 mmol, 1 eq) and K$_2$CO$_3$ (407.5 mg, 3.0 mmol, 3.00 eq) in DMF (15 mL), was added 172-2 (0.22 g, 1.1 mmol, 1.12 eq). The resulting mixture was stirred at 120° C. under N$_2$ for 3 h. LCMS detected about 74% of the desired compound. The mixture was diluted with EtOAc (30 mL), and washed with water (20 mL*3). The organic layer was dried over anhydrous Na$_2$SO$_4$, concentrated under vacuum. The residue was purified by silica gel chromatography to provide 172-4 (0.31 g, 0.6 mmol, 61.9% yield).

Step 3: 3-((5-(2-((4-(trifluoromethyl)phenyl)amino)phenyl)-2H-tetrazol-2-yl)methyl)pyrrolidin-3-ol A mixture of 172-4 (0.2 g, 0.4 mmol, 1 eq) in HCl/dioxane (4 M, 4.0 mL, 1 eq) was stirred at 15° C. for 1 h. LCMS showed the reaction was complete. The mixture was concentrated under vacuum to obtain 172-5 (0.18 g, crude, HCl salt).

Step 4: 1-phenyl-34(5-(2-((4-(trifluoromethyl)phenyl)amino)phenyl)-2H-tetrazol-2-yl)methyl)pyrrolidin-3-ol To a mixture of 172-5 (0.1 g, 0.2 mmol, 1.00 eq, HCl), 172-6 (55.3 mg, 0.5 mmol, 2.00 eq) and DIEA (117.3 mg, 1.0 mmol, 0.2 mL, 4.00 eq) in DCM (3 mL), was added Cu(OAc)$_2$ (41.2 mg, 0.2 mmol, 1.00 eq). The mixture was degassed under vacuum and purged with O$_2$ 3 times. The resulting mixture was stirred at 15° C. under O$_2$ (15 Psi) for 18 h. LCMS and HPLC showed about 20% of the desired compound, and 47% starting material remaining. The mixture was diluted with water (15 mL), and extracted with DCM (15 mL*2). The combined organic layers were dried over anhydrous Na$_2$SO$_4$, and concentrated under vacuum. The residue was purified by prep-HPLC (basic conditions) to provide Compound 172 (8.81 mg, 18.0 umol, 7.9% yield). LCMS (ESI): RT=0.922 min, mass calc. for C$_{25}$H$_{23}$F$_3$N$_6$O 480.19, m/z found 481.1 [M+H]$^+$. $^1$H NMR (400 MHz, CHLOROFORM-d) δ 9.04 (s, 1H), 8.21 (dd, J=1.3, 7.8 Hz, 1H), 7.55 (d, J=8.3 Hz, 3H), 7.44-7.38 (m, 1H), 7.31 (d, J=8.5 Hz, 2H), 7.24 (dd, J=7.7, 8.4 Hz, 2H), 7.10-7.04 (m, 1H), 6.75 (t, J=7.3 Hz, 1H), 6.56 (d, J=8.0 Hz, 2H), 5.03-4.93 (m, 2H), 3.63-3.48 (m, 3H), 3.39 (d, J=10.3 Hz, 1H), 2.91 (s, 1H), 2.24-2.12 (m, 2H).

Example 166: 2-(2-(2-methoxyethyl)-2H-tetrazol-5-yl)-N-(4-(trifluoromethyl)phenyl)aniline (Compound 173)

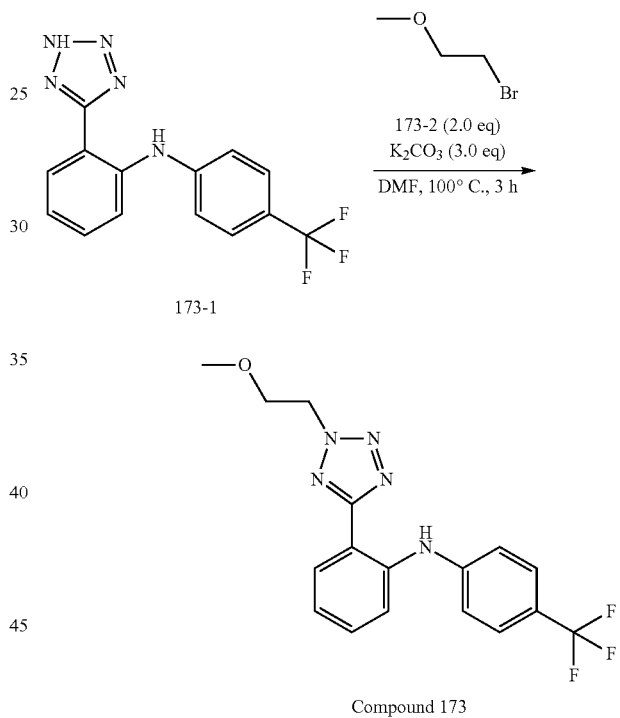

Compound 173

To a mixture of 173-1 (50 mg, 0.2 mmol, 1 eq) and K$_2$CO$_3$ (67.9 mg, 0.5 mmol, 3 eq) in DMF (2 mL), was added 173-2 (45.5 mg, 0.3 mmol, 2 eq). The resulting mixture was stirred at 100° C. for 3 h. LCMS and HPLC showed the reaction was completed. The mixture was filtered, and the solid was washed with DMF (1 mL). The filtrate was purified by prep-HPLC (basic condition) to obtain the title compound (7.03 mg, 19.4 umol, 11.8% yield). LCMS (ESI): RT=0.871 min, mass calc. for C$_{17}$H$_{16}$F$_3$N$_5$O 363.13, m/z found 364.0 [M+H]$^+$. $^1$HNMR (400 MHz, CHLOROFORM-d) δ9.09 (s, 1H), 8.22 (dd, J=1.5, 7.8 Hz, 1H), 7.57-7.51 (m, 3H), 7.41-7.35 (m, 1H), 7.30 (d, J=8.5 Hz, 2H), 7.08-7.02 (m, 1H), 4.88 (t, J=5.4 Hz, 2H), 4.00 (t, J=5.4 Hz, 2H), 3.38 (s, 3H).

435

Example 167: 2-(2-(2-phenoxyethyl)-2H-tetrazol-5-yl)-N-(4-(trifluoromethyl)phenyl)aniline (Compound 174)

436

Example 168: 2-[5-[5-fluoro-2-[4-(trifluoromethyl)anilino]phenyl]tetrazol-2-yl]ethanol (Compound 175)

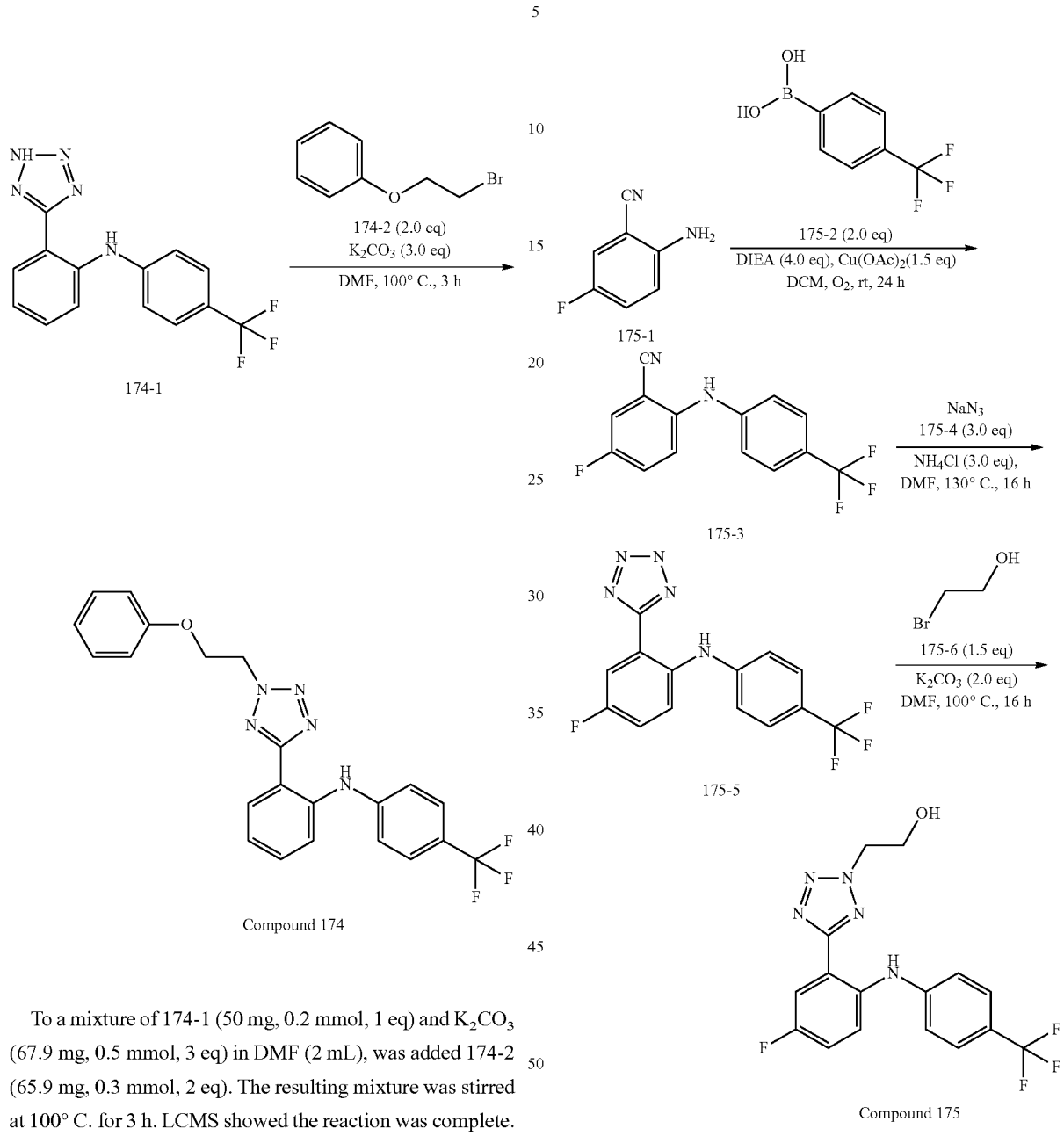

To a mixture of 174-1 (50 mg, 0.2 mmol, 1 eq) and K₂CO₃ (67.9 mg, 0.5 mmol, 3 eq) in DMF (2 mL), was added 174-2 (65.9 mg, 0.3 mmol, 2 eq). The resulting mixture was stirred at 100° C. for 3 h. LCMS showed the reaction was complete. The mixture was filtered, and the solid was washed with DMF (1 mL). The filtrate was purified by prep-HPLC (basic condition) to obtain the title compound (11.32 mg, 26.6 umol, 16.3% yield). LCMS (ESI): RT=0.950 min, mass calc. for $C_{22}H_{18}F_3N_5O$ 425.15, m/z found 426.0 [M+H]⁺. ¹HNMR (400 MHz, CHLOROFORM-d) δ 9.02 (s, 1H), 8.22 (dd, J=1.5, 7.8 Hz, 1H), 7.53 (d, J=8.5 Hz, 3H), 7.41-7.35 (m, 1H), 7.30-7.24 (m, 4H), 7.08-7.02 (m, 1H), 6.98 (t, J=7.4 Hz, 1H), 6.91-6.84 (m, 2H), 5.08 (t, J=5.4 Hz, 2H), 4.60 (t, J=5.4 Hz, 2H).

Step 1: 5-fluoro-2-[4-(trifluoromethyl)anilino]benzonitrile

To a solution of 175-1 (200.0 mg, 1.5 mmol, 1.0 eq) and 175-2 (418.8 mg, 2.2 mmol, 1.5 eq) in DCM (5.0 mL) was added DIEA (759.5 mg, 5.9 mmol, 1.0 mL, 4.0 eq) and Cu(OAc)₂ (400.3 mg, 2.2 mmol, 1.5 eq). The mixture was stirred at 20° C. for 16 hr under an O₂ atmosphere. LCMS showed the desired compound was formed. TLC (Petroleum ether:Ethyl acetate=3/1) showed a new spot appeared. The reaction was filtered and concentrated under reduced pressure to give a crude product. The crude product was purified by column chromatography over silica gel to give 175-3 (50.0 mg, 0.18 mmol, 12.1% yield). LCMS (ESI): RT=0.773 min, mass calc. for $C_{14}H_8F_4N_2$ 280.06 m/z found 280.5 $[M+H]^+$.

Step 2: 4-fluoro-2-(2H-tetrazol-5-yl)-N-[4-(trifluoromethyl)phenyl]aniline

To a solution of 175-3 (50.0 mg, 0.18 mmol, 1.00 eq) in DMF (15.0 mL) was added NH$_4$Cl (28.6 mg, 0.53 mmol, 18.7 uL, 3.0 eq) and 175-4 (34.8 mg, 0.54 mmol, 3.0 eq). The mixture was stirred at 130° C. for 16 hour under an N$_2$ atmosphere. LCMS showed the desired compound was formed. The reaction mixture was poured into HCl (1M, 4 mL) and extracted with EtOAc (10 mL*2). The combined organic layers were washed with brine (10 mL), dried over Na$_2$SO$_4$, and filtered. The solvent was removed under reduced pressure to afford the crude 175-5 (0.06 g, 0.17 mmol, 93.48% yield, HCl). The residue was directly used without further purification.

Step 3: 2-[5-[5-fluoro-2-[4-(trifluoromethyl)anilino]phenyl]tetrazol-2-yl]ethanol To a solution of 175-5 (30.0 mg, 83.4 umol, 1.0 eq, HCl) in DMF (2.0 mL) was added K$_2$CO$_3$ (23.1 mg, 0.17 mmol, 2.0 eq) and 175-6 (15.6 mg, 0.13 mmol, 8.9 uL, 1.5 eq). The mixture was stirred at 100° C. for 16 hour under an N$_2$ atmosphere. LCMS detected the desired compound was formed. The reaction was filtered to give a crude product. The crude product was purified by prep-HPLC to give Compound 175 (6.08 mg, 16.6 umol, 19.8% yield). LCMS (ESI): RT=0.802 min, mass calc. for $C_{16}H_{13}F_4N_5O$ 367.11, m/z found 368.0 $[M+H]^+$; $^1$HNMR (400 MHz, CDCl$_3$-d) δ 8.80 (s, 1H), 7.89 (dd, J=3.1, 9.2 Hz, 1H), 7.55-7.47 (m, 3H), 7.23 (d, J=8.5 Hz, 2H), 7.13 (ddd, J=3.0, 7.7, 9.1 Hz, 1H), 4.90-4.83 (m, 2H), 4.32-4.24 (m, 2H), 2.18 (s, 1H).

Example 169: 1-phenyl-34(5-(2-((4-(trifluoromethyl)phenyl)amino)phenyl)-2H-tetrazol-2-yl)methyl)piperidin-3-ol (Compound 176)

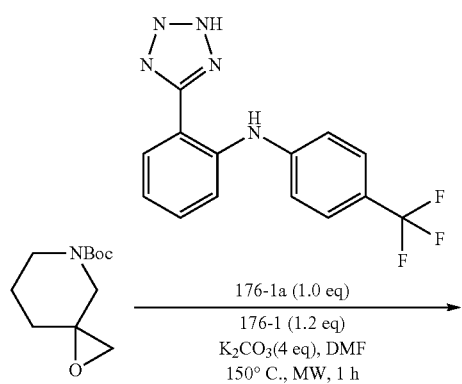

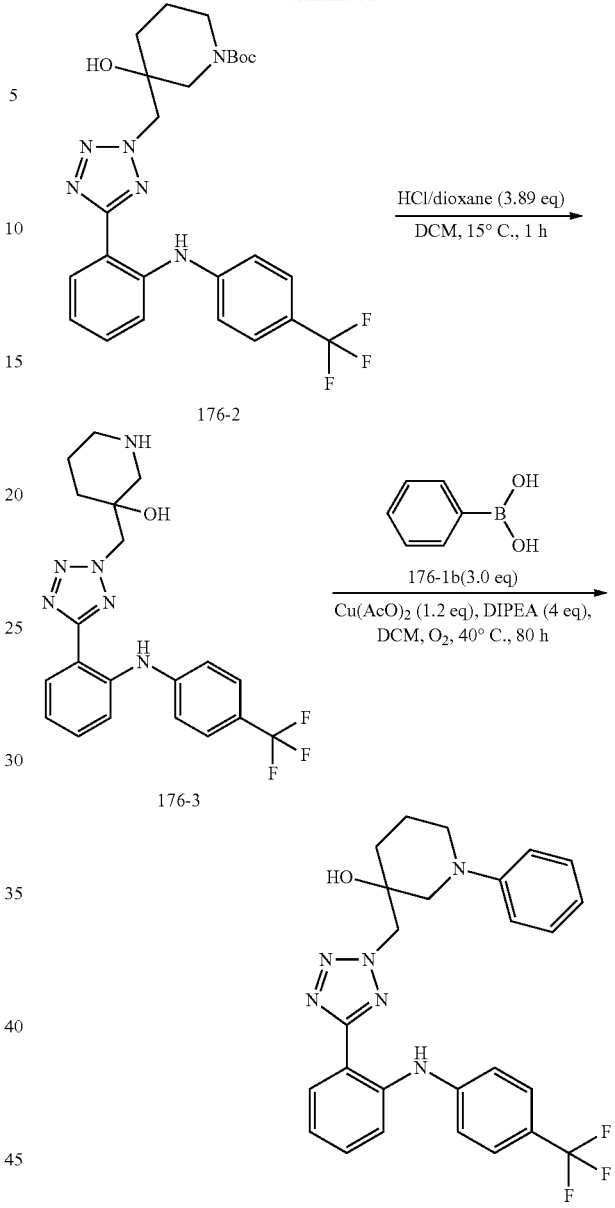

Step 1: tert-butyl 3-hydroxy-34(5-(2-((4-(trifluoromethyl)phenyl)amino)phenyl)-2H-tetrazol-2-yl)methyl)piperidine-1-carboxylate 176-1a (150.00 mg, 438.96 umol, 1.00 eq, HCl), 176-1 (112.34 mg, 526.75 umol, 1.20 eq) and K$_2$CO$_3$ (242.67 mg, 1.76 mmol, 4.00 eq) were taken up into a microwave tube in DMF (4.00 mL). The sealed tube was heated at 150° C. for 1 h under microwave conditions. The crude LCMS detected the desired product MS value. The reaction mixture was quenched by water (20 mL) and then extracted with DCM (15 mL*4). The combined organic layers were washed with brine (15 mL*2), dried over anhydrous Na$_2$SO$_4$, filtered, and concentrated under reduced pressure to give a residue. The residue was purified by flash silica gel chromatography to give provide 176-2 (0.2 g, 385.71 umol, 87.87% yield). $^1$HNMR (400 MHz, DMSO-d$_6$) δ 1.30-1.40 (m, 13H), 3.07-3.33 (m, 2H), 3.40 (br s, 2H), 4.66-4.76 (m, 2H), 5.06 (s, 1H), 7.15-7.25 (m, 3H), 7.46-7.57 (m, 4H), 8.07 (br d, J=7.50 Hz, 1H), 8.82 (s, 1H).

Step 2: 3-((5-(2-((4-(trifluoromethyl) phenyl) amino) phenyl)-2H-tetrazol-2-yl) methyl) piperidin-3-ol To a mixture of 176-2 (0.2 g, 385.71 umol, 1.00 eq) in DCM (1.5 mL) was added HCl/dioxane (1 M, 1.5 mL, 3.89 eq) at 15° C., The mixture was stirred at 15° C. for 1 hr. The crude LCMS detected the desired product MS value. The reaction mixture was concentrated to give a crude compound 176-3 (0.15 g, crude, HCl salt), which was used into the next step without further purification. $^1$HNMR (400 MHz, DMSO-$d_6$) δ 1.53-1.97 (m, 6H), 2.64-3.20 (m, 10H), 4.82 (s, 2H), 5.30-5.99 (m, 1H), 7.23 (s, 3H), 7.56 (s, 5H), 7.85-8.12 (m, 2H), 8.32 (br s, 1H), 8.81 (br s, 1H), 9.34-9.65 (m, 1H).

Step 3: 1-phenyl-3-((5-(2-((4-(trifluoromethyl)phenyl)amino)phenyl)-2H-tetrazol-2-yl)methyl)piperidin-3-ol To a mixture of 176-3 (60 mg, 131.90 umol, 1 eq, HCl) and compound 176-1b (48.25 mg, 395.71 umol, 8.82 uL, 3 eq) in DCM (2 mL) was added DIPEA (68.19 mg, 527.62 umol, 91.90 uL, 4 eq) and Cu(OAc)$_2$ (28.75 mg, 158.28 umol, 1.2 eq) in one portion at 15° C. under O$_2$. The mixture was heated to 40° C. and stirred for 40 hours. The crude LCMS showed 25% of 176-3 remained and 30% of the desired product was detected. An additional 176-1b (48.25 mg, 395.71 umol, 8.82 uL, 3 eq) was added to the reaction mixture, and the mixture was stirred at 40° C. for 40 hours. The crude LCMS showed 10% of 176-3 remained and 27% of the desired product was detected. The reaction mixture was diluted with DCM (20 mL). The reaction mixture was purified by flash silica gel chromatography to give a residue (77 mg), which was purified by prep-HPLC to give Compound 176 (4.72 mg, 9.54 umol, 7.24% yield). LCMS (ESI): RT=2.682 min, mass calc. for C$_{26}$H$_{25}$F$_3$N$_6$O 494.51, m/z found 495.00 [M+1]$^+$; $^1$HNMR (400 MHz, DMSO-$d_6$) δ 1.43-1.57 (m, 1H), 1.63-1.88 (m, 3H), 2.85-3.00 (m, 2H), 3.14-3.28 (m, 2H), 4.78-5.00 (m, 2H), 5.10 (s, 1H), 6.77 (t, J=7.15 Hz, 1H), 6.99 (d, J=7.78 Hz, 2H), 7.13-7.25 (m, 5H), 7.44-7.62 (m, 4H), 8.07 (dd, J=7.78, 1.26 Hz, 1H), 8.81 (s, 1H).

Example 170: 2-(2-(2-(2-(dimethylamino)ethoxy)ethyl)-2H-tetrazol-5-yl)-N-(4-(trifluoromethyl)phenyl)aniline (Compound 177)

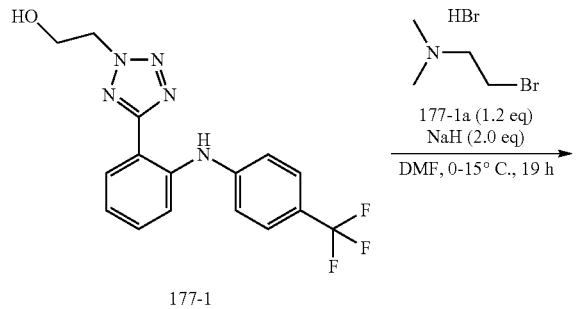

177-1

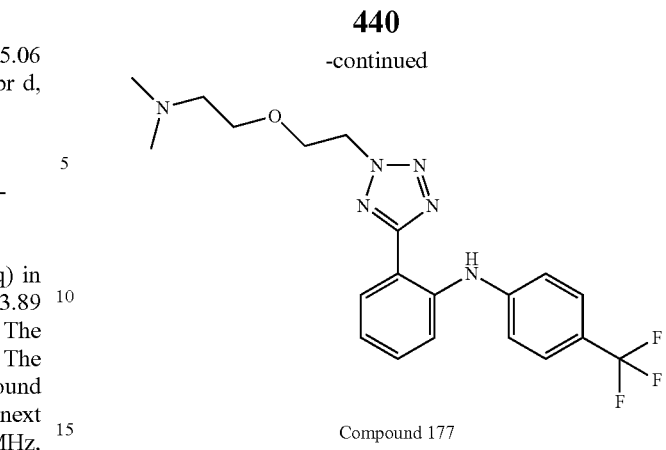

Compound 177

To a solution of 177-1 (30 mg, 85.9 umol, 1 eq) in DMF (2 mL), was added NaH (6.9 mg, 0.2 mmol, 60% purity, 2 eq) at 0° C. The mixture was stirred at 0° C. for 0.5 h. Then 177-1a (24.0 mg, 0.1 mmol, 1.2 eq, HBr) was added at 0° C. The resulting mixture was stirred at 15° C. for 2 h. LCMS detected about 17% of the desired compound, and 34% starting material remaining. The mixture was stirred at 15° C. for 17 h. LCMS detected no obvious change. The mixture was diluted with water (15 mL), and extracted with DCM (15 mL*2). The organic layer was dried over anhydrous Na$_2$SO$_4$, and concentrated under vacuum. The residue was checked by HPLC. The residue was purified by prep-HPLC (basic condition) to provide the title compound (4.03 mg, 9.6 umol, 11.2% yield). LCMS (ESI): RT=0.650 min, mass calc. for C$_{20}$H$_{23}$F$_3$N$_6$O 420.19, m/z found 421.1 [M+H]$^+$. $^1$HNMR (400 MHz, CHLOROFORM-d) δ 8.36 (dd, J=1.9, 7.4 Hz, 1H), 7.64-7.55 (m, 2H), 7.42 (d, J=8.8 Hz, 2H), 7.32 (dd, J=1.6, 7.4 Hz, 1H), 6.76 (d, J=8.8 Hz, 2H), 4.73-4.66 (m, 2H), 4.20-4.07 (m, 4H), 3.84 (s, 1H), 3.26 (t, J=8.0 Hz, 2H), 2.78 (s, 6H).

Example 171: 2-[2-[2-(4-fluorophenoxy)ethyl]tetrazol-5-yl]-N-[4-(trifluoromethyl)phenyl]aniline (Compound 178)

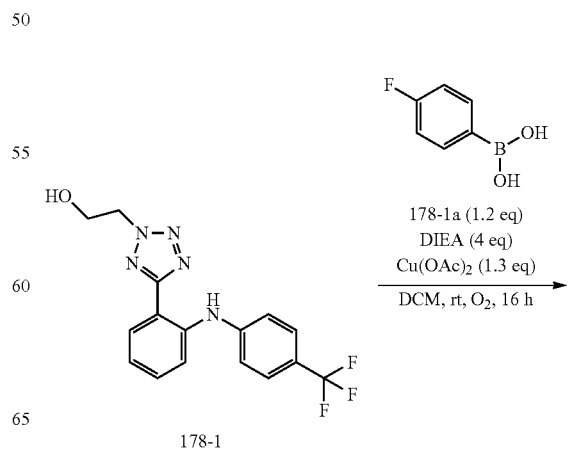

178-1

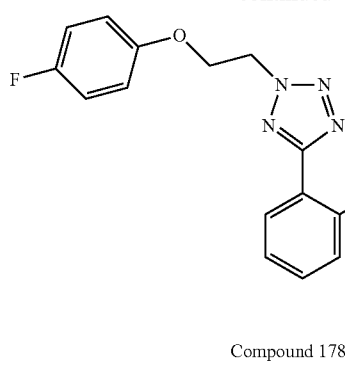

Compound 178

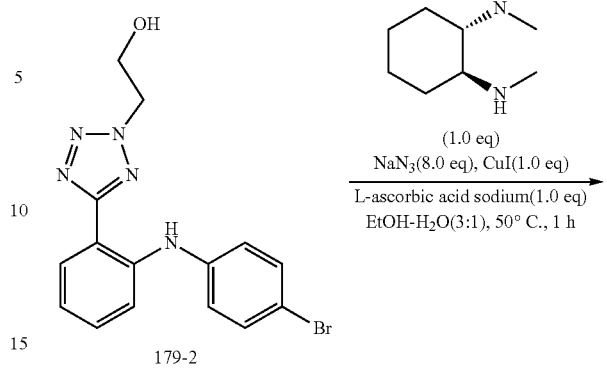

To a solution of 178-1 (40 mg, 0.114 mmol, 1 eq), (4-fluorophenyl)boronic acid 178-1a (32 mg, 0.23 mmol, 2 eq) and DIEA (59.2 mg, 0.16 mmol, 79.78 uL, 4 eq) in DCM (3 mL) was added Cu(OAc)$_2$ (27 mg, 0.15 mmol, 1.3 eq). The reaction mixture was degassed with O$_2$ three times and stirred at 20° C. for 16 hr. LCMS detected that the starting material remained and ~40% of the desired product was present. The reaction was diluted with DCM (6 mL) and washed with water (10 mL). The organic layer was dried over Na$_2$SO$_4$ and concentrated. The crude product was purified by Prep.HPLC (basic: column) to give the title compound (4.99 mg, 11.25 umol, 9.83% yield). LCMS (ESI): RT=0.935 min, mass calc. for C$_{22}$H$_{17}$F$_4$N$_5$O 443.14, m/z found 444.1 [M+H]$^+$. $^1$H NMR (400 MHz, CHLORO-FORM-d) δ 9.01 (s, 1H), 8.21 (d, J=8.0 Hz, 1H), 7.60-7.50 (m, 3H), 7.28 (d, J=8.4 Hz, 1H), 7.35-7.25 (m, 2H), 7.10-7.00 (m, 1H), 7.00-6.85 (m, 2H), 6.85-6.65 (m, 2H), 5.07 (t, J=4.8 Hz, 2H), 4.57 (t, J=5.2 Hz, 2H).

Example 172: 2-[5-[2-(4-azidoanilino)phenyl]tetrazol-2-yl]ethanol (Compound 179)

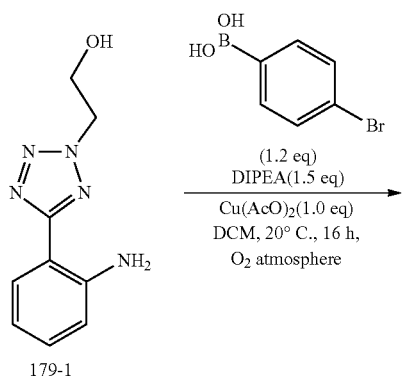

179-1

Compound 179

Step 1: 2-[5-[2-(4-bromoanilino)phenyl]tetrazol-2-yl]ethanol

To a solution of (4-bromophenyl)boronic acid (587.2 mg, 2.9 mmol, 1.2 eq) and 179-1 (500 mg, 2.4 mmol, 1.0 eq) in DCM (20.0 mL) was added Cu(OAc)$_2$ (486.8 mg, 2.7 mmol, 1.1 eq) and DIPEA (472.3 mg, 3.7 mmol, 636.6 uL, 1.5 eq). The mixture was stirred at 20° C. for 16 hr under O$_2$ atmosphere. LC-MS showed 179-1 was consumed completely and one main peak with the desired MS was detected. The reaction mixture was filtered through a Celite pad and washed with DCM (30 mL). The filtrate was concentrated to give a residue. The residue was purified by flash silica gel chromatography to give 179-2 (620 mg, 1.6 mmol, 67.1% yield). LCMS (ESI): RT=0.802 min, mass calc. for C$_{15}$H$_{14}$BrN$_5$O 359.04, m/z found 360.0 [M+H]$^+$; $^1$HNMR (400 MHz, CDCl$_3$) δ 8.85 (s, 1H), 8.16 (dd, J=1.5, 7.8 Hz, 1H), 7.45-7.40 (m, 2H), 7.39-7.29 (m, 2H), 7.18-7.11 (m, 2H), 6.99-6.92 (m, 1H), 4.92-4.80 (m, 2H), 4.33-4.21 (m, 2H), 2.29 (t, J=6.3 Hz, 1H).

Step 2: 2-[5-[2-(4-azidoanilino)phenyl]tetrazol-2-yl]ethanol

To a solution of 179-2 (50 mg, 0.14 mmol, 1.0 eq) and NaN$_3$ (72.2 mg, 1.1 mmol, 8.0 eq) in EtOH (6 mL) and Water (2 mL) was added (1R,2R)-N1,N2-dimethylcyclohexane-1,2-diamine (19.7 mg, 0.14 mmol, 1.0 eq), CuI (26.4 mg, 0.14 mmol, 1 eq) and L-sacorbic acid sodium (27.5 mg, 0.14 mmol, 1 eq). The mixture was stirred at 50° C. for 1 hr. LC-MS showed 179-2 was consumed completely and one main peak with the desired MS was detected. The reaction mixture was poured into water (30 mL) and extracted with EtOAc (10 mL*3). The combined organic layer was washed with brine (10 mL), dried over Na$_2$SO$_4$ and filtered. The filtrate was concentrated to give a residue. The residue was purified by prep-HPLC. The resulting eluent was concentrated to give a residue and the residue was lyophilized to give Compound 179 (19.70 mg, 61.12 umol, 44.03% yield). LCMS (ESI): RT=1.198 min, mass calc. for $C_{15}H_{14}N_8O$ 322.13, m/z found 323.0 [M+H]$^+$; $^1$HNMR (400 MHz, DMSO-$d_6$) δ 8.71 (s, 1H), 8.07 (dd, J=1.4, 7.9 Hz, 1H), 7.42-7.35 (m, 1H), 7.34-7.25 (m, 3H), 7.13-7.07 (m, 2H), 7.04-6.93 (m, 1H), 5.10 (t, J=5.8 Hz, 1H), 4.80 (t, J=5.3 Hz, 2H), 3.97 (q, J=5.5 Hz, 2H).

Example 173: 4-((5-(2-((4-(trifluoromethyl)phenyl) amino)phenyl)-2H-tetrazol-2-yl)methyl)oxazolidin-2-one (Compound 180)

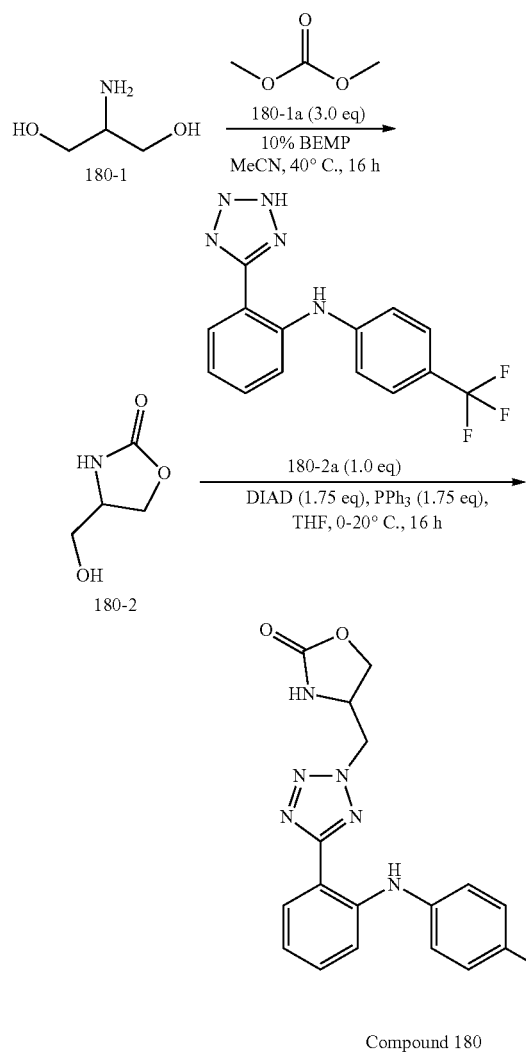

Compound 180

Step 1: 4-(hydroxymethyl)oxazolidin-2-one

To a mixture of the BEMP (301 mg, 1.10 mmol, 0.1 eq) in CH$_3$CN (10 mL) was added 180-1 (1.0 g, 10.98 mmol, 1.0 eq) and 180-1a (2.97 g, 32.93 mmol, 2.77 mL, 3.0 eq). The reaction mixture was stirred at 40° C. for 16 hour. TLC (Ethyl acetate, Rf=0.1) showed new spot was found. The reaction mixture was concentrated under vacuum to give a residue. The residue was purified by flash silica gel chromatography to give 180-2 (0.3 g, 2.56 mmol, 23% yield). $^1$HNMR ((400 MHz, DMSO-$d_6$) δ 7.61 (s, 1H), 4.98 (t, J=5.5 Hz, 1H), 4.36-4.25 (m, 1H), 4.05 (dd, J=5.0, 8.5 Hz, 1H), 3.80-3.70 (m, 1H), 3.37 (s, 1H), 3.34 (s, 1H).

Step 2: 4-((5-(2-((4-(trifluoromethyl)phenyl)amino) phenyl)-2H-tetrazol-2-yl)methyl)oxazolidin-2-one To a solution of 180-2 (34 mg, 0.293 mmol, 2.0 eq) and 180-2a (50 mg, 0.146 umol, 1.0 eq, HCl) in anhydrous THF (2 mL) was added PPh$_3$ (67 mg, 0.256 mmol, 1.75 eq) and the mixture was cooled to 0° C. under N$_2$. DIAD (51.78 mg, 256.06 umol, 49.79 uL, 1.75 eq) was added. The reaction mixture was stirred at 0° C. for 5 min and stirred at 20° C. for 16 h. LCMS showed 49% of the desired compound was found and the starting material was consumed completely. The solution was concentrated under reduced pressure to give a residue. The residue was purified by prep-HPLC to give Compound 180 (13 mg, 32 umol, 22% yield). LCMS (ESI): RT=0.795 min, mass calc. for $C_{18}H_{15}F_3N_6O_2$ 404.12, m/z found 427.0 [M+23]$^+$; $^1$HNMR (400 MHz, DMSO-$d_6$) δ 8.69 (s, 1H), 8.07 (dd, J=1.3, 7.8 Hz, 1H), 7.97 (s, 1H), 7.60-7.54 (m, 3H), 7.54-7.48 (m, 1H), 7.27-7.17 (m, 3H), 4.89 (d, J=5.3 Hz, 2H), 4.50-4.36 (m, 2H), 4.25 (dd, J=3.9, 8.2 Hz, 1H).

Example 174: 2-[5-[4-fluoro-2-[4-(trifluoromethyl) anilino]phenyl]tetrazol-2-yl]ethanol; (Compound 181)

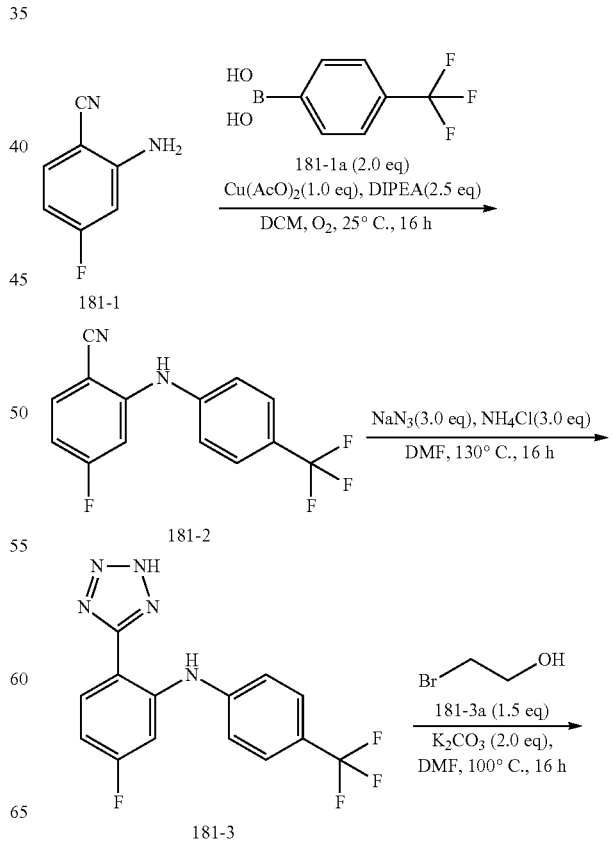

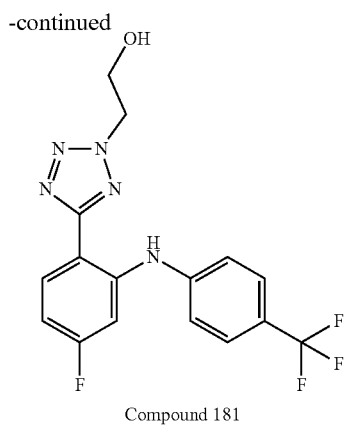

Compound 181

Step 1: 4-fluoro-2-[4-(trifluoromethyl)anilino]benzonitrile

To a mixture of 181-1 (500 mg, 3.67 mmol, 1 eq) and 181-1a (1.40 g, 7.35 mmol, 2 eq) in DCM (7 mL) was added Cu(OAc)$_2$ (667 mg, 3.67 mmol, 1 eq) and DIPEA (1.19 g, 9.18 mmol, 1.6 mL, 2.5 eq) in one portion under O$_2$ (15 Psi). The mixture was stirred at 25° C. for 18 h. LCMS showed no desired MS was detected. TLC indicated the starting material was remained. The reaction mixture was added 181-1a (400 mg) and continued stirred 24 h. The reaction mixture was filtered and concentrated under reduced pressure to give a residue. The residue was purified by flash silica gel chromatography to provide 181-2 (150 mg, 0.428 mmol, 11.7% yield). The product was used next step. $^1$H NMR (400 MHz, CHLOROFORM-d) δ7.65 (d, J=8.40 Hz, 2H), 7.59-7.54 (m, 1H), 7.32-7.27 (m, 2H), 7.02-6.96 (m, 1H), 6.72-6.63 (m, 1H), 6.55 (br s, 1H).

Step 2: 5-fluoro-2-(2H-tetrazol-5-yl)-N-[4-(trifluoromethyl)phenyl]aniline

To a mixture of 181-2 (150 mg, 0.535 umol, 1 eq) and NaN$_3$ (130 mg, 2.00 mmol, 3.74 eq) in DMF (2.5 mL) was added NH$_4$Cl (86 mg, 1.61 mmol, 3 eq) in one portion at 15° C. under N$_2$. The mixture was stirred at 130° C. for 16 h. LCMS showed no desired MS was detected. The reaction mixture was diluted with water (10 mL) and extracted with EtOAc (10 mL*3). The combined organic layers were dried with anhydrous Na$_2$SO$_4$, filtered and concentrated under vacuum. LCMS showed one main peak and 181-3 (150 mg, 408.36 umol, 76.29% yield) was used in the next step. $^1$HNMR (400 MHz, DMSO-d$_6$) δ9.42 (s, 1H), 7.95-7.90 (m, 1H), 7.64 (d, J=8.80 Hz, 2H), 7.36 (d, J=8.80 Hz, 2H), 7.32-7.27 (m, 1H), 7.05-6.99 (m, 1H).

Step 3: 2-[5-[4-fluoro-2-[4-(trifluoromethyl)anilino]phenyl]tetrazol-2-yl]ethanol To a mixture of 181-3 (50 mg, 0.155 mmol, 1 eq) and 181-3a (29 mg, 0.232 mmol, 1.5 eq) in DMF (1 mL) was added K$_2$CO$_3$ (43 mg, 0.309 mmol, 2 eq) in one portion at 15° C. under N$_2$. The mixture was stirred at 100° C. for 16 h. LCMS showed the starting material was consumed completely but no desired MS was detected. The reaction mixture was diluted with water (4 mL) and extracted with EtOAc (4 mL*3). The combined organic layers were dried with anhydrous Na$_2$SO$_4$, filtered and concentrated under vacuum. The residue was purified by prep-HPLC (basic condition) to obtain Compound 181 (7.23 mg, 19.5 umol, 12.6% yield). LCMS (ESI): RT=1.247 min, mass calcd. for C$_{16}$H$_{13}$F$_4$N$_5$O, 367.11 m/z found 368.0[M+H]$^+$. $^1$HNMR (400 MHz, DMSO-d$_6$) δ9.04 (s, 1H), 8.14-8.16 m, 1H), 7.63 (d, J=8.40 Hz, 2H), 7.36 (d, J=8.40 Hz, 2H), 7.32-7.27 (m, 1H), 7.02-6.94 (m, 1H), 5.06 (t, J=5.60 Hz, 1H), 4.78 (t, J=5.20 Hz, 2H), 3.98-3.91 (m, 2H).

Example 175: 2-[2-[2-(3-pyridyloxy)ethyl]tetrazol-5-yl]-N-[4-(trifluoromethyl)phenyl]aniline (Compound 182)

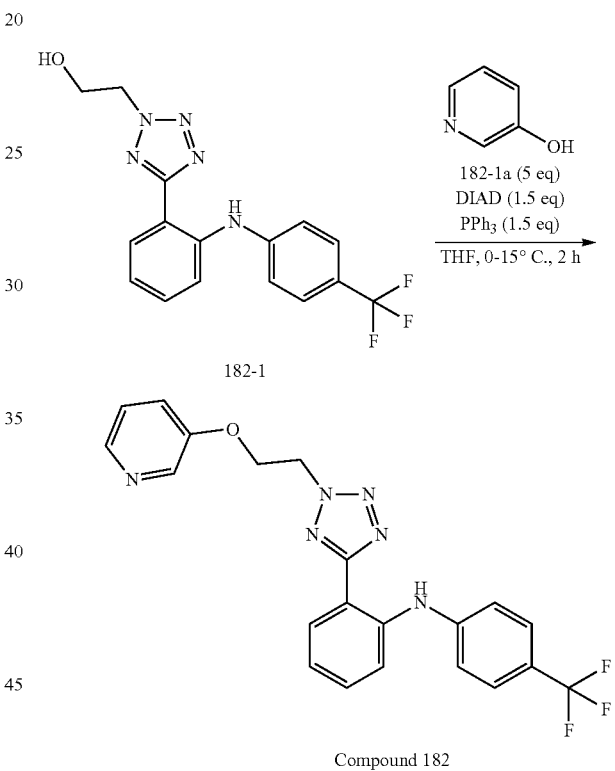

Compound 182

To a solution of 182-1 (50 mg, 0.14 mmol, 1 eq), pyridin-3-ol (68.1 mg, 0.72 mmol, 16.55 uL, 5 eq) and PPh$_3$ (56.3 mg, 0.21 mmol, 1.5 eq) in THF (1.2 mL) was added DIAD (43.4 mg, 0.21 mmol, 41.75 uL, 1.5 eq) at 0° C. The reaction mixture was stirred at 15° C. for 2 hr. LCMS showed that starting material was remained and 18% of desired product was detected. The reaction was concentrated. The crude product was purified by Prep.HPLC to give the title compound (2.51 mg, 5.57 umol, 3.89% yield). LCMS (ESI): RT=0.717 min, mass calc. for C$_{21}$H$_{17}$F$_3$N$_6$O 426.14, m/z found 427.0 [M+H]$^+$. $^1$HNMR (400 MHz, DMSO) δ 8.66 (s, 1H), 8.00 (d, J=8.4 Hz, 1H), 7.70-7.60 (m, 1H), 7.60-7.50 (m, 3H), 7.50-7.40 (m, 1H), 7.37 (s, 1H), 7.25-7.18 (m, 2H), 7.18-7.10 (m, 2H), 6.85 (d, J=8.4 Hz, 1H), 5.35 (t, J=5.2 Hz, 2H), 4.80 (t, J=5.6 Hz, 2H).

Example 176: 2-(2-(2-(difluoromethoxy)ethyl)-2H-tetrazol-5-yl)-N-(4-(trifluoromethyl) phenyl)aniline (Compound 183)

Example 177: 2-[2-[2-(2-fluorophenoxy)ethyl]tetrazol-5-yl]-N-[4-(trifluoromethyl)phenyl]aniline (Compound 184)

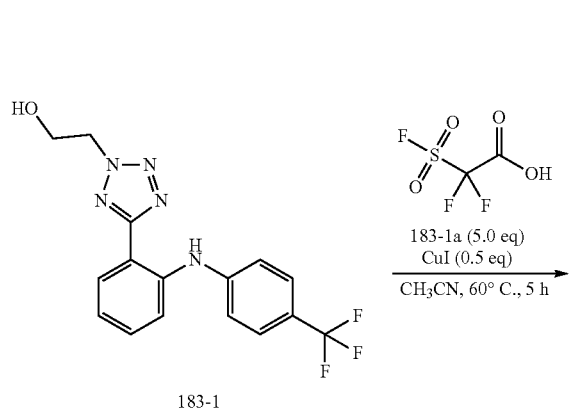

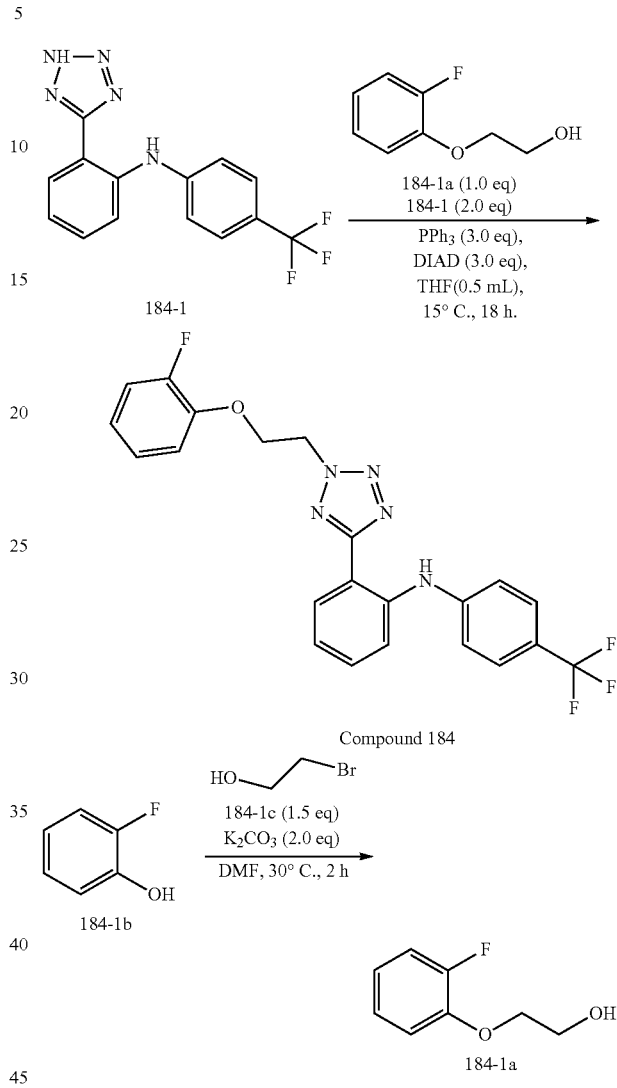

To a mixture of 183-1 (30 mg, 85.9 umol, 1 eq) in CH₃CN (4 mL), was added CuI (8.2 mg, 42.9 umol, 0.5 eq). The mixture was heated to 60° C. 183-1a (76.5 mg, 429.4 umol, 44.5 uL, 5 eq) was added dropwise. The resulting mixture was stirred at 60° C. for 5 h. LCMS and HPLC showed there's about 28% desired compound, and 23% starting material was remained. The mixture was diluted with water (10 mL), extracted with EtOAc (10 mL*3). The organic layer was dried over anhydrous Na₂SO₄, concentrated under vacuum. The residue was purified by prep-HPLC to provide the title compound (6.19 mg, 15.50 umol, 18.05% yield). LCMS (ESI): RT=0.885 min, mass calc. for $C_{17}H_{14}F_5N_5O$ 399.11, m/z found 400.0 [M+H]⁺. ¹HNMR (400 MHz, CHLOROFORM-d) δ 9.01 (s, 1H), 8.21 (dd, J=1.5, 7.8 Hz, 1H), 7.57-7.52 (m, 3H), 7.42-7.36 (m, 1H), 7.31 (d, J=8.5 Hz, 2H), 7.08-7.02 (m, 1H), 6.42-6.01 (m, 1H), 4.96 (t, J=5.5 Hz, 2H), 4.50 (t, J=5.4 Hz, 2H).

Step 1: 2-(2-fluorophenoxy)ethan-1-ol

To a suspension and mixture of 184-1b (100 mg, 0.892 mmol, 1 eq) and 184-1c (223 mg, 1.78 mmol, 2 eq) in DMF (2 mL) was added K₂CO₃ (432 mg, 3.12 mmol, 3.5 eq) in one portion. The mixture was stirred at 30° C. for 2 h. TLC showed the starting material was consumed completely and one new spot was formed. The reaction mixture was diluted with EtOAc (30 mL) and washed with water (30 mL*2), The organic phase was dried with anhydrous Na₂SO₄, filtered and concentrated under vacuum. The residue was purified by flash silica gel chromatography to provide 184-1a (45 mg, 0.242 mmol, 27.1% yield). ¹HNMR (400 MHz, CHLOROFORM-d) δ7.14-6.90 (m, 4H), 4.18-4.15 (m, 2H), 4.02-3.96 (m, 2H), 2.12 (t, J=6.40 Hz, 1H).

Step 2: 2-[2-[2-(2-fluorophenoxy)ethyl]tetrazol-5-yl]-N-[4-(trifluoromethyl)phenyl]aniline To a solution of the 184-1a (15 mg, 81 umol, 1 eq), PPh₃ (63 mg, 0.242 umol, 3 eq) and the 184-1 (49 mg, 0.161 mmol, 2 eq) in THF (0.5 mL) was added DIAD (49 mg, 0.242 mmol, 3 eq) in one portion at 0° C. under N₂. The mixture was stirred at 0° C. for 3 min, and then warmed to 15° C. for 2 h. LCMS showed only starting material was consumed completely and 23% of desired product was formed. The reaction mixture was continued stirred 16 h. The reaction mixture was concentrated under reduced pressure to remove solvent. HPLC indicated 16% of desired product was detected. The residue was purified by prep-HPLC to provide Compound 184 (6.93 mg, 15.47 umol, 19.18% yield). LCMS (ESI): RT=0.932 min, mass calcd. for C$_{22}$H$_{17}$F$_4$N$_5$O, 443.14 m/z found 444.1[M+H]⁺. ¹HNMR (400 MHz, CHLOROFORM-d) δ 9.00 (s, 1H), 8.25-8.19 (m, 1H), 7.53 (d, J=8.40 Hz, 3H), 7.43-7.35 (m, 1H), 7.30 (s, 2H), 7.09-6.99 (m, 3H), 6.98-6.90 (m, 2H), 5.11 (t, J=5.40 Hz, 2H), 4.68 (t, J=5.40 Hz, 2H).

Example 178: 2-(2-(2-(trifluoromethoxy)ethyl)-2H-tetrazol-5-yl)-N-(4-(trifluoromethyl) phenyl)aniline (Compound 185)

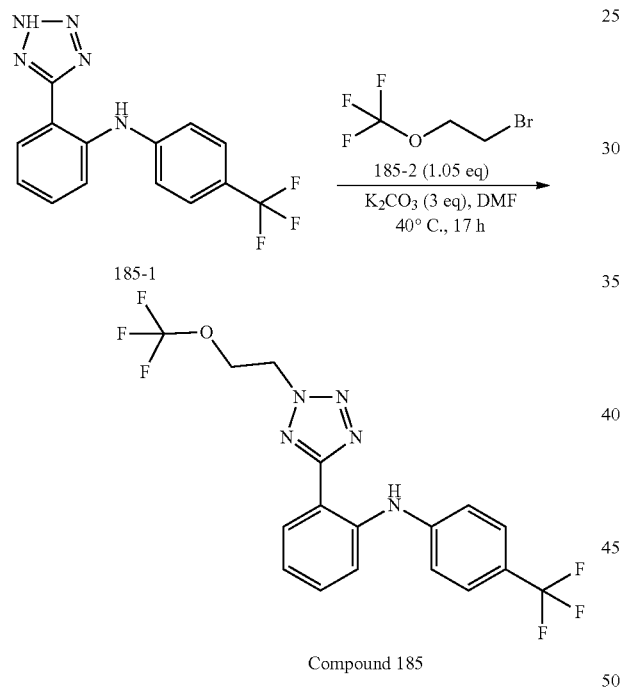

Compound 185

To a mixture of 185-1 (30 mg, 98.3 umol, 1 eq) and K$_2$CO$_3$ (40.8 mg, 0.3 mmol, 3 eq) in DMF (2 mL), was added 185-2 (19.9 mg, 0.1 mmol, 1.05 eq). The resulting mixture was stirred at 40° C. for 17 h. LCMS showed about 42% desired compound and that 56% starting material remained. The mixture was filtered, and the solid was washed with DMF (1 mL). The filtrate was checked by HPLC. The filtrate was purified by prep-HPLC to provide the title compound (3.89 mg, 9.3 umol, 9.5% yield). LCMS (ESI): RT=0.920 min, mass calc. for C$_{17}$H$_{13}$F$_6$N$_5$O 417.10, m/z found 417.9 [M+H]⁺. ¹HNMR (400 MHz, CHLOROFORM-d) δ 8.98 (s, 1H), 8.21 (d, J=7.5 Hz, 1H), 7.54 (dd, J=4.9, 8.2 Hz, 3H), 7.40 (t, J=7.4 Hz, 1H), 7.31 (d, J=8.3 Hz, 2H), 7.06 (t, J=7.5 Hz, 1H), 5.01 (t, J=5.4 Hz, 2H), 4.61 (t, J=5.4 Hz, 2H).

Example 179: 3-((5-(2-((4-(trifluoromethyl)phenyl)amino)phenyl)-2H-tetrazol-2-yl)methyl) oxetan-3-ol (Compound 186)

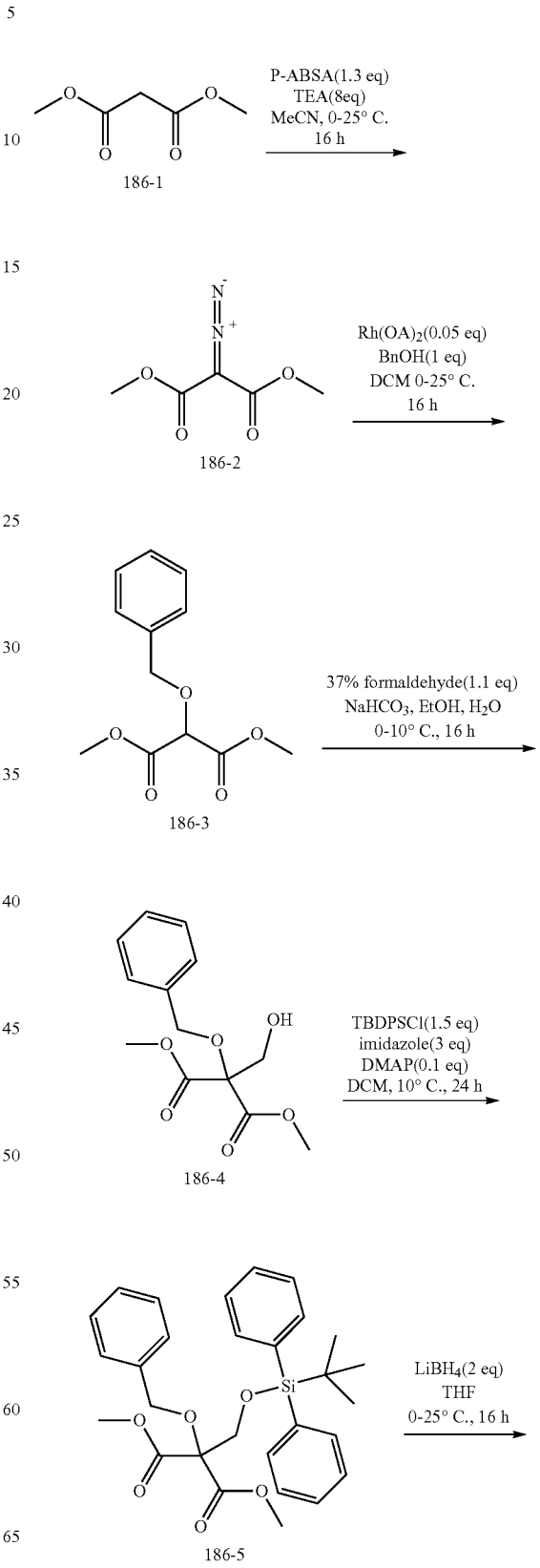

-continued

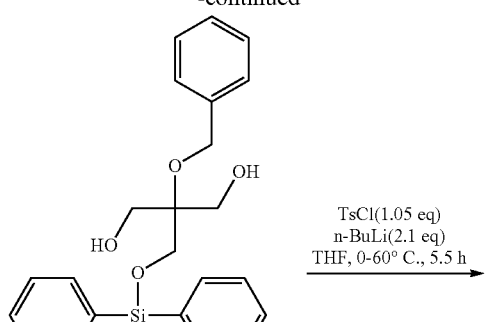
186-6

TsCl(1.05 eq)
n-BuLi(2.1 eq)
THF, 0-60° C., 5.5 h
→

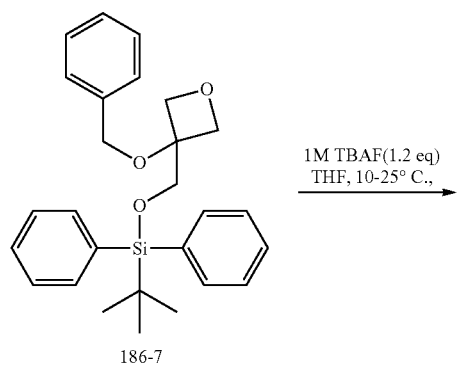
186-7

1M TBAF(1.2 eq)
THF, 10-25° C.,
→

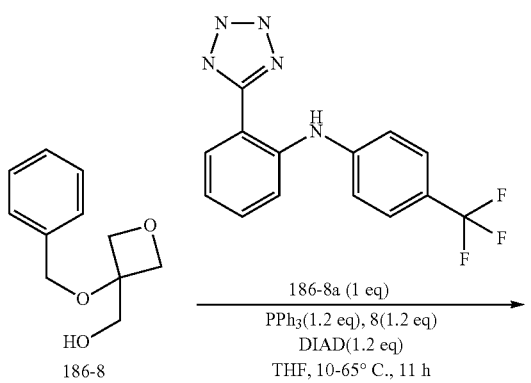
186-8

186-8a (1 eq)
PPh₃(1.2 eq), 8(1.2 eq)
DIAD(1.2 eq)
THF, 10-65° C., 11 h
→

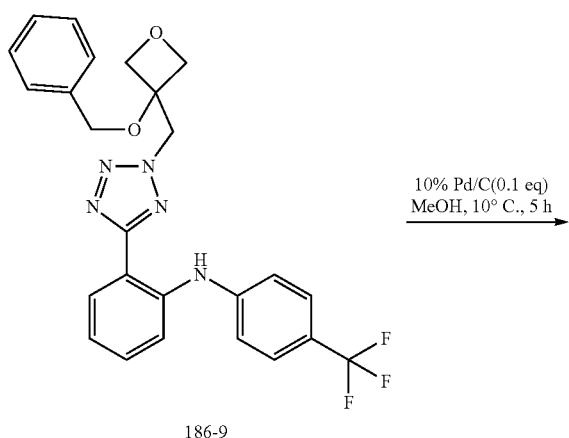
186-9

10% Pd/C(0.1 eq)
MeOH, 10° C., 5 h
→

-continued

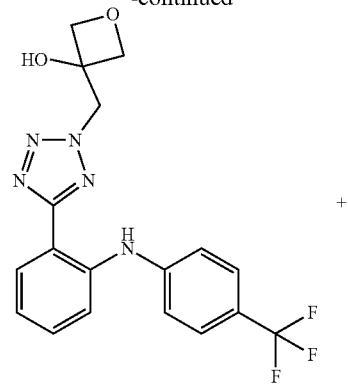
Compound 186

+

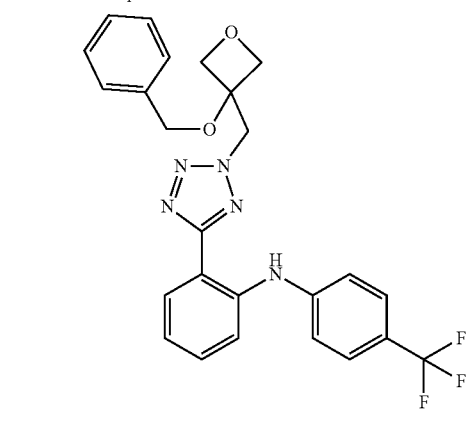
186-9

Step 1: dimethyl 2-diazomalonate

To a solution of dimethyl propanedioate 186-1 (1.5 g, 11.35 mmol, 1.30 mL, 1 eq) in MeCN (40 mL) was added N-(4-azidosulfonylphenyl)acetamide (P-ABSA) (3.55 g, 14.76 mmol, 1.3 eq) at 0° C. under nitrogen. TEA (9.19 g, 90.83 mmol, 12.6 mL, 8 eq) was then added. The resulting solution was stirred at 25° C. for 16 h, over which time lots of solid was formed. TLC (PE:EtOAc=2:1 UV) showed new spots were formed. The reaction mixture was filtered and the filtrate was evaporated carefully, but not to dryness. The reaction mixture was diluted with DCM (75 mL). This solution was washed sequentially with saturated NaHCO₃ (15 mL*2), and water (15 mL*2). The organic phase was dried over anhydrous Na₂SO₄, and gently evaporated, but not to complete dryness to give crude product dimethyl 2-diazopropanedioate 186-2 (3.4 g, crude), which was used for next step without further purification. ¹HNMR (400 MHz, CHLOROFORM-d) δ 3.83 (s, 6H).

Step 2: dimethyl 2-(benzyloxy)malonate

To a solution of dimethyl 2-diazopropanedioate 186-2 (3.4 g, 10.75 mmol, 1 eq) in DCM (7 mL) was added phenylmethanol (1.16 g, 10.75 mmol, 1.1 mL, 1 eq) at 0° C. under nitrogen. Diacetoxyrhodium (118.8 mg, 0.54 mmol, 0.05 eq) was then added. The resulting solution was stirred at 22° C. for 16 h, over which time lots of precipitation was formed. TLC (PE:EtOAc=1:1 UV) showed new spots were formed. LCMS showed two main peaks were present but no desired mass was present. The reaction mixture was diluted with DCM (50 mL) and washed with brine (15 mL). The organic phase was dried over anhydrous Na$_2$SO$_4$ and concentrated to give a residue. The residue was purified by column chromatography to give dimethyl 2-benzyloxypropanedioate 186-3 (1.9 g, 7.98 mmol, 74.18% yield). $^1$HNMR (400 MHz, CHLOROFORM-d) δ 7.43-7.33 (m, 5H), 4.73-4.68 (m, 2H), 4.57 (s, 1H), 3.83-3.78 (m, 6H).

Step 3: dimethyl 2-(benzyloxy)-2-(hydroxymethyl)malonate

To a solution of dimethyl 2-benzyloxypropanedioate 186-3 (1.9 g, 7.98 mmol, 1 eq) and NaHCO$_3$(67.0 mg, 0.8 mmol, 31.02 uL, 0.1 eq) in EtOH (8 mL) was drop-wise added formaldehyde (711.9 mg, 8.77 mmol, 0.65 mL, 1.1 eq) at 0° C. The resulting mixture was stirred at 10° C. for 16 h. TLC (PE:EtOAc=2:1 UV) showed new spots were formed and material was consumed completely. LCMS showed 82% of desired product was present. The reaction mixture was concentrated and then diluted with DCM (50 mL) and washed with brine (15 mL). The organic phase was dried over anhydrous Na$_2$SO$_4$ and concentrated to give crude product dimethyl 2-benzyloxy-2-(hydroxymethyl) propanedioate 186-4 (2.1 g, 7.83 mmol, 98.16% yield). LCMS (ESI): RT=0.647 min, mass calc. for C$_{13}$H$_{16}$O$_6$ 268.09, m/z found 290.9 [M+23]$^+$.

Step 4: dimethyl 2-(benzyloxy)-2-(((tert-butyldiphenylsilyl)oxy)methyl)malonate

To a solution of dimethyl 2-(benzyloxy)-2-(hydroxymethyl)propanedioate 186-4 (2.1 g, 7.83 mmol, 1 eq), DMAP (95.6 mg, 0.78 mmol, 0.1 eq) and imidazole (1.60 g, 23.48 mmol, 3 eq) in DMF (15 mL) was portion-wise added TBDPSCl (3.23 g, 11.74 mmol, 3.02 mL, 1.5 eq) at 10° C. The resulting solution was stirred at 10° C. under nitrogen for 24 h. TLC (PE:EtOAc=10:1 UV) showed new spots were formed and material was consumed completely. LCMS showed 56% of desired product was present. The reaction mixture was diluted with EtOAc (80 mL) and washed with brine (15 mL*4). The organic phase was dried over anhydrous Na$_2$SO$_4$ and concentrated to give a residue. The residue was purified by flash silica gel chromatography to give dimethyl 2-benzyloxy-2-[[tert-butyl(diphenyl)silyl] oxymethyl]propanedioate 186-5 (4.5, crude). LCMS (ESI): RT=1.005 min, mass calc. for C$_{29}$H$_{34}$O$_6$Si 506.21, m/z found 529.1 [M+23]$^+$.

Step 5: 2-(benzyloxy)-2-(((tert-butyldiphenylsilyl) oxy)methyl)propane-1,3-diol

To a solution of 186-5 (4.5 g, 8.88 mmol, 1 eq) in THF (50 mL) was portionwise added lithium; boranuide (406.3 mg, 18.65 mmol, 2.1 eq) at 0° C. under nitrogen (gas evolved). The reaction was allowed to warm to 25° C. and stirred at this temperature for 16 h. TLC (PE:EtOAc=1:1 UV) showed new spot was formed and material was consumed completely. LCMS showed 52% of desired product was present. The reaction mixture was quenched with water (15 mL) at 0° C. and filtered. The filtrate was diluted with EtOAc (80 mL) and washed with brine (15 mL*2). The organic phase was dried over anhydrous Na$_2$SO$_4$ and concentrated to give a residue. The residue was purified by flash silica gel chromatography to give 186-6 (2.9 g, 5.98 mmol, 67.38% yield). LCMS (ESI): RT=0.912 min, mass calc. for C$_{27}$H$_{34}$O$_4$Si 450.22, m/z found 473.1 [M+23]$^+$.

Step 6: ((3-(benzyloxy)oxetan-3-yl)methoxy)(tert-butyl)diphenylsilane

To a solution of 186-6 (2.9 g, 6.44 mmol, 1 eq) in THF (30 mL) was drop-wise added n-BuLi (2.5 M, 2.7 mL, 1.05 eq) at 0° C. After stirring for 20 min, a solution of 4-methylbenzenesulfonyl chloride (1.29 g, 6.76 mmol, 1.05 eq) in THF (5 mL) was added drop-wise. The reaction was stirred for 60 minutes at 0° C. and n-BuLi (2.5 M, 2.7 mL, 1.05 eq) was added. After stirring at 0° C. for 40 min, the reaction mixture was then heated to 60° C. and stirred at this temperature for 3.5 h. TLC (PE:EtOAc=2:1 UV) showed new spots were formed and material was consumed completely. LCMS showed 41% of desired product was present and material was consumed completely. The reaction mixture was quenched with water (15 mL) at 0° C. The mixture was diluted with EtOAc (80 mL) and washed with brine (15 mL*2). The organic phase was dried over anhydrous Na$_2$SO$_4$ and concentrated to give a residue. The residue was purified by flash silica gel chromatography to give compound 186-7(1.6 g, 3.7 mmol, 57.47% yield) as colorless oil. $^1$HNMR (400 MHz, CHLOROFORM-d) δ 7.69 (d, J=6.5 Hz, 4H), 7.47-7.28 (m, 10H), 4.73 (d, J=7.0 Hz, 2H), 4.61-4.52 (m, 4H), 4.00 (s, 2H), 1.10 (s, 8H).

Step 7: (3-(benzyloxy)oxetan-3-yl)methanol

To a solution of 186-7 (1.6 g, 3.7 mmol, 1 eq) in THF (15 mL) was added TBAF (1 M, 3.7 mL, 1 eq) at 10° C. The resulting solution was stirred at 10° C. for 2 h. LCMS showed no desired mass signal was present and 27% of material was remained. Then another batch of TBAF (1 M, 3.70 mL, 1 eq) was added and the solution was stirred at 25° C. for 1 h. TLC (PE:EtOAc=1:1 UV and stained by iodine) showed new spots were formed and some of material was remained. The reaction mixture was evaporated to dryness to give a crude product. The residue was purified by flash silica gel chromatography to give 186-8 (0.4 g, 2.06 mmol, 55.69% yield) as colorless oil. $^1$HNMR (400 MHz, CHLOROFORM-d) δ 7.43-7.29 (m, 4H), 4.82 (d, J=7.5 Hz, 2H), 4.65 (s, 2H), 4.48 (d, J=7.5 Hz, 2H), 4.00 (d, J=6.0 Hz, 2H), 1.87 (t, J=6.3 Hz, 1H).

Step 8: 2-(2-((3-(benzyloxy)oxetan-3-yl)methyl)-2H-tetrazol-5-yl)-N-(4-(trifluoromethyl) phenyl) aniline To a solution of 186-8 (0.25 g, 0.82 mmol, 1 eq), 186-8a (190.8 mg, 0.98 mmol, 1.2 eq) and PPh$_3$ (257.8 mg, 0.98 mmol, 1.2 eq) in THF (1.7 mL) was added DIAD (198.7 mg, 0.98 mmol, 0.19 mL, 1.2 eq) at 10° C. The resulting lightly yellow solution was stirred at 10° C. for 2 h. LCMS showed 17% of desired product was formed and 29% of material was remained. Then the solution was continuously stirred at 10° C. for another 3 h. LCMS showed 34% of desired product was formed and 23% of material was remained. Then the solution was stirred at 65° C. for another 6 h. LCMS showed 23% of desired product was formed and 33% of material was remained. The solution was combined with the another batch and concentrated to give a residue. The residue was purified by flash silica gel chromatography to give compound 186-9 (0.5 g, crude). LCMS (ESI): RT=0.926 min, mass calc. for C$_{25}$H$_{22}$F$_3$N$_5$O$_2$ 481.17, m/z found 482.1 [M+1]$^+$.

Step 9: 3-((5-(2-((4-(trifluoromethyl)phenyl)amino) phenyl)-2H-tetrazol-2-yl)methyl) oxetan-3-ol To a solution of 186-9 (0.4 g, 0.83 mmol, 1 eq) in MeOH (10 mL) was added Pd/C (0.35 g, 0.33 mmol, 10% purity, 0.5 eq) at 15° C. The resulting dark mixture was degassed and refilled with H₂ balloon for three times and then stirred at 15° C. for 5 h under 1 atm H₂. LCMS showed 22% desired product was formed and 11% of material was remained. TLC (PE:EtOAc=2:1 UV) showed a new spot was formed and a little of material was remained. The mixture was combined with the batch of page ES6650-78 and filtered via a pad of celite. The filter cake was washed with MeOH (20 mL). The filtrate was concentrated to give a residue. The residue was purified by prep_HPLC to give Compound 186 (41.67 mg, 0.11 mmol, 12.82% yield) and recover material 186-9 (10.8 mg, 22.4 umol, 2.70% yield).

Compound 186: LCMS (ESI): RT=1.711 min, mass calc. for $C_{18}H_{16}F_3N_5O_2$ 391.13, m/z found 392.0 [M+1]⁺. (400 MHz, DMSO-d₆) δ 8.75 (s, 1H), 8.08 (br d, J=7.5 Hz, 1H), 7.63-7.45 (m, 4H), 7.27-7.15 (m, 3H), 6.26 (s, 1H), 5.08 (s, 2H), 4.73 (d, J=7.0 Hz, 2H), 4.48 (d, J=7.0 Hz, 2H).

186-9: LCMS (ESI): RT=0.921 min, mass calc. for $C_{25}H_{22}F_3N_5O_2$ 481.17, m/z found 482.1 [M+1]⁺. ¹HNMR (400 MHz, CHLOROFORM-d) δ 8.95 (s, 1H), 8.19 (d, J=8.0 Hz, 1H), 7.52 (br d, J=8.5 Hz, 3H), 7.38 (t, J=7.8 Hz, 1H), 7.29-7.21 (m, 7H), 7.04 (t, J=7.5 Hz, 1H), 5.27 (s, 2H), 4.90-4.84 (m, 2H), 4.83-4.78 (m, 2H), 4.68 (s, 2H), 2.18 (s, 1H).

Example 180: 2-(5-(2-fluoro-6-((4-(trifluoromethyl)phenyl)amino)phenyl)-2H-tetrazol-2-yl)ethan-1-ol (Compound 187)

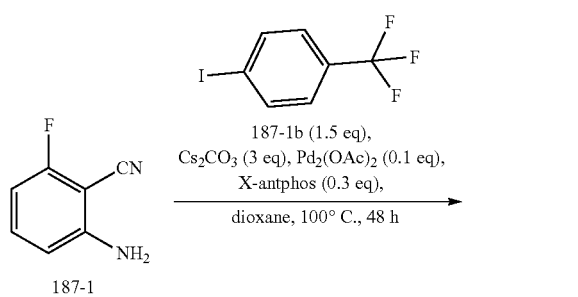

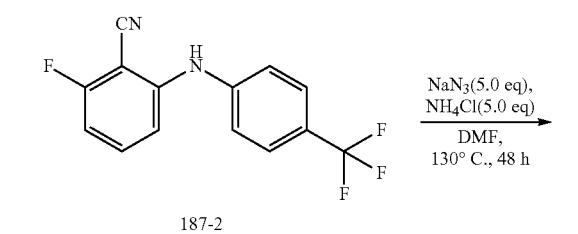

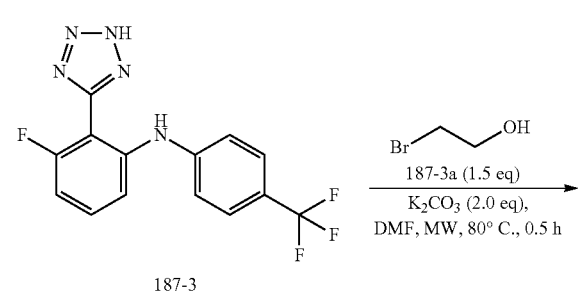

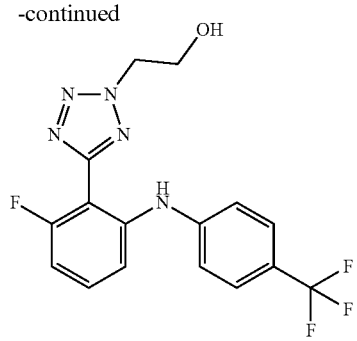

Compound 187

Step 1: 2-fluoro-6-[4-(trifluoromethyl)anilino]benzonitrile

To a mixture of 187-1 (0.2 g, 1.4 mmol, 1.0 eq), 187-1b (599.4 mg, 2.2 mmol, 0.3 uL, 1.5 eq) and Cs₂CO₃ (1.4 g, 4.4 mmol, 3.0 eq) in dioxane (10.0 mL) was added xantphos (255.0 mg, 0.4 umol, 0.3 eq) and Pd(OAc)₂ (32.9 mg, 0.1 umol, 0.1 eq) in one portion under N₂. The mixture was stirred at 100° C. for 16 h. TLC indicated 187-1 was consumed completely and two new spots formed. The reaction was clean according to TLC. The reaction mixture concentrated under reduced pressure to give a residue. The residue was purified by column chromatography (SiO2) to give 187-2 (200 mg, 0.7 mmol, 48% yield).

Step 2: 3-fluoro-2-(2H-tetrazol-5-yl)-N-[4-(trifluoromethyl)phenyl]aniline

To a mixture of 187-2 (250.0 mg, 0.9 mmol, 1.0 eq) and azidosodium (289.9 mg, 4.46 mmol, 5.0 eq) in DMF (2.0 mL) was added NH₄Cl (238.61 mg, 4.46 mmol, 0.16 mL, 5.0 eq) in one portion under N₂. The mixture was heated to 130° C. for 16 h. Several new peaks were shown on LC-MS and 35% of the desired compound was detected. The reaction mixture was added into aq.HCl (1.0 M) to give a suspension and extracted with EtOAc (10 mL*3). The combined organic layers were washed with brine (20 mL), dried over Na₂SO₄, filtered and concentrated under reduced pressure to give a residue. The residue was purified by prep-TLC (SiO₂) to give 187-3 (50 mg, crude). LCMS (ESI): RT=1.444 min, mass calc. for $C_{14}H_9F_4N_5$ 323.08, m/z found 323.9 [M+H]⁺.

Step 3: 2-(5-(2-fluoro-64(4-(trifluoromethyl)phenyl)amino)phenyl)-2H-tetrazol-2-yl)ethan-1-ol To a solution of 187-3 (20.0 mg, 61.8 umol, 1.0 eq) in DMF (2.0 mL) was added K₂CO₃ (17.1 mg, 0.1 mmol, 2.0 eq) and 187-3a (11.6 mg, 92.8 mmol, 6.5 uL, 1.5 eq). The mixture was stirred at 80° C. for 0.5 hr under microwave. Several new peaks were shown on LC-MS and 11% of the desired compound was detected. The mixture was purified by prep-HPLC to give Compound 187 (2.07 mg, 5.64 umol, 9% yield). LCMS (ESI): RT=0.781 min, mass calc. for $C_{16}H_{13}F_4N_5O$ 367.11, m/z found 367.8 [M+H]⁺; ¹H NMR (400 MHz, CDCl₃) δ (ppm) 9.04 (s, 1H), 7.54 (d, J=8.5 Hz, 2H), 7.37-7.29 (m, 2H), 7.25 (s, 1H), 6.84-6.77 (m, 1H), 4.94-4.85 (m, 2H), 4.33-4.19 (m, 2H), 2.40 (t, J=6.3 Hz, 1H).

Example 181: 2-(5-(3-fluoro-2-((4-(trifluoromethyl)phenyl)amino)phenyl)-2H-tetrazol-2-yl)ethanol (Compound 188)

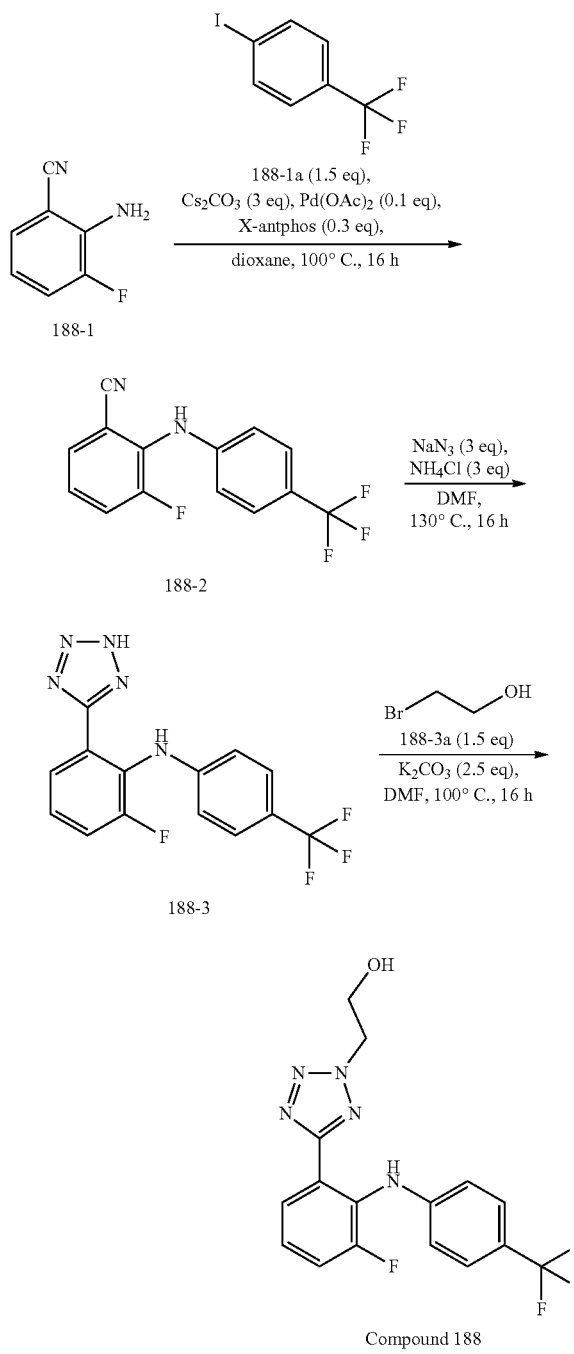

Step 1: 3-fluoro-2-((4-(trifluoromethyl)phenyl)amino)benzonitrile

To a mixture of 188-1 (400 mg, 2.94 mmol, 1 eq), 188-1a (1.20 g, 4.41 mmol, 0.648 mL, 1.5 eq) and $Cs_2CO_3$ (2.87 g, 8.82 mmol, 3 eq) in dioxane (10 mL) were added Xantphos (510.1 mg, 0.882 mmol, 0.3 eq) and Pd(OAc)$_2$ (66 mg, 0.294 mmol, 0.1 eq) in one portion under $N_2$. The mixture was stirred at 100° C. for 16 hours. The crude LCMS showed no desired product was detected but TLC (Petroleum ether:Ethyl acetate=10:1, Rf=0.15, UV 254 nm) indicated compound 188-1 remained and one major new spot had formed. The reaction mixture was quenched with water (35 mL), and extracted with EtOAc (30 mL*3). The combined organic layers were dried over anhydrous $Na_2SO_4$, filtered, and concentrated under reduced pressure to give a residue. The residue was purified by flash silica gel chromatography to give the 188-2 (239 mg, 0.853 mmol, 29.0% yield). $^1$HNMR (400 MHz, DMSO-d$_6$) δ 9.01 (s, 1H), 7.69-7.76 (m, 2H), 7.53 (d, J=8.53 Hz, 2H), 7.40 (td, J=8.09, 4.89 Hz, 1H), 6.87 (d, J=8.03 Hz, 2H).

Step 2: 2-fluoro-6-(2H-tetrazol-5-yl)-N-(4-(trifluoromethyl)phenyl)aniline

To a solution of 188-2 (139 mg, 0.496 mmol, 1 eq) in DMF (1 mL) was added NaN$_3$ (96.7 mg, 1.49 mmol, 3 eq) and NH$_4$Cl (79.6 mg, 1.49 mmol, 3 eq). The mixture was stirred at 130° C. for 16 hr. TLC (Petroleum ether:Ethyl acetate=1:1, Rf=0, UV 254 nm) indicated the compound 188-2 remained and one new spot had formed. The reaction mixture was combined with another batch, and the resulting reaction mixture was quenched with water (30 mL) and extracted with EtOAc (15 mL*3). The combined organic layers were washed with brine (15 mL), dried over anhydrous $Na_2SO_4$, filtered, and concentrated under reduced pressure to give a residue. The residue was purified by prep-TLC (Petroleum ether:Ethyl acetate=1:1) to give 188-3 (118 mg, 0.365 mmol, 42.8% yield). $^1$HNMR (400 MHz, DMSO-d$_6$) δ 10.22 (br s, 1H), 7.93-8.02 (m, 1H), 7.51 (s, 3H), 7.14-7.24 (m, 2H), 6.94 (s, 2H), 4.14 (br s, 1H).

Step 3: 2-(5-(3-fluoro-2-((4-(trifluoromethyl)phenyl)amino)phenyl)-2H-tetrazol-2-yl)ethanol To a solution of 188-3 (118 mg, 0.365 mmol, 1 eq) and 188-3a (68.4 mg, 0.548 mmol, 38.9 uL, 1.5 eq) in DMF (1 mL) was added K$_2$CO$_3$ (126.1 mg, 0.913 mmol, 2.5 eq). The mixture was stirred at 100° C. for 16 hr. The crude LCMS showed 188-3 was consumed completely and 45% of the desired product was detected. TLC (Petroleum ether:Ethyl acetate=1:1, Rf=0.46, UV 254 nm) indicated 188-3 remained and three new spots had formed. The reaction mixture was quenched with water (5 mL) and brine (5 mL) and extracted with EtOAc (10 mL*3). The combined organic layer was washed with brine (15 mL), dried over anhydrous $Na_2SO_4$, filtered, and concentrated under reduced pressure to give a residue. The residue was purified by flash silica gel chromatography to give the crude product (around 100 mg), which was diluted with MeOH (1 mL) and water (5 mL). Most of the solvent was removed by reduced pressure and the remaining aqueous fraction was lyophilized to give the Compound 188 (24.2 mg, 65.9 umol, 18.1% yield). LCMS (ESI): RT=2.134 min, mass calc. for $C_{16}H_{13}F_4N_5O$ 367.11, m/z found 368.0 [M+H]$^+$; $^1$HNMR (400 MHz, CD$_3$OD) δ 7.93-8.01 (m, 1H), 7.42 (d, J=8.53 Hz, 2H), 7.28-7.39 (m, 2H), 6.84 (dd, J=8.78, 2.01 Hz, 2H), 4.74-4.81 (m, 2H), 4.03-4.10 (m, 2H).

Example 182: tert-butyl 3-(2-(5-(2-((4-(trifluoromethyl)phenyl)amino)phenyl)-2H-tetrazol-2-yl)ethoxy)piperidine-1-carboxylate (Compound 190)

Example 183: 2-(4-(2-((4-(trifluoromethyl)phenyl)amino)phenyl)-1H-1,2,3-triazol-1-yl)ethan-1-ol (Compound 191)

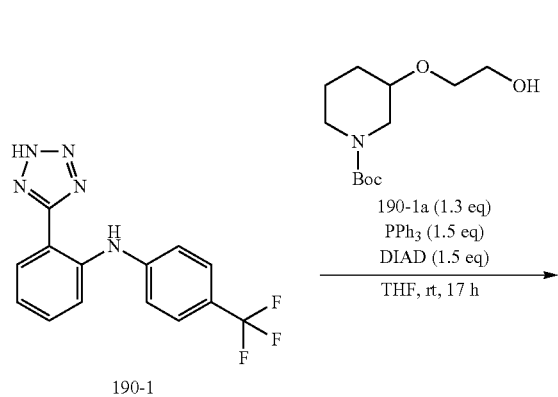

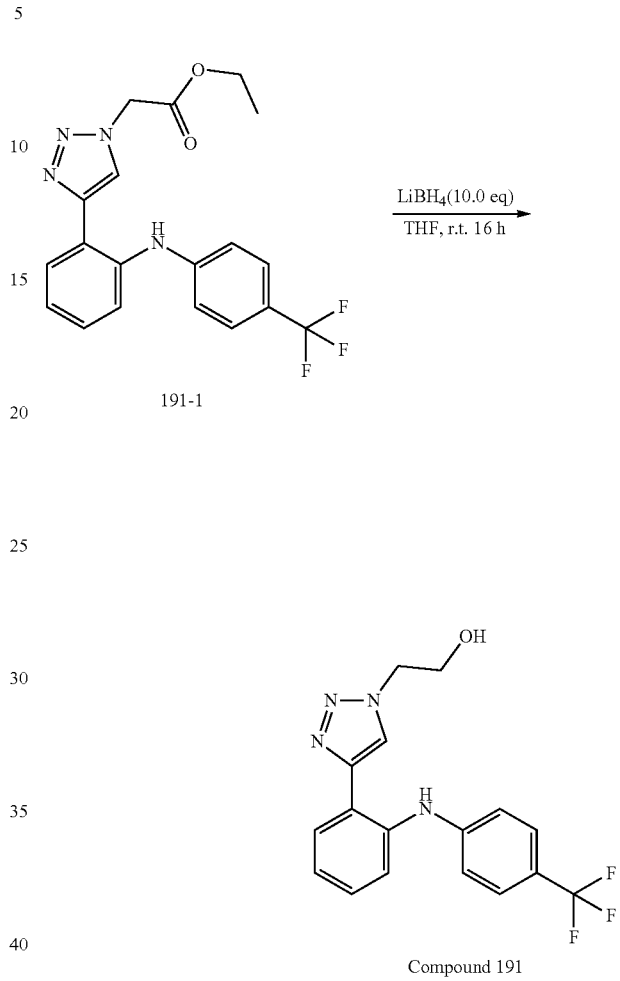

To a mixture of 190-1 (50 mg, 0.16 mmol, 1 eq), 190-1a (52.2 mg, 0.21 mmol, 1.3 eq) and PPh$_3$ (64.4 mg, 0.25 mmol, 1.5 eq) in THF (0.5 mL) was added DIAD (49.7 mg, 0.25 mmol, 48 uL, 1.5 eq). The mixture was degassed under vacuum and purged with N$_2$ for 3 times. The resulting mixture was stirred at 15° C. for 17 h. LCMS showed the reaction was completed. The mixture was concentrated in vacuum. The residue was purified by prep-HPLC to provide Compound 190 (3.49 mg, 6.6 umol, 4.0% yield), which was confirmed by LCMS and $^1$H NMR. LCMS (ESI): RT=0.964 min, mass calcd. For C$_{26}$H$_{31}$F$_3$N$_6$O$_3$ 532.24, m/z found 555.1 [M+Na]$^+$. $^1$H NMR (400 MHz, CDCl$_3$) δ 9.07 (s, 1H), 8.21 (dd, J=1.4, 7.9 Hz, 1H), 7.54 (dd, J=4.5, 8.0 Hz, 3H), 7.41-7.36 (m, 1H), 7.31 (d, J=8.5 Hz, 2H), 7.07-7.02 (m, 1H), 4.87 (t, J=5.4 Hz, 2H), 4.09 (t, J=5.5 Hz, 2H), 3.59 (dd, J=6.7, 10.2 Hz, 2H), 3.47 (tt, J=3.7, 7.7 Hz, 1H), 3.06 (ddd, J=3.5, 9.2, 13.2 Hz, 2H), 1.78-1.67 (m, 2H), 1.50-1.45 (m, 2H), 1.43 (s, 9H).

To a solution of 191-1 (180 mg, 0.46 mmol, 1 eq) in THF (10 mL) was added LiBH$_4$ (100.5 mg, 4.6 mmol, 10 eq). The mixture was stirred at 10-15° C. for 16 hr. LC-MS showed reactant was consumed completely and one main peak with desired MS was detected. The reaction was quenched by adding sat, aq. NH$_4$Cl (10 mL) and stirred for 30 min. Then the mixture was extracted with EtOAc (10 mL*2). The combined organic layer was washed with brine (10 mL), dried over Na$_2$SO$_4$ and filtered. The filtrate was concentrated to give a residue. The residue was purified by prep-HPLC to give compound Compound 191 (81.6 mg, 0.21 mmol, 46.0% yield). LCMS (ESI): RT=1.168 min, mass calc. for C$_{17}$H$_{15}$F$_3$N$_4$O 348.12, m/z found 349.0 [M+H]$^+$; $^1$H NMR (400 MHz, DMSO-d$_6$) δ 9.00 (s, 1H), 8.39 (s, 1H), 7.91 (dd, J=1.3, 7.8 Hz, 1H), 7.50 (d, J=8.5 Hz, 2H), 7.46-7.42 (m, 1H), 7.38-7.32 (m, 1H), 7.19 (t, J=7.0 Hz, 1H), 7.06 (d, J=8.5 Hz, 2H), 4.44 (t, J=5.4 Hz, 2H), 3.78 (t, J=5.4 Hz, 2H).

Example 184: (2S,3S)-3-(5-(2-((4-(trifluoromethyl)phenyl)amino)phenyl)-2H-tetrazol-2-yl)butan-2-ol (Compound 192), (2R,3R)-3-(5-(2-((4-(trifluoromethyl)phenyl)amino)phenyl)-2H-tetrazol-2-yl)butan-2-ol (Compound 193), (2R,3S)-3-(5-(2-((4-(trifluoromethyl)phenyl)amino)phenyl)-2H-tetrazol-2-yl)butan-2-ol (Compound 194), and (2S,3R)-3-(5-(2-((4-(trifluoromethyl)phenyl)amino)phenyl)-2H-tetrazol-2-yl)butan-2-ol (Compound 195)

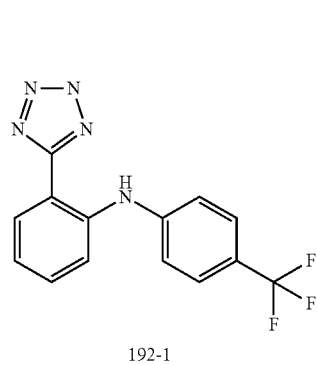

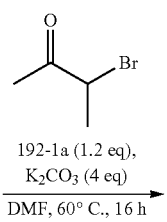

192-1a (1.2 eq), K₂CO₃ (4 eq)
DMF, 60° C., 16 h 192-1

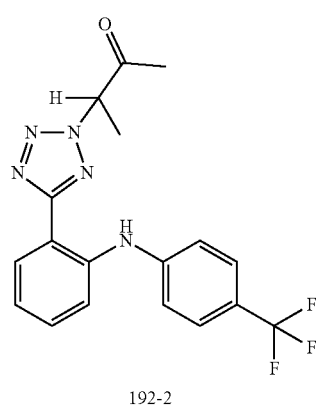

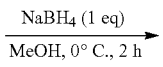

NaBH₄ (1 eq)
MeOH, 0° C., 2 h 192-2

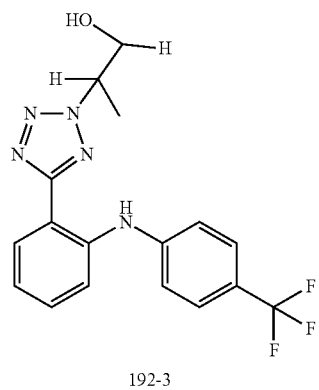

SFC 192-3

-continued

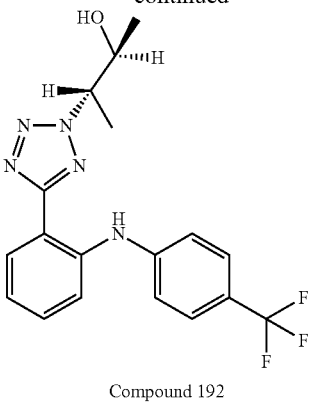

Compound 192

+

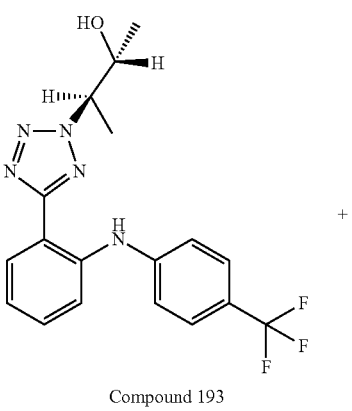

Compound 193

+

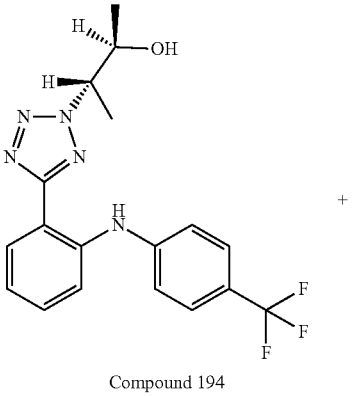

Compound 194

+

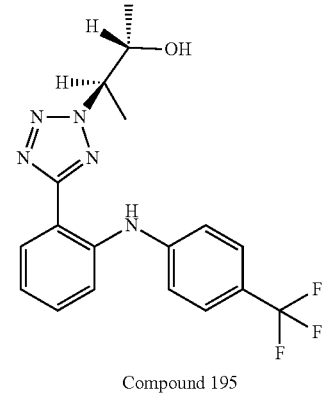

Compound 195

Step 1: 3-(5-(2-((4-(trifluoromethyl)phenyl)amino) phenyl)-2H-tetrazol-2-yl)butan-2-one To a solution of 192-1 (300 mg, 0.98 mmol, 1 eq) and 192-1a (148.4 mg, 0.98 mmol, 1 eq) in DMF (3 mL) was added K$_2$CO$_3$ (543.3 mg, 3.93 mmol, 4 eq). The mixture was stirred at 25-30° C. for 16 h. The crude LCMS showed 24% of 192-1 was remained and 53% of the desired product was detected. 192-1a (29.7 mg, 0.20 mmol, 0.2 eq) was added, the mixture was stirred at 25° C. for 16 h. The crude LCMS showed 21% of 192-1 was remained and 41% of the desired product was detected. The reaction mixture was quenched by water (25 mL), and then extracted with EtOAc (20 mL*3). The combined organic layer was washed with brine (25 mL*2), dried over anhydrous Na$_2$SO$_4$, filtered and concentrated under reduced pressure to give a residue. The residue was purified by flash silica gel chromatography to give the 192-2 (113 mg, 0.30 mmol, 30.6% yield). $^1$H NMR (400 MHz, CDCl$_3$) δ 9.02 (br s, 1H), 8.22 (dd, J=7.94, 1.54 Hz, 1H), 7.55 (d, J=7.72 Hz, 4H), 7.36-7.43 (m, 1H), 7.30 (d, J=8.38 Hz, 2H), 7.06 (t, J=7.50 Hz, 1H), 5.62 (q, J=7.28 Hz, 1H), 2.13 (s, 3H), 1.97 (d, J=7.28 Hz, 3H).

Step 2: (2S,3S)-3-(5-(2-((4-(trifluoromethyl)phenyl) amino)phenyl)-2H-tetrazol-2-yl)butan-2-ol, (2R, 3R)-3-(5-(2-((4-(trifluoromethyl)phenyl)amino)phenyl)-2H-tetrazol-2-yl)butan-2-ol, (2R,3S)-3-(5-(2-((4-(trifluoromethyl)phenyl)amino)phenyl)-2H-tetrazol-2-yl)butan-2-ol, and (2S,3R)-3-(5-(2-((4-(trifluoromethyl)phenyl)amino)phenyl)-2H-tetrazol-2-yl)butan-2-ol A mixture of 192-2 (181 mg, 0.48 mmol, 1 eq) in MeOH (2 mL) was cooled to 0° C., then NaBH$_4$ (21.9 mg, 0.58 mmol, 1.2 eq) was added, the mixture was stirred at 0° C. for 2 h. The crude LCMS showed 192-2 was consumed completely and 45% the desired product was detected. The reaction mixture was combined with another batch, and the mixture was quenched by water (15 mL), extracted with EtOAc (15 mL*3). The combined organic layer was dried over with anhydrous Na$_2$SO$_4$, filtered and concentrated under reduced pressure to give the residue as yellow oil (180 mg). The residue was purified by prep-HPLC to give an impure product (88 mg), which further purified by SFC to give Compound 192 (9.0 mg, 22.7 umol, 17.0% yield, 99.1% chiral purity), Compound 194 (4.3 mg, 11.5 umol, 8.6% yield, 99.9% chiral purity), Compound 195 (2.3 mg, 6.2 umol, 4.6% yield, 99.5% chiral purity), and Compound 193 (10.6 mg, 27.0 umol, 20.2% yield, 99.6% chiral purity).

Compound 192: LCMS (ESI): RT=2.382 min, mass calc. for C$_{18}$H$_{18}$F$_3$N$_5$O 377.15, m/z found 378.0 [M+H]$^+$; $^1$H NMR (400 MHz, CD$_3$OD) δ 8.16 (dd, J=7.91, 1.38 Hz, 1H), 7.49-7.58 (m, 3H), 7.44 (td, J=7.78, 1.51 Hz, 1H), 7.25 (d, J=8.53 Hz, 2H), 7.08-7.15 (m, 1H), 4.92-4.99 (m, 1H), 4.20 (quin, J=6.15 Hz, 1H), 1.72 (d, J=7.03 Hz, 3H), 1.11 (d, J=6.53 Hz, 3H).

Compound 193: LCMS (ESI): RT=2.381 min, mass calc. for C$_{18}$H$_{18}$F$_3$N$_5$O 377.15, m/z found 378.0 [M+H]$^+$; $^1$H NMR (400 MHz, CD$_3$OD) δ 8.16 (dd, J=7.91, 1.38 Hz, 1H), 7.49-7.59 (m, 3H), 7.44 (td, J=7.78, 1.51 Hz, 1H), 7.25 (d, J=8.53 Hz, 2H), 7.08-7.15 (m, 1H), 4.93-5.00 (m, 1H), 4.20 (quin, J=6.21 Hz, 1H), 1.72 (d, J=7.03 Hz, 3H), 1.11 (d, J=6.53 Hz, 3H).

Compound 194: LCMS (ESI): RT=2.350 min, mass calc. for C$_{18}$H$_{18}$F$_3$N$_5$O 377.15, m/z found 378.0 [M+H]$^+$; $^1$H NMR (400 MHz, CD$_3$OD) δ 8.16 (dd, J=7.78, 1.00 Hz, 1H), 7.48-7.62 (m, 3H), 7.37-7.46 (m, 1H), 7.26 (d, J=8.53 Hz, 2H), 7.09 (t, J=7.53 Hz, 1H), 4.92-4.98 (m, 1H), 4.18 (quin, J=6.59 Hz, 1H), 1.64 (d, J=6.78 Hz, 3H), 1.28 (d, J=6.27 Hz, 3H).

Compound 195: LCMS (ESI): RT=2.355 min, mass calc. for C$_{18}$H$_{18}$F$_3$N$_5$O 377.15, m/z found 378.0 [M+H]$^+$; $^1$H NMR (400 MHz, CD$_3$OD) δ 8.16 (dd, J=7.78, 1.51 Hz, 1H), 7.49-7.60 (m, 3H), 7.42 (td, J=7.78, 1.76 Hz, 1H), 7.26 (d, J=8.53 Hz, 2H), 7.06-7.13 (m, 1H), 4.91-4.98 (m, 1H), 4.18 (quin, J=6.59 Hz, 1H), 1.64 (d, J=6.78 Hz, 3H), 1.28 (d, J=6.53 Hz, 3H).

Example 185: 2-(1-methyl-3-(2-((4-(trifluoromethyl)phenyl)amino)phenyl)-1H-pyrazol-5-yl)ethan-1-ol (Compound 196)

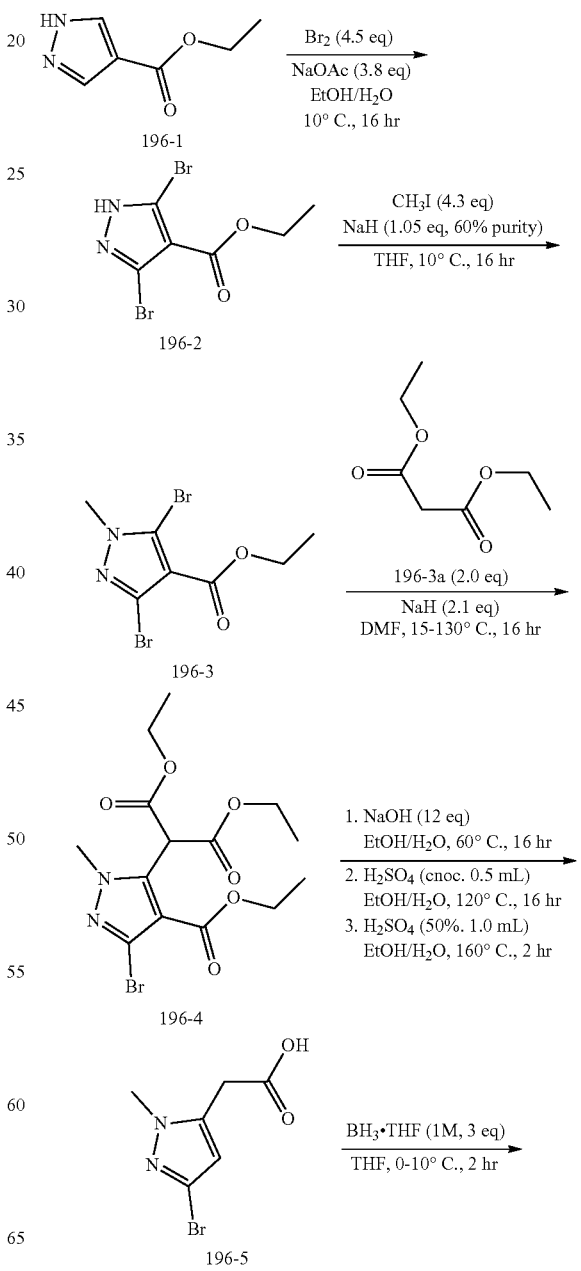

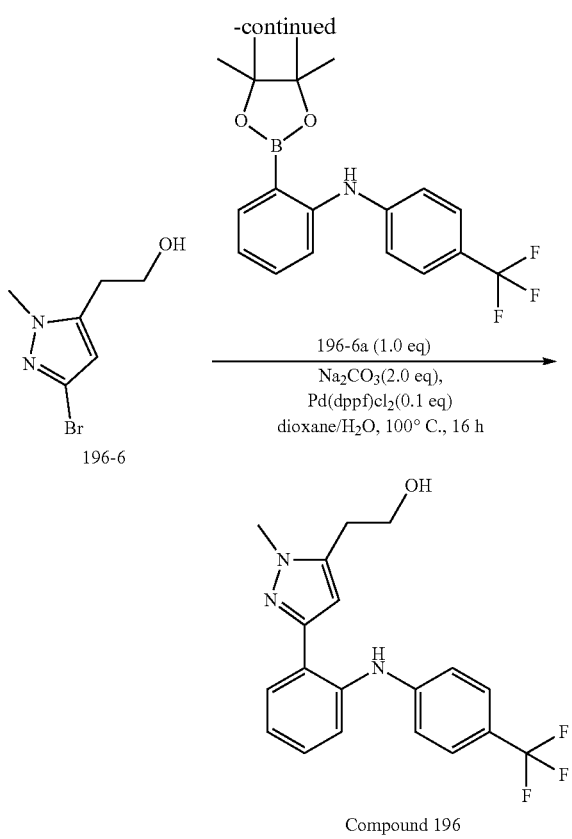

Compound 196

Step 1: ethyl 3,5-dibromo-1H-pyrazole-4-carboxylate

To the solution of 196-1 (1 g, 7.1 mmol, 1 eq) in EtOH (6 mL) and H$_2$O (10 mL) was added NaOAc (2.2 g, 27.1 mmol, 3.8 eq) and Br$_2$ (5.1 g, 32.1 mmol, 1.7 mL, 4.5 eq). The mixture was stirred at 10° C. for 16 hr. The reaction was monitored by TLC. To the reaction mixture was added sodium thiosulfate (2 g), and the solvent was evaporated under reduced pressure. The reaction mixture was poured into water, and the mixture was extracted with ethyl acetate. The extract was washed with saturated brine, and dried over Na$_2$SO$_4$. The solvent was evaporated under reduced pressure to give 196-2 (1.8 g, crude).

Step 2: ethyl 3,5-dibromo-1-methyl-1H-pyrazole-4-carboxylate

To the solution of 196-2 (1.8 g, 6.0 mmol, 1 eq) in THF (20 mL) was added NaH (254 mg, 6.4 mmol, 60% purity, 1.05 eq) at 0° C. The mixture was stirred for 1 hr at 0° C. under N$_2$ atmosphere. Then CH$_3$I (3.7 g, 26 mmol, 1.6 mL, 4.30 eq) was added to the mixture. The solution was stirred at 10° C. for 16 hr. The reaction was monitored by LCMS. The reaction solution was concentrated under reduced pressure. The residue was purified by column chromatography (SiO$_2$) to give 196-3 (700 mg, 2.2 mmol, 37% yield).

Step 3: diethyl 2-(3-bromo-4-(ethoxycarbonyl)-1-methyl-1H-pyrazol-5-yl)malonate To the solution of 196-3a (360 mg, 2.3 mmol, 0.3 mL, 2.0 eq) in DMF (2 mL) was added NaH (94 mg, 2.4 mmol, 60% purity, 2.1 eq) at 0° C. The mixture was stirred for 30 min at 15° C. Then 196-3 (350 mg, 1.1 mmol, 1 eq) was added to the solution. The mixture was stirred at 130° C. for 16 hr. The reaction was monitored by LCMS. The reaction solution was concentrated under reduced pressure. The residue was purified by column chromatography (SiO$_2$) to give 196-4 (110 mg, 0.28 mmol, 25% yield).

Step 4: 2-(3-bromo-1-methyl-1H-pyrazol-5-yl)acetic acid

To the solution of 196-4 (110 mg, 0.28 mmol, 1 eq) in EtOH (1 mL) and H$_2$O (1 mL) was added NaOH (134 mg, 3.4 mmol, 12 eq). The mixture was stirred at 60° C. for 16 hr. Then H$_2$SO$_4$ (920 mg, 9.4 mmol, 500 uL, 33 eq) was added to the mixture. The solution was stirred at 120° C. for 16 hr. Then the mixture was concentrated under reduced pressure. The residue was washed with H$_2$O (10 mL*5). The combined organic layer was dried with Na$_2$SO$_4$ and concentrated under reduced pressure. Then H$_2$SO$_4$ (920 mg, 4.7 mmol, 1 mL, 50% purity, 16.7 eq) was added to the mixture. The mixture was stirred at 160° C. for 2 hr. The reaction was monitored by LCMS. The reaction solution was dropped into ice (5 g). The mixture was extracted with EtOAc (5 mL*3). The combined organic layer was dried with Na$_2$SO$_4$ and concentrated under reduced pressure to give 196-5 (70 mg, crude).

Step 5: 2-(3-bromo-1-methyl-1H-pyrazol-5-yl)ethanol

To the solution of 196-5 (70 mg, 0.31 mmol, 1 eq) in THF (2 mL) was added BH$_3$.THF (1 M, 1 mL, 3 eq) slowly at 0° C. The mixture was warmed up to 10° C. and stirred for 2 hr at 10° C. The reaction was monitored by LCMS. The reaction solution was concentrated under reduced pressure. The residue was dissolved in EtOAc (10 mL). The solution was washed with H$_2$O (10 mL). The organic layer was dried with Na$_2$SO$_4$ and concentrated under reduced pressure to give 196-6 (55 mg, 0.27 mmol, 84% yield).

Step 6: 2-(1-methyl-3-(2-((4-(trifluoromethyl)phenyl)amino)phenyl)-1H-pyrazol-5-yl)ethanol To the solution of 196-6 (55 mg, 0.27 mmol, 1 eq) in dioxane (3 mL) and H$_2$O (0.15 mL) was added 196-6a (97 mg, 0.27 mmol, 1.0 eq) Na$_2$CO$_3$ (57 mg, 0.54 mmol, 2 eq) and Pd(dppf)Cl$_2$ (20 mg, 27 umol, 0.1 eq). The mixture was stirred at 100° C. for 16 hr. The reaction was monitored by LCMS. The reaction solution was filtered. The residue was purified by Prep-HPLC to give Compound 196 (5.3 mg, 14.4 umol, 5.4% yield). LCMS (ESI): RT=0.845 min, mass calcd. for C$_{19}$H$_{18}$F$_3$N$_3$O 361.14, m/z found 362.0 [M+H]$^+$, $^1$HNMR (400 MHz, CDCl$_3$) δ 9.71 (s, 1H), 7.61 (dd, J=1.5, 7.8 Hz, 1H), 7.53-7.46 (m, 3H), 7.27-7.20 (m, 3H), 7.01-6.93 (m, 1H), 6.46 (s, 1H), 3.96 (t, J=6.4 Hz, 2H), 3.90 (s, 3H), 2.95 (t, J=6.4 Hz, 2H).

Example 186: 2-(4-(2-((4-(trifluoromethyl)phenyl)amino)phenyl)-1H-imidazol-1-yl)ethan-1-ol (Compound 197)

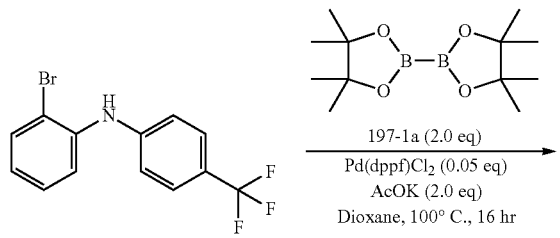

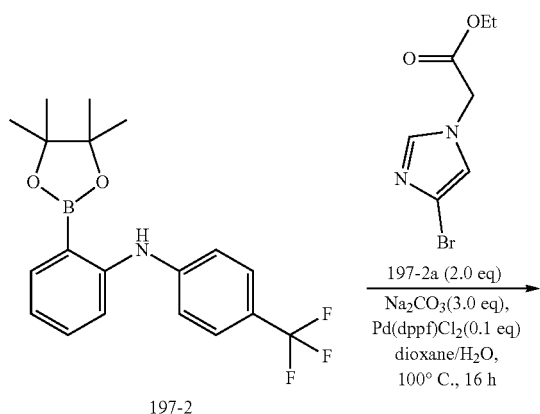

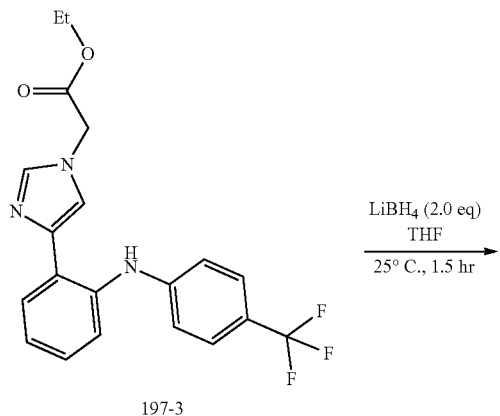

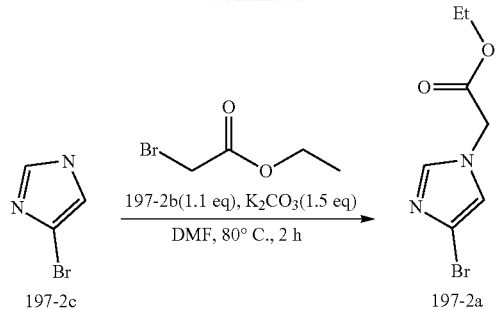

Step 1: 2-(4,4,5,5-tetramethyl-1,3,2-dioxaborolan-2-yl)-N-[4-(trifluoromethyl)phenyl]aniline To a solution of 197-1 (2.0 g, 6.3 mmol, 1.0 eq) and 197-1a (3.2 g, 12.6 mmol, 2.0 eq) in dioxane (40 mL) was added Pd(dppf)Cl$_2$ (462.9 mg, 0.6 mmol, 0.1 eq) and AcOK (1.2 g, 12.6 mmol, 2.0 eq). The mixture was stirred at 100° C. for 16 h under N$_2$ atmosphere. LC-MS showed 1 was consumed completely. Several new peaks were shown on LC-MS and 69% of desired compound was detected. The reaction mixture was filtered to give a residue. The residue was purified by column chromatography (SiO$_2$) to give 197-2 (2.0 g, crude). LCMS (ESI): RT=0.998 min, mass calc. for C$_{19}$H$_{21}$BF$_3$NO$_2$ 363.16, m/z found 364.0 [M+H]$^+$. $^1$H NMR (400 MHz, CDCl$_3$) δ 7.9 (s, 1H), 7.77 (d, J=7.3 Hz, 1H), 7.50 (d, J=8.5 Hz, 2H), 7.36 (d, J=3.3 Hz, 2H), 7.20 (d, J=8.5 Hz, 2H), 6.93-6.89 (d, J=4.0, 7.8 Hz, 1H), 1.36 (s, 12H).

Step 2: ethyl 2-(4-bromoimidazol-1-yl)acetate

To a solution of 197-2c (1.0 g, 6.8 mmol, 1.0 eq) in DMF (10.0 mL) was added K$_2$CO$_3$ (1.4 g, 10.2 mmol, 1.5 eq) and 197-2b (1.2 g, 7.4 mmol, 0.8 mL, 1.1 eq). The mixture was stirred at 80° C. for 2 h. TLC indicated 20% of 197-1 was remained, and one major new spot with lower polarity was detected. The reaction mixture was diluted with H$_2$O (20.0 mL), extracted with EtOAc (10.0 mL*3). The combined organic layers were washed with brine (30.0 mL), dried over Na$_2$SO$_4$, filtered and concentrated under reduced pressure to give a residue. The residue was purified by column chromatography (SiO$_2$) to give 197-2a (500.0 mg, 2.1 mmol, 31% yield). $^1$H NMR (400 MHz, CDCl$_3$) δ 7.38 (s, 1H), 6.94 (s, 1H), 4.69-4.61 (m, 2H), 4.30-4.20 (m, 3H), 1.35-1.26 (m, 3H).

Step 3: ethyl 2-[4-[2-[4-(trifluoromethyl)anilino]phenyl]imidazol-1-yl]acetate A mixture of 197-2 (100.0 mg, 0.3 mmol, 1.0 eq), 197-2a (128.3 mg, 0.6 mmol, 2.0 eq), Na$_2$CO$_3$ (87.5 mg, 0.8 mmol, 3.0 eq) and Pd(dppf)Cl$_2$ (20.1 mg, 27.5 umol, 0.1 eq) in dioxane (3.0 mL) and H$_2$O (0.5 mL) was degassed and purged with N$_2$ for 3 times, and then the mixture was stirred at 100° C. for 19 h under N$_2$ atmosphere. LC-MS showed 33% of 197-2 was remained. Several new peaks were shown on LC-MS and 22% of desired compound was detected. The reaction mixture was concentrated under reduced pressure to give a residue. The residue was purified by column chromatography (SiO$_2$) to give 197-3 (40 mg, 0.1 mmol, 37% yield). LCMS (ESI): RT=0.998 min, mass calc. for C$_{20}$H$_{18}$F$_3$N$_3$O$_2$ 389.14, m/z found 390.0 [M+H]$^+$. $^1$H NMR (400 MHz, CDCl$_3$) δ (ppm) 7.58 (s, 1H), 7.53-7.49 (m, 2H), 7.46 (d, J=9.3 Hz, 3H), 7.22 (d, J=10.0 Hz, 5H), 6.97-6.91 (m, 1H), 4.74 (s, 2H), 4.27 (q, J=7.1 Hz, 2H), 1.31 (t, J=7.2 Hz, 3H).

Step 4: 2-[4-[2-[4-(trifluoromethyl)anilino]phenyl]imidazol-1-yl]ethanol

To a solution of 197-3 (40.0 mg, 0.1 mmol, 1.0 eq) in THF (2.0 mL) was added LiBH$_4$ (4.4 mg, 0.2 mmol, 2.0 eq) at 25° C. The mixture was stirred at 25° C. for 1.5 h. LC-MS showed 197-3 was consumed completely. Several new peaks were shown on LC-MS and 82% of desired compound was detected. The reaction mixture was quenched by addition a.q NH$_4$Cl (2.0 mL) and concentrated under reduced pressure to give a residue. The residue was purified by prep-HPLC to give Compound 197 (2.52 mg, 7 umol, 7% yield). LCMS (ESI): RT=0.661 min, mass calc. for C$_{18}$H$_{16}$F$_3$N$_3$O 347.12, m/z found 347.9 [M+H]$^+$. $^1$H NMR (400 MHz, CDCl$_3$) δ 7.63 (s, 1H), 7.54-7.42 (m, 4H), 7.26 (s, 1H), 7.24-7.18 (m, 3H), 6.96 (t, J=7.0 Hz, 1H), 4.13 (t, J=5.0 Hz, 2H), 3.97-3.91 (m, 2H).

Example 187: 2-(2-(2-(piperidin-4-yloxy)ethyl)-2H-tetrazol-5-yl)-N-(4-(trifluoromethyl) phenyl)aniline (Compound 198)

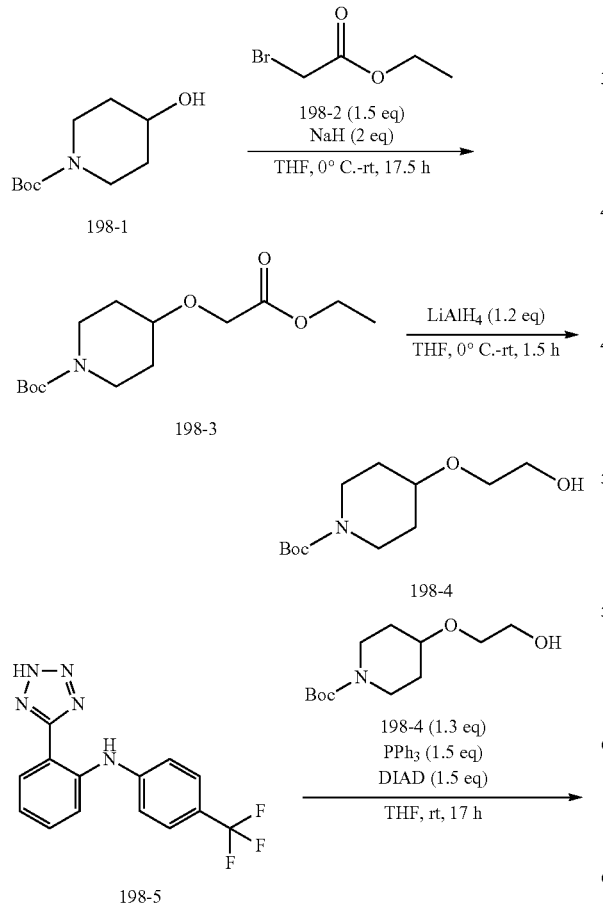

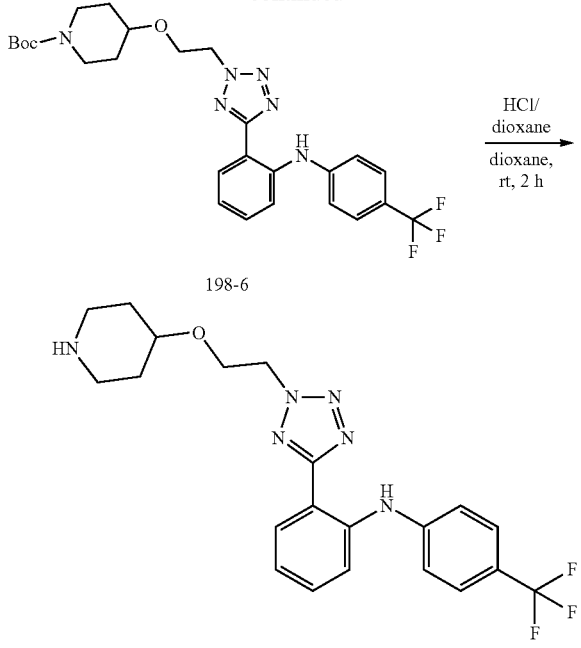

Compound 198

Step 1: tert-butyl 4-(2-ethoxy-2-oxoethoxy)piperidine-1-carboxylate

To a mixture of 198-1 (2 g, 9.94 mmol, 1 eq) in THF (20 mL) was added NaH (794.9 mg, 19.87 mmol, 60% purity, 2 eq) at 0° C. The mixture was stirred at 0° C. for 0.5 h. Then 198-2 (2.49 g, 14.9 mmol, 1.7 mL, 1.5 eq) was added at 0° C. The resulted mixture was stirred at 15° C. for 17 h. TLC showed there's a main new spot with lower polarity, and the starting material was remained. The mixture was diluted with water (30 mL), extracted with EA (20 mL*3). The organic layer was dried over anhydrous Na$_2$SO$_4$, concentrated in vacuum. The residue was purified by silica gel chromatography. 198-3 (500 mg, crude) was obtained, which was checked by $^1$H NMR. $^1$H NMR (400 MHz, CDCl$_3$) δ 4.22 (q, J=7.3 Hz, 2H), 4.12 (s, 2H), 3.85-3.74 (m, 2H), 3.59-3.53 (m, 1H), 3.08 (ddd, J=3.3, 9.4, 13.2 Hz, 2H), 1.91-1.82 (m, 2H), 1.59-1.52 (m, 2H), 1.46 (s, 9H), 1.29 (t, J=7.2 Hz, 3H).

Step 2: tert-butyl 4-(2-hydroxyethoxy)piperidine-1-carboxylate

To a mixture of LiAlH$_4$ (79.2 mg, 2.09 mmol, 1.2 eq) in THF (4 mL) was added a solution of 198-3 (500 mg, 1.74 mmol, 1 eq) in THF (6 mL) drop wise at 0° C. The resulted mixture was stirred at 0° C. for 0.5 h, 15° C. for 1 h. TLC showed the reaction was completed. Water (2.1 mL) was added to the mixture, and the mixture was stirred at 15° C. for 3 min. NaOH (25% aqueous, 2.1 mL) was added, and the mixture was stirred at 15° C. for 5 min. Then water (2.1 mL) was added, and the mixture was stirred at 15° C. for 5 min. MgSO$_4$ (1 g) was added, and the mixture was filtered. The solid was washed with EA (10 mL), the filtrate was concentrated in vacuum. The residue was purified by silica gel chromatography. 198-4 (320 mg, 1.3 mmol, 75.0% yield) was obtained, which was confirmed by $^1$H NMR. $^1$H NMR (400 MHz, CDCl$_3$) δ 3.90-3.77 (m, 2H), 3.76-3.72 (m, 2H), 3.61-3.56 (m, 2H), 3.54-3.49 (m, 1H), 3.08 (ddd, J=3.3, 9.5, 13.2 Hz, 2H), 1.86 (dd, J=3.1, 7.1 Hz, 2H), 1.57-1.50 (m, 2H), 1.46 (s, 9H).

Step 3: tert-butyl 4-(2-(5-(2-((4-(trifluoromethyl)phenyl)amino)phenyl)-2H-tetrazol-2-yl)ethoxy)piperidine-1-carboxylate To a mixture of 198-5 (150 mg, 0.49 mmol, 1 eq), 198-4 (156.7 mg, 0.64 mmol, 1.3 eq) and PPh$_3$ (193.3 mg, 0.74 mmol, 1.5 eq) in THF (1 mL) was added DIAD (149.0 mg, 0.74 mmol, 0.14 mL, 1.5 eq). The mixture was degassed under vacuum and purged with N$_2$ for 3 times. The resulting mixture was stirred at 15° C. for 17 h. LCMS showed 26% desired compound was detected. The mixture was concentrated in vacuum. The residue was purified by silica gel chromatography. 198-6 (100 mg, 0.16 mmol, 32.5% yield) was obtained, which was checked by LCMS.

Step 4: 2-(2-(2-(piperidin-4-yloxy)ethyl)-2H-tetrazol-5-yl)-N-(4-(trifluoromethyl)phenyl)aniline To a mixture of 198-6 (80 mg, 0.15 mmol, 1 eq) in dioxane (2 mL) was added HCl/dioxane (4 M, 4.8 mL, 127.81 eq). The resulting mixture was stirred at 15° C. for 2 h. LCMS showed the reaction was complete. The mixture was concentrated in vacuum. The residue was purified by pre-HPLC. This compound was checked by HPLC and purified by pre-HPLC. Compound 198 (2.69 mg, 4.9 umol, 3.3% yield, TFA) was obtained, which was confirmed by LCMS and $^1$HNMR. LCMS (ESI): RT=0.766 min, mass calcd. for C$_{21}$H$_{23}$F$_3$N$_6$O 432.19, m/z found 433.0 [M+H]$^+$. $^1$HNMR (400 MHz, DMSO-d$_6$) δ 8.80 (s, 1H), 8.43-8.16 (m, 2H), 8.06 (d, J=7.8 Hz, 1H), 7.59-7.53 (m, 3H), 7.53-7.47 (m, 1H), 7.25-7.17 (m, 3H), 4.92 (t, J=4.9 Hz, 2H), 3.99 (t, J=4.9 Hz, 2H), 3.58 (td, J=3.5, 6.8 Hz, 1H), 3.00-2.91 (m, 2H), 2.87 (dt, J=2.1, 3.8 Hz, 2H), 1.85-1.76 (m, 2H), 1.56-1.45 (m, 2H).

Example 188: 2-(2-(2-(piperidin-3-yloxy)ethyl)-2H-tetrazol-5-yl)-N-(4-(trifluoromethyl) phenyl)aniline (Compound 199)

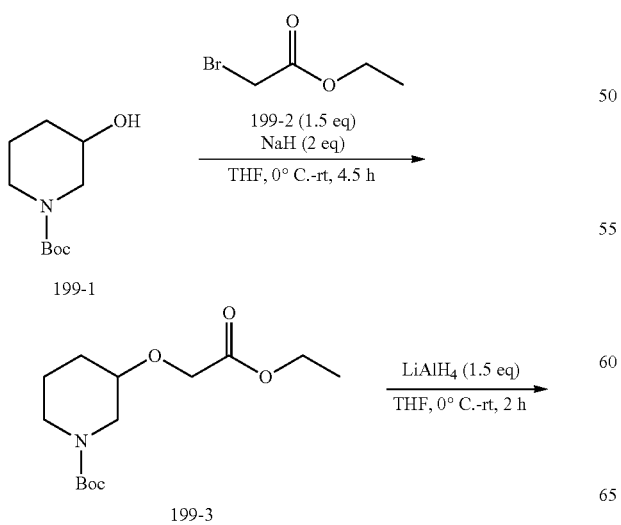

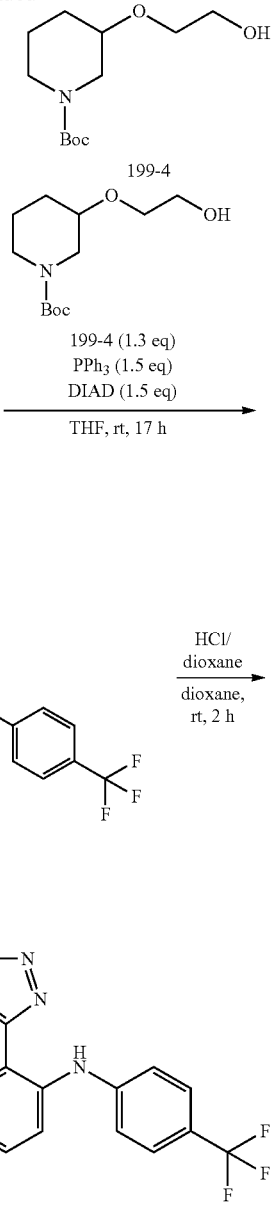

Compound 199

Step 1: tert-butyl 3-(2-ethoxy-2-oxoethoxy)piperidine-1-carboxylate

To a mixture of 199-1 (2.0 g, 9.94 mmol, 1 eq) in THF (20 mL) was added NaH (794.9 mg, 19.88 mmol, 60% purity, 2 eq) at 0° C. The mixture was stirred at 0° C. for 0.5 h. Then 199-2 (2.49 g, 14.91 mmol, 1.7 mL, 1.5 eq) was added at 0° C. The resulted mixture was stirred at 15° C. for 17 h. TLC showed there's a new spot with lower polarity, and the start material was remained. The mixture was diluted with water (30 mL) and extracted with EA (20 mL*3). The organic layer was dried over anhydrous Na$_2$SO$_4$, concentrated in vacuum. The residue was purified by silica gel chromatography. 199-3 (500 mg, crude) was obtained, which was checked by $^1$H NMR. $^1$HNMR (400 MHz, CDCl$_3$) δ 4.22 (q, J=6.9 Hz, 2H), 4.19-4.09 (m, 2H), 3.62 (td, J=4.7, 13.4 Hz, 1H), 3.41 (dt, J=4.0, 7.9 Hz, 1H), 3.16-2.94 (m, 2H), 2.04-1.94 (m, 1H), 1.82-1.72 (m, 1H), 1.64-1.54 (m, 1H), 1.46 (s, 9H), 1.43-1.36 (m, 1H), 1.33-1.23 (m, 4H).

Step 2: tert-butyl 3-(2-hydroxyethoxy)piperidine-1-carboxylate

To a mixture of LiAlH$_4$ (79.24 mg, 2.09 mmol, 1.2 eq) in THF (4 mL) was added a solution of 199-3 (500.0 mg, 1.74 mmol, 1 eq) in THF (6 mL) drop wise at 0° C. The resulted mixture was stirred at 0° C. for 0.5 h, 15° C. for 1 h. TLC showed the reaction was completed. Water (2.1 mL) was added to the mixture, and the mixture was stirred at 15° C. for 3 min. NaOH (25% aqueous, 2.1 mL) was added, and the mixture was stirred at 15° C. for 5 min. Then water (2.1 mL) was added, and the mixture was stirred at 15° C. for 5 min. MgSO$_4$ (1 g) was added, and the mixture was filtered. The solid was washed with EA (10 mL), the filtrate was concentrated in vacuum. The residue was purified by silica gel chromatography. 199-4 (380 mg, 1.55 mmol, 89.0% yield) was obtained, which was confirmed by $^1$H NMR. $^1$HNMR (400 MHz, CDCl$_3$) δ 3.74-3.68 (m, 2H), 3.68-3.58 (m, 3H), 3.37 (td, J=1.6, 3.3 Hz, 2H), 3.32-3.10 (m, 2H), 1.93-1.84 (m, 1H), 1.81-1.72 (m, 1H), 1.69-1.50 (m, 2H), 1.46 (s, 9H).

Step 3: tert-butyl 3-(2-(5-(2-((4-(trifluoromethyl)phenyl)amino)phenyl)-2H-tetrazol-2-yl)ethoxy)piperidine-1-carboxylate To a mixture of 199-5 (150 mg, 0.49 mmol, 1 eq), 199-4 (156.7 mg, 0.64 mmol, 1.3 eq) and PPh$_3$ (193.3 mg, 0.74 mmol, 1.5 eq) in THF (1 mL) was added DIAD (149.1 mg, 0.74 mmol, 0.14 mL, 1.5 eq). The mixture was degassed under vacuum and purged with N$_2$ for 3 times. The resulting mixture was stirred at 15° C. for 17 h. LCMS showed 26% desired compound was detected. The mixture was concentrated in vacuum. The residue was purified by silica gel chromatography. 199-6 (60 mg, 0.11 mmol, 22.2% yield) was obtained, which was checked by LCMS.

Step 4: 2-(2-(2-(piperidin-3-yloxy)ethyl)-2H-tetrazol-5-yl)-N-(4-(trifluoromethyl)phenyl)aniline To a mixture of 199-6 (60 mg, 0.11 mmol, 1 eq) in dioxane (2 mL) was added HCl/dioxane (4 M, 3 mL, 106.51 eq). The resulting mixture was stirred at 15° C. for 2 h. LCMS showed the reaction was complete. The mixture was concentrated in vacuum. The residue was purified by pre-HPLC. The compound was checked by HPLC and purified by pre-HPLC. Compound 199 (2.70 mg, 4.9 umol, 4.4% yield, TFA) was obtained, which was confirmed by LCMS and $^1$H NMR. LCMS (ESI): RT=0.774 min, mass calcd. for C$_{21}$H$_{23}$F$_3$N$_6$O 432.19, m/z found 433.0 [M+H]$^+$. $^1$H NMR (400 MHz, DMSO-d$_6$) δ 8.80 (s, 1H), 8.64-8.20 (m, 2H), 8.06 (dd, J=1.1, 7.9 Hz, 1H), 7.58-7.53 (m, 3H), 7.53-7.47 (m, 1H), 7.25-7.17 (m, 3H), 4.93 (t, J=4.8 Hz, 2H), 4.05 (t, J=5.1 Hz, 2H), 3.68-3.63 (m, 1H), 3.08 (dd, J=1.5, 13.1 Hz, 1H), 2.97-2.87 (m, 3H), 1.70-1.61 (m, 2H), 1.54-1.42 (m, 2H).

Example 189: (1R,2S)-2-(5-(2-((4-(trifluoromethyl)phenyl)amino)phenyl)-2H-tetrazol-2-yl)cyclopentan-1-ol (Compound 200)

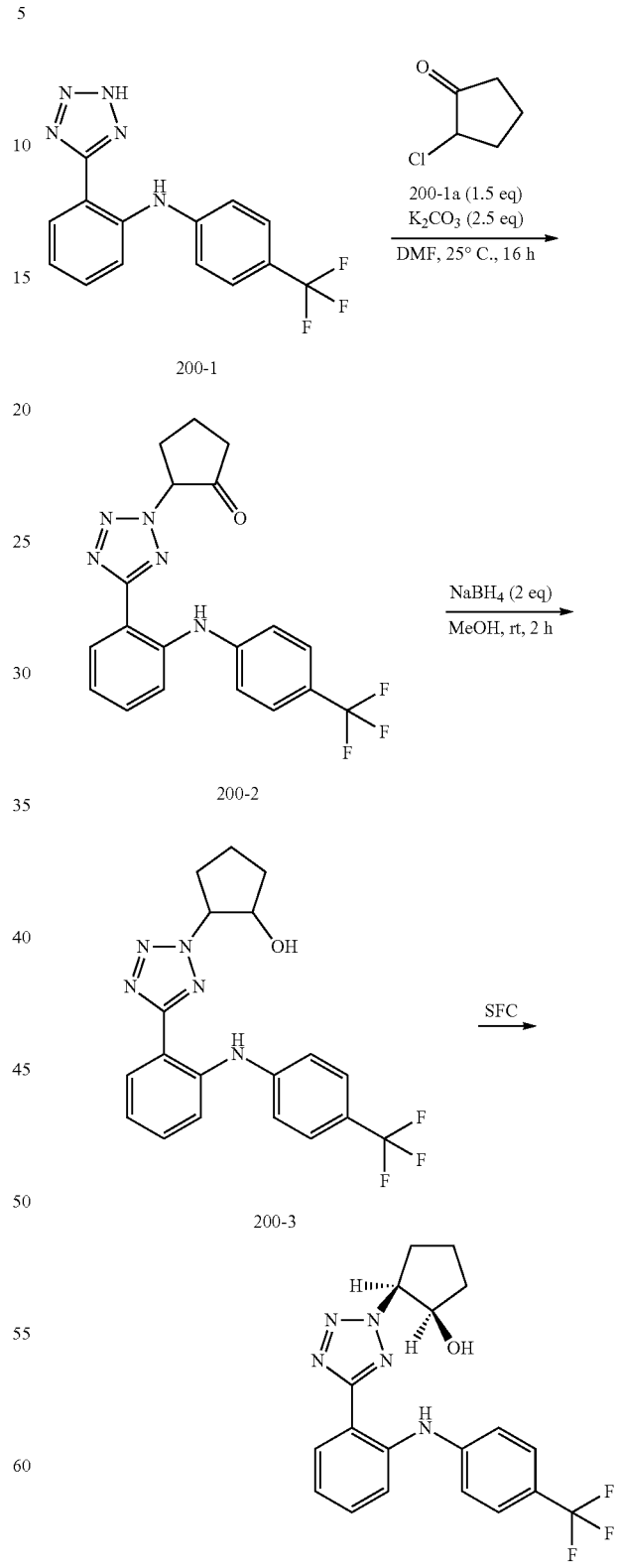

Compound 200

Step 1: 2-[5-[2-[4-(trifluoromethyl)anilino]phenyl]tetrazol-2-yl]cyclopentanone To a mixture of 200-1 (1.5 g, 4.91 mmol, 1 eq) and K$_2$CO$_3$ (2.72 g, 19.66 mmol, 4 eq) in DMF (1.5 mL) was added 200-1a (2.04 g, 17.20 mmol, 1.71 mL, 3.5 eq) in one portion. The resulting mixture was stirred at 25° C. for 16 h. LCMS showed 24% of the starting material was remained and 44% of desired product was formed. The reaction mixture was diluted with water (10 mL) and extracted with EA (10 mL*5). The combined organic layers were dried with anhydrous Na$_2$SO$_4$, filtered and concentrated in vacuum. The residue was purified by column chromatography (SiO$_2$). LCMS confirmed 200-2 (260 mg, 0.577 mmol, 11.8% yield). LCMS (ESI): RT=0.876 min, mass calcd. For C$_{19}$H$_{16}$F$_3$N$_5$O, 387.13 m/z found 388.1[M+H]$^+$.

Step 2: (1R,2S)-2-[5-[2-[4-(trifluoromethyl)anilino]phenyl]tetrazol-2-yl]cyclopentanol To a solution of 200-2 (260 mg, 0.67 mmol, 1 eq) in MeOH (3 mL) was added NaBH$_4$ (51 mg, 1.34 mmol, 2 eq) in one portion at 20° C. under N$_2$. The mixture was stirred at 20° C. for 2 h. LCMS showed the starting material was consumed completely and one main peak with desired MS was detected. The reaction mixture was concentrated under reduced pressure to remove solvent. The residue was diluted with water (15 mL) and extracted with EA (15 mL*3). The combined organic layers were dried with anhydrous Na$_2$SO$_4$, filtered and concentrated in vacuum. HPLC indicated 87% of desired product was found. LCMS showed 91% of desired product (240 mg) was formed. The product was separated by SFC. $^1$H NMR, LCMS and SFC and showed that Compound 200 was obtained (95 mg, 0.24 mmol, 36.4% yield). LCMS (ESI): RT=0.857 min, mass calcd. For C$_{19}$H$_{18}$F$_3$N$_5$O, 389.15 m/z found 390.0[M+H]$^+$. $^1$H NMR (400 MHz, CDCl$_3$) δ 9.10 (s, 1H), 8.20 (d, J=8.00 Hz, 1H), 7.54 (d, J=8.30 Hz, 3H), 7.39 (t, J=7.70 Hz, 1H), 7.30 (d, J=8.50 Hz, 2H), 7.05 (t, J=7.70 Hz, 1H), 5.10 (dt, J=4.50, 8.20 Hz, 1H), 4.69 (br s, 1H), 2.65-2.51 (m, 1H), 2.50-2.35 (m, 2H), 2.27-2.06 (m, 2H), 2.05-1.96 (m, 1H), 1.91-1.80 (m, 1H).

Example 190: (1S,2R)-2-(5-(2-((4-(trifluoromethyl)phenyl)amino)phenyl)-2H-tetrazol-2-yl)cyclopentan-1-ol (Compound 201)

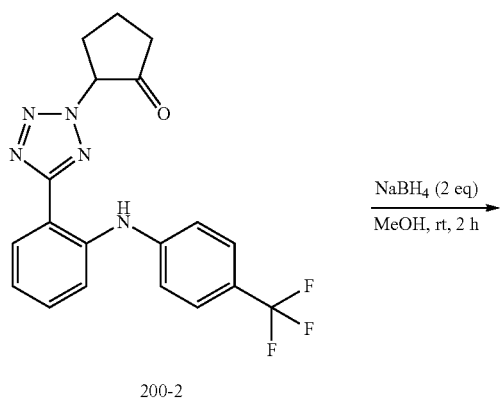

200-2

NaBH$_4$ (2 eq)
MeOH, rt, 2 h

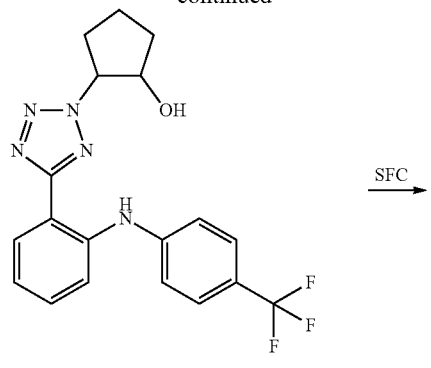

200-3

SFC

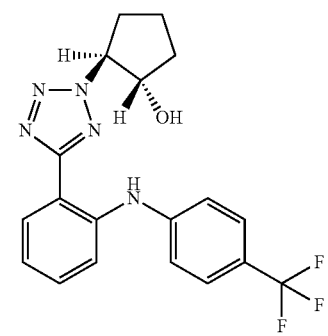

Compound 201

To a solution of the 200-2 (260 mg, 0.67 mmol, 1 eq) in MeOH (3 mL) was added NaBH$_4$ (51 mg, 1.34 mmol, 2 eq) in one portion at 20° C. under N$_2$. The mixture was stirred at 20° C. for 2 h. LCMS showed the starting material was consumed completely and one main peak with desired MS was detected. The reaction mixture was concentrated under reduced pressure to remove solvent. The residue was diluted with water (15 mL) and extracted with EA (15 mL*3). The combined organic layers were dried with anhydrous Na$_2$SO$_4$, filtered and concentrated in vacuum. HPLC indicated 87% of desired product was found. LCMS showed 91% of desired product (240 mg) was formed. The product was separated by SFC. $^1$H NMR, LCMS and SFC and showed that Compound 201 was obtained (95 mg, 0.24 mmol, 36.4% yield). LCMS (ESI): RT=0.858 min, mass calcd. For C$_{19}$H$_{18}$F$_3$N$_5$O, 389.15 m/z found 390.0[M+H]$^+$. $^1$H NMR (400 MHz, CDCl$_3$) δ 9.10 (s, 1H), 8.20 (d, J=7.80 Hz, 1H), 7.54 (d, J=8.50 Hz, 3H), 7.39 (t, J=7.70 Hz, 1H), 7.30 (d, J=8.50 Hz, 2H), 7.05 (t, J=7.50 Hz, 1H), 5.10 (dt, J=4.60, 8.20 Hz, 1H), 4.73-4.66 (m, 1H), 2.64-2.52 (m, 1H), 2.50-2.35 (m, 2H), 2.26-2.08 (m, 2H), 2.05-1.95 (m, 1H), 1.92-1.79 (m, 1H).

Example 191: ethyl 2-(4-(2-((4-(trifluoromethyl)phenyl)amino)phenyl)-1H-imidazol-1-yl)acetate (Compound 202)

Example 192: 2-(2-((1-(benzyloxy)cyclopropyl)methyl)-2H-tetrazol-5-yl)-N-(4-(trifluoromethyl)phenyl)aniline (Compound 203)

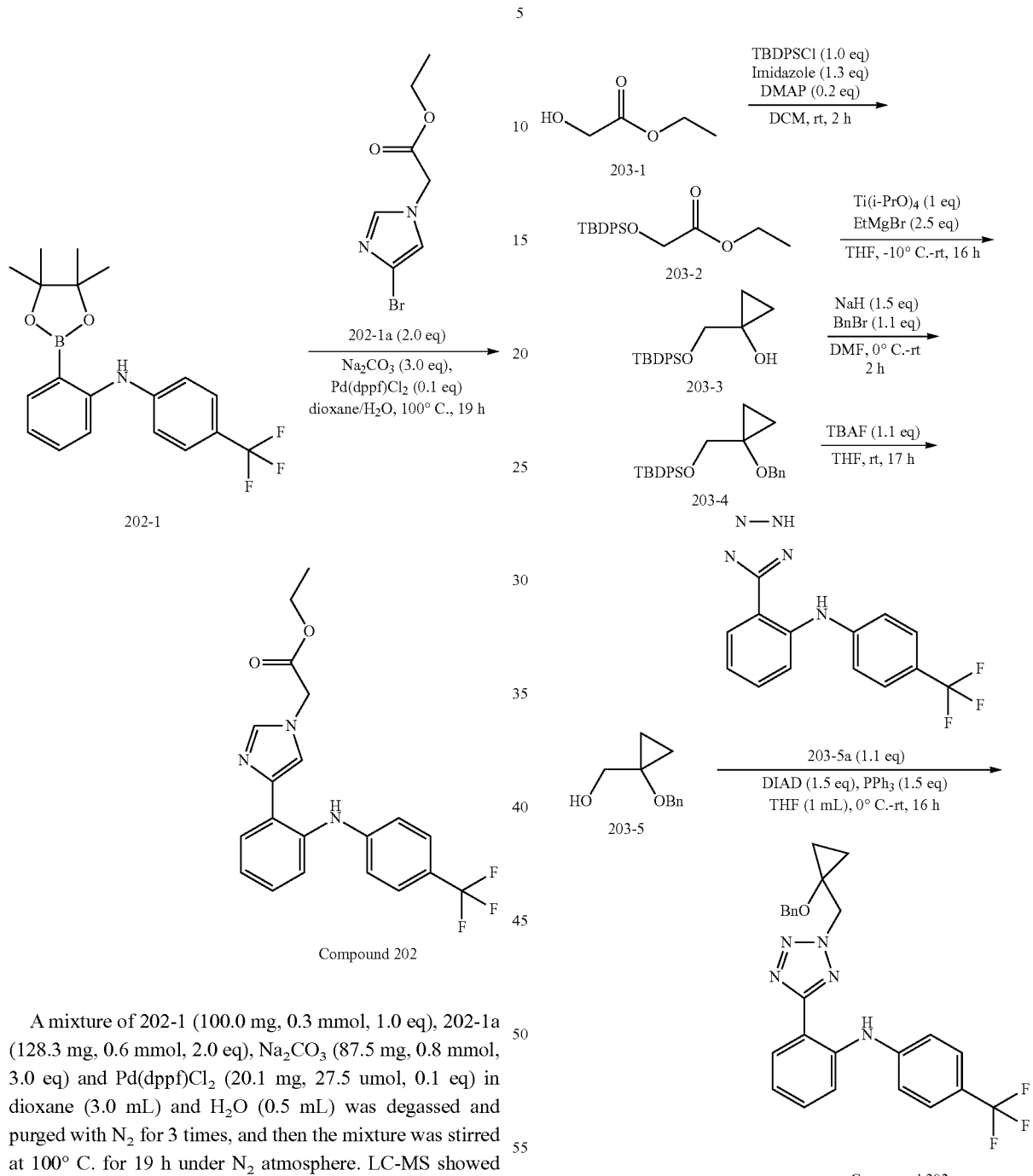

A mixture of 202-1 (100.0 mg, 0.3 mmol, 1.0 eq), 202-1a (128.3 mg, 0.6 mmol, 2.0 eq), Na$_2$CO$_3$ (87.5 mg, 0.8 mmol, 3.0 eq) and Pd(dppf)Cl$_2$ (20.1 mg, 27.5 umol, 0.1 eq) in dioxane (3.0 mL) and H$_2$O (0.5 mL) was degassed and purged with N$_2$ for 3 times, and then the mixture was stirred at 100° C. for 19 h under N$_2$ atmosphere. LC-MS showed 32% of 202-1a was remained. Several new peaks were shown on LC-MS and 23% of desired compound was detected. The mixture was purified by prep-HPLC to give Compound 202 (5.26 mg, 13.5 umol, 5% yield). LCMS (ESI): RT=0.698 min, mass calc. for C$_{20}$H$_{18}$F$_3$N$_3$O$_2$ 389.14, m/z found 390.0 [M+H]$^+$. $^1$H NMR (400 MHz, CDCl$_3$) δ 9.94 (s, 1H), 7.59 (s, 1H), 7.52-7.45 (m, 4H), 7.25-7.17 (m, 4H), 6.95 (t, J=7.5 Hz, 1H), 4.74 (s, 2H), 4.28 (q, J=7.0 Hz, 2H), 1.32 (t, J=7.2 Hz, 3H).

Step 1: ethyl 2-((tert-butyldiphenylsilyl)oxy)acetate

To a mixture of 203-1 (2 g, 19.21 mmol, 1.9 mL, 1.06 eq), 1H-imidazole (1.61 g, 23.65 mmol, 1.3 eq) and DMAP (444.5 mg, 3.64 mmol, 0.2 eq) in DCM (15 mL), was added TBDPSCl (5 g, 18.19 mmol, 4.7 mL, 1 eq) at 0° C. The resulting mixture was stirred at 15° C. for 2 h. LCMS showed the reaction was completed. The mixture was diluted with water (15 mL), extracted with DCM (15 mL*3). The organic layer was dried over anhydrous $Na_2SO_4$, concentrated in vacuum. 203-2 (5.2 g, crude) was obtained, which was checked by $^1$H NMR. $^1$H NMR (400 MHz, DMSO-$d_6$) δ 7.63 (dd, J=1.4, 7.7 Hz, 4H), 7.49-7.41 (m, 6H), 4.27 (s, 2H), 4.06 (q, J=7.0 Hz, 2H), 1.13 (t, J=7.0 Hz, 3H), 1.02 (s, 9H).

Step 2: 1-[[tert-butyl(diphenyl)silyl]oxymethyl]cyclopropanol

To a solution of 203-2 (2 g, 5.84 mmol, 1 eq) and Ti(i-PrO)$_4$ (1.16 g, 4.09 mmol, 1.2 mL, 0.7 eq) in THF (20 mL) was added Ethyl magnesium bromide (3 M, 4.9 mL, 2.53 eq) dropwise at −10° C. The reaction was warmed to 20° C. for 16 hr. TLC (EA:PE=1:5) showed that starting material was consumed and a new spot was detected. The reaction was quenched by sat. NH4Cl (20 mL). The THF was removed. The residue was extracted with EA (3*50 mL). The organic layer was dried over $Na_2SO_4$ and concentrated. 203-3 (1.7 g, 5.21 mmol, 89.17% yield) was used for next step directly. $^1$HNMR showed that desired product was obtained. $^1$HNMR (400 MHz, CDCl$_3$) δ 7.80-7.65 (m, 4H), 7.50-7.30 (m, 6H), 3.69 (s, 2H), 2.00 (s, 1H), 1.08 (s, 9H), 0.80-0.60 (m, 2H), 0.50-0.30 (m, 2H).

Step 3: (1-benzyloxycyclopropyl)methoxy-tert-butyl-diphenyl-silane

To a solution of 203-3 (1.2 g, 3.68 mmol, 1 eq) in DMF (10 mL) was added NaH (220.5 mg, 5.51 mmol, 60% purity, 1.5 eq) at 0° C., followed by BnBr (691.5 mg, 4.04 mmol, 0.5 mL, 1.1 eq). The reaction was stirred at 15° C. for 16 hr. LCMS showed that 46% of desired MS signal was detected. The reaction was concentrated. The crude product was purified by CombiFlash to give 203-4 (0.8 g, 1.92 mmol, 52.3% yield).

Step 4: (1-benzyloxycyclopropyl)methanol

To a solution of 203-4 (0.19 g, 4.56 mmol, 1 eq) in THF (4 mL) was added TBAF (1 M, 0.7 mL, 1.5 eq) at 0° C. The reaction was warmed to 25° C. for 2 hr. TLC (EA:PE=1:10) showed that starting material was consumed completely and two new spots were detected. LCMS showed that starting material was consumed. The reaction was concentrated. The crude product was purified by CombiFlash to give 203-5 (80 mg, 0.45 mmol, 98.4% yield).

Step 5: 2-[2-[(1-benzyloxycyclopropyl)methyl]tetrazol-5-yl]-N-[4-(trifluoromethyl)phenyl]aniline To a solution of 203-5a (85.6 mg, 0.28 mmol, 1 eq), 203-5 (50 mg, 0.28 mmol, 1 eq) and PPh$_3$ (110.4 mg, 0.42 mmol, 1.5 eq) in THF (1 mL) was added DIAD (85.1 mg, 0.42 mmol, 82 uL, 1.5 eq) at 0° C. The reaction was stirred at 20° C. for 12 hr. LCMS showed that 20% of desired product was detected. The reaction was concentrated. The crude product was purified by Prep.HPLC to give Compound 203 (19 mg, 39 umol, 13.9% yield). H NMR and LCMS confirmed that desired product was obtained. LCMS (ESI): RT=0.969 min, mass calcd. for $C_{25}H_{22}F_3N_5O$ 465.18, m/z found 466.3 [M+H]$^+$. $^1$H NMR (400 MHz, DMSO) δ 8.64 (s, 1H), 8.10 (d, J=7.6 Hz, 1H), 7.65-7.45 (m, 4H), 7.25-7.10 (m, 9H), 5.11 (s, 2H), 4.59 (s, 2H), 0.99 (m, 4H).

Example 193: 1-((5-(2-((4-(trifluoromethyl)phenyl)amino)phenyl)-2H-tetrazol-2-yl)methyl) cyclopropan-1-ol (Compound 204)

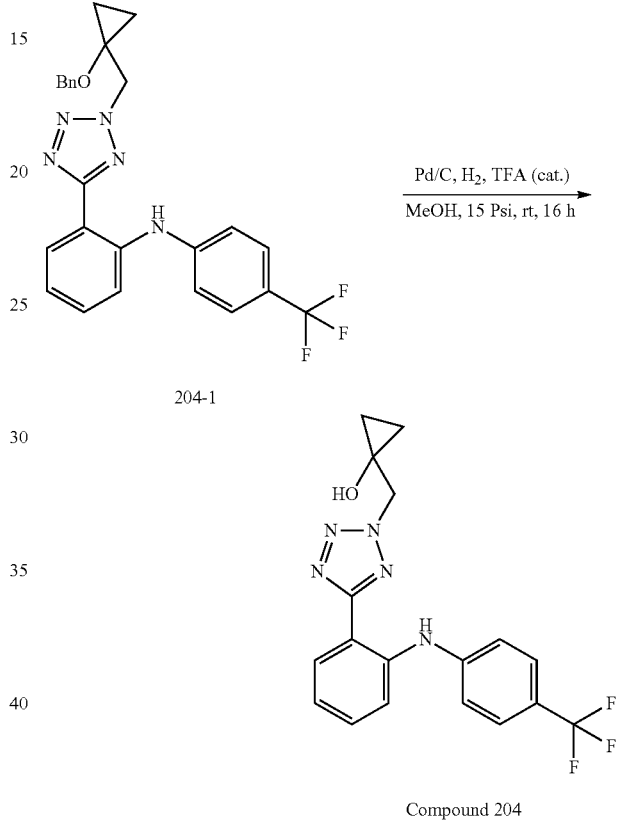

Compound 204

To a solution of 204-1 (13 mg, 27.9 umol, 1 eq) in MeOH (5 mL) was added dry Pd/C (3 mg, 10% purity, 1.00 eq) under $N_2$. The suspension was degassed under vacuum and purged with $H_2$ several times. The mixture was stirred under $H_2$ (15 psi) at 20° C. for 16 hours. LCMS showed that 95% of starting material was remained and 5% of desired MS signal was detected. To the reaction was added TFA (0.2 mL) and the reaction was stirred at 20° C. for 16 hr. LCMS showed that 95% of desired product was detected. The reaction was filtered and concentrated. The crude product was purified by Prep.HPLC to give Compound 204 (3 mg, 7.6 umol, 27.2% yield). LCMS and HNMR confirmed that desired product was obtained. LCMS (ESI): RT=0.833 min, mass calcd. for $C_{18}H_{16}F_3N_5O$ 375.13, m/z found 376.0 [M+H]$^+$. $^1$H NMR (400 MHz, CDCl$_3$) δ 9.07 (s, 1H), 8.21 (d, J=8.0 Hz, 1H), 7.65-7.45 (m, 3H), 7.45-7.35 (m, 1H), 7.35-7.20 (m, 2H), 7.06 (t, J=7.6 Hz, 1H), 4.82 (s, 2H), 3.04 (s, 1H), 1.07 (t, J=6.8 Hz, 2H), 0.92 (t, J=7.2 Hz, 2H).

Example 194: 2-(1-methyl-3-(2-((4-(trifluoromethyl)phenyl)amino)phenyl)-1H-1,2,4-triazol-5-yl)ethan-1-ol (Compound 205)
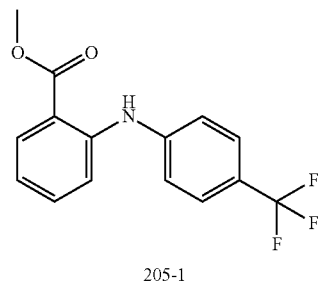
205-1
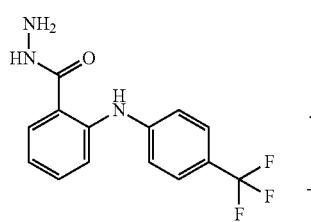
205-2
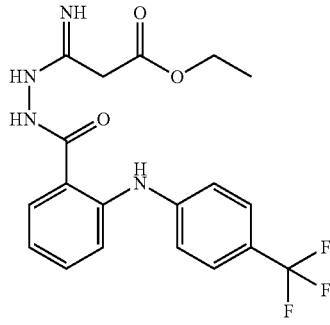
205-3
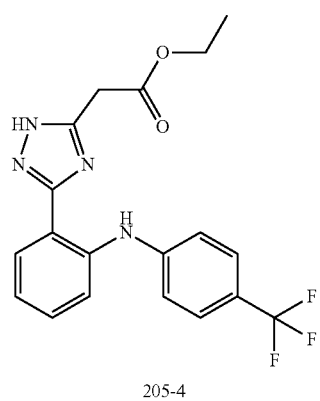
205-4
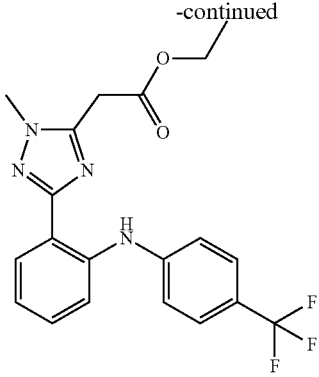
205-5
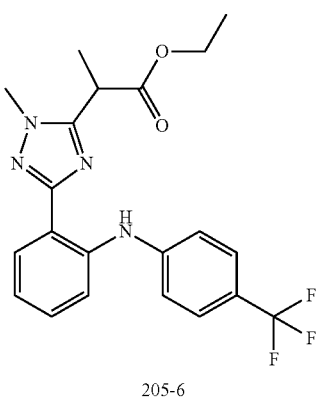
205-6
205-5
Compound 205
Step 1: 2-((4-(trifluoromethyl)phenyl)amino)benzohydrazide
To a mixture of 205-1 (1 g, 3.39 mmol, 1 eq) in EtOH (10 mL) was added $NH_2NH_2 \cdot H_2O$ (2.06 g, 34.98 mmol, 2 mL, 85% purity, 10.33 eq). The resulted mixture was stirred at 80° C. for 17 h. LCMS and TLC showed the reaction was complete. The mixture was concentrated in vacuum. The residue was purified by silica gel chromatography. 205-2 (600 mg, 1.77 mmol, 52.2% yield) was obtained, which was checked by LCMS.

Step 2: ethyl 3-imino-3-(2-(2-((4-(trifluoromethyl) phenyl)amino)benzoyl)hydrazinyl) Propanoate To a mixture of 205-2 (600 mg, 2.03 mmol, 1 eq) in MeOH (8 mL) was added 205-1a (485.2 mg, 3.05 mmol, 1.5 eq). The resulted mixture was stirred at 70° C. for 1 h. LCMS showed the reaction was complete. The mixture was concentrated in vacuum. The residue was diluted with EA (10 mL), filtered, and the solid was dried in vacuum. 205-3 (350 mg, crude) was obtained.

Step 3: ethyl 2-(3-(2-((4-(trifluoromethyl)phenyl) amino)phenyl)-1H-1,2,4-triazol-5-yl)acetate 205-3 (350 mg, 0.86 mmol, 1 eq) was stirred at 180° C. under $N_2$ for 0.5 h. LCMS showed the reaction was complete. The mixture was purified by pre-TLC. 205-4 (80 mg, 0.18 mmol, 20.8% yield) was obtained, which was checked by LCMS.

Step 4: ethyl 2-(1-methyl-3-(2-((4-(trifluoromethyl) phenyl)amino)phenyl)-1H-1,2,4-triazol-5-yl)acetate To a mixture of 205-4 (160 mg, 0.41 mmol, 1 eq) and $K_2CO_3$ (113.3 mg, 0.82 mmol, 2 eq) in DMF (2 mL), was added MeI (87.3 mg, 0.61 mmol, 38 uL, 1.5 eq). The resulting mixture was stirred at 15° C. for 2 h. LCMS showed the starting material was consumed complete. The mixture was concentrated in vacuum. The residue was diluted with water (15 mL), extracted with EA (15 mL*3). The organic layer was dried over anhydrous $Na_2SO_4$, concentrated in vacuum. The residue was checked by LCMS, purified by pre-HPLC to give 205-5 (10 mg, 24.7 umol, 6.0% yield) and 205-6 (about 10 mg), which were checked by LCMS.

Step 5: 2-(1-methyl-3-(2-((4-(trifluoromethyl)phenyl)amino)phenyl)-1H-1,2,4-triazol-5-yl)ethanol To a mixture of 205-5 (10 mg, 24.7 umol, 1 eq) in THF (2 mL) was added $LiBH_4$ (2.69 mg, 0.12 mmol, 5 eq) at 0° C. The resulted mixture was stirred at 15° C. for 5 h. LCMS showed the reaction was completed. The mixture was filtered, and the filtrate was diluted with MeOH (2 mL), concentrated in vacuum. The residue was checked by HPLC, purified by pre-HPLC. Compound 205 (2.95 mg, 8.14 umol) was obtained, which was checked by LCMS, $^1$H NMR and NOE. LCMS (ESI): RT=0.783 min, mass calcd. For $C_{18}H_{17}F_3N_4O$ 362.14, m/z found 362.9 [M+H]$^+$. $^1$H NMR (400 MHz, DMSO-d$_6$) δ 9.96 (s, 1H), 8.07 (d, J=7.6 Hz, 1H), 7.60 (d, J=8.4 Hz, 2H), 7.51 (d, J=8.0 Hz, 1H), 7.45-7.40 (m, 3H), 7.03 (d, J=7.6 Hz, 1H), 3.91 (s, 3H), 3.82 (t, J=6.4 Hz, 2H), 3.00 (t, J=6.8 Hz, 2H).

Example 195: 2-(1-methyl-3-(2-((4-(trifluoromethyl)phenyl)amino)phenyl)-1H-1,2,4-triazol-5-yl) propan-1-ol (Compound 206)

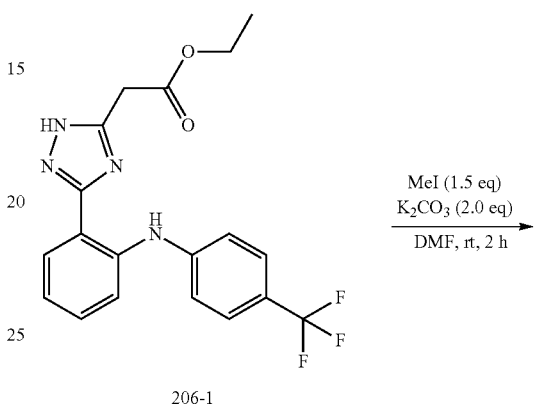

206-1

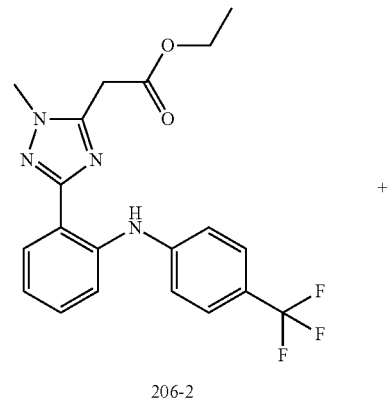

206-2

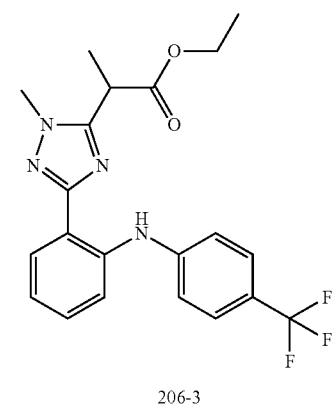

206-3

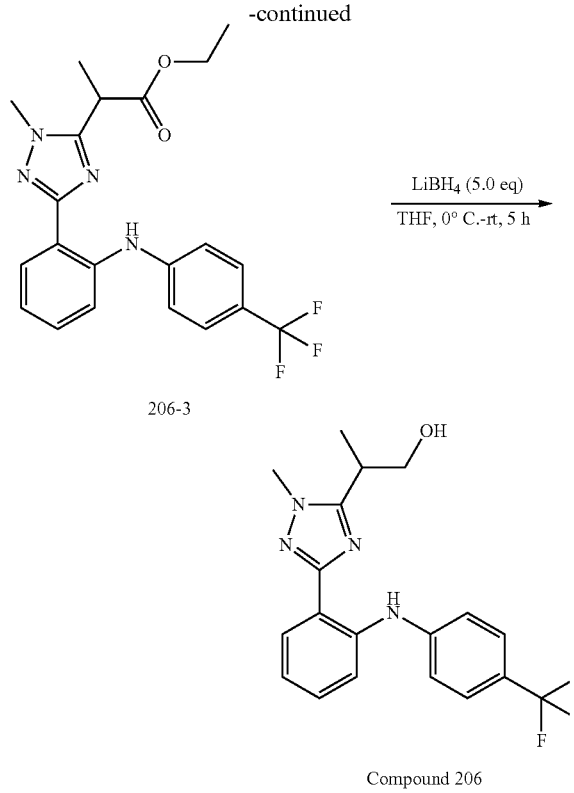

206-3

Compound 206

Step 1: ethyl 2-(1-methyl-3-(2-((4-(trifluoromethyl)
phenyl)amino)phenyl)-1H-1,2,4-triazol-5-yl)acetate To a mixture of 206-1 (160 mg, 0.41 mmol, 1 eq) and K$_2$CO$_3$ (113.3 mg, 0.82 mmol, 2 eq) in DMF (2 mL), was added MeI (87.3 mg, 0.61 mmol, 38 uL, 1.5 eq). The resulting mixture was stirred at 15° C. for 2 h. LCMS showed the starting material was consumed complete. The mixture was concentrated in vacuum. The residue was diluted with water (15 mL), extracted with EA (15 mL*3). The organic layer was dried over anhydrous Na$_2$SO$_4$, concentrated in vacuum. The residue was checked by LCMS, purified by pre-HPLC to give 206-2 (10 mg, 24.7 umol, 6.0% yield) and 206-3 (about 10 mg), which were checked by LCMS.

Step 2: 2-(1-methyl-3-(2-((4-(trifluoromethyl)phe-
nyl)amino)phenyl)-1H-1,2,4-triazol-5-yl)propan-1-ol To a mixture of 206-3 (10 mg, 24.7 umol, 1 eq) in THF (2 mL) was added LiBH$_4$ (2.69 mg, 0.12 mmol, 5 eq) at 0° C. The resulted mixture was stirred at 15° C. for 5 h. LCMS showed the reaction was completed. The mixture was filtered, and the filtrate was diluted with MeOH (2 mL), concentrated in vacuum. The residue was checked by HPLC, purified by pre-HPLC. Compound 206 (5.5 mg, 14.61 umol) was obtained, which was confirmed by LCMS, $^1$H NMR and NOE. LCMS (ESI): RT=0.818 min, mass calcd. For C$_{19}$H$_{19}$F$_3$N$_4$O 376.15, m/z found 376.9 [M+H]$^+$. $^1$H NMR (400 MHz, DMSO-d$_6$) δ 10.13 (s, 1H), 8.07 (dd, J=8.0, 1.6 Hz, 1H), 7.60 (d, J=8.4 Hz, 2H), 7.51 (d, J=8.0 Hz, 1H), 7.45-7.40 (m, 3H), 7.03 (d, J=7.6 Hz, 1H), 3.92 (s, 3H), 3.70-3.50 (m, 2H), 3.40-3.20 (m, 1H), 1.28 (d, J=7.2 Hz, 3H).

Example 196: 2-(5-(2-((4-bromophenyl)amino)phe-
nyl)-2H-tetrazol-2-yl)ethan-1-ol (Compound 207)

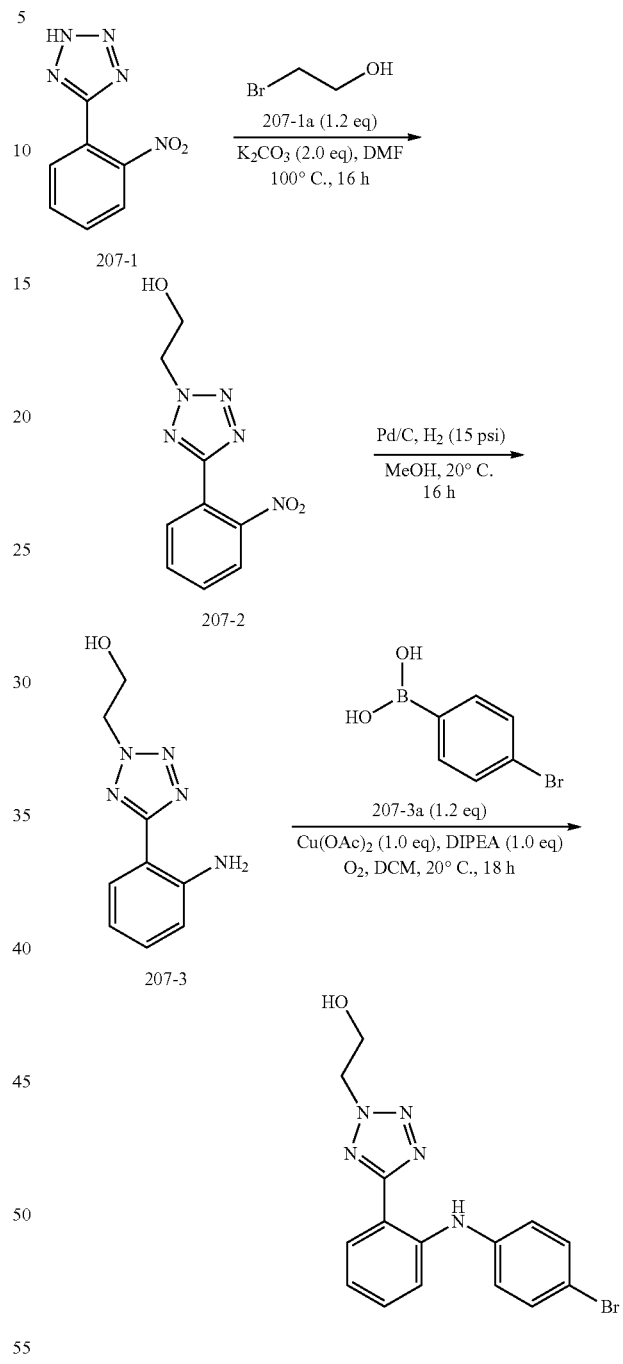

Compound 207

Step 1: 2-(5-(2-nitrophenyl)-2H-tetrazol-2-yl)etha-
nol

To a solution of 207-1 (3.0 g, 15.69 mmol, 1 eq) in DMF (15 mL) were added K$_2$CO$_3$ (4.34 g, 31.4 mmol, 2.0 eq) and 207-1a (2.35 g, 18.83 mmol, 1.3 mL, 1.2 eq). The mixture was stirred at 100° C. for 16 hr. TLC showed the starting material was consumed completely, and one major new spot was detected (Petroleum ether:Ethyl acetate=1/1, $R_f$=0.35). The mixture was cooled to 20° C. and H$_2$O (15 mL) was added to quench the reaction. The aqueous phase was extracted with ethyl acetate (30 mL*3). The combined organic phase was washed with brine (15 mL*1), dried with anhydrous Na$_2$SO$_4$, filtered and concentrated in vacuum. The residue was purified by silica gel chromatography to give 207-2 (2.1 g, 8.21 mmol, 52% yield), which was confirmed by HNMR. $^1$HNMR (400 MHz, CDCl$_3$) δ 7.99 (dd, J=7.8, 1.2 Hz, 1H), 7.89 (dd, J=7.9, 1.1 Hz, 1H), 7.63-7.75 (m, 2H), 4.81-4.84 (m, 2H), 4.22 (t, J=4.6 Hz, 2H), 2.54 (brs, 1H).

Step 2: 2-(5-(2-aminophenyl)-2H-tetrazol-2-yl)ethanol

To a solution of 2-[5-(2-nitrophenyl)tetrazol-2-yl]ethanol (2.0 g, 8.50 mmol, 1 eq) in MeOH (20 mL) was added Pd/C (0.2 g, 8.50 mmol, 20% purity, 1 eq) under N$_2$. The suspension was degassed under vacuum and purged with H$_2$ for 3 times. Then the mixture was stirred under H$_2$ (15 psi) at 20° C. for 16 hr. LCMS showed that no starting material exist. The reaction mixture was filtered and the filter was concentrated to provide 207-3, which was used in next step directly without further purification. $^1$H NMR (400 MHz, CDCl$_3$) δ 8.08 (dd, J=7.9, 1.4 Hz, 1H), 7.22-7.26 (m, 1H), 6.78-6.82 (m, 2H), 5.42 (brs, 2H), 4.79-4.82 (m, 2H), 4.22 (t, J=4.8 Hz, 2H), 2.62 (brs, 1H).

Step 3: 2-(5-(2((4-bromophenyl)amino)phenyl)-2H-tetrazol-2-yl)ethanol

To a solution of 207-3 (100 mg, 0.49 mmol, 1 eq) and 207-3a (117.4 mg, 0.58 mmol, 1.2 eq) in DCM (5 mL) was added Cu(OAc)$_2$ (88.5 mg, 0.49 mmol, 1 eq) and DIPEA (63 mg, 0.49 mmol, 85 uL, 1 eq). The mixture was stirred at 20° C. under O$_2$ for 18 hr. TLC(Petroleum ether:Ethyl acetate=2/1, $R_f$=0.2) showed the starting material was consumed completely, and one major new spot was detected. H$_2$O (5 mL) was added to quench the reaction. The aqueous phase was extracted with ethyl acetate (10 mL*3). The combined organic phase was washed with brine (10 mL*1), dried with anhydrous Na$_2$SO$_4$, filtered and concentrated in vacuum. The residue was purified by silica gel chromatography to give Compound 207 (18.1 mg, 50 umol, 10.2% yield). LCMS (ESI): RT=1.732 min, mass calc. for C$_{15}$H$_{14}$ClN$_6$O 359.04, m/z found 359.8 [M+1]$^+$; $^1$H NMR (400 MHz, CDCl$_3$) δ 8.83 (s, 1H), 8.16 (dd, J=8.0, 1.2 Hz, 1H), 7.41-7.44 (m, 2H), 7.30-7.37 (m, 2H), 7.13-7.16 (m, 2H), 6.94-6.98 (m, 1H), 4.83-4.86 (m, 2H), 4.24-4.28 (m, 2H), 2.40 (t, J=6.3 Hz, 1H).

Example 197: 2-(5-(2-((4-chlorophenyl)amino)phenyl)-2H-tetrazol-2-yl)ethan-1-ol (Compound 208)

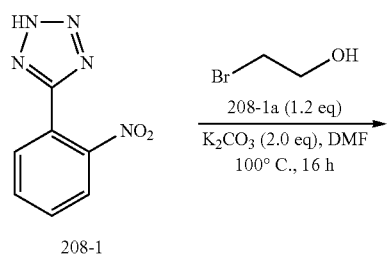

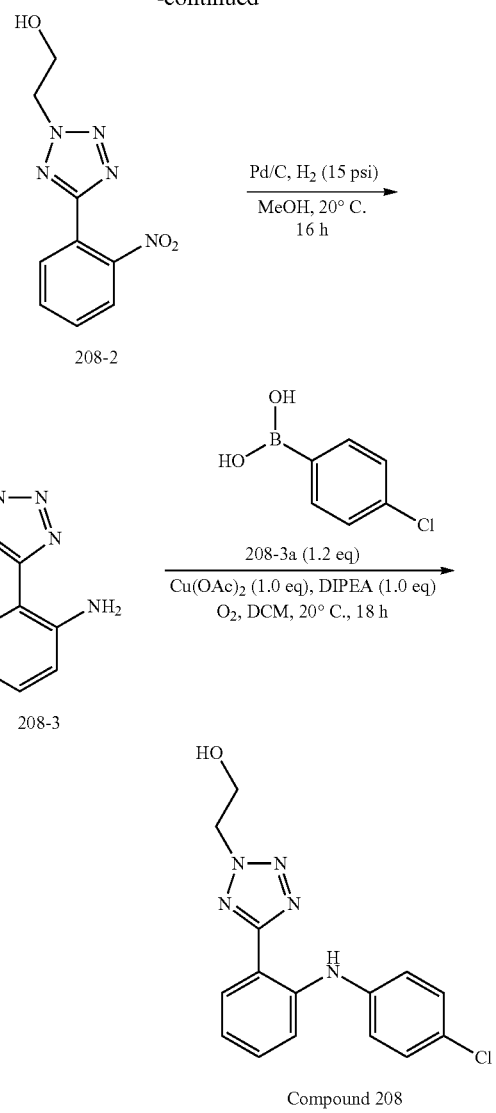

Step 1: 2-(5-(2-nitrophenyl)-2H-tetrazol-2-yl)ethanol

To a solution of 208-1 (3.0 g, 15.69 mmol, 1 eq) in DMF (15 mL) were added K$_2$CO$_3$ (4.34 g, 31.39 mmol, 2.0 eq) and 208-1a (2.35 g, 18.83 mmol, 1.3 mL, 1.2 eq). The mixture was stirred at 100° C. for 16 hr. TLC (Petroleum ether:Ethyl acetate=1/1, $R_f$=0.35) showed the starting material was consumed completely, and one major new spot was detected. The mixture was cooled to 20° C. and H$_2$O (15 mL) was added to quench the reaction. The aqueous phase was extracted with ethyl acetate (30 mL*3). The combined organic phase was washed with brine (15 mL*1), dried with anhydrous Na$_2$SO$_4$, filtered and concentrated in vacuum. The residue was purified by silica gel chromatography to give the desired 208-2 (2.1 g, 8.21 mmol, 52% yield), which was confirmed by $^1$H NMR. $^1$H NMR (400 MHz, CDCl$_3$) δ 7.99 (dd, J=7.8, 1.2 Hz, 1H), 7.89 (dd, J=7.9, 1.1 Hz, 1H), 7.63-7.75 (m, 2H), 4.81-4.84 (m, 2H), 4.22 (t, J=4.6 Hz, 2H), 2.54 (brs, 1H).

Step 2: 2-(5-(2-aminophenyl)-2H-tetrazol-2-yl)ethanol

To a solution of 208-2 (2.0 g, 8.50 mmol, 1 eq) in MeOH (20 mL) was added Pd/C (0.2 g, 8.50 mmol, 20% purity, 1 eq) under N2. The suspension was degassed under vacuum and purged with $H_2$ for 3 times. Then the mixture was stirred under $H_2$ (15 psi) at 20° C. for 16 hr. LCMS showed that no starting material existed. The reaction mixture was filtered and the filter was concentrated to get 208-3, which was used in next step directly without further purification. $^1$H NMR (400 MHz, CDCl$_3$) δ 8.08 (dd, J=7.9, 1.4 Hz, 1H), 7.22-7.26 (m, 1H), 6.78-6.82 (m, 2H), 5.42 (brs, 2H), 4.79-4.82 (m, 2H), 4.22 (t, J=4.8 Hz, 2H), 2.62 (brs, 1H).

Step 3: 2-(5-(2-((4-chlorophenyl)amino)phenyl)-2H-tetrazol-2-yl)ethanol

To a solution of 208-3 (100 mg, 0.49 mmol, 1 eq) and (4-chlorophenyl)boronic acid (91.4 mg, 0.58 mmol, 1.2 eq) in DCM (5 mL) was added Cu(OAc)$_2$ (88.5 mg, 0.49 mmol, 1 eq) and DIPEA (62.9 mg, 0.49 mmol, 85 uL, 1 eq). The mixture was stirred at 20° C. under O$_2$ for 18 hr. TLC(PE/EA=2/1) showed there's no starting material. H$_2$O (5 mL) was added to quench the reaction. The aqueous phase was extracted with ethyl acetate (10 mL*3). The combined organic phase was washed with brine (10 mL*1), dried with anhydrous Na$_2$SO$_4$, filtered and concentrated in vacuum. The residue was purified by silica gel chromatography to give Compound 208 (13.85 mg, 42.6 umol, 8.74% yield). LCMS (ESI): RT=1.732 min, mass calc. for C$_{15}$H$_{14}$ClN$_6$O 315.09, m/z found 316.0 [M+1]$^+$; $^1$H NMR (400 MHz, CDCl$_3$) δ 8.84 (s, 1H), 8.16 (dd, J=7.8, 1.0 Hz, 1H), 7.28-7.36 (m, 4H), 7.18-7.21 (m, 2H), 6.93-6.97 (m, 1H), 4.84-4.86 (m, 2H), 4.24-4.28 (m, 2H), 2.31 (t, J=6.4 Hz, 1H).

Example 198: 2-(1-benzyl-3-(2-((4-(trifluoromethyl)phenyl)amino)phenyl)-1H-pyrazol-5-yl)ethan-1-ol (Compound 209)

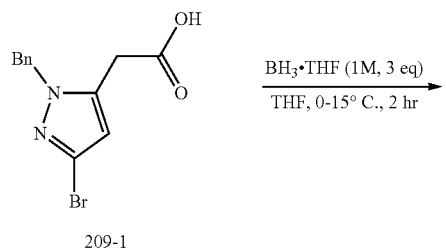

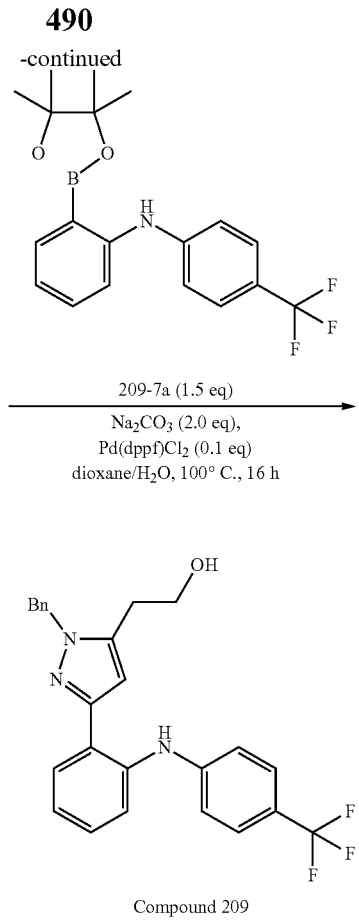

Compound 209

Step 1: 2-(1-benzyl-3-bromo-1H-pyrazol-5-yl)ethanol

To the solution of 209-1 (130 mg, 0.44 mmol, 1 eq) in THF (4 mL) was added BH3.THF (1 M, 1.3 mL, 3 eq) at 0° C. The mixture was warmed up to 15° C. and stirred for 2 hr. The reaction solution was quenched with H$_2$O (15 mL). The mixture was extracted with EtOAc (10 mL*2). The combined organic layers were dried with Na$_2$SO$_4$ and concentrated under reduced pressure to give 209-2 (45 mg, 0.16 mmol, 36% yield).

Step 2: 2-(1-benzyl-3-(2-((4-(trifluoromethyl)phenyl)amino)phenyl)-1H-pyrazol-5-yl)ethanol To the solution of 209-2 (20 mg, 71.1 umol, 1 eq) in dioxane (3 mL) and H$_2$O (0.15 mL) were added compound 209-7a (25. mg, 71.1 umol, 1 eq), Pd(PPh$_3$)$_4$ (8.2 mg, 7.1 umol, 0.1 eq) and Cs$_2$CO$_3$ (34.8 mg, 0.11 mmol, 1.5 eq). The mixture was stirred at 100° C. for 16 hr. LCMS showed that a little of starting material was remained and one main peak with desired MS. The reaction solution was concentrated under reduced pressure. The residue was purified by column chromatography (SiO$_2$) to give compound 209.5 mg of the crude was re-purified by Prep-HPLC to give Compound 209 (2.66 mg, 6.1 umol, 8.6% yield). LCMS (ESI): RT=0.890 min, mass calcd. for C$_{25}$H$_{22}$F$_3$N$_3$O 437.17, m/z found 438.1 [M+H]$^+$, $^1$H NMR (400 MHz, CDCl$_3$) δ 7.63 (dd, J=1.3, 7.8 Hz, 1H), 7.53-7.47 (m, 1H), 7.43 (d, J=8.5 Hz, 2H), 7.35-7.29 (m, 3H), 7.26-7.21 (m, 1H), 7.19-7.15 (m, 2H), 7.09 (d, J=8.5 Hz, 2H), 6.98 (t, J=7.4 Hz, 1H), 6.51 (s, 1H), 5.38 (s, 2H), 3.86 (t, J=6.4 Hz, 2H), 2.90 (t, J=6.4 Hz, 2H).

Example 199: 2-(2-((2S,3S)-3-methoxybutan-2-yl)-2H-tetrazol-5-yl)-N-(4-(trifluoro methyl)phenyl)aniline (Compound 210), 2-(2-((2S,3R)-3-methoxybutan-2-yl)-2H-tetrazol-5-yl)-N-(4-(trifluoromethyl)phenyl)aniline (Compound 211), 2-(2-((2R,3S)-3-methoxybutan-2-yl)-2H-tetrazol-5-yl)-N-(4-(trifluoromethyl)phenyl)aniline (Compound 212), and 2-(2-((2R,3R)-3-methoxybutan-2-yl)-2H-tetrazol-5-yl)-N-(4-(trifluoromethyl)phenyl)aniline (Compound 213)

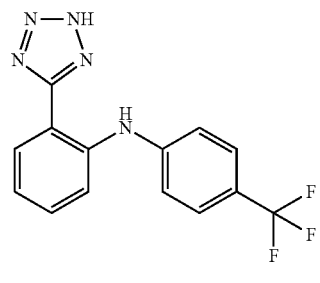
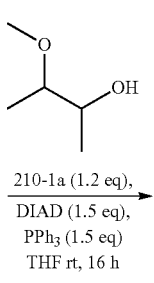

210-1a (1.2 eq), DIAD (1.5 eq), PPh₃ (1.5 eq) THF rt, 16 h

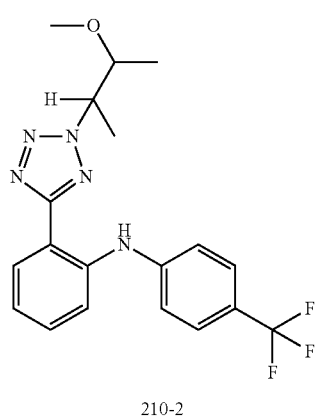

210-2

SFC

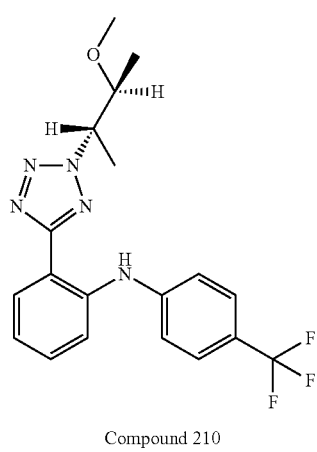

Compound 210

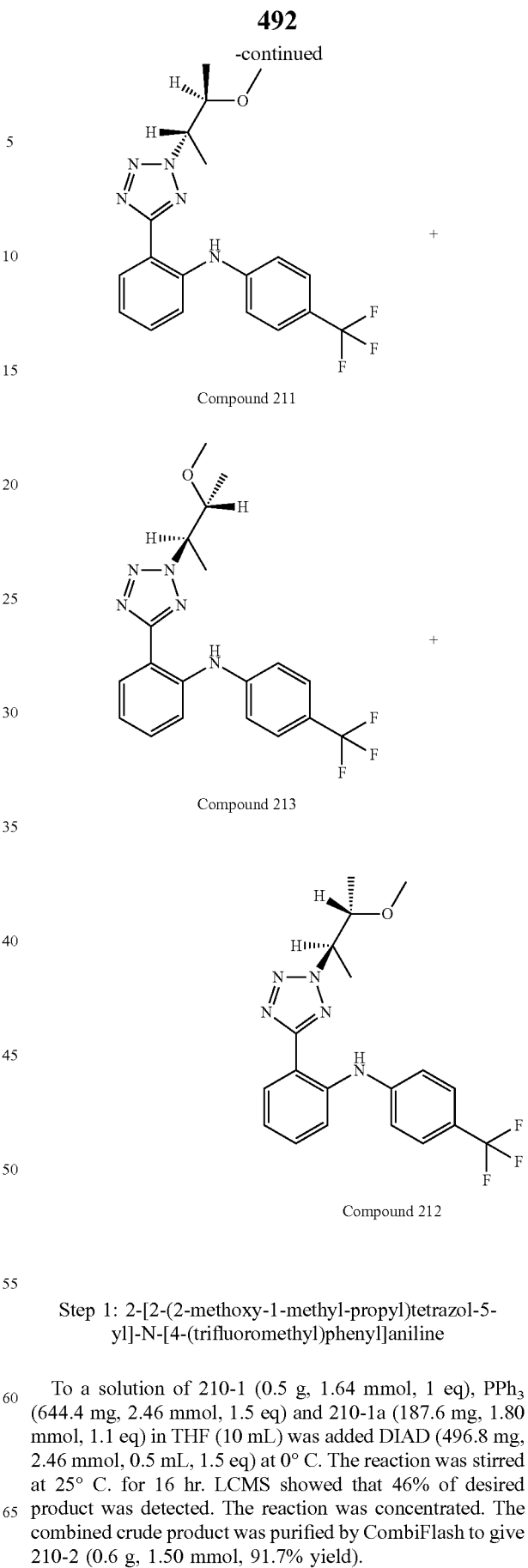

Compound 211

Compound 213

Compound 212

Step 1: 2-[2-(2-methoxy-1-methyl-propyl)tetrazol-5-yl]-N-[4-(trifluoromethyl)phenyl]aniline To a solution of 210-1 (0.5 g, 1.64 mmol, 1 eq), PPh₃ (644.4 mg, 2.46 mmol, 1.5 eq) and 210-1a (187.6 mg, 1.80 mmol, 1.1 eq) in THF (10 mL) was added DIAD (496.8 mg, 2.46 mmol, 0.5 mL, 1.5 eq) at 0° C. The reaction was stirred at 25° C. for 16 hr. LCMS showed that 46% of desired product was detected. The reaction was concentrated. The combined crude product was purified by CombiFlash to give 210-2 (0.6 g, 1.50 mmol, 91.7% yield).

Step 2: 2-(2-((2S,3S)-3-methoxybutan-2-yl)-2H-tetrazol-5-yl)-N-(4-(trifluoromethyl)phenyl) aniline, 2-(2-((2R,3R)-3-methoxybutan-2-yl)-2H-tetrazol-5-yl)-N-(4-(trifluoromethyl)phenyl) aniline, 2-(2-((2S,3R)-3-methoxybutan-2-yl)-2H-tetrazol-5-yl)-N-(4-(trifluoromethyl)phenyl) aniline, and 2-(2-((2R,3S)-3-methoxybutan-2-yl)-2H-tetrazol-5-yl)-N-(4-(trifluoromethyl) phenyl)aniline 210-2 (0.6 g, 1.53 mmol, 1 eq) was separated by SFC. About 150 mg crude product was separated by chiral SFC again.

Compound 210 (38.38 mg, 96.1 umol, 6.3% yield). LCMS (ESI): RT=0.929 min, mass calcd. For $C_{19}H_{20}F_3N_5O$, 391.16 m/z found 392.0[M+H]$^+$. $^1$H NMR (400 MHz, CDCl$_3$) δ 9.14 (s, 1H), 8.22 (d, J=7.6 Hz, 1H), 7.60-7.50 (m, 3H), 7.37 (t, J=7.20 Hz, 1H), 7.30 (d, J=7.6 Hz, 2H), 7.04 (t, J=7.20 Hz, 1H), 5.10-5.02 (m, 1H), 3.85-3.66 (m, 1H), 3.37 (s, 3H), 1.77 (d, J=6.8 Hz, 3H), 1.12 (d, J=6.8 Hz, 3H).

Compound 213 (30 mg, 76.7 umol, 5.0% yield). LCMS (ESI): RT=0.924 min, mass calcd. For $C_{19}H_{20}F_3N_5O$, 391.16 m/z found 392.0[M+H]$^+$. $^1$H NMR (400 MHz, CDCl$_3$) δ 9.14 (s, 1H), 8.22 (d, J=7.6 Hz, 1H), 7.60-7.50 (m, 3H), 7.37 (t, J=7.20 Hz, 1H), 7.30 (d, J=7.6 Hz, 2H), 7.04 (t, J=7.20 Hz, 1H), 5.10-5.02 (m, 1H), 3.85-3.66 (m, 1H), 3.37 (s, 3H), 1.77 (d, J=6.8 Hz, 3H), 1.12 (d, J=6.8 Hz, 3H).

Compound 211 (135.21 mg, 0.33 mmol, 21.4% yield). LCMS (ESI): RT=0.935 min, mass calcd. For $C_{19}H_{20}F_3N_5O$, 391.16 m/z found 392.0[M+H]$^+$. $^1$H NMR (400 MHz, CDCl$_3$) δ 9.17 (s, 1H), 8.23 (dd, J=8.0, 2.0 Hz, 1H), 7.54 (d, J=8.00 Hz, 3H), 7.40-7.30 (m, 1H), 7.29 (br d, J=8.40 Hz, 2H), 7.04 (t, J=8.0 Hz, 1H), 5.10-5.02 (m, 1H), 3.90-3.75 (m, 1H), 3.23 (s, 3H), 1.67 (d, J=6.8 Hz, 3H), 1.27 (d, J=6.0 Hz, 3H).

Compound 212 (179.88 mg, 0.45 mmol, 29.4% yield). LCMS (ESI): RT=0.927 min, mass calcd. For $C_{19}H_{20}F_3N_5O$, 391.16 m/z found 392.0[M+H]$^+$. $^1$H NMR (400 MHz, CDCl$_3$) δ 9.17 (s, 1H), 8.23 (dd, J=8.0, 2.0 Hz, 1H), 7.54 (d, J=8.00 Hz, 3H), 7.40-7.30 (m, 1H), 7.29 (br d, J=8.40 Hz, 2H), 7.04 (t, J=8.0 Hz, 1H), 5.10-5.02 (m, 1H), 3.90-3.75 (m, 1H), 3.23 (s, 3H), 1.67 (d, J=6.8 Hz, 3H), 1.27 (d, J=6.0 Hz, 3H).

Example 200: 2-(2-(2-methoxycyclopentyl)-2H-tetrazol-5-yl)-N-(4-(trifluoromethyl)phenyl) Aniline (Compound 214)

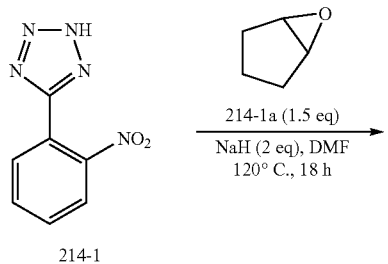

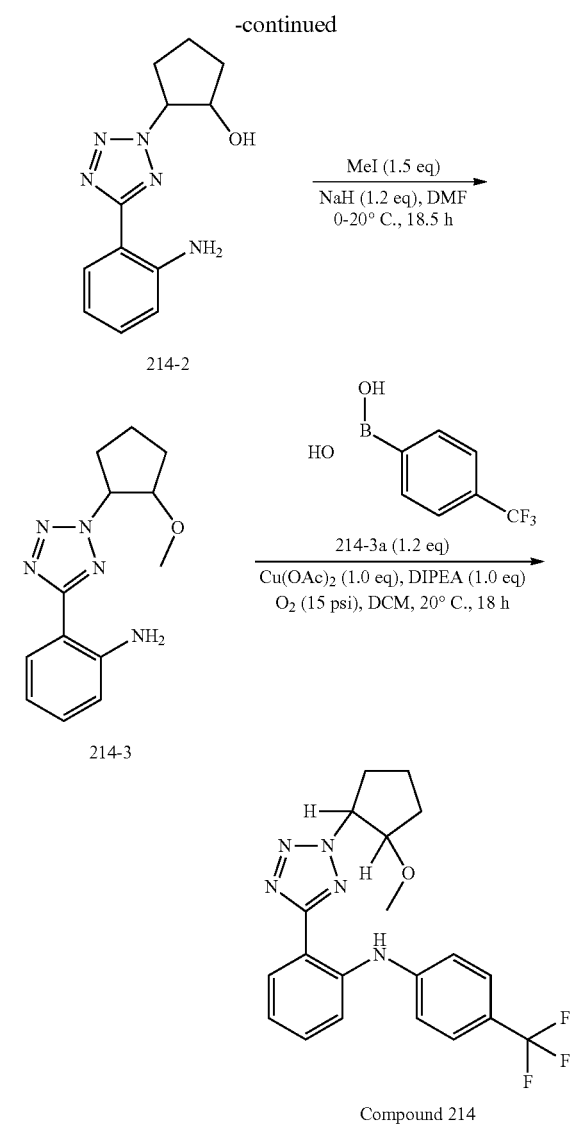

Step 1: 2-(5-(2-aminophenyl)-2H-tetrazol-2-yl)cyclopentanol

To a mixture of 214-1 (1.0 g, 5.2 mmol, 1 eq) and 214-1a (880.1 mg, 10.5 mmol, 0.9 mL, 2 eq) in DMF (15 mL) was added NaH (418.4 mg, 10.5 mmol, 60% purity, 2 eq). The reaction mixture was stirred at 120° C. under N$_2$ for 18 hr. TLC and LCMS showed the desired product was generated, the starting material wasn't consumed completely. The reaction was quenched with H$_2$O (5 mL) and extracted with EA (10 mL*3), the combined organic phase was washed with brine (10 mL) and dried over Na$_2$SO$_4$, filtered and concentrated in vacuum. The residue was purified by silica gel chromatography. 214-2 (220 mg, 0.90 mmol, 17.2% yield) was obtained. $^1$H NMR (400 MHz, CDCl$_3$) δ 8.08 (dd, J=1.3, 7.8 Hz, 1H), 7.23 (dt, J=1.6, 7.7 Hz, 1H), 6.88-6.71 (m, 2H), 5.42 (br s, 2H), 5.01 (dt, J=5.8, 7.9 Hz, 1H), 4.68 (q, J=6.5 Hz, 1H), 2.73-2.60 (m, 1H), 2.57-2.45 (m, 1H), 2.37-2.19 (m, 2H), 2.03-1.92 (m, 2H), 1.88-1.76 (m, 1H).

Step 2: 2-(2-(2-methoxycyclopentyl)-2H-tetrazol-5-yl)aniline

To a solution of 214-2 (210 mg, 0.86 mmol, 1 eq) in DMF (2 mL) was added NaH (41.1 mg, 1.0 mmol, 60% purity, 1.2 eq) at 0° C. under $N_2$. The mixture was stirred at 0° C. for 30 min followed by adding MeI (430 mg, 3.0 mmol, 0.19 mL, 3.5 eq). After that, the reaction mixture was stirred at 20° C. under $N_2$ for 18 hr. LCMS showed the desired product was generated, no starting material existed. The reaction was quenched with $H_2O$ (5 mL), the aqueous phase was extracted with ethyl acetate (10 mL*3). The combined organic phase was washed with brine (5 mL*1), dried with anhydrous $Na_2SO_4$, filtered and concentrated in vacuum. The residue was purified by silica gel chromatography. 214-3 (143 mg, 0.55 mmol, 64.4% yield) was obtained. $^1$HNMR (400 MHz, $CDCl_3$) δ 8.12 (dd, J=1.3, 8.0 Hz, 1H), 7.24 (dt, J=1.6, 7.7 Hz, 1H), 6.87-6.75 (m, 2H), 5.45 (br s, 2H), 5.21 (m, 1H), 4.25 (td, J=4.5, 6.5 Hz, 1H), 3.35 (s, 3H), 2.52-2.38 (m, 1H), 2.35-2.15 (m, 2H), 2.09-1.91 (m, 2H), 1.90-1.79 (m, 1H)

Step 3: 2-(2-(2-methoxycyclopentyl)-2H-tetrazol-5-yl)-N-(4-(trifluoromethyl)phenyl)aniline To a solution of 214-3 (71 mg, 0.27 mmol, 1 eq) and 214-3a (62.4 mg, 0.33 mmol, 1.2 eq) in DCM (5 mL) were added $Cu(OAc)_2$ (49.7 mg, 0.27 mmol, 1.0 eq) and DIPEA (35.4 mg, 0.27 mmol, 48 uL, 1.0 eq). The mixture was stirred at 20° C. under $O_2$ for 18 hr. LCMS showed the desired product was generated, starting material was consumed completely. $H_2O$ (10 mL) was added to quench the reaction, the aqueous phase was extracted with ethyl acetate (20 mL*3). The combined organic phase was washed with brine (20 mL*2), dried with anhydrous $Na_2SO_4$, filtered and concentrated in vacuum. The residue was purified by prep-HPLC. Compound 214 (38.6 mg, 96 umol, 35.0% yield) was obtained. LCMS (ESI): RT=0.944 min, mass calc. for $C_{20}H_{20}F_3N_5O$ 403.16, m/z found 403.9 [M+H]$^+$; $^1$H NMR (400 MHz, $CDCl_3$) δ 9.10 (s, 1H), 8.21 (dd, J=1.5, 7.8 Hz, 1H), 7.54 (d, J=8.3 Hz, 3H), 7.44-7.35 (m, 1H), 7.29 (d, J=8.5 Hz, 2H), 7.11-7.00 (m, 1H), 5.22 (m, 1H), 4.24 (m, 1H), 3.35 (s, 3H), 2.54-2.40 (m, 1H), 2.36-2.25 (m, 1H), 2.25-2.17 (m, 1H), 2.04-1.93 (m, 2H), 1.92-1.79 (m, 1H).

Example 201: methyl 2-(1-benzyl-3-(2-((4-(trifluoromethyl)phenyl)amino)phenyl)-1H-pyrazol-5-yl)acetate (Compound 215)

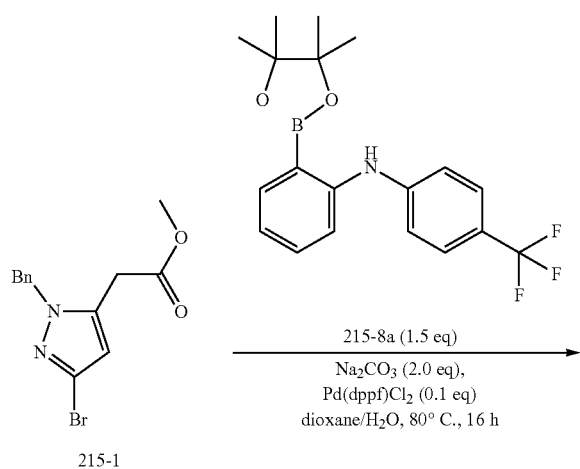

Compound 215

To the solution of 215-1 (200 mg, 0.65 mmol, 1 eq) in dioxane (4 mL) and $H_2O$ (2 mL) were added 215-8a (235 mg, 0.65 mmol, 1 eq), $Pd(PPh_3)_4$ (75 mg, 64.7 umol, 0.1 eq) and $Cs_2CO_3$ (316 mg, 0.97 mmol, 1.5 eq). The mixture was stirred at 80° C. for 16 hr. The reaction was monitored by LCMS. LCMS showed that the starting material was consumed and the peak with the desired MS was observed. The reaction solution was concentrated under reduced pressure. The residue was purified by column chromatography ($SiO_2$) to give Compound 215 (100 mg, 0.20 mmol, 31% yield). 10 mg of the crude product was re-purified by Prep-HPLC to give Compound 215 (2.50 mg, 5.3 umol, 8.14e-1% yield). LCMS (ESI): RT=0.951 min, mass calcd. for $C_{26}H_{22}F_3N_3O_2$ 465.17, m/z found 466.0 [M+H]$^+$, $^1$HNMR (400 MHz, $CDCl_3$) δ 9.64 (s, 1H), 7.62 (d, J=7.8 Hz, 1H), 7.53-7.40 (m, 3H), 7.32 (s, 3H), 7.17 (d, J=5.3 Hz, 2H), 7.08 (d, J=8.5 Hz, 2H), 6.97 (t, J=7.7 Hz, 1H), 6.60 (s, 1H), 5.38 (s, 2H), 3.71-3.61 (m, 1H), 3.71-3.61 (m, 1H), 3.71-3.61 (m, 5H).

Example 202: 2-(2-(3-aminopropyl)-2H-tetrazol-5-yl)-N-(4-(trifluoromethyl)phenyl)aniline (Compound 216)

-continued

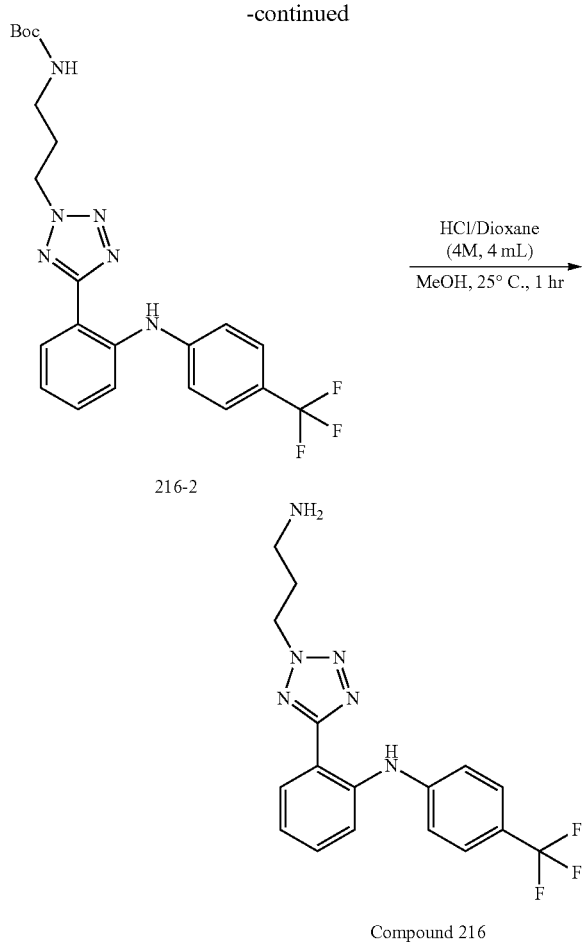

216 (4.16 mg, 11.5 umol, 5% yield). LCMS (ESI): RT=0.689 min, mass calcd. for $C_{17}H_{17}F_3N_6$ 362.15, m/z found 342.9 [M−F−1]$^+$, $^1$HNMR (400 MHz, CDCl$_3$) δ 9.04 (s, 1H), 8.18 (d, J=6.5 Hz, 1H), 7.56-7.48 (m, 3H), 7.36 (t, J=7.2 Hz, 1H), 7.32-7.26 (m, 2H), 7.03 (t, J=7.4 Hz, 1H), 4.91-4.72 (m, 2H), 2.91-2.77 (m, 2H), 2.28-2.19 (m, 2H).

Example 203: tert-butyl 3-(5-(2-((4-(trifluoromethyl)phenyl)amino)phenyl)-2H-tetrazol-2-yl)azetidine-1-carboxylate (Compound 217)

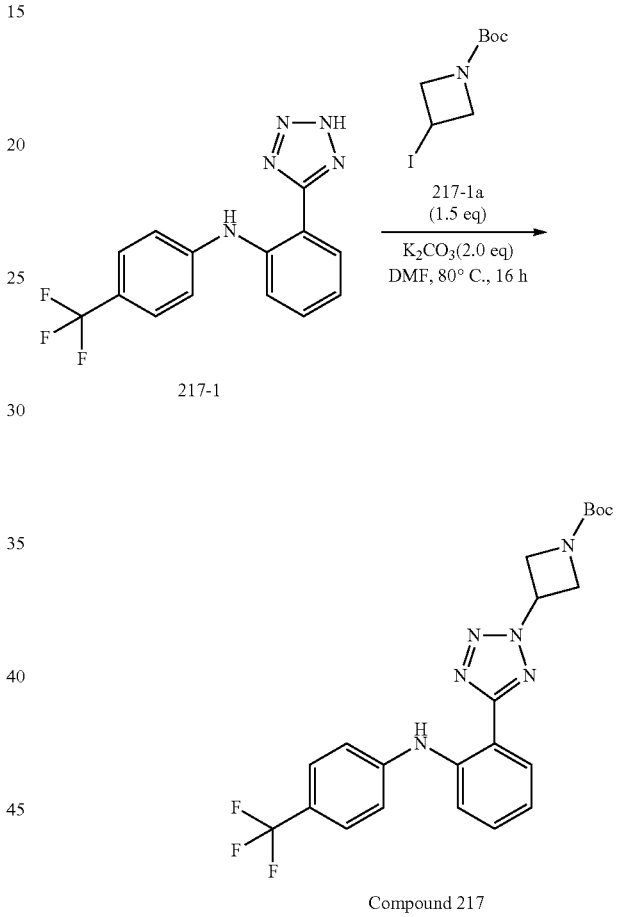

Step 1: tert-butyl (3-(5-(2-((4-(trifluoromethyl)phenyl)amino)phenyl)-2H-tetrazol-2-yl)propyl) carbamate To the solution of 216-1 (50 mg, 0.16 mmol, 1 eq) in THF (1 mL) was added 216-1a (37 mg, 0.2 mmol, 37 uL, 1.3 eq) and PPh$_3$ (129 mg, 0.49 mmol, 3 eq) at 0° C. Then DIAD (99 mg, 0.49 mmol, 96 uL, 3 eq) was added to the mixture. The solution was warmed up to 30° C. and stirred for 16 hr. The reaction was monitored by LCMS. LCMS showed that the starting material was consumed and the main peak was the desired MS. The reaction solution was concentrated under reduced pressure. The residue was purified by column chromatography (SiO$_2$) to give 216-2 (100 mg, crude).

Step 2: 2-(2-(3-aminopropyl)-2H-tetrazol-5-yl)-N-(4-(trifluoromethyl)phenyl)aniline To the solution of 216-2 (100 mg, 0.22 mmol, 1 eq) in MeOH (4 mL) was added HCl/dioxane (4 M, 4 mL, 74 eq). The mixture was stirred at 25° C. for 1 hr. The reaction was monitored by LCMS. LCMS showed that the starting material remained a little and the desired MS was observed. The reaction solution was concentrated under reduced pressure. The residue was purified by Prep-HPLC to give Compound To a solution of 217-1 (100 mg, 0.3 mmol, 1.0 eq) in DMF (3.0 mL) was added K$_2$CO$_3$ (90.5 mg, 0.6 mmol, 2.0 eq) and 217-1a (139.1 mg, 0.5 mmol, 1.5 eq). The mixture was stirred at 80° C. for 16 h. LC-MS showed 37% of 217-1 remained. Several new peaks were shown on LC-MS and 48% of desired compound was detected. The mixture was purified by prep-HPLC to give Compound 217 (25.9 mg, 56.3 umol, 17% yield). LCMS (ESI): RT=0.935 min, mass calc. for $C_{22}H_{23}F_3N_6O$ 460.18 m/z found 483.17 [M+Na]$^+$; $^1$HNMR (400 MHz, CDCl$_3$) δ 8.99 (s, 1H), 8.24-8.21 (d, J=1.5, 8.0 Hz, 1H), 7.54 (d, J=8.5 Hz, 3H), 7.44-7.37 (m, 1H), 7.29 (d, J=8.5 Hz, 2H), 7.10-7.03 (m, 1H), 5.73-5.66 (m, J=5.5, 7.6 Hz, 1H), 4.62-4.48 (m, 4H), 1.53-1.48 (m, 9H).

Example 204: 2-(2-(1-aminopropan-2-yl)-2H-tetrazol-5-yl)-N-(4-(trifluoromethyl)phenyl) Aniline (Compound 218)

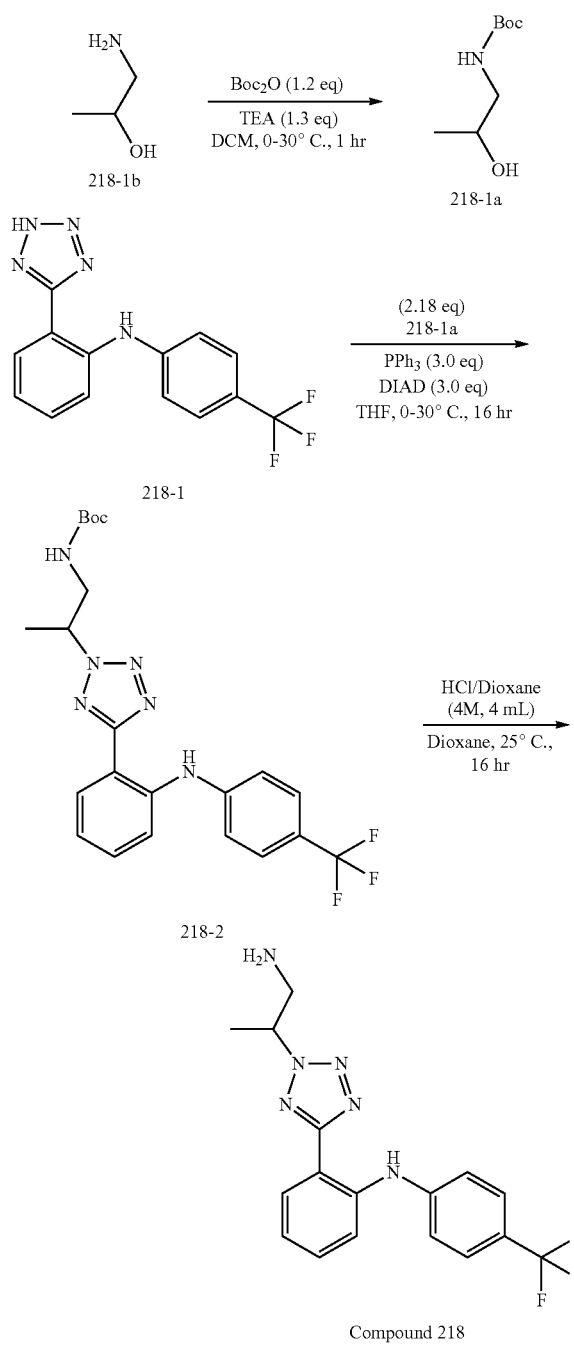

Compound 218

Step 1: tert-butyl (2-hydroxypropyl)carbamate

To the solution of 218-1b (100 mg, 1.3 mmol, 0.1 mL, 1 eq) in DCM (1 mL) were added TEA (175 mg, 1.7 mmol, 0.2 mL, 1.3 eq) and Boc$_2$O (349 mg, 1.6 mmol, 0.4 mL, 1.2 eq) at 0° C. The reaction solution was warmed up to 30° C. and stirred for 1 hr. The reaction was monitored by TLC. TLC (PE:EA=3:1) showed that the starting material was consumed and several new spots with smaller polarity was observed. The reaction was concentrated under reduced pressure. The residue was purified by column chromatography (SiO$_2$) to give 218-1a (250 mg, crude). $^1$HNMR (400 MHz, CDCl$_3$) δ 3.96-3.85 (m, 1H), 3.34-3.21 (m, 1H), 3.07-2.95 (m, 1H), 1.45 (s, 9H), 1.18 (d, J=6.5 Hz, 3H).

Step 2: tert-butyl (2-(5-(2-((4-(trifluoromethyl)phenyl)amino)phenyl)-2H-tetrazol-2-yl)propyl)carbamate To the solution of 218-1a (250 mg, 1.4 mmol, 2.2 eq) in THF (2 mL) was added PPh$_3$ (516 mg, 2.0 mmol, 3 eq) and 218-1 (200 mg, 0.66 mmol, 1 eq) at 0° C. Then DIAD (397 mg, 2.0 mmol, 0.4 mL, 3 eq) was added to the mixture. The solution was warmed up to 30° C. and stirred for 16 hr. The reaction was monitored by LCMS. LCMS showed that the starting material was consumed and the main peak was the desired MS. The reaction was concentrated under reduced pressure. The residue was purified by column chromatography (SiO$_2$) to give 218-2 (180 mg, 0.35 mmol, 54% yield). $^1$H NMR (400 MHz, CDCl$_3$) δ 9.04 (s, 1H), 8.20 (d, J=6.5 Hz, 1H), 7.54 (d, J=8.5 Hz, 3H), 7.41-7.35 (m, 1H), 7.30 (d, J=8.5 Hz, 2H), 7.05 (t, J=7.5 Hz, 1H), 5.24-5.12 (m, 1H), 4.85-4.75 (m, 1H), 3.84-3.64 (m, 2H), 1.69 (d, J=6.8 Hz, 3H), 1.40-1.36 (m, 9H).

Step 3: 2-(2-(1-aminopropan-2-yl)-2H-tetrazol-5-yl)-N-(4-(trifluoromethyl)phenyl)aniline To the solution of 218-2 (50 mg, 0.11 mmol, 1 eq) in dioxane (2 mL) was added HCl/dioxane (4 M, 2 mL, 74 eq). The mixture was stirred at 25° C. for 16 hr. The reaction was monitored by LCMS. LCMS showed that the starting material was consumed and one main peak with desired MS. The reaction solution was concentrated under reduced pressure. The residue was purified by prep-HPLC to give Compound 218 (16.08 mg, 39.5 umol, 36.6% yield, HCl). LCMS (ESI): RT=0.689 min, mass calcd. for C$_{17}$H$_{17}$F$_3$N$_6$ 362.15, m/z found 342.9 [M−F−1]$^-$, $^1$H NMR (400 MHz, DMSO-d$_6$) δ 8.79 (s, 1H), 8.17 (br, 3H), 8.06 (dd, J=1.3, 7.8 Hz, 1H), 7.59-7.51 (m, 4H), 7.25-7.19 (m, 3H), 5.41-5.31 (m, 1H), 3.49-3.44 (m, 2H), 1.60 (d, J=6.8 Hz, 3H).

Example 205: 2-(2-(2-(methylamino)ethyl)-2H-tetrazol-5-yl)-N-(4-(trifluoromethyl)phenyl) Aniline (Compound 219)

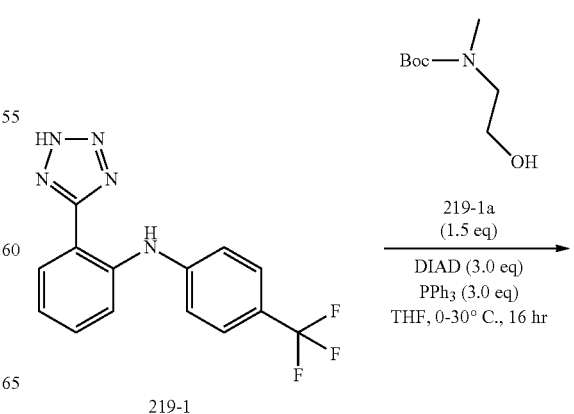

Example 206: 2-(2-(3-(methylamino)propyl)-2H-tetrazol-5-yl)-N-(4-(trifluoromethyl)phenyl) Aniline (Compound 220)

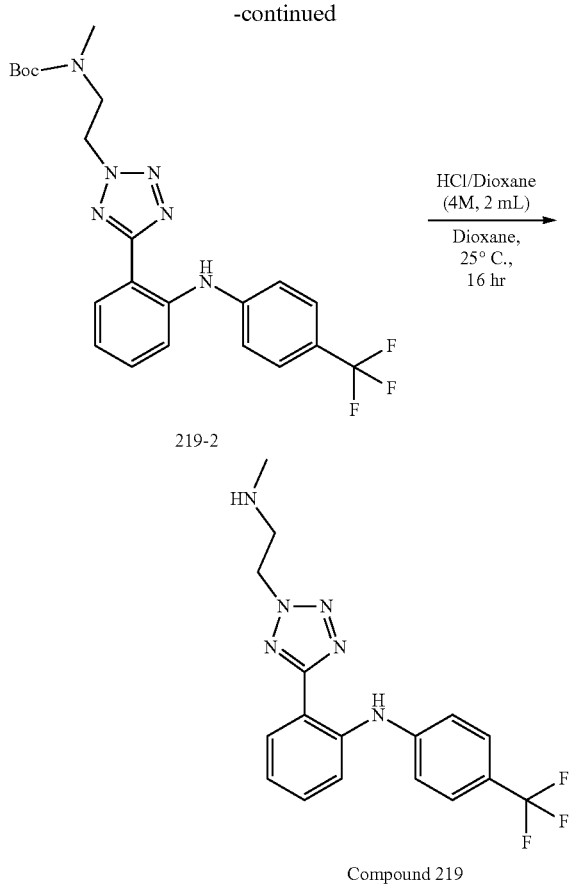

Compound 219

Step 1: tert-butyl methyl(2-(5-(2-((4-(trifluoromethyl)phenyl)amino)phenyl)-2H-tetrazol-2-yl)ethyl)carbamate To the solution of 219-1 (200 mg, 0.66 mmol, 1 eq) in THF (2 mL) were added PPh$_3$ (516 mg, 2.0 mmol, 3 eq) and 219-1a (172 mg, 0.98 mmol, 59 uL, 1.5 eq) at 0° C. Then DIAD (397 mg, 2.0 mmol, 0.4 mL, 3 eq) was added to the mixture. The reaction solution was warmed up to 30° C. and stirred for 16 hr. The reaction was monitored by LCMS. LCMS showed that the starting material was consumed and the desired MS was observed. The reaction was concentrated under reduced pressure. The residue was purified by prep-TLC (SiO$_2$) to give 219-2 (45 mg, 97 umol, 15% yield).

Step 2: 2-(2-(2-(methylamino)ethyl)-2H-tetrazol-5-yl)-N-(4-(trifluoromethyl)phenyl)aniline To the solution of 219-2 (40 mg, 86 umol, 1 eq) in dioxane (2 mL) was added HCl/dioxane (4 M, 2 mL, 92 eq). The mixture was stirred at 25° C. for 16 hr. The reaction was monitored by LCMS. LCMS showed that the starting material was consumed and the main peak was the desired MS. The reaction solution was concentrated under reduced pressure. The residue was purified by prep-HPLC to give Compound 219 (2.76 mg, 6.9 umol, 8.0% yield, HCl). LCMS (ESI): RT=0.693 min, mass calcd. for $C_{17}H_{17}F_3N_6$ 362.15, m/z found 342.9 [M−F−1]$^-$, $^1$H NMR (400 MHz, DMSO-d$_6$) δ 9.17 (br, 2H), 8.80 (s, 1H), 8.03 (d, J=6.8 Hz, 1H), 7.60-7.48 (m, 4H), 7.27 (d, J=8.5 Hz, 2H), 7.21 (t, J=7.2 Hz, 1H), 5.12 (t, J=5.6 Hz, 2H), 3.63-3.54 (m, 2H), 2.60 (t, J=5.0 Hz, 3H).

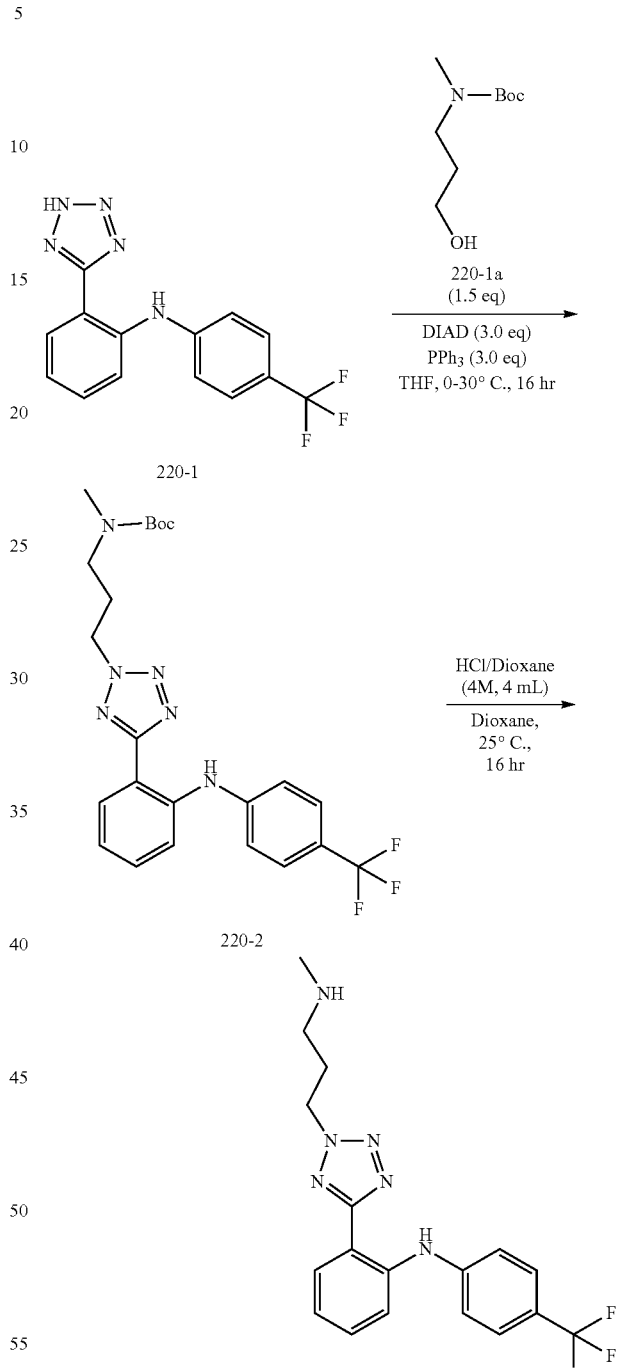

Compound 220

Step 1: tert-butyl methyl(3-(5-(2-((4-(trifluoromethyl)phenyl)amino)phenyl)-2H-tetrazol-2-yl)propyl)carbamate To the solution of 220-1 (200 mg, 0.66 mmol, 1 eq) in THF (2 mL) was added PPh$_3$ (516 mg, 2.0 mmol, 3 eq) and 220-1a (186 mg, 0.98 mmol, 1.5 eq) at 0° C. Then DIAD (397 mg, 2.0 mmol, 0.4 mL, 3 eq) was added to the mixture. The reaction solution was warmed up to 30° C. and stirred for 16 hr. The reaction was monitored by LCMS. LCMS showed that the starting material was consumed and the desired MS was observed. The reaction was concentrated under reduced pressure. The residue was purified by prep-TLC (SiO$_2$) to give 220-2 (241 mg, 0.48 mmol, 73% yield). $^1$H NMR (400 MHz, CDCl$_3$) δ 9.04 (s, 1H), 8.19 (d, J=6.5 Hz, 1H), 7.53 (dd, J=2.9, 8.7 Hz, 3H), 7.37 (t, J=8.5 Hz, 1H), 7.30 (d, J=8.5 Hz, 2H), 7.04 (t, J=7.5 Hz, 1H), 4.72 (t, J=7.2 Hz, 2H), 3.44-3.35 (m, 2H), 2.89 (s, 3H), 2.39-2.27 (m, 2H), 1.44 (br s, 9H).

Step 2: 2-(2-(3-(methylamino)propyl)-2H-tetrazol-5-yl)-N-(4-(trifluoromethyl)phenyl)aniline To the solution of 220-2 (50 mg, 0.1 mmol, 1 eq) in dioxane (2 mL) was added HCl/dioxane (4 M, 4 mL, 152 eq). The mixture was stirred at 25° C. for 16 hr. The reaction was monitored by LCMS. LCMS showed that the starting material was consumed and the main peak was the desired MS. The reaction solution was concentrated under reduced pressure. The residue was purified by prep-HPLC to give Compound 220 (6.49 mg, 16.9 umol, 16.1% yield). LCMS (ESI): RT=0.707 min, mass calcd. for C$_{18}$H$_{19}$F$_3$N$_6$ 376.16, m/z found 376.9[M+1]$^+$, $^1$HNMR (400 MHz, DMSO-d$_6$) δ 8.98 (br, 2H), 8.76 (s, 1H), 8.03 (dd, J=1.4, 7.9 Hz, 1H), 7.59-7.47 (m, 4H), 7.25-7.16 (m, 3H), 4.87 (t, J=6.9 Hz, 2H), 3.04-2.93 (m, 2H), 2.54-2.52 (m, 2H), 2.37-2.27 (m, 2H).

Example 207: 2-(2-(azetidin-3-yl)-2H-tetrazol-5-yl)-N-(4-(trifluoromethyl)phenyl)aniline (Compound 221)

To a solution of 221-1 (20.0 mg, 43.4 umol, 1.0 eq) in DCM (1.0 mL) was added TFA (770 mg, 6.7 mmol, 0.5 mL, 155.4 eq). The mixture was stirred at 25° C. for 0.5 h. LC-MS showed 221-1 was consumed completely and one main peak with desired MS was detected. The reaction mixture was concentrated under reduced pressure to give a residue. The residue was purified by prep-HPLC to give Compound 221 (5.52 mg, 15.3 umol, 35% yield). LCMS (ESI): RT=0.696 min, mass calc. for C$_{17}$H$_{15}$F$_3$N$_6$ 360.13 m/z found 340.9 [M−F]$^+$; $^1$H NMR (400 MHz, CDCl$_3$) δ 9.04 (s, 1H), 8.22 (d, J=7.5 Hz, 1H), 7.54 (d, J=8.0 Hz, 3H), 7.39 (t, J=7.5 Hz, 1H), 7.30 (d, J=8.0 Hz, 2H), 7.06 (t, J=7.4 Hz, 1H), 5.86-5.79 (m, J=7.2 Hz, 1H), 4.40 (t, J=7.7 Hz, 2H), 4.17 (t, J=8.2 Hz, 2H).

Example 208: 2-(1-methyl-4-(2-((4-(trifluoromethyl)phenyl)amino)phenyl)-1H-imidazol-2-yl)ethan-1-ol (Compound 222)

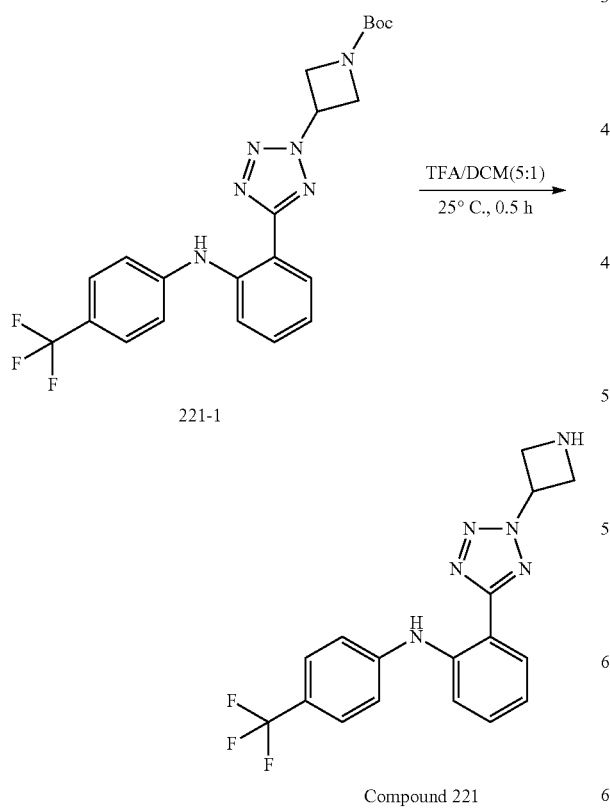

Compound 221

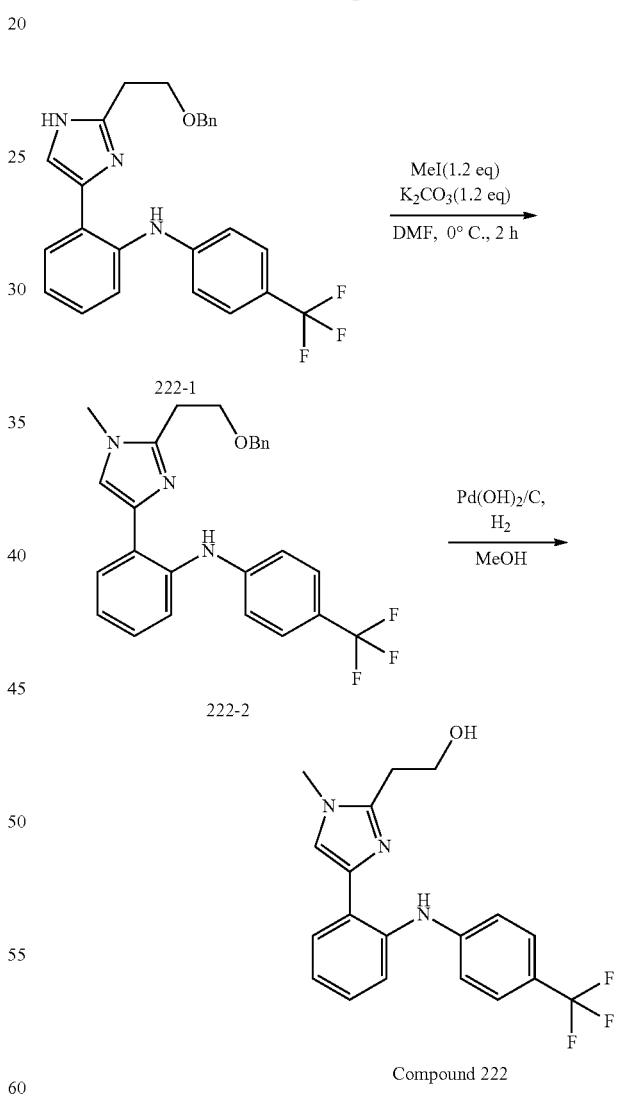

Compound 222

Step 1: 2-[2-(2-benzyloxyethyl)-1-methyl-imidazol-4-yl]-N-[4-(trifluoromethyl)phenyl]aniline To a solution of 222-1 (80 mg, 0.18 mmol, 1 eq) and K$_2$CO$_3$ (37.9 mg, 0.27 mmol, 1.5 eq) in DMF (3 mL) was added MeI (31.2 mg, 0.22 mmol, 14 uL, 1.2 eq) at 0° C. The mixture was stirred at 0° C. for 2 hr. TLC showed reactant was consumed completely and one main spot was formed. The reaction mixture was poured into water (10 mL), extracted with EtOAc (5 mL*3). The combined organic layer was washed with brine (5 mL), dried over $Na_2SO_4$ and filtered. The filtrate was concentrated to give 222-2 (85 mg, crude), which was used in the next step directly without further purification.

Step 2: 2-[1-methyl-5-[2-[4-(trifluoromethyl)anilino]phenyl]imidazol-2-yl]ethanol To a solution of 222-2 (85 mg, 0.19 mmol, 1 eq) in MeOH (2 mL) was added $Pd(OH)_2/C$ (20%, 20 mg) under $N_2$. The suspension was degassed under vacuum and purged with $H_2$ several times. The mixture was stirred under $H_2$ (15 psi) at 50° C. for 16 hours. To the mixture was added ammonium formate (237.4 mg, 3.77 mmol, 20 eq) and the mixture was stirred for 16 h at 70° C. The reaction mixture was filtered to remove $Pd(OH)_2/C$, and the filtrate was concentrated to give a residue. The residue was dissolved in MeOH (5 mL) and $Pd(OH)_2/C$ (10%, 20 mg) was added under $N_2$. The suspension was degassed under vacuum and purged with $H_2$ several times. The mixture was stirred under $H_2$ (15 psi) at 20-30° C. for 16 hours. The reaction mixture was stirred for another 6 h at 20-30° C. LC-MS showed ~30% of 222-2 was remained and ~60% of desired compound was detected. The reaction mixture was filtered and the residue was concentrated to give a residue. The residue was purified by prep-HPLC to give Compound 222 (6.15 mg, 17.0 umol, 9.0% yield), which was confirmed by H NMR and NOE. LCMS (ESI): RT=0.658 min, mass calc. for $C_{19}H_{18}F_3N_3O$ 361.14, m/z found 361.9 [M+H]$^+$; $^1$H NMR (400 MHz, DMSO-$d_6$) δ 10.49 (s, 1H), 7.66 (d, J=7.0 Hz, 1H), 7.54-7.46 (m, 3H), 7.39 (d, J=8.0 Hz, 1H), 7.20-7.12 (m, 3H), 6.99 (t, J=7.4 Hz, 1H), 4.84 (t, J=5.3 Hz, 1H), 3.80 (q, J=6.5 Hz, 2H), 3.62 (s, 3H), 2.86 (t, J=6.7 Hz, 2H).

Example 209: tert-butyl (2-(5-(2-((4-(trifluoromethyl)phenyl)amino)phenyl)-2H-tetrazol-2-yl)propyl)carbamate (Compound 223)

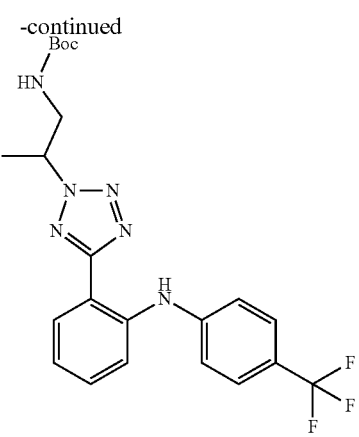

Compound 223

To the solution of 223-1a (250 mg, 1.4 mmol, 2.2 eq) in THF (2 mL) was added $PPh_3$ (516 mg, 2.0 mmol, 3 eq) and compound 223-1 (200 mg, 0.66 mmol, 1 eq) at 0° C. Then DIAD (397 mg, 2.0 mmol, 0.4 mL, 3 eq) was added to the mixture. The solution was warmed up to 30° C. and stirred for 16 hr. The reaction was monitored by LCMS. LCMS showed that the starting material was consumed and one main peak with desired MS. The reaction was concentrated under reduced pressure. The residue was purified by column chromatography ($SiO_2$) to give Compound 223 (180 mg, 0.35 mmol, 54% yield). LCMS (ESI): RT=0.922 min, mass calcd. for $C_{22}H_{25}F_3N_6O_2$ 462.20, m/z found 485.0 [M+Na]$^+$, $^1$H NMR (400 MHz, CDCl$_3$) δ 9.04 (s, 1H), 8.20 (d, J=6.5 Hz, 1H), 7.54 (d, J=8.5 Hz, 3H), 7.41-7.35 (m, 1H), 7.30 (d, J=8.5 Hz, 2H), 7.05 (t, J=7.5 Hz, 1H), 5.24-5.12 (m, 1H), 4.85-4.75 (m, 1H), 3.84-3.64 (m, 2H), 1.69 (d, J=6.8 Hz, 3H), 1.40-1.36 (m, 9H).

Example 210: tert-butyl methyl(2-(5-(2-((4-(trifluoromethyl)phenyl)amino)phenyl)-2H-tetrazol-2-yl)ethyl)carbamate (Compound 224)

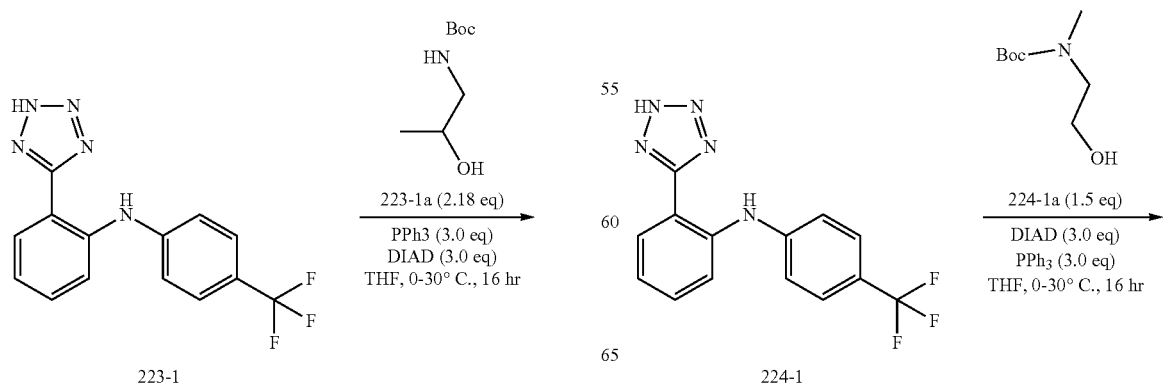

Compound 224

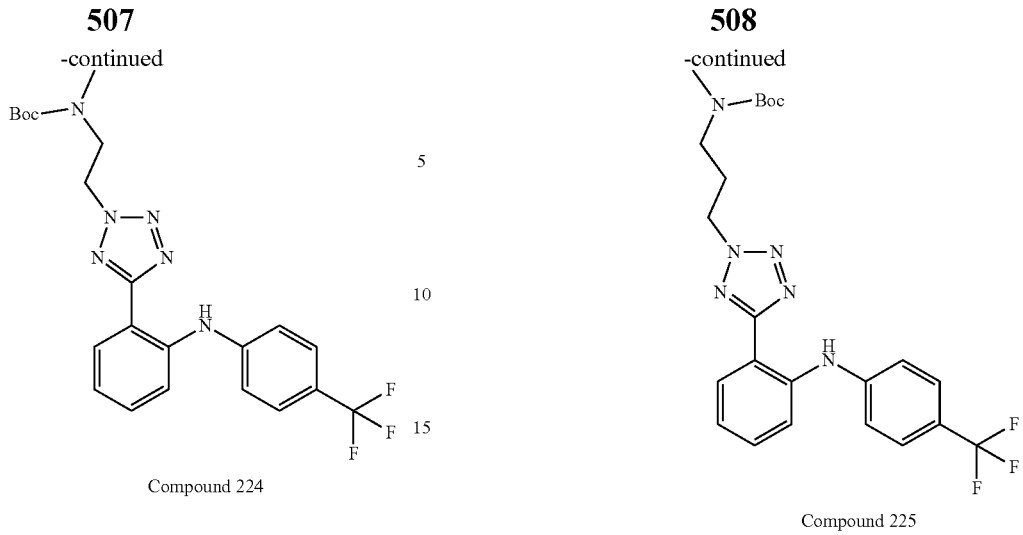

Compound 224

To the solution of 224-1 (200 mg, 0.66 mmol, 1 eq) in THF (2 mL) was added PPh$_3$ (516 mg, 2.0 mmol, 3 eq) and 224-1a (172 mg, 0.98 mmol, 59 uL, 1.5 eq) at 0° C. Then DIAD (397 mg, 2.0 mmol, 0.4 mL, 3 eq) was added to the mixture. The reaction solution was warmed up to 30° C. and stirred for 16 hr. The reaction was monitored by LCMS. LCMS showed that the starting material was consumed and the desired MS was observed. The reaction was concentrated under reduced pressure. The residue was purified by prep-TLC (SiO$_2$) to give compound the crude product. 20 mg of the crude product was re-purified by prep-HPLC to give Compound 224 (2.84 mg, 6.08 umol, 9.28e-1% yield). LCMS (ESI): RT=0.908 min, mass calcd. for C$_{22}$H$_{25}$F$_3$N$_6$O$_2$ 462.20, m/z found 485.1 [M+Na]$^+$, $^1$HNMR (400 MHz, CDCl$_3$) δ 8.96 (s, 1H), 8.20 (dd, J=1.5, 7.8 Hz, 1H), 7.56-7.50 (m, 3H), 7.40-7.34 (m, 1H), 7.30 (d, J=8.3 Hz, 2H), 7.07-7.00 (m, 1H), 4.92-4.79 (m, 2H), 3.91-3.81 (m, 2H), 2.93-2.67 (m, 3H), 1.39-1.30 (m, 9H).

Example 211: tert-butyl methyl(3-(5-(2-((4-(trifluoromethyl)phenyl)amino)phenyl)-2H-tetrazol-2-yl)propyl)carbamate (Compound 225)

Compound 225

Compound 225

To the solution of 225-1 (200 mg, 0.66 mmol, 1 eq) in THF (2 mL) was added PPh$_3$ (516 mg, 2.0 mmol, 3 eq) and 225-1a (186 mg, 0.98 mmol, 1.5 eq) at 0° C. Then DIAD (397 mg, 2.0 mmol, 0.4 mL, 3 eq) was added to the mixture. The reaction solution was warmed up to 30° C. and stirred for 16 hr. The reaction was monitored by LCMS. LCMS showed that the starting material was consumed and the desired MS was observed. The reaction was concentrated under reduced pressure. The residue was purified by prep-TLC (SiO$_2$) to give Compound 225 (241 mg, 0.48 mmol, 73% yield). LCMS (ESI): RT=0.944 min, mass calcd. for C$_{23}$H$_{27}$F$_3$N$_6$O$_2$ 476.21, m/z found 499.1[M+Na]$^+$, $^1$HNMR (400 MHz, CDCl$_3$) δ 9.04 (s, 1H), 8.19 (d, J=6.5 Hz, 1H), 7.53 (dd, J=2.9, 8.7 Hz, 3H), 7.37 (t, J=8.5 Hz, 1H), 7.30 (d, J=8.5 Hz, 2H), 7.04 (t, J=7.5 Hz, 1H), 4.72 (t, J=7.2 Hz, 2H), 3.44-3.35 (m, 2H), 2.89 (s, 3H), 2.39-2.27 (m, 2H), 1.44 (br s, 9H).

Example 212: tert-butyl 3-(5-(2-((4-(trifluoromethyl)phenyl)amino)phenyl)-2H-tetrazol-2-yl)pyrrolidine-1-carboxylate (Compound 226)

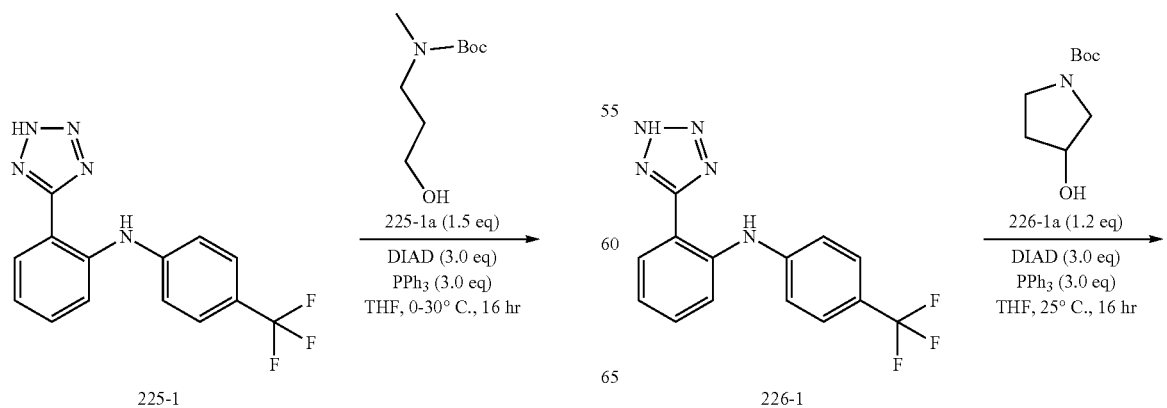

225-1

226-1

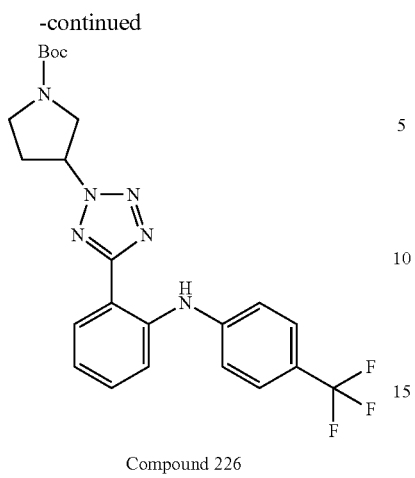

Compound 226

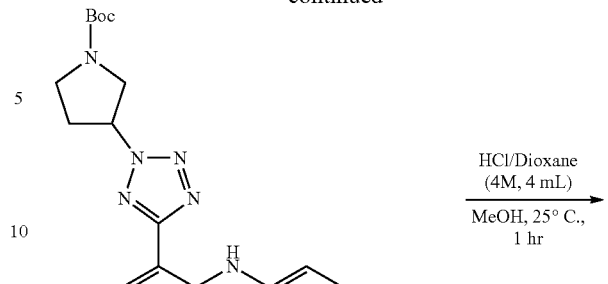

227-2

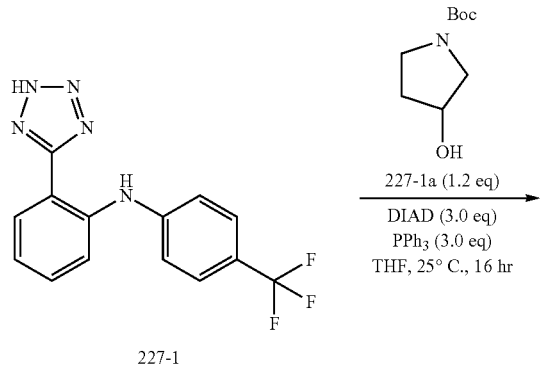

Compound 227

To a solution of 226-1 (100.0 mg, 0.3 mmol, 1.0 eq), 226-1a (73.6 mg, 0.4 mmol, 32 uL, 1.2 eq), PPh$_3$ (257.7 mg, 1.0 mmol, 3.0 eq) in THF (2.0 mL) was added dropwise DIAD (198.7 mg, 1.0 mmol, 0.2 mL, 3.0 eq) at 0° C. over 10 min. After addition, the mixture was stirred for 16 h at 25° C. LC-MS showed 19% of 1 was remained and 40% of desired compound was detected. The reaction mixture was concentrated under reduced pressure to give a residue which was purified by column chromatography (SiO$_2$) to give Compound 226 (70 mg, 0.1 mmol, 42% yield). 20 mg was repurified by prep-HPLC to give Compound 226 (2.93 mg). LCMS (ESI): RT=0.928 min, mass calc. for C$_{23}$H$_{25}$F$_3$N$_6$O$_2$ 474.20 m/z found 497.1 [M+Na]$^+$; $^1$H NMR (400 MHz, CDCl$_3$) δ 8.98 (s, 1H), 8.21 (d, J=7.0 Hz, 1H), 7.54 (d, J=8.5 Hz, 3H), 7.39 (t, J=7.7 Hz, 1H), 7.30 (d, J=8.3 Hz, 2H), 7.05 (t, J=7.4 Hz, 1H), 5.50 (s, 1H), 4.19-3.92 (m, 2H), 3.85-3.56 (m, 2H), 2.81-2.46 (m, 2H), 1.47 (s, 9H).

Example 213: 2-(2-(pyrrolidin-3-yl)-2H-tetrazol-5-yl)-N-(4-(trifluoromethyl)phenyl)aniline (Compound 227)

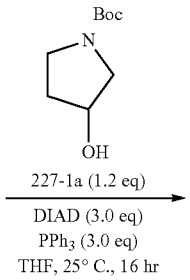

Step 1: tert-butyl 3-hydroxypyrrolidine-1-carboxylate

To a solution of 227-1b (0.7 g, 8.0 mmol, 0.6 uL, 1.0 eq) in DCM (10.0 mL) were added TEA (1.2 g, 12.0 mmol, 1.6 mL, 1.5 eq) and Boc$_2$O (2.1 g, 9.6 mmol, 2.2 mL, 1.2 eq). The mixture was stirred at 25° C. for 16 h. TLC (Petroleum ether:Ethyl acetate=3:1) indicated 227-1b was consumed completely and many new spots formed. The reaction mixture was concentrated under reduced pressure to give a residue which was purified by column chromatography (SiO$_2$) to give 227-1a (1.4 g, 7.5 mmol, 93% yield).

Step 2: tert-butyl 3-[5-[2-[4-(trifluoromethyl)anilino]phenyl]tetrazol-2-yl]azetidine-1-carboxylate To a solution of 227-1 (100.0 mg, 0.3 mmol, 1.0 eq), 227-1a (73.6 mg, 0.4 mmol, 31.7 uL, 1.2 eq), PPh$_3$ (257.7 mg, 1.0 mmol, 3.0 eq) in THF (2.0 mL) was added drop-wise DIAD (198.7 mg, 1.0 mmol, 0.2 mL, 3.0 eq) at 0° C. over 10 min. After addition, the mixture was stirred at this temperature for 16 h at 25° C. LC-MS showed 19% of 227-1 was remained and 40% of desired compound was detected. The reaction mixture concentrated under reduced pressure to give a residue. The residue was purified by column chromatography (SiO$_2$) to give 227-2 (70 mg, 0.1 mmol, 42% yield). 20 mg was re-purified by prep-HPLC to give 227-2 (2.93 mg). LCMS (ESI): RT=0.928 min, mass calc. for C$_{23}$H$_{25}$F$_3$N$_6$O$_2$ 474.20 m/z found 497.1 [M+Na]$^+$; $^1$H NMR (400 MHz, CDCl$_3$) δ 8.98 (s, 1H), 8.21 (d, J=7.0 Hz, 1H), 7.54 (d, J=8.5 Hz, 3H), 7.39 (t, J=7.7 Hz, 1H), 7.30 (d, J=8.3 Hz, 2H), 7.05 (t, J=7.4 Hz, 1H), 5.50 (s, 1H), 4.19-3.92 (m, 2H), 3.85-3.56 (m, 2H), 2.81-2.46 (m, 2H), 1.47 (s, 9H).

Step 3: 2-(2-pyrrolidin-3-yltetrazol-5-yl)-N-[4-(trifluoromethyl)phenyl]aniline

To a solution of 227-2 (35.0 mg, 73.7 umol, 1.0 eq) in dioxane (1.0 mL) was added HCl/dioxane (3.0 mL). The mixture was stirred at 25° C. for 1 hr. LC-MS showed 227-2 was consumed completely and one main peak with desired MS was detected. The reaction mixture was concentrated under reduced pressure to give a residue. The residue was purified by prep-HPLC to give Compound 227 (11.09 mg, 29.6 umol, 40% yield). LCMS (ESI): RT=0.692 min, mass calc. for C$_{18}$H$_{17}$N$_3$F$_3$N$_6$ 374.15 m/z found 374.9 [M+H]$^+$; $^1$H NMR (400 MHz, CDCl$_3$) δ 9.03 (s, 1H), 8.15 (d, J=7.8 Hz, 1H), 7.51 (d, J=8.3 Hz, 3H), 7.35 (t, J=7.8 Hz, 1H), 7.24 (d, J=3.5 Hz, 2H), 7.02 (t, J=7.4 Hz, 1H), 5.56-5.26 (m, 1H), 3.54-3.45 (m, 1H), 3.44-3.29 (m, 2H), 3.21-3.03 (m, 1H), 2.54-2.33 (m, 2H).

Example 214: 2-(2-(2-aminoethyl)-2H-tetrazol-5-yl)-N-(4-(trifluoromethyl)phenyl)aniline (Compound 228)

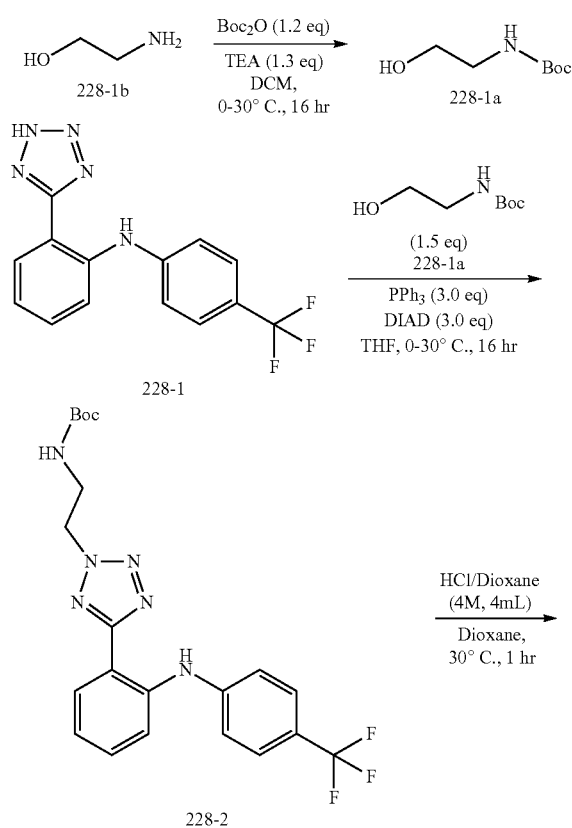

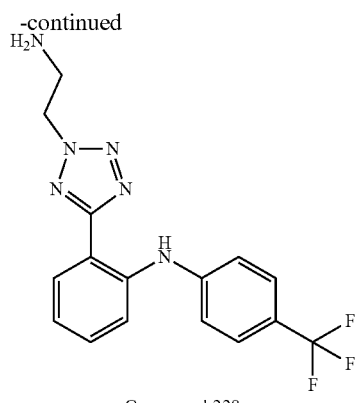

Compound 228

Step 1: tert-butyl (2-hydroxyethyl)carbamate

To the solution of 228-1b (0.5 g, 8.2 mmol, 0.5 mL, 1 eq) in DCM (10 mL) was added TEA (1.1 g, 10.7 mmol, 1.5 mL, 1.3 eq). Then Boc$_2$O (2.1 g, 9.8 mmol, 2.3 mL, 1.2 eq) was added to the mixture at 0° C. The solution was warmed up to 30° C. and stirred for 16 hr. The reaction was monitored by TLC. TLC (PE:EA=1:1) showed that the starting material was consumed and a new spot with smaller polarity was observed. The reaction solution was concentrated under reduced pressure. The residue was purified by column chromatography (SiO$_2$) to give 228-1a (900 mg, 5.6 mmol, 68% yield).

Step 2: tert-butyl (2-(5-(2-((4-(trifluoromethyl)phenyl)amino)phenyl)-2H-tetrazol-2-yl)ethyl)carbamate To the solution of 228-1a (79 mg, 0.50 mmol, 76 uL, 1.5 eq) in THF (2 mL) were added 228-1 (100 mg, 0.33 mmol, 1 eq) and PPh$_3$ (258 mg, 0.98 mmol, 3 eq) at 0° C. Then DIAD (199 mg, 0.98 mmol, 0.2 mL, 3 eq) was added to the mixture at 0° C. The solution was warmed up to 30° C. and stirred for 16 hr. The reaction was monitored by TLC. TLC (PE:EA=4:1) showed that the starting material was consumed and a new spot with smaller polarity was observed. The reaction solution was concentrated under reduced pressure. The residue was purified by column chromatography (SiO$_2$) to give 228-2 (60 mg, 0.13 mmol, 40.4% yield).

Step 3: 2-(2-(2-aminoethyl)-2H-tetrazol-5-yl)-N-(4-(trifluoromethyl)phenyl)aniline To the solution of 228-2 (40 mg, 89 umol, 1 eq) in dioxane (4 mL) was added HCl/dioxane (4 M, 4 mL, 179 eq). The mixture was stirred at 30° C. for 1 hr. The reaction was monitored by LCMS. LCMS showed that the starting material was consumed and the main peak was the desired MS. The reaction solution was concentrated under reduced pressure. The residue was purified by prep-HPLC to give Compound 228 (2.87 mg, 7.5 umol, 8.4% yield, HCl). LCMS (ESI): RT=0.682 min, mass calcd. for C$_{16}$H$_{15}$F$_3$N$_6$ 348.13, m/z found 328.9[M−F−1]$^-$, $^1$H NMR (400 MHz, DMSO-d$_6$) δ 8.80 (s, 1H), 8.40 (br, 3H), 8.03 (d, J=7.5 Hz, 1H), 7.61-7.47 (m, 4H), 7.32-7.17 (m, 3H), 5.05 (t, J=5.5 Hz, 2H), 3.54-3.46 (m, 2H).

Example 215: 2-(2-(2-aminopropyl)-2H-tetrazol-5-yl)-N-(4-(trifluoromethyl)phenyl)aniline (Compound 229)

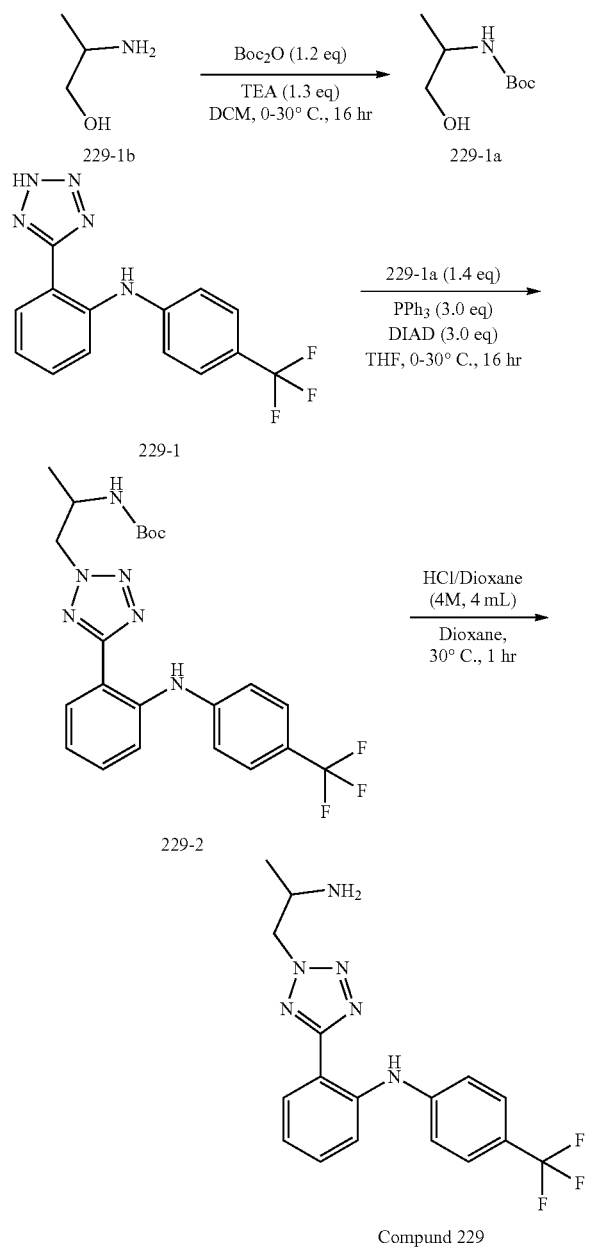

Compund 229

Step 1: tert-butyl (1-hydroxypropan-2-yl)carbamate

To the solution of 229-1b (100 mg, 1.3 mmol, 0.1 mL, 1 eq) in DCM (1 mL) was added TEA (175 mg, 1.7 mmol, 0.2 mL, 1.3 eq) and Boc$_2$O (349 mg, 1.6 mmol, 0.4 mL, 1.2 eq) at 0° C. The reaction solution was warmed up to 30° C. and stirred for 16 hr. The reaction was monitored by TLC. TLC (PE:EA=3:1) showed that the starting material was consumed and several new spots with smaller polarity was observed. The reaction solution was concentrated under reduced pressure. The residue was purified by column chromatography (SiO$_2$) to give 229-1a (163 mg, 0.93 mmol, 70% yield). $^1$H NMR (400 MHz, CDCl$_3$) δ 4.62 (br, 1H), 3.78 (s, 1H), 3.65 (d, J=8.8 Hz, 1H), 3.51 (dd, J=6.4, 10.9 Hz, 1H), 2.52 (br, 1H), 1.46 (s, 9H), 1.15 (d, J=6.8 Hz, 3H).

Step 2: tert-butyl (1-(5-(2-((4-(trifluoromethyl)phenyl)amino)phenyl)-2H-tetrazol-2-yl)propan-2-yl) carbamate To the solution of 229-1a (163 mg, 0.93 mmol, 1.4 eq) in THF (2 mL) were added 229-1 (200 mg, 0.66 mmol, 1 eq) and PPh$_3$ (516 mg, 2.0 mmol, 3 eq) at 0° C. Then DIAD (397 mg, 2.0 mmol, 0.4 mL, 3 eq) was added to the mixture at 0° C. The solution was warmed up to 30° C. and stirred for 16 hr. The reaction was monitored by TLC. TLC (PE:EA=4:1) showed that the starting material was consumed and a new spot with smaller polarity was observed. The reaction solution was concentrated under reduced pressure. The residue was purified by column chromatography (SiO$_2$) to give 229-2 (145 mg, 0.31 mmol, 47.9% yield).

Step 3: 2-(2-(2-aminopropyl)-2H-tetrazol-5-yl)-N-(4-(trifluoromethyl)phenyl)aniline To the solution of 229-2 (20 mg, 43 umol, 1 eq) in dioxane (2 mL) was added HCl/dioxane (4 M, 4 mL, 369.97 eq). The mixture was stirred at 30° C. for 1 hr. The reaction was monitored by LCMS. LCMS showed that the starting material was consumed and one main peak with desired MS. The reaction solution was concentrated under reduced pressure. The residue was purified by prep-HPLC to give Compound 229 (2.01 mg, 5 umol, 11.4% yield, HCl). LCMS (ESI): RT=0.698 min, mass calcd. for C$_{17}$H$_{17}$F$_3$N$_6$ 362.15, m/z found 342.9[M−F−1]$^-$, $^1$H NMR (400 MHz, DMSO-d$_6$) δ 8.80 (s, 1H), 8.47-8.29 (m, 3H), 8.03 (d, J=7.5 Hz, 1H), 7.60-7.48 (m, 5H), 7.30-7.17 (m, 4H), 4.98 (d, J=6.0 Hz, 2H), 3.91-3.80 (m 1H), 1.28 (d, J=6.8 Hz, 3H).

Example 216: 2-(1-(2-aminoethyl)-1H-1,2,4-triazol-3-yl)-N-(4-(trifluoromethyl)phenyl)aniline (Compound 230)

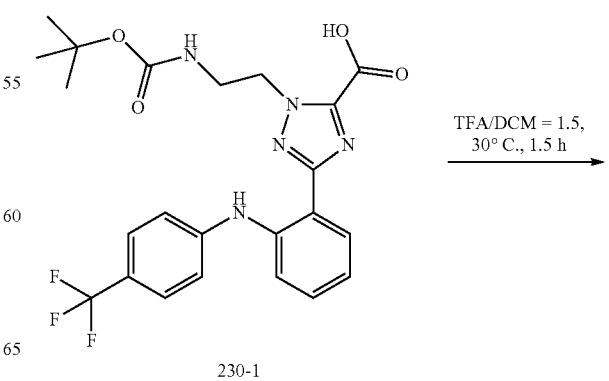

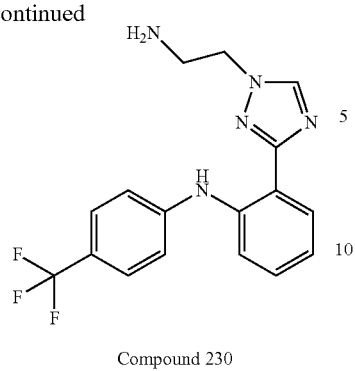

Compound 230

A solution of 230-1 (7 mg, 14.2 umol, 1 eq), TFA (812.03 mg, 7.12 mmol, 0.5 mL, 500 eq) in DCM (2.5 mL) was stirred at 30° C. for 1.5 h. LCMS showed no starting material was remained, no desired product was detected and one peak with mass 347.9 at 0.687 min was present. The solution was concentrated and then combined with another batch to give a residue. The residue was purified by prep-HPLC. The desired fractions were collected and most of organic solvent was removed under vacuum. The remained mixture was lyophilized to dryness to give Compound 230 (6.03 mg, 15.5 umol, 108.5% yield, HCl). LCMS (ESI): RT=1.661 min, mass calc. for $C_{17}H_{16}F_3N_5$ 347.14, m/z found 348.0 [M+1]$^+$. $^1$H NMR (400 MHz, MeOD) δ 8.83 (s, 1H), 8.13 (dd, J=1.3, 7.8 Hz, 1H), 7.55 (d, J=8.5 Hz, 3H), 7.45-7.38 (m, 1H), 7.32 (d, J=8.5 Hz, 2H), 7.08 (t, J=7.5 Hz, 1H), 4.70 (t, J=5.8 Hz, 2H), 3.58 (t, J=5.8 Hz, 2H).

Example 217: tert-butyl (3R,4R)-3-hydroxy-4-(5-(2-((4-(trifluoromethyl)phenyl)amino)phenyl)-2H-tetrazol-2-yl)pyrrolidine-1-carboxylate (Compound 231)

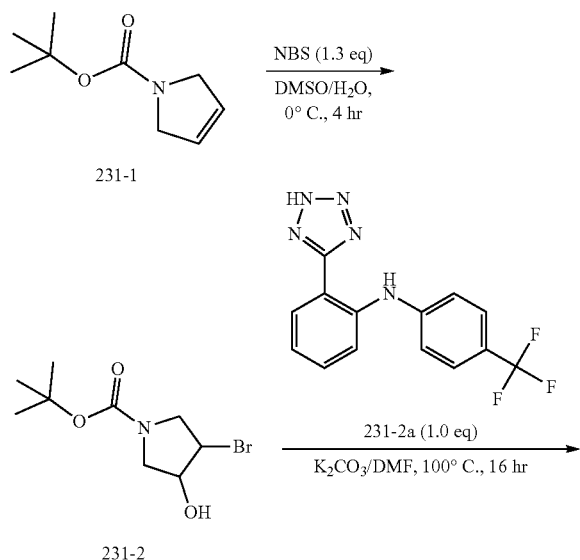

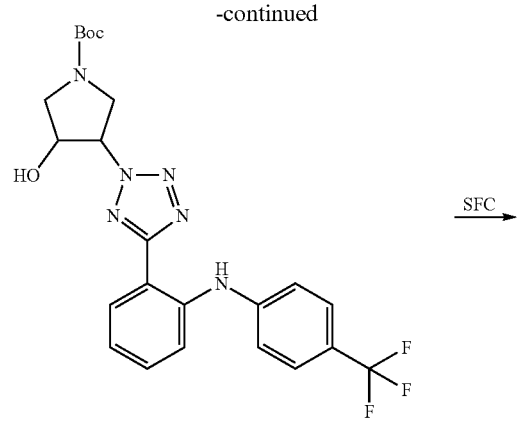

Compound 231

Step 1: tert-butyl 3-bromo-4-hydroxypyrrolidine-1-carboxylate

To a solution of 231-1 (2.0 g, 12 mmol, 1.0 eq) in DMSO (26 mL) and H$_2$O (1.6 mL) at 0° C. was added NBS (2.7 g, 15 mmol, 1.3 eq). The reaction mixture was warmed to 25° C. and stirred for 4 hr under N$_2$. TLC (PE/EA=3/1) showed a new spot was generated. H$_2$O (10 mL) was added to quench the reaction, the aqueous phase was extracted with ethyl acetate (20 mL*3). The combined organic phase was washed with brine (20 mL*2), dried with anhydrous Na$_2$SO$_4$, filtered and concentrated in vacuum. The residue was purified by silica gel chromatography to afford compound 231-2 (2.45 g, 78% yield). $^1$HNMR (400 MHz, CDCl$_3$) δ 4.34-4.19 (m, 1H), 4.07 (d, J=3.5 Hz, 1H), 3.89 (dd, J=4.8, 13.1 Hz, 1H), 3.71-3.54 (m, 2H), 3.25 (t, J=12.3 Hz, 1H), 1.33 (s, 9H).

Step 2: tert-butyl 3-hydroxy-4-(5-(2-((4-(trifluoromethyl)phenyl)amino)phenyl)-2H-tetrazol-2-yl)pyrrolidine-1-carboxylate To a solution of 231-2 (1.0 g, 3.8 mmol, 1.0 eq) and 231-2a (1.2 g, 3.8 mmol, 1.0 eq) in DMF (3 mL) was added K$_2$CO$_3$ (1.0 g, 7.5 mmol, 2.0 eq). The reaction mixture was stirred for 16 hr at 100° C. under N$_2$. TLC (PE/EA=3/1) showed a new spot was generated. H$_2$O (50 mL) was added to quench the reaction; the aqueous phase was extracted with ethyl acetate (100 mL*3). The combined organic phase was washed with brine (50 mL*2), dried with anhydrous Na₂SO₄, filtered and concentrated in vacuum. The residue was purified by silica gel chromatography to afford compound 231-3 (560 mg, 30% yield). ¹HNMR (400 MHz, CDCl₃) δ 8.90 (s, 1H), 8.16 (d, J=7.5 Hz, 1H), 7.95 (s, 2H), 7.50 (dd, J=4.1, 8.2 Hz, 4H), 7.39-7.31 (m, 1H), 7.28-7.24 (m, 2H), 7.01 (t, J=7.5 Hz, 1H), 5.36-5.24 (m, 1H), 4.83 (d, J=4.0 Hz, 1H), 4.18-4.09 (m, 1H), 4.08-3.81 (m, 2H), 3.62-3.47 (m, 1H), 1.44 (s, 9H).

Step 3: tert-butyl (3R,4R)-3-hydroxy-4-(5-(2-((4-(trifluoromethyl)phenyl)amino)phenyl)-2H-tetrazol-2-yl)pyrrolidine-1-carboxylate 231-3 (90 mg) was purified by SFC. The mixture was concentrated under reduced pressure. The residue was re-suspended in water (10 mL) and the resulting mixture was lyophilized to dryness to remove the solvent residue completely. Compound 231 (42 mg, 46% yield) was obtained. ¹H NMR (400 MHz, CDCl₃) δ 8.92 (s, 1H), 8.17 (dd, J=1.4, 7.9 Hz, 1H), 7.57-7.50 (m, 3H), 7.38 (t, J=7.2 Hz, 1H), 7.28 (d, J=8.5 Hz, 2H), 7.04 (t, J=7.5 Hz, 1H), 5.36-5.24 (m, 1H), 4.89 (s, 1H), 4.27-3.85 (m, 3H), 3.62-3.47 (m, 1H), 2.56 (s, 1H), 1.47 (s, 9H)

Example 218: tert-butyl (3S,4S)-3-hydroxy-4-(5-(2-((4-(trifluoromethyl)phenyl)amino)phenyl)-2H-tetrazol-2-yl)pyrrolidine-1-carboxylate (Compound 232)

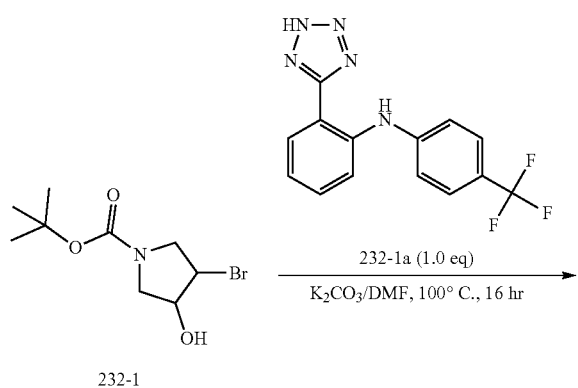

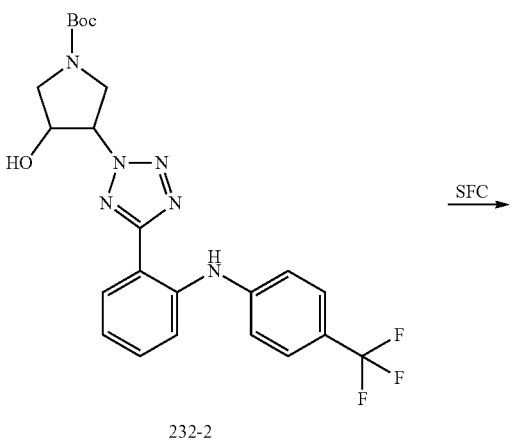

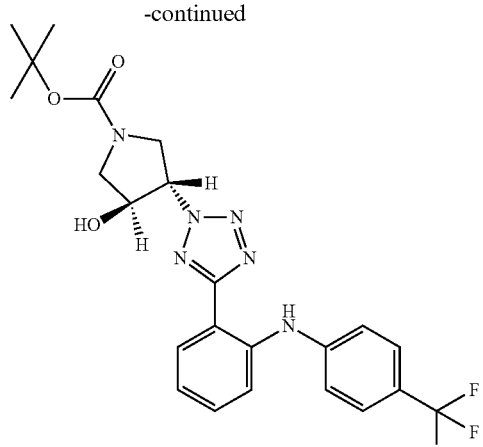

Compound 232

Step 1: tert-butyl-3-hydroxy-4-(5-(2-((4-(trifluoromethyl)phenyl)amino)phenyl)-2H-tetrazol-2-yl)pyrrolidine-1-carboxylate To a solution of 232-1 (1.0 g, 3.8 mmol, 1.0 eq) and 232-1a (1.2 g, 3.8 mmol, 1.0 eq) in DMF (3 mL) was added K₂CO₃ (1.0 g, 7.5 mmol, 2.0 eq). The reaction mixture was stirred for 16 hr at 100° C. under N₂. TLC (PE/EA=3/1) showed a new spot was generated. H₂O (50 mL) was added to quench the reaction; the aqueous phase was extracted with ethyl acetate (100 mL*3). The combined organic phase was washed with brine (50 mL*2), dried with anhydrous Na₂SO₄, filtered and concentrated in vacuum. The residue was purified by silica gel chromatography to afford 232-1 (560 mg, 30% yield). ¹HNMR (400 MHz, CDCl₃) δ 8.90 (s, 1H), 8.16 (d, J=7.5 Hz, 1H), 7.95 (s, 2H), 7.50 (dd, J=4.1, 8.2 Hz, 4H), 7.39-7.31 (m, 1H), 7.28-7.24 (m, 2H), 7.01 (t, J=7.5 Hz, 1H), 5.36-5.24 (m, 1H), 4.83 (d, J=4.0 Hz, 1H), 4.18-4.09 (m, 1H), 4.08-3.81 (m, 2H), 3.62-3.47 (m, 1H), 1.44 (s, 9H).

Step 2: tert-butyl (3S,4S)-3-hydroxy-4-(5-(2-((4-(trifluoromethyl)phenyl)amino)phenyl)-2H-tetrazol-2-yl)pyrrolidine-1-carboxylate 232-2 (90 mg) was purified by SFC. The mixture was concentrated under reduced pressure. The residue was re-suspended in water (10 mL) and the resulting mixture was lyophilized to dryness to remove the solvent residue completely. Compound 232 (40 mg, 44% yield) was obtained. 1H NMR (400 MHz, CDCl₃) δ 8.92 (s, 1H), 8.17 (dd, J=1.3, 7.8 Hz, 1H), 7.56-7.50 (m, 3H), 7.38 (t, J=7.3 Hz, 1H), 7.29 (d, J=8.5 Hz, 2H), 7.04 (t, J=7.5 Hz, 1H), 5.36-5.27 (m, 1H), 4.89 (s, 1H), 4.28-3.84 (m, 3H), 3.62-3.47 (m, 1H), 2.52 (d, J=3.0 Hz, 1H), 1.47 (s, 9H).

Example 219: (3R,4R)-4-(5-(2-((4-(trifluoromethyl)phenyl)amino)phenyl)-2H-tetrazol-2-yl)pyrrolidin-3-ol (Compound 233)

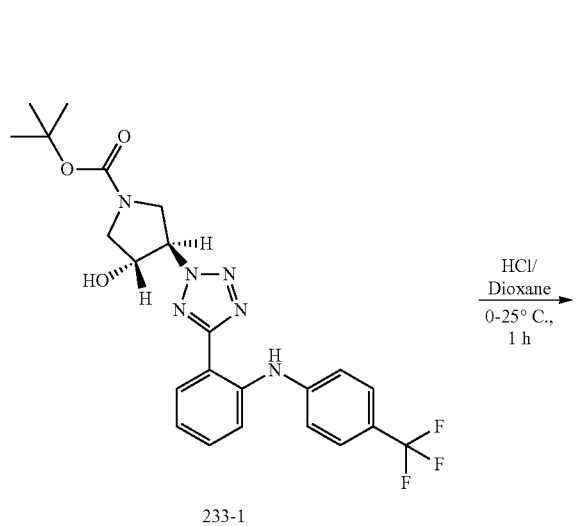

233-1

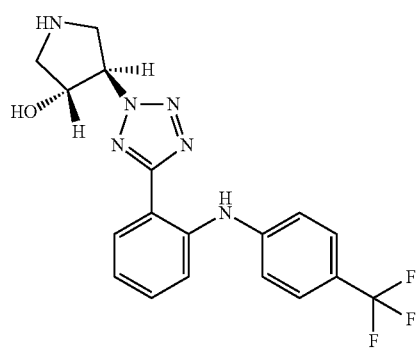

Compound 233

A mixture of HCl/dioxane (4 mL) was cooled to 0° C., and then 233-1 (36 mg, 73 umol, 1.0 eq) was added. The reaction mixture was allowed to warm up to 25° C. for 1 hour. LC-MS showed 233-1 was consumed completely and no desired MS was detected. The reaction mixture was concentrated under reduced pressure. The residue was purified by prep-HPLC to obtain Compound 233 (5.04 mg, 17.4% yield). $^1$H NMR (400 MHz, CDCl$_3$) δ 9.00 (s, 1H), 8.16 (d, J=6.8 Hz, 1H), 7.53 (dd, J=2.8, 8.5 Hz, 3H), 7.38 (t, J=7.2 Hz, 1H), 7.29 (s, 2H), 7.04 (t, J=7.4 Hz, 1H), 5.30-5.22 (m, 1H), 4.82-4.74 (m, 1H), 3.80-3.65 (m, 1H), 3.61-3.41 (m, 2H), 3.12-3.04 (m, 1H).

Example 220: (3S,4S)-4-(5-(2-((4-(trifluoromethyl)phenyl)amino)phenyl)-2H-tetrazol-2-yl)pyrrolidin-3-ol (Compound 234)

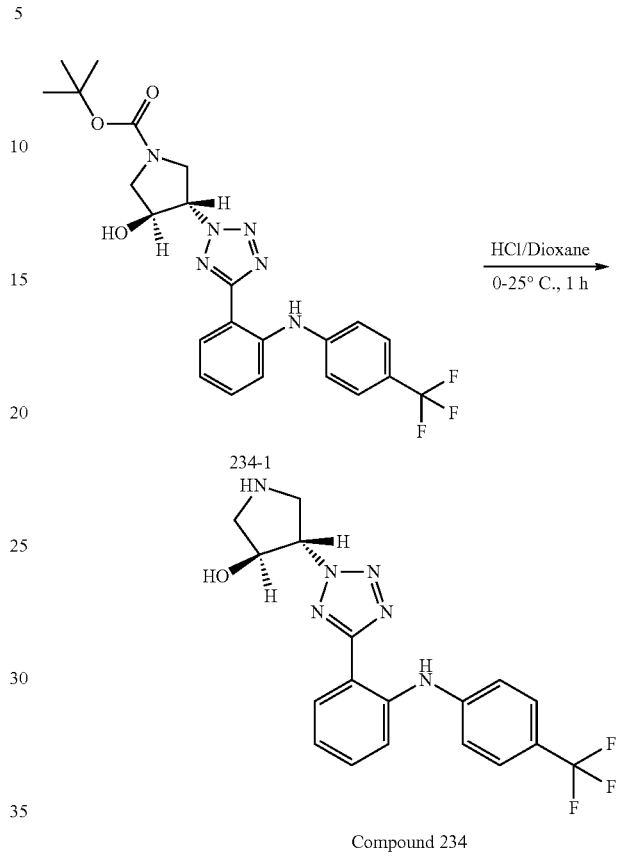

A mixture of HCl/dioxane (4 mL) was cooled to 0° C., and then 234-1 (34 mg, 69 umol, 1.0 eq) was added. The reaction mixture was allowed to warm up to 25° C. for 1 hour. LC-MS showed reactant 234-1 was consumed completely and no desired MS was detected. The reaction mixture was concentrated under reduced pressure. The residue was purified by prep-HPLC to obtain Compound 234 (5.26 mg, 19% yield). $^1$H NMR (400 MHz, CDCl$_3$) δ 8.99 (s, 1H), 8.15 (d, J=7.8 Hz, 1H), 7.53 (dd, J=3.4, 8.4 Hz, 3H), 7.38 (t, J=7.5 Hz, 1H), 7.29 (s, 2H), 7.04 (t, J=7.5 Hz, 1H), 5.38-5.15 (m, 1H), 4.90-4.65 (m, 1H), 4.22-2.53 (m, 4H).

Example 221: 2-(2-((3-(benzyloxy)thietan-3-yl)methyl)-2H-tetrazol-5-yl)-N-(4-(trifluoromethyl)phenyl)aniline (Compound 235)

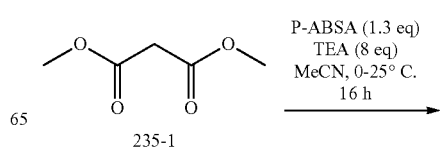

235-1

521
-continued
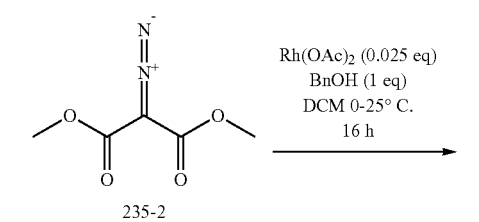
235-2
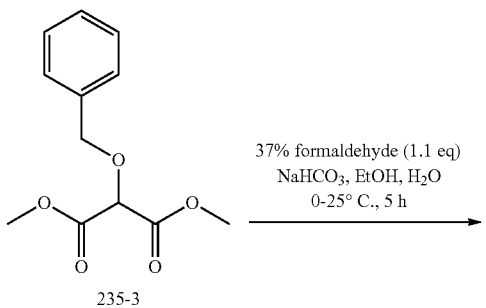
235-3
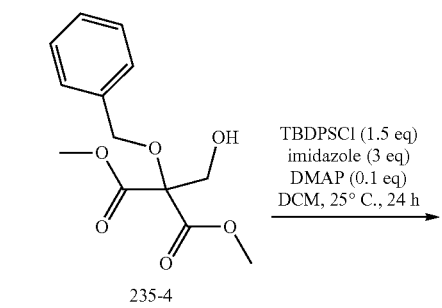
235-4
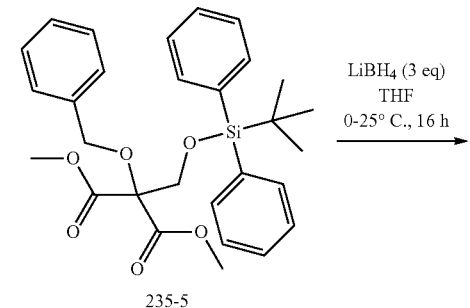
235-5
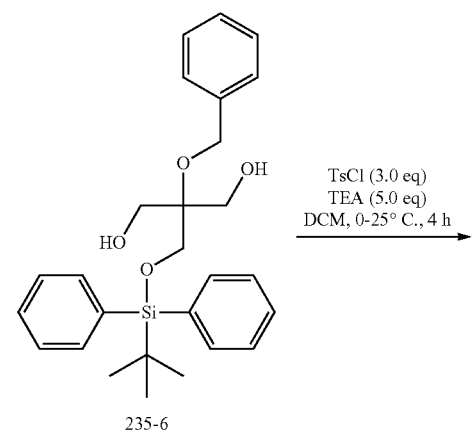
235-6
522
-continued
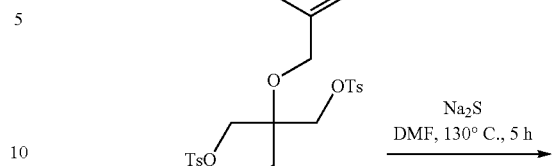
235-7
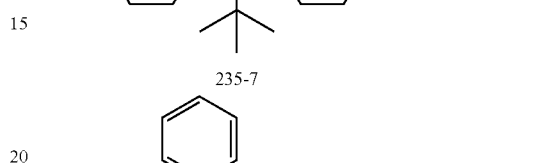
235-8
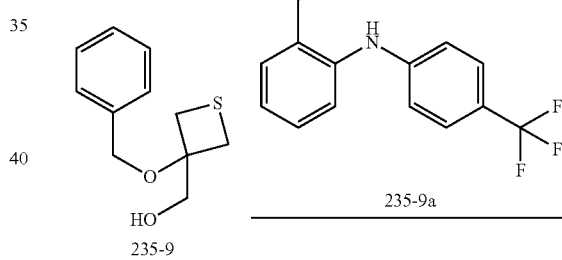
235-9
235-9a
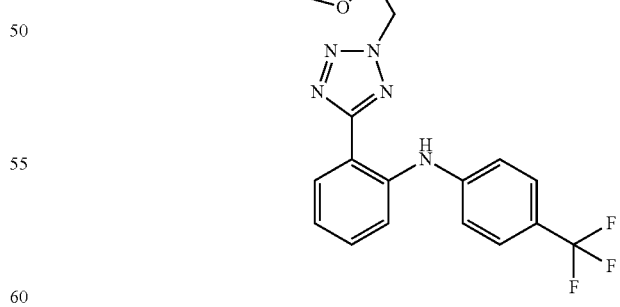
Compound 235
Step 1: dimethyl 2-diazopropanedioate
To a solution of 235-1 (5 g, 37.8 mmol, 4.3 mL, 1 eq) in MeCN (50 mL) was added P-ABSA (10.0 g, 41.6 mmol, 1.1 eq) at 0° C. under nitrogen. TEA (19.15 g, 189.2 mmol, 26.3 mL, 5 eq) was then added. The resulting solution was stirred at 25° C. for 16 hr. TLC (PE:EA=3:1 UV) indicated ~10% of reactant 235-1 was remained, and one major new spot with lower polarity was detected. The reaction mixture was filtered and the filtrate was evaporated carefully, but not to dryness. The reaction mixture was diluted with DCM (75 mL). This solution was washed sequentially with saturated NaHCO$_3$ (50 mL*2), and water (50 mL*2). The organic phase was dried over anhydrous Na$_2$SO$_4$, and gently evaporated, but not to complete dryness to give crude product of 235-2 (13.2 g, crude), which was used for next step without further purification. $^1$H NMR (400 MHz, CDCl$_3$) δ 3.85-3.78 (m, 6H).

Step 2: dimethyl 2-benzyloxypropanedioate

To a solution of 235-2 (12.1 g, 76.5 mmol, 1 eq) in DCM (80 mL) was added BnOH (8.28 g, 76.5 mmol, 7.9 mL, 1 eq) at 0° C. under nitrogen. diacetoxyrhodium (845.6 mg, 1.9 mmol, 0.025 eq) was then added. The resulting solution was stirred at 25° C. for 16 hr, over which time lots of precipitate was formed. TLC (PE:EA=3:1, stained by KMnO$_4$) indicated reactant 235-2 was consumed completely and one new spot formed. The residue was poured into ice water (20 mL) and stirred for 5 min. The aqueous phase was extracted with ethyl acetate (8 mL*3). The combined organic phase was washed with brine (20 mL), dried with anhydrous Na$_2$SO$_4$, filtered and concentrated in vacuum to give the crude product of 235-3 (17.55 g, crude). The crude product solution was used for next step without further purification. $^1$H NMR (400 MHz, CDCl$_3$) δ 7.40-7.34 (m, 5H), 5.29 (s, 1H), 4.70 (s, 2H), 4.58 (s, 1H), 3.79 (s, 6H).

Step 3: dimethyl 2-benzyloxy-2-(hydroxymethyl)propanedioate

To a solution of 235-3 (15.5 g, 65.0 mmol, 1 eq) and NaHCO$_3$ (546.5 mg, 6.5 mmol, 0.25 mL, 0.1 eq) in EtOH (100 mL) and H$_2$O (50 mL) was dropwise added HCHO (5.81 g, 71.5 mmol, 5.3 mL, 1.1 eq) at 0° C. The resulting mixture was stirred at 25° C. for 5 h. TLC (PE/EA=2/1) indicated reactant 235-3 was consumed completely and one main spot formed. LCMS showed reactant 235-3 was consumed completely and ~76% of desired compound was detected (m/z=290.9; RT: 0.62 min). The reaction mixture was concentrated under reduced pressure to remove EtOH. H$_2$O (150 mL) was added. The mixture was extracted with EA (60 mL*3). The combined organic phase was washed with saturated brine (30 mL), dried over Na$_2$SO$_4$, filtered and concentrated in vacuum. The residue was purified by flash silica gel chromatography to give 235-4 (10.5 g, 34.0 mmol, 52.3% yield). LCMS (ESI): RT=0.63 min, mass calc. for C$_{13}$H$_{16}$O$_6$ 268.09, m/z found 290.8 [M+Na].

Step 4: dimethyl 2-benzyloxy-2-[[tert-butyl(diphenyl)silyl]oxymethyl]propanedioate To a solution of 235-4 (6 g, 22.3 mmol, 1 eq), DMAP (273.2 mg, 2.2 mmol, 0.1 eq) and imidazole (4.57 g, 67.1 mmol, 3 eq) in DMF (30 mL) was portion-wise added TBDPSCl (9.22 g, 33.5 mmol, 8.62 mL, 1.5 eq) at 25° C. The resulting solution was stirred at 25° C. under nitrogen for 24 h. TLC (PE/EA=10/1, UV) indicated reactant 235-4 was consumed completely and one new spot formed. LCMS showed 72% of desired compound was found (m/z=529.9; RT: 0.99 min). The residue was poured into ice-water (150 mL) and stirred for 5 min. The aqueous phase was extracted with ethyl acetate (80 mL*3). The combined organic phase was washed with brine (150 mL), dried with anhydrous Na$_2$SO$_4$, filtered and concentrated under vacuum to give crude product of 235-5 (13.6 g, crude). The product was used for next step without further purification. LCMS (ESI): RT=0.99 min, mass calc. for C$_{29}$H$_{34}$O$_6$Si 506.21, m/z found 529.0 [M+Na].

Step 5: 2-benzyloxy-2-[[tert-butyl(diphenyl)silyl]oxymethyl]propane-1,3-diol

To a solution of 235-5 (13 g, 25.6 mmol, 1 eq) in THF (100 mL) was portion-wise added LiBH$_4$ (1.68 g, 76.9 mmol, 3 eq) at 0° C. under nitrogen (gas evolved). The reaction was allowed to warm to 25° C. and stirred at this temperature for 16 h. TLC (PE/EA=3/1) indicated reactant 235-5 was consumed completely and one new spot formed. The residue was poured into saturated NH$_4$Cl (150 mL) solution and stirred for 5 min. The aqueous phase was extracted with ethyl acetate (60 mL*3). The combined organic phase was washed with brine (150 mL), dried with anhydrous Na$_2$SO$_4$, filtered and concentrated in vacuum. The residue was purified by flash silica gel chromatography to give 235-6 (6.4 g, 13.07 mmol, 50.9% yield). LCMS (ESI): RT=0.88 min, mass calc. for C$_{27}$H$_{34}$O$_4$Si 450.22, m/z found 473.0 [M+Na]; $^1$H NMR (400 MHz, DMSO-d$_6$) δ 7.69-7.64 (m, 4H), 7.47-7.25 (m, 11H), 4.68 (s, 2H), 4.57 (t, J=5.3 Hz, 2H), 3.78 (s, 2H), 3.66 (d, J=5.3 Hz, 4H), 1.01 (s, 9H).

Step 6: [2-benzyloxy-2-[[tert-butyl(diphenyl)silyl]oxymethyl]-3-(p-tolylsulfonyloxy)propyl]4-methylbenzenesulfonate To a solution of 235-6 (7 g, 15.5 mmol, 1 eq) in DCM (70 mL) was added TEA (7.86 g, 77.6 mmol, 10.8 mL, 5 eq) at 0° C. under N$_2$. The mixture was stirred at this temperature for 0.5 hr, and then TosCl (8.88 g, 46.6 mmol, 3 eq) was added. The resulting mixture was stirred at 25° C. for 3.5 hr. TLC (PE/EA=3/1, UV) indicated reactant 235-6 was consumed completely and one new main spot formed. The residue was poured into ice-water (150 mL) and stirred for 5 min. The aqueous phase was extracted with ethyl acetate (60 mL*3). The combined organic phase was washed with brine (100 mL), dried with anhydrous Na$_2$SO$_4$, filtered and concentrated under vacuum. The residue was purified by flash silica gel chromatography to give 235-7 (9.5 g, 12.5 mmol, 80.5% yield).

Step 7: (3-benzyloxythietan-3-yl)methoxy-tert-butyl-diphenyl-silane

To a solution of 235-7 (5 g, 6.5 mmol, 1 eq) in DMF (40 mL) was added Na$_2$S (1.03 g, 13.8 mmol, 0.55 mL, 2 eq). The mixture was stirred at 70° C. for 4 hr. TLC (PE/EA=10/1, UV (254)) indicated reactant 235-7 was consumed completely and one main new spots formed. The residue was poured into ice-water (100 mL) and stirred for 5 min. The aqueous phase was extracted with ethyl acetate (50 mL*3). The combined organic phase was washed with H$_2$O (50 mL*2), brine (50 mL), dried with anhydrous Na$_2$SO$_4$, filtered and concentrated in vacuum. The residue was purified by flash silica gel chromatography to give 235-8 (950 mg, 2.12 mmol, 32.1% yield).

Step 8: (3-benzyloxythietan-3-yl)methanol

To a solution of 235-8 (1.5 g, 3.3 mmol, 1 eq) in THF (15 mL) was added TBAF (1 M, 4.0 mL, 1.2 eq). The mixture was stirred at 25° C. for 2 hr. TLC (PE/EA=5/1, stained by I$_2$) indicated reactant 235-8 was consumed completely and many new spots formed. The residue was poured into ice-water (30 mL) and stirred for 5 min. The aqueous phase was extracted with ethyl acetate (10 mL*3). The combined organic phase was washed with brine (20 mL), dried with anhydrous Na$_2$SO$_4$, filtered and concentrated in vacuum. The residue was purified by flash silica gel chromatography to give 235-9 (601 mg, 2.86 mmol, 85.4% yield).

Step 9: 2-[2-[(3-benzyloxythietan-3-yl)methyl]tetrazol-5-yl]-N-[4-(trifluoromethyl)phenyl]aniline To a solution of 2-(2H-tetrazol-5-yl)-N-[4-(trifluoromethyl)phenyl]aniline 235-9a (762.0 mg, 2.5 mmol, 1.5 eq) in THF (10 mL) were added 235-9 (350 mg, 1.66 mmol, 1 eq), PPh$_3$ (654.8 mg, 2.5 mmol, 1.5 eq) under N$_2$. The mixture was stirred at 25° C. for 0.5 hr. Then DIAD (673.0 mg, 3.3 mmol, 0.64 mL, 2 eq) was added at 0° C. The resulting mixture was stirred at 25° C. for 2 hr. TLC (PE/EA=5/1, UV) indicated reactant 235-9a was consumed completely and one new main spot formed. LCMS showed reactant 235-9a was consumed completely and ~92% of desired compound was detected (m/z=498.0; RT: 0.97 min). The residue was poured into ice-water (35 mL) and stirred for 5 min. The aqueous phase was extracted with EA (20 mL*3). The combined organic phase was washed with brine (30 mL), dried with anhydrous Na$_2$SO$_4$, filtered and concentrated in vacuum. The residue was purified by flash silica gel chromatography to afford Compound 235 (650 mg, 1.29 mmol, 77.7% yield). Part of it (30 mg) was purified by Pre-HPLC to afford the desired pure Compound 235 (8.5 mg). LCMS (ESI): RT=0.97 min, mass calc. for C$_{25}$H$_{22}$F$_3$N$_5$OS 497.15, m/z found 498.1 [M+H]$^+$; $^1$HNMR (400 MHz, DMSO-d$_6$) δ 8.89-8.63 (m, 1H), 8.07 (br d, J=7.8 Hz, 1H), 7.66-7.44 (m, 4H), 7.32-7.04 (m, 8H), 5.45 (s, 1H), 5.39 (s, 1H), 4.61 (s, 2H), 3.55 (d, J=9.8 Hz, 2H), 3.26 (d, J=9.8 Hz, 2H).

Example 222: 3-(benzyloxy)-34(5-(2-((4-(trifluoromethyl)phenyl)amino)phenyl)-2H-tetrazol-2-yl)methyl)thietane-1-oxide (Compound 236)

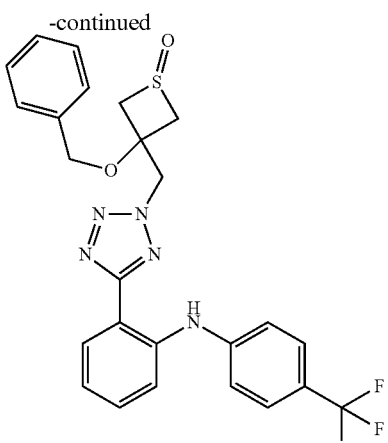

Compound 236

To a solution of 236-1 (300 mg, 0.60 mmol, 1 eq) in DCM (10 mL) was added m-CPBA (97.9 mg, 0.48 mmol, 85% purity, 0.8 eq). The mixture was stirred at 25° C. for 2 hr. TLC (PE/EA=3/1, UV) indicated reactant 236-1 was consumed completely and one new spot formed. LCMS showed reactant 236-1 was consumed completely and ~63% of desired compound was detected (m/z=536.0; RT: 0.86 min). The reaction mixture was diluted with DCM (30 mL). This solution was washed sequentially with saturated Na$_2$SO$_3$ solution (20 mL*2), saturated NaHCO$_3$ solution (20 mL*2), and brine (30 mL). The organic phase was dried over anhydrous Na$_2$SO$_4$, filtered and concentrated in vacuum. The residue was purified by flash silica gel chromatography to afford Compound 236 (265 mg, 0.47 mmol, 79.1% yield, HCl). Part of it (30 mg) was purified by Prep-HPLC to afford the desired Compound 236 (12.5 mg, HCl salt). LCMS (ESI): RT=0.868 min, mass calc. for C$_{25}$H$_{22}$F$_3$N$_5$O$_2$S 513.14, m/z found 536.1 [M+Na]; $^1$H NMR (400 MHz, DMSO-d$_6$) δ 8.72 (s, 1H), 8.09-8.04 (m, 1H), 7.56-7.47 (m, 4H), 7.27-7.12 (m, 8H), 5.44 (s, 1H), 5.32 (s, 1H), 5.13 (s, 1H), 4.68-4.60 (m, 2H), 4.23-4.15 (m, 1H), 3.93-3.85 (m, 1H), 3.57-3.36 (m, 2H).

Example 223: 3-(benzyloxy)-34(5-(2-((4-(trifluoromethyl)phenyl)amino)phenyl)-2H-tetrazol-2-yl)methyl)thietane-1,1-dioxide (Compound 237)

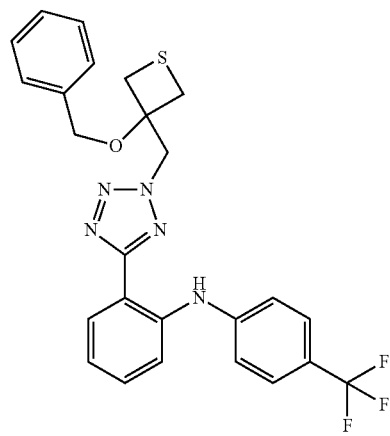

236-1 m-CPBA (0.8 eq)
DCM, 25° C., 2 h 237-1 m-CPBA (1.5 eq)
DCM, 25° C., 2 h

-continued

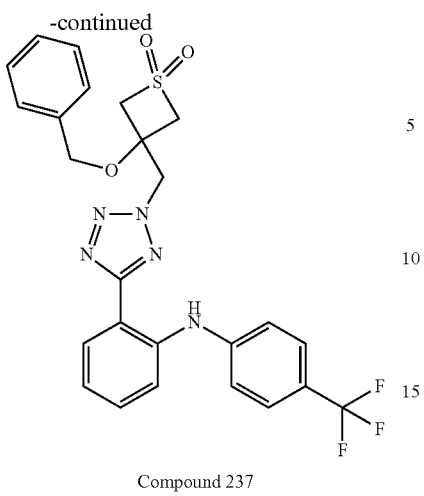

Compound 237

To a solution of 237-1 (100 mg, 0.2 mmol, 1 eq) in DCM (3 mL) was added m-CPBA (61.2 mg, 0.3 mmol, 85% purity, 1.5 eq). The mixture was stirred at 25° C. for 2 hr. TLC (PE/EA=5/1, UV) indicated reactant 237-1 was consumed completely and one new spot formed. LCMS showed reactant 237-1 was consumed completely and ~65% of desired compound was detected (m/z=530.0; RT: 0.89 min). The reaction mixture was diluted with DCM (30 mL). This solution was washed sequentially with saturated $Na_2SO_3$ (20 mL*2), saturated $NaHCO_3$ (20 mL*2) and brine (30 mL). The organic phase was dried over anhydrous $Na_2SO_4$, filtered and concentrated in vacuum. The residue was purified by prep-HPLC to afford Compound 237 (41.2 mg, 72.7 umol, 36.2% yield, HCl salt). LCMS (ESI): RT=0.889 min, mass calc. for $C_{25}H_{22}F_3N_5O_3S$ 529.14, m/z found 530.3 [M+H]$^+$; $^1$HNMR (400 MHz, DMSO-$d_6$) δ 8.66 (s, 1H), 8.07 (d, J=7.5 Hz, 1H), 7.56-7.48 (m, 4H), 7.26-7.18 (m, 6H), 7.14 (d, J=8.5 Hz, 2H), 5.51 (s, 2H), 4.68 (s, 2H), 4.59 (d, J=15.3 Hz, 2H), 4.36 (d, J=15.3 Hz, 2H).

Example 224: 2-(5-(5-chloro-2-((4-(trifluoromethyl)phenyl)amino)phenyl)-2H-tetrazol-2-yl)ethanol (Compound 238)

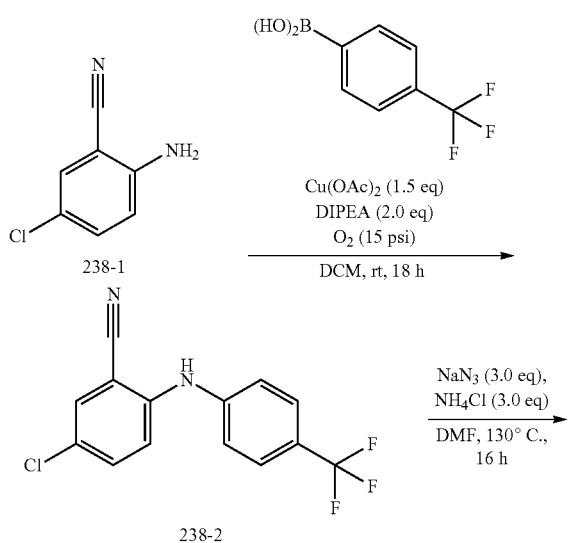

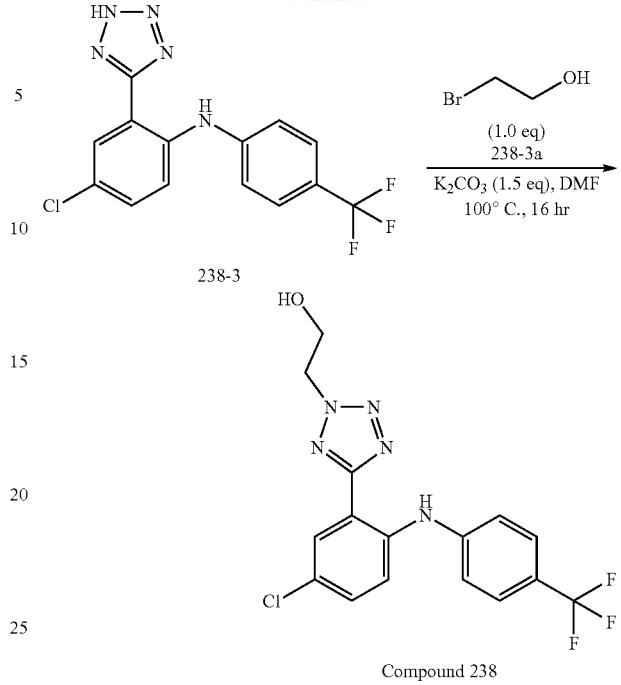

Compound 238

Step 1: 5-chloro-2-((4-(trifluoromethyl)phenyl)amino)benzonitrile

To a solution of compound 238-1 (2.0 g, 13 mmol, 1.0 eq) and [4-(trifluoromethyl)phenyl]boronic acid (3.73 g, 19.7 mmol, 1.5 eq) in DCM (20 mL) was added DIPEA (3.39 g, 26.2 mmol, 4.6 mL, 2.0 eq) and Cu(OAc)$_2$ (3.57 g, 19.6 mmol, 1.5 eq) under $N_2$. The suspension was degassed under vacuum and purged with $O_2$ for several times. The mixture was stirred under $O_2$ (15 psi) at 25° C. for 18 hours. TLC (Petroleum ether/Ethyl acetate=5:1, UV) showed that the starting material was remained and two new spots were formed. LCMS showed that the desired mass was detected. The reaction mixture was filtered and the filter was concentrated in vacuum. The residue was purified by column chromatography. Compound 238-2 (540 mg, 1.8 mmol, 13.9% yield) was obtained. $^1$H NMR (400 MHz, CDCl$_3$) δ 7.58 (d, J=8.52 Hz, 2H), 7.48-7.55 (m, 1H), 7.39 (dd, J=9.02, 2.26 Hz, 1H), 7.23-7.26 (m, 1H), 7.19 (d, J=8.28 Hz, 2H), 6.43 (br s, 1H).

Step 2: 4-chloro-2-(2H-tetrazol-5-yl)-N-(4-(trifluoromethyl)phenyl)aniline

To a solution of compound 238-2 (300 mg, 1.0 mmol, 1.0 eq) in DMF (3 mL) were added NaN$_3$ (197.2 mg, 3.0 mmol, 3.0 eq) and NH$_4$Cl (162.2 mg, 3.0 mmol, 0.1 mL, 3.0 eq). The reaction mixture was heated at 130° C. for 16 hr. LCMS indicated that 90% desired product was detected. The reaction mixture was poured into the aq HCl (1 M), then the aqueous phase was extracted with ethyl acetate (15 mL*4), the combined organic phase was washed with brine (5 mL), dried over Na$_2$SO$_4$, filtered and concentrated in vacuum. The crude product was used for the next step without further purification. Compound 238-3 (353 mg, crude) was obtained.

Step 3: 2-(5-(5-chloro-2-((4-(trifluoromethyl)phenyl)amino)phenyl)-2H-tetrazol-2-yl)ethanol To a solution of compound 238-3 (100 mg, 0.3 mmol, 1.0 eq) in DMF (2 mL) were added compound 238-3a (40.4 mg, 0.3 mmol, 23.0 uL, 1.1 eq) and K$_3$PO$_4$ (62.5 mg, 0.3 mmol, 1.5 eq). The mixture was stirred at 100° C. for 16 hr. LCMS indicated that the starting material was consumed completely and 75% of desired product was detected. The reaction mixture was diluted with ethyl acetate (20 mL). Then the mixture was washed with water (5 mL) and brine (5 mL). The organic phase was dried over Na$_2$SO$_4$, filtered and concentrated in vacuum. The residue was purified by prep-HPLC. Compound 238 (52 mg, 0.14 mmol, 45.6% yield) was obtained. LCMS (ESI): RT=0.830 min, mass calcd. For C$_{16}$H$_{13}$ClF$_3$N$_5$O, 383.08 m/z found 383.9 [M+H]$^+$; $^1$H NMR (400 MHz, CDCl$_3$) δ 9.05 (s, 1H), 8.17 (d, J=2.52 Hz, 1H), 7.56 (d, J=8.28 Hz, 2H), 7.46 (d, J=9.02 Hz, 1H), 7.32 (dd, J=8.92, 2.38 Hz, 1H), 7.29 (s, 2H), 4.83-4.94 (m, 2H), 4.24-4.35 (m, 2H), 2.20 (t, J=6.16 Hz, 1H).

Example 225: 2-(5-(4-chloro-2-((4-(trifluoromethyl)phenyl)amino)phenyl)-2H-tetrazol-2-yl)ethanol (Compound 239)

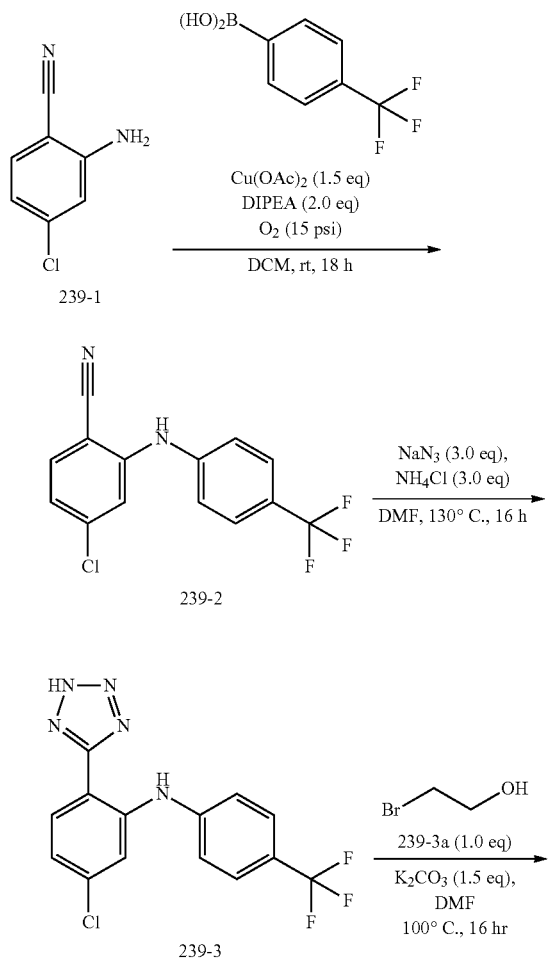

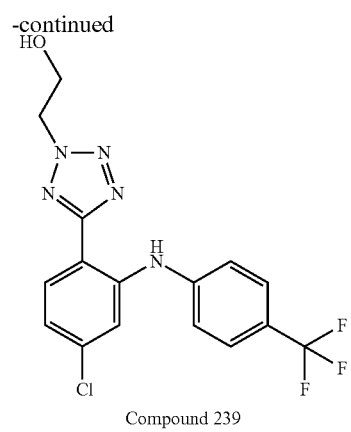

Compound 239

Step 1: 4-chloro-2-((4-(trifluoromethyl)phenyl)amino)benzonitrile

To a solution of compound 239-1 (1.3 g, 8.5 mmol, 1.0 eq) and [4-(trifluoromethyl)phenyl]boronic acid (2.43 g, 12.8 mmol, 1.5 eq) in DCM (20 mL) was added DIPEA (2.20 g, 17 mmol, 3 mL, 2.0 eq) and Cu(OAc)$_2$ (2.32 g, 12.78 mmol, 1.5 eq) under N$_2$. The suspension was degassed under vacuum and purged with O$_2$ several times. The mixture was stirred under O$_2$ (15 psi) at 25° C. for 18 hours. TLC (Petroleum ether/Ethyl acetate=5/1, UV) indicated that the staring material was remained and two new spots were formed. LCMS showed that 16% of desired mass was detected. The reaction mixture was filtered and the filter was concentrated in vacuum. The residue was purified by column chromatography (SiO$_2$). Compound 239-2 (330 mg, 1.11 mmol, 13% yield) was obtained. $^1$HNMR (400 MHz, CDCl$_3$) δ 7.64 (d, J=8.52 Hz, 2H), 7.49 (d, J=8.52 Hz, 1H), 7.26-7.29 (m, 3H), 6.94 (dd, J=8.42, 1.88 Hz, 1H), 6.55 (s, 1H).

Step 2: 5-chloro-2-(2H-tetrazol-5-yl)-N-(4-(trifluoromethyl)phenyl)aniline

To a solution of compound 239-2 (200 mg, 0.67 mmol, 1.0 eq) in DMF (3 mL) were added NaN$_3$ (131.5 mg, 2.0 mmol, 3.0 eq) and NH$_4$Cl (108.2 mg, 2.0 mmol, 70.7 uL, 3.0 eq). The reaction mixture was heated at 130° C. for 16 hr. LCMS showed that 82% of desired product was detected. The reaction mixture was poured into the aq. HCl (1 M), then the aqueous phase was extracted with ethyl acetate (15 mL*4), the combined organic phase was washed with brine (5 mL), dried over Na$_2$SO$_4$, filtered and concentrated in vacuum. The crude product was used for the next step without further purification. The compound 239-3 (297 mg, crude) was obtained.

Step 3: 2-(5-(4-chloro-2-((4-(trifluoromethyl)phenyl)amino)phenyl)-2H-tetrazol-2-yl)ethanol To a solution of compound 239-3 (100 mg, 0.3 mmol, 1 eq) in DMF (2 mL) were added compound 239-3a (40.5 mg, 0.33 mmol, 23 uL, 1.1 eq) and K$_3$PO$_4$ (125 mg, 0.59 mmol, 2.0 eq). The mixture was stirred at 100° C. for 16 hr. LCMS showed that 68% of desired product was detected. The reaction mixture was diluted with ethyl acetate (20 mL), washed with water (5 mL) and brine (5 mL). Then the organic phase was dried over Na$_2$SO$_4$, filtered and concentrated in vacuum. The crude product was purified by prep-HPLC. Compound 239 (41 mg, 0.1 mmol, 36% yield) was obtained. LCMS (ESI): RT=0.828 min, mass calcd. For $C_{16}H_{13}ClF_3N_5O$, 383.08 m/z found 383.9 [M+H]$^+$; $^1$H NMR (400 MHz, CDCl$_3$) δ 9.18 (s, 1H), 8.12 (d, J=8.52 Hz, 1H), 7.60 (d, J=8.52 Hz, 2H), 7.46 (d, J=1.76 Hz, 1H), 7.34 (d, J=8.52 Hz, 2H), 6.99 (dd, J=8.52, 2.00 Hz, 1H), 4.84-4.89 (m, 2H), 4.25-4.31 (m, 2H), 2.23 (t, J=6.28 Hz, 1H).

Example 226: 2-[5-[5-methoxy-2-[4-(trifluoromethyl)anilino]phenyl]tetrazol-2-yl]ethanol (Compound 240)

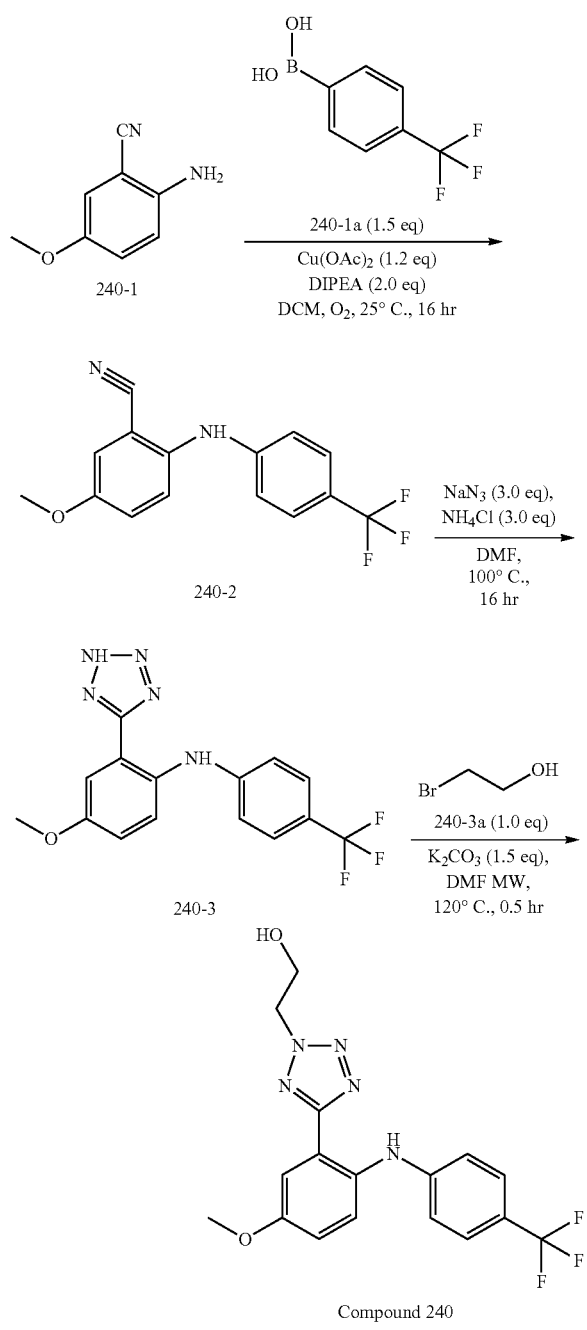

Compound 240

Step 1: 5-methoxy-2-[4-(trifluoromethyl)anilino]benzonitrile

To a solution of compound 240-1 (500 mg, 3.3 mmol, 1.0 eq), compound 240-1a (961 mg, 5.0 mmol, 1.5 eq), Cu(OAc)$_2$ (736 mg, 4.0 mmol, 1.2 eq) in DCM (10 mL) was added DIPEA (872 mg, 6.7 mmol, 2.0 eq). The reaction mixture was stirred at 25° C. for 16 hours under O$_2$. LC-MS showed one main peak with desired MS was detected. TLC (Petroleum ether:Ethyl acetate=5:1) indicated reactant 240-1 was remained, and one major new spot with lower polarity was detected. The reaction mixture was concentrated under reduce pressure. The residue was purified by flash silica gel chromatography to obtain compound 240-2 (650 mg, 66% yield). $^1$HNMR (400 MHz, CDCl$_3$) δ 7.59-7.49 (m, 3H), 7.37 (d, J=9.03 Hz, 1H), 7.15-7.11 (m, 1H), 7.06 (d, J=8.53 Hz, 2H), 6.93 (d, J=8.53 Hz, 1H), 3.85 (s, 3H).

Step 2: 4-methoxy-2-(2H-tetrazol-5-yl)-N-[4-(trifluoromethyl)phenyl]aniline

To a solution of compound 240-2 (300 mg, 1.0 mmol, 1.0 eq) and NH$_4$Cl (165 mg, 3.0 mmol, 3.0 eq) in DMF (5 mL) was added NaN$_3$ (230 mg, 3.5 mmol, 3.4 eq). The reaction mixture was stirred at 100° C. for 16 hours. LC-MS showed reactant 240-2 was consumed completely and one main peak with desired m/z was detected. The reaction mixture was cooled to room temperature. The suspension was added to HCl (15 mL, 1 M), and then filtered to obtain compound 240-3 (260 mg, crude).

Step 3: 2-[5-[5-methoxy-2-[4-(trifluoromethyl)anilino]phenyl]tetrazol-2-yl]ethanol To a solution of compound 240-3 (50 mg, 0.15 mmol, 1.0 eq), compound 240-3a (19 mg, 0.15 mmol, 1.0 eq) and K$_2$CO$_3$ (31 mg, 0.22 mmol, 1.5 eq) were taken up into a microwave tube in DMF (1.5 mL). The sealed tube was heated at 120° C. for 30 min under microwave. LC-MS showed reactant 240-3 was consumed completely and one main peak with desired m/z was detected. The reaction mixture was concentrated under reduce pressure. The residue was purified by prep-HPLC to obtain Compound 240 (18.06 mg, 32% yield). LCMS (ESI): RT=0.785 min, mass calcd. for $C_{17}H_{16}F_3N_5O_2$ 379.13, m/z found 379.9 [M+H]$^+$, $^1$HNMR (400 MHz, CDCl$_3$) δ 8.47 (s, 1H), 7.69 (d, J=3.01 Hz, 1H), 7.47 (dd, J=8.66, 2.38 Hz, 3H), 7.14 (d, J=8.28 Hz, 2H), 7.02 (dd, J=9.03, 3.01 Hz, 1H), 4.88-4.81 (m, 2H), 4.25 (t, J=4.64 Hz, 2H), 3.89 (s, 3H), 2.23 (s, 1H).

Example 227: 2-[5-[4-methoxy-2-[4-(trifluoromethyl)anilino]phenyl]tetrazol-2-yl]ethanol (Compound 241)

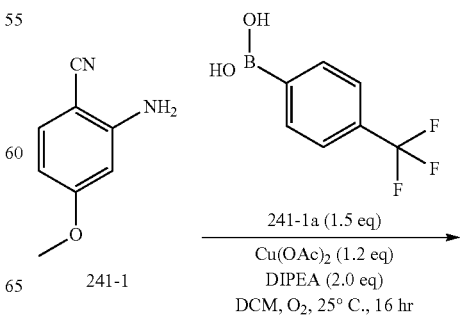

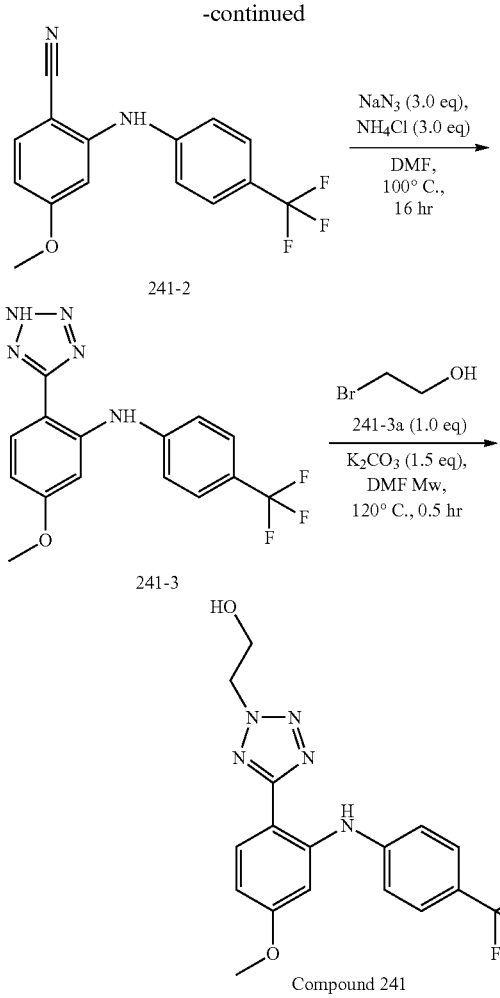

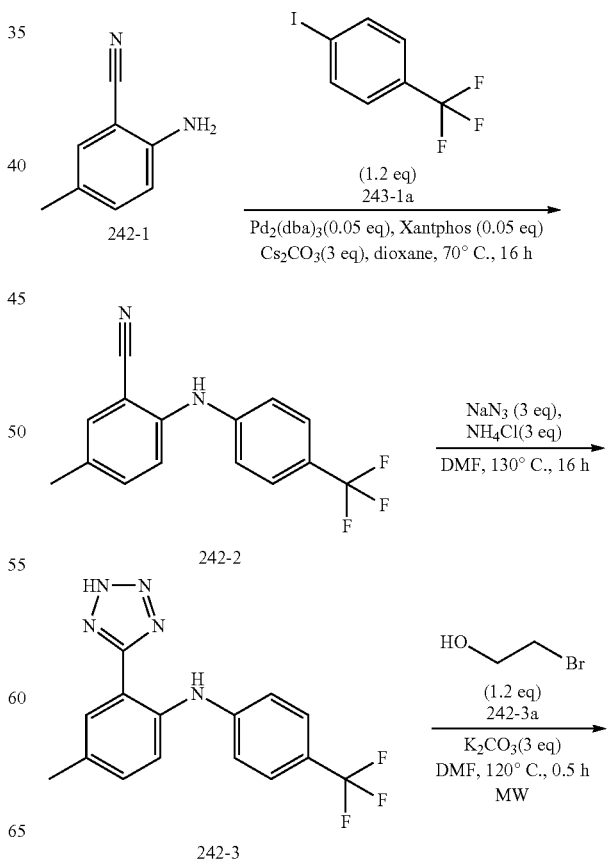

Step 1: 4-methoxy-2-[4-(trifluoromethyl)anilino]benzonitrile

To a solution of compound 241-1 (500 mg, 3.37 mmol, 1 eq), compound 241-1a (961 mg, 5.06 mmol, 1.5 eq), Cu(OAc)$_2$ (736 mg, 4.05 mmol, 1.2 eq) in DCM (10 mL) was added DIPEA (872 mg, 6.75 mmol, 2.0 eq). The reaction mixture was stirred at 25° C. for 16 hours under O$_2$. LC-MS showed one main peak with desired MS was detected. TLC (Petroleum ether:Ethyl acetate=5:1) indicated reactant 241-1 was remained, and one major new spot with lower polarity was detected. The reaction mixture was concentrated under reduced pressure. The residue was purified by flash silica gel chromatography to give compound 241-2 (600 mg, crude). $^1$H NMR (400 MHz, CDCl$_3$) δ ppm, 7.59 (d, J=8.53 Hz, 2H), 7.49 (dd, J=8.66, 2.38 Hz, 4H), 7.24 (s, 2H), 6.91 (d, J=8.28 Hz, 3H), 6.82 (m, 2H), 6.52 (dd, J=8.66, 2.38 Hz, 1H), 6.45 (s, 1H), 3.80 (s, 3H).

Step 2: 5-methoxy-2-(2H-tetrazol-5-yl)-N-[4-(trifluoromethyl)phenyl]aniline

To a solution of compound 241-2 (300 mg, 1.03 mmol, 1 eq) and NH$_4$Cl (165 mg, 3.08 mmol, 3.0 eq) in DMF (5 mL) was added NaN$_3$ (230 mg, 3.54 mmol, 3.45 eq). The reaction mixture was stirred at 100° C. for 16 hours. LC-MS showed reactant 241-2 was consumed completely and one main peak with desired m/z was detected. The reaction mixture was cooled to room temperature. The suspension was added to HCl (15 mL, 1 M), and then filtered to obtain compound 241-3 (300 mg, crude).

Step 3: 2-[5-[4-methoxy-2-[4-(trifluoromethyl)anilino]phenyl]tetrazol-2-yl]ethanol A solution of compound 241-3 (100 mg, 0.29 mmol, 1.0 eq), compound 241-3a (37.3 mg, 0.29 mmol, 1.0 eq) and K$_2$CO$_3$ (62 mg, 0.45 mmol, 1.5 eq) were taken up into a microwave tube in DMF (1.5 mL). The sealed tube was heated at 120° C. for 30 min under microwave. LC-MS showed reactant 241-3 was consumed completely and one main peak with desired m/z was detected. The reaction mixture was concentrated under reduced pressure. The residue was purified by prep-HPLC to give Compound 241 (3.87 mg, 3.4% yield). LCMS (ESI): RT=0.797 min, mass calcd. for C$_{17}$H$_{16}$F$_3$N$_5$O$_2$ 379.13, m/z found 380.2 [M+H]$^+$; $^1$HNMR (400 MHz, CDCl$_3$) δ 9.10 (s, 1H), 8.10 (d, J=8.78 Hz, 1H), 7.55 (d, J=8.28 Hz, 2H), 7.33 (d, J=8.28 Hz, 2H), 7.01 (d, J=2.51 Hz, 1H), 6.60 (dd, J=8.78, 2.26 Hz, 1H), 4.83 (m, 2H), 4.32-4.18 (d, J=4.52 Hz, 2H), 3.82 (s, 3H), 2.35 (s, 1H).

Example 228: 2-(5-(5-methyl-2-((4-(trifluoromethyl)phenyl)amino)phenyl)-2H-tetrazol-2-yl)ethanol (Compound 242)

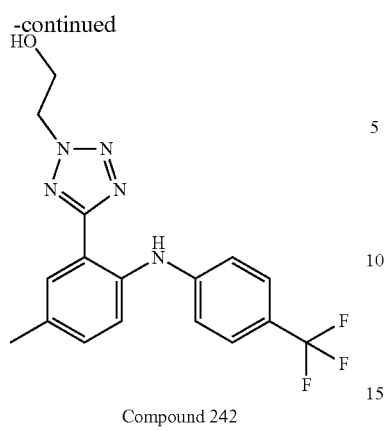

Compound 242

Step 1: 5-methyl-2-((4-(trifluoromethyl)phenyl)amino)benzonitrile

A mixture of compound 242-1 (0.1 g, 0.76 mmol, 1 eq), 1-iodo-4-(trifluoromethyl)benzene 242-1a (247.0 mg, 0.91 mmol, 0.13 mL, 1.2 eq), $Cs_2CO_3$ (739.6 mg, 2.27 mmol, 3 eq), $Pd_2(dba)_3$ (34.6 mg, 37.8 umol, 0.05 eq) and Xantphos (43.7 mg, 75.6 umol, 0.1 eq) in dioxane (3 mL) was bubbled with nitrogen for 1 min, sealed and heated at 70° C. for 16 hours. LCMS showed the reaction was complete and no peak with desired mass was detected. TLC (PE:EA=5:1 UV) showed one main new spot. The reaction was filtered via a pad of celite and concentrated to give a residue. The residue was purified by column chromatography ($SiO_2$) to give compound 242-1 (0.85 g, crude). $^1H$ NMR (400 MHz, $CDCl_3$) δ 7.63 (dd, J=2.8, 6.8 Hz, 1H), 7.55 (d, J=8.5 Hz, 2H), 7.42 (dd, J=1.8, 4.8 Hz, 1H), 7.38 (s, 1H), 7.29 (d, J=1.0 Hz, 2H), 7.18-7.13 (m, 2H), 6.36 (s, 1H), 2.32 (s, 3H).

Step 2: 4-methyl-2-(2H-tetrazol-5-yl)-N-(4-(trifluoromethyl)phenyl)aniline

To a mixture of compound 242-2 (0.9 g, 3.26 mmol, 1 eq) and $NH_4Cl$ (522.8 mg, 9.77 mmol, 0.34 mL, 3 eq) in DMF (15 mL) was added $NaN_3$ (635.4 mg, 9.77 mmol, 3 eq). The reaction was heated at 130° C. for 16 hr. TLC (PE:EA=5:1 UV) showed the reaction was complete. The mixture was added into a stirred 1 M HCl (20 mL), along with lots of solid was formed. Then the mixture was filtered. The filter cake was washed with water (5 mL) and 10 mL of a mix solution of PE:EA=10:1 in turns, dried under vacuum to give compound 242-3 (0.35 g, 1.10 mmol, 33.7% yield), which was used directly without further purification. $^1HNMR$ (400 MHz, $CDCl_3$) δ 7.81 (s, 1H), 7.51 (br d, J=8.0 Hz, 2H), 7.46 (d, J=8.5 Hz, 1H), 7.28-7.18 (m, 3H), 2.35 (s, 3H).

Step 3: 2-(5-(5-methyl-2-((4-(trifluoromethyl)phenyl)amino)phenyl)-2H-tetrazol-2-yl)ethanol To a mixture of compound 242-3 (0.05 g, 0.16 mmol, 1 eq) and $K_2CO_3$ (64.9 mg, 0.47 mmol, 3 eq) in DMF (2 mL) was added 2-bromoethanol 242-3a (21.5 mg, 0.17 mmol, 12.2 uL, 1.1 eq). The reaction was heated at 120° C. for 0.5 hr under microwave. TLC (PE:EA=1:1 UV) showed one new spot was formed and some starting material was remained. LCMS showed 58% of desired product was formed and 30% of starting material was remained. The mixture was filtered. The filtrate was purified by prep-HPLC to give Compound 242 (15.15 mg, 41.62 umol, 26.6% yield). LCMS (ESI): RT=0.821 min, mass calc. for $C_{17}H_{16}F_3N_5O$ 363.13, m/z found 363.9 $[M+1]^+$; $^1H$ NMR (400 MHz, $CDCl_3$) δ 8.80 (br s, 1H), 7.99 (s, 1H), 7.54-7.40 (m, 3H), 7.25-7.17 (m, 3H), 4.84 (br t, J=4.9 Hz, 2H), 4.26 (br s, 2H), 2.39 (s, 3H).

Example 229: 2-(5-(4-methyl-2-((4-(trifluoromethyl)phenyl)amino)phenyl)-2H-tetrazol-2-yl)ethanol (Compound 243)

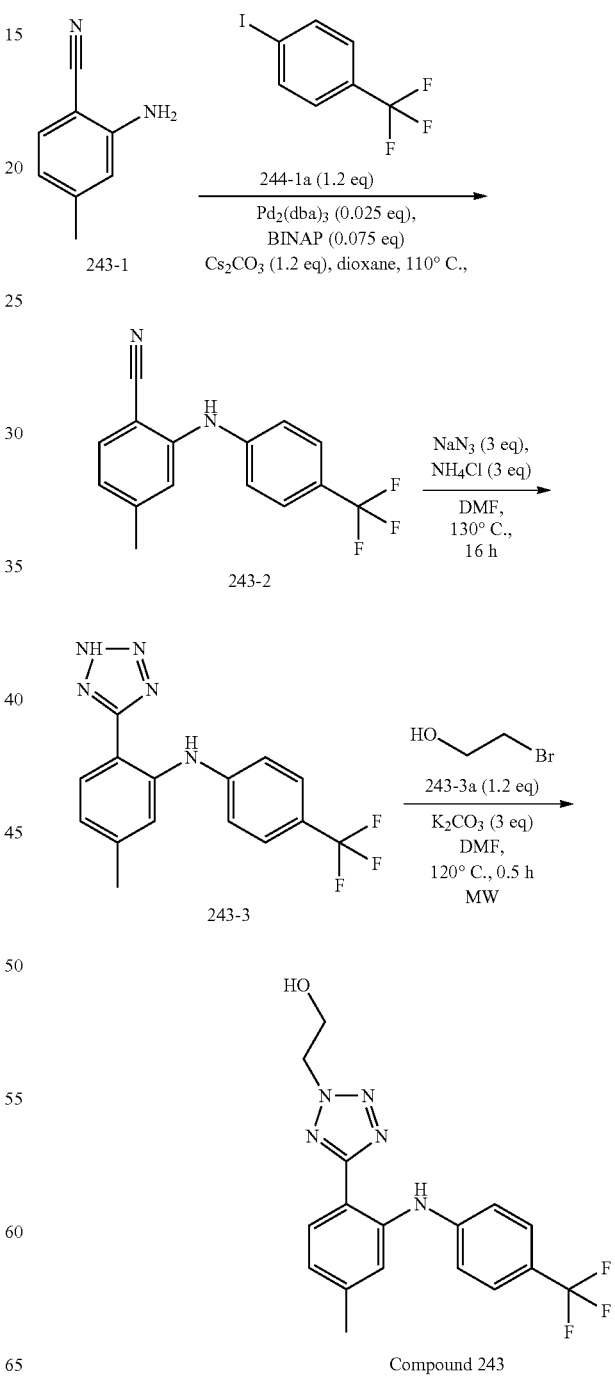

Compound 243

Step 1: 4-methyl-2-((4-(trifluoromethyl)phenyl)amino)benzonitrile

A mixture of 2-amino-4-methyl-benzonitrile 243-1 (1 g, 7.57 mmol, 1 eq), 243-1a (2.06 g, 7.57 mmol, 1.1 mL, 1 eq), $Cs_2CO_3$ (2.96 g, 9.08 mmol, 1.2 eq), $Pd_2(dba)_3$ (173.2 mg, 0.19 mmol, 0.025 eq), and BINAP (353.4 mg, 0.57 mmol, 0.075 eq) in dioxane (30 mL) was degassed and refilled with nitrogen for 3 times and heated at 110° C. for 16 hours under $N_2$. TLC (PE:EA=5:1 UV) showed one main new spot was formed and some of starting material was remained. The mixture was filtered via a pad of celite and concentrated to give a residue. The residue was purified by column chromatography ($SiO_2$) to give compound 243-2 (1.1 g, 3.98 mmol, 52.6% yield). $^1$H NMR (400 MHz, $CDCl_3$) δ 7.59 (d, J=8.5 Hz, 2H), 7.46 (d, J=8.0 Hz, 1H), 7.22 (d, J=8.5 Hz, 2H), 7.17 (s, 1H), 6.81 (d, J=7.5 Hz, 1H), 6.41 (br s, 1H), 2.40-2.30 (m, 3H).

Step 2: 5-methyl-2-(2H-tetrazol-5-yl)-N-(4-(trifluoromethyl)phenyl)aniline

To a mixture of compound 243-2 (1.1 g, 3.98 mmol, 1 eq) and $NH_4Cl$ (638.9 mg, 11.95 mmol, 0.41 mL, 3 eq) in DMF (15 mL) was added $NaN_3$ (776.6 mg, 11.95 mmol, 3 eq). The reaction was heated at 130° C. for 16 hr. TLC (PE:EA=5:1 UV) showed the reaction was complete. The mixture was added into a stirred 1 M HCl (20 mL), along with lots of solid was formed. Then the mixture was filtered. The filter cake was washed with water (15 mL) and 10 mL of a mix solution of PE:EA=10:1, dried under vacuum to give compound 243-3 (1.2 g, 3.76 mmol, 94.3% yield), which was used directly without further purification. $^1$HNMR (400 MHz, $CDCl_3$) δ 9.34 (br s, 1H), 7.76 (br d, J=8.0 Hz, 1H), 7.56 (d, J=8.5 Hz, 2H), 7.40-7.28 (m, 3H), 6.84 (d, J=8.0 Hz, 1H), 2.36 (s, 3H).

Step 3: 2-(5-(4-methyl-2-((4-(trifluoromethyl)phenyl)amino)phenyl)-2H-tetrazol-2-yl)ethanol A mixture of compound 243-3 (0.2 g, 0.63 mmol, 1 eq), 243-3a (78.2 mg, 0.63 mmol, 44.4 uL, 1 eq), $K_2CO_3$ (259.7 mg, 1.88 mmol, 3 eq) in DMF (3 mL) was stirred at 120° C. under microwave for 0.5 hour. TLC (PE:EA=1:2 UV) showed some of starting material was remained and one mainly new spot formed. LCMS showed one main peak with desired mass. The mixture was filtered. The filtrate was purified by prep-HPLC. The desired fractions were collected and most of organic solvent was removed under vacuum. The remained mixture was lyophilized to dryness to give Compound 243 (61.27 mg, 0.17 mmol, 26.9% yield). LCMS (ESI): RT=0.820 min, mass calc. for $C_{17}H_{16}F_3N_5O$ 363.13, m/z found 364.0 [M+1]$^+$; $^1$H NMR (400 MHz, DMSO-$d_6$) δ 8.79 (s, 1H), 7.95 (d, J=8.0 Hz, 1H), 7.57 (d, J=8.5 Hz, 2H), 7.37 (s, 1H), 7.25 (d, J=8.5 Hz, 2H), 7.00 (d, J=8.0 Hz, 1H), 5.08 (t, J=5.5 Hz, 1H), 4.76 (t, J=5.3 Hz, 2H), 3.94 (q, J=5.5 Hz, 2H), 2.35 (s, 3H).

Example 230: 3-[[5-[2-[4-(trifluoromethyl)anilino]phenyl]tetrazol-2-yl]methyl]thietan-3-ol (Compound 244)

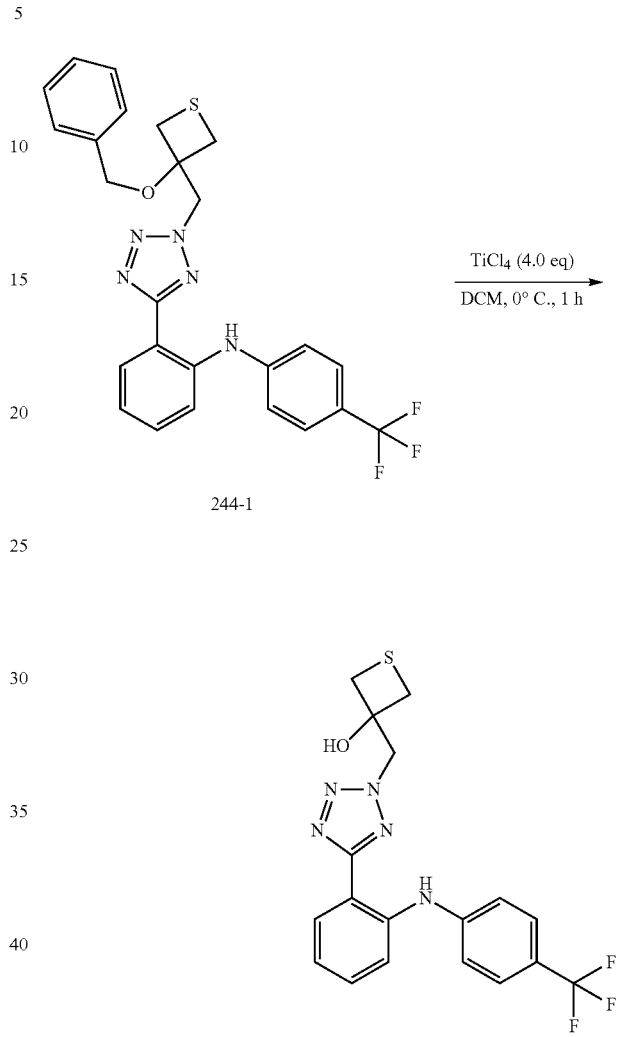

To a solution of compound 244-1 (50 mg, 0.1 mmol, 1 eq) in DCM (1 mL), a solution of $TiCl_4$ (76.2 mg, 0.40 mmol, 4 eq) in DCM (1 mL) was added at 0° C. under $N_2$. The mixture was stirred at 0° C. for 1 hr. LCMS showed reactant 244-1 was consumed completely and ~55% of desired compound was detected (m/z=407.8; RT: 0.84 min). The residue was poured into ice-water (25 mL) and stirred for 5 min. The aqueous phase was extracted with EA (10 mL*3). The combined organic phase was washed with brine (20 mL), dried with anhydrous $Na_2SO_4$, filtered and concentrated in vacuum. The residue was purified by prep-HPLC to give Compound 244 (11.8 mg, 0.026 mmol, 26.4% yield, HCl). LCMS (ESI): RT=0.847 min, mass calc. for $C_{18}H_{16}F_3N_5OS$ 407.10, m/z found 408.1 [M+H]$^+$; $^1$HNMR (400 MHz, DMSO-$d_6$) δ 8.78 (s, 1H), 8.08 (dd, J=1.0, 7.8 Hz, 1H), 7.60-7.47 (m, 4H), 7.26-7.15 (m, 3H), 6.40 (s, 1H), 5.08 (s, 2H), 3.38-3.28 (m, 4H).

Example 231: 1-oxo-3-[[5-[2-[4-(trifluoromethyl)anilino]phenyl]tetrazol-2-yl]methyl]thietan-3-ol (Compound 245)

Example 232: 2-(5-(2-((3-chloro-4-(trifluoromethyl)phenyl) amino) phenyl)-2H-tetrazol-2-yl)ethanol (Compound 246)

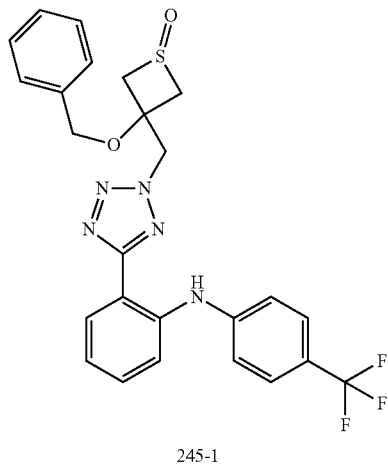

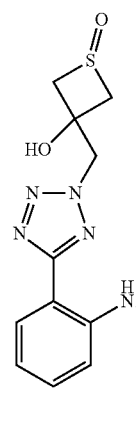

Compound 245

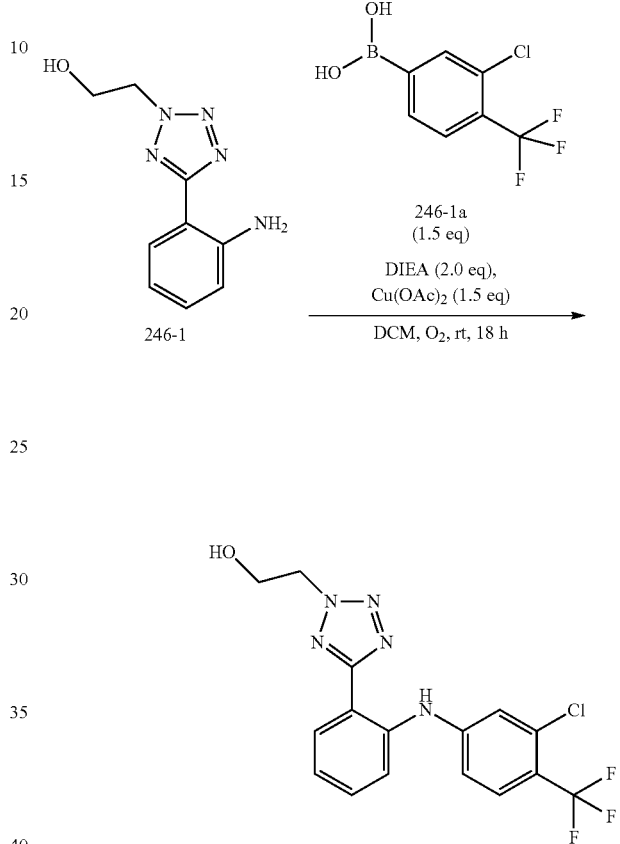

Compound 246

To a solution of compound 245-1 (40 mg, 0.078 mmol, 1 eq) in DCM (1 mL), a solution TiCl$_4$ (44.3 mg, 0.23 mmol, 3 eq) in DCM (1 mL) was added at 0° C. under N$_2$. The mixture was stirred at 0° C. for 4 hr. LCMS showed ~33% of reactant 245-1 was remained and ~33% of desired compound was detected (m/z=445.8; RT: 0.75 min). The reaction mixture was diluted with DCM (15 mL). This solution was washed with brine (10 mL*3). The organic phase was dried over anhydrous Na$_2$SO$_4$, filtered and concentrated in vacuum. The residue was purified by prep-HPLC to give Compound 245 (5.6 mg, 12.1 umol, 15.6% yield, HCl). LCMS (ESI): RT=0.914 min, mass calc. for C$_{18}$H$_{16}$F$_3$N$_5$O$_2$S 423.10, m/z found 446.2 [M+Na]$^+$; $^1$HNMR (400 MHz, CD$_3$OD) δ 8.25-8.16 (m, 1H), 7.63-7.52 (m, 3H), 7.51-7.43 (m, 1H), 7.30 (d, J=8.3 Hz, 2H), 7.14 (t, J=7.7 Hz, 1H), 5.08 (s, 2H), 3.80-3.72 (m, 2H), 3.63-3.55 (m, 2H).

To a solution of compound 246-1 (200 mg, 0.98 mmol, 1.0 eq) in DCM (5 mL) were added DIEA (251.9 mg, 1.95 mmol, 0.34 mL, 2.0 eq), Cu(OAc)$_2$ (265.5 mg, 1.46 mmol, 1.5 eq) and compound 246-1a (328.0 mg, 1.46 mmol, 1.5 eq). The suspension was degassed under vacuum and purged with O$_2$ several times. The mixture was stirred under O$_2$ (15 psi) at 25° C. for 18 hours. LCMS indicated that 66% of desired product was detected. The reaction mixture was filtered and the filter was concentrated in vacuum. The crude product was purified by prep-HPLC to give Compound 246 (176 mg, 0.45 mmol, 45.6% yield). LCMS (ESI): RT=0.811 min, mass calcd. For C$_{16}$H$_{13}$ClF$_3$N$_5$O, 383.08 m/z found 383.9 [M+H]$^+$; $^1$H NMR (400 MHz, CDCl$_3$) δ 9.07 (s, 1H), 8.19 (dd, J=7.78, 1.51 Hz, 1H), 7.55 (t, J=7.66 Hz, 2H), 7.44 (t, J=7.68 Hz, 1H), 7.32 (d, J=1.76 Hz, 1H), 7.09-7.16 (m, 2H), 4.84-4.90 (m, 2H), 4.24-4.31 (m, 2H), 2.25 (t, J=6.14 Hz, 1H).

Example 233: 1,1-dioxo-3-[[5-[2-[4-(trifluoromethyl)anilino]phenyl]tetrazol-2-yl]methyl]thietan-3-ol (Compound 247)

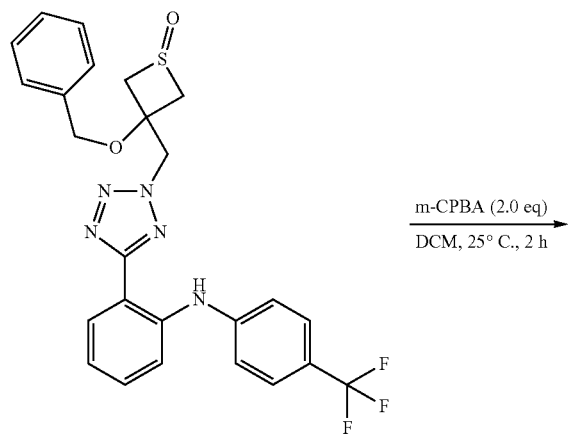

247-1 m-CPBA (2.0 eq)
DCM, 25° C., 2 h

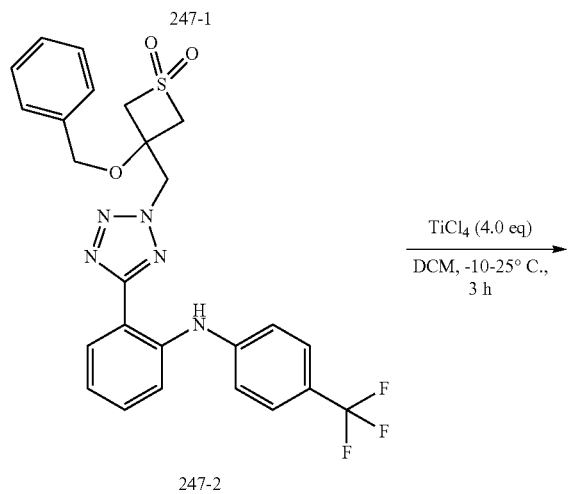

247-2

TiCl₄ (4.0 eq)
DCM, -10-25° C., 3 h

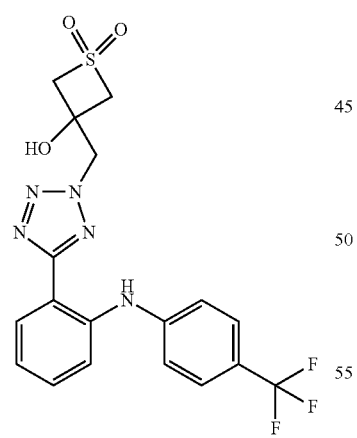

Compound 247

Step 1: 2-[2-[(3-benzyloxy-1,1-dioxo-thietan-3-yl)methyl]tetrazol-5-yl]-N-[4-(trifluoromethyl)phenyl]aniline To a solution of compound 247-1 (60 mg, 0.11 mmol, 1 eq) in DCM (3 mL) was added m-CPBA (47.4 mg, 0.23 mmol, 85% purity, 2 eq). The mixture was stirred at 25° C. for 2 hr. TLC (PE/EA=3/1, UV) indicated reactant 247-1 was almost consumed completely and one new spot formed. LCMS showed reactant 247-1 was consumed completely and ~48% of desired compound was detected (m/z=530.0; RT: 0.90 min). The reaction mixture was diluted with DCM (30 mL). This solution was washed sequentially with saturated Na₂SO₃ (20 mL*2), NaHCO₃ (20 mL*2), and brine (30 mL). The organic phase was dried over anhydrous Na₂SO₄, filtered and concentrated in vacuum. The residue was purified by flash silica gel chromatography to give compound 247-2 (55 mg, 0.1 mol, 88.9% yield). LCMS (ESI): RT=1.093 min, mass calc. for $C_{25}H_{22}F_3N_5O_3S$ 529.14, m/z found 530.3 [M+H]⁺.

Step 2: 1,1-dioxo-3-[[5-[2-[4-(trifluoromethyl)anilino]phenyl]tetrazol-2-yl]methyl]thietan-3-ol To a solution of compound 247-2 (50 mg, 94.4 umol, 1 eq) in DCM (0.5 mL), a solution TiCl₄ (71.6 mg, 0.37 mmol, 4 eq) in DCM (0.5 mL) was added at -10° C. under N₂. The mixture was stirred at -10° C. for 2 hr. And then the resulting mixture was warm to 25° C. and stirred for 1 hr. LCMS showed ~36% of reactant 247-2 was remained and ~37% of desired compound was detected (m/z=440.0; RT: 0.78 min). The reaction mixture was diluted with DCM (15 mL). This solution was washed with brine (10 mL*3). The organic phase was dried over anhydrous Na₂SO₄, filtered and concentrated in vacuum. The residue was purified by prep-HPLC to give Compound 247 (6.5 mg, 13.3 umol, 14.1% yield, HCl). LCMS (ESI): RT=0.979 min, mass calc. for $C_{18}H_{16}F_3N_5O_2S$ 439.09, m/z found 440.2 [M+H]⁺; ¹H NMR (400 MHz, DMSO-d₆) δ 8.70 (s, 1H), 8.09 (d, J=7.8 Hz, 1H), 7.63-7.45 (m, 4H), 7.28-7.15 (m, 3H), 6.56 (s, 1H), 5.13 (s, 2H), 4.63 (d, J=14.3 Hz, 2H), 4.06 (d, J=14.3 Hz, 2H).

Example 234: 2-(5-(2-((4-((trifluoromethyl)thio)phenyl)amino)phenyl)-2H-tetrazol-2-yl)ethanol (Compound 248)

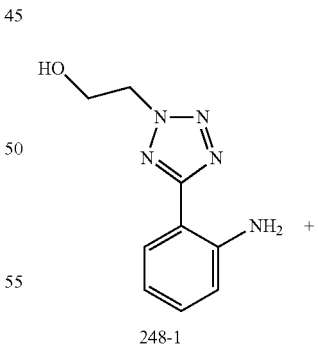

248-1

+

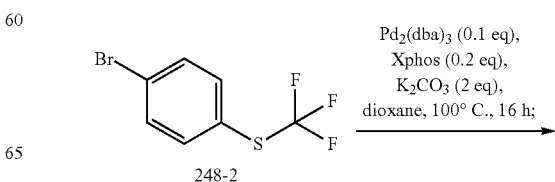

248-2

Pd₂(dba)₃ (0.1 eq),
Xphos (0.2 eq),
K₂CO₃ (2 eq),
dioxane, 100° C., 16 h;

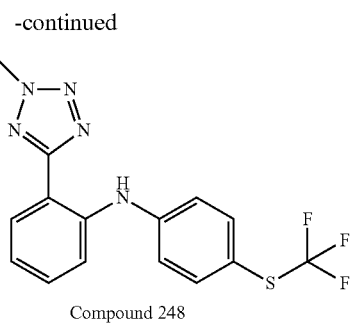

Compound 248

The mixture of compound 248-1 (50 mg, 0.24 mmol, 1 eq), compound 248-2 (94.0 mg, 0.36 mmol, 54.9 uL, 1.5 eq), Pd$_2$(dba)$_3$ (22.3 mg, 24.4 umol, 0.1 eq), XPhos (23.2 mg, 48.7 umol, 0.2 eq) and K$_2$CO$_3$ (67.4 mg, 0.49 mmol, 2 eq) in dioxane (3 mL) at 30° C. was purged and degassed with N$_2$ for 3 times, and then stirred at 100° C. under N$_2$ for 16 h. LCMS showed starting material was consumed completely and 70% of desired product was formed. The mixture was concentrated to give a residue. The residue was purified by prep-HPLC to give Compound 248 (47.86 mg, 0.13 mmol, 51.5% yield). LCMS (ESI): RT=0.822 min, mass calc. for C$_{16}$H$_{14}$F$_3$N$_5$OS 381.09, m/z found 381.9[M+1]$^+$; $^1$H NMR (400 MHz, DMSO-d$_6$) δ 8.83 (s, 1H), 8.06 (d, J=6.8 Hz, 1H), 7.55 (d, J=8.5 Hz, 3H), 7.52-7.46 (m, 1H), 7.22 (d, J=8.5 Hz, 2H), 7.20-7.14 (m, 1H), 5.10 (t, J=5.6 Hz, 1H), 4.77 (t, J=5.3 Hz, 2H), 3.95 (q, J=5.5 Hz, 2H).

Example 235: 2-[5-[2-[3,5-bis(trifluoromethyl)anilino]phenyl]tetrazol-2-yl]ethanol (Compound 249)

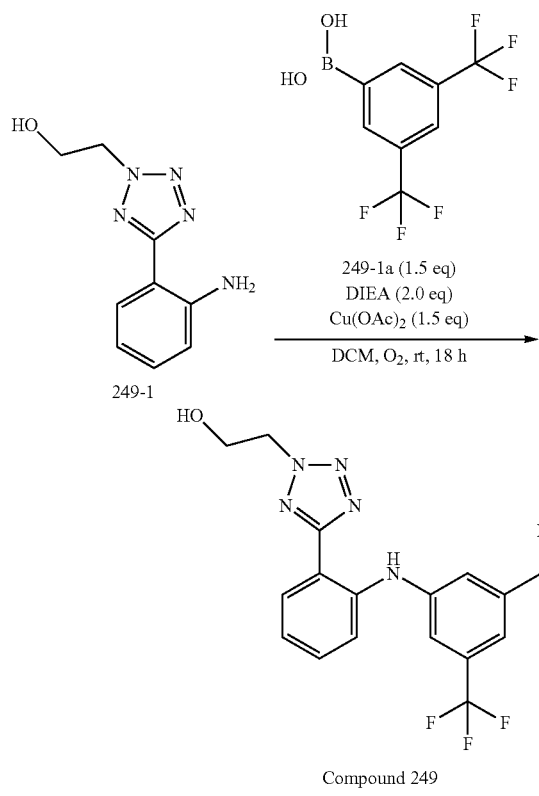

Compound 249

To a solution of compound 249-1 (100 mg, 0.49 mmol, 1.0 eq) in DCM (5 mL) were added DIEA (125.9 mg, 0.97 mmol, 0.17 mL, 2.0 eq), Cu(OAc)$_2$ (132.7 mg, 0.73 mmol, 1.5 eq) and compound 249-1a (188.5 mg, 0.73 mmol, 1.5 eq). The suspension was degassed under vacuum and purged with O$_2$ several times. The mixture was stirred under O$_2$ (15 psi) at 25° C. for 18 hours. LCMS indicated that 69% of desired product was detected. The reaction mixture was filtered and the filtrate was concentrated in vacuum. Then the residue was diluted with EA (20 mL), washed with brine (5 mL), dried over Na$_2$SO$_4$, filtered and concentrated under reduced pressure. The crude product was purified by prep-HPLC. Compound 249 (86 mg, 0.20 mmol, 41.9% yield) was obtained. LCMS (ESI): RT=0.838 min, mass calcd. For C17H13F6N5O, 417.10 m/z found 417.9 [M+H]$^+$; $^1$H NMR (400 MHz, CDCl$_3$) δ 9.18 (s, 1H), 8.21 (dd, J=7.91, 1.12 Hz, 1H), 7.63 (s, 2H), 7.41-7.50 (m, 3H), 7.09-7.15 (m, 1H), 4.85-4.90 (m, 2H), 4.25-4.32 (m, 2H), 2.27 (t, J=6.14 Hz, 1H), 1.59 (s, 2H).

Example 236: 2-(5-(2-((3-chlorophenyl)amino)phenyl)-2H-tetrazol-2-yl)ethanol (Compound 250)

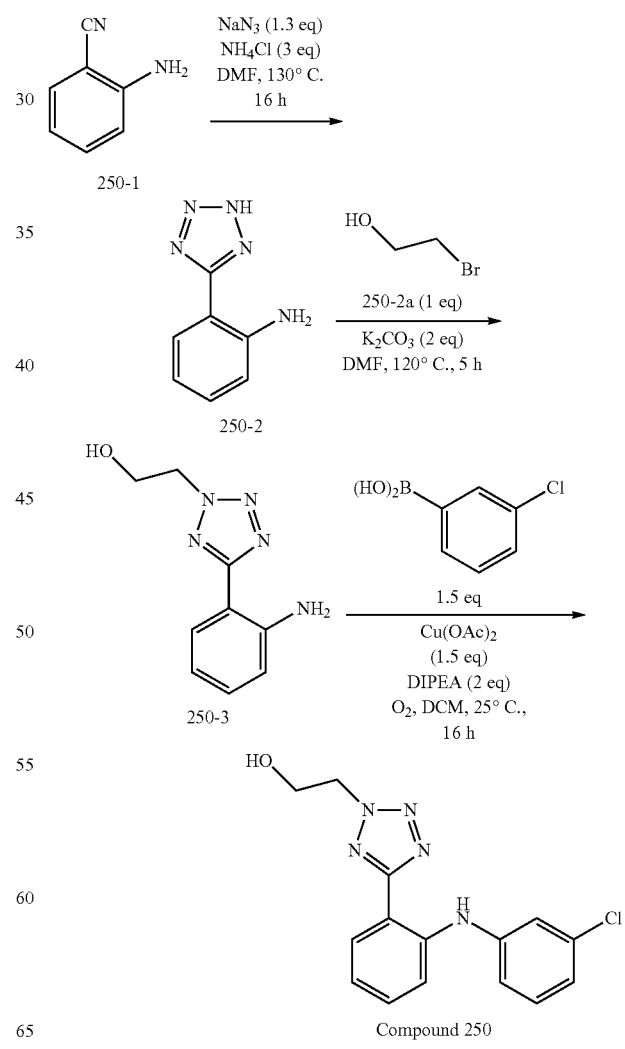

Compound 250

Step 1: 2-(2H-tetrazol-5-yl)aniline

A suspension of 250-1 (12.5 g, 105.8 mmol, 1 eq), NaN₃ (8.94 g, 137.5 mmol, 1.3 eq) and NH₄Cl (16.98 g, 317.4 mmol, 11.1 mL, 3 eq) in DMF (50 mL) was stirred at 130° C. for 16 hours. TLC (Dichloromethane:Methanol=10:1, UV) showed reactant 250-1 was consumed, and new spots were detected. LCMS showed reactant 250-1 was consumed completely and 40% of desired product was formed. The mixture was added into a flask containing 0.5 M HCl, but no solid was formed. The pH of the mixture was adjusted from 2 to 8 with 1 M NaOH. Then the mixture was concentrated, along with a lot of solid formed. Then the resulting residue was dissolved in 50 mL of methanol and filtered. The filtrate was concentrated to give crude product 250-2 (50 g, crude), which was used directly without further purification. $^1$H NMR (400 MHz, DMSO-$d_6$) δ 7.86 (d, J=7.8 Hz, 1H), 7.15-7.06 (m, 1H), 6.84-6.79 (m, 1H), 6.65-6.57 (m, 1H), 2.76 (s, 1H).

Step 2: 2-(5-(2-aminophenyl)-2H-tetrazol-2-yl)ethanol

A suspension of compound 250-2 (20 g, 62.0 mmol, 1 eq), 250-2a (7.75 g, 62.0 mmol, 4.4 mL, 1 eq), and K₂CO₃ (17.15 g, 124.1 mmol, 2 eq) in DMF (40 mL) was stirred at 120° C. for 5 hours. TLC (EA:PE=2:1, UV) showed compound 250-2 was consumed and new spots were detected. The mixture was filtered and concentrated to give residue. The residue was purified by column chromatography (SiO₂) to give compound 250-3 (3.8 g, 18.52 mmol, 29.8% yield). $^1$H NMR (400 MHz, DMSO-$d_6$) δ 7.95 (br d, J=8.0 Hz, 1H), 7.28-7.17 (m, 1H), 6.88 (d, J=8.0 Hz, 1H), 6.68 (t, J=7.4 Hz, 1H), 6.32 (br s, 2H), 5.11 (br s, 1H), 4.78 (t, J=5.1 Hz, 2H), 3.99 (br s, 2H).

Step 3: 2-(5-(2-((3-chlorophenyl)amino)phenyl)-2H-tetrazol-2-yl)ethanol

A suspension of compound 250-3 (0.2 g, 0.97 mmol, 1 eq), (3-chlorophenyl)boronic acid (228.6 mg, 1.46 mmol, 1.5 eq), DIPEA (251.9 mg, 1.95 mmol, 0.34 mL, 2 eq) and Cu(OAc)₂ (265.5 mg, 1.46 mmol, 1.5 eq) in DCM (5 mL) was stirred at 25° C. for 16 hours under O₂ in balloon. LCMS showed 6% of compound 250-3 was remained and 56% of desired compound was detected. TLC (PE:EA=1:1 UV) showed one main new spot was formed. The reaction mixture was filtered and concentrated to give a residue. The residue was purified by column chromatography (SiO₂) to give Compound 250 (110.81 mg, 0.35 mmol, 35.8% yield). LCMS (ESI): RT=0.774 min, mass calc. for C₁₅H₁₄ClN₅O 315.09, m/z found 315.9 [M+1]⁺; $^1$H NMR (400 MHz, DMSO-$d_6$) δ 8.68 (s, 1H), 8.06 (d, J=7.8 Hz, 1H), 7.45 (d, J=3.5 Hz, 2H), 7.34-7.26 (m, 1H), 7.21 (t, J=2.0 Hz, 1H), 7.16-7.06 (m, 2H), 6.97 (dd, J=1.1, 7.9 Hz, 1H), 5.08 (t, J=5.6 Hz, 1H), 4.79 (t, J=5.3 Hz, 2H), 3.97 (q, J=5.5 Hz, 2H).

Example 237: 2-(5-(2-((3,4-dichlorophenyl)amino)phenyl)-2H-tetrazol-2-yl)ethanol (Compound 251)

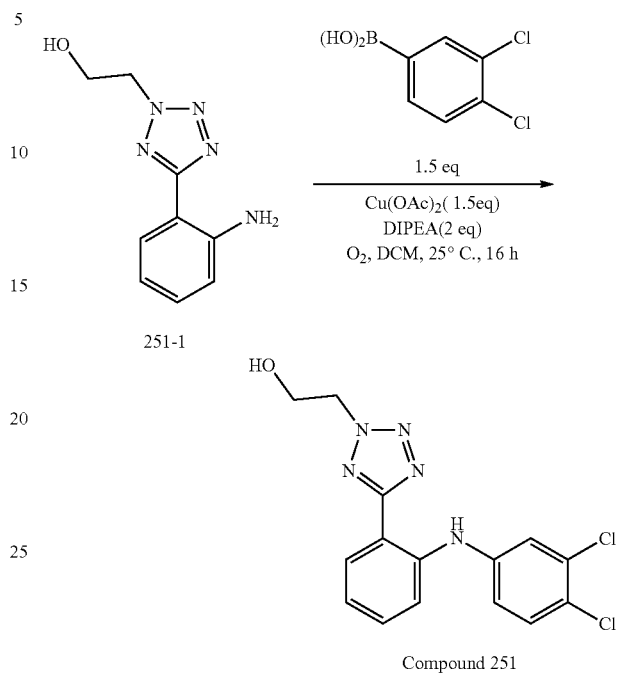

Compound 251

A suspension of compound 251-1 (0.2 g, 0.97 mmol, 1 eq), (3,4-dichlorophenyl)boronic acid (278.9 mg, 1.46 mmol, 1.5 eq), DIPEA (251.9 mg, 1.95 mmol, 0.34 mL, 2 eq) and Cu(OAc)₂ (265.5 mg, 1.46 mmol, 1.5 eq) in DCM (5 mL) was stirred at 25° C. for 16 hours under O₂ in balloon. LCMS showed 10% of reactant 251-1 was remained and 64% of desired compound was detected. The reaction mixture was filtered and concentrated to give a residue. The residue was purified by column chromatography (SiO₂) to give Compound 251 (149.6 mg, 0.42 mmol, 43.0% yield). LCMS (ESI): RT=0.847 min, mass calc. for C₁₅H₁₃Cl₂N₅O 349.05, m/z found 383.8 [M+1]⁺. $^1$H NMR (400 MHz, DMSO-$d_6$) δ 8.67 (s, 1H), 8.15-7.99 (m, 1H), 7.50-7.42 (m, 3H), 7.36 (d, J=2.8 Hz, 1H), 7.21-7.03 (m, 2H), 5.08 (t, J=5.6 Hz, 1H), 4.79 (t, J=5.3 Hz, 2H), 3.96 (q, J=5.3 Hz, 2H).

Example 238: 2-(5-(2-((3,5-dichlorophenyl)amino)phenyl)-2H-tetrazol-2-yl)ethanol (Compound 252)

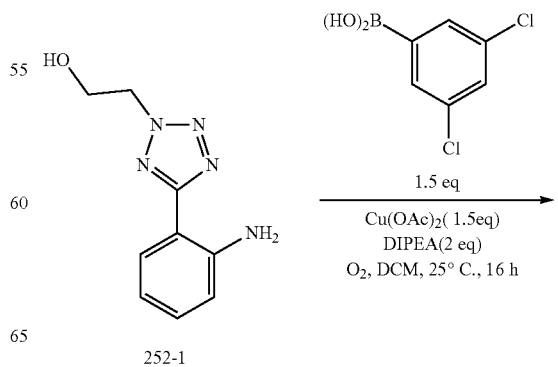

252-1

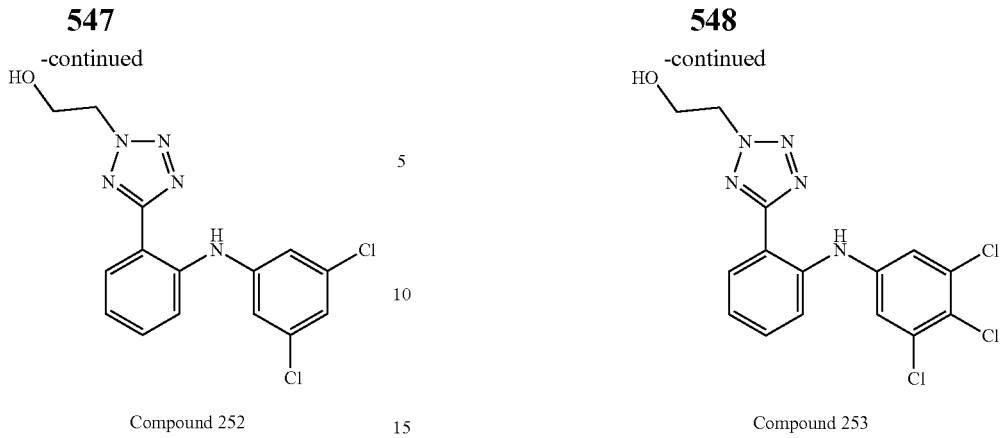

Compound 252

Compound 253

A suspension of compound 252-1 (0.2 g, 0.97 mmol, 1 eq), (3,5-dichlorophenyl)boronic acid (278.9 mg, 1.46 mmol, 1.5 eq), DIPEA (251.9 mg, 1.95 mmol, 0.34 mL, 2 eq) and Cu(OAc)$_2$ (265.5 mg, 1.46 mmol, 1.5 eq) in DCM (5 mL) was stirred at 25° C. for 16 hours under O$_2$ in balloon. LCMS showed no compound 252-1 was remained and 48% of desired compound was detected. The reaction mixture was filtered and concentrated to give a residue. The residue was purified by column chromatography (SiO$_2$) to give Compound 252 (114.29 mg, 0.32 mmol, 33.2% yield). LCMS (ESI): RT=0.814 min, mass calc. for C$_{15}$H$_{13}$Cl$_2$N$_5$O 349.05, m/z found 349.9 [M+1]$^+$; $^1$H NMR (400 MHz, DMSO-d$_6$) δ 8.67 (s, 1H), 8.04 (d, J=7.5 Hz, 1H), 7.58-7.46 (m, 2H), 7.26-7.16 (m, 1H), 7.06 (d, J=1.8 Hz, 2H), 7.03-6.96 (m, 1H), 5.08 (t, J=5.8 Hz, 1H), 4.77 (t, J=5.3 Hz, 2H), 3.95 (q, J=5.5 Hz, 2H), 3.17 (d, J=5.3 Hz, 1H).

Example 239: 2-(5-(2-((3,4,5-trichlorophenyl)amino)phenyl)-2H-tetrazol-2-yl)ethanol (Compound 253)

A suspension of compound 253-1 (0.2 g, 0.97 mmol, 1 eq), (3,4,5-trichlorophenyl)boronic acid (329.3 mg, 1.46 mmol, 1.5 eq), DIPEA (251.9 mg, 1.95 mmol, 0.34 mL, 2 eq) and Cu(OAc)$_2$ (265.5 mg, 1.46 mmol, 1.5 eq) in DCM (5 mL) was stirred at 25° C. for 16 hours under O$_2$ in balloon. LCMS showed no compound 253-1 was remained and 70% of desired compound was detected. The reaction mixture was filtered and concentrated to give a residue. The residue was purified by column chromatography (SiO$_2$) to give Compound 253 (171.37 mg, 0.44 mmol, 44.9% yield). LCMS (ESI): RT=0.808 min, mass calc. for C$_{15}$H$_{12}$Cl$_3$N$_5$O 383.01, m/z found 349.9 [M−Cl+1]$^+$; $^1$H NMR (400 MHz, DMSO-d$_6$) δ 8.68 (s, 1H), 8.10-7.92 (m, 1H), 7.57-7.44 (m, 2H), 7.32-7.15 (m, 3H), 5.07 (t, J=5.8 Hz, 1H), 4.77 (t, J=5.3 Hz, 2H), 3.95 (q, J=5.5 Hz, 2H), 1.99 (s, 1H).

Example 240: 2-[5-[5-bromo-2-[4-(trifluoromethyl)anilino]phenyl]tetrazol-2-yl]ethanol (Compound 254)

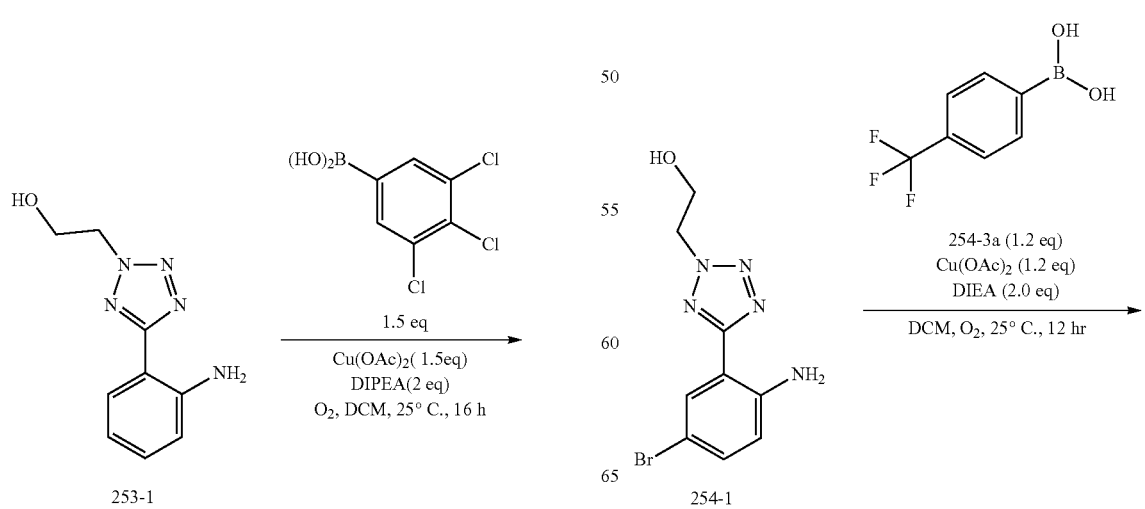

-continued

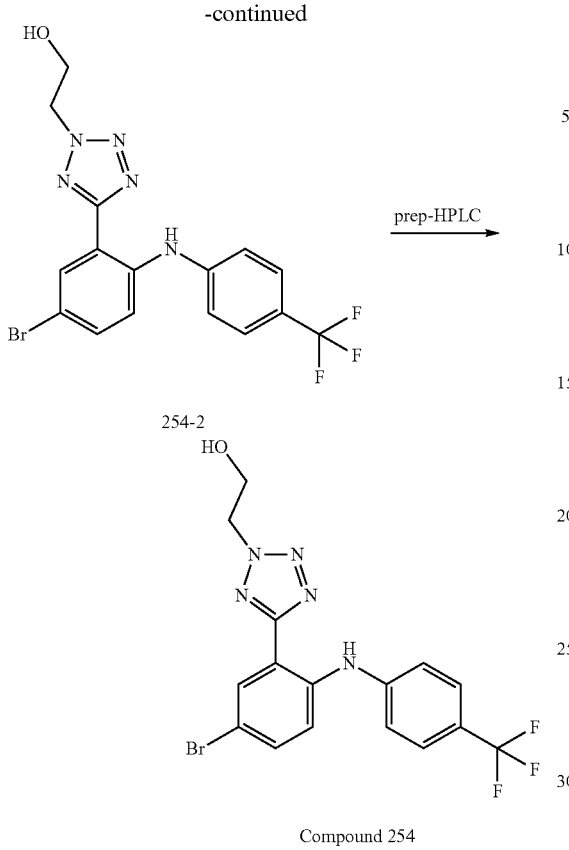

Compound 254

Step 1: 2-[5-[5-bromo-2-[4-(trifluoromethyl)anilino]phenyl]tetrazol-2-yl]ethanol To a mixture of compound 254-1 (3.5 g, 12.3 mmol, 1 eq) and compound 254-3a (2.81 g, 14.7 mmol, 1.2 eq) in DCM (20 mL) was added Cu(OAc)$_2$ (4.48 g, 24.6 mmol, 2 eq) and DIPEA (7.96 g, 61.6 mmol, 10.7 mL, 5 eq) in one portion at 25° C. under O$_2$. The mixture was stirred for 18 hrs under O$_2$(15 psi). TLC (PE/EA=3/1) showed the reaction was finished. The mixture was quenched by EA (30 mL). The mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by column chromatography (SiO$_2$) to give crude compound 254-2 (7 g, 16.3 mmol, 66.3% yield).

Step 2: 2-[5-[5-bromo-2-[4-(trifluoromethyl)anilino]phenyl]tetrazol-2-yl]ethanol Compound 254-2 (0.03 g, 70.0 umol, 1 eq) was re-purified by prep-HPLC to give desired Compound 254 (17.72 mg, 0.041 mmol). LCMS (ESI): RT=0.838 min, mass calc. for: C$_{16}$H$_{13}$BrF$_3$N$_5$O 427.03, m/z found 429.7 [M+H]$^+$; $^1$HNMR (400 MHz, DMSO-d$_6$) δ 8.84 (s, 1H), 8.15 (d, J=2.3 Hz, 1H), 7.65-7.58 (m, 3H), 7.50 (d, J=9.0 Hz, 1H), 7.28 (d, J=8.3 Hz, 2H), 5.07 (t, J=5.6 Hz, 1H), 4.79 (t, J=5.1 Hz, 2H), 3.95 (q, J=5.5 Hz, 2H).

Example 241: 2-(5-(5-cyclopropyl-2-((4-(trifluoromethyl)phenyl)amino)phenyl)-2H-tetrazol-2-yl)ethanol (Compound 255)

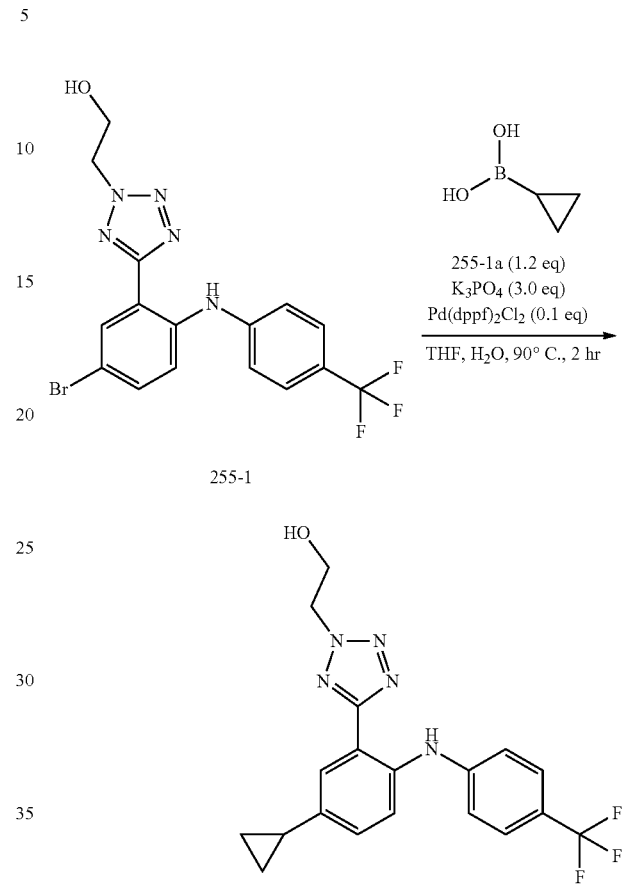

Compound 255

To a mixture of 255-1 (200 mg, 0.47 mmol, 1.0 eq) and 255-1a (48.1 mg, 0.56 mmol, 1.2 eq) in THF (3 mL) was added K$_3$PO$_4$ (297.4 mg, 1.40 mmol, 3 eq), Pd(dppf)Cl$_2$ (34.1 mg, 0.046 mmol, 0.1 eq) and H$_2$O (8.4 mg, 0.47 mmol, 8.4 uL, 1 eq) in one portion. The mixture was stirred at 90° C. for 15 min under microwave. LCMS showed the starting material was consumed completely and the desired mass was detected. The reaction mixture was filtered. H$_2$O (3 mL) was added into the reaction. The mixture was extracted with ethyl acetate (3 mL*3). The combined organic layers were washed with brine (4 mL*2), dried with anhydrous Na$_2$SO$_4$, filtered and concentrated in vacuum. The residue was purified by prep-HPLC. Compound 255 (7.08 mg, 16.46 umol, 3.52% yield) was obtained. LCMS (ESI): RT=0.842 min, mass calc. for C$_{19}$H$_{18}$F$_3$N$_5$O 389.37, m/z found 390.0 [M+H]$^+$; $^1$H NMR (400 MHz, DMSO-d$_6$) δ 8.64 (s, 1H), 7.77 (d, J=2.3 Hz, 1H), 7.52 (d, J=8.5 Hz, 2H), 7.44 (d, J=8.5 Hz, 1H), 7.20 (dd, J=2.3, 8.5 Hz, 1H), 7.14 (d, J=8.5 Hz, 2H), 5.06 (t, J=5.5 Hz, 1H), 4.76 (t, J=5.3 Hz, 2H), 3.93 (br d, J=5.3 Hz, 2H), 2.09-1.96 (m, 1H), 1.01-0.91 (m, 2H), 0.74-0.65 (m, 2H).

Example 242: 2-[5-[5-ethyl-2-[4-(trifluoromethyl)anilino]phenyl]tetrazol-2-yl]ethanol (Compound 256)

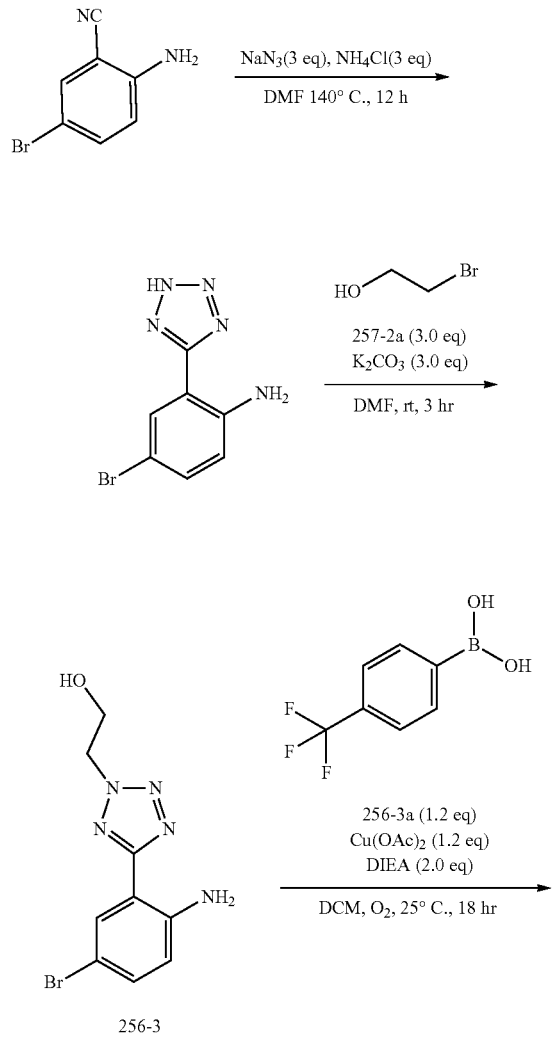

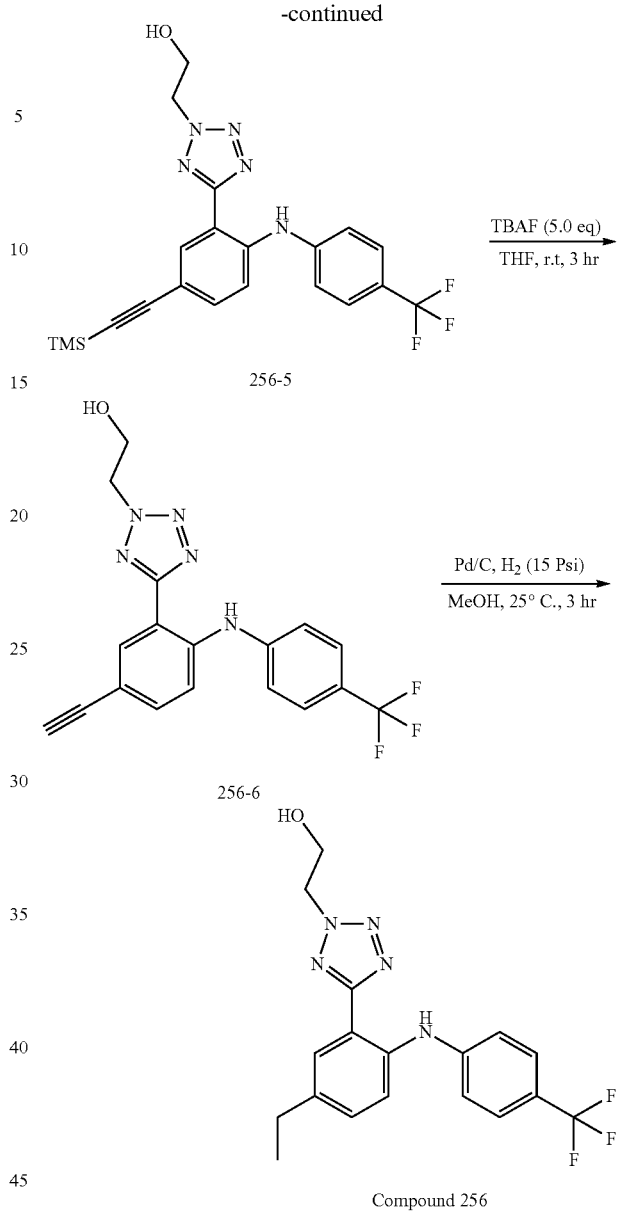

Step 1: 4-bromo-2-(2H-tetrazol-5-yl)aniline

To the solution of compound 256-1 (8 g, 40.6 mmol, 1 eq) in DMF (50 mL) was added NaN₃ (16.96 g, 260.8 mmol, 6.4 eq) and NH₄Cl (6.52 g, 121.8 mmol, 4.2 mL, 3 eq). The mixture was stirred at 140° C. for 12 hr. TLC (PE/EA=3/1) showed that the reaction was complete. The reaction solution was added to H₂O (200 mL). The aqueous phase was adjust to pH=5 and extracted with ethyl acetate (150 mL*3). The combined organic phase was washed with brine (50 mL*5), dried with anhydrous Na₂SO₄, filtered and concentrated in vacuum to give compound 256-2 (20 g, crude), which was used for the next step without further purification.

Step 2: 2-[5-(2-amino-5-bromo-phenyl)tetrazol-2-yl]ethanol

To the solution of compound 256-2 (8 g, 33.3 mmol, 1 eq) in DMF (100 mL) was added 256-2a (8.33 g, 66.6 mmol, 4.7 mL, 2 eq) and K$_2$CO$_3$ (13.82 g, 99.9 mmol, 3 eq). The mixture was stirred at 130° C. for 3 hr. TLC (PE/EA=1/1) showed the reaction was complete. The reaction solution was added to H$_2$O (100 mL). The mixture was extracted with ethyl acetate (50 mL*3). The combined organic phase was washed with brine (50 mL*5), dried with anhydrous Na$_2$SO$_4$, filtered and concentrated in vacuum. The residue was purified by column chromatography (SiO$_2$) to give compound 256-3 (8 g, 21.6 mmol, 65.0% yield).

Step 3: 2-[5-[5-bromo-2-[4-(trifluoromethyl)anilino]phenyl]tetrazol-2-yl]ethanol To a mixture of compound 256-3 (3.5 g, 12.3 mmol, 1 eq) and compound 256-3a (2.81 g, 14.7 mmol, 1.2 eq) in DCM (20 mL) was added Cu(OAc)$_2$ (4.48 g, 24.6 mmol, 2 eq) and DIPEA (7.96 g, 61.6 mmol, 10.7 mL, 5 eq) in one portion at 25° C. under O$_2$. The mixture was stirred for 18 hours under O$_2$(15 psi). TLC (PE/EA=3/1) showed the reaction was finished. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by column chromatography (SiO$_2$). Compound 256-4 (7 g, 16.3 mmol, 66.3% yield) was obtained.

Step 4: 2-[5-[2-[4-(trifluoromethyl)anilino]-5-(2-trimethylsilylethynyl)phenyl]tetrazol-2-yl]ethanol To a mixture of compound 256-4 (0.3 g, 0.7 mmol, 1 eq) and 256-4a (82.5 mg, 0.84 mmol, 0.1 mL, 1.2 eq) in dioxane (2 mL) was added Pd(dppf)Cl$_2$ (51.2 mg, 0.07 mmol, 0.1 eq), CuI (13.3 mg, 0.07 mmol, 0.1 eq) and DIPEA (90.5 mg, 0.70 mmol, 0.1 mL, 1 eq). The mixture was stirred for 10 hrs at 100° C. LCMS The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by column chromatography (SiO$_2$). Compound 256-5 (0.15 g, 0.33 mmol, 48.0% yield) was obtained.

Step 5: 2-[5-[5-ethynyl-2-[4-(trifluoromethyl)anilino]phenyl]tetrazol-2-yl]ethanol To the solution of compound 256-5 (50 mg, 0.11 mmol, 1 eq) was added TBAF (1 M, 1.1 mL, 10 eq). The mixture was stirred at 25° C. for 3 hr. TLC (PE/EA=3/1) and LCMS showed the reaction was complete. The reaction solution was added to H$_2$O (30 mL). The mixture was extracted with ethyl acetate (10 mL*3). The combined organic phase was washed with brine (10 mL*5), dried with anhydrous Na$_2$SO$_4$, filtered and concentrated in vacuum. The residue was purified by column chromatography (SiO$_2$). Compound 256-6 (0.03 g, 0.08 mmol, 71.6% yield) was obtained.

Step 6: 2-[5-[5-ethyl-2-[4-(trifluoromethyl)anilino]phenyl]tetrazol-2-yl]ethanol To a solution of compound 256-6 (0.03 g, 0.08 mmol, 1 eq) in MeOH (2 mL) was added Pd/C (30 mg, 0.08 mmol, 10% purity, 1.00 eq) under N$_2$. The suspension was degassed under vacuum and purged with H$_2$ several times. The mixture was stirred under H$_2$ (15 psi) at 25° C. for 3 hrs. LCMS showed the reaction was complete. The reaction solution was filtered and the filtered was concentrated in vacuum. The residue was purified by prep-HPLC. Compound 256 (12.79 mg, 0.03 mmol, 38.4% yield, HCl) was obtained. LCMS (ESI): RT=0.847 min, mass calc. for: C$_{18}$H$_{18}$F$_3$N$_5$O 377.15, m/z found 378.0 [M+H]$^+$; $^1$H NMR (400 MHz, DMSO-d$_6$) δ 8.68 (s, 1H), 7.88 (d, J=2.0 Hz, 1H), 7.55-7.46 (m, 3H), 7.36 (dd, J=2.0, 8.5 Hz, 1H), 7.17 (d, J=8.5 Hz, 2H), 5.06 (br s, 1H), 4.76 (t, J=5.3 Hz, 2H), 3.94 (t, J=5.3 Hz, 2H), 2.68 (q, J=7.5 Hz, 2H), 1.23 (t, J=7.5 Hz, 3H).

Example 243: methyl 3-((tert-butoxycarbonyl)amino)-2-(5-(2-((4-(trifluoromethyl)phenyl)amino)phen-yl)-2H-tetrazol-2-yl)propanoate (Compound 257)

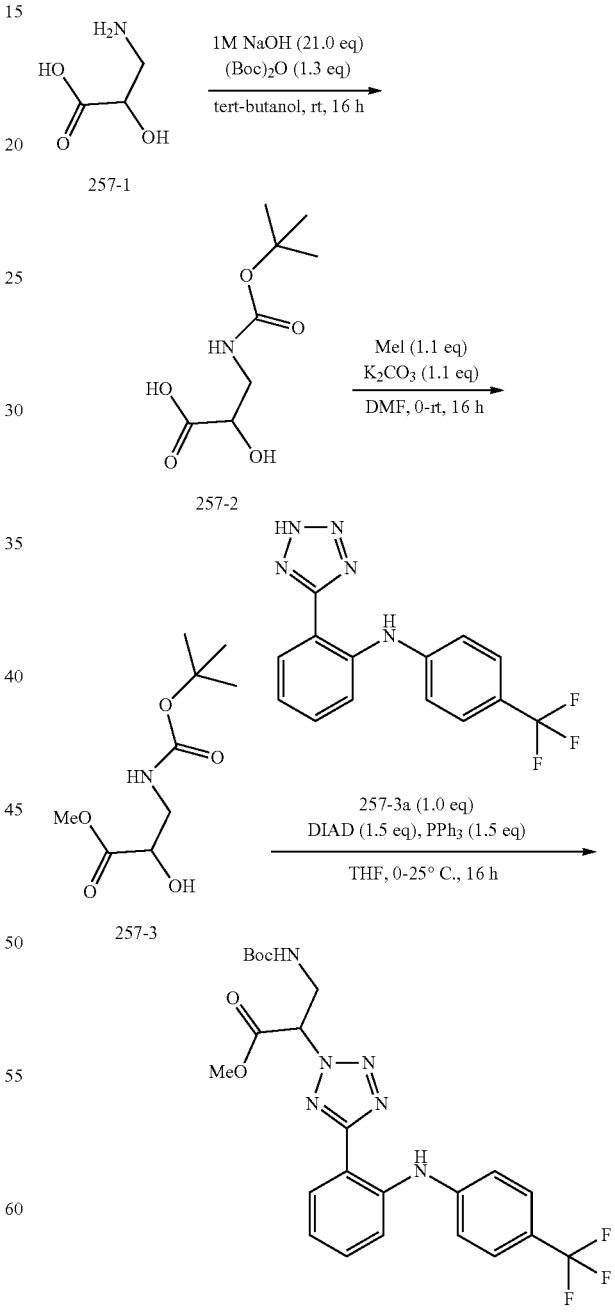

Compound 257

Step 1: 3-((tert-butoxycarbonyl)amino)-2-hydroxypropanoic acid

To a solution of compound 257-1 (1 g, 9.52 mmol, 1 eq) in tert-butanol (40 mL) and NaOH (1 M, 20 mL, 21.0 eq) solution was added (Boc)$_2$O (2.70 g, 12.3 mmol, 2.8 mL, 1.3 eq) at 0° C. Then the mixture was stirred at 25° C. for 16 hr. The reaction mixture was concentrated in vacuum and then the aqueous phase was extracted with EA (15 mL*3) and 1N HCl (15 mL). The combined organic phase was washed with brine (5 mL), filtered and concentrated in vacuum. The crude compound 257-2 (1.2 g, 5.85 mmol, 61.5% yield) was obtained and was used for the next step without further purification. $^1$H NMR (400 MHz, CDCl$_3$) δ 5.32 (br s, 1H), 4.32 (br s, 1H), 3.44-3.65 (m, 2H), 1.43 (br s, 9H).

Step 2: methyl 3-((tert-butoxycarbonyl)amino)-2-hydroxypropanoate

To a solution of compound 257-2 (800 mg, 3.90 mmol, 1 eq) in DMF (6 mL) were added MeI (1.4 g, 9.86 mmol, 0.6 mL, 2.5 eq) and K$_2$CO$_3$ (592.7 mg, 4.29 mmol, 1.1 eq) at 0° C. Then the mixture was stirred at 25° C. for 16 hr. TLC (PE/EA=1/1, I$_2$) showed that one new spot was formed. The reaction mixture was quenched by water (15 mL), extracted with EA (15 mL*3). The combined organic phase was washed with brine (5 mL*2), dried over Na$_2$SO$_4$, filtered and concentrated in vacuum. Compound 257-3 (700 mg, 3.19 mmol, 81.9% yield) was obtained and was used for the next step without further purification. $^1$H NMR (400 MHz, CDCl$_3$) δ 5.11 (br s, 1H), 4.24 (t, J=4.64 Hz, 1H), 3.75 (s, 3H), 3.34-3.57 (m, 3H), 1.39 (s, 9H).

Step 3: methyl 3-((tert-butoxycarbonyl)amino)-2-(5-(2-((4-(trifluoromethyl)phenyl)amino) phen-yl)-2H-tetrazol-2-yl)propanoate To a mixture of compound 257-3 (150 mg, 0.68 mmol, 1 eq), compound 257-3a (208.9 mg, 0.69 mmol, 1 eq) and PPh$_3$ (269.2 mg, 1.03 mmol, 1.5 eq) in THF (2 mL), DIAD (207.5 mg, 1.03 mmol, 0.2 mL, 1.5 eq) was added dropwise at 0° C. The mixture was stirred at 25° C. for 16 hr. LCMS showed that 39% of desired product was detected. TLC (PE/EA=3/1, UV) indicated that several spots were formed. The reaction mixture was quenched with water (10 mL), extracted with EA (15 mL*3). The combined organic phase was washed with brine (5 mL), dried over Na$_2$SO$_4$, filtered and concentrated in vacuum. The crude product was purified by prep-HPLC. Compound 257 (155 mg, 0.3 mmol, 43.4% yield) was obtained. LCMS (ESI): RT=0.956 min, mass calcd. For C$_{23}$H$_{25}$F$_3$N$_6$O$_4$, 506.19 m/z found 529.1 [M+Na]$^+$; $^1$H NMR (400 MHz, CDCl$_3$) δ 8.96 (s, 1H), 8.21 (d, J=7.03 Hz, 1H), 7.55 (dd, J=8.66, 2.89 Hz, 3H), 7.40 (t, J=7.74 Hz, 1H), 7.31 (d, J=8.53 Hz, 2H), 7.02-7.09 (m, 1H), 5.87 (dd, J=7.91, 4.64 Hz, 1H), 5.00 (br s, 1H), 4.04-4.28 (m, 1H), 4.04-4.28 (m, 1H), 3.82 (s, 3H), 1.40 (s, 9H).

Example 244: tert-butyl (3-hydroxy-2-(5-(2-((4-(trifluoromethyl)phenyl)amino)phenyl)-2H-tetrazol-2-yl)propyl)carbamate (Compound 258)

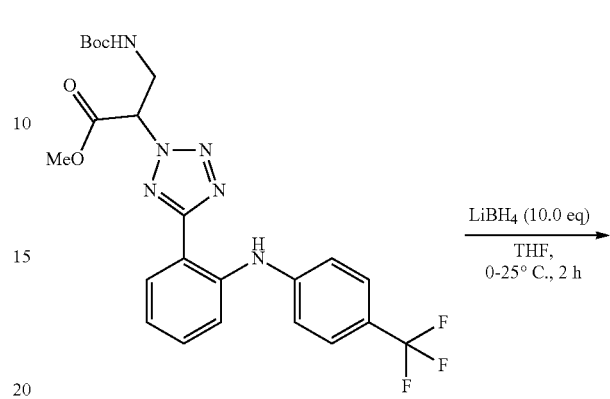

Compound 257

Compound 258

To a solution of Compound 257 (50 mg, 98.7 umol, 1 eq) in THF (1 mL) was added LiBH$_4$ (21.5 mg, 0.99 mmol, 10 eq) at 0° C. Then the reaction mixture was warmed to 25° C. and stirred for 2 hr. LCMS showed that 98% of desired product was detected. TLC (PE/EA=3/1, UV) showed that the starting material was consumed completely and one new spot was formed. The reaction mixture was quenched with water (10 mL), extracted with EA (15 mL*3). The organic phase was washed with brine (5 mL), dried over Na$_2$SO$_4$, filtered and concentrated in vacuum. The crude product was purified by prep-TLC. Compound 258 (37 mg, 77.3 umol, 78.3% yield) was obtained. LCMS (ESI): RT=0.894 min, mass calcd. For C$_{22}$H$_{25}$F$_3$N$_6$O$_3$, 478.19 m/z found 501.1 [M+Na]$^+$; $^1$H NMR (400 MHz, CDCl$_3$) δ 9.00 (s, 1H), 8.19 (dd, J=7.78, 1.25 Hz, 1H), 7.54 (d, J=8.28 Hz, 3H), 7.40 (t, J=7.73 Hz, 1H), 7.29 (d, J=8.53 Hz, 2H), 7.03-7.09 (m, 1H), 5.00-5.11 (m, 2H), 4.14-4.25 (m, 1H), 4.08 (td, J=12.17, 6.02 Hz, 2H), 3.88 (dt, J=15.31, 4.89 Hz, 1H), 3.77 (dd, J=8.78, 5.77 Hz, 1H), 1.45 (s, 9H).

Example 245: 3-amino-2-(5-(2-((4-(trifluoromethyl)phenyl)amino)phenyl)-2H-tetrazol-2-yl)propan-1-ol (Compound 259)

Example 246: 2-(5-(5-(difluoromethoxy)-2-((4-(trifluoromethyl)phenyl)amino)phenyl)-2H-tetrazol-2-yl)ethanol (Compound 260)

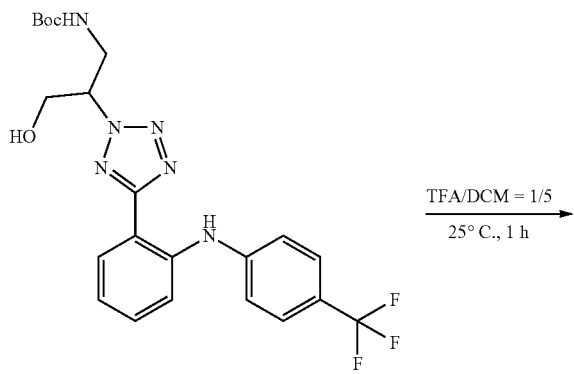

Compound 258

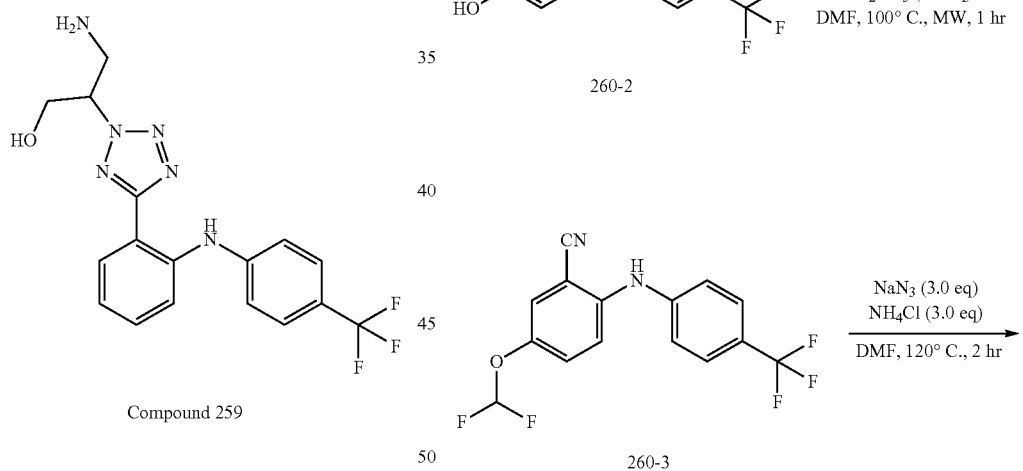

Compound 259

To a solution of Compound 258 (15 mg, 31.4 umol, 1 eq) in DCM (1 mL) was added TFA (308.0 mg, 2.70 mmol, 0.2 mL, 86.1 eq). The mixture was stirred at 25° C. for 1 hr. LCMS showed that 86% of desired product was detected. The reaction mixture was concentrated in vacuum. The crude product was purified by prep-HPLC. Compound 259 (8.50 mg, 20.9 umol, 66.6% yield) was obtained. LCMS (ESI): RT=0.824 min, mass calcd. For $C_{19}H_{16}F_3NO_2$, 347.11 m/z found 347.9 [M+H]+; $^1$HNMR (400 MHz, CDCl$_3$) δ 9.03 (br s, 1H), 8.17 (br d, J=7.53 Hz, 1H), 7.53 (br d, J=8.28 Hz, 3H), 7.38 (t, J=7.65 Hz, 1H), 7.29 (s, 2H), 7.04 (br t, J=7.28 Hz, 1H), 4.97 (br s, 1H), 4.30 (br s, 2H), 3.42-3.76 (m, 2H).

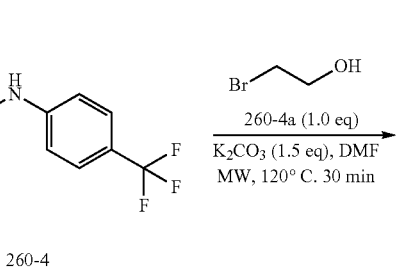

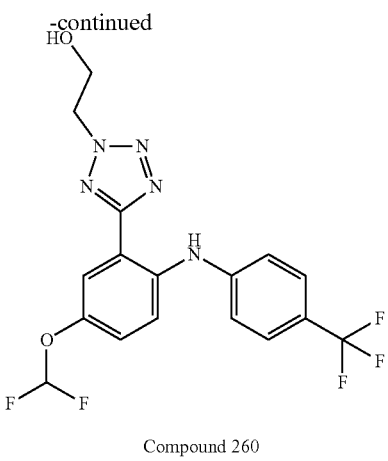

Compound 260

Step 1: 5-hydroxy-2-((4-(trifluoromethyl)phenyl)amino)benzonitrile

A solution of compound 260-1 (100 mg, 0.74 mmol, 1.0 eq), compound 260-1a (201 mg, 0.89 mmol, 1.2 eq), compound 260-1b (6.0 mg, 7.5 umol, 0.01 eq) and t-BuONa (143 mg, 1.49 mmol, 2.0 eq) in Dioxane (3 mL) was stirred at 90° C. for 1 hour under $N_2$. TLC (Petroleum ether:Ethyl acetate=1:1) showed the starting material was consumed and one main new spot was formed. The reaction mixture was concentrated under reduced pressure. The mixture was diluted with $H_2O$ (10 mL), and then the mixture was adjusted with HCl (1M) to pH=6. The resultant mixture was extracted with EA (50 mL*3). The combined organic layers were dried over $Na_2SO_4$, filtered and concentrated to dryness under reduced pressure. The residue was purified by column chromatography over silica gel to afford compound 260-2 (100 mg, 48% yield). $^1$H NMR (400 MHz, $CDCl_3$) δ 7.52 (d, J=8.5 Hz, 2H), 7.30 (d, J=9.0 Hz, 1H), 7.10-7.01 (m, 4H), 6.12 (s, 1H), 5.48 (s, 1H).

Step 2: 5-(difluoromethoxy)-2-((4-(trifluoromethyl)phenyl)amino)benzonitrile Compound 260-2 (250 mg, 0.89 mmol, 1.0 eq), compound 260-2a (411 mg, 2.70 mmol, 3.0 eq) and $Cs_2CO_3$ (878 mg, 2.70 mmol, 3 eq) were taken up into a microwave tube in DMF (4 mL). The sealed tube was heated at 100° C. for 1 hour under microwave. TLC (Petroleum ether:Ethyl acetate=5:1) showed the starting material was remained and two new spots were formed. The reaction mixture was concentrated under reduced pressure. The mixture was diluted with water (20 mL) and the resultant mixture was extracted with EA (50 mL*3). The combined organic layers were dried over $Na_2SO_4$, filtered and concentrated to dryness under reduced pressure. The residue was purified by column chromatography over silica gel to afford compound 260-3 (200 mg, 68% yield).

Step 3: 4-(difluoromethoxy)-2-(2H-tetrazol-5-yl)-N-(4-(trifluoromethyl)phenyl)aniline A solution of compound 260-3 (50 mg, 0.15 mmol, 1.0 eq), $NaN_3$ (30 mg, 0.46 mmol, 3.0 eq) and $NH_4Cl$ (24 mg, 0.46 mmol, 3.0 eq) in DMF (2 mL) was stirred at 120° C. for 2 hours. LC-MS showed Reactant 260-3 was consumed completely and one main peak with desired MS was detected. The reaction mixture was concentrated under reduced pressure. The mixture was diluted with water (20 mL) and the resultant mixture was extracted with EA (40 mL*3). The combined organic layers were dried over $Na_2SO_4$, filtered and concentrated to dryness under reduced pressure to obtain compound 260-4 (50 mg, crude). LCMS (ESI): RT=0.998 min, mass calcd. for $C_{15}H_{10}F_5N_5O$ 371.08, m/z found 371.3 [M+H]$^+$.

Step 4: 2-(5-(5-(difluoromethoxy)-2-((4-(trifluoromethyl)phenyl)amino)phenyl)-2H-tetrazol-2-yl)ethanol Compound 260-4 (50 mg, 0.13 mmol, 1.0 eq), compound 260-4a (17 mg, 0.13 mmol, 1.0 eq) and $K_2CO_3$ (28 mg, 0.20 mmol, 1.5 eq) were taken up into a microwave tube in DMF (1 mL). The sealed tube was heated at 120° C. for 30 min under microwave. LC-MS showed reactant 260-4 was consumed completely and one main peak with desired MS was detected. The reaction mixture was concentrated under reduced pressure. The mixture was diluted with water (10 mL) and the resultant mixture was extracted with EA (30 mL*3). The combined organic layers were dried over $Na_2SO_4$, filtered and concentrated to dryness under reduced pressure. The residue was purified by prep-HPLC to obtain Compound 260 (15.0 mg, 27% yield). LCMS (ESI): RT=1.040 min, mass calcd. for $C_{19}H_{18}F_3N_5O$ 415.11, m/z found 416.0 [M+H]$^+$; $^1$HNMR (400 MHz, $CDCl_3$) δ 9.00 (s, 1H), 7.99 (d, J=2.8 Hz, 1H), 7.57 (d, J=8.5 Hz, 2H), 7.52 (d, J=9.0 Hz, 1H), 7.32-7.28 (m, 2H), 7.20 (dd, J=2.8, 9.0 Hz, 1H), 6.75-6.35 (m, 1H), 4.92-4.86 (m, 2H), 4.34-4.26 (m, 2H), 2.19 (t, J=6.1 Hz, 1H).

Example 247: 2-(5-(5-(trifluoromethoxy)-2-((4-(trifluoromethyl)phenyl)amino)phenyl)-2H-tetrazol-2-yl)ethanol (Compound 261)

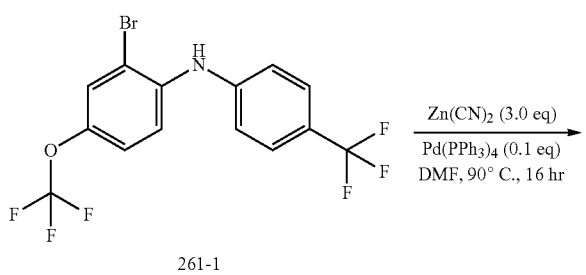

261-1

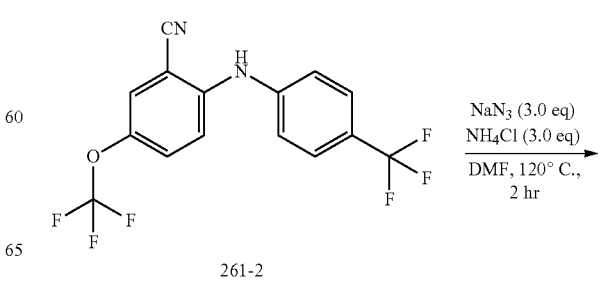

261-2

-continued

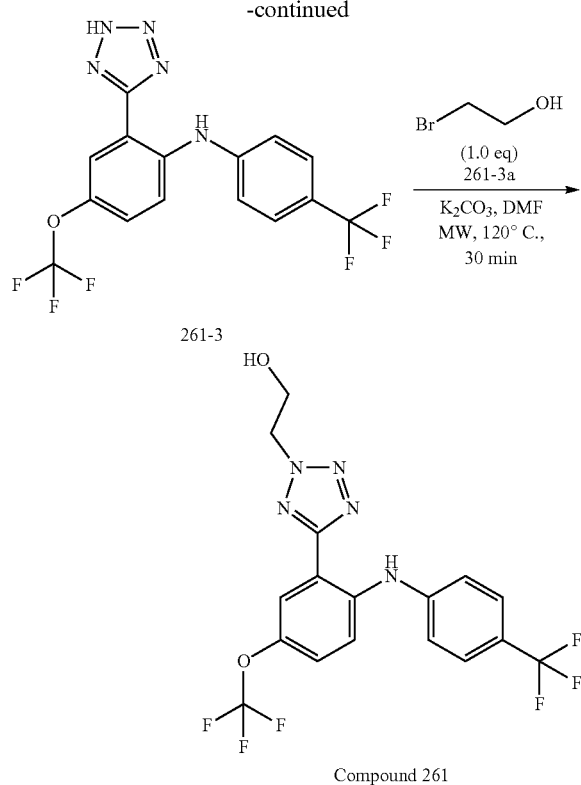

261-3

Compound 261

Step 1: 5-(trifluoromethoxy)-2-((4-(trifluoromethyl)phenyl)amino)benzonitrile A solution of compound 261-1 (100 mg, 0.250 mmol, 1.0 eq), Zn(CN)$_2$ (88 mg, 0.75 mmol, 3.0 eq) and Pd(PPh$_3$)$_4$ (29 mg, 25 umol, 0.1 eq) in DMF (2 mL) was degassed under vacuum and purged with N$_2$ several times. The reaction mixture was stirred at 90° C. for 16 hours under N$_2$. TLC (Petroleum ether:Ethyl acetate=10:1) showed the starting material was consumed and two new spots were detected. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by column chromatography over silica gel to afford compound 261-2 (60 mg, 69.3% yield). $^1$H NMR (400 MHz, CDCl$_3$) δ 7.63 (d, J=8.5 Hz, 2H), 7.44 (s, 1H), 7.37-7.30 (m, 2H), 7.25 (d, J=8.5 Hz, 2H), 6.51 (s, 1H).

Step 2: 2-(2H-Tetrazol-5-yl)-4-(trifluoromethoxy)-N-(4-(trifluoromethyl)phenyl)aniline A solution of compound 261-2 (60 mg, 0.17 mmol, 1.0 eq), NaN$_3$ (34 mg, 0.52 mmol, 3.0 eq) and NH$_4$Cl (28 mg, 0.52 mmol, 3.0 eq) in DMF (2 mL) was stirred at 120° C. for 2 hours. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure to obtain compound 261-3 (60 mg, crude).

Step 3: 2-(5-(5-(Trifluoromethoxy)-2-((4-(trifluoromethyl)phenyl)amino)phenyl)-2H-tetrazol-2-yl)ethanol Compound 261-3 (60 mg, 0.15 mmol, 1.0 eq), compound 261-3a (19 mg, 0.15 mmol, 1.0 eq) and K$_2$CO$_3$ (32 mg, 0.23 mmol, 1.5 eq) were taken up into a microwave tube in DMF (1 mL). The sealed tube was heated at 120° C. for 30 min under microwave. LC-MS showed reactant 261-3 was consumed completely and one main peak with desired MS was detected. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by prep-HPLC to obtain compound 261 as a crude product. The crude product was purified by Prep-TLC, and then the residue was repurified by prep-HPLC to give Compound 261 (9.63 mg, 14% yield). LCMS (ESI): RT=0.914 min, mass calcd. for C$_{17}$H$_{13}$F$_6$N$_5$O$_2$ 433.10, m/z found 434.0 [M+H]$^+$; $^1$H NMR (400 MHz, CDCl$_3$) δ 9.10 (s, 1H), 8.07 (d, J=2.6 Hz, 1H), 7.57 (d, J=8.5 Hz, 2H), 7.50 (d, J=9.1 Hz, 1H), 7.31 (d, J=8.5 Hz, 2H), 7.24 (dd, J=2.5, 9.1 Hz, 1H), 4.91-4.85 (m, 2H), 4.29 (q, J=5.3 Hz, 2H), 2.18 (t, J=5.8 Hz, 1H).

Example 248: 2-(5-(5-(trifluoromethyl)-2-((4-(trifluoromethyl)phenyl)amino)phenyl)-2H-tetrazol-2-yl)ethanol (Compound 262)

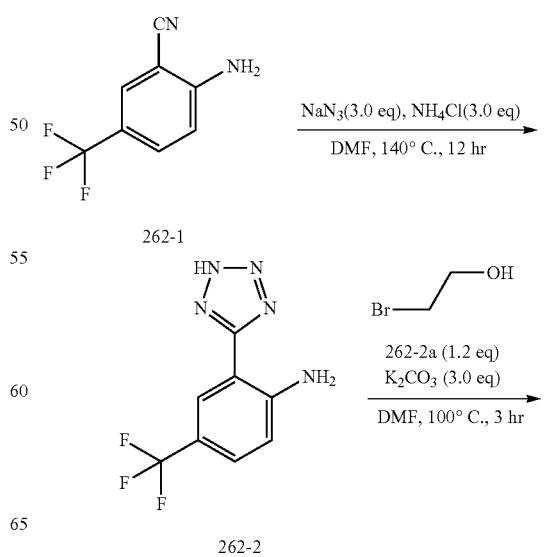

262-1

262-2

Step 3: 2-(5-(5-(trifluoromethyl)-2-((4-(trifluoromethyl)phenyl)amino)phenyl)-2H-tetrazol-2-yl)ethanol To a solution of 262-3 (0.2 g, 0.73 mmol, 1 eq) and 262-3a (166.8 mg, 0.88 mmol, 1.2 eq) in DCM (3 mL) was added Cu(OAc)$_2$ (159.5 mg, 0.88 mmol, 1.2 eq) and DIEA (94.6 mg, 0.73 mmol, 0.13 mL, 2 eq) under O$_2$(15 psi). The mixture was stirred at 25° C. for 12 hr. LCMS showed the desired mass was detected. The reaction mixture was filtered. The filtered cake was washed with ethyl acetate (10 ml*3) and the combined organic layers was washed by NaCl (15 mL*3) then concentrated in vacuum to give crude product. The residue was purified by prep-HPLC. Compound 262 (22.1 mg, 48.6 umol, 6.6% yield, HCl) was obtained. (ESI): RT=0.901 min, mass calc. for C$_{17}$H$_{13}$F$_6$N$_5$O 417.31, m/z found 418.0 [M+H]$^+$; $^1$H NMR (400 MHz, DMSO-d$_6$) δ 9.25 (s, 1H), 8.31 (d, J=1.8 Hz, 1H), 7.76 (dd, J=2.0, 8.8 Hz, 1H), 7.72-7.64 (m, 3H), 7.46 (d, J=8.5 Hz, 2H), 5.18-5.00 (m, 1H), 4.83 (t, J=5.3 Hz, 2H), 3.98 (t, J=5.1 Hz, 2H).

Example 249: 2-(2-(1,3-dioxan-5-yl)-2H-tetrazol-5-yl)-N-(4-(trifluoromethyl)phenyl)aniline (Compound 263)

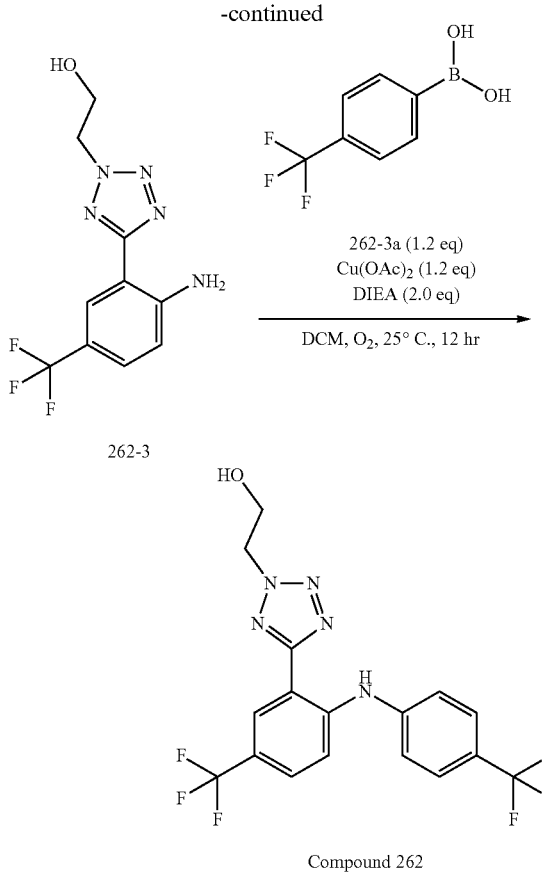

Step 1: 2-(2H-tetrazol-5-yl)-4-(trifluoromethyl)aniline

To a solution of 262-1 (1 g, 5.37 mmol, 1 eq) in DMF (10 mL) was added NaN$_3$ (1.05 g, 16.12 mmol, 3 eq), NH$_4$Cl (862.2 mg, 16.12 mmol, 0.56 mL, 3 eq). The mixture was stirred at 140° C. for 2 hr. LCMS showed the starting material was consumed and the desired mass was detected. The reaction mixture was quenched by addition H$_2$O (25 mL). The mixture was extracted with ethyl acetate (30 mL*3). The combined organic layers were washed with brine (50 mL*2), dried over anhydrous Na$_2$SO$_4$, filtered and concentrated in vacuum. Compound 262-2 (1.2 g, crude) was obtained and used into the next step without further purification.

Step 2: 2-(5-(2-amino-5-(trifluoromethyl)phenyl)-2H-tetrazol-2-yl)ethanol

To a solution of 262-2 (0.4 g, 1.75 mmol, 1 eq) and 262-2a (261.8 mg, 2.09 mmol, 0.15 mL, 1.2 eq) in DMF (2 mL) was added K$_2$CO$_3$ (723.7 mg, 5.24 mmol, 3 eq). The mixture was stirred at 130° C. for 1 hr. LCMS showed the desired mass was detected. The reaction mixture was combined with ES7927-140 to workup. H$_2$O (8 mL) was added to the solution. The mixture was extracted with ethyl acetate (15 mL*3). The combined organic layers were washed with brine (25 mL*2), dried over anhydrous Na$_2$SO$_4$, filtered and concentrated in vacuum. Compound 262-3 (0.4 g, 1.46 mmol, 83.8% yield) was obtained.

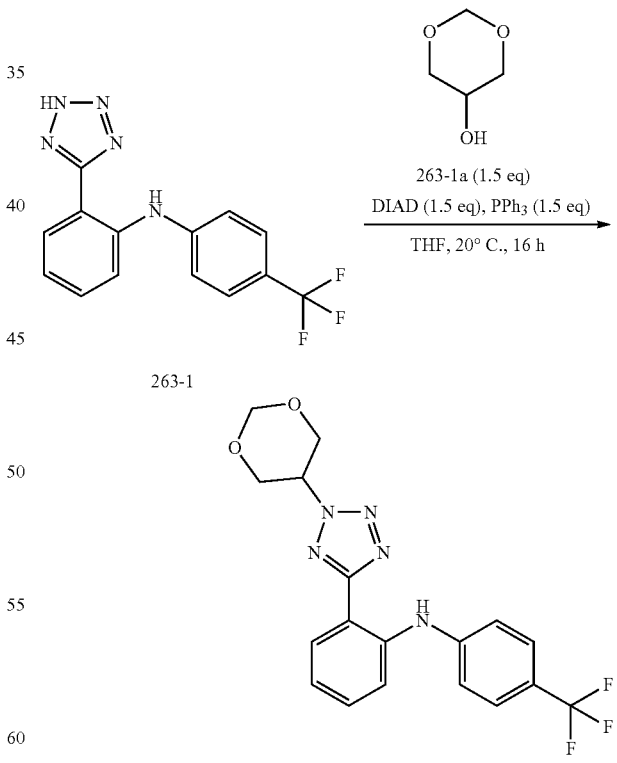

To a solution of compound 263-1 (2 g, 6.55 mmol, 1 eq) in THF (2 mL) were added compound 263-1a (1.02 g, 9.83 mmol, 1.5 eq) and PPh$_3$ (2.58 g, 9.83 mmol, 1.5 eq). The mixture was degassed with N₂ for 3 times. Then DIAD (1.99 g, 9.83 mmol, 1.9 mL, 1.5 eq) was added to the mixture dropwised at 0° C. The mixture was stirred at 20° C. for 16 hr. LCMS showed that the starting material was remained and 33% of desired product was detected. TLC (PE/EA=3/1, UV) showed that several spots were formed. The reaction mixture was concentrated in vacuum and the residue was diluted with EA (20 mL), washed with water (5 mL) and brine (5 mL). The organic phase was dried over Na₂SO₄, filtered and concentrated in vacuum. The crude product was purified by column chromatography (SiO₂). Compound 263 (1.3 g, 2.79 mmol, 42.6% yield) was obtained. LCMS (ESI): RT=0.885 min, mass calcd. For $C_{18}H_{16}F_3N_5O_2$, 391.13 m/z found 392.0 [M+H]⁺; ¹H NMR (400 MHz, CDCl₃) δ 9.02 (s, 1H), 8.20 (dd, J=7.92, 1.38 Hz, 1H), 7.51-7.58 (m, 3H), 7.35-7.42 (m, 1H), 7.30 (d, J=8.54 Hz, 2H), 7.03-7.08 (m, 1H), 5.12 (s, 1H), 4.85-4.94 (m, 2H), 4.65-4.80 (m, 2H), 4.00-4.07 (m, 2H).

Example 250: 2-(5-(2-((4-(trifluoromethyl)phenyl)amino)phenyl)-2H-tetrazol-2-yl)propane-1,3-diol (Compound 264)

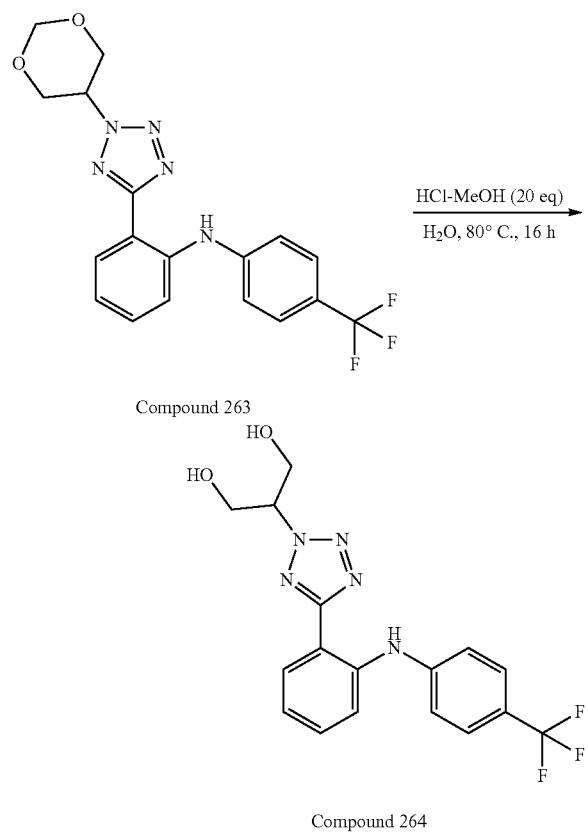

Compound 263

Compound 264

A solution of Compound 263 (1.2 g, 3.07 mmol, 1 eq) in HCl/MeOH (10 mL) and H₂O (1 mL) was stirred at 80° C. for 16 hr. LCMS showed that the starting material was remained and ~40% of desired product was detected. The reaction mixture was concentrated in vacuum. The residue was purified by column chromatography (SiO₂). Compound 264 (340 mg, 0.88 mmol, 28.9% yield) was obtained. LCMS (ESI): RT=0.799 min, mass calcd. For $C_{17}H_{16}F_3N_5O_2$, 379.13 m/z found 379.9 [M+H]⁺; ¹H NMR (400 MHz, CDCl₃) δ 9.00 (s, 1H), 8.18 (dd, J=1.4, 7.9 Hz, 1H), 7.53 (dd, J=5.8, 8.0 Hz, 3H), 7.42-7.35 (m, 1H), 7.29 (br d, J=8.5 Hz, 2H), 7.05 (t, J=7.7 Hz, 1H), 4.91-4.81 (m, 2H), 4.44-4.30 (m, 1H), 3.89-3.80 (m, 1H), 3.79-3.69 (m, 1H), 2.94 (br d, J=5.3 Hz, 1H), 2.15 (br t, J=5.5 Hz, 1H).

Example 251: 2-(2-(1-methyl-1H-pyrazol-4-yl)-2H-tetrazol-5-yl)-N-(4-(trifluoromethyl)phenyl)aniline (Compound 265)

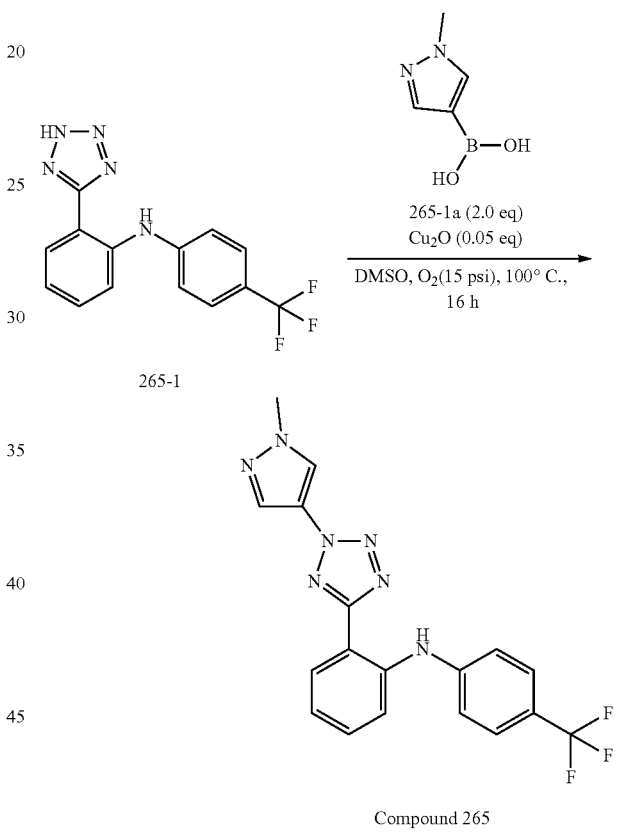

Compound 265

To a solution of compound 265-1 (50 mg, 0.16 mmol, 1 eq) in DMSO (1 mL) were added compound 265-1a (41.2 mg, 0.33 mmol, 2 eq) and Cu₂O (1.2 mg, 8.2 umol, 0.05 eq). The mixture was degassed and purged with O₂ (15 psi) for 3 times and stirred at 100° C. for 16 hr. LCMS showed that 57% of desired product was detected. The reaction mixture was filtered and concentrated in vacuum. The crude product was purified by prep-HPLC. Compound 265 (19 mg, 49.3 umol, 30.1% yield) was obtained. LCMS (ESI): RT=0.918 min, mass calcd. For $C_{18}H_{14}F_3N_7$, 385.13 m/z found 386.0 [M+H]⁺; ¹H NMR (400 MHz, CDCl₃) δ 9.05 (s, 1H), 8.27 (dd, J=1.5, 8.0 Hz, 1H), 8.10 (d, J=4.8 Hz, 2H), 7.56 (br d, J=8.8 Hz, 3H), 7.41 (t, J=7.8 Hz, 1H), 7.32 (d, J=8.5 Hz, 2H), 7.07 (t, J=7.2 Hz, 1H), 4.05 (s, 3H).

Example 252: 2-[5-[5-(difluoromethyl)-2-[4-(trifluoromethyl)anilino]phenyl]tetrazol-2-yl]ethanol (Compound 266)
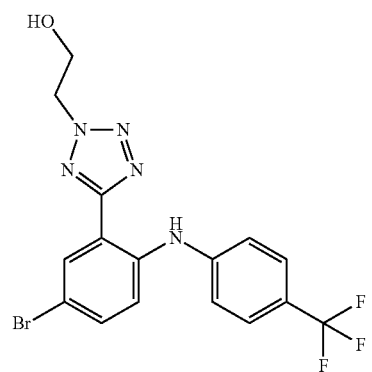
266-1
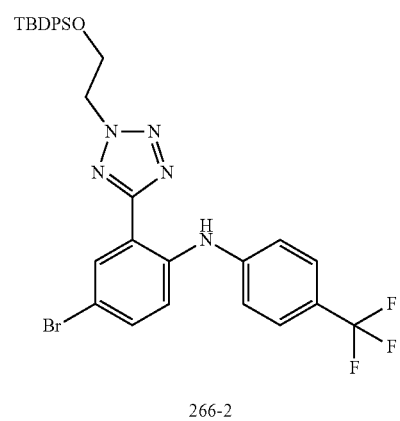
266-2
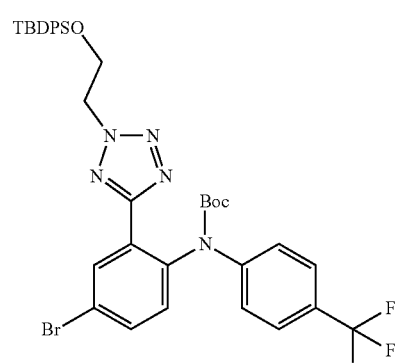
266-3
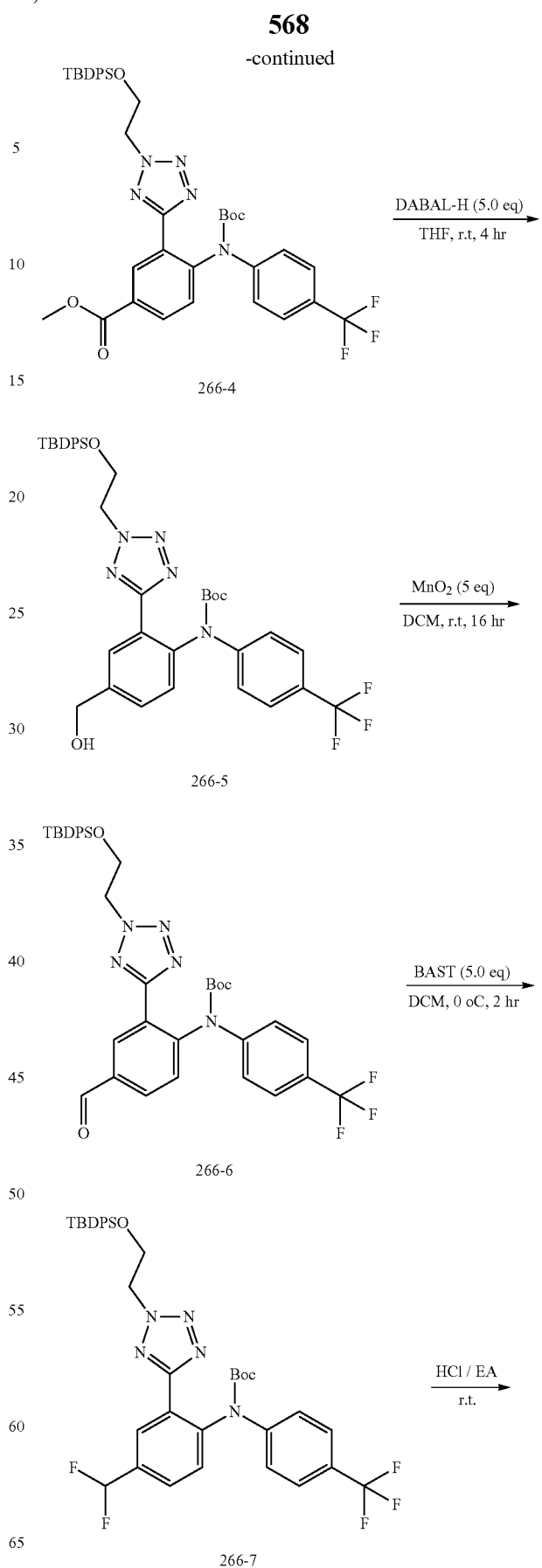

-continued

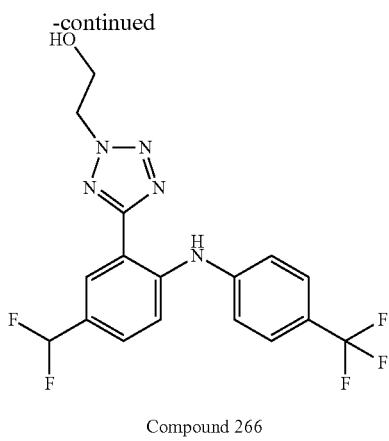

Compound 266

Step 1: 4-bromo-2-[2-[2-[tert-butyl(diphenyl)silyl]oxyethyl]tetrazol-5-yl]-N-[4-(trifluoromethyl)phenyl]aniline To a solution of compound 266-1 (1.6 g, 3.7 mmol, 1 eq) in DCM (20 mL) was added imidazole (763.1 mg, 11.2 mmol, 3 eq) and TBDPSCl (1.5 g, 5.6 mmol, 1.4 mL, 1.5 eq) at 25° C. under $N_2$. The mixture was heated to 40° C. and stirred for 4 hrs. LCMS showed 36% starting material was remained and 44% desired compound was detected. The reaction mixture was quenched by addition of water (20 mL) and extracted with DCM (20 mL*2). The combined organic layers were washed with brine (20 mL), dried over $Na_2SO_4$, filtered and concentrated under reduced pressure to give compound 266-2 (3.5 g, crude), which was used into the next step without further purification. LCMS (ESI): RT=1.192 min, mass calcd for $C_{32}H_{31}BrF_3N_5OSi$ 665.14, m/z found 666.0 [M+H]$^+$.

Step 2: tert-butyl N-[4-bromo-2-[2-[2-[tert-butyl(diphenyl)silyl]oxyethyl]tetrazol-5-yl]phenyl]-N-[4-(trifluoromethyl)phenyl]carbamate To a mixture of compound 266-2 (3 g, 4.5 mmol, 1 eq) and tert-butoxycarbonyl tert-butyl carbonate (2.9 g, 13.5 mmol, 3.1 mL, 3 eq) in DCM (40 mL) was added DMAP (1.1 g, 9.0 mmol, 2 eq) and DIPEA (1.74 g, 13.5 mmol, 2.3 mL, 3 eq) at 25° C. The mixture was stirred at 40° C. for 3 hrs. LCMS showed the starting material was consumed completely and one main peak with desired mass detected. TLC (Petroleum ether:Ethyl acetate=5:1 UV 254 nm) indicated the starting material was consumed completely and two new spots formed. The reaction mixture was quenched by addition of water (50 mL) and extracted with DCM (50 mL*2). The combined organic layers were washed with brine (40 mL), dried over $Na_2SO_4$, filtered and concentrated under reduced pressure to give a residue. The residue was purified by column chromatography ($SiO_2$) to give compound 266-3 (3 g, 2.59 mmol, 57.4% yield). LCMS (ESI): RT=1.176 min, mass calcd for $C_{37}H_{39}BrF_3N_5O_3Si$ 766.72, m/z found 790.2 [M+Na]$^+$.

Step 3: methyl 4-[N-tert-butoxycarbonyl-4-(trifluoromethyl)anilino]-3-[2-[2-[tert-butyl(diphenyl)silyl]oxyethyl]tetrazol-5-yl]benzoate To a solution of compound 266-3 (3 g, 3.9 mmol, 1 eq) in DMSO (25 mL) and MeOH (5 mL) was added Pd(dba)$_2$ (224 mg, 0.39 mmol, 0.1 eq), Xantphos (226 mg, 0.39 mmol, 0.1 eq) and AcOK (1.15 g, 11.7 mmol, 3 eq) at 25° C. under CO (45 psi). The mixture was heated to 80° C. and stirred for 16 hrs. LCMS showed the starting material was consumed completely and one main peak with desired mass. TLC (Petroleum ether:Ethyl acetate=5:1 UV 254 nm) indicated the starting material was consumed completely and two new spots formed. The reaction mixture was filtered and the filter was quenched by addition water (50 mL) and extracted with EA (100 mL*2). The combined organic layers were washed with brine (50 mL*2), dried over $Na_2SO_4$, filtered and concentrated under reduced pressure to give a residue. The residue was purified by column chromatography ($SiO_2$) to give compound 266-4 (600 mg, 0.79 mmol, 20.3% yield). LCMS (ESI): RT=1.122 min, mass calcd for $C_{39}H_{42}F_3N_5O_5S$ 745.86, m/z found 768.3 [M+Na]$^+$.

Step 4: tert-butyl N-[2-[2-[2-[tert-butyl(diphenyl)silyl]oxyethyl]tetrazol-5-yl]-4-(hydroxymethyl)phenyl]-N-[4-(trifluoromethyl)phenyl]carbamate To a solution of compound 266-4 (500 mg, 670 umol, 1 eq) in THF (5 mL) was added DIBAL-H (1 M, 3.3 mL, 5 eq) in one portion at 30° C. under $N_2$. The mixture was stirred at 30° C. for 4 hrs. LCMS showed the starting material was consumed completely and one main peak with desired mass. The reaction mixture was combined with ES7564-262. The mixture was quenched by addition of water (20 mL) and extracted with EA (40 mL*2). The reaction mixture was filtered and the combined organic layers were washed with brine (20 mL), dried over $Na_2SO_4$, filtered and concentrated under reduced pressure to give compound 266-5 (430 mg, 0.38 mmol, 57.1% yield), which was used into the next step without further purification. LCMS (ESI): RT=1.071 min, mass calcd for $C_{38}H_{42}F_3N_5O_4Si$ 717.85, m/z found 740.2 [M+Na]$^+$.

Step 5: tert-butyl N-[2-[2-[2-[tert-butyl(diphenyl)silyl]oxyethyl]tetrazol-5-yl]-4-formyl-phenyl]-N-[4-(trifluoromethyl)phenyl]carbamate To a solution of compound 266-5 (430 mg, 0.59 mmol, 1 eq) in DCM (5 mL) was added $MnO_2$ (260 mg, 3.0 mmol, 5 eq) at 30° C. The mixture was stirred at 30° C. for 16 hrs. LCMS showed the starting material was consumed completely and one main peak with desired mass. The reaction mixture was filtered and the filter was concentrated to give crude compound 266-6 (420 mg, crude), which was used into the next step without further purification. LCMS (ESI): RT=1.101 min, mass calcd for $C_{38}H_{40}F_3N_5O_4Si$ 715.84, m/z found 738.2 [M+Na]$^+$.

Step 6: tert-butyl N-[2-[2-[2-[tert-butyl(diphenyl)silyl]oxyethyl]tetrazol-5-yl]-4-(difluoromethyl)phenyl]-N-[4-(trifluoromethyl)phenyl]carbamate To a solution of compound 266-6 (350 mg, 0.48 mmol, 1 eq) in DCM (5 mL) was added BAST (540.8 mg, 2.44 mmol, 0.53 mL, 5 eq) in one portion at 0° C. under $N_2$. The mixture was stirred at 0° C. for 2 hrs. LCMS showed the starting material was consumed completely and one main peak with desired mass. The reaction mixture was quenched by addition of water (10 mL) and extracted with EA (30 mL*2). The combined organic layers were washed with brine (10 mL), dried over $Na_2SO_4$, filtered and concentrated under reduced pressure to give compound 266-7 (400 mg, 0.45 mmol, 92.6% yield), which was used into the next step without further purification. LCMS (ESI): RT=1.112 min, mass calcd for $C_{38}H_{40}F_5N_5O_3Si$ 737.83, m/z found 760.3 [M+Na]$^+$.

Step 7: 2-[5-[5-(difluoromethyl)-2-[4-(trifluoromethyl)anilino]phenyl]tetrazol-2-yl]ethanol To a mixture of compound 266-7 (100 mg, 0.13 mmol, 1 eq) in DCM (2 mL) was added HCl/MeOH (4 M, 1.7 mL, 50 eq) at 25° C. The mixture was stirred at 25° C. for 1 hr. LCMS showed the starting material was consumed completely and one main peak with desired mass. The reaction mixture was quenched by addition of water (10 mL) and extracted with EA (30 mL*2). The combined organic layers were washed with brine (10 mL), dried over $Na_2SO_4$, filtered and concentrated under reduced pressure to give a residue. The residue was purified by prep-HPLC to give Compound 266 (10.1 mg, 23.1 umol, 17.1% yield, HCl). LCMS (ESI): RT=0.861 min, mass calcd for $C_{17}H_{14}F_5N_5O$ 399.32, m/z found 400 [M+H]$^+$. $^1$H NMR (400 MHz, DMSO-d$_6$) δ 9.11 (s, 1H), 8.26 (s, 1H), 7.69-7.63 (m, 4H), 7.40 (d, J=8.3 Hz, 2H), 7.26 (s, 1H), 7.12 (s, 1H), 6.98 (s, 1H), 5.10 (t, J=5.6 Hz, 1H), 4.81 (t, J=5.3 Hz, 2H), 3.97 (q, J=5.5 Hz, 2H).

II. Biological Evaluation

Example A1: YAP Reporter Assay

HEK293T cells stably transfected with 8XTBD luciferase reporter and pRLTK in 384-well plates were treated with the test compounds, starting from 3 μM (final concentration in assay plate), 1:3 dilution, and 10 points in quadruplicates. Post 24-hr incubation with compounds at 37° C. and 5% CO2, cells were lysed and 8XTBD-driven firefly luciferase and control TK-driven *renilla* luciferase activities were measured using Promega Dual-Luciferase Reporter Assay System.

Reagents: The reagents used for this study are: DMEM: Invitrogen #11960077, Dual-Glo Luciferase Assay System: Promega-E2980, Puromycin Dihydrochloride: Invitrogen-A1113803, 384-well plate: PerkinElmer-6007480, L-GLUTAMINE: Invitrogen-25030164, Hygromycin B: Invitrogen-10687010, and Penicillin-Streptomycin: Merk-TMS-AB2-C Media: The media used for this assay were: Culture Medium: DMEM+1 ug/mL puromycin+200 ug/mL hygromycin (with 10% FBS+1 mM L-glutamine); and Assay Medium: DMEM (with 10% FBS+1 mM L-glutamine+1× P/S).

Cell Plating: The appropriate media was warmed at 37° C. by water bath: Culture Medium, Assay Medium, 1*D-PBS, 0.05% trypsin-EDTA. The cells were trypsinized after removing all media, then washed with 1*sterile D-PBS and then with 2 ml 0.05% trypsin-EDTA. The cells were then incubated at RT for one minute. Then 10 ml/75 cm2 flask Assay Medium was added to each flask. Using a 10 ml pipette, the cells were then gently resuspended in the media, until the clumps completely disappeared. The cells were then transferred into 50 ml centrifuge tubes and were centrifuged at 800 rpm for 5 mins. The medium was removed and the cells were resuspended with Assay Medium. An aliquot of cells was used to count the cell density (cells/nil). The cell suspension was then diluted with Assay Medium to a concentration of 6×104 cells/ml. 50 ul cells suspension was then plated to 384-well plate (PerkinElmer-6007480), 3×103 cells/well and the cells were incubated in an incubator at 37° C., 5% CO2.

Compound Treatment: In the afternoon (incubation of the plate with 3-4 hrs), the test compounds were added by Echo, starting from 3 uM (final concentration in the assay plate), 1:3 dilution, 10 points, quadruplicates. The plate was placed at 37° C., 5% CO2 incubator for 24 hrs.

Detection: The Dual-Glo Luciferase Reagent was prepared by transferring the contents of one bottle of Dual-Glo Luciferase Buffer to one bottle of Dual-Glo Luciferase Substrate to create the Dual-Glo Luciferase Reagent. Mixing was performed by inversion until the substrate was thoroughly dissolved. After mixing, the reagent was aliquoted into 15 ml tubes. In the afternoon (24 hrs post compound treatment), the DMEM+ medium in the 384 well plates were aspirated by Microplate Washer.

Measuring firefly luciferase activity: 20 ul Dual-Glo Luciferase Reagent was added to the 384-well plates. The plates were protected from light to prevent interference with the assay. The plates were shaken for 1 min followed centrifuging plates at 1000 rpm for 30 seconds. After waiting at least 10 minutes, the firefly luminescence was measured by Envision.

Measuring *renilla* luciferase activity: 20 ul Stop-Glo Reagent was added to the 384-well plates. The plates were shaken for 1min and then centrifuged at 1000 rpm for 30 seconds. After waiting at least 10 minutes, the *renilla* luminescence was measured by Envision.

Compound IC$_{50}$ and maximum inhibition on the firefly luciferase and *renilla* luciferase activities were reported separately. IC$_{50}$ for firefly luciferase activity are shown in the table below.

| Compound No. | Name | Firefly Luciferase IC$_{50}$ (μM) |
| --- | --- | --- |
| 3 | 2-[5-[2-[3-(trifluoromethyl)anilino]phenyl]tetrazol-2-yl]ethanol | C |
| 5 | 2-[2-(2-methoxyethyl)tetrazol-5-yl]-N-[3-(trifluoromethyl)phenyl]aniline | C |
| 7 | ethyl 2-[5-[2-(4-fluoroanilino)phenyl]tetrazol-2-yl]acetate | B |
| 8 | 2-[5-[2-(4-fluoroanilino)phenyl]tetrazol-2-yl]ethanol | B |
| 9 | 2-[5-[2-(4-ethylanilino)phenyl]tetrazol-2-yl]ethanol | B |
| 10 | 2-(5-(2-((3-fluorophenyl)amino)phenyl)-2H-tetrazol-2-yl)ethanol | B |
| 11 | 2-(5-(2-((4-(Trifluoromethoxy)phenyl)amino)phenyl)-2H-tetrazol-2-yl)ethanol | A |
| 12 | 2-[5-[2-(4-methoxyanilino)phenyl]tetrazol-2-yl]ethanol | B |
| 13 | 3-[5-[2-[3-(trifluoromethyl)anilino]phenyl]tetrazol-2-yl]propan-1-ol | B |
| 17 | 2-[5-[2-(3-ethylanilino)phenyl]tetrazol-2-yl]ethanol | B |
| 18 | Ethyl 2-[4-[2-[3-(trifluoromethyl)anilino]phenyl]triazol-1-yl]acetate | C |
| 23 | 2-(5-(2-((4-(Trifluoromethyl)phenyl)amino)phenyl)-2H-tetrazol-2-yl)ethanol | A |
| 24 | 2-(5-(2-((3-(Trifluoromethoxy)phenyl)amino)phenyl)-2H-tetrazol-2-yl)ethanol | B |
| 25 | 2-[5-[2-(3,4-difluoroanilino)phenyl]tetrazol-2-yl]ethanol | B |
| 28 | 2-(5-(2-[2,4-difluorophenyl)amino)phenyl)-2H-tetrazol-2-yl)ethan-1-ol | B |

-continued

| Compound No. | Name | Firefly Luciferase IC$_{50}$ (μM) |
|---|---|---|
| 31 | 2-[5-[2-[4-(difluoromethylsulfanyl)anilino]phenyl]tetrazol-2-yl]ethanol | B |
| 36 | 2-(5-(2-[2-fluorophenyl)amino)phenyl)-2H-tetrazol-2-yl)ethanol | C |
| 39 | 2-(3-(2-((3-(trifluoromethyl)phenyl)amino)phenyl)-1H-1,2,4-triazol-1-yl)ethanol | C |
| 40 | 2-[2-(3-pyridylmethyl)tetrazol-5-yl]-N-[4-(trifluoromethyl)phenyl]aniline | B |
| 41 | 2-[2-(4-pyridylmethyl)tetrazol-5-yl]-N-[4-(trifluoromethyl)phenyl]aniline | B |
| 42 | N-methyl-2-[5-[2-[4-(trifluoromethyl)anilino]phenyl]tetrazol-2-yl]acetamide | A |
| 43 | N,N-dimethyl-2-[5-[2-[4-(trifluoromethyl)anilino]phenyl]tetrazol-2-yl]acetamide | B |
| 44 | N,N-diethyl-2-[5-[2-[4-(trifluoromethyl)anilino]phenyl]tetrazol-2-yl]acetamide | C |
| 45 | 1-pyrrolidin-1-yl-2-[5-[2-[4-(trifluoromethyl)anilino]phenyl]tetrazol-2-yl]ethanone | B |
| 46 | N-methyl-2-[5-[2-[4-(trifluoromethoxy)anilino]phenyl]tetrazol-2-yl]acetamide | B |
| 50 | 2-[2-[2-(dimethylamino)ethyl]tetrazol-5-yl]-N-[4-(trifluoromethyl)phenyl]aniline | B |
| 51 | 2-[2-(3-pyridylmethyl)tetrazol-5-yl]-N-[4-(trifluoromethoxy)phenyl]aniline | C |
| 52 | 2-[2-(2-pyridylmethyl)tetrazol-5-yl]-N-[4-(trifluoromethyl)phenyl]aniline | B |
| 53 | 2-[2-(4-pyridylmethyl)tetrazol-5-yl]-N-[4-(trifluoromethoxy)phenyl]aniline | C |
| 54 | 2-[2-(2-pyridylmethyl)tetrazol-5-yl]-N-[4-(trifluoromethoxy)phenyl]aniline | C |
| 57 | 2-[4-[2-[3-(trifluoromethyl)anilino]phenyl]pyrazol-1-yl]ethanol | B |
| 58 | ethyl 2-(4-(2-((3-(trifluoromethyl)phenyl)amino)phenyl)-1H-pyrazol-1-yl)acetate | B |
| 60 | ethyl 2-(4-(2-((4-(trifluoromethyl)phenyl)amino)phenyl)-1H-pyrazol-1-yl)acetate | A |
| 61 | 2-(4-(2-((4-(trifluoromethyl)phenyl)amino)phenyl)-1H-pyrazol-1-yl)acetic acid | B |
| 62 | 2-(2-(3-(dimethylamino)propyl)-2H-tetrazol-5-yl)-N-(4-(trifluoromethyl)phenyl)aniline | C |
| 63 | 2-(2-(3-(dimethylamino)propyl)-2H-tetrazol-5-yl)-N-(4-(trifluoromethoxy)phenyl)aniline | C |
| 69 | 2-(5-(2-((4-(trifluoromethyl)phenyl)amino)pyridin-3-yl)-2H-tetrazol-2-yl)ethanol | B |
| 75 | 2-(5-(2-((4-(trifluoromethoxy)phenyl)amino)pyridin-3-yl)-2H-tetrazol-2-yl)ethanol | B |
| 76 | ethyl 2-[3-methyl-4-[2-[4-(trifluoromethyl)anilino]phenyl]pyrazol-1-yl]acetate | B |
| 77 | ethyl 2-[5-methyl-4-[2-[4-(trifluoromethyl)anilino]phenyl]pyrazol-1-yl]acetate | A |
| 78 | 2-[5-[4-[4-(trifluoromethyl)anilino]-3-pyridyl]tetrazol-2-yl]ethanol | C |
| 83 | 2-[3-methyl-4-[2-[4-(trifluoromethyl)anilino]phenyl]pyrazol-1-yl]ethanol | C |
| 84 | 2-[5-methyl-4-[2-[4-(trifluoromethyl)anilino]phenyl]pyrazol-1-yl]ethanol | C |
| 90 | ethyl 2-(5-methyl-4-(2-((3-(trifluoromethyl)phenyl)amino)phenyl)-1H-pyrazol-1-yl)acetate | C |
| 92 | N-[2-[5-[2-[4-(trifluoromethyl)anilino]phenyl]tetrazol-2-yl]ethyl]acetamide | B |
| 93 | N-[2-[5-[2-[4-(trifluoromethyl)anilino]phenyl]tetrazol-2-yl]ethyl]methanesulfonamide | C |
| 98 | 3-(5-(2-((4-(trifluoromethyl)phenyl)amino)phenyl)-2H-tetrazol-2-yl)propan-1-ol | A |
| 99 | 2-[2-(sulfamoylamino)ethyl]-5-[2-[4-(trifluoromethyl)anilino]phenyl]tetrazole | C |
| 101 | (5-(2-((4-(trifluoromethyl)phenyl)amino)phenyl)-2H-tetrazol-2-yl)methanesulfonamide | B |
| 102 | 2-[5-[2-[4-(trifluoromethyl)anilino]phenyl]tetrazol-2-yl]acetamide | A |
| 105 | 1-[5-[2-[4-(trifluoromethyl)anilino]phenyl]tetrazol-2-yl]propan-2-ol | A |
| 106 | 1-[5-[2-[4-(trifluoromethyl)anilino]phenyl]tetrazol-2-yl]propan-2-ol | A |
| 108 | 2-[5-[2-[4-(trifluoromethyl)anilino]phenyl]tetrazol-2-yl]ethylurea | A |
| 109 | N-(3-(5-(2-((4-(trifluoromethyl)phenyl)amino)phenyl)-2H-tetrazol-2-yl)propyl)methanesulfonamide | C |
| 111 | N-[3-[5-[2-[4-(trifluoromethyl)anilino]phenyl]tetrazol-2-yl]propyl]acetamide | B |
| 113 | 2-[5-[2-[4-(trifluoromethyl)anilino]phenyl]tetrazol-2-yl]ethanehydroxamic acid | B |
| 114 | 3-(5-(2-((4-(trifluoromethyl)phenyl)amino)phenyl)-2H-tetrazol-2-yl)propane-1,2-diol | A |
| 116 | ethyl 2-[5-[2-[4-(trifluoromethyl)anilino]phenyl]tetrazol-2-yl]propanoate | A |
| 117 | 2-[2-(2-fluoroethyl)tetrazol-5-yl]-N-[4-(trifluoromethyl)phenyl]aniline | B |
| 119 | 2-(2-(tetrahydrofuran-3-yl)-2H-tetrazol-5-yl)-N-(4-(trifluoromethyl)phenyl)aniline | A |
| 120 | 2-(2-tetrahydropyran-3-yltetrazol-5-yl)-N-[4-(trifluoromethyl)phenyl]aniline | B |
| 121 | 1-cyclopropyl-2-[5-[2-[4-(trifluoromethyl)anilino]phenyl]tetrazol-2-yl]ethanone | B |
| 122 | 2-(2-tetrahydropyran-4-yltetrazol-5-yl)-N-[4-(trifluoromethyl)phenyl]aniline | B |
| 123 | 2-[2-(oxetan-3-yl)tetrazol-5-yl]-N-[4-(trifluoromethyl)phenyl]aniline | A |
| 124 | 2-[5-[2-[4-(trifluoromethyl)anilino]phenyl]tetrazol-2-yl]ethyl carbamate | A |
| 125 | 2-[5-[2-[4-(trifluoromethyl)anilino]phenyl]tetrazol-2-yl]propan-1-ol | A |
| 126 | 2-[2-(3-fluoropropyl)tetrazol-5-yl]-N-[4-(trifluoromethyl)phenyl]aniline | B |
| 127 | 1-cyclopropyl-2-[5-[2-[4-[5-(trifluoromethyl)anilino]phenyl]tetrazol-2-yl]ethanol | A |
| 128 | 3-methyl-1-[5-[2-[4-(trifluoromethyl)anilino]phenyl]tetrazol-2-yl]butan-2-one | B |
| 129 | 2-(2-(1-methoxypropan-2-yl)-2H-tetrazol-5-yl)-N-(4-(trifluoromethyl)phenyl)aniline | A |
| 130 | 1-phenyl-2-[5-[2-[4-(trifluoromethyl)anilino]phenyl]tetrazol-2-yl]ethanone | C |

| Compound No. | Name | Firefly Luciferase IC$_{50}$ (μM) |
|---|---|---|
| 131 | 1,1,1-trifluoro-3-[5-[2-[4-(trifluoromethyl)anilino]phenyl]tetrazol-2-yl]propan-2-ol | A |
| 132 | (4R)-3-[(1R)-1-phenylethyl]-4-[[5-[2-[4-(trifluoromethyl)anilino]phenyl]tetrazol-2-yl]methyl]oxazolidin-2-one3 | B |
| 133 | 1-[[5-[2-[4-(trifluoromethyl)anilino]phenyl]tetrazol-2-yl]methyl]cyclohexanol | B |
| 135 | 4-[[5-[2-[4-(trifluoromethyl)anilino]phenyl]tetrazol-2-yl]methyl]piperidin-4-ol | C |
| 136 | 5-((5-(2-((4-(trifluoromethyl)phenyl)amino)phenyl)-2H-tetrazol-2-yl)methyl)oxazolidin-2-one | B |
| 138 | 4-[[5-[2-[4-(trifluoromethyl)anilino]phenyl]tetrazol-2-yl]methyl]tetrahydropyran-4-ol | B |
| 139 | 1-(5-(2-(4-(trifluoromethyl)phenyl)amino)phenyl)-2H-tetrazol-2-yl)butan-2-ol | A |
| 140 | 2-[2-(2-pyridyl)tetrazol-5-yl]-N-[4-(trifluoromethyl)phenyl]aniline | B |
| 141 | 3-methyl-1-[5-[2-[4-(trifluoromethyl)anilino]phenyl]tetrazol-2-yl]butan-2-ol | B |
| 142 | 3-[[5-[2-[4-(trifluoromethyl)anilino]phenyl]tetrazol-2-yl]methyl]tetrahydropyran-3-ol | B |
| 143 | 1-phenyl-2-[5-[2-[4-(trifluoromethyl)anilino]phenyl]tetrazol-2-yl]ethanol | C |
| 147 | tert-butyl 3-hydroxy-3-((5-(2-((4-(trifluoromethyl)phenyl)amino)phenyl)-2H-tetrazol-2-yl)methyl)piperidine-1-carboxylate | C |
| 151 | 3-[[5-[2-[4-(trifluoromethyl)anilino]phenyl]tetrazol-2-yl]methyl]tetrahydrofuran-3-ol | A |
| 152 | 1-((5-(2-((4-(Trifluoromethyl)phenyl)amino)phenyl)-2H-tetrazol-2-yl)methyl)cyclopentanol | A |
| 153 | 3-((5-(2-((4-(trifluoromethyl)phenyl)amino)phenyl)-2H-tetrazol-2-yl)methyl)pyrrolidin-3-ol | B |
| 154 | 1-(3-hydroxy-3-((5-(2-((4-(trifluoromethyl)phenyl)amino)phenyl)-2H-tetrazol-2-yl)methyl)pyrrolidin-1-yl)ethanone | B |
| 155 | 1-(3-hydroxy-3-((5-(2-((4-(trifluoromethyl)phenyl) amino) phenyl)-2H-tetrazol-2-yl) methyl piperidin-1-yl) ethanone | B |
| 156 | 3-((5-(2-((4-(tri fluorom ethyl) phenyl) amino) phenyl)-2H-tetrazol-2-yl) methyl) piperidin-3-ol | B |
| 157 | 3-[[5-[2-[4-(trifluoromethyl)anilino]phenyl]tetrazol-2-yl]methyl]azetidin-3-ol | B |
| 158 | (R)-4-((5-(2-((4-(trifluoromethyl)phenyl)amino)phenyl)-2H-tetrazol-2-yl)methyl)oxazolidin-2-one | B |
| 161 | 1-[3-hydroxy-3-[[5-[2-[4-(trifluoromethyl)anilino]phenyl]tetrazol-2-yl]methyl]azetidin-1-yl]ethanone | B |
| 162 | [1-acetyl-3-[[5-[2-[4-(trifluoromethyl)anilino]phenyl]tetrazol-2-yl]methyl]azetidin-3-yl]acetate | C |
| 165 | 2-[2-(3-pyridyl)tetrazol-5-yl]-N-[4-(trifluoromethyl)phenyl]aniline | C |
| 166 | 2-(2-(oxetan-3-ylmethyl)-2H-tetrazol-5-yl)-N-(4-(trifluoromethyl) phenyl) aniline | B |
| 167 | 4-((5-(2-((4-(trifluoromethyl)phenyl)amino)phenyl)-2H-tetrazol-2-yl)methyl)imidazolidin-2-one | B |
| 169 | 1-((5-(2-((4-(Trifluoromethyl)phenyl)amino)phenyl)-2H-tetrazol-2-yl)methyl)cyclobutanol | A |
| 170 | 2-(2-(Cyclobutylmethyl)-2H-tetrazol-5-yl)-N-(4-(trifluoromethyl)phenyl)aniline | B |
| 171 | 2-(2-methyltetrazol-5-yl)-N-[4-(trifluoromethyl)phenyl]aniline | B |
| 172 | 1-phenyl-3-[(5-(2-((4-(trifluoromethyl)phenyl)amino)phenyl)-2H-tetrazol-2-yl)methyl)pyrrolidin-3-ol | C |
| 173 | 2-(2-(2-methoxyethyl)-2H-tetrazol-5-yl)-N-(4-(trifluoromethyl)phenyl)aniline | A |
| 175 | 2-[5-[5-fluoro-2-[4-(trifluoromethyl)anilino]phenyl]tetrazol-2-yl]ethanol | A |
| 176 | 1-phenyl-3-[(5-(2-((4-(trifluoromethyl)phenyl)amino)phenyl)-2H-tetrazol-2-yl)methyl)piperidin-3-ol | B |
| 179 | 2-[5-[2-(4-azidoanilino)phenyl]tetrazol-2-yl]ethanol | B |
| 180 | 4-((5-(2-((4-(trifluoromethyl)phenyl)amino)phenyl)-2H-tetrazol-2-yl)methyl)oxazolidin-2-one | B |
| 181 | 2-[5-[4-fluoro-2-[4-(trifluoromethyl)anilino]phenyl]tetrazol-2-yl]ethanol; | A |
| 183 | 2-(2-(2-(difluoromethoxy)ethyl)-2H-tetrazol-5-yl)-N-(4-(trifluoromethyl)phenyl)aniline | B |
| 185 | 2-(2-(2-(trifluoromethoxy)ethyl)-2H-tetrazol-5-yl)-N-(4-(trifluoromethyl)phenyl)aniline | B |
| 186 | 3-((5-(2-((4-(trifluoromethyl)phenyl)amino)phenyl)-2H-tetrazol-2-yl)methyl)oxetan-3-ol | A |
| 187 | 2-(5-(2-fluoro-6-((4-(trifluoromethyl)phenyl)amino)phenyl)-2H-tetrazol-2-yl)ethan-1-ol | A |
| 188 | 2-(5-(3-fluoro-2-((4-(trifluoromethyl)phenyl)amino)phenyl)-2H-tetrazol-2-yl)ethanol | A |
| 191 | 2-(4-(2-((4-(trifluoromethyl)phenyl)amino)phenyl)-1H-1,2,3-triazol-1-yl)ethan-1-ol | A |
| 192 | (2S,3S)-3-(5-(2-((4-(trifluoromethyl)phenyl)amino)phenyl)-2H-tetrazol-2-yl)butan-2-ol | A |
| 193 | (2R,3R)-3-(5-(2-((4-(trifluoromethyl)phenyl)amino)phenyl)-2H-tetrazol-2-yl)butan-2-ol | A |
| 194 | (2R,3S)-3-(5-(2-((4-(trifluoromethyl)phenyl)amino)phenyl)-2H-tetrazol-2-yl)butan-2-ol | A |
| 195 | (2S,3R)-3-(5-(2-((4-(trifluoromethyl)phenyl)amino)phenyl)-2H-tetrazol-2-yl)butan-2-ol | A |
| 196 | 2-(1-methyl-3-(2-((4-(trifluoromethyl)phenyl)amino)phenyl)-1H-pyrazol-5-yl)ethan-1-ol | C |
| 197 | 2-(4-(2-((4-(trifluoromethyl)phenyl)amino)phenyl)-1H-imidazol-1-yl)ethan-1-ol | B |
| 198 | 2-(2-(2-(piperidin-4-yloxy)ethyl)-2H-tetrazol-5-yl)-N-(4-(trifluoromethyl)phenyl)aniline | B |
| 200 | (1R,2S)-2-(5-(2-((4-(trifluoromethyl)phenyl)amino)phenyl)-2H-tetrazol-2-yl)cyclopentan-1-ol | B |
| 201 | (1S,2R)-2-(5-(2-((4-(trifluoromethyl)phenyl)amino)phenyl)-2H-tetrazol-2-yl)cyclopentan-1-ol | A |
| 202 | ethyl 2-(4-(2-((4-(trifluoromethyl)phenyl)amino)phenyl)-1H-imidazol-1-yl)acetate | B |
| 204 | 1-((5-(2-((4-(trifluoromethyl)phenyl)amino)phenyl)-2H-tetrazol-2-yl)methyl)cyclopropan-1-ol | A |
| 205 | 2-(1-methyl-3-(2-((4-(trifluoromethyl)phenyl)amino)phenyl)-1H-1,2,4-triazol-5-yl)ethan-1-ol | C |

| Compound No. | Name | Firefly Luciferase IC$_{50}$ (μM) |
|---|---|---|
| 206 | 2-(1-methyl-3-(2-((4-(trifluoromethyl)phenyl)amino)phenyl)-1H-1,2,4-triazol-5-yl)propan-1-ol | C |
| 207 | 2-(5-(2-((4-bromophenyl)amino)phenyl)-2H-tetrazol-2-yl)ethan-1-ol | B |
| 208 | 2-(5-(2-((4-chlorophenyl)amino)phenyl)-2H-tetrazol-2-yl)ethan-1-ol | B |
| 210 | 2-(2-(((2S,3S)-3-methoxybutan-2-yl)-2H-tetrazol-5-yl)-N-(4-(trifluoromethyl)phenyl)aniline | A |
| 211 | 2-(2-(((2S,3R)-3-methoxybutan-2-yl)-2H-tetrazol-5-yl)-N-(4-(trifluoromethyl)phenyl)aniline | B |
| 212 | 2-(2-(((2R,3S)-3-methoxybutan-2-yl)-2H-tetrazol-5-yl)-N-(4-(trifluoromethyl)phenyl)aniline | A |
| 213 | 2-(2-(((2R,3R)-3-methoxybutan-2-yl)-2H-tetrazol-5-yl)-N-(4-(trifluoromethyl)phenyl)aniline | B |
| 214 | 2-(2-(2-methoxycyclopentyl)-2H-tetrazol-5-yl)-N-(4-(trifluoromethyl)phenyl)aniline | B |
| 216 | 2-(2-(3-aminopropyl)-2H-tetrazol-5-yl)-N-(4-(trifluoromethyl)phenyl)aniline | B |
| 218 | 2-(2-(1-aminopropan-2-yl)-2H-tetrazol-5-yl)-N-(4-(trifluoromethyl)phenyl)aniline | A |
| 219 | 2-(2-(2-(methylamino)ethyl)-2H-tetrazol-5-yl)-N-(4-(trifluoromethyl)phenyl)aniline | B |
| 220 | 2-(2-(3-(methylamino)propyl)-2H-tetrazol-5-yl)-N-(4-(trifluoromethyl)phenyl)aniline | C |
| 221 | 2-(2-(azetidin-3-yl)-2H-tetrazol-5-yl)-N-(4-(trifluoromethyl)phenyl)aniline | C |
| 227 | 2-(2-(pyrrolidin-3-yl)-2H-tetrazol-5-yl)-N-(4-(trifluoromethyl)phenyl)aniline | B |
| 228 | 2-(2-(2-aminoethyl)-2H-tetrazol-5-yl)-N-(4-(trifluoromethyl)phenyl)aniline | B |
| 229 | 2-(2-(2-aminopropyl)-2H-tetrazol-5-yl)-N-(4-(trifluoromethyl)phenyl)aniline | B |
| 230 | 2-(1-(2-aminoethyl)-1H-1,2,4-triazol-3-yl)-N-(4-(trifluoromethyl)phenyl)aniline | B |
| 233 | (3R,4R)-4-(5-(2-((4-(trifluoromethyl)phenyl)amino)phenyl)-2H-tetrazol-2-yl)pyrrolidin-3-ol | B |
| 234 | (3S,4S)-4-(5-(2-((4-(trifluoromethyl)phenyl)amino)phenyl)-2H-tetrazol-2-yl)pyrrolidin-3-ol | B |
| 238 | 2-(5-(5-chloro-2-((4-(trifluoromethyl)phenyl)amino)phenyl)-2H-tetrazol-2-yl)ethanol | A |
| 239 | 2-(5-(4-chloro-2-((4-(trifluoromethyl)phenyl)amino)phenyl)-2H-tetrazol-2-yl)ethanol | A |
| 240 | 2-[5-[5-methoxy-2-[4-(trifluoromethyl)anilino]phenyl]tetrazol-2-yl]ethanol | A |
| 241 | 2-[5-[4-methoxy-2-[4-(trifluoromethyl)anilino]phenyl]tetrazol-2-yl]ethanol | A |
| 242 | 2-(5-(5-methyl-2-((4-(trifluoromethyl)phenyl)amino)phenyl)-2H-tetrazol-2-yl)ethanol | A |
| 243 | 2-(5-(4-methyl-2-((4-(trifluoromethyl)phenyl)amino)phenyl)-2H-tetrazol-2-yl)ethanol | A |
| 244 | 3-[[5-[2-[4-(trifluoromethyl)anilino]phenyl]tetrazol-2-yl]methyl]thietan-3-ol | A |
| 245 | 1-oxo-3-[[5-[2-[4-(trifluoromethyl)anilino]phenyl]tetrazol-2-yl]methyl]thietan-3-ol | B |
| 246 | 2-(5-(2-((3-chloro-4-(trifluoromethyl)phenyl)amino)phenyl)-2H-tetrazol-2-yl)ethanol | A |
| 248 | 2-(5-(2-((4-((trifluoromethyl)thio)phenyl)amino)phenyl)-2H-tetrazol-2-yl)ethanol | B |
| 250 | 2-(5-(2-((3-chlorophenyl)amino)phenyl)-2H-tetrazol-2-yl)ethanol | C |
| 251 | 2-(5-(2-((3,4-dichlorophenyl)amino)phenyl)-2H-tetrazol-2-yl)ethanol | B |
| 253 | 2-(5-(2-((3,4,5-trichlorophenyl)amino)phenyl)-2H-tetrazol-2-yl)ethanol | C |
| 254 | 2-[5-[5-bromo-2-[4-(trifluoromethyl)anilino]phenyl]tetrazol-2-yl]ethanol | A |
| 255 | 2-(5-(5-cyclopropyl-2-((4-(trifluoromethyl)phenyl)amino)phenyl)-2H-tetrazol-2-yl)ethanol | A |
| 256 | 2-[5-[5-ethyl-2-[4-(trifluoromethyl)anilino]phenyl]tetrazol-2-yl]ethanol | A |
| 259 | 3-amino-2-(5-(2-((4-(trifluoromethyl)phenyl)amino)phenyl)-2H-tetrazol-2-yl)propan-1-ol | B |
| 260 | 2-(5-(5-(difluoromethoxy)-2-((4-(trifluoromethyl)phenyl)amino)phenyl)-2H-tetrazol-2-yl)ethanol | A |
| 261 | 2-(5-(5-(trifluoromethoxy)-2-((4-(trifluoromethyl)phenyl)amino)phenyl)-2H-tetrazol-2-yl)ethanol | B |
| 262 | 2-(5-(5-(trifluoromethyl)-2-((4-(trifluoromethyl)phenyl)amino)phenyl)-2H-tetrazol-2-yl)ethanol | B |
| 263 | 2-(2-(1,3-dioxan-5-yl)-2H-tetrazol-5-yl)-N-(4-(trifluoromethyl)phenyl)aniline | A |
| 264 | 2-(5-(2-((4-(trifluoromethyl)phenyl)amino)phenyl)-2H-tetrazol-2-yl)propane-1,3-diol | A |
| 266 | 2-[5-[5-(difluoromethyl)-2-[4-(trifluoromethyl)anilino]phenyl]tetrazol-2-yl]ethanol | B |

Note:
Biochemical assay IC$_{50}$ data are designated within the following ranges:
A: ≤0.100 μM
B: >0.100 μM to ≤1.000 μM
C: >1.000 μM to ≤5.000 μM
D: >5.000 μM Example A2: Tumor Suppression Assay The procedures described herein for the tumor suppression assay is as described in PCT/US2013/043752 (WO 2013/188138). Mouse procedures are performed according to the guidelines of approved animal protocol and based on the methods. After the cells are grown to 90%>confluence, these cells are harvested by trypsinization, washed in phosphate-buffered saline (PBS), and resuspended in PBS supplemented with 50% matrigel (BD Biosciences). An appropriate amount of cells is prepared for administration, such as 200 μL per injection site. Immuno-compromised mice are injected on the dorsolateral sites subcutaneously. Any one of the compounds described herein is formulated accordingly and is then administered at a suitable dose. Control mice received vehicle alone. The average tumor diameter (two perpendicular axes of the tumor are measured) are recorded. The data are expressed in tumor volume estimated by ([width]2×length/2). Paired, two-tailed Student's t-test is performed to access the statistical significance.

Example A3: Cell Proliferation Assay

Cancer cell lines are plated in 384-well plates 24 h before drug treatment. Post incubation for various time periods

What is claimed is:

1. A compound of Formula (III), or a pharmaceutically acceptable salt thereof:

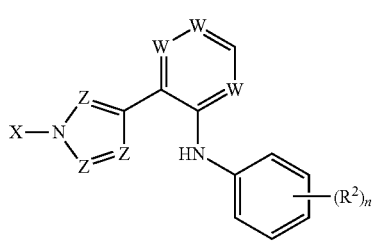

Formula (III)

wherein:
each Z is independently N or CR$^z$;
each R$^z$ is independently H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
X is substituted or unsubstituted C$_1$-C$_6$alkyl, substituted or unsubstituted C$_1$-C$_6$haloalkyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl, -L$^1$-Y$^1$, or -L$^2$-L$^3$-Y$^2$;
L$^1$ is substituted or unsubstituted C$_1$-C$_6$alkylene;
Y$^1$ is substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl;
L$^2$ is absent or substituted or unsubstituted C$_1$-C$_6$alkylene;
L$^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—(C=O)—, —(C=O)—NR$^3$(SO$_2$)NR$^3$—, —O(C=O)—NR$^3$(SO$_2$)—NR$^3$—, or —NR$^3$(SO$_2$)NR$^3$—(C=O)O—;
each R$^3$ is independently H or substituted or unsubstituted C$_1$-C$_6$alkyl;
Y$^2$ is H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl;
or R$^3$ and Y$^2$ on the same N atom are taken together with the N atom to which they are attached to form a substituted or unsubstituted N-containing heterocycle;
each W is CR$^1$ or N with the provision that one W is N;
each R$^1$ is independently H, halogen, —CN, —OR$^4$, —SR$^4$, —N(R$^4$)$_2$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
n is 0, 1, 2, 3, 4, or 5;
each R$^2$ is independently H, halogen, —N$_3$, —CN, —OR$^5$, —SR$^5$, —(SO$_2$)R$^5$, —N(R$^5$)$_2$, —CO$_2$R$^5$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, substituted or unsubstituted heteroaryl, or

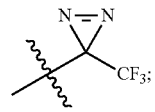

each R$^4$ is independently H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and
each R$^5$ is independently H, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
wherein "substituted" means that the referenced group is substituted with one or more substituents each independently selected from D, halogen, —CN, —NH$_2$, —OH, =O, —NH(CH$_3$), —N(CH$_3$)$_2$, —CH$_3$, —CH$_2$CH$_3$, —CF$_3$, —OCH$_3$, and —OCF$_3$.

2. The compound, or pharmaceutically acceptable salt thereof, of claim 1, wherein:

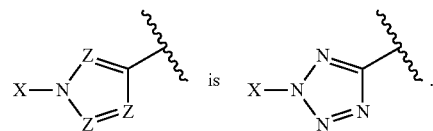

3. The compound, or pharmaceutically acceptable salt thereof, of claim 1, wherein:
    each $R^z$ is independently H or substituted or unsubstituted $C_1$-$C_6$alkyl.

4. The compound, or pharmaceutically acceptable salt thereof, of claim 1, wherein:
    X is substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

5. The compound, or pharmaceutically acceptable salt thereof, of claim 1, wherein:
    X is -$L^1$-$Y^1$; wherein:
    $L^1$ is substituted or unsubstituted $C_1$-$C_4$alkylene; and
    $Y^1$ is substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl.

6. The compound, or pharmaceutically acceptable salt thereof, of claim 1, wherein:

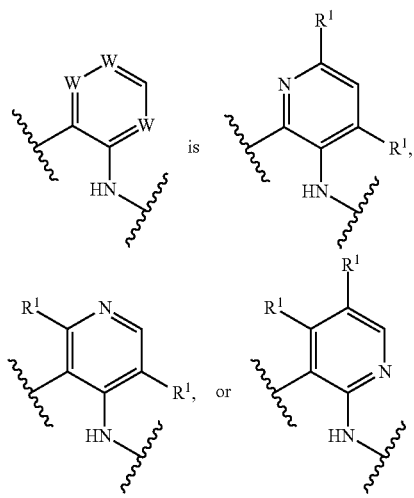

7. The compound, or pharmaceutically acceptable salt thereof, of claim 6, wherein:
    each $R^1$ is independently H, halogen, —CN, —$OR^4$, —$SR^4$, —$N(R^4)_2$, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted aryl, or substituted or unsubstituted heteroaryl.

8. The compound, or pharmaceutically acceptable salt thereof, of claim 1, wherein:

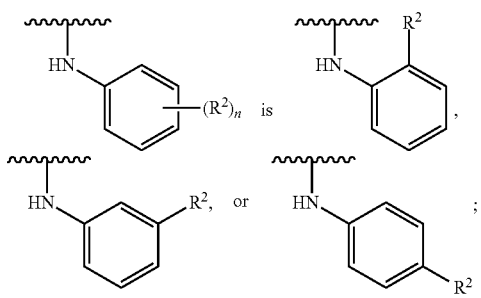

and
$R^2$ is halogen, —$N_3$, —$OR^5$, —$(SO_2)R^5$, —$CO_2R^5$, substituted or unsubstituted $C_1$-$C_6$alkyl, substituted or unsubstituted $C_1$-$C_6$haloalkyl, or

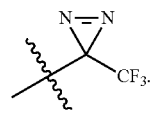

9. The compound, or pharmaceutically acceptable salt thereof, of claim 1, wherein:

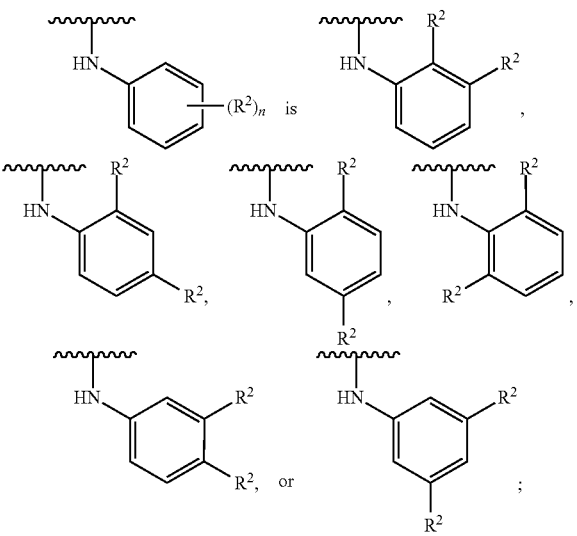

and
each $R^2$ is independently halogen, —$N_3$, —$OR^5$, —$(SO_2)R^5$, —$CO_2R^5$, substituted or unsubstituted $C_1$-$C_6$alkyl, substituted or unsubstituted $C_1$-$C_6$haloalkyl, or

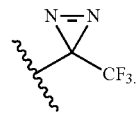

10. The compound, or pharmaceutically acceptable salt thereof, of claim 1, wherein the compound has the structure of Formula (IIIa), or a pharmaceutically acceptable salt thereof:

Formula (IIIa)

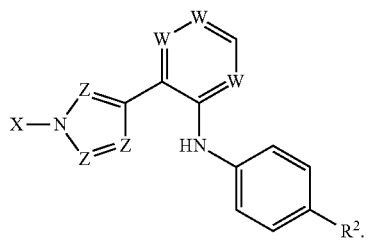

11. The compound, or pharmaceutically acceptable salt thereof, of claim 1, wherein the compound has the structure of Formula (IIIb), or a pharmaceutically acceptable salt thereof:

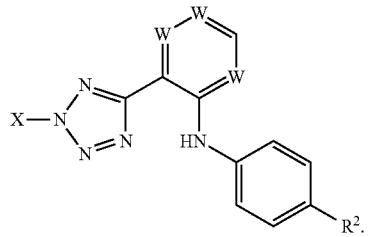

Formula (IIIb)

12. A pharmaceutical composition comprising a pharmaceutically acceptable excipient and a compound of claim 1, or a pharmaceutically acceptable salt thereof.

13. A method of treating cancer in a subject in need thereof comprising administering to the subject in need thereof a therapeutically effective amount of a compound of claim 1, or a pharmaceutically acceptable salt thereof; wherein the cancer is selected from mesothelioma, hepatocellular carcinoma, meningioma, malignant peripheral nerve sheath tumor, lung cancer, prostate cancer, pancreatic cancer, adenosquamous carcinoma, thyroid cancer, gastric cancer, esophageal cancer, ovarian cancer, melanoma, and breast cancer.

14. The compound, or pharmaceutically acceptable salt thereof, of claim 1, wherein each $R^2$ is independently F, Cl, —$CF_3$ or —$OCF_3$.

15. The compound, or pharmaceutically acceptable salt thereof, of claim 14, wherein $R^2$ is —$CF_3$.

16. A method of inhibiting transcriptional coactivator with PDZ binding motif/Yes-associated protein transcriptional coactivator (TAZ/YAP) in a subject, comprising administering to the subject a compound of claim 1, or a pharmaceutically acceptable salt thereof.

17. The compound, or pharmaceutically acceptable salt thereof, of claim 10, wherein:

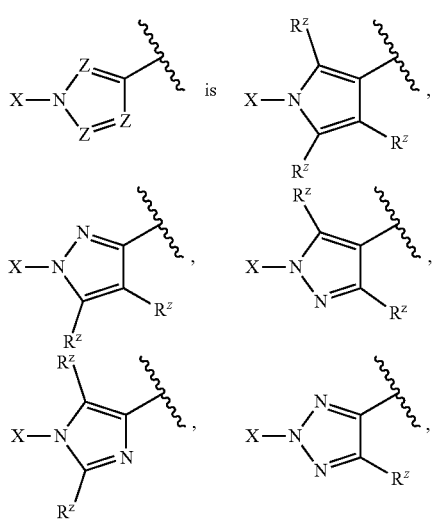

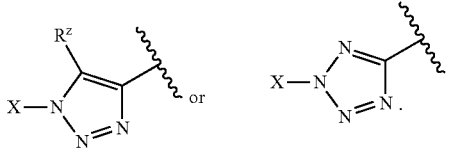

18. The compound, or pharmaceutically acceptable salt thereof, of claim 11, wherein:

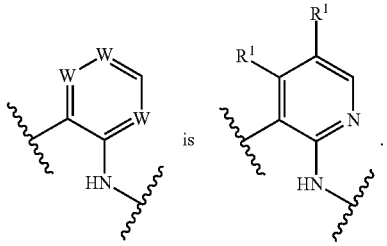

19. The compound, or pharmaceutically acceptable salt thereof, of claim 18, wherein:
each $R^1$ is H; and
$R^2$ is independently F, Cl, —$CF_3$ or —$OCF_3$.

20. The compound, or pharmaceutically acceptable salt thereof, of claim 19, wherein:
X is substituted or unsubstituted $C_2$-$C_6$alkyl;
or X is substituted or unsubstituted cyclopropyl, substituted or unsubstituted cyclobutyl, substituted or unsubstituted cyclopentyl, or substituted or unsubstituted cyclohexyl;
or X is substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted thietanyl, substituted or unsubstituted tetrahydrothienyl, substituted or unsubstituted tetrahydrothiopyranyl, substituted or unsubstituted morpholinyl, or substituted or unsubstituted piperazinyl, substituted or unsubstituted 1,3-dioxolanyl, substituted or unsubstituted oxazolidinonyl, or substituted or unsubstituted imidazolidin-2-onyl;
or X is phenyl;
or X is substituted or unsubstituted pyridinyl, substituted or unsubstituted imidazolyl, substituted or unsubstituted pyrimidinyl, substituted or unsubstituted pyrazolyl, substituted or unsubstituted triazolyl, substituted or unsubstituted pyrazinyl, substituted or unsubstituted tetrazolyl, substituted or unsubstituted furyl, substituted or unsubstituted thienyl, substituted or unsubstituted isoxazolyl, substituted or unsubstituted thiazolyl, substituted or unsubstituted oxazolyl, substituted or unsubstituted isothiazolyl, substituted or unsubstituted pyrrolyl, substituted or unsubstituted pyridazinyl, substituted or unsubstituted triazinyl, substituted or unsubstituted oxadiazolyl, substituted or unsubstituted thiadiazolyl, or substituted or unsubstituted furazanyl.

21. The compound, or pharmaceutically acceptable salt thereof, of claim 19, wherein:
X is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dionyl, pyrrolidinonyl, imidazolidinyl, imidazolidin-2-onyl, or thiazolidin-2-onyl.
22. A compound that has one of the following structures:
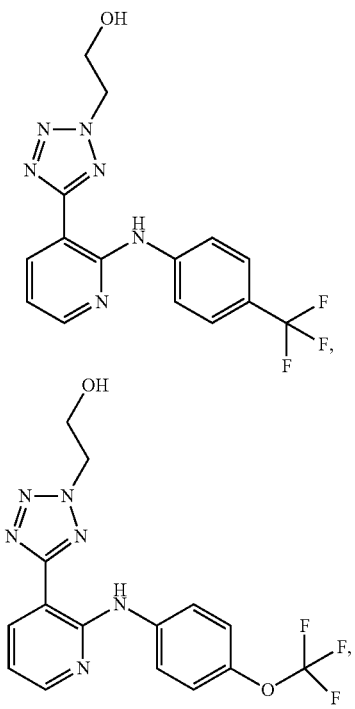
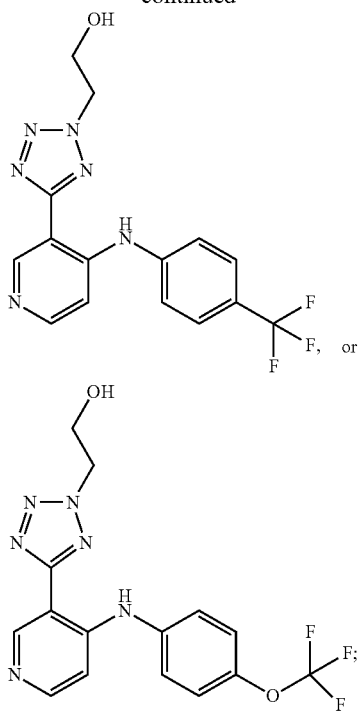
or a pharmaceutically acceptable salt thereof of any one of the preceding compounds.
* * * * *